(12) United States Patent
Gross et al.

(10) Patent No.: US 11,660,315 B2
(45) Date of Patent: May 30, 2023

(54) UNIVERSAL PLATFORM FOR PREPARING AN INHIBITORY CHIMERIC ANTIGEN RECEPTOR (ICAR)

(71) Applicants: ImmPACT-Bio Ltd., Ness Ziona (IL); GAVISH-GALILEE BIO APPLICATIONS LTD., Kiryat Shmona (IL)

(72) Inventors: Gideon Gross, Moshav Almagor (IL); Will Gibson, Boston, MA (US); Dvir Dahary, Tel Aviv (IL); Merav Beiman, Ness Ziona (IL)

(73) Assignees: ImmPACT-Bio Ltd., Ness Ziona (IL); Gavish-Galilee Bio Applications Ltd., Kiryat Shmona (IL)

( * ) Notice: Subject to any disclaimer, the term of this patent is extended or adjusted under 35 U.S.C. 154(b) by 150 days.

(21) Appl. No.: 16/652,019

(22) PCT Filed: Sep. 28, 2018

(86) PCT No.: PCT/US2018/053583
§ 371 (c)(1),
(2) Date: Mar. 27, 2020

(87) PCT Pub. No.: WO2019/068007
PCT Pub. Date: Apr. 4, 2019

(65) Prior Publication Data
US 2020/0261499 A1 Aug. 20, 2020

Related U.S. Application Data

(60) Provisional application No. 62/649,429, filed on Mar. 28, 2018, provisional application No. 62/564,454, filed on Sep. 28, 2017.

(51) Int. Cl.
| | | |
|---|---|---|
| *A61K 35/00* | (2006.01) | |
| *A61K 35/12* | (2015.01) | |
| *A61P 35/00* | (2006.01) | |
| *C07K 14/725* | (2006.01) | |
| *C07K 14/705* | (2006.01) | |
| *C07K 16/28* | (2006.01) | |
| *C12N 15/10* | (2006.01) | |
| *A61K 39/00* | (2006.01) | |
| *A61K 35/17* | (2015.01) | |
| *C07K 16/30* | (2006.01) | |

(52) U.S. Cl.
CPC ............ *A61K 35/12* (2013.01); *A61P 35/00* (2018.01); *C07K 14/7051* (2013.01); *C07K 14/70521* (2013.01); *C07K 14/70578* (2013.01); *C07K 16/2803* (2013.01); *C12N 15/1055* (2013.01); *C12N 15/1093* (2013.01); *A61K 35/17* (2013.01); *A61K 2039/5156* (2013.01); *C07K 16/2833* (2013.01); *C07K 16/30* (2013.01); *C07K 2317/622* (2013.01); *C07K 2317/73* (2013.01); *C07K 2319/02* (2013.01); *C07K 2319/03* (2013.01); *C07K 2319/33* (2013.01)

(58) Field of Classification Search
CPC ..... A61K 35/12; A61P 35/00; C07K 14/7051; C07K 16/2833; C07K 16/30
See application file for complete search history.

(56) References Cited

U.S. PATENT DOCUMENTS

| | | | |
|---|---|---|---|
| 9,745,368 | B2 | 8/2017 | Milone et al. |
| 11,267,901 | B2 * | 3/2022 | Fedorov .................. A61P 13/08 |
| 2015/0376296 | A1 | 12/2015 | Fedorov et al. |
| 2016/0289293 | A1 | 10/2016 | Pule |
| 2019/0290691 | A1 | 9/2019 | Jackel |

FOREIGN PATENT DOCUMENTS

| | | |
|---|---|---|
| JP | 2012501652 A | 1/2012 |
| JP | 2017-503472 A | 2/2017 |
| JP | 2017-504623 A | 2/2017 |
| WO | WO 2014145252 A2 | 9/2014 |
| WO | WO 2015075468 A1 | 5/2015 |
| WO | WO 2015142314 A1 | 9/2015 |
| WO | WO 2016075612 A1 | 5/2016 |
| WO | WO 2016097231 A2 | 6/2016 |
| WO | WO 2016126608 A1 | 8/2016 |
| WO | WO 2016138034 A1 | 9/2016 |
| WO | WO 2018061012 A1 | 4/2018 |
| WO | WO 2018/204546 A2 | 11/2018 |
| WO | WO 2018211245 A1 | 11/2018 |
| WO | 2019/068007 A1 | 4/2019 |
| WO | 2020/065406 A1 | 4/2020 |
| WO | WO 2020/092554 A1 | 5/2020 |

OTHER PUBLICATIONS

Abecasis et al. "A map of human genome variation from population-scale sequencing." Nature—1000 Genomes Project Consortium. 467.7319 (2010): 1061-1073.
Abeyweera, Thushara P., Ernesto Merino, and Morgan Huse. "Inhibitory signaling blocks activating receptor clustering and induces cytoskeletal retraction in natural killer cells." Journal of Cell Biology 192.4 (2011): 675-690.
Auton et al. "A global reference for human genetic variation." Nature—1000 Genomes Project Consortium. 526.7571 (2015): 68-74.
Barrett, Michael T., et al. "Evolution of neoplastic cell lineages in Barrett oesophagus." Nature genetics 22.1 (1999): 106-109.

(Continued)

*Primary Examiner* — Jeanette M Lieb
(74) *Attorney, Agent, or Firm* — McDermott Will & Emery LLP; Brennen P. Baylor

(57) ABSTRACT

The present invention provides a method of identifying a target for preparing an inhibitory chimeric antigen receptor (iCAR) or a protective chimeric antigen receptor (pCAR) capable of preventing or attenuating undesired activation of an effector immune cell. Also provided are a list of iCAR targets, as well as vectors and transduced effector immune cells comprising the nucleic acid molecule and methods for treatment of cancer comprising administering the transduced effector immune cells are further provided.

11 Claims, 79 Drawing Sheets
Specification includes a Sequence Listing.

(56) References Cited

OTHER PUBLICATIONS

Bausch-Fluck, Damaris, et al. "A mass spectrometric-derived cell surface protein atlas." PloS one 10.4 (2015) 1-22.
Bayle, J. Henri, et al. "Rapamycin analogs with differential binding specificity permit orthogonal control of protein activity." Chemistry & biology 13.1 (2006): 99-107.
Bergbold, Nina, and Marius K. Lemberg. "Emerging role of rhomboid family proteins in mammalian biology and disease." Biochimica et Biophysica Acta (BBA)-Biomembranes 1828.12 (2013): 2840-2848.
Blankenstein, Thomas, et al. "Targeting cancer-specific mutations by T cell receptor gene therapy." Current opinion in immunology 33 (2015): 112-119.
Boczkowski, David, et al. "Induction of tumor immunity and cytotoxic T lymphocyte responses using dendritic cells transfected with messenger RNA amplified from tumor cells." Cancer research 60.4 (2000): 1028-1034.
Burrell, Rebecca A., et al. "The causes and consequences of genetic heterogeneity in cancer evolution." Nature 501.7467 (2013): 338-345.
Caescu, Cristina I., Grace R. Jeschke, and Benjamin E. Turk. "Active-site determinants of substrate recognition by the metalloproteinases TACE and ADAM10." Biochemical Journal 424.1 (2009): 79-88.
Carney, W. P., et al. "Monoclonal antibody specific for an activated RAS protein." Proceedings of the National Academy of Sciences 83.19 (1986): 7485-7489.
Cerami, Ethan, et al. "The eBio cancer genomics portal: an open platform for exploring multidimensional cancer genomics data." 2 (2012): 401-404.
Chao, Ginger, et al. "Isolating and engineering human antibodies using yeast surface display." Nature protocols 1.2 (2006): 755-768.
Chess, Andrew. "Mechanisms and consequences of widespread random monoallelic expression." Nature Reviews Genetics 13.6 (2012): 421-428.
Chicaybam et al. (2014) "Construction and validation of an activating and inhibitory chimeric antigen receptor (CAR) system," Cancer Research. vol. 74, Issue 19, Abstract 2797, 4 pages.
Chicaybam et al. (2015) "Construction and validation of an activating and inhibitory chimeric antigen receptor (CAR) system." Cancer Research. vol. 75, Issue 15, Abstract 3156, 4 pages.
Da Cunha, J. P. C., et al. "Bioinformatics construction of the human cell surfaceome." Proceedings of the National Academy of Sciences 106.39 (2009): 16752-16757.
Devilee, Peter, Anne-Marie Cleton-Jansen, and Cees J. Cornelisse. "Ever since Knudson." Trends in genetics 17.10 (2001): 569-573.
Dotti, Gianpietro, et al. "Design and development of therapies using chimeric antigen receptor-expressing T cells." Immunological reviews 257.1 (2014): 107-126.
Ebsen, Henriette, et al. "Differential surface expression of ADAM10 and ADAM17 on human T lymphocytes and tumor cells." PloS one 8.10 (2013) e76853, 1-16.
Eriksson, Mikael, et al. "Inhibitory receptors alter natural killer cell interactions with target cells yet allow simultaneous killing of susceptible targets." The Journal of experimental medicine 190.7 (1999): 1005-1012.
European Search Report corresponding to European Patent Application No. 17855171.9, dated Mar. 26, 2020, 8 pages.
Fedorov et al. (2013) "PD-1-and CTLA-4-based inhibitory chimeric antigen receptors (iCARs) divert off-target immunotherapy responses." Science translational medicine. 5(215-172):1-25.
Feenstra, M., et al. "HLA class I expression and chromosomal deletions at 6p and 15q in head and neck squamous cell carcinomas." Tissue antigens 54.3 (1999): 235-245.
Gao, Jianjiong, et al. "Integrative analysis of complex cancer genomics and clinical profiles using the cBioPortal." Sci. Signal. 6.269 (2013): 1-34.
Gill, Saar, and Carl H. June. "Going viral: chimeric antigen receptor T-cell therapy for hematological malignancies." Immunological reviews 263.1 (2015): 68-89.
Gordon, Wendy R., et al. "Mechanical allostery: evidence for a force requirement in the proteolytic activation of Notch." Developmental cell 33.6 (2015): 729-736.
Graef, Isabella A., et al. "Proximity and orientation underlie signaling by the non-receptortyrosine kinase ZAP70." The EMBO journal 16.18 (1997): 5618-5628.
Gross et al. (2016) "Therapeutic Potential of T Cell Chimeric Antigen Receptors (CARs) in Cancer Treatment: Counteracting Off-Tumor Toxicities for Safe Car T Cell Therapy," Annu. Rev. Pharmacol. Toxicol. 56:59-83.
Gross, Gideon, Tova Waks, and Zelig Eshhar. "Expression of immunoglobulin-T-cell receptor chimeric molecules as functional receptors with antibody-type specificity." Proceedings of the National Academy of Sciences 86.24 (1989): 10024-10028.
GTEx Consortium. "The Genotype-Tissue Expression (GTEx) pilot analysis: multitissue gene regulation in humans." Science 348.6235 (2015): 648-660.
Haapasalo, Annakaisa, and Dora M. Kovacs. "The many substrates of presenilin/γ-secretase." Journal of Alzheimer's disease 25.1 (2011): 3-28.
Hamburger et al. (2020) "Engineered T cells directed at tumors with defined allelic loss," Molecular Immunology. 128:298-310.
Hanes, Jozef, and Andreas Pluckthun. "In vitro selection and evolution of functional proteins by using ribosome display." Proceedings of the National Academy of Sciences 94.10 (1997): 4937-4942.
Heemskerk, Bianca, Pia Kvistborg, and Ton NM Schumacher. "The cancer antigenome." The EMBO journal 32.2 (2013): 194-203.
Hemming, Matthew L., et al. "Identification of β-secretase (BACE1) substrates using quantitative proteomics." PloS one 4.12 (2009) e8477, 1-14.
Huse, Morgan, S. Catherine Milanoski, and Thushara P. Abeyweera. "Building tolerance by dismantling synapses: inhibitory receptor signaling in natural killer cells." Immunological reviews 251.1 (2013): 143-153.
International Search Report with Written Opinion corresponding to International Patent Application No. PCT/IL17/51102, dated Jan. 14, 2018, 8 pages.
Jiménez, Pilar, et al. "Chromosome loss is the most frequent mechanism contributing to HLA haplotype loss in human tumors." International journal of cancer 83.1 (1999): 91-97.
Klebanoff, Christopher A., Steven A. Rosenberg, and Nicholas P. Restifo. "Prospects for gene-engineered T cell immunotherapy for solid cancers." Nature medicine 22.1 (2016): 26-36.
Kloss, Christopher C., et al. "Combinatorial antigen recognition with balanced signaling promotes selective tumor eradication by engineered T cells." Nature biotechnology 31.1 (2013): 71-75.
Knudson, Alfred G. "Mutation and cancer: statistical study of retinoblastoma." Proceedings of the National Academy of Sciences 68.4 (1971): 820-823.
Lanitis, Evripidis, et al. "Chimeric antigen receptor T Cells with dissociated signaling domains exhibit focused antitumor activity with reduced potential for toxicity in vivo." Cancer immunology research 1.1 (2013): 43-53.
Lawrence et al. (2014) "Discovery and saturation analysis of cancer genes across 21 tumour types," Nature. 505:495-501.
Lawrence, Michael S., et al. "Mutational heterogeneity in cancer and the search for new cancer-associated genes." Nature 499.7457 (2013): 214-218.
Lee, Andria, et al. "Distribution analysis of nonsynonymous polymorphisms within the G-protein-coupled receptor gene family." Genomics 81.3 (2003): 245-248.
Lek, Monkol, et al. "Analysis of protein-coding genetic variation in 60,706 humans." Nature 536.7616 (2016): 285-291.
Lengauer, Christoph, Kenneth W. Kinzler, and Bert Vogelstein. "Genetic instabilities in human cancers." Nature 396.6712 (1998): 643-649.
Li, Hongsheng, et al. "A preliminary study of the relationship between breast cancer metastasis and loss of heterozygosity by using exome sequencing." Scientific reports 4 (2014): 5460 1-6.

(56) References Cited

OTHER PUBLICATIONS

Liberles, Stephen D., et al. "Inducible gene expression and protein translocation using nontoxic ligands identified by a mammalian three-hybrid screen." Proceedings of the National Academy of Sciences 94.15 (1997): 7825-7830.

Lindblad-Toh, Kerstin, et al. "Loss-of-heterozygosity analysis of small-cell lung carcinomas using single-nucleotide polymorphism arrays." Nature biotechnology 18.9 (2000): 1001-1005.

Lo, Ken C., et al. "Comprehensive analysis of loss of heterozygosity events in glioblastoma using the 100K SNP mapping arrays and comparison with copy number abnormalities defined by BAC array comparative genomic hybridization." Genes, Chromosomes and Cancer 47.3 (2008): 221-237.

Long, Eric O., et al. "Controlling natural killer cell responses: integration of signals for activation and inhibition." Annual review of immunology 31 (2013): 227-258.

Maleno, Isabel, et al. "Distribution of HLA class I altered phenotypes in colorectal carcinomas: high frequency of HLA haplotype loss associated with loss of heterozygosity in chromosome region 6p21." Immunogenetics 56.4 (2004): 244-253.

Maleno, Isabel, et al. "Frequent loss of heterozygosity in the β2-microglobulin region of chromosome 15 in primary human tumors." Immunogenetics 63.2 (2011): 65-71.

Maleno, Isabel, et al. "LOH at 6p21.3 region and HLA class altered phenotypes in bladder carcinomas." Immunogenetics 58.7 (2006): 503-510.

Maleno, Isabel, et al. "Multiple mechanisms generate HLA class I altered phenotypes in laryngeal carcinomas: high frequency of HLA haplotype loss associated with loss of heterozygosity in chromosome region 6p21." Cancer Immunology, Immunotherapy 51.7 (2002): 389-396.

Mcgranahan, Nicholas, et al. "Cancer chromosomal instability: therapeutic and diagnostic challenges." EMBO reports 13.6 (2012): 528-538.

Medintz et al. (2000) "Loss of heterozygosity assay for molecular detection of cancer using energy-transfer primers and capillary array electrophoresis," Genome research. 10(8):1211-1218.

Morsut, Leonardo, et al. "Engineering customized cell sensing and response behaviors using synthetic notch receptors." Cell 164.4 (2016): 780-791.

Ng, Pauline C., and Steven Henikoff. "SIFT: Predicting amino acid changes that affect protein function." Nucleic acids research 31.13 (2003): 3812-3814.

Nirschl, Christopher J., and Charles G. Drake. "Molecular pathways: coexpression of immune checkpoint molecules: signaling pathways and implications for cancer immunotherapy." Clinical cancer research 19.18 (2013): 4917-4924.

Ohgaki, Hiroko, et al. "Genetic pathways to glioblastoma: a population-based study." Cancer research 64.19 (2004): 6892-6899.

O'Keefe, Christine, Michael A. McDevitt, and Jaroslaw P. Maciejewski. "Copy neutral loss of heterozygosity: a novel chromosomal lesion in myeloid malignancies." Blood, The Journal of the American Society of Hematology 115.14 (2010): 2731-2739.

Overwijk, Willem W., et al. "Mining the mutanome: developing highly personalized Immunotherapies based on mutational analysis of tumors." Journal for immunotherapy of cancer 1.1 (2013): 11.

Patel et al. (2014) "Cancer CARtography: charting out a new approach to cancer immunotherapy," Immunotherapy. 6(6):675-678.

Rana, Brinda K., Tetsuo Shiina, and Paul A. Insel. "Genetic variations and polymorphisms of G protein-coupled receptors: functional and therapeutic implications." Annual review of pharmacology and toxicology 41.1 (2001): 593-624.

Rawson, Robert B. "The site-2 protease." Biochimica et Biophysica Acta (BBA)-Biomembranes 1828.12 (2013): 2801-2807.

Rosenberg, Steven A. "Finding suitable targets is the major obstacle to cancer gene therapy." Cancer gene therapy 21.2 (2014): 45-47.

Rosenberg, Steven A., and Nicholas P. Restifo. "Adoptive cell transfer as personalized immunotherapy for human cancer." Science 348.6230 (2015): 62-68.

Roybal et al. (2016) "Precision Tumor Recognition by T Cells with Combinatorial Antigen-Sensing Circuits," Cell. 164:770-779.

Sathirapongsasuti, Jarupon Fah, et al. "Exome sequencing-based copy-number variation and loss of heterozygosity detection: ExomeCNV." Bioinformatics 27.19 (2011): 2648-2654.

Savage, Peter A. "Tumor antigenicity revealed." Trends in immunology 35.2 (2014): 47-48.

Savova, Virginia, et al. "Genes with monoallelic expression contribute disproportionately to genetic diversity in humans." Nature genetics 48.3 (2016): 231-237.

Schumacher, Ton N., and Robert D. Schreiber. "Neoantigens in cancer immunotherapy." Science 348.6230 (2015): 69-74.

Sela-Culang, Inbal, et al. "PEASE: predicting B-cell epitopes utilizing antibody sequence." Bioinformatics 31.8 (2015): 1313-1315.

Sela-Culang, Inbal, Yanay Ofran, and Bjoern Peters. "Antibody specific epitope prediction—emergence of a new paradigm." Current opinion in virology 11 (2015): 98-102.

Skora, Andrew D., et al. "Generation of MANAbodies specific to HLA-restricted epitopes encoded by somatically mutated genes." Proceedings of the National Academy of Sciences 112.32 (2015): 9967-9972.

Stark, Mitchell, and Nicholas Hayward. "Genome-wide loss of heterozygosity and copy number analysis in melanoma using high-density single-nucleotide polymorphism arrays." Cancer research 67.6 (2007): 2632-2642.

Stark, Susan E., and Andrew J. Caton. "Antibodies that are specific for a single amino acid interchange in a protein epitope use structurally distinct variable regions." The Journal of experimental medicine 174.3 (1991): 613-624.

Teo, Shu Mei, et al. "Statistical challenges associated with detecting copy number variations with next-generation sequencing." Bioinformatics 28.21 (2012): 2711-2718.

Thul, Peter J., et al. "A subcellular map of the human proteome." Science 356.6340 (2017): eaal3321, 1-14.

Treanor, Bebhinn, et al. "Microclusters of inhibitory killer immunoglobulin-like receptor signaling at natural killer cell immunological synapses." The Journal of cell biology 174.1 (2006): 153-161.

Uhlén, Mathias, et al. "Tissue-based map of the human proteome." Science 347.6220(2015): 1260419 1-11.

Van Buuren, Marit M., Jorg JA Calis, and Ton NM Schumacher. "High sensitivity of cancer exome-based CD8 T cell neo-antigen identification." Oncoimmunology 3.5 (2014): e28836, 1-7.

Vogelstein, Bert, et al. "Allelotype of colorectal carcinomas." Science 244.4901 (1989): 207-211.

Vogelstein, Bert, et al. "Cancer genome landscapes." Science 339. 6127 (2013): 1546-1558.

Voss, Matthias, Bernd Schröder, and Regina Fluhrer. "Mechanism, specificity, and physiology of signal peptide peptidase (SPP) and SPP-like proteases." Biochimica Et Biophysica Acta (BBA)-Biomembranes 1828.12 (2013): 2828-2839.

Vyas, Yatin M., et al. "Spatial organization of signal transduction molecules in the NK cell immune synapses during MHC class I-regulated noncytolytic and cytolytic interactions." The Journal of Immunology 167.8 (2001): 4358-4367.

Wang, Zhigang C., et al. "Loss of heterozygosity and its correlation with expression profiles in subclasses of invasive breast cancers." Cancer research 64.1 (2004): 64-71.

Wilkie, Scott, et al. "Dual targeting of ErbB2 and MUC1 in breast cancer using chimeric antigen receptors engineered to provide complementary signaling." Journal of clinical immunology 32.5 (2012): 1059-1070.

Wu, Chia-Yung, et al. "Remote control of therapeutic T cells through a small molecule-gated chimeric receptor." Science 350. 6258 (2015): aab4077 1-21.

Yeung, Jacky T., et al. "LOH in the HLA class I region at 6p21 is associated with shorter survival in newly diagnosed adult glioblastoma." Clinical Cancer Research 19.7 (2013): 1816-1826.

MacDonald et al. (J Clin Invest. 2016;126(4):1413-1424. (Year: 2016).

Sergeeva et al., Blood (2008, 112(11), 2545). (Year: 2008).

Bellon et al. (J Immunol 2002; 168:3351-3359), (Year: 2002).

Binstadt et al. (Immunity Dec. 1996;5(6):629-38) (Year: 1996).

Ellis et al. (Human Immunology, 61, 334-340 (2000)). (Year: 2000).

(56) References Cited

OTHER PUBLICATIONS

McEvoy et al. (Tissue Antigens, 2002, 60: 235-243). (Year: 2002).
Morgan et al. (MolecularTherapy, vol. 18 No. 4, 843-851, 2010). (Year: 2010).
Sayos et al. (Biochem Biophys Res Commun. Nov. 12, 2004;324(2):640-7). (Year: 2004).
Sun et al. (Breast Cancer Research 2014, 16:R61). (Year: 2014).
Burlingham, et al., "Hla (A*0201) Mimicry by Anti-Idiotypic Monoclonal Antibodies," J. Immunol., 1998, 161:6705-6714.
International Search Report and Written Opinion for International Application No. PCT/US21/49315, dated Feb. 23, 2022.
Cordoba, et al. "The large ectodomains of CD45 and CD148 regulate their segregation from and inhibition of ligated T-cell receptor." Blood 121.21 (2013): 4295-4302.
Irles, et al. "CD45 ectodomain controls interaction with GEMs and Lck activity for optimal TCR signaling." Nature immunology 4.2 (2003): 189-197.
JPO—Japanese Search Report dated Jul. 25, 2022 for related Japenese Appl. No. 2020-518009, 16 pgs. English-Japanese translations.
Betts and Koup, "Detection of T-Cell Degranulation: CD107a and b," Methods in Cell Biology, 2004, 75:497-512.
Campoli, et al., "HLA Antigen Changes in Malignant Cells: Epigenetic Mechanisms and Biologic Significance." Ocogene (2008) 27:5869-5885.
Chen, et al., "Structural and Functional Distinctiveness of HLA-2 Aallelic Variants" Immunol. Res. (2012) 53:182-190.
Compagno, M., et al., "Mutations of Multiple Genes Cause Deregulation of NF-kB in Diffuse Large B-cell-Lymphoma," Nature, Jun. 2009, 459(7247):717-721.
Gerlinger M., M.D et al., "Intratumor Heterogeneity and Branched Evolution Revealed by Multiregion Sequencing," New England Journal of Medicine, 2012, 366(10):883-892.
Hilton, et al., "Direct binding to antigen-coated beads refines the specificity and cross-reactivity of four monoclonal antibodies that recognize polymorphic epitopes of HLA class I molecules." Tissue Antigens (Apr. 2013) 81(4):212-220.
Hudecek, et al. "The nonsignaling extracellular spacer domain of chimeric antigen receptors is decisive for in vivo antitumor activity." Cancer Immunol. Res. (2014) 3(2)—pp. 125-135.
Matali, et al., "Selective Changes in Expression of HLA Class I Polymorphic Determinants in Human Solid Tumors." Proc. Natl. Acad. Sci. USA (Sep. 1989) 86:6719-6723.
Norell, Hakan, et al., "Frequent Loss of HLA-A2 Expression in Metastasizing Ovarian Carcinomas Associated with Genomic Haplotype Loss and HLA-A2-Restricted HER-2/neu-Specific Immunity." Cancer Res. (2006) 66 (12):6397-6394.
Ramos and Amorim, "Molecular biology techniques for loss of heterozygosity detection: the glioma example," J. Bras Patol. Med. Lab., Jun. 2015, 51 (3):198-196.
Saverino, et al., "The CD85/LIR-1/ILT2 Inhibitory Receptor Is Expressed by All Human T Lymphocytes and Down-Regulates Their Functions." J. Immunol (2000) 165:3742-3755.
Song, et al., "Full Screening and Accurate Subtyping of HLA-A*02 Alleles Through Group-Specific Amplification and Mono-Allelic Sequencing." Cellular & Molecular Immunology. (2013) 10; pp. 490-496.
Zack T. et al., "Pan-cancer patterns of somatic copy-number alteration," Nature Genetics, Oct. 2013, 45 (10):1134-1140.
Zheng S. et al., "Comprehensive Pan-Genomic Characterization of Adrenocortical Carcinoma," Cancer Cell, May 2016, 29(5):723-736.
International Preliminary Report on Patentability for International Application No. PCT/US2018/053583, dated Apr. 9, 2020, 9 pgs.
International Search Report with Written Opinion corresponding to International Patent Application No. PCT/US2018/053583, dated Feb. 25, 2019, 12 pages.

* cited by examiner

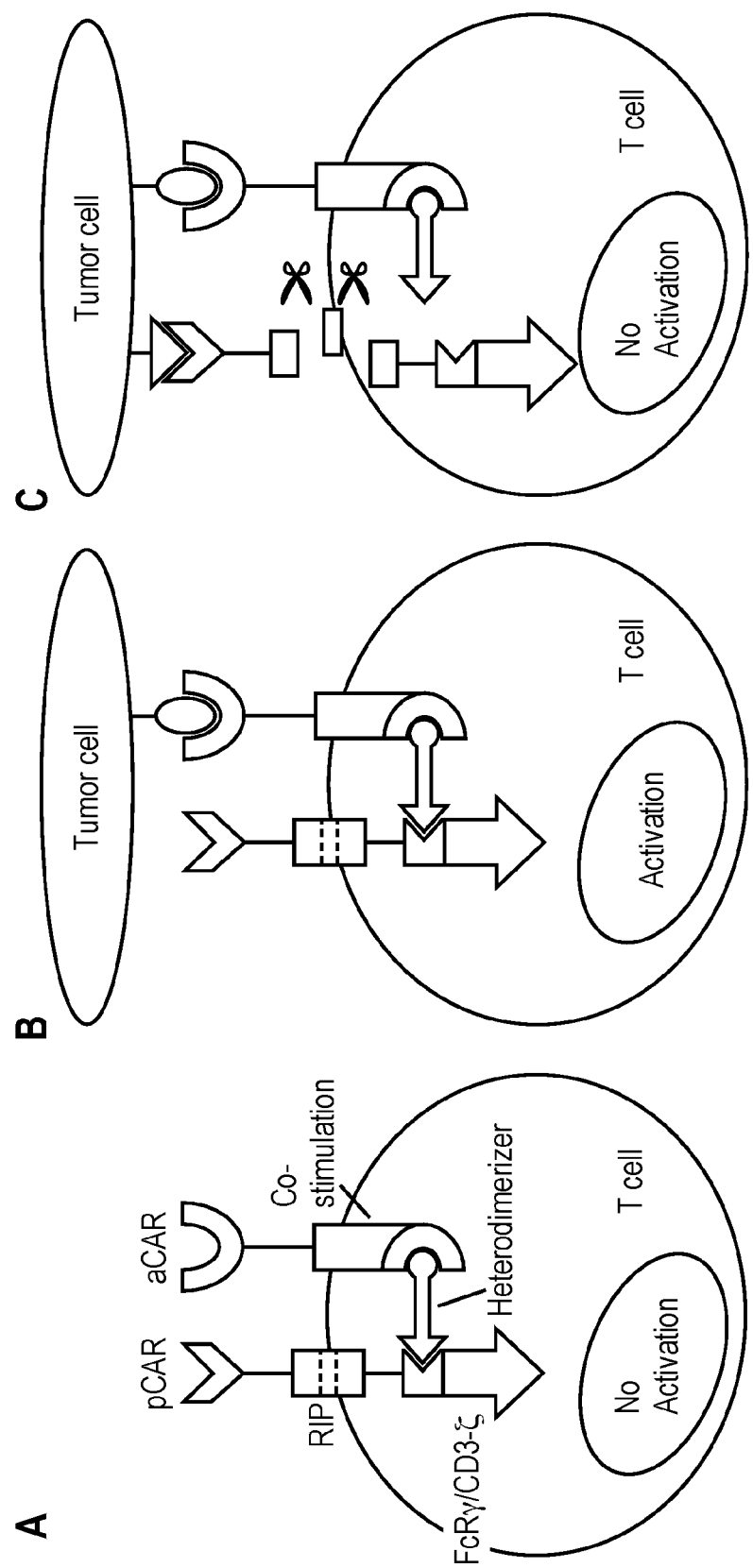

HLA-G (gene upstream)

HLA-A

ZNRD1 (gene downstream)

Loss of Heterozygosity of HLA proteins across cancers

HLA-A

HLA-B

HLA-C

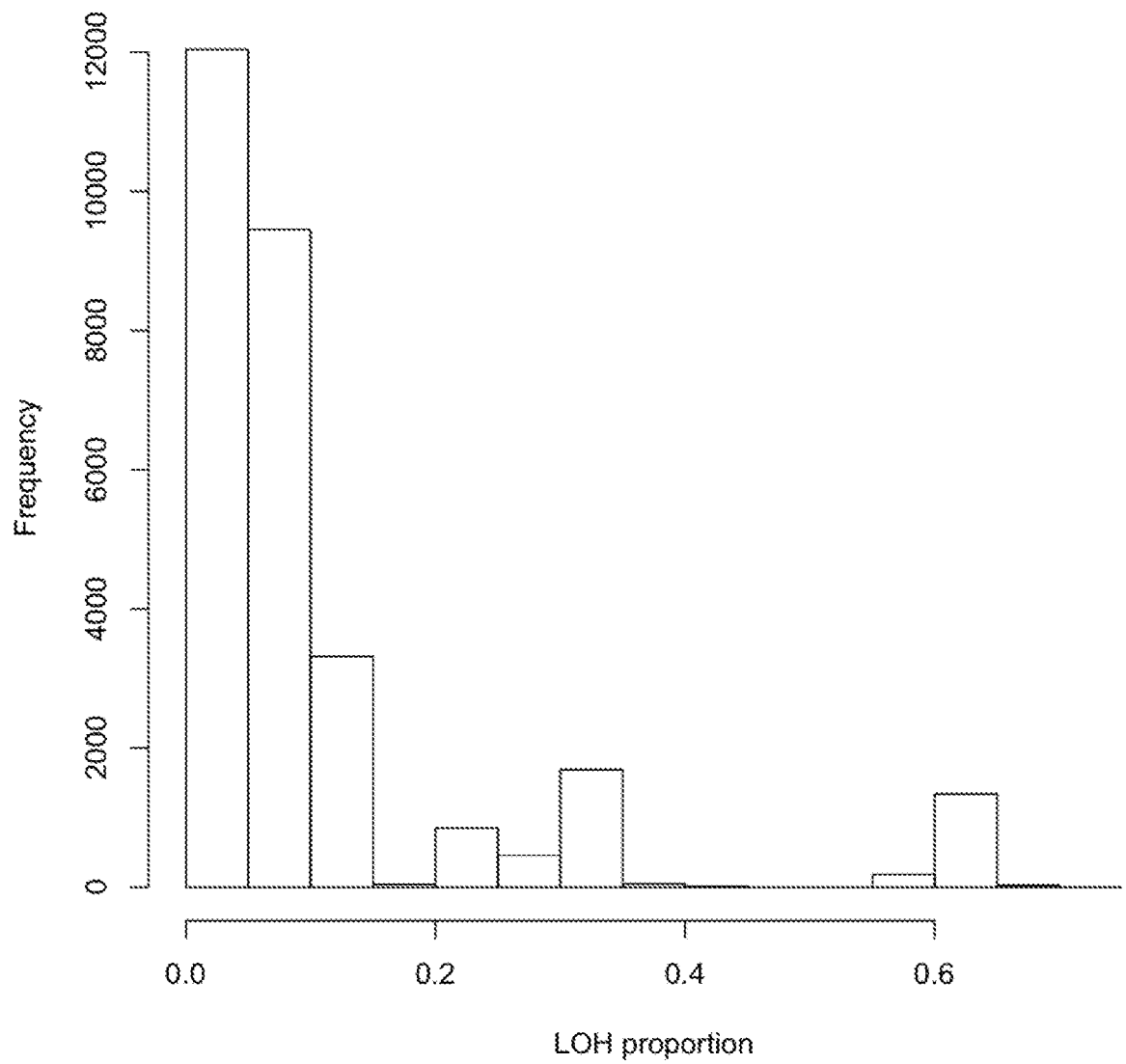

Figure 13

TCGA Study Abbreviations

| Study Abbreviation | Study Name |
|---|---|
| LAML | Acute Myeloid Leukemia |
| ACC | Adrenocortical carcinoma |
| BLCA | Bladder Urothelial Carcinoma |
| LGG | Brain Lower Grade Glioma |
| BRCA | Breast invasive carcinoma |
| CESC | Cervical squamous cell carcinoma and endocervical adenocarcinoma |
| CHOL | Cholangiocarcinoma |
| LCML | Chronic Myelogenous Leukemia |
| COAD | Colon adenocarcinoma |
| CNTL | Controls |
| ESCA | Esophageal carcinoma |
| FPPP FFPE | Pilot Phase II |
| GBM | Glioblastoma multiforme |
| HNSC | Head and Neck squamous cell carcinoma |
| KICH | Kidney Chromophobe |
| KIRC | Kidney renal clear cell carcinoma |
| KIRP | Kidney renal papillary cell carcinoma |
| LIHC | Liver hepatocellular carcinoma |
| LUAD | Lung adenocarcinoma |
| LUSC | Lung squamous cell carcinoma |
| DLBC | Lymphoid Neoplasm Diffuse Large B-cell Lymphoma |
| MESO | Mesothelioma |
| MISC | Miscellaneous |
| OV | Ovarian serous cystadenocarcinoma |
| PAAD | Pancreatic adenocarcinoma |
| PCPG | Pheochromocytoma and Paraganglioma |
| PRAD | Prostate adenocarcinoma |
| READ | Rectum adenocarcinoma |
| SARC | Sarcoma |
| SKCM | Skin Cutaneous Melanoma |
| STAD | Stomach adenocarcinoma |
| TGCT | Testicular Germ Cell Tumors |
| THYM | Thymoma |
| THCA | Thyroid carcinoma |
| UCS | Uterine Carcinosarcoma |
| UCEC | Uterine Corpus Endometrial Carcinoma |
| UVM | Uveal Melanoma |

Figure 16
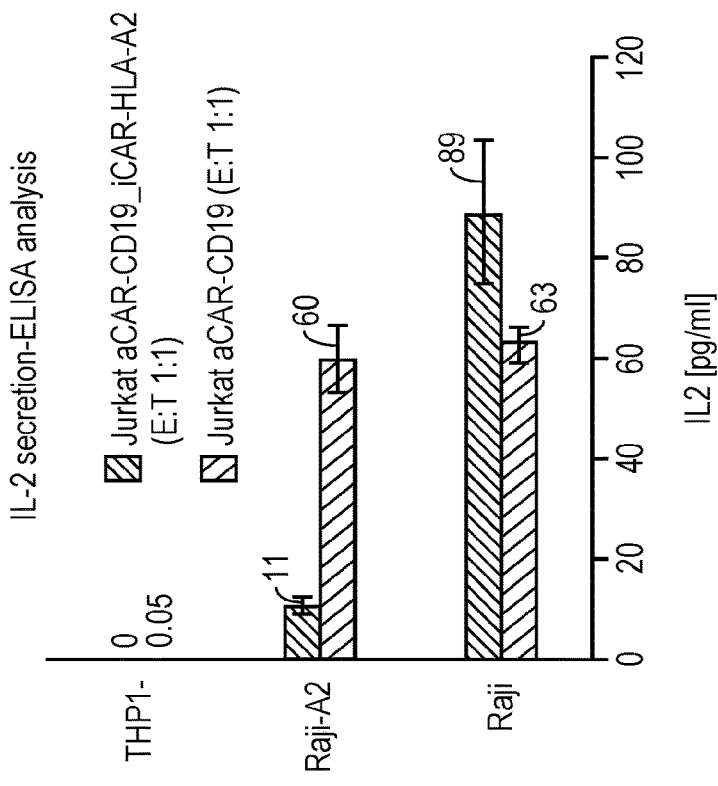
B IL-2 secretion as measured by ELISA
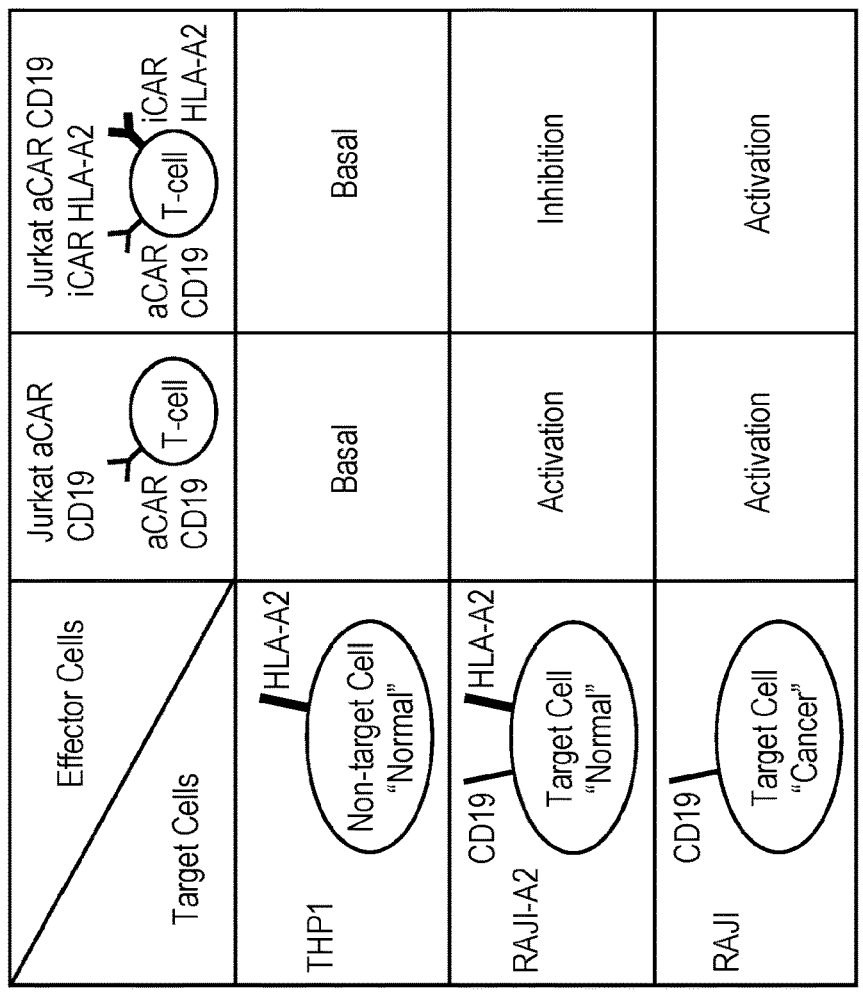
A Schematic illustration of the assay

Figure 17
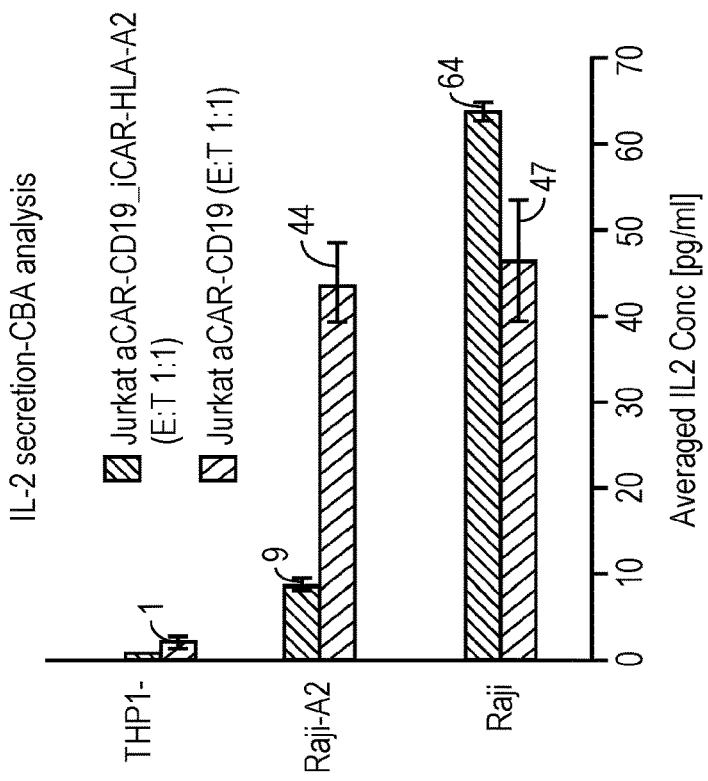
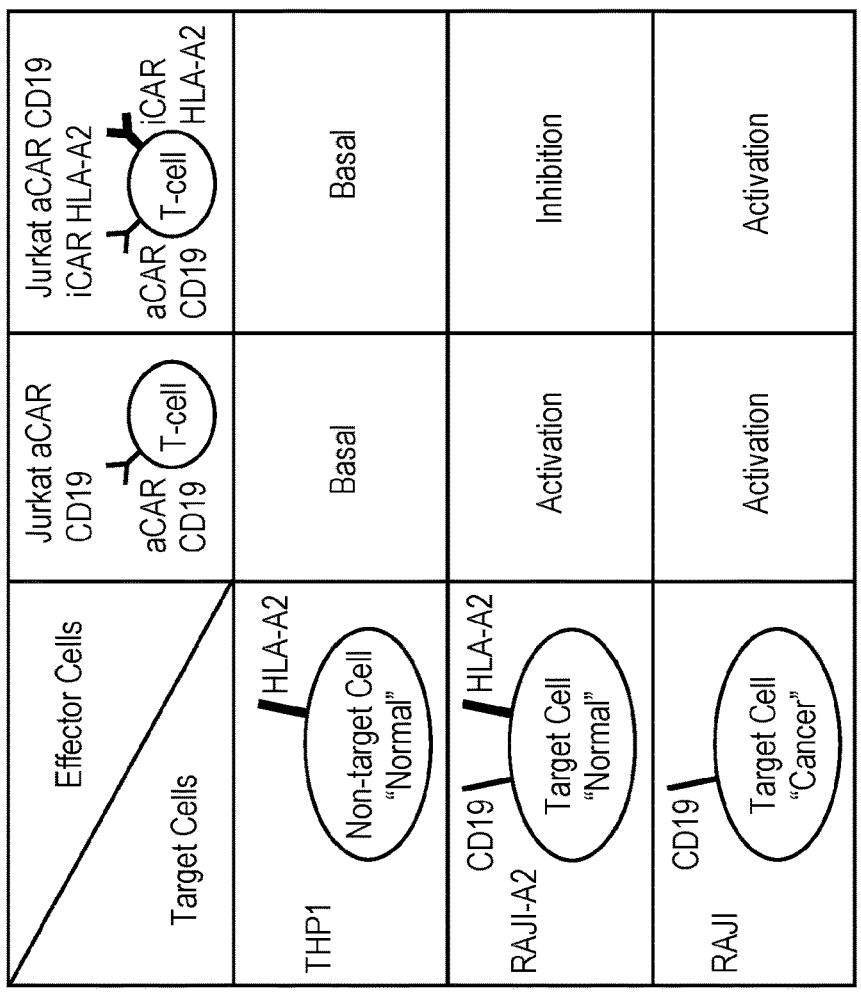

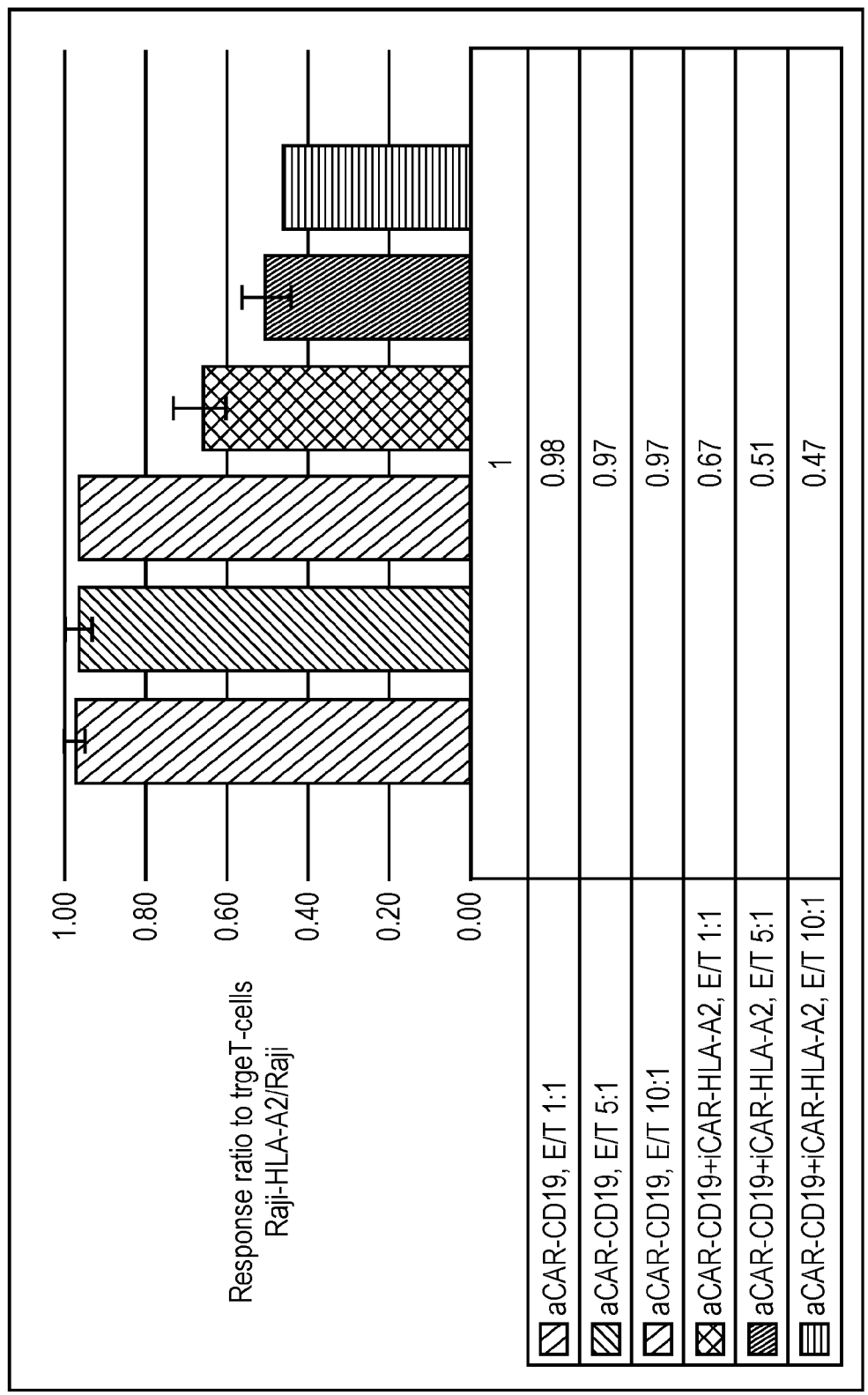

FIGURE 21 A

CD19 aCAR_IRES_RFP_P2A_Puro- DNA sequence
ATGGCCTTACCAGTGACCGCCTTGCTCCTGCCGCTGGCCTTGCTGCTCCACGCCGCCAGG
CCGGACATCCAGATGACACAGACTACATCCTCCCTGTCTGCCTCTCTGGGAGACAGAGTC
ACCATCAGTTGCAGGGCAAGTCAGGACATTAGTAAATATTTAAATTGGTATCAGCAGAAA
CCAGATGGAACTGTTAAACTCCTGATCTACCATACATCAAGATTACACTCAGGAGTCCCA
TCAAGGTTCAGTGGCAGTGGGTCTGGAACAGATTATTCTCTCACCATTAGCAACCTGGAG
CAAGAAGATATTGCCACTTACTTTTGCCAACAGGGTAATACGCTTCCGTACACGTTCGGA
GGGGGGACCAAGCTGGAGATCACAGGTGGCGGTGGCTCGGGCGGTGGTGGGTCGGGTGGC
GGCGGATCTGAGGTGAAACTGCAGGAGTCAGGACCTGGCCTGGTGGCGCCCTCACAGAGC
CTGTCCGTCACATGCACTGTCTCAGGGGTCTCATTACCCGACTATGGTGTAAGCTGGATT
CGCCAGCCTCCACGAAAGGGTCTGGAGTGGCTGGGAGTAATATGGGGTAGTGAAACCACA
TACTATAATTCAGCTCTCAAATCCAGACTGACCATCATCAAGGACAACTCCAAGAGCCAA
GTTTTCTTAAAAATGAACAGTCTGCAAACTGATGACACAGCCATTTACTACTGTGCCAAA
CATTATTACTACGGTGGTAGCTATGCTATGGACTACTGGGGCCAAGGAACCTCAGTCACC
GTCTCCTCAACCACTACCCCAGCACCGAGGCCACCCACCCCGGCTCCTACCATCGCCTCC
CAGCCTCTGTCCCTGCGTCCGGAGGCATGTAGACCCGCAGCTGGTGGGGCCGTGCATACC
CGGGGTCTTGACTTCGCCTGCGATATCTACATTTGGGCCCCTCTGGCTGGTACTTGCGGG
GTCCTGCTGCTTTCACTCGTGATCACTCTTTACTGTAAGCGCGGTCGGAAGAAGCTGCTG
TACATCTTTAAGCAACCCTTCATGAGGCCTGTGCAGACTACTCAAGAGGAGGACGGCTGT
TCATGCCGGTTCCCAGAGGAGGAGGAAGGCGGCTGCGAACTGCGCGTGAAATTCAGCCGC
AGCGCAGATGCTCCAGCCTACAAGCAGGGGCAGAACCAGCTCTACAACGAACTCAATCTT
GGTCGGAGAGAGGAGTACGACGTGCTGGACAAGCGGAGAGGACGGGACCCAGAAATGGGC
GGGAAGCCGCGCAGAAAGAATCCCCAAGAGGGCCTGTACAACGAGCTCCAAAAGGATAAG
ATGGCAGAAGCCTATAGCGAGATTGGTATGAAAGGGGAACGCAGAAGAGGCAAAGGCCAC
GACGGACTGTACCAGGGACTCAGCACCGCCACCAAGGACACCTATGACGCTCTTCACATG
CAGGCCCTGCCGCCTCGGTGAGCGGCCGCAAATTCCGCCCCTCTCCCTCCCCCCCCCCTA
ACGTTACTGGCCGAAGCCGCTTGGAATAAGGCCGGTGTGCGTTTGTCTATATGTTATTTT
CCACCATATTGCCGTCTTTTGGCAATGTGAGGGCCCGGAAACCTGGCCCTGTCTTCTTGA
CGAGCATTCCTAGGGGTCTTTCCCCTCTCGCCAAAGGAATGCAAGGTCTGTTGAATGTCG
TGAAGGAAGCAGTTCCTCTGGAAGCTTCTTGAAGACAAACAACGTCTGTAGCGACCCTTT
GCAGGCAGCGGAACCCCCACCTGGCGACAGGTGCCTCTGCGGCCAAAAGCCACGTGTAT
AAGATACACCTGCAAAGGCGGCACAACCCCAGTGCCACGTTGTGAGTTGGATAGTTGTGG
AAAGAGTCAAATGGCTCTCCTCAAGCGTATTCAACAAGGGGCTGAAGGATGCCCAGAAGG
TACCCCATTGTATGGGATCTGATCTGGGGCCTCGGTGCACATGCTTTACATGTGTTTAGT
CGAGGTTAAAAAAACGTCTAGGCCCCCCGAACCACGGGGACGTGGTTTTCCTTTGAAAAA
CACGATAATACCATGGTGTCTAAGGGCGAAGAGCTGATTAAGGAGAACATGCACATGAAG
CTGTACATGGAGGGCACCGTGAACAACCACCACTTCAAGTGCACATCCGAGGGCGAAGGC
AAGCCCTACGAGGGCACCCAGACCATGAGAATCAAGGTGGTCGAGGGCGGCCCTCTCCCC
TTCGCCTTCGACATCCTGGCTACCAGCTTCATGTACGGCAGCAGAACCTTCATCAACCAC
ACCCAGGGCATCCCCGACTTCTTTAAGCAGTCCTTCCCTGAGGGCTTCACATGGGAGAGA
GTCACCACATACGAAGACGGGGCGTGCTGACCGCTACCCAGGACACCAGCCTCCAGGAC
GGCTGCCTCATCTACAACGTCAAGATCAGAGGGGTGAACTTCCCATCCAACGGCCCTGTG
ATGCAGAAGAAAACACTCGGCTGGGAGGCCAACACCGAGATGCTGTACCCCGCTGACGGC
GGCCTGGAAGGCAGAAGCGACATGGCCCTGAAGCTCGTGGGCGGGGCCACCTGATCTGC
AACTTCAAGACCACATACAGATCCAAGAAACCCGCTAAGAACCTCAAGATGCCCGGCGTC
TACTATGTGGACCACAGACTGGAAAGAATCAAGGAGGCCGACAAAGAGACCTACGTCGAG
CAGCACGAGGTGGCTGTGGCCAGATACTGCGACCTCCCTAGCAAACTGGGGCACAAACTT
AATGGATCCGGCGCGACAAACTTTAGCTTGCTGAAGCAAGCTGGTGACGTGGAGGAGAAT
CCCGGCCCTATGGCCACCGAGTACAAGCCCACGGTGCGCCTCGCCACCCGCGACGACGTC
CCCGGGCCGTACGCACCCTCGCCGCCGCGTTCGCCGACTACCCCGCCACGCGCCACACC
GTCGATCCGGACCGCCACATCGAGCGGGTCACCGAGCTGCAAGAACTCTTCCTCACGCGC
GTCGGGCTCGACATCGGCAAGGTGTGGGTCGCGGACGACGGCGCCGCGGTGGCGGTCTGG

FIGURE 21 B (Continued)

```
ACCACGCCGGAGAGCGTCGAAGCGGGGCGGTGTTCGCCGAGATCGGCCCGCGCATGGCC
GAGTTGAGCGGTTCCCGGCTGGCCGCGCAGCAACAGATGGAAGGCCTCCTGGCGCCGCAC
CGGCCCAAGGAGCCCGCGTGGTTCCTGGCCACCGTCGGCGTCTCGCCCGACCACCAGGGC
AAGGGTCTGGGCAGCGCCGTCGTGCTCCCCGGAGTGGAGGCGGCCGAGCGCGCCGGGGTG
CCCGCCTTCCTGGAGACCTCCGCGCCCCGCAACCTCCCCTTCTACGAGCGGCTCGGCTTC
ACCGTCACCGCCGACGTCGAGGTGCCCGAAGGACCGCGCACCTGGTGCATGACCCGCAAG
CCCGGTGCCTGA

CD19 aCAR- protein sequence
MALPVTALLLPLALLLHAARPDIQMTQTTSSLSASLGDRVTISCRASQDI
SKYLNWYQQKPDGTVKLLIYHTSRLHSGVPSRFSGSGSGTDYSLTISNLE
QEDIATYFCQQGNTLPYTFGGGTKLEITGGGGSGGGGSGGGGSEVKLQES
GPGLVAPSQSLSVTCTVSGVSLPDYGVSWIRQPPRKGLEWLGVIWGSETT
YYNSALKSRLTIIKDNSKSQVFLKMNSLQTDDTAIYYCAKHYYYGGSYAM
DYWGQGTSVTVSSTTTPAPRPPTPAPTIASQPLSLRPEACRPAAGGAVHT
RGLDFACDIYIWAPLAGTCGVLLLSLVITLYCKRGRKKLLYIFKQPFMRP
VQTTQEEDGCSCRFPEEEEGGCELRVKFSRSADAPAYKQGQNQLYNELNL
GRREEYDVLDKRRGRDPEMGGKPRRKNPQEGLYNELQKDKMAEAYSEIGM
KGERRRGKGHDGLYQGLSTATKDTYDALHMQALPPR RFP-protein sequence
MVSKGEELIKENMHMKLYMEGTVNNHHFKCTSEGEGKPYEGTQTMRIKVV
EGGPLPFAFDILATSFMYGSRTFINHTQGIPDFFKQSFPEGFTWERVTTY
EDGGVLTATQDTSLQDGCLIYNVKIRGVNFPSNGPVMQKKTLGWEANTEM
LYPADGGLEGRSDMALKLVGGGHLICNFKTTYRSKKPAKNLKMPGVYYVD
HRLERIKEADKETYVEQHEVAVARYCDLPSKLGHKLN Puromycin resistance-protein sequence
MATEYKPTVRLATRDDVPRAVRTLAAAFADYPATRHTVDPDRHIERVTEL
QELFLTRVGLDIGKVWVADDGAAVAVWTTPESVEAGAVFAEIGPRMAELS
GSRLAAQQQMEGLLAPHRPKEPAWFLATVGVSPDHQGKGLGSAVVLPGVE
AAERAGVPAFLETSAPRNLPFYERLGFTVTADVEVPEGPRTWCMTRKPGA CD20 iCAR_IRES_GFP_P2A_Hygro- DNA sequence
ATGGCACTGCCTGTGACCGCCCTGCTGCTGCCACTGGCCCTGCTGCTGCACGCAGCCAGG
CCCGACATCGTGCTGACACAGAGCCCAGCAATCCTGTCCGCCTCTCCTGGAGAGAAGGTG
ACCATGACATGCCGCGCCAGCTCCTCTGTGAACTACATGGATTGGTATCAGAAGAAGCCT
GGCAGCTCCCCAAAGCCCTGGATCTACGCCACCAGCAATCTGGCCTCCGGCGTGCCAGCA
CGGTTCAGCGGCTCCGGCTCTGGCACCAGCTATTCCCTGACAATCTCCAGAGTGGAGGCA
GAGGACGCAGCAACCTACTATTGCCAGCAGTGGTCTTTCAACCCCCCTACCTTTGGCGGC
GGCACAAAGCTGGAGATCAAGGGCTCTACAAGCGAGGAGGCTCTGGAGGAGGCAGCGGA
GGCGGCGGCTCTAGCGAGGTGCAGCTGCAGCAGAGCGGAGCAGAGCTGGTGAAGCCTGGA
GCCTCCGTGAAGATGTCTTGTAAGGCCAGCGGCTACACCTTCACATCCTATAATATGCAC
TGGGTGAAGCAGACCCCAGGACAGGGCCTGGAGTGGATCGGAGCAATCTACCCAGGAAAC
GGCGACACAAGCTATAATCAGAAGTTTAAGGGCAAGGCCACCCTGACAGCCGATAAGTCC
TCTAGCACCGCCTACATGCAGCTGTCCTCTCTGACATCCGAGGACTCTGCCGATTACTAT
TGTGCCCGGTCCAACTACTATGGCAGCTCCTACTGGTTCTTTGACGTGTGGGGAGCAGGC
ACCACAGTGACCGTGTCTAGCACCGAGAGGAGAGCAGAGGTGCCCACAGCACACCCATCT
CCAAGCCCTAGGCCAGCAGGACAGTTCCAGACCCTGGTGGTGGGAGTGGTGGGAGGCCTG
CTGGGCTCTCTGGTGCTGCTGGTGTGGGTGCTGGCCGTGATCTGCAGCAGGGCCGCCCGC
GGCACCATCGGCGCCAGGCGCACAGGCCAGCCTCTGAAGGAGGACCCTTCCGCCGTGCCA
GTGTTCTCTGTGGACTACGGCGAGCTGGATTTTCAGTGGCGGGAGAAAACCCCAGAGCCA
CCTGTGCCCTGCGTGCCTGAGCAGACCGAGTATGCCACAATCGTGTTTCCATCCGGAATG
GGCACAAGCTCCCCTGCAAGGAGAGGCAGCGCCGACGGACCACGGTCCGCCCAGCCACTG
CGGCCCGAGGATGGCCACTGTTCTTGGCCCCTGTGACGCCCCTCTCCCCCCCCCCCCTCT
CCCTCCCCCCCCCCTAACGTTACTGGCCGAAGCCGCTTGGAATAAGGCCGGTGTGCGTTT
GTCTATATGTTATTTTCCACCATATTGCCGTCTTTTGGCAATGTGAGGGCCCGGAAACCT
```

FIGURE 21 C (Continued)

```
GGCCCTGTCTTCTTGACGAGCATTCCTAGGGGTCTTTCCCCTCTCGCCAAAGGAATGCAA
GGTCTGTTGAATGTCGTGAAGGAAGCAGTTCCTCTGGAAGCTTCTTGAAGACAAACAACG
TCTGTAGCGACCCTTTGCAGGCAGCGGAACCCCCACCTGGCGACAGGTGCCTCTGCGGC
CAAAAGCCACGTGTATAAGATACACCTGCAAAGGCGGCACAACCCCAGTGCCACGTTGTG
AGTTGGATAGTTGTGGAAAGAGTCAAATGGCTCTCCTCAAGCGTATTCAACAAGGGGCTG
AAGGATGCCCAGAAGGTACCCCATTGTATGGATCTGATCTGGGGCCTCGGTGCACATGC
TTTACATGTGTTTAGTCGAGGTTAAAAAAACGTCTAGGCCCCCGAACCACGGGGACGTG
GTTTTCCTTTGAAAAACACGATGATAAGGCTTGCCACAACCCGTACCAAAGATGGTGTCC
AAGGGAGAGGAGCTGTTCACCGGAGTGGTGCCCATCCTGGTGGAGCTGGACGGCGATGTG
AATGGCCACAAGTTTAGCGTGTCCGGAGAGGGAGAGGGCGACGCAACCTACGGCAAGCTG
ACACTGAAGTTCATCTGCACCACAGGCAAGCTGCCCGTGCCTTGGCCAACCCTGGTGACC
ACACTGACATACGGCGTGCAGTGTTTTCTCGCTATCCCGACCACATGAAGCAGCACGAT
TTCTTTAAGAGCGCCATGCCTGAGGGCTACGTGCAGGAGCGGACCATCTTCTTTAAGGAC
GATGGCAACTATAAGACCAGAGCCGAGGTGAAGTTCGAGGGCGACACACTGGTGAACAGG
ATCGAGCTGAAGGGCATCGACTTTAAGGAGGATGGCAATATCCTGGGCCACAAGCTGGAG
TACAACTATAATTCCCACAACGTGTACATCATGGCCGATAAGCAGAAGAACGGCATCAAG
GTCAATTTCAAGATCAGACACAATATCGAGGACGGCTCTGTGCAGCTGGCCGATCACTAC
CAGCAGAACACCCCAATCGGCGACGGACCCGTGCTGCTGCCTGATAATCACTATCTGTCT
ACACAGAGCGCCCTGTCCAAGGACCCCAACGAGAAGAGGGATCACATGGTGCTGCTGGAG
TTTGTGACCGCAGCAGGAATCACACTGGGAATGGACGAGCTGTATAAGGGCAGCGGCGCC
ACCAACTTCTCCCTGCTGAAGCAGGCAGGCGACGTGGAGGAGAATCCAGGACCTATGGAT
AGAAGCGGCAAGCCAGAGCTGACCGCCACATCCGTGGAGAAGTTCCTGATCGAGAAGTTT
GACTCTGTGAGCGATCTGATGCAGCTGTCCGAGGGAGAGGAGTCCAGGGCCTTCTCTTTT
GATGTGGGCGGCAGGGGATACGTGCTGAGGGTGAATAGCTGCGCCGACGGCTTCTATAAG
GATAGATACGTGTATAGACACTTTGCCTCCGCCGCCCTGCCAATCCCAGAGGTGCTGGAC
ATCGGCGAGTTTTCCGAGTCTCTGACCTACTGTATCAGCCGGAGAGCCCAGGGAGTGACC
CTGCAGGATCTGCCTGAGACAGAGCTGCCAGCCGTGCTGCAGCCAGTGGCAGAGGCTATG
GACGCAATCGCCGCCGCCGACCTGTCTCAGACAAGCGGCTTCGGCCCTTTTGGCCCACAG
GGCATCGGCCAGTACACCACATGGAGGGACTTCATCTGCGCCATCGCCGATCCTCACGTG
TATCACTGGCAGACCGTGATGGACGATACAGTGAGCGCCTCCGTGGCACAGGCCCTGGAC
GAGCTGATGCTGTGGGCCGAGGATTGTCCAGAGGTGCGCCACCTGGTGCACGCAGACTTT
GGCAGCAACAATGTGCTGACCGATAATGGCCGGATCACAGCCGTGATCGACTGGTCCGAG
GCCATGTTCGGCGATTCTCAGTACGAGGTGGCCAACATCTTCTTTTGGAGGCCTTGGCTG
GCCTGCATGGAGCAGCAGACCCGCTATTTTGAGAGGCGCCACCCTGAGCTGGCCGGCTCT
CCACGGCTGAGAGCATACATGCTGCGCATCGGCCTGGACCAGCTGTATCAGAGCCTGGTG
GATGGCAATTTCGACGATGCAGCATGGGCACAGGGCCGGTGCGACGCAATCGTGAGATCC
GGCGCCGGCACCGTGGGCCGGACACAGATCGCACGGCGGAGCGCCGCCGTGTGGACCGAC
GGATGCGTGGAGGTGCTGGCCGATTCTGGCAACAGGCGCCCAAGCACAAGGCCCCGCGCC
AAGGAGTGA
```

CD20 iCAR -protein sequence
MALPVTALLLPLALLLHAARPDIVLTQSPAILSASPGEKVTMTCRASSSV
NYMDWYQKKPGSSPKPWIYATSNLASGVPARFSGSGSGTSYSLTISRVEA
EDAATYYCQQWSFNPPTFGGGTKLEIKGSTSGGGSGGGSGGGGSSEVQLQ
QSGAELVKPGASVKMSCKASGYTFTSYNMHWVKQTPGQGLEWIGAIYPGN
GDTSYNQKFKGKATLTADKSSSTAYMQLSSLTSEDSADYYCARSNYYGSS
YWFFDVWGAGTTVTVSSTERRAEVPTAHPSPSPRPAGQFQTLVVGVVGGL
LGSLVLLVWVLAVICSRAARGTIGARRTGQPLKEDPSAVPVFSVDYGELD
FQWREKTPEPPVPCVPEQTEYATIVFPSGMGTSSPARRGSADGPRSAQPL
RPEDGHCSWPL GFP--protein sequence
MVSKGEELFTGVVPILVELDGDVNGHKFSVSGEGEGDATYGKLTLKFICT
TGKLPVPWPTLVTTLTYGVQCFSRYPDHMKQHDFFKSAMPEGYVQERTIF
FKDDGNYKTRAEVKFEGDTLVNRIELKGIDFKEDGNILGHKLEYNYNSHN
VYIMADKQKNGIKVNFKIRHNIEDGSVQLADHYQQNTPIGDGPVLLPDNH
YLSTQSALSKDPNEKRDHMVLLEFVTAAGITLGMDELYK

FIGURE 21 D (Continued)

Hygromycin resistance--protein sequence
MDRSGKPELTATSVEKFLIEKFDSVSDLMQLSEGEESRAFSFDVGGRGYV
LRVNSCADGFYKDRYVYRHFASAALPIPEVLDIGEFSESLTYCISRRAQG
VTLQDLPETELPAVLQPVAEAMDAIAAADLSQTSGFGPFGPQGIGQYTTW
RDFICAIADPHVYHWQTVMDDTVSASVAQALDELMLWAEDCPEVRHLVHA
DFGSNNVLTDNGRITAVIDWSEAMFGDSQYEVANIFFWRPWLACMEQQTR
YFERRHPELAGSPRLRAYMLRIGLDQLYQSLVDGNFDDAAWAQGRCDAIV
RSGAGTVGRTQIARRSAAVWTDGCVEVLADSGNRRPSTRPRAKE HLA-A2 iCAR_IRES_ GFP_P2A_Hygro- DNA sequence
ATGGCACTGCCAGTGACCGCCCTGCTGCTGCCTCTGGCCCTGCTGCTGCACGCAGCCAGA
CCCGAGCAGAAGCTGATCTCCGAGGAGGACCTGCAGGTGCAGCTGCAGCAGTCTGGACCT
GAGCTGGTGAAGCCAGGAGCCTCCGTGAAGATGTCTTGCAAGGCCAGCGGCTACACCTTC
ACATCTTATCACATCCAGTGGGTGAAGCAGCGGCCCGGACAGGGCCTGGAGTGGATCGGA
TGGATCTACCCAGGCGACGGCTCCACACAGTATAACGAGAAGTTCAAGGGCAAGACCACA
CTGACCGCCGATAAGAGCAGCAGCACCGCCTACATGCTGCTGAGCAGCCTGACCAGCGAG
GACAGCGCCATCTACTTTTGCGCCAGGGAGGGCACATACTATGCTATGGACTATTGGGGC
CAGGGCACCAGCGTGACAGTGTCTAGCGGAGGAGGAGGCTCCGGAGGAGGAGGCTCTGGC
GGCGGCGGCAGCGACGTGCTGATGACCCAGACACCACTGAGCCTGCCCGTGAGCCTGGGC
GATCAGGTGAGCATCTCCTGTAGATCCTCTCAGAGCATCGTGCACTCCAACGGCAATACC
TACCTGGAGTGGTATCTGCAGAAGCCAGGCCAGTCCCCCAAGCTGCTGATCTATAAGGTG
TCTAATCGGTTCAGCGGCGTGCCTGACAGATTTTCTGGCAGCGGCTCCGGCACCGACTTC
ACCCTGAAGATCAGCCGGGTGGAGGCAGAGGATCTGGGCGTGTACTATTGTTTCCAGGGC
TCCCACGTGCCACGCACCTTTGGCGGCGGCACAAAGCTGGAGATCAAGACCGAGAGGAGA
GCAGAGGTGCCCACAGCACACCCATCTCCAAGCCCTAGGCCAGCAGGACAGTTCCAGACC
CTGGTGGTGGGAGTGGTGGGAGGCCTGCTGGGCTCTCTGGTGCTGCTGGTGTGGGTGCTG
GCCGTGATCTGCAGCAGGGCCGCCCGCGGCACCATCGGCGCCAGGCGCACAGGCCAGCCT
CTGAAGGAGGACCCTTCCGCCGTGCCAGTGTTCTCTGTGGACTACGGCGAGCTGGATTTT
CAGTGGCGGGAGAAAACCCCAGAGCCACCTGTGCCCTGCGTGCCTGAGCAGACCGAGTAT
GCCACAATCGTGTTTCCATCGGAATGGGCACAAGCTCCCCTGCAAGGAGAGGCAGCGCC
GACGGACCACGGTCCGCCCAGCCACTGCGGCCCGAGGATGGCCACTGTTCTTGGCCCCTG
TGACGCCCCTCTCCCCCCCCCCCTCTCCCTCCCCCCCCCCTAACGTTACTGGCCGAAGC
CGCTTGGAATAAGGCCGGTGTGCGTTTGTCTATATGTTATTTTCCACCATATTGCCGTCT
TTTGGCAATGTGAGGGCCCGGAAACCTGGCCCTGTCTTCTTGACGAGCATTCCTAGGGGT
CTTTCCCCTCTCGCCAAAGGAATGCAAGGTCTGTTGAATGTCGTGAAGGAAGCAGTTCCT
CTGGAAGCTTCTTGAAGACAAACAACGTCTGTAGCGACCCTTTGCAGGCAGCGGAACCCC
CCACCTGGCGACAGGTGCCTCTGCGGCCAAAAGCCACGTGTATAAGATACACCTGCAAAG
GCGGCACAACCCCAGTGCCACGTTGTGAGTTGGATAGTTGTGGAAAGAGTCAAATGGCTC
TCCTCAAGCGTATTCAACAAGGGGCTGAAGGATGCCCAGAAGGTACCCCATTGTATGGGA
TCTGATCTGGGGCCTCGGTGCACATGCTTTACATGTGTTTAGTCGAGGTTAAAAAAACGT
CTAGGCCCCCGAACCACGGGGACGTGGTTTTCCTTTGAAAAACACGATGATAAGGCTTG
CCACAACCCGTACCAAAGATGGTGTCCAAGGGAGAGGAGCTGTTCACCGGAGTGGTGCCC
ATCCTGGTGGAGCTGGACGGCGATGTGAATGGCCACAAGTTTAGCGTGTCCGGAGAGGGA
GAGGGCGACGCAACCTACGGCAAGCTGACACTGAAGTTCATCTGCACCACAGGCAAGCTG
CCCGTGCCTTGGCCAACCCTGGTGACCACACTGACATACGGCGTGCAGTGTTTTTCTCGC
TATCCCGACCACATGAAGCAGCACGATTTCTTTAAGAGCGCCATGCCTGAGGGCTACGTG
CAGGAGCGGACCATCTTCTTTAAGGACGATGGCAACTATAAGACCAGAGCCGAGGTGAAG
TTCGAGGGCGACACTGGTGAACAGGATCGAGCTGAAGGGCATCGACTTTAAGGAGGAT
GGCAATATCCTGGGCCACAAGCTGGAGTACAACTATAATTCCCACAACGTGTACATCATG
GCCGATAAGCAGAAGAACGGCATCAAGGTCAATTTCAAGATCAGACACAATATCGAGGAC
GGCTCTGTGCAGCTGGCCGATCACTACCAGCAGAACACCCCAATCGGCGACGGACCCGTG
CTGCTGCCTGATAATCACTATCTGTCTACACAGAGCGCCCTGTCCAAGGACCCCAACGAG
AAGAGGGATCACATGGTGCTGCTGGAGTTTGTGACCGCAGCAGGAATCACACTGGGAATG
GACGAGCTGTATAAGGGCAGCGGCGCCACCAACTTCTCCCTGCTGAAGCAGGCAGGCGAC
GTGGAGGAGAATCCAGGACCTATGGATAGAAGCGGCAAGCCAGAGCTGACCGCCACATCC
GTGGAGAAGTTCCTGATCGAGAAGTTTGACTCTGTGAGCGATCTGATGCAGCTGTCCGAG

FIGURE 21 E (Continued)

```
GGAGAGGAGTCCAGGGCCTTCTCTTTTGATGTGGGCGGCAGGGGATACGTGCTGAGGGTG
AATAGCTGCGCCGACGGCTTCTATAAGGATAGATACGTGTATAGACACTTTGCCTCCGCC
GCCCTGCCAATCCCAGAGGTGCTGGACATCGGCGAGTTTTCCGAGTCTCTGACCTACTGT
ATCAGCCGGAGAGCCCAGGGAGTGACCCTGCAGGATCTGCCTGAGACAGAGCTGCCAGCC
GTGCTGCAGCCAGTGGCAGAGGCTATGGACGCAATCGCCGCCGCCGACCTGTCTCAGACA
AGCGGCTTCGGCCCTTTTGGCCCACAGGGCATCGGCCAGTACACCACATGGAGGGACTTC
ATCTGCGCCATCGCCGATCCTCACGTGTATCACTGGCAGACCGTGATGGACGATACAGTG
AGCGCCTCCGTGGCACAGGCCCTGGACGAGCTGATGCTGTGGGCCGAGGATTGTCCAGAG
GTGCGCCACCTGGTGCACGCAGACTTTGGCAGCAACAATGTGCTGACCGATAATGGCCGG
ATCACAGCCGTGATCGACTGGTCCGAGGCCATGTTCGGCGATTCTCAGTACGAGGTGGCC
AACATCTTCTTTTGGAGGCCTTGGCTGGCCTGCATGGAGCAGCAGACCCGCTATTTTGAG
AGGCGCCACCCTGAGCTGGCCGGCTCTCCACGGCTGAGAGCATACATGCTGCGCATCGGC
CTGGACCAGCTGTATCAGAGCCTGGTGGATGGCAATTTCGACGATGCAGCATGGGCACAG
GGCCGGTGCGACGCAATCGTGAGATCCGGCGCCGGCACCGTGGGCCGGACACAGATCGCA
CGGCGGAGCGCCGCCGTGTGGACCGACGGATGCGTGGAGGTGCTGGCCGATTCTGGCAAC
AGGCGCCCAAGCACAAGGCCCCGCGCCAAGGAGTGA
```

HLA-A2 iCAR --protein sequence
MALPVTALLLPLALLLHAARPEQKLISEEDLQVQLQQSGPELVKPGASVK
MSCKASGYTFTSYHIQWVKQRPGQGLEWIGWIYPGDGSTQYNEKFKGKTT
LTADKSSSTAYMLLSSLTSEDSAIYFCAREGTYYAMDYWGQGTSVTVSSG
GGGSGGGGSGGGGSDVLMTQTPLSLPVSLGDQVSISCRSSQSIVHSNGNT
YLEWYLQKPGQSPKLLIYKVSNRFSGVPDRFSGSGSGTDFTLKISRVEAE
DLGVYYCFQGSHVPRTFGGGTKLEIKTERRAEVPTAHPSPSPRPAGQFQT
LVVGVVGGLLGSLVLLVWVLAVICSRAARGTIGARRTGQPLKEDPSAVPV
FSVDYGELDFQWREKTPEPPVPCVPEQTEYATIVFPSGMGTSSPARRGSA
DGPRSAQPLRPEDGHCSWPL

Figure 22

| Chr | Gene |
|---|---|
| 1 | ABCA4 |
| 1 | ADAM30 |
| 1 | ASTN1 |
| 1 | C1orf101 |
| 1 | CACNA1S |
| 1 | CATSPER4 |
| 1 | CD101 |
| 1 | CD164L2 |
| 1 | CD1A |
| 1 | CD1C |
| 1 | CD244 |
| 1 | CD34 |
| 1 | CELSR2 |
| 1 | CHRNB2 |
| 1 | CLCA2 |
| 1 | CLSTN1 |
| 1 | CR1 |
| 1 | CR2 |
| 1 | CRB1 |
| 1 | CSF3R |
| 1 | CSMD2 |
| 1 | ECE1 |
| 1 | ELTD1 |
| 1 | EMC1 |
| 1 | EPHA10 |
| 1 | EPHA2 |
| 1 | ERMAP |
| 1 | FCAMR |
| 1 | FCER1A |
| 1 | FCGR1B |
| 1 | FCGR2A |
| 1 | FCGR2B |
| 1 | FCGR3A |
| 1 | FCRL1 |
| 1 | FCRL3 |
| 1 | FCRL4 |
| 1 | FCRL5 |
| 1 | FCRL6 |
| 1 | GJB4 |
| 1 | GPA33 |
| 1 | GPR157 |
| 1 | GPR37L1 |
| 1 | GPR88 |
| 1 | HCRTR1 |

| Chr | Gene |
|---|---|
| 1 | IGSF3 |
| 1 | IGSF9 |
| 1 | IL22RA1 |
| 1 | ITGA10 |
| 1 | KIAA1324 |
| 1 | KIAA2013 |
| 1 | LDLRAD2 |
| 1 | LEPR |
| 1 | LRIG2 |
| 1 | LRP8 |
| 1 | LRRC52 |
| 1 | LRRC8B |
| 1 | LRRN2 |
| 1 | LY9 |
| 1 | MR1 |
| 1 | MUC1 |
| 1 | MXRA8 |
| 1 | NCSTN |
| 1 | NFASC |
| 1 | NOTCH2 |
| 1 | NPR1 |
| 1 | NTRK1 |
| 1 | OPN3 |
| 1 | OR10J1 |
| 1 | OR10J4 |
| 1 | OR10K1 |
| 1 | OR10R2 |
| 1 | OR10T2 |
| 1 | OR10X1 |
| 1 | OR11L1 |
| 1 | OR14A16 |
| 1 | OR14I1 |
| 1 | OR14K1 |
| 1 | OR2AK2 |
| 1 | OR2C3 |
| 1 | OR2G2 |
| 1 | OR2G3 |
| 1 | OR2L2 |
| 1 | OR2M7 |
| 1 | OR2T1 |
| 1 | OR2T12 |
| 1 | OR2T27 |
| 1 | OR2T29 |
| 1 | OR2T3 |

| Chr | Gene |
|---|---|
| 1 | OR2T33 |
| 1 | OR2T34 |
| 1 | OR2T35 |
| 1 | OR2T4 |
| 1 | OR2T5 |
| 1 | OR2T6 |
| 1 | OR2T7 |
| 1 | OR2T8 |
| 1 | OR2W3 |
| 1 | OR6F1 |
| 1 | OR6K2 |
| 1 | OR6K3 |
| 1 | OR6K6 |
| 1 | OR6N1 |
| 1 | OR6P1 |
| 1 | OR6Y1 |
| 1 | PEAR1 |
| 1 | PIGR |
| 1 | PLXNA2 |
| 1 | PTCH2 |
| 1 | PTCHD2 |
| 1 | PTGFRN |
| 1 | PTPRC |
| 1 | PTPRF |
| 1 | PVRL4 |
| 1 | RXFP4 |
| 1 | S1PR1 |
| 1 | SCNN1D |
| 1 | SDC3 |
| 1 | SELE |
| 1 | SELL |
| 1 | SELP |
| 1 | SEMA4A |
| 1 | SEMA6C |
| 1 | SLAMF7 |
| 1 | SLAMF9 |
| 1 | SLC2A7 |
| 1 | SLC5A9 |
| 1 | TACSTD2 |
| 1 | TAS1R2 |
| 1 | TIE1 |
| 1 | TLR5 |
| 1 | TMEM81 |
| 1 | TNFRSF14 |

Figure 22 (Continued)

| Chr | Gene |
|---|---|
| 1 | TNFRSF1B |
| 1 | TRABD2B |
| 1 | USH2A |
| 1 | VCAM1 |
| 1 | ZP4 |
| 2 | ABCG5 |
| 2 | ALK |
| 2 | ASPRV1 |
| 2 | ATRAID |
| 2 | CD207 |
| 2 | CHRNG |
| 2 | CLEC4F |
| 2 | CNTNAP5 |
| 2 | CRIM1 |
| 2 | CXCR1 |
| 2 | DNER |
| 2 | DPP10 |
| 2 | EDAR |
| 2 | EPCAM |
| 2 | GPR113 |
| 2 | GPR148 |
| 2 | GPR35 |
| 2 | GPR39 |
| 2 | IL1RL1 |
| 2 | ITGA4 |
| 2 | ITGA6 |
| 2 | ITGAV |
| 2 | LCT |
| 2 | LHCGR |
| 2 | LRP1B |
| 2 | LRP2 |
| 2 | LY75 |
| 2 | MARCO |
| 2 | MERTK |
| 2 | NRP2 |
| 2 | OR6B2 |
| 2 | PLA2R1 |
| 2 | PLB1 |
| 2 | PROKR1 |
| 2 | PROM2 |
| 2 | SCN7A |
| 2 | SDC1 |
| 2 | TGOLN2 |
| 2 | THSD7B |

| Chr | Gene |
|---|---|
| 2 | TMEFF2 |
| 2 | TMEM178A |
| 2 | TPO |
| 2 | TRABD2A |
| 3 | ACKR2 |
| 3 | ALCAM |
| 3 | ANO10 |
| 3 | ATP13A4 |
| 3 | CACNA1D |
| 3 | CACNA2D2 |
| 3 | CACNA2D3 |
| 3 | CASR |
| 3 | CCRL2 |
| 3 | CD200 |
| 3 | CD200R1 |
| 3 | CD86 |
| 3 | CD96 |
| 3 | CDCP1 |
| 3 | CDHR4 |
| 3 | CELSR3 |
| 3 | CHL1 |
| 3 | CLDN11 |
| 3 | CLDN18 |
| 3 | CLSTN2 |
| 3 | CSPG5 |
| 3 | CX3CR1 |
| 3 | CXCR6 |
| 3 | DCBLD2 |
| 3 | DRD3 |
| 3 | EPHB3 |
| 3 | GABRR3 |
| 3 | GP5 |
| 3 | GPR128 |
| 3 | GPR15 |
| 3 | GPR27 |
| 3 | GRM2 |
| 3 | GRM7 |
| 3 | HEG1 |
| 3 | HTR3C |
| 3 | HTR3D |
| 3 | HTR3E |
| 3 | IGSF11 |
| 3 | IL17RC |
| 3 | IL17RD |

| Chr | Gene |
|---|---|
| 3 | IL17RE |
| 3 | IL5RA |
| 3 | IMPG2 |
| 3 | ITGA9 |
| 3 | ITGB5 |
| 3 | KCNMB3 |
| 3 | LRIG1 |
| 3 | LRRC15 |
| 3 | LRRN1 |
| 3 | MST1R |
| 3 | NAALADL2 |
| 3 | NRROS |
| 3 | OR5AC1 |
| 3 | OR5H1 |
| 3 | OR5H14 |
| 3 | OR5H15 |
| 3 | OR5H6 |
| 3 | OR5K2 |
| 3 | OR5K3 |
| 3 | OR5K4 |
| 3 | PLXNB1 |
| 3 | PLXND1 |
| 3 | PRRT3 |
| 3 | PTPRG |
| 3 | ROBO2 |
| 3 | RYK |
| 3 | SEMA5B |
| 3 | SIDT1 |
| 3 | SLC22A14 |
| 3 | SLC33A1 |
| 3 | SLC4A7 |
| 3 | SLITRK3 |
| 3 | STAB1 |
| 3 | SUSD5 |
| 3 | TFRC |
| 3 | TLR9 |
| 3 | TMEM44 |
| 3 | TMPRSS7 |
| 3 | TNFSF10 |
| 3 | UPK1B |
| 3 | VIPR1 |
| 3 | ZPLD1 |
| 4 | ANTXR2 |
| 4 | BTC |

Figure 22 (Continued)

| Chr | Gene |
|---|---|
| 4 | CNGA1 |
| 4 | CORIN |
| 4 | EGF |
| 4 | EMCN |
| 4 | ENPEP |
| 4 | EPHA5 |
| 4 | ERVMER34-1 |
| 4 | EVC2 |
| 4 | FAT1 |
| 4 | FAT4 |
| 4 | FGFRL1 |
| 4 | FRAS1 |
| 4 | GPR125 |
| 4 | GRID2 |
| 4 | GYPA |
| 4 | GYPB |
| 4 | KDR |
| 4 | KIAA0922 |
| 4 | KLB |
| 4 | MFSD8 |
| 4 | PARM1 |
| 4 | PDGFRA |
| 4 | RNF150 |
| 4 | TENM3 |
| 4 | TLR1 |
| 4 | TLR10 |
| 4 | TLR6 |
| 4 | TMEM156 |
| 4 | TMPRSS11A |
| 4 | TMPRSS11B |
| 4 | TMPRSS11E |
| 4 | TMPRSS11F |
| 4 | UNC5C |
| 5 | ADAM19 |
| 5 | ADRB2 |
| 5 | BTNL3 |
| 5 | BTNL8 |
| 5 | BTNL9 |
| 5 | C5orf15 |
| 5 | CATSPER3 |
| 5 | CD180 |
| 5 | CDH12 |
| 5 | CDHR2 |

| Chr | Gene |
|---|---|
| 5 | COL23A1 |
| 5 | CSF1R |
| 5 | F2RL2 |
| 5 | FAM174A |
| 5 | FAT2 |
| 5 | FGFR4 |
| 5 | FLT4 |
| 5 | GABRA6 |
| 5 | GABRG2 |
| 5 | GPR151 |
| 5 | GPR98 |
| 5 | GRM6 |
| 5 | HAVCR1 |
| 5 | HAVCR2 |
| 5 | IL31RA |
| 5 | IL6ST |
| 5 | IL7R |
| 5 | ITGA1 |
| 5 | ITGA2 |
| 5 | KCNMB1 |
| 5 | LIFR |
| 5 | LNPEP |
| 5 | MEGF10 |
| 5 | NIPAL4 |
| 5 | OR2V1 |
| 5 | OR2Y1 |
| 5 | OSMR |
| 5 | PCDH1 |
| 5 | PCDH12 |
| 5 | PCDHA1 |
| 5 | PCDHA2 |
| 5 | PCDHA4 |
| 5 | PCDHA8 |
| 5 | PCDHA9 |
| 5 | PCDHB10 |
| 5 | PCDHB11 |
| 5 | PCDHB13 |
| 5 | PCDHB14 |
| 5 | PCDHB15 |
| 5 | PCDHB16 |
| 5 | PCDHB2 |
| 5 | PCDHB3 |
| 5 | PCDHB4 |
| 5 | PCDHB5 |

| Chr | Gene |
|---|---|
| 5 | PCDHB6 |
| 5 | PCDHGA1 |
| 5 | PCDHGA4 |
| 5 | PDGFRB |
| 5 | PRLR |
| 5 | SEMA5A |
| 5 | SEMA6A |
| 5 | SGCD |
| 5 | SLC1A3 |
| 5 | SLC22A4 |
| 5 | SLC22A5 |
| 5 | SLC36A3 |
| 5 | SLC6A18 |
| 5 | SLC6A19 |
| 5 | SLCO6A1 |
| 5 | SV2C |
| 5 | TENM2 |
| 5 | TIMD4 |
| 5 | UGT3A1 |
| 6 | BAI3 |
| 6 | BTN1A1 |
| 6 | BTN2A1 |
| 6 | BTN2A2 |
| 6 | BTN3A2 |
| 6 | BTNL2 |
| 6 | CD83 |
| 6 | DCBLD1 |
| 6 | DLL1 |
| 6 | DPCR1 |
| 6 | ENPP1 |
| 6 | ENPP3 |
| 6 | ENPP4 |
| 6 | EPHA7 |
| 6 | GABBR1 |
| 6 | GABRR1 |
| 6 | GCNT6 |
| 6 | GFRAL |
| 6 | GJB7 |
| 6 | GLP1R |
| 6 | GPR110 |
| 6 | GPR111 |
| 6 | GPR116 |
| 6 | GPR126 |
| 6 | GPR63 |

Figure 22 (Continued)

| Chr | Gene |
|---|---|
| 6 | GPRC6A |
| 6 | HFE |
| 6 | HLA-A |
| 6 | HLA-B |
| 6 | HLA-C |
| 6 | HLA-DPA1 |
| 6 | HLA-DPB1 |
| 6 | HLA-DQA1 |
| 6 | HLA-DQA2 |
| 6 | HLA-DQB1 |
| 6 | HLA-DQB2 |
| 6 | HLA-DRB1 |
| 6 | HLA-DRB5 |
| 6 | HLA-E |
| 6 | HLA-F |
| 6 | HLA-G |
| 6 | IL20RA |
| 6 | ITPR3 |
| 6 | KIAA0319 |
| 6 | LMBRD1 |
| 6 | LRFN2 |
| 6 | LRP11 |
| 6 | MAS1L |
| 6 | MEP1A |
| 6 | MICA |
| 6 | MICB |
| 6 | MUC21 |
| 6 | MUC22 |
| 6 | NCR2 |
| 6 | NOTCH4 |
| 6 | OPRM1 |
| 6 | OR10C1 |
| 6 | OR12D2 |
| 6 | OR12D3 |
| 6 | OR14J1 |
| 6 | OR2B2 |
| 6 | OR2B6 |
| 6 | OR2J1 |
| 6 | OR2W1 |
| 6 | OR5V1 |
| 6 | PKHD1 |
| 6 | PTCRA |
| 6 | RAET1E |
| 6 | RAET1G |

| Chr | Gene |
|---|---|
| 6 | ROS1 |
| 6 | SDIM1 |
| 6 | SLC22A1 |
| 6 | SLC44A4 |
| 6 | TAAR2 |
| 6 | TREM1 |
| 6 | TREML1 |
| 6 | TREML2 |
| 7 | AQP1 |
| 7 | CD36 |
| 7 | CDHR3 |
| 7 | CNTNAP2 |
| 7 | DPP6 |
| 7 | EGFR |
| 7 | EPHA1 |
| 7 | EPHB6 |
| 7 | ERVW-1 |
| 7 | GHRHR |
| 7 | GJC3 |
| 7 | GPNMB |
| 7 | GRM8 |
| 7 | HYAL4 |
| 7 | KIAA1324L |
| 7 | LRRN3 |
| 7 | MET |
| 7 | MUC12 |
| 7 | MUC17 |
| 7 | NPC1L1 |
| 7 | NPSR1 |
| 7 | OR2A12 |
| 7 | OR2A14 |
| 7 | OR2A2 |
| 7 | OR2A25 |
| 7 | OR2A42 |
| 7 | OR2A7 |
| 7 | OR2AE1 |
| 7 | OR2F2 |
| 7 | OR6V1 |
| 7 | PILRA |
| 7 | PKD1L1 |
| 7 | PLXNA4 |
| 7 | PODXL |
| 7 | PTPRN2 |
| 7 | PTPRZ1 |

| Chr | Gene |
|---|---|
| 7 | RAMP3 |
| 7 | SLC29A4 |
| 7 | SMO |
| 7 | TAS2R16 |
| 7 | TAS2R4 |
| 7 | TAS2R40 |
| 7 | TFR2 |
| 7 | THSD7A |
| 7 | TMEM213 |
| 7 | TTYH3 |
| 7 | ZAN |
| 7 | ZP3 |
| 8 | ADAM18 |
| 8 | ADAM28 |
| 8 | ADAM32 |
| 8 | ADAM7 |
| 8 | ADAM9 |
| 8 | CDH17 |
| 8 | CHRNA2 |
| 8 | CSMD1 |
| 8 | CSMD3 |
| 8 | DCSTAMP |
| 8 | FZD6 |
| 8 | GPR124 |
| 8 | NRG1 |
| 8 | OR4F21 |
| 8 | PKHD1L1 |
| 8 | PRSS55 |
| 8 | SCARA3 |
| 8 | SCARA5 |
| 8 | SDC2 |
| 8 | SLC10A5 |
| 8 | SLC39A14 |
| 8 | SLC39A4 |
| 8 | SLCO5A1 |
| 8 | TNFRSF10A |
| 8 | TNFRSF10B |
| 9 | ABCA1 |
| 9 | AQP7 |
| 9 | C9orf135 |
| 9 | CA9 |
| 9 | CD72 |
| 9 | CNTNAP3 |
| 9 | CNTNAP3B |

Figure 22 (Continued)

| Chr | Gene |
|---|---|
| 9 | ENTPD8 |
| 9 | GPR144 |
| 9 | GRIN3A |
| 9 | IZUMO3 |
| 9 | KIAA1161 |
| 9 | MAMDC4 |
| 9 | MEGF9 |
| 9 | MUSK |
| 9 | NOTCH1 |
| 9 | OR13C2 |
| 9 | OR13C3 |
| 9 | OR13C5 |
| 9 | OR13C8 |
| 9 | OR13C9 |
| 9 | OR13D1 |
| 9 | OR13F1 |
| 9 | OR1B1 |
| 9 | OR1J2 |
| 9 | OR1K1 |
| 9 | OR1L1 |
| 9 | OR1L3 |
| 9 | OR1L6 |
| 9 | OR1L8 |
| 9 | OR1N1 |
| 9 | OR1N2 |
| 9 | OR1Q1 |
| 9 | OR2S2 |
| 9 | PCSK5 |
| 9 | PLGRKT |
| 9 | PTPRD |
| 9 | ROR2 |
| 9 | SEMA4D |
| 9 | SLC31A1 |
| 9 | TEK |
| 9 | TLR4 |
| 9 | TMEM2 |
| 9 | VLDLR |
| 10 | ABCC2 |
| 10 | ADAM8 |
| 10 | ADRB1 |
| 10 | ANTXRL |
| 10 | ATRNL1 |
| 10 | C10orf54 |
| 10 | CDH23 |

| Chr | Gene |
|---|---|
| 10 | CDHR1 |
| 10 | CNNM2 |
| 10 | COL13A1 |
| 10 | COL17A1 |
| 10 | ENTPD1 |
| 10 | FGFR2 |
| 10 | FZD8 |
| 10 | GPR158 |
| 10 | GRID1 |
| 10 | IL15RA |
| 10 | IL2RA |
| 10 | ITGA8 |
| 10 | ITGB1 |
| 10 | MRC1 |
| 10 | NPFFR1 |
| 10 | NRP1 |
| 10 | OPN4 |
| 10 | PCDH15 |
| 10 | PKD2L1 |
| 10 | PLXDC2 |
| 10 | PRLHR |
| 10 | RGR |
| 10 | SLC29A3 |
| 10 | SLC39A12 |
| 10 | TACR2 |
| 10 | TCTN3 |
| 10 | TSPAN15 |
| 10 | UNC5B |
| 10 | VSTM4 |
| 11 | AMICA1 |
| 11 | ANO3 |
| 11 | APLP2 |
| 11 | C11orf24 |
| 11 | CCKBR |
| 11 | CD248 |
| 11 | CD44 |
| 11 | CD5 |
| 11 | CD6 |
| 11 | CDON |
| 11 | CLMP |
| 11 | CRTAM |
| 11 | DCHS1 |
| 11 | DSCAML1 |
| 11 | FAT3 |

| Chr | Gene |
|---|---|
| 11 | FOLH1 |
| 11 | GDPD4 |
| 11 | GDPD5 |
| 11 | GRIK4 |
| 11 | HEPHL1 |
| 11 | HTR3B |
| 11 | IFITM10 |
| 11 | IL10RA |
| 11 | KIRREL3 |
| 11 | LGR4 |
| 11 | LRP4 |
| 11 | LRP5 |
| 11 | LRRC32 |
| 11 | MCAM |
| 11 | MFRP |
| 11 | MPEG1 |
| 11 | MRGPRE |
| 11 | MRGPRF |
| 11 | MRGPRG |
| 11 | MRGPRX2 |
| 11 | MRGPRX3 |
| 11 | MRGPRX4 |
| 11 | MS4A4A |
| 11 | MTNR1B |
| 11 | MUC15 |
| 11 | NAALAD2 |
| 11 | NAALADL1 |
| 11 | NCAM1 |
| 11 | NRXN2 |
| 11 | OR10A2 |
| 11 | OR10A5 |
| 11 | OR10A6 |
| 11 | OR10D3 |
| 11 | OR10G4 |
| 11 | OR10G7 |
| 11 | OR10G8 |
| 11 | OR10G9 |
| 11 | OR10Q1 |
| 11 | OR10S1 |
| 11 | OR1S1 |
| 11 | OR2AG1 |
| 11 | OR2AG2 |
| 11 | OR2D2 |
| 11 | OR4A15 |

Figure 22 (Continued)

| Chr | Gene |
|---|---|
| 11 | OR4A47 |
| 11 | OR4A5 |
| 11 | OR4A8P |
| 11 | OR4C11 |
| 11 | OR4C13 |
| 11 | OR4C15 |
| 11 | OR4C16 |
| 11 | OR4C3 |
| 11 | OR4C46 |
| 11 | OR4C5 |
| 11 | OR4D6 |
| 11 | OR4D9 |
| 11 | OR4S2 |
| 11 | OR4X1 |
| 11 | OR51E1 |
| 11 | OR51L1 |
| 11 | OR52A1 |
| 11 | OR52E1 |
| 11 | OR52E2 |
| 11 | OR52E4 |
| 11 | OR52E6 |
| 11 | OR52I1 |
| 11 | OR52I2 |
| 11 | OR52J3 |
| 11 | OR52L1 |
| 11 | OR52N1 |
| 11 | OR52N2 |
| 11 | OR52N4 |
| 11 | OR52W1 |
| 11 | OR56B1 |
| 11 | OR56B4 |
| 11 | OR5A1 |
| 11 | OR5A2 |
| 11 | OR5AK2 |
| 11 | OR5AR1 |
| 11 | OR5B17 |
| 11 | OR5B3 |
| 11 | OR5D14 |
| 11 | OR5D16 |
| 11 | OR5D18 |
| 11 | OR5F1 |
| 11 | OR5I1 |
| 11 | OR5L2 |
| 11 | OR5M11 |

| Chr | Gene |
|---|---|
| 11 | OR5M3 |
| 11 | OR5P2 |
| 11 | OR5R1 |
| 11 | OR5T2 |
| 11 | OR5T3 |
| 11 | OR5W2 |
| 11 | OR6A2 |
| 11 | OR6T1 |
| 11 | OR6X1 |
| 11 | OR8A1 |
| 11 | OR8B12 |
| 11 | OR8B2 |
| 11 | OR8B3 |
| 11 | OR8B4 |
| 11 | OR8D1 |
| 11 | OR8D2 |
| 11 | OR8H1 |
| 11 | OR8H2 |
| 11 | OR8H3 |
| 11 | OR8I2 |
| 11 | OR8J1 |
| 11 | OR8J2 |
| 11 | OR8J3 |
| 11 | OR8K1 |
| 11 | OR8K3 |
| 11 | OR8K5 |
| 11 | OR8U1 |
| 11 | OR9G1 |
| 11 | OR9G4 |
| 11 | OR9Q2 |
| 11 | P2RX3 |
| 11 | PTPRJ |
| 11 | ROBO3 |
| 11 | SIGIRR |
| 11 | SLC22A10 |
| 11 | SLC3A2 |
| 11 | SLC5A12 |
| 11 | SLCO2B1 |
| 11 | SORL1 |
| 11 | ST14 |
| 11 | SYT8 |
| 11 | TENM4 |
| 11 | TMEM123 |
| 11 | TMPRSS4 |

| Chr | Gene |
|---|---|
| 11 | TMPRSS5 |
| 11 | TRPM5 |
| 11 | TSPAN18 |
| 11 | ZP1 |
| 12 | ANO4 |
| 12 | AVPR1A |
| 12 | CACNA2D4 |
| 12 | CD163 |
| 12 | CD163L1 |
| 12 | CD27 |
| 12 | CD4 |
| 12 | CLEC12A |
| 12 | CLEC2A |
| 12 | CLEC4C |
| 12 | CLEC7A |
| 12 | CLECL1 |
| 12 | CLSTN3 |
| 12 | GPR133 |
| 12 | GPRC5D |
| 12 | ITGA7 |
| 12 | ITGB7 |
| 12 | KLRB1 |
| 12 | KLRC2 |
| 12 | KLRC3 |
| 12 | KLRC4 |
| 12 | KLRF1 |
| 12 | KLRF2 |
| 12 | LRP1 |
| 12 | LRP6 |
| 12 | MANSC1 |
| 12 | MANSC4 |
| 12 | OLR1 |
| 12 | OR10AD1 |
| 12 | OR10P1 |
| 12 | OR2AP1 |
| 12 | OR6C1 |
| 12 | OR6C2 |
| 12 | OR6C3 |
| 12 | OR6C4 |
| 12 | OR6C6 |
| 12 | OR6C74 |
| 12 | OR6C76 |
| 12 | OR8S1 |
| 12 | OR9K2 |

Figure 22 (Continued)

| Chr | Gene |
|---|---|
| 12 | ORAI1 |
| 12 | P2RX4 |
| 12 | P2RX7 |
| 12 | PTPRB |
| 12 | PTPRQ |
| 12 | SCNN1A |
| 12 | SELPLG |
| 12 | SLC38A4 |
| 12 | SLC5A8 |
| 12 | SLC6A15 |
| 12 | SLC8B1 |
| 12 | SLCO1B1 |
| 12 | SLCO1B7 |
| 12 | SSPN |
| 12 | STAB2 |
| 12 | TAS2R10 |
| 12 | TAS2R13 |
| 12 | TAS2R20 |
| 12 | TAS2R30 |
| 12 | TAS2R31 |
| 12 | TAS2R42 |
| 12 | TAS2R43 |
| 12 | TAS2R46 |
| 12 | TAS2R7 |
| 12 | TMEM119 |
| 12 | TMEM132B |
| 12 | TMEM132C |
| 12 | TMEM132D |
| 12 | TMPRSS12 |
| 12 | TNFRSF1A |
| 12 | TSPAN8 |
| 12 | VSIG10 |
| 13 | ATP4B |
| 13 | ATP7B |
| 13 | FLT3 |
| 13 | FREM2 |
| 13 | KL |
| 13 | PCDH8 |
| 13 | SGCG |
| 13 | SHISA2 |
| 13 | SLC15A1 |
| 13 | SLITRK6 |
| 13 | TNFRSF19 |
| 14 | ADAM21 |

| Chr | Gene |
|---|---|
| 14 | BDKRB2 |
| 14 | C14orf37 |
| 14 | CLEC14A |
| 14 | DLK1 |
| 14 | FLRT2 |
| 14 | GPR135 |
| 14 | GPR137C |
| 14 | JAG2 |
| 14 | LTB4R2 |
| 14 | MMP14 |
| 14 | OR11G2 |
| 14 | OR11H12 |
| 14 | OR11H6 |
| 14 | OR4K1 |
| 14 | OR4K15 |
| 14 | OR4K5 |
| 14 | OR4L1 |
| 14 | OR4N2 |
| 14 | OR4N5 |
| 14 | OR4Q2 |
| 14 | SLC24A4 |
| 14 | SYNDIG1L |
| 15 | ANPEP |
| 15 | CD276 |
| 15 | CHRNA7 |
| 15 | CHRNB4 |
| 15 | CSPG4 |
| 15 | DUOX1 |
| 15 | DUOX2 |
| 15 | FAM174B |
| 15 | GLDN |
| 15 | IGDCC4 |
| 15 | ITGA11 |
| 15 | LCTL |
| 15 | LTK |
| 15 | LYSMD4 |
| 15 | MEGF11 |
| 15 | NRG4 |
| 15 | OCA2 |
| 15 | OR4F4 |
| 15 | OR4M2 |
| 15 | OR4N4 |
| 15 | PRTG |
| 15 | RHCG |

| Chr | Gene |
|---|---|
| 15 | SCAMP5 |
| 15 | SEMA4B |
| 15 | SEMA6D |
| 15 | SLC24A1 |
| 15 | SLC28A1 |
| 15 | TRPM1 |
| 15 | TYRO3 |
| 16 | ATP2C2 |
| 16 | CACNA1H |
| 16 | CD19 |
| 16 | CDH11 |
| 16 | CDH16 |
| 16 | CDH3 |
| 16 | CDH5 |
| 16 | CNGB1 |
| 16 | CNTNAP4 |
| 16 | GDPD3 |
| 16 | GPR56 |
| 16 | GPR97 |
| 16 | IL4R |
| 16 | ITFG3 |
| 16 | ITGAL |
| 16 | ITGAM |
| 16 | ITGAX |
| 16 | KCNG4 |
| 16 | MMP15 |
| 16 | MSLNL |
| 16 | NOMO1 |
| 16 | NOMO3 |
| 16 | OR2C1 |
| 16 | PKD1 |
| 16 | PKD1L2 |
| 16 | SCNN1B |
| 16 | SEZ6L2 |
| 16 | SLC22A31 |
| 16 | SLC5A11 |
| 16 | SLC7A6 |
| 16 | SPN |
| 16 | TMC5 |
| 16 | TMC7 |
| 16 | TMEM204 |
| 16 | TMEM219 |
| 16 | TMEM8A |
| 17 | ABCC3 |

Figure 22 (Continued)

| Chr | Gene |
|---|---|
| 17 | ACE |
| 17 | AOC3 |
| 17 | ASGR2 |
| 17 | C17orf80 |
| 17 | CD300A |
| 17 | CD300C |
| 17 | CD300E |
| 17 | CD300LG |
| 17 | CHRNB1 |
| 17 | CLEC10A |
| 17 | CNTNAP1 |
| 17 | CPD |
| 17 | CXCL16 |
| 17 | FAM171A2 |
| 17 | GCGR |
| 17 | GLP2R |
| 17 | GP1BA |
| 17 | GPR142 |
| 17 | GUCY2D |
| 17 | ITGA2B |
| 17 | ITGA3 |
| 17 | ITGAE |
| 17 | ITGB3 |
| 17 | KCNJ12 |
| 17 | LRRC37A |
| 17 | LRRC37A2 |
| 17 | LRRC37A3 |
| 17 | LRRC37B |
| 17 | MRC2 |
| 17 | NGFR |
| 17 | OR1A2 |
| 17 | OR1D2 |
| 17 | OR1G1 |
| 17 | OR3A1 |
| 17 | OR3A2 |
| 17 | OR4D1 |
| 17 | OR4D2 |
| 17 | RNF43 |
| 17 | SCN4A |
| 17 | SDK2 |
| 17 | SECTM1 |
| 17 | SEZ6 |
| 17 | SLC26A11 |
| 17 | SPACA3 |

| Chr | Gene |
|---|---|
| 17 | TMEM102 |
| 17 | TMEM132E |
| 17 | TNFSF12 |
| 17 | TRPV3 |
| 17 | TTYH2 |
| 17 | TUSC5 |
| 18 | APCDD1 |
| 18 | CDH19 |
| 18 | CDH20 |
| 18 | CDH7 |
| 18 | COLEC12 |
| 18 | DCC |
| 18 | DSC1 |
| 18 | DSG1 |
| 18 | DSG3 |
| 18 | DYNAP |
| 18 | MEP1B |
| 18 | PTPRM |
| 18 | SIGLEC15 |
| 18 | TNFRSF11A |
| 19 | ABCA7 |
| 19 | ACPT |
| 19 | BCAM |
| 19 | C19orf38 |
| 19 | C19orf59 |
| 19 | C5AR1 |
| 19 | CATSPERD |
| 19 | CATSPERG |
| 19 | CD320 |
| 19 | CD33 |
| 19 | CD97 |
| 19 | CEACAM1 |
| 19 | CEACAM19 |
| 19 | CEACAM21 |
| 19 | CEACAM3 |
| 19 | CEACAM4 |
| 19 | CLEC4M |
| 19 | DLL3 |
| 19 | EMR1 |
| 19 | EMR2 |
| 19 | EMR3 |
| 19 | ERVV-1 |
| 19 | ERVV-2 |
| 19 | FAM187B |

| Chr | Gene |
|---|---|
| 19 | FCAR |
| 19 | FFAR3 |
| 19 | FPR1 |
| 19 | GFY |
| 19 | GP6 |
| 19 | GPR42 |
| 19 | GRIN3B |
| 19 | ICAM3 |
| 19 | IGFLR1 |
| 19 | IL12RB1 |
| 19 | IL27RA |
| 19 | KIR2DL1 |
| 19 | KIR2DL3 |
| 19 | KIR2DL4 |
| 19 | KIR3DL1 |
| 19 | KIR3DL2 |
| 19 | KIR3DL3 |
| 19 | KIRREL2 |
| 19 | KISS1R |
| 19 | LAIR1 |
| 19 | LDLR |
| 19 | LILRA1 |
| 19 | LILRA2 |
| 19 | LILRA4 |
| 19 | LILRA6 |
| 19 | LILRB1 |
| 19 | LILRB2 |
| 19 | LILRB3 |
| 19 | LILRB4 |
| 19 | LILRB5 |
| 19 | LINGO3 |
| 19 | LPHN1 |
| 19 | LRP3 |
| 19 | MADCAM1 |
| 19 | MAG |
| 19 | MEGF8 |
| 19 | MUC16 |
| 19 | NCR1 |
| 19 | NOTCH3 |
| 19 | NPHS1 |
| 19 | OR10H1 |
| 19 | OR10H2 |
| 19 | OR10H3 |
| 19 | OR10H4 |

Figure 22 (Continued)

| Chr | Gene |
|---|---|
| 19 | OR1I1 |
| 19 | OR2Z1 |
| 19 | OR7A10 |
| 19 | OR7C1 |
| 19 | OR7D4 |
| 19 | OR7E24 |
| 19 | OR7G1 |
| 19 | OR7G2 |
| 19 | OR7G3 |
| 19 | PLVAP |
| 19 | PTGIR |
| 19 | PTPRH |
| 19 | PTPRS |
| 19 | PVR |
| 19 | SCN1B |
| 19 | SHISA7 |
| 19 | SIGLEC10 |
| 19 | SIGLEC11 |
| 19 | SIGLEC12 |
| 19 | SIGLEC5 |
| 19 | SIGLEC6 |
| 19 | SIGLEC8 |
| 19 | SIGLEC9 |
| 19 | SLC44A2 |
| 19 | SLC5A5 |
| 19 | SLC7A9 |
| 19 | TARM1 |
| 19 | TGFBR3L |
| 19 | TMC4 |
| 19 | TMEM91 |
| 19 | TMPRSS9 |
| 19 | TNFSF14 |
| 19 | TNFSF9 |
| 19 | TRPM4 |
| 19 | VN1R2 |
| 19 | VSIG10L |
| 19 | VSTM2B |
| 20 | ABHD12 |

| Chr | Gene |
|---|---|
| 20 | ADAM33 |
| 20 | ADRA1D |
| 20 | APMAP |
| 20 | ATRN |
| 20 | CD40 |
| 20 | CD93 |
| 20 | CDH22 |
| 20 | CDH26 |
| 20 | CDH4 |
| 20 | FLRT3 |
| 20 | GCNT7 |
| 20 | GGT7 |
| 20 | JAG1 |
| 20 | LRRN4 |
| 20 | NPBWR2 |
| 20 | OCSTAMP |
| 20 | PTPRA |
| 20 | PTPRT |
| 20 | SEL1L2 |
| 20 | SIGLEC1 |
| 20 | SIRPA |
| 20 | SIRPB1 |
| 20 | SIRPG |
| 20 | SLC24A3 |
| 20 | SLC2A10 |
| 20 | SSTR4 |
| 20 | THBD |
| 21 | CLDN8 |
| 21 | DSCAM |
| 21 | ICOSLG |
| 21 | IFNAR1 |
| 21 | IFNGR2 |
| 21 | IGSF5 |
| 21 | ITGB2 |
| 21 | KCNJ15 |
| 21 | NCAM2 |
| 21 | TMPRSS15 |
| 21 | TMPRSS2 |

| Chr | Gene |
|---|---|
| 21 | TMPRSS3 |
| 21 | TRPM2 |
| 21 | UMODL1 |
| 22 | CACNA1I |
| 22 | CELSR1 |
| 22 | COMT |
| 22 | CSF2RB |
| 22 | GGT1 |
| 22 | GGT5 |
| 22 | IL2RB |
| 22 | KREMEN1 |
| 22 | MCHR1 |
| 22 | OR11H1 |
| 22 | P2RX6 |
| 22 | PKDREJ |
| 22 | PLXNB2 |
| 22 | SCARF2 |
| 22 | SEZ6L |
| 22 | SSTR3 |
| 22 | SUSD2 |
| 22 | TMPRSS6 |
| 22 | TNFRSF13C |
| X | ATP6AP2 |
| X | ATP7A |
| X | EDA2R |
| X | FMR1NB |
| X | GLRA4 |
| X | GPR112 |
| X | GUCY2F |
| X | HEPH |
| X | P2RY10 |
| X | P2RY4 |
| X | PLXNA3 |
| X | PLXNB3 |
| X | VSIG4 |
| X | XG |

Figure 23

| Chr | Position | ref | alt | Gene |
|---|---|---|---|---|
| 1 | 101005090 | G | A | GPR88 |
| 1 | 101197012 | A | G | VCAM1 |
| 1 | 101704572 | C | A | S1PR1 |
| 1 | 109735398 | A | C | KIAA1324 |
| 1 | 109801674 | A | C | CELSR2 |
| 1 | 109806313 | T | C | CELSR2 |
| 1 | 113650307 | G | A | LRIG2 |
| 1 | 11561593 | G | A | PTCHD2 |
| 1 | 11584109 | C | G | PTCHD2 |
| 1 | 11585308 | C | T | PTCHD2 |
| 1 | 117122130 | T | C | IGSF3 |
| 1 | 117142613 | C | T | IGSF3 |
| 1 | 117142641 | G | A | IGSF3 |
| 1 | 117503940 | G | A | PTGFRN |
| 1 | 117554421 | A | G | CD101 |
| 1 | 117559726 | A | G | CD101 |
| 1 | 117560058 | C | G | CD101 |
| 1 | 117568200 | G | A | CD101 |
| 1 | 11986011 | T | C | KIAA2013 |
| 1 | 120437884 | A | G | ADAM30 |
| 1 | 120469147 | T | C | NOTCH2 |
| 1 | 120572547 | T | C | NOTCH2 |
| 1 | 120572572 | C | T | NOTCH2 |
| 1 | 120934449 | C | T | FCGR1B |
| 1 | 120934573 | C | T | FCGR1B |
| 1 | 1221001 | A | G | SCNN1D |
| 1 | 1222598 | C | T | SCNN1D |
| 1 | 12252955 | T | G | TNFRSF1B |
| 1 | 1291085 | C | T | MXRA8 |
| 1 | 145533877 | C | G | ITGA10 |
| 1 | 145535814 | C | T | ITGA10 |
| 1 | 145536082 | G | A | ITGA10 |
| 1 | 145541460 | C | T | ITGA10 |
| 1 | 151107304 | C | G | SEMA6C |
| 1 | 151108137 | T | G | SEMA6C |
| 1 | 151112483 | T | C | SEMA6C |
| 1 | 153653757 | G | C | NPR1 |
| 1 | 154541971 | T | G | CHRNB2 |
| 1 | 155161702 | GT | G | MUC1 |
|   |   | GT |   |   |
|   |   | CC |   |   |
|   |   | GG |   |   |
|   |   | GG |   |   |
|   |   | CC |   |   |

| Chr | Position | ref | alt | Gene |
|---|---|---|---|---|
|   |   |   | GA |   |
|   |   |   | GG |   |
|   |   |   | TG |   |
|   |   |   | AC |   |
|   |   |   | AC |   |
|   |   |   | CG |   |
|   |   |   | TG |   |
|   |   |   | GG |   |
|   |   |   | CT |   |
|   |   |   | GG |   |
|   |   |   | GG |   |
|   |   |   | GG |   |
|   |   |   | GC |   |
|   |   |   | GG |   |
|   |   |   | TG |   |
|   |   |   | GA |   |
|   |   |   | GC |   |
|   |   |   | CC |   |
|   |   |   | GG |   |
|   |   |   | GG |   |
|   |   |   | CT |   |
|   |   |   | GG |   |
|   |   |   | CT |   |
|   |   |   | TG |   |
|   |   |   | T |   |
| 1 | 155161714 | G | A | MUC1 |
| 1 | 155911517 | C | A | RXFP4 |
| 1 | 156144971 | G | A | SEMA4A |
| 1 | 156838432 | C | T | NTRK1 |
| 1 | 156877457 | T | C | PEAR1 |
| 1 | 156878044 | G | A | PEAR1 |
| 1 | 156878473 | C | T | PEAR1 |
| 1 | 157504422 | C | T | FCRL5 |
| 1 | 157508882 | C | T | FCRL5 |
| 1 | 157508908 | T | C | FCRL5 |
| 1 | 157508997 | G | T | FCRL5 |
| 1 | 157509025 | C | T | FCRL5 |
| 1 | 157514091 | C | T | FCRL5 |
| 1 | 157514097 | A | G | FCRL5 |
| 1 | 157559122 | C | T | FCRL4 |
| 1 | 157668194 | A | C | FCRL3 |
| 1 | 157668390 | T | C | FCRL3 |
| 1 | 157772404 | C | T | FCRL1 |
| 1 | 158225019 | C | G | CD1A |
| 1 | 158261071 | A | C | CD1C |

Figure 23 (Continued)

| Chr | Position | ref | alt | Gene |
|---|---|---|---|---|
| 1 | 158263011 | T | C | CD1C |
| 1 | 158368964 | C | T | OR10T2 |
| 1 | 158368974 | A | G | OR10T2 |
| 1 | 158369210 | A | G | OR10T2 |
| 1 | 158435928 | G | A | OR10K1 |
| 1 | 158449749 | A | G | OR10R2 |
| 1 | 158450238 | G | A | OR10R2 |
| 1 | 158450314 | A | G | OR10R2 |
| 1 | 158517585 | G | A | OR6Y1 |
| 1 | 158517891 | G | A | OR6Y1 |
| 1 | 158532605 | C | A | OR6P1 |
| 1 | 158532614 | G | A | OR6P1 |
| 1 | 158532908 | T | C | OR6P1 |
| 1 | 158549082 | A | T | OR10X1 |
| 1 | 158670426 | C | T | OR6K2 |
| 1 | 158687896 | C | T | OR6K3 |
| 1 | 158724722 | G | C | OR6K6 |
| 1 | 158724750 | C | T | OR6K6 |
| 1 | 158725194 | T | C | OR6K6 |
| 1 | 158725237 | C | T | OR6K6 |
| 1 | 158735691 | T | C | OR6N1 |
| 1 | 158735892 | A | G | OR6N1 |
| 1 | 158736445 | C | T | OR6N1 |
| 1 | 159273892 | A | G | FCER1A |
| 1 | 159273943 | G | A | FCER1A |
| 1 | 159275786 | C | G | FCER1A |
| 1 | 159402547 | T | C | OR10J4 |
| 1 | 159409857 | A | G | OR10J1 |
| 1 | 159409870 | T | G | OR10J1 |
| 1 | 159778910 | G | A | FCRL6 |
| 1 | 159779464 | T | C | FCRL6 |
| 1 | 159779465 | C | T | FCRL6 |
| 1 | 159912899 | C | T | IGSF9 |
| 1 | 159922175 | C | T | SLAMF9 |
| 1 | 159923111 | T | G | SLAMF9 |
| 1 | 159923234 | C | T | SLAMF9 |
| 1 | 160318829 | G | C | NCSTN |
| 1 | 160719757 | C | T | SLAMF7 |
| 1 | 160719843 | A | C | SLAMF7 |
| 1 | 160784275 | A | C | LY9 |
| 1 | 160811488 | T | C | CD244 |
| 1 | 161049509 | G | T | PVRL4 |
| 1 | 161049662 | A | G | PVRL4 |
| 1 | 161476204 | C | T | FCGR2A |

| Chr | Position | ref | alt | Gene |
|---|---|---|---|---|
| 1 | 161476205 | A | G | FCGR2A |
| 1 | 161479745 | A | G | FCGR2A |
| 1 | 161518214 | T | C | FCGR3A |
| 1 | 161518336 | C | T | FCGR3A |
| 1 | 161642774 | T | G | FCGR2B |
| 1 | 16464489 | C | T | EPHA2 |
| 1 | 165532746 | T | A | LRRC52 |
| 1 | 167032895 | C | A | GPA33 |
| 1 | 169563951 | T | G | SELP |
| 1 | 169565346 | C | A | SELP |
| 1 | 169566313 | C | T | SELP |
| 1 | 169580885 | C | T | SELP |
| 1 | 169581595 | G | A | SELP |
| 1 | 169582317 | C | T | SELP |
| 1 | 169676486 | A | G | SELL |
| 1 | 169696946 | G | A | SELE |
| 1 | 177030344 | T | C | ASTN1 |
| 1 | 181018236 | A | G | MR1 |
| 1 | 19175846 | T | C | TAS1R2 |
| 1 | 19181015 | G | C | TAS1R2 |
| 1 | 19181393 | T | C | TAS1R2 |
| 1 | 19186093 | G | A | TAS1R2 |
| 1 | 19565338 | C | T | EMC1 |
| 1 | 19565344 | C | G | EMC1 |
| 1 | 19566382 | A | G | EMC1 |
| 1 | 197396761 | G | A | CRB1 |
| 1 | 198671653 | A | G | PTPRC |
| 1 | 201052310 | A | T | CACNA1S |
| 1 | 202092332 | C | G | GPR37L1 |
| 1 | 202092360 | G | A | GPR37L1 |
| 1 | 204588700 | C | G | LRRN2 |
| 1 | 204589066 | C | T | LRRN2 |
| 1 | 204924020 | C | T | NFASC |
| 1 | 204944474 | T | G | NFASC |
| 1 | 204966402 | A | G | NFASC |
| 1 | 205053150 | A | G | TMEM81 |
| 1 | 205053219 | C | T | TMEM81 |
| 1 | 207106478 | G | A | PIGR |
| 1 | 207107806 | G | A | PIGR |
| 1 | 207109116 | C | T | PIGR |
| 1 | 207134226 | C | T | FCAMR |
| 1 | 207134410 | T | G | FCAMR |
| 1 | 207646462 | G | A | CR2 |
| 1 | 207646923 | G | A | CR2 |

Figure 23 (Continued)

| Chr | Position | ref | alt | Gene |
|---|---|---|---|---|
| 1 | 207707637 | A | C | CR1 |
| 1 | 207715740 | T | C | CR1 |
| 1 | 207715866 | G | A | CR1 |
| 1 | 207741193 | T | C | CR1 |
| 1 | 207753621 | A | G | CR1 |
| 1 | 207760773 | C | T | CR1 |
| 1 | 208073205 | C | A | CD34 |
| 1 | 208252715 | A | C | PLXNA2 |
| 1 | 208252777 | G | C | PLXNA2 |
| 1 | 208252778 | C | A | PLXNA2 |
| 1 | 208272313 | A | C | PLXNA2 |
| 1 | 208390162 | T | C | PLXNA2 |
| 1 | 208390469 | C | T | PLXNA2 |
| 1 | 208391098 | T | C | PLXNA2 |
| 1 | 208391131 | C | T | PLXNA2 |
| 1 | 21573855 | G | A | ECE1 |
| 1 | 215808007 | G | A | USH2A |
| 1 | 215808022 | T | C | USH2A |
| 1 | 215821909 | C | T | USH2A |
| 1 | 215916563 | G | A | USH2A |
| 1 | 215960153 | A | C | USH2A |
| 1 | 215960167 | T | G | USH2A |
| 1 | 215987222 | T | C | USH2A |
| 1 | 216011361 | T | C | USH2A |
| 1 | 216011408 | T | C | USH2A |
| 1 | 216051125 | G | A | USH2A |
| 1 | 216172299 | C | G | USH2A |
| 1 | 216172380 | A | G | USH2A |
| 1 | 216219781 | A | G | USH2A |
| 1 | 216258213 | A | G | USH2A |
| 1 | 216348764 | C | T | USH2A |
| 1 | 216373416 | A | C | USH2A |
| 1 | 216462662 | T | A | USH2A |
| 1 | 216595306 | C | T | USH2A |
| 1 | 22141206 | A | C | LDLRAD2 |
| 1 | 223284528 | A | G | TLR5 |
| 1 | 223284599 | T | C | TLR5 |
| 1 | 223285200 | G | A | TLR5 |
| 1 | 223285833 | G | T | TLR5 |
| 1 | 223285946 | T | G | TLR5 |
| 1 | 238046056 | G | A | ZP4 |
| 1 | 238053226 | G | A | ZP4 |
| 1 | 241767708 | C | T | OPN3 |
| 1 | 24454688 | C | T | IL22RA1 |

| Chr | Position | ref | alt | Gene |
|---|---|---|---|---|
| 1 | 24460844 | A | G | IL22RA1 |
| 1 | 244723989 | C | A | C1orf101 |
| 1 | 244724277 | C | T | C1orf101 |
| 1 | 247695756 | T | C | OR2C3 |
| 1 | 247751731 | C | G | OR2G2 |
| 1 | 247752161 | T | C | OR2G2 |
| 1 | 247768948 | C | T | OR2G3 |
| 1 | 247769425 | G | A | OR2G3 |
| 1 | 247876020 | A | G | OR6F1 |
| 1 | 247902448 | G | A | OR14K1 |
| 1 | 247902693 | G | T | OR14K1 |
| 1 | 247978517 | A | G | OR14A16 |
| 1 | 247978541 | AAGG | A | OR14A16 |
| 1 | 248004660 | T | G | OR11L1 |
| 1 | 248004687 | C | G | OR11L1 |
| 1 | 248059150 | T | C | OR2W3 |
| 1 | 248059151 | G | A | OR2W3 |
| 1 | 248059394 | G | C | OR2W3 |
| 1 | 248059423 | C | T | OR2W3 |
| 1 | 248059703 | T | A | OR2W3 |
| 1 | 248084579 | G | A | OR2T8 |
| 1 | 248084825 | C | T | OR2T8 |
| 1 | 248084854 | A | G | OR2T8 |
| 1 | 248084909 | T | G | OR2T8 |
| 1 | 248085124 | G | A | OR2T8 |
| 1 | 248128745 | A | G | OR2AK2 |
| 1 | 248128929 | G | A | OR2AK2 |
| 1 | 248129240 | G | A | OR2AK2 |
| 1 | 248129486 | C | T | OR2AK2 |
| 1 | 248202344 | G | C | OR2L2 |
| 1 | 248436582 | T | C | OR2T33 |
| 1 | 248436611 | G | A | OR2T33 |
| 1 | 248436857 | C | T | OR2T33 |
| 1 | 248458875 | CT | C | OR2T12 |
| 1 | 248487300 | C | T | OR2M7 |
| 1 | 248487338 | C | A | OR2M7 |
| 1 | 248487834 | G | T | OR2M7 |
| 1 | 248524937 | ATGGGACTCTTC | A | OR2T4 |

Figure 23 (Continued)

| Chr | Position | ref | alt | Gene |
|---|---|---|---|---|
| | | AGACAATCCAAACATCCAATGGCCAATATCACCTGGATGGCCAACCACACTGGATGGTCGCGGATTTCATATCCTGT | | |
| 1 | 248524974 | A | G | OR2T4 |
| 1 | 248550976 | T | G | OR2T6 |
| 1 | 248569369 | A | G | OR2T1 |
| 1 | 248604542 | C | T | OR2T7 |
| 1 | 248604971 | T | C | OR2T7 |
| 1 | 248605007 | ACTT | A | OR2T7 |
| 1 | 248636713 | G | C | OR2T3 |

| Chr | Position | ref | alt | Gene |
|---|---|---|---|---|
| 1 | 248636934 | G | T | OR2T3 |
| 1 | 248637480 | A | G | OR2T3 |
| 1 | 248651905 | A | T | OR2T5 |
| 1 | 248652175 | G | A | OR2T5 |
| 1 | 248722507 | C | T | OR2T29 |
| 1 | 248722723 | G | A | OR2T29 |
| 1 | 248722777 | T | A | OR2T29 |
| 1 | 248737230 | T | C | OR2T34 |
| 1 | 248801778 | A | T | OR2T35 |
| 1 | 248813650 | CAGA | C | OR2T27 |
| 1 | 248813695 | A | G | OR2T27 |
| 1 | 248845097 | C | T | OR14I1 |
| 1 | 248845356 | G | T | OR14I1 |
| 1 | 2491306 | G | A | TNFRSF14 |
| 1 | 26520292 | G | T | CATSPER4 |
| 1 | 27709020 | T | C | CD164L2 |
| 1 | 27709044 | T | C | CD164L2 |
| 1 | 31347320 | G | A | SDC3 |
| 1 | 31349647 | C | T | SDC3 |
| 1 | 31381313 | CCAG | C | SDC3 |
| 1 | 32084861 | T | C | HCRTR1 |
| 1 | 34238283 | T | C | CSMD2 |
| 1 | 34401453 | A | G | CSMD2 |
| 1 | 35227005 | CT | C | GJB4 |
| 1 | 35227007 | TTGTC | T | GJB4 |
| 1 | 36937701 | T | C | CSF3R |
| 1 | 38197152 | C | T | EPHA10 |
| 1 | 38227086 | A | T | EPHA10 |
| 1 | 38227268 | G | T | EPHA10 |
| 1 | 43296456 | G | A | ERMAP |
| 1 | 43770692 | C | T | TIE1 |
| 1 | 44057042 | A | G | PTPRF |
| 1 | 45292937 | T | G | PTCH2 |
| 1 | 48241061 | G | A | TRABD2B |
| 1 | 48694594 | G | A | SLC5A9 |
| 1 | 48697277 | C | T | SLC5A9 |
| 1 | 53746346 | T | G | LRP8 |
| 1 | 53792651 | A | C | LRP8 |
| 1 | 59042311 | T | G | TACSTD2 |
| 1 | 59042388 | C | G | TACSTD2 |

Figure 23 (Continued)

| Chr | Position | ref | alt | Gene |
|---|---|---|---|---|
| 1 | 66036441 | A | G | LEPR |
| 1 | 66058513 | A | G | LEPR |
| 1 | 66075952 | G | C | LEPR |
| 1 | 79392756 | C | A | ELTD1 |
| 1 | 86900372 | C | G | CLCA2 |
| 1 | 86909582 | G | A | CLCA2 |
| 1 | 90049071 | G | A | LRRC8B |
| 1 | 9079301 | C | T | SLC2A7 |
| 1 | 9083094 | G | T | SLC2A7 |
| 1 | 9188876 | T | C | GPR157 |
| 1 | 94496053 | G | A | ABCA4 |
| 1 | 94544234 | T | C | ABCA4 |
| 1 | 94564483 | C | T | ABCA4 |
| 1 | 9804693 | C | T | CLSTN1 |
| 2 | 102955468 | C | A | IL1RL1 |
| 2 | 109545691 | T | C | EDAR |
| 2 | 112686988 | G | A | MERTK |
| 2 | 112722854 | G | A | MERTK |
| 2 | 112751928 | G | A | MERTK |
| 2 | 112754942 | A | G | MERTK |
| 2 | 116503671 | G | A | DPP10 |
| 2 | 116510817 | G | C | DPP10 |
| 2 | 116525960 | G | A | DPP10 |
| 2 | 116548675 | G | A | DPP10 |
| 2 | 119739063 | T | C | MARCO |
| 2 | 125281910 | C | T | CNTNAP5 |
| 2 | 125320888 | A | C | CNTNAP5 |
| 2 | 131486765 | C | G | GPR148 |
| 2 | 133175250 | A | G | GPR39 |
| 2 | 136555659 | T | C | LCT |
| 2 | 136567203 | T | C | LCT |
| 2 | 136575534 | T | C | LCT |
| 2 | 137872746 | G | A | THSD7B |
| 2 | 137917922 | T | A | THSD7B |
| 2 | 137928320 | C | T | THSD7B |
| 2 | 137988626 | C | T | THSD7B |
| 2 | 137990678 | C | T | THSD7B |
| 2 | 138420996 | A | G | THSD7B |
| 2 | 141116447 | G | T | LRP1B |
| 2 | 141242918 | T | C | LRP1B |
| 2 | 141259399 | A | C | LRP1B |
| 2 | 141457962 | C | T | LRP1B |
| 2 | 142567910 | T | C | LRP1B |
| 2 | 1481155 | G | T | TPO |

| Chr | Position | ref | alt | Gene |
|---|---|---|---|---|
| 2 | 1481231 | G | C | TPO |
| 2 | 1488616 | A | C | TPO |
| 2 | 1497657 | G | A | TPO |
| 2 | 1499870 | A | G | TPO |
| 2 | 1499927 | A | C | TPO |
| 2 | 160673519 | G | A | LY75 |
| 2 | 160673526 | A | G | LY75 |
| 2 | 160676350 | T | C | LY75 |
| 2 | 160676427 | C | A | LY75 |
| 2 | 160710153 | T | G | LY75 |
| 2 | 160711045 | G | C | LY75 |
| 2 | 160729005 | C | T | LY75 |
| 2 | 160743040 | T | A | LY75 |
| 2 | 160808075 | C | T | PLA2R1 |
| 2 | 160843746 | GC | G | PLA2R1 |
| 2 | 160843748 | T | G | PLA2R1 |
| 2 | 160879259 | C | T | PLA2R1 |
| 2 | 160885418 | G | C | PLA2R1 |
| 2 | 160885442 | T | C | PLA2R1 |
| 2 | 160898583 | G | T | PLA2R1 |
| 2 | 167279922 | C | A | SCN7A |
| 2 | 170003432 | T | G | LRP2 |
| 2 | 170010985 | T | C | LRP2 |
| 2 | 170053505 | C | T | LRP2 |
| 2 | 170060512 | C | G | LRP2 |
| 2 | 170070172 | C | T | LRP2 |
| 2 | 170097707 | T | G | LRP2 |
| 2 | 170175334 | T | C | LRP2 |
| 2 | 173339808 | G | A | ITGA6 |
| 2 | 173352507 | G | T | ITGA6 |
| 2 | 173355958 | G | A | ITGA6 |
| 2 | 182376480 | T | A | ITGA4 |
| 2 | 182395345 | G | A | ITGA4 |
| 2 | 187466842 | A | C | ITGAV |
| 2 | 187511466 | A | G | ITGAV |
| 2 | 192922499 | G | A | TMEFF2 |
| 2 | 20403794 | A | T | SDC1 |
| 2 | 206581033 | G | A | NRP2 |
| 2 | 219029108 | C | G | CXCR1 |
| 2 | 219029843 | A | C | CXCR1 |
| 2 | 230341874 | T | G | DNER |
| 2 | 233406178 | G | A | CHRNG |
| 2 | 240969312 | A | G | OR6B2 |
| 2 | 241558397 | G | A | GPR35 |

Figure 23 (Continued)

| Chr | Position | ref | alt | Gene | Chr | Position | ref | alt | Gene |
|---|---|---|---|---|---|---|---|---|---|
| 2 | 26534801 | G | A | GPR113 | 3 | 102181131 | A | G | ZPLD1 |
| 2 | 26534813 | A | G | GPR113 | 3 | 105258861 | A | G | ALCAM |
| 2 | 26534872 | C | T | GPR113 | 3 | 111286375 | G | C | CD96 |
| 2 | 26536694 | C | T | GPR113 | 3 | 111780727 | C | A | TMPRSS7 |
| 2 | 26536727 | C | T | GPR113 | 3 | 111780741 | C | T | TMPRSS7 |
| 2 | 26539204 | C | A | GPR113 | 3 | 111799845 | A | T | TMPRSS7 |
| 2 | 26539806 | A | G | GPR113 | 3 | 112059768 | C | G | CD200 |
| 2 | 27435165 | G | A | ATRAID | 3 | 112063850 | C | A | CD200 |
| 2 | 27435250 | A | G | ATRAID | 3 | 112647832 | A | C | CD200R1 |
| 2 | 28814033 | A | G | PLB1 | 3 | 112648127 | T | G | CD200R1 |
| 2 | 28827625 | C | T | PLB1 | 3 | 112648222 | T | C | CD200R1 |
| 2 | 28843148 | G | A | PLB1 | 3 | 113251935 | G | A | SIDT1 |
| 2 | 28854958 | C | T | PLB1 | 3 | 113251962 | C | A | SIDT1 |
| 2 | 29448410 | T | G | ALK | 3 | 113890815 | C | T | DRD3 |
| 2 | 36744583 | A | C | CRIM1 | 3 | 118649060 | G | T | IGSF11 |
| 2 | 39893305 | A | C | TMEM178A | 3 | 118909159 | A | G | UPK1B |
| 2 | 44040401 | G | C | ABCG5 | 3 | 118909892 | A | G | UPK1B |
| 2 | 47601106 | T | C | EPCAM | 3 | 121825197 | G | A | CD86 |
| 2 | 47604176 | C | T | EPCAM | 3 | 121981215 | A | G | CASR |
| 2 | 48921375 | T | C | LHCGR | 3 | 122631896 | A | T | SEMA5B |
| 2 | 48921438 | T | C | LHCGR | 3 | 122632436 | A | G | SEMA5B |
| 2 | 68873071 | A | G | PROKR1 | 3 | 122634665 | G | C | SEMA5B |
| 2 | 70188531 | C | T | ASPRV1 | 3 | 122640851 | G | C | SEMA5B |
| 2 | 71036417 | T | C | CLEC4F | 3 | 122646828 | A | G | SEMA5B |
| 2 | 71036482 | T | C | CLEC4F | 3 | 122694930 | C | T | SEMA5B |
| 2 | 71043407 | A | G | CLEC4F | 3 | 124515498 | T | C | ITGB5 |
| 2 | 71043461 | C | T | CLEC4F | 3 | 124515636 | C | T | ITGB5 |
| 2 | 71043728 | T | A | CLEC4F | 3 | 124728626 | A | G | HEG1 |
| 2 | 71044076 | T | C | CLEC4F | 3 | 124731485 | C | G | HEG1 |
| 2 | 71058230 | T | A | CD207 | 3 | 124731689 | T | A | HEG1 |
| 2 | 71058306 | T | C | CD207 | 3 | 124731944 | T | G | HEG1 |
| 2 | 71060111 | G | A | CD207 | 3 | 124732618 | A | G | HEG1 |
| 2 | 71060936 | G | C | CD207 | 3 | 129293256 | T | C | PLXND1 |
| 2 | 71061001 | T | A | CD207 | 3 | 129304797 | G | A | PLXND1 |
| 2 | 71061145 | C | T | CD207 | 3 | 129305459 | C | A | PLXND1 |
| 2 | 85059227 | C | T | TRABD2A | 3 | 129305460 | C | T | PLXND1 |
| 2 | 85097590 | C | T | TRABD2A | 3 | 133941320 | C | T | RYK |
| 2 | 85554080 | G | A | TGOLN2 | 3 | 137743508 | A | T | CLDN18 |
| 2 | 95947085 | A | G | PROM2 | 3 | 140178381 | T | C | CLSTN2 |
| 2 | 95947099 | G | A | PROM2 | 3 | 140178485 | G | A | CLSTN2 |
| 3 | 100354524 | A | G | GPR128 | 3 | 155571275 | T | C | SLC33A1 |
| 3 | 100368546 | A | G | GPR128 | 3 | 164906806 | T | C | SLITRK3 |
| 3 | 100963154 | G | A | IMPG2 | 3 | 170136972 | A | C | CLDN11 |
| 3 | 102157417 | A | G | ZPLD1 | 3 | 172232780 | G | T | TNFSF10 |

Figure 23 (Continued)

| Chr | Position | ref | alt | Gene |
|---|---|---|---|---|
| 3 | 174951756 | T | C | NAALADL2 |
| 3 | 175345143 | C | G | NAALADL2 |
| 3 | 175455116 | A | G | NAALADL2 |
| 3 | 175473047 | T | C | NAALADL2 |
| 3 | 178961025 | G | C | KCNMB3 |
| 3 | 178961038 | T | C | KCNMB3 |
| 3 | 183753777 | G | A | HTR3D |
| 3 | 183754278 | C | G | HTR3D |
| 3 | 183774762 | C | A | HTR3C |
| 3 | 183822145 | C | T | HTR3E |
| 3 | 183824398 | G | A | HTR3E |
| 3 | 184293716 | A | C | EPHB3 |
| 3 | 193171979 | T | A | ATP13A4 |
| 3 | 193209178 | T | C | ATP13A4 |
| 3 | 194080916 | G | A | LRRC15 |
| 3 | 194080983 | C | T | LRRC15 |
| 3 | 194117911 | C | G | GP5 |
| 3 | 194337901 | T | C | TMEM44 |
| 3 | 194353875 | G | T | TMEM44 |
| 3 | 195800811 | C | T | TFRC |
| 3 | 196388099 | G | C | NRROS |
| 3 | 27472936 | C | T | SLC4A7 |
| 3 | 27473156 | T | A | SLC4A7 |
| 3 | 3139957 | T | C | IL5RA |
| 3 | 33194990 | C | A | SUSD5 |
| 3 | 33195309 | A | G | SUSD5 |
| 3 | 33255592 | A | G | SUSD5 |
| 3 | 37559040 | A | G | ITGA9 |
| 3 | 37574951 | G | A | ITGA9 |
| 3 | 37695260 | A | G | ITGA9 |
| 3 | 38347851 | A | G | SLC22A14 |
| 3 | 38350543 | A | G | SLC22A14 |
| 3 | 3886665 | G | A | LRRN1 |
| 3 | 391100 | A | G | CHL1 |
| 3 | 39323163 | A | C | CX3CR1 |
| 3 | 42555275 | A | C | VIPR1 |
| 3 | 42906116 | T | C | ACKR2 |
| 3 | 43602803 | C | T | ANO10 |
| 3 | 439963 | A | G | CHL1 |
| 3 | 45134822 | T | C | CDCP1 |
| 3 | 45987980 | G | A | CXCR6 |
| 3 | 46449164 | G | A | CCRL2 |
| 3 | 46449175 | G | A | CCRL2 |
| 3 | 46449581 | A | G | CCRL2 |

| Chr | Position | ref | alt | Gene |
|---|---|---|---|---|
| 3 | 46450070 | T | A | CCRL2 |
| 3 | 46450072 | G | A | CCRL2 |
| 3 | 47618953 | C | A | CSPG5 |
| 3 | 47619025 | G | C | CSPG5 |
| 3 | 48461437 | G | A | PLXNB1 |
| 3 | 48461530 | G | A | PLXNB1 |
| 3 | 48463856 | G | A | PLXNB1 |
| 3 | 48691316 | T | C | CELSR3 |
| 3 | 48697654 | C | G | CELSR3 |
| 3 | 49832788 | G | A | CDHR4 |
| 3 | 49933240 | G | A | MST1R |
| 3 | 49933461 | C | T | MST1R |
| 3 | 49936102 | T | C | MST1R |
| 3 | 49936608 | T | C | MST1R |
| 3 | 49940078 | C | T | MST1R |
| 3 | 50513613 | C | T | CACNA2D2 |
| 3 | 51747288 | G | A | GRM2 |
| 3 | 52258319 | G | A | TLR9 |
| 3 | 52551973 | C | T | STAB1 |
| 3 | 53700459 | T | G | CACNA1D |
| 3 | 54420749 | T | G | CACNA2D3 |
| 3 | 54420752 | A | G | CACNA2D3 |
| 3 | 57138419 | G | A | IL17RD |
| 3 | 61975382 | T | C | PTPRG |
| 3 | 62189189 | G | A | PTPRG |
| 3 | 62189385 | A | G | PTPRG |
| 3 | 66434643 | T | C | LRIG1 |
| 3 | 66436546 | C | T | LRIG1 |
| 3 | 71803448 | CG<br>GC<br>CG<br>CG<br>GC<br>GG<br>G | C | GPR27 |
| 3 | 7494417 | A | T | GRM7 |
| 3 | 75986717 | G | A | ROBO2 |
| 3 | 75986741 | G | T | ROBO2 |
| 3 | 97726747 | T | A | GABRR3 |
| 3 | 97783335 | T | C | OR5AC1 |
| 3 | 97783823 | C | G | OR5AC1 |
| 3 | 97783851 | T | C | OR5AC1 |
| 3 | 97852083 | C | T | OR5H1 |
| 3 | 97868795 | A | G | OR5H14 |

Figure 23 (Continued)

| Chr | Position | ref | alt | Gene |
|---|---|---|---|---|
| 3 | 97888322 | T | TG | OR5H15 |
| 3 | 97888337 | C | T | OR5H15 |
| 3 | 97983231 | C | T | OR5H6 |
| 3 | 97983664 | C | T | OR5H6 |
| 3 | 97983699 | C | A | OR5H6 |
| 3 | 97983711 | T | C | OR5H6 |
| 3 | 97983723 | C | T | OR5H6 |
| 3 | 97983981 | G | A | OR5H6 |
| 3 | 98072715 | C | A | OR5K4 |
| 3 | 98109529 | C | T | OR5K3 |
| 3 | 98110287 | C | T | OR5K3 |
| 3 | 98217050 | C | A | OR5K2 |
| 3 | 98251211 | A | G | GPR15 |
| 3 | 98600385 | T | C | DCBLD2 |
| 3 | 9953258 | C | T | IL17RE |
| 3 | 9959410 | G | A | IL17RC |
| 3 | 9960070 | C | T | IL17RC |
| 3 | 9991101 | C | G | PRRT3 |
| 3 | 9991163 | A | G | PRRT3 |
| 3 | 9991388 | G | C | PRRT3 |
| 3 | 9991429 | G | A | PRRT3 |
| 4 | 101386643 | C | T | EMCN |
| 4 | 101401161 | TAAC | T | EMCN |
| 4 | 1018705 | C | A | FGFRL1 |
| 4 | 110864533 | C | T | EGF |
| 4 | 110883121 | G | A | EGF |
| 4 | 110901198 | G | A | EGF |
| 4 | 110902111 | A | T | EGF |
| 4 | 110908933 | T | C | EGF |
| 4 | 110914427 | A | T | EGF |
| 4 | 111398208 | A | G | ENPEP |
| 4 | 111409705 | T | C | ENPEP |
| 4 | 126241335 | C | G | FAT4 |
| 4 | 126371814 | C | T | FAT4 |
| 4 | 126372742 | G | A | FAT4 |
| 4 | 126373570 | C | T | FAT4 |
| 4 | 126373653 | A | G | FAT4 |
| 4 | 128842876 | C | G | MFSD8 |
| 4 | 142053488 | G | A | RNF150 |
| 4 | 142053711 | C | G | RNF150 |
| 4 | 144920596 | G | A | GYPB |
| 4 | 145041720 | A | G | GYPA |
| 4 | 154513627 | A | G | KIAA0922 |

| Chr | Position | ref | alt | Gene |
|---|---|---|---|---|
| 4 | 154514965 | T | C | KIAA0922 |
| 4 | 183601761 | G | A | TENM3 |
| 4 | 187524464 | G | A | FAT1 |
| 4 | 187531022 | A | G | FAT1 |
| 4 | 187539323 | C | T | FAT1 |
| 4 | 187540635 | T | G | FAT1 |
| 4 | 187542755 | T | C | FAT1 |
| 4 | 187542927 | T | C | FAT1 |
| 4 | 187549428 | C | T | FAT1 |
| 4 | 187557893 | T | C | FAT1 |
| 4 | 187627792 | T | C | FAT1 |
| 4 | 187629140 | G | C | FAT1 |
| 4 | 187629770 | A | C | FAT1 |
| 4 | 187630590 | G | A | FAT1 |
| 4 | 187630597 | C | G | FAT1 |
| 4 | 187630905 | C | T | FAT1 |
| 4 | 22404391 | G | A | GPR125 |
| 4 | 38776070 | C | T | TLR10 |
| 4 | 38776235 | A | G | TLR10 |
| 4 | 38776320 | C | T | TLR10 |
| 4 | 38776491 | T | G | TLR10 |
| 4 | 38776725 | C | A | TLR10 |
| 4 | 38799399 | G | T | TLR1 |
| 4 | 38799710 | T | C | TLR1 |
| 4 | 38800214 | C | G | TLR1 |
| 4 | 38800323 | A | G | TLR1 |
| 4 | 38829675 | C | T | TLR6 |
| 4 | 38829702 | C | T | TLR6 |
| 4 | 38829815 | A | G | TLR6 |
| 4 | 38830116 | C | T | TLR6 |
| 4 | 38830350 | A | G | TLR6 |
| 4 | 38830736 | A | G | TLR6 |
| 4 | 39000305 | A | G | TMEM156 |
| 4 | 39000475 | T | C | TMEM156 |
| 4 | 39448529 | G | A | KLB |
| 4 | 39448586 | C | T | KLB |
| 4 | 47663760 | T | G | CORIN |
| 4 | 47663799 | G | A | CORIN |
| 4 | 47667064 | T | C | CORIN |
| 4 | 47695024 | G | T | CORIN |
| 4 | 47945295 | C | T | CNGA1 |
| 4 | 53610402 | G | A | ERVMER34-1 |

Figure 23 (Continued)

| Chr | Position | ref | alt | Gene |
|---|---|---|---|---|
| 4 | 53611484 | C | T | ERVMER34-1 |
| 4 | 55133806 | G | A | PDGFRA |
| 4 | 55139771 | T | C | PDGFRA |
| 4 | 55972974 | T | A | KDR |
| 4 | 55979558 | C | T | KDR |
| 4 | 5690902 | T | C | EVC2 |
| 4 | 66467418 | A | C | EPHA5 |
| 4 | 66509085 | T | G | EPHA5 |
| 4 | 68784774 | T | C | TMPRSS11A |
| 4 | 68938185 | C | T | TMPRSS11F |
| 4 | 69094507 | T | A | TMPRSS11B |
| 4 | 69095197 | T | C | TMPRSS11B |
| 4 | 69337325 | C | G | TMPRSS11E |
| 4 | 69343287 | A | G | TMPRSS11E |
| 4 | 75695301 | G | A | BTC |
| 4 | 75937971 | C | T | PARM1 |
| 4 | 78987157 | A | G | FRAS1 |
| 4 | 79158715 | G | C | FRAS1 |
| 4 | 79166478 | A | T | FRAS1 |
| 4 | 79186200 | C | T | FRAS1 |
| 4 | 79186257 | T | C | FRAS1 |
| 4 | 79188027 | A | G | FRAS1 |
| 4 | 79188584 | C | T | FRAS1 |
| 4 | 79205699 | T | A | FRAS1 |
| 4 | 79284694 | C | T | FRAS1 |
| 4 | 79285146 | C | G | FRAS1 |
| 4 | 79300993 | G | A | FRAS1 |
| 4 | 79373353 | C | T | FRAS1 |
| 4 | 79373436 | G | A | FRAS1 |
| 4 | 79373499 | G | A | FRAS1 |
| 4 | 79387464 | A | G | FRAS1 |
| 4 | 79394702 | G | A | FRAS1 |
| 4 | 79434685 | T | G | FRAS1 |
| 4 | 79443837 | A | T | FRAS1 |
| 4 | 79443850 | G | A | FRAS1 |
| 4 | 79447763 | T | C | FRAS1 |
| 4 | 80977133 | G | A | ANTXR2 |
| 4 | 94006294 | T | G | GRID2 |
| 4 | 96171659 | T | G | UNC5C |
| 5 | 101724448 | G | C | SLCO6A1 |
| 5 | 101748741 | G | C | SLCO6A1 |
| 5 | 115811248 | G | T | SEMA6A |
| 5 | 115811273 | C | T | SEMA6A |

| Chr | Position | ref | alt | Gene |
|---|---|---|---|---|
| 5 | 1213668 | G | A | SLC6A19 |
| 5 | 1240749 | A | G | SLC6A18 |
| 5 | 1245997 | C | A | SLC6A18 |
| 5 | 126732256 | A | C | MEGF10 |
| 5 | 126732427 | G | A | MEGF10 |
| 5 | 131630568 | G | C | SLC22A4 |
| 5 | 131630571 | A | C | SLC22A4 |
| 5 | 131705926 | A | C | SLC22A5 |
| 5 | 133295334 | T | C | C5orf15 |
| 5 | 134343766 | T | G | CATSPER3 |
| 5 | 140166953 | A | G | PCDHA1 |
| 5 | 140167175 | T | C | PCDHA1 |
| 5 | 140174622 | G | A | PCDHA2 |
| 5 | 140174865 | G | C | PCDHA2 |
| 5 | 140186937 | G | T | PCDHA4 |
| 5 | 140187322 | C | T | PCDHA4 |
| 5 | 140187664 | A | G | PCDHA4 |
| 5 | 140188354 | C | G | PCDHA4 |
| 5 | 140221098 | C | G | PCDHA8 |
| 5 | 140221139 | G | A | PCDHA8 |
| 5 | 140229086 | C | G | PCDHA9 |
| 5 | 140229368 | G | C | PCDHA9 |
| 5 | 140229581 | G | C | PCDHA9 |
| 5 | 140229794 | G | C | PCDHA9 |
| 5 | 140230122 | G | A | PCDHA9 |
| 5 | 140474756 | G | A | PCDHB2 |
| 5 | 140480852 | G | A | PCDHB3 |
| 5 | 140481333 | T | G | PCDHB3 |
| 5 | 140481475 | A | T | PCDHB3 |
| 5 | 140481594 | T | C | PCDHB3 |
| 5 | 140482013 | G | A | PCDHB3 |
| 5 | 140502083 | A | G | PCDHB4 |
| 5 | 140502343 | C | T | PCDHB4 |
| 5 | 140502344 | C | T | PCDHB4 |
| 5 | 140502841 | G | A | PCDHB4 |
| 5 | 140503237 | A | G | PCDHB4 |
| 5 | 140503531 | C | T | PCDHB4 |
| 5 | 140515483 | T | C | PCDHB5 |
| 5 | 140516407 | G | A | PCDHB5 |
| 5 | 140530529 | G | A | PCDHB6 |
| 5 | 140531592 | C | T | PCDHB6 |
| 5 | 140531667 | T | C | PCDHB6 |
| 5 | 140531746 | C | G | PCDHB6 |
| 5 | 140562739 | G | A | PCDHB16 |

Figure 23 (Continued)

| Chr | Position | ref | alt | Gene |
|---|---|---|---|---|
| 5 | 140563173 | G | T | PCDHB16 |
| 5 | 140563656 | G | A | PCDHB16 |
| 5 | 140564048 | G | C | PCDHB16 |
| 5 | 140564088 | C | T | PCDHB16 |
| 5 | 140572763 | C | G | PCDHB10 |
| 5 | 140573754 | A | C | PCDHB10 |
| 5 | 140574079 | C | T | PCDHB10 |
| 5 | 140574103 | T | G | PCDHB10 |
| 5 | 140580931 | C | G | PCDHB11 |
| 5 | 140581076 | C | T | PCDHB11 |
| 5 | 140595625 | G | A | PCDHB13 |
| 5 | 140604419 | G | A | PCDHB14 |
| 5 | 140625897 | G | A | PCDHB15 |
| 5 | 140626566 | A | C | PCDHB15 |
| 5 | 140626627 | G | A | PCDHB15 |
| 5 | 140626855 | C | T | PCDHB15 |
| 5 | 140627020 | G | T | PCDHB15 |
| 5 | 140627184 | C | G | PCDHB15 |
| 5 | 140710705 | G | A | PCDHGA1 |
| 5 | 140710810 | G | A | PCDHGA1 |
| 5 | 140735215 | G | A | PCDHGA4 |
| 5 | 140736689 | G | A | PCDHGA4 |
| 5 | 140736814 | G | C | PCDHGA4 |
| 5 | 141244356 | C | T | PCDH1 |
| 5 | 141335498 | C | T | PCDH12 |
| 5 | 145895558 | G | A | GPR151 |
| 5 | 148206440 | G | A | ADRB2 |
| 5 | 148206473 | G | C | ADRB2 |
| 5 | 149450132 | T | C | CSF1R |
| 5 | 149509508 | G | A | PDGFRB |
| 5 | 150666907 | A | G | SLC36A3 |
| 5 | 150897236 | A | G | FAT2 |
| 5 | 150901261 | C | T | FAT2 |
| 5 | 150901613 | A | G | FAT2 |
| 5 | 150908812 | C | T | FAT2 |
| 5 | 150908813 | G | A | FAT2 |
| 5 | 150930186 | C | T | FAT2 |
| 5 | 150930345 | C | T | FAT2 |
| 5 | 150942969 | G | A | FAT2 |
| 5 | 150945483 | C | T | FAT2 |
| 5 | 150945518 | C | T | FAT2 |
| 5 | 150946436 | A | G | FAT2 |
| 5 | 150946773 | G | A | FAT2 |
| 5 | 150948147 | T | G | FAT2 |

| Chr | Position | ref | alt | Gene |
|---|---|---|---|---|
| 5 | 155935708 | G | A | SGCD |
| 5 | 156376703 | A | G | TIMD4 |
| 5 | 156378666 | G | A | TIMD4 |
| 5 | 156479426 | T | C | HAVCR1 |
| 5 | 156479443 | CTTG | C | HAVCR1 |
| 5 | 156479488 | G | A | HAVCR1 |
| 5 | 156479509 | A | G | HAVCR1 |
| 5 | 156531736 | C | A | HAVCR2 |
| 5 | 156887270 | C | T | NIPAL4 |
| 5 | 156918850 | C | T | ADAM19 |
| 5 | 156936364 | T | C | ADAM19 |
| 5 | 161116672 | C | T | GABRA6 |
| 5 | 161529571 | A | G | GABRG2 |
| 5 | 161529631 | G | T | GABRG2 |
| 5 | 167642193 | A | G | TENM2 |
| 5 | 169805866 | G | A | KCNMB1 |
| 5 | 169810796 | C | T | KCNMB1 |
| 5 | 175995711 | C | A | CDHR2 |
| 5 | 176002734 | G | A | CDHR2 |
| 5 | 176004476 | T | C | CDHR2 |
| 5 | 176011579 | T | C | CDHR2 |
| 5 | 176017455 | C | T | CDHR2 |
| 5 | 176517797 | C | T | FGFR4 |
| 5 | 177683377 | T | C | COL23A1 |
| 5 | 177683905 | G | A | COL23A1 |
| 5 | 177987740 | C | T | COL23A1 |
| 5 | 178409927 | G | A | GRM6 |
| 5 | 178421594 | G | T | GRM6 |
| 5 | 178421770 | T | G | GRM6 |
| 5 | 180049808 | T | C | FLT4 |
| 5 | 180057293 | T | C | FLT4 |
| 5 | 180058762 | G | T | FLT4 |
| 5 | 180166256 | C | T | OR2Y1 |
| 5 | 180338368 | A | G | BTNL8 |
| 5 | 180374523 | G | A | BTNL8 |
| 5 | 180420155 | T | C | BTNL3 |
| 5 | 180424423 | G | C | BTNL3 |
| 5 | 180477168 | T | G | BTNL9 |
| 5 | 180551775 | T | C | OR2V1 |
| 5 | 21765178 | A | G | CDH12 |
| 5 | 21817206 | T | C | CDH12 |
| 5 | 22078584 | C | T | CDH12 |
| 5 | 35084647 | T | C | PRLR |

Figure 23 (Continued)

| Chr | Position | ref | alt | Gene |
|---|---|---|---|---|
| 5 | 35861068 | T | C | IL7R |
| 5 | 35871190 | G | A | IL7R |
| 5 | 35965970 | A | C | UGT3A1 |
| 5 | 36677083 | G | C | SLC1A3 |
| 5 | 38486065 | C | T | LIFR |
| 5 | 38496637 | C | T | LIFR |
| 5 | 38527308 | G | A | LIFR |
| 5 | 38884071 | T | G | OSMR |
| 5 | 38921788 | G | A | OSMR |
| 5 | 52201722 | C | T | ITGA1 |
| 5 | 52214581 | G | A | ITGA1 |
| 5 | 52229745 | T | G | ITGA1 |
| 5 | 52240810 | A | G | ITGA1 |
| 5 | 52351838 | G | A | ITGA2 |
| 5 | 52358757 | G | A | ITGA2 |
| 5 | 55168132 | A | G | IL31RA |
| 5 | 55250727 | A | G | IL6ST |
| 5 | 55251931 | G | C | IL6ST |
| 5 | 55264153 | C | G | IL6ST |
| 5 | 66479383 | T | C | CD180 |
| 5 | 66480374 | G | C | CD180 |
| 5 | 66481777 | G | C | CD180 |
| 5 | 75591710 | C | G | SV2C |
| 5 | 75594743 | G | A | SV2C |
| 5 | 75913784 | T | C | F2RL2 |
| 5 | 89914925 | T | G | GPR98 |
| 5 | 89920969 | C | A | GPR98 |
| 5 | 89925169 | T | C | GPR98 |
| 5 | 89949754 | G | A | GPR98 |
| 5 | 89979518 | C | T | GPR98 |
| 5 | 89979589 | G | A | GPR98 |
| 5 | 89979698 | C | T | GPR98 |
| 5 | 89979750 | G | T | GPR98 |
| 5 | 89985882 | A | G | GPR98 |
| 5 | 89988504 | A | G | GPR98 |
| 5 | 89989802 | A | G | GPR98 |
| 5 | 89990324 | A | G | GPR98 |
| 5 | 90006849 | G | A | GPR98 |
| 5 | 90012379 | G | A | GPR98 |
| 5 | 90016871 | G | A | GPR98 |
| 5 | 90021035 | T | C | GPR98 |
| 5 | 90024735 | G | A | GPR98 |
| 5 | 90052289 | G | A | GPR98 |
| 5 | 90085654 | T | C | GPR98 |

| Chr | Position | ref | alt | Gene |
|---|---|---|---|---|
| 5 | 90107108 | A | G | GPR98 |
| 5 | 90119324 | G | A | GPR98 |
| 5 | 90151589 | G | A | GPR98 |
| 5 | 9050549 | T | C | SEMA5A |
| 5 | 96322360 | G | A | LNPEP |
| 5 | 96350710 | G | A | LNPEP |
| 5 | 96363459 | A | G | LNPEP |
| 5 | 99871518 | A | G | FAM174A |
| 6 | 10647272 | C | T | GCNT6 |
| 6 | 117130544 | A | C | GPRC6A |
| 6 | 117130704 | G | A | GPRC6A |
| 6 | 117150008 | G | A | GPRC6A |
| 6 | 117650532 | C | G | ROS1 |
| 6 | 117665231 | T | C | ROS1 |
| 6 | 117683821 | G | A | ROS1 |
| 6 | 117710661 | T | C | ROS1 |
| 6 | 117724379 | C | T | ROS1 |
| 6 | 117725448 | T | G | ROS1 |
| 6 | 117860508 | A | G | DCBLD1 |
| 6 | 132047245 | G | A | ENPP3 |
| 6 | 132061420 | G | A | ENPP3 |
| 6 | 132172368 | A | C | ENPP1 |
| 6 | 132206079 | C | T | ENPP1 |
| 6 | 132939217 | C | T | TAAR2 |
| 6 | 137338202 | T | C | IL20RA |
| 6 | 14131854 | A | G | CD83 |
| 6 | 142688969 | A | G | GPR126 |
| 6 | 142689042 | T | A | GPR126 |
| 6 | 142691549 | A | C | GPR126 |
| 6 | 150158558 | C | T | LRP11 |
| 6 | 150164259 | A | C | LRP11 |
| 6 | 150174278 | A | C | LRP11 |
| 6 | 150184601 | G | A | LRP11 |
| 6 | 150184684 | AG | A | LRP11 |
|   |   | CA |   |   |
|   |   | CG |   |   |
|   |   | GC |   |   |
|   |   | TG |   |   |
|   |   | CC |   |   |
|   |   | GG |   |   |
|   |   | GG |   |   |
|   |   | GC |   |   |
|   |   | GC |   |   |
|   |   | GG |   |   |

Figure 23 (Continued)

| Chr | Position | ref | alt | Gene |
|---|---|---|---|---|
|  |  | GG |  |  |
|  |  | CG |  |  |
|  |  | CC |  |  |
|  |  | GG |  |  |
| 6 | 150184882 | G | C | LRP11 |
| 6 | 150210681 | G | A | RAET1E |
| 6 | 150210685 | C | T | RAET1E |
| 6 | 150210723 | C | T | RAET1E |
| 6 | 150211071 | C | T | RAET1E |
| 6 | 150211123 | A | T | RAET1E |
| 6 | 150239484 | C | T | RAET1G |
| 6 | 150240829 | G | C | RAET1G |
| 6 | 154360569 | C | T | OPRM1 |
| 6 | 154360797 | A | G | OPRM1 |
| 6 | 160543148 | C | T | SLC22A1 |
| 6 | 166307718 | T | C | SDIM1 |
| 6 | 166307982 | C | T | SDIM1 |
| 6 | 170593037 | C | T | DLL1 |
| 6 | 24564540 | A | G | KIAA0319 |
| 6 | 24564544 | T | C | KIAA0319 |
| 6 | 24576631 | C | T | KIAA0319 |
| 6 | 24596433 | A | C | KIAA0319 |
| 6 | 24596478 | T | G | KIAA0319 |
| 6 | 26091179 | C | G | HFE |
| 6 | 26093141 | G | A | HFE |
| 6 | 26370630 | T | G | BTN3A2 |
| 6 | 26370657 | A | G | BTN3A2 |
| 6 | 26370660 | G | A | BTN3A2 |
| 6 | 26370748 | G | A | BTN3A2 |
| 6 | 26388405 | G | A | BTN2A2 |
| 6 | 26463574 | G | T | BTN2A1 |
| 6 | 26463575 | G | T | BTN2A1 |
| 6 | 26463660 | G | A | BTN2A1 |
| 6 | 26505362 | G | A | BTN1A1 |
| 6 | 27879551 | C | G | OR2B2 |
| 6 | 27925827 | A | G | OR2B6 |
| 6 | 29012712 | T | C | OR2W1 |
| 6 | 29068759 | C | A | OR2J1 |
| 6 | 29069264 | T | C | OR2J1 |
| 6 | 29069299 | C | T | OR2J1 |
| 6 | 29274486 | T | C | OR14J1 |
| 6 | 29323905 | A | C | OR5V1 |
| 6 | 29342775 | G | A | OR12D3 |
| 6 | 29364508 | T | C | OR12D2 |

| Chr | Position | ref | alt | Gene |
|---|---|---|---|---|
| 6 | 29364951 | G | A | OR12D2 |
| 6 | 29407800 | C | A | OR10C1 |
| 6 | 29408275 | C | A | OR10C1 |
| 6 | 29408313 | C | A | OR10C1 |
| 6 | 29455465 | G | A | MAS1L |
| 6 | 29600104 | G | A | GABBR1 |
| 6 | 29693011 | C | T | HLA-F |
| 6 | 29795913 | A | T | HLA-G |
| 6 | 29796376 | C | A | HLA-G |
| 6 | 29910557 | T | A | HLA-A |
| 6 | 29910566 | G | A | HLA-A |
| 6 | 29910660 | A | G | HLA-A |
| 6 | 29910688 | A | G | HLA-A |
| 6 | 29910693 | A | G | HLA-A |
| 6 | 29910698 | G | A | HLA-A |
| 6 | 29910721 | G | C | HLA-A |
| 6 | 29910750 | C | T | HLA-A |
| 6 | 29910761 | G | A | HLA-A |
| 6 | 29910767 | G | C | HLA-A |
| 6 | 29910801 | C | A | HLA-A |
| 6 | 29911064 | A | G | HLA-A |
| 6 | 29911086 | T | C | HLA-A |
| 6 | 29911092 | G | T | HLA-A |
| 6 | 29911098 | T | C | HLA-A |
| 6 | 29911198 | T | C | HLA-A |
| 6 | 29911207 | G | A | HLA-A |
| 6 | 29911218 | G | A | HLA-A |
| 6 | 29911222 | C | T | HLA-A |
| 6 | 29911271 | G | C | HLA-A |
| 6 | 29911296 | G | A | HLA-A |
| 6 | 29911306 | C | T | HLA-A |
| 6 | 29911970 | G | A | HLA-A |
| 6 | 29912028 | AG | A | HLA-A |
| 6 | 29912030 | G | C | HLA-A |
| 6 | 29912042 | G | A | HLA-A |
| 6 | 29912085 | C | T | HLA-A |
| 6 | 29912153 | A | G | HLA-A |
| 6 | 29912297 | A | G | HLA-A |
| 6 | 30458064 | G | A | HLA-E |
| 6 | 30459165 | C | T | HLA-E |
| 6 | 30916705 | A | G | DPCR1 |
| 6 | 30917212 | T | C | DPCR1 |
| 6 | 30917482 | C | T | DPCR1 |
| 6 | 30954245 | T | C | MUC21 |

Figure 23 (Continued)

| Chr | Position | ref | alt | Gene |
|---|---|---|---|---|
| 6 | 30954356 | C | T | MUC21 |
| 6 | 30954389 | GG GC TA GC AC AG CC AC CA AC TC TG AC TC CA GC AC AA CC | G | MUC21 |
| 6 | 30954559 | A | C | MUC21 |
| 6 | 30954560 | C | T | MUC21 |
| 6 | 30954684 | G | C | MUC21 |
| 6 | 30954909 | C | G | MUC21 |
| 6 | 30955010 | C | T | MUC21 |
| 6 | 30955247 | C | T | MUC21 |
| 6 | 30955250 | A | G | MUC21 |
| 6 | 30993377 | T | A | MUC22 |
| 6 | 30993440 | G | A | MUC22 |
| 6 | 30993494 | G | C | MUC22 |
| 6 | 30993533 | A | G | MUC22 |
| 6 | 30993590 | A | G | MUC22 |
| 6 | 30993719 | A | G | MUC22 |
| 6 | 30993776 | A | T | MUC22 |
| 6 | 30993813 | G | A | MUC22 |
| 6 | 30993866 | A | T | MUC22 |
| 6 | 30993880 | G | C | MUC22 |
| 6 | 30994022 | AC CA CA GG CT | A | MUC22 |
| 6 | 30994025 | A | G | MUC22 |
| 6 | 30994034 | GA GA | G | MUC22 |

| Chr | Position | ref | alt | Gene |
|---|---|---|---|---|
|  |  | CC AC TA CA AT CC TG AT TA |  |  |
| 6 | 30994059 | C | G | MUC22 |
| 6 | 30994248 | C | G | MUC22 |
| 6 | 30994253 | G | A | MUC22 |
| 6 | 30994259 | A | T | MUC22 |
| 6 | 30994283 | G | A | MUC22 |
| 6 | 30994412 | G | A | MUC22 |
| 6 | 30994431 | C | T | MUC22 |
| 6 | 30994470 | C | G | MUC22 |
| 6 | 30994532 | G | T | MUC22 |
| 6 | 30994617 | C | G | MUC22 |
| 6 | 30994635 | C | T | MUC22 |
| 6 | 30994730 | G | A | MUC22 |
| 6 | 30995114 | AC | A | MUC22 |
| 6 | 30995178 | C | T | MUC22 |
| 6 | 30995187 | T | C | MUC22 |
| 6 | 30995297 | A | G | MUC22 |
| 6 | 30995532 | T | C | MUC22 |
| 6 | 30995786 | A | G | MUC22 |
| 6 | 30995894 | A | T | MUC22 |
| 6 | 30996132 | C | T | MUC22 |
| 6 | 30996154 | TG AG AC CA CC AC AG CC TC TA CT GA AG GC TC C | T | MUC22 |

Figure 23 (Continued)

| Chr | Position | ref | alt | Gene |
|---|---|---|---|---|
| 6 | 30996314 | A | G | MUC22 |
| 6 | 30996354 | C | T | MUC22 |
| 6 | 30996487 | GACC | G | MUC22 |
| 6 | 30996509 | G | A | MUC22 |
| 6 | 30996699 | A | C | MUC22 |
| 6 | 30996959 | G | A | MUC22 |
| 6 | 30996981 | T | TCA | MUC22 |
| 6 | 30996984 | C | A | MUC22 |
| 6 | 30997334 | A | G | MUC22 |
| 6 | 30997352 | A | G | MUC22 |
| 6 | 30997517 | A | T | MUC22 |
| 6 | 30997692 | G | C | MUC22 |
| 6 | 30997824 | T | C | MUC22 |
| 6 | 30997877 | G | C | MUC22 |
| 6 | 30999997 | T | C | MUC22 |
| 6 | 31000005 | T | A | MUC22 |
| 6 | 31237862 | T | C | HLA-C |
| 6 | 31238002 | G | A | HLA-C |
| 6 | 31238027 | C | A | HLA-C |
| 6 | 31238053 | G | C | HLA-C |
| 6 | 31238068 | C | T | HLA-C |
| 6 | 31238155 | G | A | HLA-C |
| 6 | 31238232 | G | A | HLA-C |
| 6 | 31238868 | C | T | HLA-C |
| 6 | 31238880 | C | T | HLA-C |
| 6 | 31238886 | A | G | HLA-C |
| 6 | 31238925 | C | T | HLA-C |
| 6 | 31238970 | T | A | HLA-C |
| 6 | 31239006 | G | T | HLA-C |
| 6 | 31239060 | A | G | HLA-C |
| 6 | 31239116 | G | A | HLA-C |
| 6 | 31239407 | G | T | HLA-C |
| 6 | 31239417 | C | T | HLA-C |
| 6 | 31239430 | C | T | HLA-C |
| 6 | 31239449 | C | G | HLA-C |
| 6 | 31239501 | G | T | HLA-C |
| 6 | 31239543 | C | T | HLA-C |
| 6 | 31239585 | C | T | HLA-C |
| 6 | 31239607 | G | A | HLA-C |
| 6 | 31239616 | C | A | HLA-C |
| 6 | 31239630 | C | T | HLA-C |
| 6 | 31322980 | C | T | HLA-B |

| Chr | Position | ref | alt | Gene |
|---|---|---|---|---|
| 6 | 31323115 | T | C | HLA-B |
| 6 | 31323202 | T | C | HLA-B |
| 6 | 31323262 | G | A | HLA-B |
| 6 | 31323321 | G | A | HLA-B |
| 6 | 31323337 | T | C | HLA-B |
| 6 | 31323953 | C | G | HLA-B |
| 6 | 31323958 | T | G | HLA-B |
| 6 | 31323991 | C | G | HLA-B |
| 6 | 31324022 | TCC | T | HLA-B |
| 6 | 31324064 | T | A | HLA-B |
| 6 | 31324100 | G | T | HLA-B |
| 6 | 31324210 | G | A | HLA-B |
| 6 | 31324492 | GC | G | HLA-B |
| 6 | 31324506 | C | T | HLA-B |
| 6 | 31324524 | GCC | G | HLA-B |
| 6 | 31324542 | T | C | HLA-B |
| 6 | 31324549 | T | C | HLA-B |
| 6 | 31324552 | G | C | HLA-B |
| 6 | 31324580 | T | C | HLA-B |
| 6 | 31324582 | T | C | HLA-B |
| 6 | 31324599 | T | G | HLA-B |
| 6 | 31324615 | C | T | HLA-B |
| 6 | 31324641 | T | A | HLA-B |
| 6 | 31324647 | T | C | HLA-B |
| 6 | 31324674 | C | T | HLA-B |
| 6 | 31324702 | C | T | HLA-B |
| 6 | 31378388 | G | A | MICA |
| 6 | 31378864 | A | G | MICA |
| 6 | 31378932 | G | A | MICA |
| 6 | 31378956 | C | G | MICA |
| 6 | 31378977 | G | A | MICA |
| 6 | 31379043 | A | G | MICA |
| 6 | 31379109 | G | A | MICA |
| 6 | 31379115 | G | A | MICA |
| 6 | 31379134 | C | G | MICA |
| 6 | 31379795 | A | G | MICA |
| 6 | 31379807 | C | T | MICA |
| 6 | 31379817 | T | C | MICA |
| 6 | 31379823 | C | G | MICA |
| 6 | 31379931 | G | A | MICA |
| 6 | 31473546 | A | G | MICB |
| 6 | 31473561 | A | G | MICB |

Figure 23 (Continued)

| Chr | Position | ref | alt | Gene |
|---|---|---|---|---|
| 6 | 31473957 | C | G | MICB |
| 6 | 31474000 | G | A | MICB |
| 6 | 31474820 | C | T | MICB |
| 6 | 31475056 | G | A | MICB |
| 6 | 31836976 | G | A | SLC44A4 |
| 6 | 31839309 | C | T | SLC44A4 |
| 6 | 32178570 | C | T | NOTCH4 |
| 6 | 32185796 | C | T | NOTCH4 |
| 6 | 32188383 | T | C | NOTCH4 |
| 6 | 32188640 | T | C | NOTCH4 |
| 6 | 32188823 | G | A | NOTCH4 |
| 6 | 32188943 | G | A | NOTCH4 |
| 6 | 32190390 | T | G | NOTCH4 |
| 6 | 32362703 | G | T | BTNL2 |
| 6 | 32362741 | C | T | BTNL2 |
| 6 | 32362745 | G | A | BTNL2 |
| 6 | 32363816 | T | C | BTNL2 |
| 6 | 32363888 | C | T | BTNL2 |
| 6 | 32364011 | T | C | BTNL2 |
| 6 | 32364046 | T | A | BTNL2 |
| 6 | 32370816 | G | A | BTNL2 |
| 6 | 32370835 | T | C | BTNL2 |
| 6 | 32370879 | C | T | BTNL2 |
| 6 | 32370927 | G | A | BTNL2 |
| 6 | 32370969 | TG | T | BTNL2 |
| 6 | 32370975 | C | T | BTNL2 |
| 6 | 32370993 | C | T | BTNL2 |
| 6 | 32372863 | A | T | BTNL2 |
| 6 | 32487165 | G | C | HLA-DRB5 |
| 6 | 32487170 | G | A | HLA-DRB5 |
| 6 | 32487215 | C | T | HLA-DRB5 |
| 6 | 32487242 | G | A | HLA-DRB5 |
| 6 | 32487294 | C | T | HLA-DRB5 |
| 6 | 32487309 | T | C | HLA-DRB5 |
| 6 | 32487353 | T | C | HLA-DRB5 |
| 6 | 32487398 | C | T | HLA-DRB5 |
| 6 | 32487402 | C | A | HLA-DRB5 |
| 6 | 32489708 | C | A | HLA-DRB5 |
| 6 | 32489711 | A | G | HLA-DRB5 |
| 6 | 32489732 | T | A | HLA-DRB5 |
| 6 | 32489733 | A | C | HLA-DRB5 |
| 6 | 32489735 | G | T | HLA-DRB5 |
| 6 | 32489786 | T | G | HLA-DRB5 |
| 6 | 32489792 | G | T | HLA-DRB5 |

| Chr | Position | ref | alt | Gene |
|---|---|---|---|---|
| 6 | 32489796 | C | T | HLA-DRB5 |
| 6 | 32489813 | G | C | HLA-DRB5 |
| 6 | 32489825 | T | A | HLA-DRB5 |
| 6 | 32489888 | A | T | HLA-DRB5 |
| 6 | 32489919 | G | A | HLA-DRB5 |
| 6 | 32489949 | G | A | HLA-DRB5 |
| 6 | 32497914 | C | T | HLA-DRB5 |
| 6 | 32548628 | G | A | HLA-DRB1 |
| 6 | 32548632 | T | A | HLA-DRB1 |
| 6 | 32549340 | C | G | HLA-DRB1 |
| 6 | 32549357 | G | A | HLA-DRB1 |
| 6 | 32549424 | C | T | HLA-DRB1 |
| 6 | 32549475 | T | C | HLA-DRB1 |
| 6 | 32549481 | C | T | HLA-DRB1 |
| 6 | 32549520 | T | C | HLA-DRB1 |
| 6 | 32549525 | C | G | HLA-DRB1 |
| 6 | 32549531 | T | C | HLA-DRB1 |
| 6 | 32549540 | C | T | HLA-DRB1 |
| 6 | 32549579 | TG | T | HLA-DRB1 |
| 6 | 32549588 | G | A | HLA-DRB1 |
| 6 | 32549589 | A | C | HLA-DRB1 |
| 6 | 32551886 | C | T | HLA-DRB1 |
| 6 | 32551915 | A | G | HLA-DRB1 |
| 6 | 32551939 | G | T | HLA-DRB1 |
| 6 | 32551990 | T | G | HLA-DRB1 |
| 6 | 32551996 | G | T | HLA-DRB1 |
| 6 | 32552000 | C | T | HLA-DRB1 |
| 6 | 32552029 | A | T | HLA-DRB1 |
| 6 | 32552048 | C | T | HLA-DRB1 |
| 6 | 32552075 | A | G | HLA-DRB1 |
| 6 | 32552092 | A | T | HLA-DRB1 |
| 6 | 32552123 | G | A | HLA-DRB1 |
| 6 | 32552143 | C | T | HLA-DRB1 |
| 6 | 32552146 | AG | A | HLA-DRB1 |
| 6 | 32605309 | A | G | HLA-DQA1 |
| 6 | 32609105 | G | A | HLA-DQA1 |
| 6 | 32609126 | T | C | HLA-DQA1 |
| 6 | 32609147 | A | T | HLA-DQA1 |
| 6 | 32609150 | C | G | HLA-DQA1 |
| 6 | 32609173 | C | G | HLA-DQA1 |
| 6 | 32609192 | A | G | HLA-DQA1 |
| 6 | 32609195 | G | A | HLA-DQA1 |
| 6 | 32609207 | C | T | HLA-DQA1 |
| 6 | 32609213 | G | A | HLA-DQA1 |

Figure 23 (Continued)

| Chr | Position | ref | alt | Gene |
|---|---|---|---|---|
| 6 | 32609216 | G | T | HLA-DQA1 |
| 6 | 32609220 | TGA | T | HLA-DQA1 |
| 6 | 32609221 | G | C | HLA-DQA1 |
| 6 | 32609222 | A | T | HLA-DQA1 |
| 6 | 32609224 | T | TTC | HLA-DQA1 |
| 6 | 32609229 | C | A | HLA-DQA1 |
| 6 | 32609231 | A | G | HLA-DQA1 |
| 6 | 32609238 | AGGT | A | HLA-DQA1 |
| 6 | 32609239 | G | A | HLA-DQA1 |
| 6 | 32609254 | G | T | HLA-DQA1 |
| 6 | 32609255 | G | T | HLA-DQA1 |
| 6 | 32609264 | G | C | HLA-DQA1 |
| 6 | 32609276 | TGG | T | HLA-DQA1 |
| 6 | 32609806 | C | T | HLA-DQA1 |
| 6 | 32609874 | T | G | HLA-DQA1 |
| 6 | 32609952 | T | C | HLA-DQA1 |
| 6 | 32609964 | G | T | HLA-DQA1 |
| 6 | 32609965 | C | A | HLA-DQA1 |
| 6 | 32609969 | T | G | HLA-DQA1 |
| 6 | 32609974 | T | G | HLA-DQA1 |
| 6 | 32610401 | G | A | HLA-DQA1 |
| 6 | 32629755 | G | A | HLA-DQB1 |
| 6 | 32629764 | C | T | HLA-DQB1 |
| 6 | 32629891 | C | T | HLA-DQB1 |
| 6 | 32629905 | T | C | HLA-DQB1 |
| 6 | 32629920 | C | T | HLA-DQB1 |
| 6 | 32629931 | C | G | HLA-DQB1 |
| 6 | 32629935 | C | G | HLA-DQB1 |
| 6 | 32629936 | C | T | HLA-DQB1 |
| 6 | 32629963 | C | T | HLA-DQB1 |
| 6 | 32632593 | C | T | HLA-DQB1 |
| 6 | 32632599 | A | G | HLA-DQB1 |
| 6 | 32632605 | C | A | HLA-DQB1 |
| 6 | 32632608 | C | G | HLA-DQB1 |
| 6 | 32632650 | C | T | HLA-DQB1 |
| 6 | 32632659 | C | T | HLA-DQB1 |
| 6 | 32632660 | T | G | HLA-DQB1 |
| 6 | 32632700 | T | A | HLA-DQB1 |
| 6 | 32632703 | G | A | HLA-DQB1 |
| 6 | 32632721 | A | T | HLA-DQB1 |

| Chr | Position | ref | alt | Gene |
|---|---|---|---|---|
| 6 | 32632724 | C | T | HLA-DQB1 |
| 6 | 32632745 | G | A | HLA-DQB1 |
| 6 | 32632748 | T | A | HLA-DQB1 |
| 6 | 32632769 | T | C | HLA-DQB1 |
| 6 | 32632775 | G | C | HLA-DQB1 |
| 6 | 32632790 | C | A | HLA-DQB1 |
| 6 | 32632818 | T | G | HLA-DQB1 |
| 6 | 32632832 | A | T | HLA-DQB1 |
| 6 | 32634282 | A | G | HLA-DQB1 |
| 6 | 32713784 | C | A | HLA-DQA2 |
| 6 | 32726753 | G | A | HLA-DQB2 |
| 6 | 32726788 | T | C | HLA-DQB2 |
| 6 | 32726803 | C | T | HLA-DQB2 |
| 6 | 33036853 | A | C | HLA-DPA1 |
| 6 | 33036951 | A | G | HLA-DPA1 |
| 6 | 33036999 | T | C | HLA-DPA1 |
| 6 | 33037424 | T | C | HLA-DPA1 |
| 6 | 33037474 | A | G | HLA-DPA1 |
| 6 | 33037522 | T | C | HLA-DPA1 |
| 6 | 33037579 | A | T | HLA-DPA1 |
| 6 | 33037580 | T | G | HLA-DPA1 |
| 6 | 33037639 | G | A | HLA-DPA1 |
| 6 | 33037640 | C | T | HLA-DPA1 |
| 6 | 33053577 | G | A | HLA-DPB1 |
| 6 | 33659472 | C | G | ITPR3 |
| 6 | 39033595 | G | A | GLP1R |
| 6 | 40400288 | C | T | LRFN2 |
| 6 | 41119109 | CTCT | C | TREML1 |
| 6 | 41162518 | T | C | TREML2 |
| 6 | 41162562 | G | C | TREML2 |
| 6 | 41166021 | C | T | TREML2 |
| 6 | 41166149 | A | G | TREML2 |
| 6 | 41166154 | G | C | TREML2 |
| 6 | 41250466 | T | A | TREM1 |
| 6 | 41303995 | A | G | NCR2 |
| 6 | 41309552 | T | C | NCR2 |
| 6 | 42891022 | G | A | PTCRA |
| 6 | 46108083 | A | G | ENPP4 |
| 6 | 46801071 | G | T | MEP1A |
| 6 | 46801092 | A | G | MEP1A |
| 6 | 46803018 | A | T | MEP1A |
| 6 | 46803102 | A | G | MEP1A |
| 6 | 46827073 | A | G | GPR116 |

Figure 23 (Continued)

| Chr | Position | ref | alt | Gene |
|---|---|---|---|---|
| 6 | 46827239 | C | T | GPR116 |
| 6 | 46834685 | G | A | GPR116 |
| 6 | 46977458 | T | C | GPR110 |
| 6 | 46977783 | C | T | GPR110 |
| 6 | 47624239 | A | G | GPR111 |
| 6 | 47624299 | A | G | GPR111 |
| 6 | 47626833 | C | A | GPR111 |
| 6 | 47646748 | T | C | GPR111 |
| 6 | 47646842 | A | G | GPR111 |
| 6 | 47649265 | T | A | GPR111 |
| 6 | 47649574 | A | G | GPR111 |
| 6 | 51497519 | C | T | PKHD1 |
| 6 | 51612837 | C | T | PKHD1 |
| 6 | 51777251 | G | A | PKHD1 |
| 6 | 51875250 | A | C | PKHD1 |
| 6 | 51890823 | G | A | PKHD1 |
| 6 | 51910905 | T | C | PKHD1 |
| 6 | 51914956 | G | A | PKHD1 |
| 6 | 51920465 | A | C | PKHD1 |
| 6 | 55196587 | C | T | GFRAL |
| 6 | 69349073 | A | G | BAI3 |
| 6 | 69666684 | A | G | BAI3 |
| 6 | 70407465 | A | T | LMBRD1 |
| 6 | 87994504 | C | T | GJB7 |
| 6 | 89926962 | T | C | GABRR1 |
| 6 | 89926966 | T | C | GABRR1 |
| 6 | 94120219 | G | A | EPHA7 |
| 6 | 94120639 | T | C | EPHA7 |
| 6 | 97247547 | C | T | GPR63 |
| 7 | 100218631 | C | T | TFR2 |
| 7 | 100230864 | G | C | TFR2 |
| 7 | 100350763 | T | G | ZAN |
| 7 | 100353013 | TACA | T | ZAN |
| 7 | 100361675 | G | A | ZAN |
| 7 | 100361819 | C | T | ZAN |
| 7 | 100366284 | T | C | ZAN |
| 7 | 100367573 | T | C | ZAN |
| 7 | 100371114 | C | T | ZAN |
| 7 | 100371358 | G | A | ZAN |
| 7 | 100371417 | G | A | ZAN |
| 7 | 100371474 | G | A | ZAN |
| 7 | 100373077 | C | G | ZAN |
| 7 | 100373367 | G | C | ZAN |

| Chr | Position | ref | alt | Gene |
|---|---|---|---|---|
| 7 | 100374087 | A | G | ZAN |
| 7 | 100377082 | T | C | ZAN |
| 7 | 100377138 | A | AGGGC | ZAN |
| 7 | 100377364 | G | A | ZAN |
| 7 | 100385532 | A | C | ZAN |
| 7 | 100385578 | G | C | ZAN |
| 7 | 100385714 | G | A | ZAN |
| 7 | 100386900 | T | C | ZAN |
| 7 | 100389590 | C | T | ZAN |
| 7 | 100395003 | G | C | ZAN |
| 7 | 100612952 | G | A | MUC12 |
| 7 | 100612955 | A | ACTG | MUC12 |
| 7 | 100612961 | G | C | MUC12 |
| 7 | 100634356 | G | A | MUC12 |
| 7 | 100634358 | C | T | MUC12 |
| 7 | 100634821 | A | G | MUC12 |
| 7 | 100634838 | C | A | MUC12 |
| 7 | 100634877 | C | T | MUC12 |
| 7 | 100634892 | G | A | MUC12 |
| 7 | 100634933 | G | C | MUC12 |
| 7 | 100634964 | C | A | MUC12 |
| 7 | 100635205 | C | T | MUC12 |
| 7 | 100635375 | A | C | MUC12 |
| 7 | 100635535 | C | T | MUC12 |
| 7 | 100635661 | T | C | MUC12 |
| 7 | 100635679 | C | G | MUC12 |
| 7 | 100635767 | G | C | MUC12 |
| 7 | 100636147 | C | T | MUC12 |
| 7 | 100636383 | G | A | MUC12 |
| 7 | 100636408 | G | A | MUC12 |
| 7 | 100636446 | G | A | MUC12 |
| 7 | 100636447 | A | G | MUC12 |
| 7 | 100636461 | C | A | MUC12 |
| 7 | 100636551 | C | T | MUC12 |
| 7 | 100636584 | T | C | MUC12 |
| 7 | 100637008 | C | A | MUC12 |
| 7 | 100637035 | A | C | MUC12 |
| 7 | 100637193 | C | A | MUC12 |
| 7 | 100637547 | G | A | MUC12 |
| 7 | 100637556 | G | A | MUC12 |
| 7 | 100637605 | A | C | MUC12 |

Figure 23 (Continued)

| Chr | Position | ref | alt | Gene |
|---|---|---|---|---|
| 7 | 100637839 | C | G | MUC12 |
| 7 | 100637887 | A | G | MUC12 |
| 7 | 100638135 | G | A | MUC12 |
| 7 | 100638279 | T | C | MUC12 |
| 7 | 100638444 | G | A | MUC12 |
| 7 | 100638484 | A | T | MUC12 |
| 7 | 100638828 | C | T | MUC12 |
| 7 | 100638856 | A | G | MUC12 |
| 7 | 100639012 | C | T | MUC12 |
| 7 | 100639054 | G | A | MUC12 |
| 7 | 100639066 | C | T | MUC12 |
| 7 | 100639147 | A | G | MUC12 |
| 7 | 100639153 | C | T | MUC12 |
| 7 | 100639177 | C | T | MUC12 |
| 7 | 100639203 | A | C | MUC12 |
| 7 | 100639632 | G | A | MUC12 |
| 7 | 100639708 | C | T | MUC12 |
| 7 | 100641130 | C | T | MUC12 |
| 7 | 100641631 | C | T | MUC12 |
| 7 | 100641744 | C | T | MUC12 |
| 7 | 100641745 | G | A | MUC12 |
| 7 | 100641798 | C | G | MUC12 |
| 7 | 100641913 | G | A | MUC12 |
| 7 | 100641922 | C | G | MUC12 |
| 7 | 100642455 | G | A | MUC12 |
| 7 | 100642924 | G | A | MUC12 |
| 7 | 100642986 | G | A | MUC12 |
| 7 | 100643073 | C | A | MUC12 |
| 7 | 100643080 | C | T | MUC12 |
| 7 | 100643088 | A | G | MUC12 |
| 7 | 100643104 | C | T | MUC12 |
| 7 | 100643155 | A | T | MUC12 |
| 7 | 100643490 | G | T | MUC12 |
| 7 | 100643638 | C | G | MUC12 |
| 7 | 100643832 | C | G | MUC12 |
| 7 | 100644027 | C | A | MUC12 |
| 7 | 100644059 | G | C | MUC12 |
| 7 | 100644082 | G | A | MUC12 |
| 7 | 100644089 | C | A | MUC12 |
| 7 | 100644090 | G | A | MUC12 |
| 7 | 100644167 | T | G | MUC12 |
| 7 | 100644184 | C | T | MUC12 |
| 7 | 100644303 | G | A | MUC12 |
| 7 | 100644660 | G | A | MUC12 |

| Chr | Position | ref | alt | Gene |
|---|---|---|---|---|
| 7 | 100644772 | C | T | MUC12 |
| 7 | 100644793 | C | T | MUC12 |
| 7 | 100645453 | C | T | MUC12 |
| 7 | 100645525 | A | C | MUC12 |
| 7 | 100645569 | T | A | MUC12 |
| 7 | 100645825 | C | A | MUC12 |
| 7 | 100646199 | T | C | MUC12 |
| 7 | 100646322 | C | A | MUC12 |
| 7 | 100646364 | G | A | MUC12 |
| 7 | 100646676 | A | G | MUC12 |
| 7 | 100646712 | A | C | MUC12 |
| 7 | 100647276 | C | A | MUC12 |
| 7 | 100647338 | C | A | MUC12 |
| 7 | 100647339 | G | A | MUC12 |
| 7 | 100647553 | G | A | MUC12 |
| 7 | 100647565 | C | T | MUC12 |
| 7 | 100647646 | A | G | MUC12 |
| 7 | 100647652 | C | T | MUC12 |
| 7 | 100647702 | A | C | MUC12 |
| 7 | 100647819 | C | T | MUC12 |
| 7 | 100648029 | G | A | MUC12 |
| 7 | 100648117 | C | G | MUC12 |
| 7 | 100648476 | T | C | MUC12 |
| 7 | 100675128 | G | A | MUC17 |
| 7 | 100675376 | A | C | MUC17 |
| 7 | 100675512 | G | A | MUC17 |
| 7 | 100675976 | G | A | MUC17 |
| 7 | 100676409 | C | T | MUC17 |
| 7 | 100677279 | G | C | MUC17 |
| 7 | 100677285 | G | A | MUC17 |
| 7 | 100677333 | C | G | MUC17 |
| 7 | 100677405 | G | A | MUC17 |
| 7 | 100677429 | G | A | MUC17 |
| 7 | 100677455 | G | A | MUC17 |
| 7 | 100677516 | A | G | MUC17 |
| 7 | 100677523 | A | C | MUC17 |
| 7 | 100677572 | A | G | MUC17 |
| 7 | 100677630 | C | T | MUC17 |
| 7 | 100677642 | C | T | MUC17 |
| 7 | 100677645 | C | A | MUC17 |
| 7 | 100677704 | C | T | MUC17 |
| 7 | 100677710 | A | G | MUC17 |
| 7 | 100677714 | C | T | MUC17 |
| 7 | 100677816 | G | A | MUC17 |

Figure 23 (Continued)

| Chr | Position | ref | alt | Gene |
|---|---|---|---|---|
| 7 | 100677944 | T | C | MUC17 |
| 7 | 100677974 | A | G | MUC17 |
| 7 | 100677995 | A | G | MUC17 |
| 7 | 100678013 | G | A | MUC17 |
| 7 | 100678029 | G | C | MUC17 |
| 7 | 100678032 | T | C | MUC17 |
| 7 | 100678173 | C | T | MUC17 |
| 7 | 100678370 | C | T | MUC17 |
| 7 | 100678421 | T | A | MUC17 |
| 7 | 100678433 | A | T | MUC17 |
| 7 | 100678434 | C | A | MUC17 |
| 7 | 100678464 | C | T | MUC17 |
| 7 | 100678481 | A | T | MUC17 |
| 7 | 100678527 | G | T | MUC17 |
| 7 | 100678568 | A | T | MUC17 |
| 7 | 100678610 | A | T | MUC17 |
| 7 | 100678616 | G | A | MUC17 |
| 7 | 100678622 | G | A | MUC17 |
| 7 | 100678740 | T | C | MUC17 |
| 7 | 100679136 | T | C | MUC17 |
| 7 | 100679316 | T | A | MUC17 |
| 7 | 100679318 | A | C | MUC17 |
| 7 | 100679366 | A | G | MUC17 |
| 7 | 100679388 | A | C | MUC17 |
| 7 | 100679390 | A | G | MUC17 |
| 7 | 100679550 | G | A | MUC17 |
| 7 | 100679754 | C | G | MUC17 |
| 7 | 100679760 | G | A | MUC17 |
| 7 | 100680132 | G | A | MUC17 |
| 7 | 100680137 | C | T | MUC17 |
| 7 | 100680256 | A | C | MUC17 |
| 7 | 100680268 | A | G | MUC17 |
| 7 | 100680269 | G | C | MUC17 |
| 7 | 100680286 | T | G | MUC17 |
| 7 | 100680521 | G | A | MUC17 |
| 7 | 100680761 | G | A | MUC17 |
| 7 | 100680939 | C | A | MUC17 |
| 7 | 100680983 | G | A | MUC17 |
| 7 | 100681172 | A | G | MUC17 |
| 7 | 100681751 | A | G | MUC17 |
| 7 | 100683036 | T | C | MUC17 |
| 7 | 100683050 | T | G | MUC17 |
| 7 | 100683053 | A | G | MUC17 |
| 7 | 100683864 | C | T | MUC17 |

| Chr | Position | ref | alt | Gene |
|---|---|---|---|---|
| 7 | 100684593 | G | A | MUC17 |
| 7 | 100686491 | G | C | MUC17 |
| 7 | 100686777 | C | T | MUC17 |
| 7 | 100695138 | G | A | MUC17 |
| 7 | 105615406 | G | A | CDHR3 |
| 7 | 105615426 | G | C | CDHR3 |
| 7 | 105658451 | G | A | CDHR3 |
| 7 | 110762920 | G | A | LRRN3 |
| 7 | 11500372 | C | T | THSD7A |
| 7 | 11581121 | T | C | THSD7A |
| 7 | 116340262 | A | G | MET |
| 7 | 11676065 | G | C | THSD7A |
| 7 | 11871406 | G | C | THSD7A |
| 7 | 121653250 | G | A | PTPRZ1 |
| 7 | 121653398 | G | A | PTPRZ1 |
| 7 | 122635173 | A | C | TAS2R16 |
| 7 | 123514896 | G | T | HYAL4 |
| 7 | 126173902 | G | C | GRM8 |
| 7 | 126542667 | A | T | GRM8 |
| 7 | 128843396 | G | A | SMO |
| 7 | 131191476 | C | T | PODXL |
| 7 | 131193739 | C | T | PODXL |
| 7 | 131194255 | G | C | PODXL |
| 7 | 131195712 | G | A | PODXL |
| 7 | 131195959 | C | T | PODXL |
| 7 | 132193371 | G | A | PLXNA4 |
| 7 | 138486096 | G | C | TMEM213 |
| 7 | 141478308 | T | C | TAS2R4 |
| 7 | 141478800 | G | A | TAS2R4 |
| 7 | 142563253 | T | G | EPHB6 |
| 7 | 142749439 | T | C | OR6V1 |
| 7 | 142749919 | G | A | OR6V1 |
| 7 | 142749928 | T | C | OR6V1 |
| 7 | 142750243 | G | A | OR6V1 |
| 7 | 142919731 | C | A | TAS2R40 |
| 7 | 143097100 | A | G | EPHA1 |
| 7 | 143632618 | C | T | OR2F2 |
| 7 | 143632833 | A | G | OR2F2 |
| 7 | 143771557 | T | C | OR2A25 |
| 7 | 143792991 | G | A | OR2A12 |
| 7 | 143806688 | C | A | OR2A2 |
| 7 | 143826697 | C | G | OR2A14 |
| 7 | 143826729 | ACTT | A | OR2A14 |

Figure 23 (Continued)

| Chr | Position | ref | alt | Gene |
|---|---|---|---|---|
| 7 | 143929434 | G | C | OR2A42 |
| 7 | 143956181 | A | C | OR2A7 |
| 7 | 147183121 | A | C | CNTNAP2 |
| 7 | 147674989 | A | C | CNTNAP2 |
| 7 | 147926842 | A | C | CNTNAP2 |
| 7 | 154684153 | T | C | DPP6 |
| 7 | 157931091 | C | T | PTPRN2 |
| 7 | 157931144 | C | T | PTPRN2 |
| 7 | 157931151 | C | G | PTPRN2 |
| 7 | 157959794 | T | C | PTPRN2 |
| 7 | 157959895 | C | T | PTPRN2 |
| 7 | 157959911 | A | G | PTPRN2 |
| 7 | 157959965 | C | T | PTPRN2 |
| 7 | 157985149 | C | G | PTPRN2 |
| 7 | 23300255 | C | T | GPNMB |
| 7 | 23300345 | C | T | GPNMB |
| 7 | 2692639 | A | G | TTYH3 |
| 7 | 30915263 | A | G | AQP1 |
| 7 | 31008686 | G | A | GHRHR |
| 7 | 31009576 | G | T | GHRHR |
| 7 | 34818113 | A | T | NPSR1 |
| 7 | 44578836 | T | C | NPC1L1 |
| 7 | 45216926 | G | A | RAMP3 |
| 7 | 45217015 | T | C | RAMP3 |
| 7 | 47840310 | C | G | PKD1L1 |
| 7 | 47840387 | C | T | PKD1L1 |
| 7 | 47847865 | G | A | PKD1L1 |
| 7 | 47851623 | C | T | PKD1L1 |
| 7 | 47852837 | C | T | PKD1L1 |
| 7 | 47886583 | T | C | PKD1L1 |
| 7 | 47913579 | T | C | PKD1L1 |
| 7 | 47925525 | G | T | PKD1L1 |
| 7 | 47927650 | G | A | PKD1L1 |
| 7 | 47927744 | C | T | PKD1L1 |
| 7 | 47930180 | T | C | PKD1L1 |
| 7 | 47933494 | C | T | PKD1L1 |
| 7 | 47968927 | C | A | PKD1L1 |
| 7 | 5327517 | A | C | SLC29A4 |
| 7 | 55229255 | G | A | EGFR |
| 7 | 76054372 | G | A | ZP3 |
| 7 | 76069811 | T | C | ZP3 |
| 7 | 76069881 | A | G | ZP3 |
| 7 | 76069886 | A | G | ZP3 |
| 7 | 76069902 | G | C | ZP3 |

| Chr | Position | ref | alt | Gene |
|---|---|---|---|---|
| 7 | 76071228 | A | G | ZP3 |
| 7 | 80300449 | T | G | CD36 |
| 7 | 86539251 | A | C | KIAA1324L |
| 7 | 86539302 | G | C | KIAA1324L |
| 7 | 92098776 | C | T | ERVW-1 |
| 7 | 92099196 | A | G | ERVW-1 |
| 7 | 99473858 | G | C | OR2AE1 |
| 7 | 99526754 | G | A | GJC3 |
| 7 | 99971849 | A | G | PILRA |
| 8 | 10390452 | C | T | PRSS55 |
| 8 | 10396056 | G | C | PRSS55 |
| 8 | 10411495 | T | C | PRSS55 |
| 8 | 10411512 | TG | T | PRSS55 |
| 8 | 104312432 | A | G | FZD6 |
| 8 | 104336788 | C | G | FZD6 |
| 8 | 105361354 | G | C | DCSTAMP |
| 8 | 105367121 | A | G | DCSTAMP |
| 8 | 110397780 | A | G | PKHD1L1 |
| 8 | 110406671 | T | A | PKHD1L1 |
| 8 | 110413762 | T | C | PKHD1L1 |
| 8 | 110437443 | T | C | PKHD1L1 |
| 8 | 110441582 | A | G | PKHD1L1 |
| 8 | 110448635 | A | G | PKHD1L1 |
| 8 | 110455184 | C | T | PKHD1L1 |
| 8 | 110455187 | A | T | PKHD1L1 |
| 8 | 110455321 | C | A | PKHD1L1 |
| 8 | 110457011 | A | G | PKHD1L1 |
| 8 | 110460488 | G | T | PKHD1L1 |
| 8 | 110476776 | G | A | PKHD1L1 |
| 8 | 110492279 | G | A | PKHD1L1 |
| 8 | 110495303 | T | C | PKHD1L1 |
| 8 | 110504218 | A | G | PKHD1L1 |
| 8 | 110510993 | C | A | PKHD1L1 |
| 8 | 110523026 | T | G | PKHD1L1 |
| 8 | 110527429 | C | T | PKHD1L1 |
| 8 | 113241088 | T | G | CSMD3 |
| 8 | 113299353 | A | G | CSMD3 |
| 8 | 114186003 | T | C | CSMD3 |
| 8 | 116725 | T | G | OR4F21 |
| 8 | 145640235 | C | T | SLC39A4 |
| 8 | 145640411 | A | G | SLC39A4 |
| 8 | 145641328 | C | T | SLC39A4 |
| 8 | 145641417 | G | A | SLC39A4 |
| 8 | 145642002 | C | T | SLC39A4 |

Figure 23 (Continued)

| Chr | Position | ref | alt | Gene |
|---|---|---|---|---|
| 8 | 22262321 | T | C | SLC39A14 |
| 8 | 22886020 | A | G | TNFRSF10B |
| 8 | 22900701 | G | A | TNFRSF10B |
| 8 | 23058220 | T | G | TNFRSF10A |
| 8 | 23059324 | C | G | TNFRSF10A |
| 8 | 23060256 | T | C | TNFRSF10A |
| 8 | 23082369 | C | G | TNFRSF10A |
| 8 | 23082477 | G | A | TNFRSF10A |
| 8 | 24178738 | G | T | ADAM28 |
| 8 | 24199218 | C | A | ADAM28 |
| 8 | 24339679 | G | A | ADAM7 |
| 8 | 24356818 | A | C | ADAM7 |
| 8 | 27324822 | T | C | CHRNA2 |
| 8 | 27516955 | G | A | SCARA3 |
| 8 | 27528446 | T | C | SCARA3 |
| 8 | 27729527 | C | T | SCARA5 |
| 8 | 27767231 | C | G | SCARA5 |
| 8 | 27779093 | G | A | SCARA5 |
| 8 | 27779612 | G | A | SCARA5 |
| 8 | 2909992 | G | A | CSMD1 |
| 8 | 3000108 | C | G | CSMD1 |
| 8 | 3076959 | T | C | CSMD1 |
| 8 | 3245054 | C | T | CSMD1 |
| 8 | 32453358 | G | A | NRG1 |
| 8 | 37654907 | A | G | GPR124 |
| 8 | 37690619 | A | C | GPR124 |
| 8 | 38879190 | C | T | ADAM9 |
| 8 | 39080632 | C | G | ADAM32 |
| 8 | 39112033 | T | C | ADAM32 |
| 8 | 39564367 | A | G | ADAM18 |
| 8 | 70594420 | C | A | SLCO5A1 |
| 8 | 82607068 | C | G | SLC10A5 |
| 8 | 95143186 | C | G | CDH17 |
| 8 | 95188850 | T | C | CDH17 |
| 8 | 97614625 | G | A | SDC2 |
| 8 | 97614661 | T | A | SDC2 |
| 9 | 104385711 | C | T | GRIN3A |
| 9 | 104433235 | C | T | GRIN3A |
| 9 | 104433255 | C | T | GRIN3A |
| 9 | 107266596 | T | C | OR13F1 |
| 9 | 107267352 | T | C | OR13F1 |
| 9 | 107299001 | C | A | OR13C3 |
| 9 | 107331504 | C | A | OR13C8 |
| 9 | 107360910 | G | A | OR13C5 |

| Chr | Position | ref | alt | Gene |
|---|---|---|---|---|
| 9 | 107361111 | T | C | OR13C5 |
| 9 | 107361129 | C | T | OR13C5 |
| 9 | 107361460 | G | A | OR13C5 |
| 9 | 107361642 | G | A | OR13C5 |
| 9 | 107367392 | TGTTA | T | OR13C2 |
| 9 | 107367664 | AGC | A | OR13C2 |
| 9 | 107367841 | A | T | OR13C2 |
| 9 | 107379895 | G | T | OR13C9 |
| 9 | 107380215 | T | A | OR13C9 |
| 9 | 107456763 | T | C | OR13D1 |
| 9 | 107562804 | T | C | ABCA1 |
| 9 | 107620835 | G | A | ABCA1 |
| 9 | 107620867 | C | T | ABCA1 |
| 9 | 113538122 | G | A | MUSK |
| 9 | 116018501 | C | G | SLC31A1 |
| 9 | 120475302 | A | G | TLR4 |
| 9 | 120475602 | C | T | TLR4 |
| 9 | 123476303 | A | C | MEGF9 |
| 9 | 125273574 | G | A | OR1J2 |
| 9 | 125289521 | G | A | OR1N1 |
| 9 | 125315557 | T | C | OR1N2 |
| 9 | 125316028 | T | C | OR1N2 |
| 9 | 125330714 | G | A | OR1L8 |
| 9 | 125377087 | A | G | OR1Q1 |
| 9 | 125377505 | A | G | OR1Q1 |
| 9 | 125391241 | G | A | OR1B1 |
| 9 | 125424189 | C | G | OR1L1 |
| 9 | 125437482 | G | A | OR1L3 |
| 9 | 125512193 | C | A | OR1L6 |
| 9 | 125512245 | C | T | OR1L6 |
| 9 | 125512770 | T | C | OR1L6 |
| 9 | 125562651 | G | A | OR1K1 |
| 9 | 125563212 | T | C | OR1K1 |
| 9 | 127215344 | A | G | GPR144 |
| 9 | 127215772 | C | T | GPR144 |
| 9 | 127215778 | C | T | GPR144 |
| 9 | 127220392 | G | C | GPR144 |
| 9 | 127220938 | G | C | GPR144 |
| 9 | 127231554 | G | A | GPR144 |
| 9 | 127231579 | A | G | GPR144 |
| 9 | 139399320 | C | T | NOTCH1 |

Figure 23 (Continued)

| Chr | Position | ref | alt | Gene |
|---|---|---|---|---|
| 9 | 139413097 | T | G | NOTCH1 |
| 9 | 139417464 | T | G | NOTCH1 |
| 9 | 139748483 | G | A | MAMDC4 |
| 9 | 139751164 | G | A | MAMDC4 |
| 9 | 139751649 | G | A | MAMDC4 |
| 9 | 140332478 | A | G | ENTPD8 |
| 9 | 24543732 | C | T | IZUMO3 |
| 9 | 24545451 | G | A | IZUMO3 |
| 9 | 2635545 | G | A | VLDLR |
| 9 | 27168571 | T | C | TEK |
| 9 | 27190655 | G | A | TEK |
| 9 | 27203078 | G | A | TEK |
| 9 | 33385698 | A | G | AQP7 |
| 9 | 33385733 | C | T | AQP7 |
| 9 | 33387044 | T | A | AQP7 |
| 9 | 33387047 | T | G | AQP7 |
| 9 | 33387060 | C | G | AQP7 |
| 9 | 34371788 | A | T | KIAA1161 |
| 9 | 34372347 | G | T | KIAA1161 |
| 9 | 35612978 | G | A | CD72 |
| 9 | 35674347 | A | T | CA9 |
| 9 | 35679251 | A | G | CA9 |
| 9 | 35957615 | T | C | OR2S2 |
| 9 | 35957831 | G | A | OR2S2 |
| 9 | 35958047 | T | C | OR2S2 |
| 9 | 39085808 | T | C | CNTNAP3 |
| 9 | 39088517 | C | A | CNTNAP3 |
| 9 | 39100130 | G | C | CNTNAP3 |
| 9 | 39102655 | A | G | CNTNAP3 |
| 9 | 39103743 | C | T | CNTNAP3 |
| 9 | 39118196 | C | A | CNTNAP3 |
| 9 | 39133031 | C | A | CNTNAP3 |
| 9 | 43800940 | G | A | CNTNAP3B |
| 9 | 43822668 | C | T | CNTNAP3B |
| 9 | 43822704 | G | A | CNTNAP3B |
| 9 | 43822762 | C | T | CNTNAP3B |
| 9 | 43844281 | G | C | CNTNAP3B |
| 9 | 43849812 | T | G | CNTNAP3B |
| 9 | 43853583 | CT | C | CNTNAP3B |
| 9 | 43861081 | T | G | CNTNAP3B |
| 9 | 43891504 | A | T | CNTNAP3B |
| 9 | 43891683 | G | A | CNTNAP3B |
| 9 | 5431913 | A | G | PLGRKT |
| 9 | 72459437 | C | T | C9orf135 |

| Chr | Position | ref | alt | Gene |
|---|---|---|---|---|
| 9 | 74305098 | C | T | TMEM2 |
| 9 | 74319677 | T | C | TMEM2 |
| 9 | 74332970 | G | A | TMEM2 |
| 9 | 74349846 | A | T | TMEM2 |
| 9 | 74360096 | C | T | TMEM2 |
| 9 | 74360234 | C | T | TMEM2 |
| 9 | 78853916 | G | C | PCSK5 |
| 9 | 78854033 | T | A | PCSK5 |
| 9 | 78910241 | A | C | PCSK5 |
| 9 | 78910273 | G | A | PCSK5 |
| 9 | 78923638 | C | T | PCSK5 |
| 9 | 78936358 | G | A | PCSK5 |
| 9 | 78936492 | A | G | PCSK5 |
| 9 | 78937974 | C | T | PCSK5 |
| 9 | 78938043 | G | A | PCSK5 |
| 9 | 78938186 | G | C | PCSK5 |
| 9 | 78969059 | C | A | PCSK5 |
| 9 | 8485787 | C | G | PTPRD |
| 9 | 8518052 | G | C | PTPRD |
| 9 | 91994101 | G | A | SEMA4D |
| 9 | 91994433 | C | T | SEMA4D |
| 9 | 92003679 | C | T | SEMA4D |
| 9 | 94493330 | G | C | ROR2 |
| 9 | 94495608 | T | C | ROR2 |
| 10 | 101560169 | G | A | ABCC2 |
| 10 | 102056790 | G | A | PKD2L1 |
| 10 | 102057262 | C | T | PKD2L1 |
| 10 | 102057362 | A | C | PKD2L1 |
| 10 | 104678350 | G | A | CNNM2 |
| 10 | 105810400 | T | C | COL17A1 |
| 10 | 115804036 | A | G | ADRB1 |
| 10 | 117075090 | T | G | ATRNL1 |
| 10 | 120353843 | G | A | PRLHR |
| 10 | 123310871 | A | G | FGFR2 |
| 10 | 135084781 | G | A | ADAM8 |
| 10 | 135086766 | G | A | ADAM8 |
| 10 | 15573050 | A | G | ITGA8 |
| 10 | 15649698 | T | G | ITGA8 |
| 10 | 15649710 | G | A | ITGA8 |
| 10 | 15719621 | C | G | ITGA8 |
| 10 | 18116531 | C | T | MRC1 |
| 10 | 18138639 | A | G | MRC1 |
| 10 | 18183217 | G | A | MRC1 |
| 10 | 18242311 | A | G | SLC39A12 |

Figure 23 (Continued)

| Chr | Position | ref | alt | Gene |
|---|---|---|---|---|
| 10 | 20506418 | G | A | PLXDC2 |
| 10 | 25464527 | C | A | GPR158 |
| 10 | 33199278 | T | G | ITGB1 |
| 10 | 33475282 | C | T | NRP1 |
| 10 | 35929254 | GC | G | FZD8 |
|  |  | CC |  |  |
|  |  | GC |  |  |
|  |  | GC |  |  |
|  |  | CC |  |  |
|  |  | GC |  |  |
|  |  | GC |  |  |
|  |  | CC |  |  |
|  |  | GC |  |  |
|  |  | CG |  |  |
|  |  | CG |  |  |
|  |  | CC |  |  |
|  |  | CG |  |  |
|  |  | CG |  |  |
|  |  | CC |  |  |
|  |  | CG |  |  |
|  |  | CC |  |  |
|  |  | GC |  |  |
|  |  | CG |  |  |
|  |  | CG |  |  |
|  |  | CC |  |  |
|  |  | GC |  |  |
|  |  | CC |  |  |
|  |  | GC |  |  |
|  |  | GC |  |  |
|  |  | CC |  |  |
|  |  | CC |  |  |
|  |  | AG |  |  |
|  |  | CG |  |  |
|  |  | CC |  |  |
|  |  | C |  |  |
| 10 | 35929308 | AG | A | FZD8 |
|  |  | CG |  |  |
|  |  | CC |  |  |
|  |  | CC |  |  |
|  |  | CC |  |  |
| 10 | 47658590 | G | C | ANTXRL |
| 10 | 47658597 | T | G | ANTXRL |
| 10 | 47669277 | C | G | ANTXRL |
| 10 | 47674009 | G | A | ANTXRL |
| 10 | 50315893 | A | G | VSTM4 |

| Chr | Position | ref | alt | Gene |
|---|---|---|---|---|
| 10 | 55755491 | C | T | PCDH15 |
| 10 | 55892642 | T | C | PCDH15 |
| 10 | 55955444 | T | G | PCDH15 |
| 10 | 55955610 | C | T | PCDH15 |
| 10 | 6002368 | T | G | IL15RA |
| 10 | 6063567 | C | T | IL2RA |
| 10 | 71176012 | A | G | TACR2 |
| 10 | 71176066 | T | C | TACR2 |
| 10 | 71265955 | A | G | TSPAN15 |
| 10 | 71582188 | C | T | COL13A1 |
| 10 | 71690231 | G | A | COL13A1 |
| 10 | 72015429 | C | A | NPFFR1 |
| 10 | 73046617 | A | G | UNC5B |
| 10 | 73103969 | T | C | SLC29A3 |
| 10 | 73111408 | C | T | SLC29A3 |
| 10 | 73199595 | C | T | CDH23 |
| 10 | 73434888 | G | C | CDH23 |
| 10 | 73434906 | G | A | CDH23 |
| 10 | 73515221 | T | C | C10orf54 |
| 10 | 73520632 | A | C | C10orf54 |
| 10 | 73544086 | G | A | CDH23 |
| 10 | 73550117 | C | G | CDH23 |
| 10 | 73558128 | G | A | CDH23 |
| 10 | 73558886 | G | A | CDH23 |
| 10 | 73558952 | C | T | CDH23 |
| 10 | 73571765 | T | C | CDH23 |
| 10 | 85960404 | G | C | CDHR1 |
| 10 | 85962824 | C | T | CDHR1 |
| 10 | 86017740 | C | T | RGR |
| 10 | 87489317 | T | C | GRID1 |
| 10 | 88414569 | C | T | OPN4 |
| 10 | 97453464 | T | G | TCTN3 |
| 10 | 97607266 | G | A | ENTPD1 |
| 11 | 102272839 | C | A | TMEM123 |
| 11 | 102272884 | C | T | TMEM123 |
| 11 | 112832299 | C | T | NCAM1 |
| 11 | 112832308 | A | AG | NCAM1 |
| 11 | 113561054 | A | G | TMPRSS5 |
| 11 | 113567640 | TG | T | TMPRSS5 |
| 11 | 113803028 | A | C | HTR3B |
| 11 | 113803666 | G | A | HTR3B |
| 11 | 117403235 | G | T | DSCAML1 |
| 11 | 117864063 | A | G | IL10RA |
| 11 | 117864846 | A | G | IL10RA |

Figure 23 (Continued)

| Chr | Position | ref | alt | Gene |
|---|---|---|---|---|
| 11 | 117978578 | G | A | TMPRSS4 |
| 11 | 117982464 | A | G | TMPRSS4 |
| 11 | 117988105 | C | T | TMPRSS4 |
| 11 | 118074337 | A | G | AMICA1 |
| 11 | 118081345 | A | T | AMICA1 |
| 11 | 119181832 | C | G | MCAM |
| 11 | 119185677 | T | C | MCAM |
| 11 | 119215586 | C | T | MFRP |
| 11 | 119216504 | C | T | MFRP |
| 11 | 119216555 | T | C | MFRP |
| 11 | 120811161 | G | A | GRIK4 |
| 11 | 121393684 | G | A | SORL1 |
| 11 | 121437819 | C | G | SORL1 |
| 11 | 121491782 | G | A | SORL1 |
| 11 | 122722440 | C | A | CRTAM |
| 11 | 122726430 | A | G | CRTAM |
| 11 | 122955402 | C | T | CLMP |
| 11 | 123624425 | T | C | OR6X1 |
| 11 | 123624658 | G | T | OR6X1 |
| 11 | 123814478 | A | G | OR6T1 |
| 11 | 123847558 | C | T | OR10S1 |
| 11 | 123848121 | T | C | OR10S1 |
| 11 | 123886307 | C | T | OR10G4 |
| 11 | 123886550 | C | T | OR10G4 |
| 11 | 123886822 | C | T | OR10G4 |
| 11 | 123886865 | T | A | OR10G4 |
| 11 | 123893745 | C | T | OR10G9 |
| 11 | 123893988 | C | T | OR10G9 |
| 11 | 123894234 | A | G | OR10G9 |
| 11 | 123894246 | A | G | OR10G9 |
| 11 | 123900385 | C | A | OR10G8 |
| 11 | 123900916 | C | T | OR10G8 |
| 11 | 123909650 | C | G | OR10G7 |
| 11 | 123909653 | G | T | OR10G7 |
| 11 | 123909656 | G | A | OR10G7 |
| 11 | 123909671 | G | A | OR10G7 |
| 11 | 123909695 | G | C | OR10G7 |
| 11 | 124056566 | G | A | OR10D3 |
| 11 | 124180082 | A | G | OR8D1 |
| 11 | 124189306 | G | A | OR8D2 |
| 11 | 124190036 | G | A | OR8D2 |
| 11 | 124252750 | G | A | OR8B2 |
| 11 | 124253170 | G | A | OR8B2 |
| 11 | 124266697 | A | AG | OR8B3 |
| 11 | 124267177 | T | C | OR8B3 |
| 11 | 124294236 | A | G | OR8B4 |
| 11 | 124294703 | T | C | OR8B4 |
| 11 | 124413261 | A | T | OR8B12 |
| 11 | 124440617 | C | T | OR8A1 |
| 11 | 124742365 | G | A | ROBO3 |
| 11 | 124746180 | C | T | ROBO3 |
| 11 | 125864206 | T | C | CDON |
| 11 | 125871715 | G | A | CDON |
| 11 | 125885283 | G | C | CDON |
| 11 | 125889526 | C | T | CDON |
| 11 | 125891269 | C | T | CDON |
| 11 | 125891295 | T | C | CDON |
| 11 | 126343227 | T | C | KIRREL3 |
| 11 | 130010313 | G | A | APLP2 |
| 11 | 130058437 | G | A | ST14 |
| 11 | 130060569 | G | A | ST14 |
| 11 | 130064567 | A | G | ST14 |
| 11 | 1769226 | G | T | IFITM10 |
| 11 | 18158993 | T | C | MRGPRX3 |
| 11 | 18159254 | A | G | MRGPRX3 |
| 11 | 18159455 | T | C | MRGPRX3 |
| 11 | 18194827 | C | G | MRGPRX4 |
| 11 | 18194878 | T | G | MRGPRX4 |
| 11 | 18195051 | T | C | MRGPRX4 |
| 11 | 18195537 | A | G | MRGPRX4 |
| 11 | 1855821 | G | C | SYT8 |
| 11 | 1856344 | C | A | SYT8 |
| 11 | 19077904 | T | G | MRGPRX2 |
| 11 | 2432666 | C | T | TRPM5 |
| 11 | 26586801 | G | A | MUC15 |
| 11 | 26660708 | T | G | ANO3 |
| 11 | 26743240 | C | T | SLC5A12 |
| 11 | 27390220 | T | C | LGR4 |
| 11 | 27393886 | G | A | LGR4 |
| 11 | 3239559 | G | A | MRGPRG |
| 11 | 3239818 | C | T | MRGPRG |
| 11 | 3249984 | C | T | MRGPRE |
| 11 | 35226155 | A | G | CD44 |
| 11 | 35229673 | T | C | CD44 |
| 11 | 408174 | G | T | SIGIRR |
| 11 | 44940828 | G | A | TSPAN18 |
| 11 | 4608116 | T | C | OR52I2 |
| 11 | 4615767 | A | G | OR52I1 |

Figure 23 (Continued)

| Chr | Position | ref | alt | Gene |
|---|---|---|---|---|
| 11 | 4615771 | A | G | OR52I1 |
| 11 | 4615837 | G | A | OR52I1 |
| 11 | 4615857 | G | A | OR52I1 |
| 11 | 4616062 | C | T | OR52I1 |
| 11 | 4674282 | A | G | OR51E1 |
| 11 | 46886077 | A | T | LRP4 |
| 11 | 46897446 | G | A | LRP4 |
| 11 | 46898771 | T | C | LRP4 |
| 11 | 46916179 | T | G | LRP4 |
| 11 | 46917868 | A | G | LRP4 |
| 11 | 48145375 | A | C | PTPRJ |
| 11 | 48146522 | G | A | PTPRJ |
| 11 | 48146622 | G | A | PTPRJ |
| 11 | 48149352 | G | A | PTPRJ |
| 11 | 48166267 | G | C | PTPRJ |
| 11 | 48285906 | C | T | OR4X1 |
| 11 | 48285981 | CCTT | C | OR4X1 |
| 11 | 48346523 | C | T | OR4C3 |
| 11 | 48346541 | A | T | OR4C3 |
| 11 | 48346547 | C | T | OR4C3 |
| 11 | 48346551 | C | A | OR4C3 |
| 11 | 48346962 | A | G | OR4C3 |
| 11 | 48346996 | G | A | OR4C3 |
| 11 | 48347014 | G | A | OR4C3 |
| 11 | 48347067 | C | T | OR4C3 |
| 11 | 48347267 | T | C | OR4C3 |
| 11 | 48387186 | A | G | OR4C5 |
| 11 | 48387201 | G | A | OR4C5 |
| 11 | 48387424 | G | T | OR4C5 |
| 11 | 48387668 | C | G | OR4C5 |
| 11 | 48387683 | GT | G | OR4C5 |
| 11 | 48387689 | T | C | OR4C5 |
| 11 | 48387705 | C | T | OR4C5 |
| 11 | 48387890 | T | C | OR4C5 |
| 11 | 48387894 | C | T | OR4C5 |
| 11 | 48387900 | G | A | OR4C5 |
| 11 | 48387917 | AT | A | OR4C5 |
| 11 | 48387930 | T | C | OR4C5 |
| 11 | 48387945 | C | CCA | OR4C5 |
| 11 | 48387960 | T | C | OR4C5 |
| 11 | 48387978 | T | A | OR4C5 |
| 11 | 48387983 | T | C | OR4C5 |

| Chr | Position | ref | alt | Gene |
|---|---|---|---|---|
| 11 | 48510919 | C | A | OR4A47 |
| 11 | 49186274 | G | A | FOLH1 |
| 11 | 49204779 | C | T | FOLH1 |
| 11 | 49208267 | G | A | FOLH1 |
| 11 | 49227620 | A | G | FOLH1 |
| 11 | 49973979 | C | T | OR4C13 |
| 11 | 5020799 | C | T | OR51L1 |
| 11 | 5068297 | G | A | OR52J3 |
| 11 | 5080068 | G | A | OR52E2 |
| 11 | 5080337 | T | C | OR52E2 |
| 11 | 5080359 | G | A | OR52E2 |
| 11 | 5080844 | T | C | OR52E2 |
| 11 | 5091576 | A | AC | OR52E1 |
| 11 | 51411914 | T | C | OR4A5 |
| 11 | 51412327 | T | A | OR4A5 |
| 11 | 51412353 | A | T | OR4A5 |
| 11 | 51412379 | T | C | OR4A5 |
| 11 | 51435852 | G | T | OR4A8P |
| 11 | 51435866 | A | G | OR4A8P |
| 11 | 51515834 | C | A | OR4C46 |
| 11 | 5172786 | A | G | OR52A1 |
| 11 | 5172795 | A | AC | OR52A1 |
| 11 | 55135435 | C | T | OR4A15 |
| 11 | 55136219 | C | T | OR4A15 |
| 11 | 55321823 | T | A | OR4C15 |
| 11 | 55339652 | C | T | OR4C16 |
| 11 | 55340170 | A | C | OR4C16 |
| 11 | 55340379 | T | C | OR4C16 |
| 11 | 55371381 | G | A | OR4C11 |
| 11 | 55371807 | A | T | OR4C11 |
| 11 | 55371828 | G | T | OR4C11 |
| 11 | 55418620 | G | A | OR4S2 |
| 11 | 55563602 | G | A | OR5D14 |
| 11 | 55587914 | A | G | OR5D18 |
| 11 | 55594936 | T | G | OR5L2 |
| 11 | 55606472 | T | C | OR5D16 |
| 11 | 55681566 | G | A | OR5W2 |
| 11 | 55703861 | T | C | OR5I1 |
| 11 | 55761528 | T | C | OR5F1 |
| 11 | 55861277 | GT | G | OR8I2 |
| 11 | 55861297 | A | G | OR8I2 |
| 11 | 55861306 | CA | C | OR8I2 |
| 11 | 55873013 | A | T | OR8H2 |
| 11 | 55873026 | G | T | OR8H2 |

Figure 23 (Continued)

| Chr | Position | ref | alt | Gene |
|---|---|---|---|---|
| 11 | 55873293 | T | C | OR8H2 |
| 11 | 55889895 | C | T | OR8H3 |
| 11 | 55890356 | G | T | OR8H3 |
| 11 | 55904382 | A | C | OR8J3 |
| 11 | 55927763 | C | T | OR8K5 |
| 11 | 55978721 | G | A | OR8J2 |
| 11 | 55979047 | T | G | OR8J2 |
| 11 | 55979246 | G | A | OR8J2 |
| 11 | 55999737 | G | C | OR5T2 |
| 11 | 56000471 | G | A | OR5T2 |
| 11 | 56000600 | G | T | OR5T2 |
| 11 | 56020049 | T | C | OR5T3 |
| 11 | 56058474 | T | A | OR8H1 |
| 11 | 56058535 | C | T | OR8H1 |
| 11 | 56086299 | G | A | OR8K3 |
| 11 | 56113516 | T | C | OR8K1 |
| 11 | 56113575 | A | G | OR8K1 |
| 11 | 56113593 | C | A | OR8K1 |
| 11 | 56113764 | G | A | OR8K1 |
| 11 | 56127971 | T | G | OR8J1 |
| 11 | 56143103 | G | A | OR8U1 |
| 11 | 56143108 | C | G | OR8U1 |
| 11 | 56143113 | A | G | OR8U1 |
| 11 | 56143125 | C | T | OR8U1 |
| 11 | 56143158 | A | G | OR8U1 |
| 11 | 56143370 | G | A | OR8U1 |
| 11 | 56143371 | T | G | OR8U1 |
| 11 | 56143394 | A | G | OR8U1 |
| 11 | 56143592 | C | T | OR8U1 |
| 11 | 56185224 | A | G | OR5R1 |
| 11 | 56185689 | A | G | OR5R1 |
| 11 | 56237966 | T | C | OR5M3 |
| 11 | 56310222 | C | T | OR5M11 |
| 11 | 56431216 | C | T | OR5AR1 |
| 11 | 56431667 | G | A | OR5AR1 |
| 11 | 56468155 | T | G | OR9G1 |
| 11 | 56468368 | C | T | OR9G1 |
| 11 | 56468416 | G | A | OR9G1 |
| 11 | 56468449 | A | T | OR9G1 |
| 11 | 56511160 | A | G | OR9G4 |
| 11 | 56756398 | G | T | OR5AK2 |
| 11 | 56756399 | G | T | OR5AK2 |
| 11 | 56756664 | G | A | OR5AK2 |
| 11 | 56756915 | A | G | OR5AK2 |

| Chr | Position | ref | alt | Gene |
|---|---|---|---|---|
| 11 | 57114109 | G | A | P2RX3 |
| 11 | 5758051 | G | A | OR56B1 |
| 11 | 5758270 | G | A | OR56B1 |
| 11 | 5776479 | A | C | OR52N4 |
| 11 | 5776779 | T | C | OR52N4 |
| 11 | 57958497 | T | C | OR9Q2 |
| 11 | 57982229 | A | G | OR1S1 |
| 11 | 57982763 | A | G | OR1S1 |
| 11 | 57982832 | T | A | OR1S1 |
| 11 | 57995777 | G | A | OR10Q1 |
| 11 | 5809241 | T | C | OR52N1 |
| 11 | 5809548 | G | A | OR52N1 |
| 11 | 5809746 | C | T | OR52N1 |
| 11 | 5809806 | GA | G | OR52N1 |
| 11 | 5809811 | G | T | OR52N1 |
| 11 | 58125774 | A | G | OR5B17 |
| 11 | 58126305 | A | T | OR5B17 |
| 11 | 58170342 | C | T | OR5B3 |
| 11 | 58170374 | T | C | OR5B3 |
| 11 | 5842356 | A | G | OR52N2 |
| 11 | 5842384 | C | G | OR52N2 |
| 11 | 5862845 | A | G | OR52E6 |
| 11 | 58978684 | G | A | MPEG1 |
| 11 | 58978940 | C | T | MPEG1 |
| 11 | 58979393 | G | A | MPEG1 |
| 11 | 5906048 | G | A | OR52E4 |
| 11 | 59189912 | G | A | OR5A2 |
| 11 | 59211188 | G | A | OR5A1 |
| 11 | 59224464 | G | C | OR4D6 |
| 11 | 59224720 | A | G | OR4D6 |
| 11 | 59225221 | T | C | OR4D6 |
| 11 | 59282960 | C | G | OR4D9 |
| 11 | 60070176 | A | G | MS4A4A |
| 11 | 6007613 | T | G | OR52L1 |
| 11 | 60637164 | C | T | ZP1 |
| 11 | 60775227 | C | T | CD6 |
| 11 | 60776186 | C | T | CD6 |
| 11 | 60776209 | C | T | CD6 |
| 11 | 60776306 | C | T | CD6 |
| 11 | 60777073 | G | A | CD6 |
| 11 | 60886913 | C | T | CD5 |
| 11 | 6129837 | C | T | OR56B4 |
| 11 | 6221249 | A | G | OR52W1 |
| 11 | 62656046 | A | C | SLC3A2 |

Figure 23 (Continued)

| Chr | Position | ref | alt | Gene |
|---|---|---|---|---|
| 11 | 6291120 | G | A | CCKBR |
| 11 | 63057925 | G | A | SLC22A10 |
| 11 | 64480930 | A | T | NRXN2 |
| 11 | 64820695 | T | G | NAALADL1 |
| 11 | 66083129 | T | C | CD248 |
| 11 | 6646584 | C | T | DCHS1 |
| 11 | 6647461 | A | T | DCHS1 |
| 11 | 6648388 | G | A | DCHS1 |
| 11 | 6648424 | G | A | DCHS1 |
| 11 | 6790106 | T | C | OR2AG2 |
| 11 | 68030173 | C | A | C11orf24 |
| 11 | 6806827 | G | T | OR2AG1 |
| 11 | 68115489 | A | G | LRP5 |
| 11 | 6816875 | G | A | OR6A2 |
| 11 | 68174189 | G | A | LRP5 |
| 11 | 68201295 | C | T | LRP5 |
| 11 | 6867167 | C | A | OR10A5 |
| 11 | 6867199 | C | T | OR10A5 |
| 11 | 68777323 | T | C | MRGPRF |
| 11 | 6891758 | A | C | OR10A2 |
| 11 | 6912921 | ATT | A | OR2D2 |
| 11 | 6913243 | T | C | OR2D2 |
| 11 | 6913244 | A | G | OR2D2 |
| 11 | 6913482 | G | A | OR2D2 |
| 11 | 74907582 | C | T | SLCO2B1 |
| 11 | 75152243 | C | T | GDPD5 |
| 11 | 76371418 | C | T | LRRC32 |
| 11 | 76371705 | C | G | LRRC32 |
| 11 | 76954788 | T | TA | GDPD4 |
| 11 | 76954812 | T | C | GDPD4 |
| 11 | 76954833 | G | A | GDPD4 |
| 11 | 76979550 | T | C | GDPD4 |
| 11 | 7818471 | C | T | OR5P2 |
| 11 | 78525384 | T | G | TENM4 |
| 11 | 78565314 | C | G | TENM4 |
| 11 | 7949707 | A | G | OR10A6 |
| 11 | 89880604 | G | A | NAALAD2 |
| 11 | 89883708 | A | G | NAALAD2 |
| 11 | 89883726 | C | T | NAALAD2 |
| 11 | 89902154 | A | G | NAALAD2 |
| 11 | 92086513 | C | T | FAT3 |
| 11 | 92086662 | A | G | FAT3 |
| 11 | 92531356 | A | G | FAT3 |

| Chr | Position | ref | alt | Gene |
|---|---|---|---|---|
| 11 | 92533057 | A | G | FAT3 |
| 11 | 92534442 | A | G | FAT3 |
| 11 | 92702962 | G | A | MTNR1B |
| 11 | 93797619 | A | G | HEPHL1 |
| 12 | 10041364 | G | A | KLRF2 |
| 12 | 10046052 | C | A | KLRF2 |
| 12 | 10069302 | C | T | CLEC2A |
| 12 | 101336201 | G | C | ANO4 |
| 12 | 10137557 | A | C | CLEC12A |
| 12 | 101560328 | C | A | SLC5A8 |
| 12 | 10279261 | G | T | CLEC7A |
| 12 | 10313448 | C | G | OLR1 |
| 12 | 104062457 | T | G | STAB2 |
| 12 | 104069795 | G | A | STAB2 |
| 12 | 104124018 | A | C | STAB2 |
| 12 | 104139034 | C | A | STAB2 |
| 12 | 104153004 | C | G | STAB2 |
| 12 | 10560957 | T | C | KLRC4 |
| 12 | 10571091 | T | G | KLRC3 |
| 12 | 10571658 | C | T | KLRC3 |
| 12 | 10587111 | A | G | KLRC2 |
| 12 | 108985945 | A | G | TMEM119 |
| 12 | 108985976 | G | A | TMEM119 |
| 12 | 108986017 | G | A | TMEM119 |
| 12 | 109017264 | T | C | SELPLG |
| 12 | 109017266 | G | A | SELPLG |
| 12 | 109017411 | GA GT GG TC TG TG CC TC CA TG GC TG CT GG TG GA GT GG | G | SELPLG |

Figure 23 (Continued)

| Chr | Position | ref | alt | Gene |
|---|---|---|---|---|
|  |  | TC |  |  |
|  |  | TG |  |  |
|  |  | TG |  |  |
|  |  | CT |  |  |
|  |  | TC |  |  |
|  |  | CA |  |  |
|  |  | TG |  |  |
|  |  | GC |  |  |
|  |  | TG |  |  |
|  |  | CT |  |  |
|  |  | GG |  |  |
|  |  | TG |  |  |
|  |  | C |  |  |
| 12 | 109017650 | GG | G | SELPLG |
|  |  | AG |  |  |
|  |  | TG |  |  |
|  |  | GT |  |  |
|  |  | CT |  |  |
|  |  | GT |  |  |
|  |  | GC |  |  |
|  |  | CT |  |  |
|  |  | CC |  |  |
|  |  | GT |  |  |
|  |  | GG |  |  |
|  |  | GC |  |  |
|  |  | AC |  |  |
|  |  | TG |  |  |
|  |  | GT |  |  |
|  |  | T |  |  |
| 12 | 109017898 | C | T | SELPLG |
| 12 | 10954383 | T | A | TAS2R7 |
| 12 | 10954632 | C | A | TAS2R7 |
| 12 | 10954916 | A | G | TAS2R7 |
| 12 | 10978402 | G | A | TAS2R10 |
| 12 | 11061122 | T | C | TAS2R13 |
| 12 | 11149711 | C | A | TAS2R20 |
| 12 | 11149720 | A | G | TAS2R20 |
| 12 | 11150033 | G | T | TAS2R20 |
| 12 | 11150240 | T | C | TAS2R20 |
| 12 | 11183427 | T | G | TAS2R31 |
| 12 | 11183484 | C | G | TAS2R31 |
| 12 | 11183642 | A | G | TAS2R31 |
| 12 | 11183676 | C | T | TAS2R31 |
| 12 | 11183697 | C | A | TAS2R31 |
| 12 | 11214437 | T | C | TAS2R46 |

| Chr | Position | ref | alt | Gene |
|---|---|---|---|---|
| 12 | 11244299 | A | G | TAS2R43 |
| 12 | 11244303 | T | C | TAS2R43 |
| 12 | 11244309 | A | G | TAS2R43 |
| 12 | 11244378 | C | G | TAS2R43 |
| 12 | 11244603 | T | A | TAS2R43 |
| 12 | 11286088 | A | C | TAS2R30 |
| 12 | 11338750 | T | C | TAS2R42 |
| 12 | 11339020 | T | A | TAS2R42 |
| 12 | 113753203 | G | A | SLC8B1 |
| 12 | 113758166 | G | A | SLC8B1 |
| 12 | 118511726 | C | T | VSIG10 |
| 12 | 121592689 | T | C | P2RX7 |
| 12 | 121600253 | T | C | P2RX7 |
| 12 | 121666646 | A | G | P2RX4 |
| 12 | 122079295 | A | G | ORAI1 |
| 12 | 12301898 | C | T | LRP6 |
| 12 | 12483134 | T | A | MANSC1 |
| 12 | 12483764 | C | T | MANSC1 |
| 12 | 12496086 | C | T | MANSC1 |
| 12 | 125834697 | A | T | TMEM132B |
| 12 | 126137060 | C | T | TMEM132B |
| 12 | 126138520 | G | A | TMEM132B |
| 12 | 128899673 | A | G | TMEM132C |
| 12 | 128899675 | G | A | TMEM132C |
| 12 | 128899748 | G | A | TMEM132C |
| 12 | 128899885 | G | A | TMEM132C |
| 12 | 128900005 | G | A | TMEM132C |
| 12 | 129153986 | G | A | TMEM132C |
| 12 | 129189702 | C | G | TMEM132C |
| 12 | 129189941 | G | A | TMEM132C |
| 12 | 129559086 | C | A | TMEM132D |
| 12 | 129559421 | C | T | TMEM132D |
| 12 | 130185054 | A | T | TMEM132D |
| 12 | 13103266 | G | T | GPRC5D |
| 12 | 131456080 | T | G | GPR133 |
| 12 | 131498802 | T | G | GPR133 |
| 12 | 1910786 | C | T | CACNA2D4 |
| 12 | 21207389 | T | C | SLCO1B7 |
| 12 | 21329738 | A | G | SLCO1B1 |
| 12 | 21329813 | C | A | SLCO1B1 |
| 12 | 26383834 | G | A | SSPN |
| 12 | 27916224 | A | G | MANSC4 |
| 12 | 47186770 | C | T | SLC38A4 |
| 12 | 48596484 | A | T | OR10AD1 |

Figure 23 (Continued)

| Chr | Position | ref | alt | Gene |
|---|---|---|---|---|
| 12 | 48596546 | C | T | OR10AD1 |
| 12 | 48597053 | A | G | OR10AD1 |
| 12 | 48919659 | T | C | OR8S1 |
| 12 | 51236931 | G | A | TMPRSS12 |
| 12 | 51237816 | G | A | TMPRSS12 |
| 12 | 53591647 | T | A | ITGB7 |
| 12 | 55523586 | AT | A | OR9K2 |
| 12 | 55523685 | C | T | OR9K2 |
| 12 | 55523860 | A | C | OR9K2 |
| 12 | 55524172 | G | A | OR9K2 |
| 12 | 55641075 | A | G | OR6C74 |
| 12 | 55641328 | G | A | OR6C74 |
| 12 | 55688448 | G | A | OR6C6 |
| 12 | 55688454 | G | C | OR6C6 |
| 12 | 55714876 | C | G | OR6C1 |
| 12 | 55725746 | A | T | OR6C3 |
| 12 | 55820104 | G | A | OR6C76 |
| 12 | 55846538 | C | G | OR6C2 |
| 12 | 55945258 | T | C | OR6C4 |
| 12 | 55968994 | G | C | OR2AP1 |
| 12 | 56030938 | C | T | OR10P1 |
| 12 | 56089357 | C | T | ITGA7 |
| 12 | 56090126 | C | T | ITGA7 |
| 12 | 57578673 | G | A | LRP1 |
| 12 | 63544601 | C | T | AVPR1A |
| 12 | 6443001 | G | A | TNFRSF1A |
| 12 | 6464581 | C | T | SCNN1A |
| 12 | 6554628 | G | A | CD27 |
| 12 | 6925294 | T | C | CD4 |
| 12 | 6925407 | C | T | CD4 |
| 12 | 70963619 | G | A | PTPRB |
| 12 | 70970293 | T | C | PTPRB |
| 12 | 70983895 | A | C | PTPRB |
| 12 | 71002893 | C | T | PTPRB |
| 12 | 71016340 | C | T | PTPRB |
| 12 | 71029733 | C | T | PTPRB |
| 12 | 71533622 | C | T | TSPAN8 |
| 12 | 7288432 | A | G | CLSTN3 |
| 12 | 7527124 | A | G | CD163L1 |
| 12 | 7548996 | C | G | CD163L1 |
| 12 | 7549009 | C | T | CD163L1 |
| 12 | 7586017 | C | T | CD163L1 |
| 12 | 7586260 | T | C | CD163L1 |
| 12 | 7637769 | G | A | CD163 |

| Chr | Position | ref | alt | Gene |
|---|---|---|---|---|
| 12 | 7640079 | A | T | CD163 |
| 12 | 7649484 | T | C | CD163 |
| 12 | 7890040 | G | T | CLEC4C |
| 12 | 7894056 | G | A | CLEC4C |
| 12 | 80818876 | A | G | PTPRQ |
| 12 | 80828843 | A | G | PTPRQ |
| 12 | 80855803 | G | A | PTPRQ |
| 12 | 80855825 | C | T | PTPRQ |
| 12 | 80878310 | C | G | PTPRQ |
| 12 | 80878317 | G | A | PTPRQ |
| 12 | 80889829 | T | A | PTPRQ |
| 12 | 80899901 | C | A | PTPRQ |
| 12 | 80933609 | A | G | PTPRQ |
| 12 | 80935345 | T | C | PTPRQ |
| 12 | 80935411 | G | C | PTPRQ |
| 12 | 81007527 | T | C | PTPRQ |
| 12 | 85266484 | G | A | SLC6A15 |
| 12 | 9750669 | A | G | KLRB1 |
| 12 | 9885578 | G | A | CLECL1 |
| 12 | 9985915 | G | T | KLRF1 |
| 13 | 114303822 | G | A | ATP4B |
| 13 | 23824818 | G | A | SGCG |
| 13 | 24167505 | T | A | TNFRSF19 |
| 13 | 26624789 | C | T | SHISA2 |
| 13 | 26624935 | C | T | SHISA2 |
| 13 | 28624294 | G | A | FLT3 |
| 13 | 33590718 | G | A | KL |
| 13 | 33628138 | T | G | KL |
| 13 | 33628193 | G | C | KL |
| 13 | 33629393 | C | T | KL |
| 13 | 39263646 | G | A | FREM2 |
| 13 | 39264083 | C | G | FREM2 |
| 13 | 39264597 | T | A | FREM2 |
| 13 | 39264690 | T | C | FREM2 |
| 13 | 39343822 | C | T | FREM2 |
| 13 | 39424253 | C | G | FREM2 |
| 13 | 39430314 | C | T | FREM2 |
| 13 | 39452993 | C | T | FREM2 |
| 13 | 52523808 | C | T | ATP7B |
| 13 | 53420344 | A | G | PCDH8 |
| 13 | 53421473 | T | C | PCDH8 |
| 13 | 86369403 | T | C | SLITRK6 |
| 13 | 99356611 | C | T | SLC15A1 |
| 13 | 99358401 | C | G | SLC15A1 |

Figure 23 (Continued)

| Chr | Position | ref | alt | Gene |
|---|---|---|---|---|
| 13 | 99376181 | C | T | SLC15A1 |
| 14 | 101195359 | A | T | DLK1 |
| 14 | 101200860 | G | A | DLK1 |
| 14 | 105609836 | G | A | JAG2 |
| 14 | 105614675 | T | G | JAG2 |
| 14 | 105614734 | C | T | JAG2 |
| 14 | 105617042 | C | T | JAG2 |
| 14 | 19377881 | G | A | OR11H12 |
| 14 | 19377907 | A | C | OR11H12 |
| 14 | 19378189 | G | T | OR11H12 |
| 14 | 20295627 | C | G | OR4N2 |
| 14 | 20389039 | A | G | OR4K5 |
| 14 | 20389541 | T | C | OR4K5 |
| 14 | 20389543 | T | C | OR4K5 |
| 14 | 20404076 | A | T | OR4K1 |
| 14 | 20404091 | G | A | OR4K1 |
| 14 | 20404395 | G | A | OR4K1 |
| 14 | 20404614 | C | A | OR4K1 |
| 14 | 20444012 | A | T | OR4K15 |
| 14 | 20444026 | T | G | OR4K15 |
| 14 | 20470852 | CT | C | OR4Q2 |
| 14 | 20528250 | G | T | OR4L1 |
| 14 | 20528448 | TC AT AG AT TT GC TC AC TG AC | T | OR4L1 |
| 14 | 20528682 | T | C | OR4L1 |
| 14 | 20612465 | A | G | OR4N5 |
| 14 | 20612672 | T | C | OR4N5 |
| 14 | 20665538 | C | T | OR11G2 |
| 14 | 20665627 | A | G | OR11G2 |
| 14 | 20665640 | G | A | OR11G2 |
| 14 | 20665840 | G | A | OR11G2 |
| 14 | 20691888 | C | A | OR11H6 |
| 14 | 20691962 | C | G | OR11H6 |
| 14 | 20692188 | T | C | OR11H6 |
| 14 | 20692453 | G | T | OR11H6 |
| 14 | 23312594 | G | A | MMP14 |

| Chr | Position | ref | alt | Gene |
|---|---|---|---|---|
| 14 | 24780016 | G | A | LTB4R2 |
| 14 | 38724185 | C | T | CLEC14A |
| 14 | 53019944 | A | G | GPR137C |
| 14 | 53019964 | CG CT GC AG CC TC AG GC GC CG CG | C | GPR137C |
| 14 | 58563694 | G | C | C14orf37 |
| 14 | 58605043 | G | A | C14orf37 |
| 14 | 58605072 | C | G | C14orf37 |
| 14 | 59931931 | T | G | GPR135 |
| 14 | 70924955 | A | C | ADAM21 |
| 14 | 70925501 | G | C | ADAM21 |
| 14 | 74876355 | G | C | SYNDIG1L |
| 14 | 86089315 | G | A | FLRT2 |
| 14 | 92958522 | A | C | SLC24A4 |
| 14 | 96703484 | C | T | BDKRB2 |
| 15 | 100269635 | G | C | LYSMD4 |
| 15 | 100269680 | G | C | LYSMD4 |
| 15 | 100269737 | G | A | LYSMD4 |
| 15 | 102462478 | TT AT C | T | OR4F4 |
| 15 | 22368855 | T | C | OR4M2 |
| 15 | 22368862 | G | A | OR4M2 |
| 15 | 22369132 | G | A | OR4M2 |
| 15 | 22382728 | C | T | OR4N4 |
| 15 | 22383249 | G | A | OR4N4 |
| 15 | 28260053 | G | A | OCA2 |
| 15 | 31369123 | A | G | TRPM1 |
| 15 | 31453147 | G | A | TRPM1 |
| 15 | 32446127 | G | A | CHRNA7 |
| 15 | 41803754 | G | A | LTK |
| 15 | 41860490 | T | A | TYRO3 |
| 15 | 45392075 | G | A | DUOX2 |
| 15 | 45399075 | G | A | DUOX2 |
| 15 | 45403967 | A | G | DUOX2 |

Figure 23 (Continued)

| Chr | Position | ref | alt | Gene |
|---|---|---|---|---|
| 15 | 45404066 | G | A | DUOX2 |
| 15 | 45427488 | C | T | DUOX1 |
| 15 | 48056219 | A | G | SEMA6D |
| 15 | 48058071 | G | A | SEMA6D |
| 15 | 51676020 | T | G | GLDN |
| 15 | 51696856 | G | A | GLDN |
| 15 | 55929515 | C | G | PRTG |
| 15 | 55972797 | T | C | PRTG |
| 15 | 65688138 | A | G | IGDCC4 |
| 15 | 65689267 | T | C | IGDCC4 |
| 15 | 65916527 | A | T | SLC24A1 |
| 15 | 65917355 | T | G | SLC24A1 |
| 15 | 66411441 | C | T | MEGF11 |
| 15 | 66850362 | C | T | LCTL |
| 15 | 68605169 | G | A | ITGA11 |
| 15 | 68609647 | G | T | ITGA11 |
| 15 | 68628049 | T | G | ITGA11 |
| 15 | 68628163 | C | T | ITGA11 |
| 15 | 73994806 | C | T | CD276 |
| 15 | 73995173 | C | T | CD276 |
| 15 | 73996066 | G | A | CD276 |
| 15 | 73996101 | G | A | CD276 |
| 15 | 75310766 | A | G | SCAMP5 |
| 15 | 75969335 | C | T | CSPG4 |
| 15 | 75970070 | C | T | CSPG4 |
| 15 | 75981550 | C | T | CSPG4 |
| 15 | 75981551 | G | A | CSPG4 |
| 15 | 75981803 | G | A | CSPG4 |
| 15 | 75981816 | C | T | CSPG4 |
| 15 | 75981841 | ACCTCCAGCACCAG | A | CSPG4 |
| 15 | 75981860 | C | T | CSPG4 |
| 15 | 75982058 | T | A | CSPG4 |
| 15 | 75982072 | G | A | CSPG4 |
| 15 | 75982085 | C | T | CSPG4 |
| 15 | 75982271 | C | T | CSPG4 |
| 15 | 75982492 | G | A | CSPG4 |
| 15 | 75982513 | A | G | CSPG4 |
| 15 | 75982581 | G | C | CSPG4 |

| Chr | Position | ref | alt | Gene |
|---|---|---|---|---|
| 15 | 75982670 | G | A | CSPG4 |
| 15 | 75985464 | C | T | CSPG4 |
| 15 | 75985469 | A | C | CSPG4 |
| 15 | 76254311 | C | T | NRG4 |
| 15 | 78922229 | T | C | CHRNB4 |
| 15 | 85448875 | C | A | SLC28A1 |
| 15 | 85478696 | C | T | SLC28A1 |
| 15 | 85478729 | G | A | SLC28A1 |
| 15 | 90039643 | T | C | RHCG |
| 15 | 90335788 | C | T | ANPEP |
| 15 | 90344352 | T | C | ANPEP |
| 15 | 90347814 | G | A | ANPEP |
| 15 | 90349558 | C | T | ANPEP |
| 15 | 90764219 | G | A | SEMA4B |
| 15 | 90768942 | C | T | SEMA4B |
| 15 | 93198678 | TTGGAGC | T | FAM174B |
| 15 | 93198784 | A | G | FAM174B |
| 16 | 1250389 | A | G | CACNA1H |
| 16 | 14956982 | G | A | NOMO1 |
| 16 | 14960480 | A | G | NOMO1 |
| 16 | 14988868 | A | G | NOMO1 |
| 16 | 1584438 | G | C | TMEM204 |
| 16 | 1584446 | G | C | TMEM204 |
| 16 | 16358944 | G | A | NOMO3 |
| 16 | 16367613 | G | T | NOMO3 |
| 16 | 19041595 | G | A | TMC7 |
| 16 | 19471571 | G | A | TMC5 |
| 16 | 19475099 | C | A | TMC5 |
| 16 | 2140554 | G | A | PKD1 |
| 16 | 2152387 | A | G | PKD1 |
| 16 | 2152865 | C | G | PKD1 |
| 16 | 2153414 | A | T | PKD1 |
| 16 | 2155426 | T | C | PKD1 |
| 16 | 2158672 | G | A | PKD1 |
| 16 | 2158680 | C | T | PKD1 |
| 16 | 2159341 | C | T | PKD1 |
| 16 | 2160973 | A | G | PKD1 |
| 16 | 2161666 | G | A | PKD1 |
| 16 | 2161744 | G | A | PKD1 |
| 16 | 2162361 | A | G | PKD1 |
| 16 | 2164211 | G | A | PKD1 |

Figure 23 (Continued)

| Chr | Position | ref | alt | Gene |
|---|---|---|---|---|
| 16 | 2164808 | C | T | PKD1 |
| 16 | 2165395 | G | A | PKD1 |
| 16 | 2166538 | G | A | PKD1 |
| 16 | 23388540 | G | T | SCNN1B |
| 16 | 24902299 | C | G | SLC5A11 |
| 16 | 27356203 | A | G | IL4R |
| 16 | 28944396 | C | G | CD19 |
| 16 | 29675114 | C | T | SPN |
| 16 | 29675326 | A | G | SPN |
| 16 | 29899123 | G | T | SEZ6L2 |
| 16 | 29979430 | T | C | TMEM219 |
| 16 | 30124072 | C | G | GDPD3 |
| 16 | 30492823 | C | T | ITGAL |
| 16 | 30516565 | C | A | ITGAL |
| 16 | 30518041 | G | C | ITGAL |
| 16 | 309998 | C | T | ITFG3 |
| 16 | 31276811 | G | A | ITGAM |
| 16 | 31336888 | C | T | ITGAM |
| 16 | 31367318 | T | C | ITGAX |
| 16 | 31371674 | G | A | ITGAX |
| 16 | 31374535 | C | G | ITGAX |
| 16 | 31391120 | T | C | ITGAX |
| 16 | 318822 | G | T | ITFG3 |
| 16 | 3405986 | G | A | OR2C1 |
| 16 | 426329 | A | C | TMEM8A |
| 16 | 426432 | T | C | TMEM8A |
| 16 | 427479 | T | C | TMEM8A |
| 16 | 57689805 | A | C | GPR56 |
| 16 | 57710156 | C | T | GPR97 |
| 16 | 57718325 | G | A | GPR97 |
| 16 | 57935442 | G | A | CNGB1 |
| 16 | 57935470 | C | T | CNGB1 |
| 16 | 57937788 | T | C | CNGB1 |
| 16 | 58079165 | G | A | MMP15 |
| 16 | 65022234 | C | T | CDH11 |
| 16 | 65025718 | G | A | CDH11 |
| 16 | 66432381 | T | C | CDH5 |
| 16 | 66432423 | T | C | CDH5 |
| 16 | 66944180 | C | T | CDH16 |
| 16 | 66945947 | C | T | CDH16 |
| 16 | 66948130 | G | A | CDH16 |
| 16 | 68325203 | T | A | SLC7A6 |
| 16 | 68719113 | G | A | CDH3 |
| 16 | 68721533 | G | C | CDH3 |

| Chr | Position | ref | alt | Gene |
|---|---|---|---|---|
| 16 | 76482747 | C | G | CNTNAP4 |
| 16 | 76501304 | G | C | CNTNAP4 |
| 16 | 76532583 | A | G | CNTNAP4 |
| 16 | 76587202 | T | G | CNTNAP4 |
| 16 | 81180988 | C | G | PKD1L2 |
| 16 | 81180995 | T | C | PKD1L2 |
| 16 | 81181097 | G | T | PKD1L2 |
| 16 | 81181783 | T | C | PKD1L2 |
| 16 | 81181821 | T | C | PKD1L2 |
| 16 | 81181869 | T | C | PKD1L2 |
| 16 | 81183325 | T | A | PKD1L2 |
| 16 | 81185412 | C | T | PKD1L2 |
| 16 | 81190598 | T | C | PKD1L2 |
| 16 | 81190613 | A | G | PKD1L2 |
| 16 | 81190669 | T | C | PKD1L2 |
| 16 | 81193358 | C | G | PKD1L2 |
| 16 | 81194335 | T | C | PKD1L2 |
| 16 | 81199520 | T | C | PKD1L2 |
| 16 | 81199538 | T | C | PKD1L2 |
| 16 | 81199544 | G | A | PKD1L2 |
| 16 | 81208203 | G | T | PKD1L2 |
| 16 | 81208348 | G | T | PKD1L2 |
| 16 | 81208473 | G | T | PKD1L2 |
| 16 | 81208515 | G | A | PKD1L2 |
| 16 | 81241100 | G | C | PKD1L2 |
| 16 | 81242102 | G | A | PKD1L2 |
| 16 | 81242194 | T | C | PKD1L2 |
| 16 | 81242198 | G | A | PKD1L2 |
| 16 | 81249892 | T | C | PKD1L2 |
| 16 | 81249927 | C | T | PKD1L2 |
| 16 | 81249954 | T | A | PKD1L2 |
| 16 | 81253759 | A | G | PKD1L2 |
| 16 | 81253917 | A | G | PKD1L2 |
| 16 | 824270 | C | A | MSLNL |
| 16 | 824473 | G | A | MSLNL |
| 16 | 824927 | T | C | MSLNL |
| 16 | 825234 | C | T | MSLNL |
| 16 | 825628 | G | A | MSLNL |
| 16 | 828760 | G | C | MSLNL |
| 16 | 84256103 | C | T | KCNG4 |
| 16 | 84256410 | C | T | KCNG4 |
| 16 | 84256422 | C | T | KCNG4 |
| 16 | 84256619 | C | T | KCNG4 |
| 16 | 84474484 | G | A | ATP2C2 |

Figure 23 (Continued)

| Chr | Position | ref | alt | Gene |
|---|---|---|---|---|
| 16 | 84476200 | A | T | ATP2C2 |
| 16 | 84485677 | T | A | ATP2C2 |
| 16 | 84495704 | G | C | ATP2C2 |
| 16 | 89262657 | G | A | SLC22A31 |
| 17 | 1183338 | C | T | TUSC5 |
| 17 | 1183354 | T | C | TUSC5 |
| 17 | 1183464 | A | G | TUSC5 |
| 17 | 21319007 | G | A | KCNJ12 |
| 17 | 21319121 | C | T | KCNJ12 |
| 17 | 27284194 | T | C | SEZ6 |
| 17 | 27284443 | A | G | SEZ6 |
| 17 | 27286851 | T | C | SEZ6 |
| 17 | 27287531 | C | T | SEZ6 |
| 17 | 28706114 | C | T | CPD |
| 17 | 28749880 | A | G | CPD |
| 17 | 2996217 | C | T | OR1D2 |
| 17 | 3030582 | C | G | OR1G1 |
| 17 | 30372739 | C | T | LRRC37B |
| 17 | 3101590 | C | T | OR1A2 |
| 17 | 31323899 | G | A | SPACA3 |
| 17 | 3181644 | G | C | OR3A2 |
| 17 | 3181662 | G | C | OR3A2 |
| 17 | 3182172 | C | T | OR3A2 |
| 17 | 3195603 | T | A | OR3A1 |
| 17 | 32956086 | A | C | TMEM132E |
| 17 | 32957114 | G | A | TMEM132E |
| 17 | 32961994 | T | G | TMEM132E |
| 17 | 3431403 | C | G | TRPV3 |
| 17 | 3635740 | C | G | ITGAE |
| 17 | 3657159 | C | T | ITGAE |
| 17 | 3657175 | T | C | ITGAE |
| 17 | 40841001 | G | C | CNTNAP1 |
| 17 | 41003859 | C | T | AOC3 |
| 17 | 41004637 | G | A | AOC3 |
| 17 | 41004681 | C | T | AOC3 |
| 17 | 41008373 | G | A | AOC3 |
| 17 | 41931375 | A | G | CD300LG |
| 17 | 42437000 | G | A | FAM171A2 |
| 17 | 42453065 | A | C | ITGA2B |
| 17 | 44372608 | G | A | LRRC37A |
| 17 | 44405764 | A | C | LRRC37A |
| 17 | 44407828 | C | T | LRRC37A |
| 17 | 44408406 | A | G | LRRC37A |
| 17 | 44409165 | G | A | LRRC37A |
| 17 | 44409255 | A | G | LRRC37A |
| 17 | 44590284 | G | A | LRRC37A2 |
| 17 | 44623627 | A | C | LRRC37A2 |
| 17 | 44625834 | C | G | LRRC37A2 |
| 17 | 44625866 | A | C | LRRC37A2 |
| 17 | 44625928 | C | A | LRRC37A2 |
| 17 | 44626347 | T | C | LRRC37A2 |
| 17 | 44626866 | T | C | LRRC37A2 |
| 17 | 44627027 | G | A | LRRC37A2 |
| 17 | 44627117 | A | G | LRRC37A2 |
| 17 | 45360730 | T | C | ITGB3 |
| 17 | 4638563 | G | A | CXCL16 |
| 17 | 4638737 | A | G | CXCL16 |
| 17 | 47587819 | C | T | NGFR |
| 17 | 48149503 | A | T | ITGA3 |
| 17 | 48155425 | G | A | ITGA3 |
| 17 | 4836381 | C | T | GP1BA |
| 17 | 4837202 | ACCACCCCCAGAGCCCAC | A | GP1BA |
| 17 | 48712329 | G | A | ABCC3 |
| 17 | 48712336 | G | C | ABCC3 |
| 17 | 56233034 | C | A | OR4D1 |
| 17 | 56247575 | C | T | OR4D2 |
| 17 | 56492800 | T | C | RNF43 |
| 17 | 60741917 | G | A | MRC2 |
| 17 | 60744158 | G | T | MRC2 |
| 17 | 60758296 | A | C | MRC2 |
| 17 | 60767015 | G | A | MRC2 |
| 17 | 61584720 | A | T | ACE |
| 17 | 62020348 | T | C | SCN4A |
| 17 | 62856153 | G | A | LRRC37A3 |
| 17 | 62856621 | T | C | LRRC37A3 |
| 17 | 62890818 | C | T | LRRC37A3 |
| 17 | 62890867 | C | T | LRRC37A3 |
| 17 | 62891154 | G | A | LRRC37A3 |
| 17 | 62892071 | G | C | LRRC37A3 |
| 17 | 62892159 | G | T | LRRC37A3 |

Figure 23 (Continued)

| Chr | Position | ref | alt | Gene |
|---|---|---|---|---|
| 17 | 62892181 | G | C | LRRC37A3 |
| 17 | 62892442 | G | C | LRRC37A3 |
| 17 | 6980273 | C | T | CLEC10A |
| 17 | 7012079 | C | T | ASGR2 |
| 17 | 71238433 | G | A | C17orf80 |
| 17 | 71380062 | G | A | SDK2 |
| 17 | 71380087 | G | C | SDK2 |
| 17 | 71384080 | G | C | SDK2 |
| 17 | 71426656 | G | T | SDK2 |
| 17 | 71434193 | C | T | SDK2 |
| 17 | 71452153 | A | G | SDK2 |
| 17 | 72233559 | G | A | TTYH2 |
| 17 | 72240168 | G | A | TTYH2 |
| 17 | 72240177 | T | G | TTYH2 |
| 17 | 72363857 | GC | G | GPR142 |
| 17 | 72469966 | G | A | CD300A |
| 17 | 72540936 | G | A | CD300C |
| 17 | 72610089 | C | T | CD300E |
| 17 | 72610164 | T | C | CD300E |
| 17 | 7339627 | C | T | TMEM102 |
| 17 | 7348625 | A | G | CHRNB1 |
| 17 | 7462969 | A | G | TNFSF12 |
| 17 | 78215587 | C | T | SLC26A11 |
| 17 | 7906519 | G | T | GUCY2D |
| 17 | 79768748 | A | C | GCGR |
| 17 | 80282566 | C | T | SECTM1 |
| 17 | 9729445 | A | T | GLP2R |
| 18 | 10471732 | G | A | APCDD1 |
| 18 | 10485612 | A | C | APCDD1 |
| 18 | 28720072 | G | A | DSC1 |
| 18 | 28720147 | C | T | DSC1 |
| 18 | 28919779 | A | C | DSG1 |
| 18 | 28919794 | C | A | DSG1 |
| 18 | 28919884 | A | C | DSG1 |
| 18 | 28919911 | A | G | DSG1 |
| 18 | 28919913 | G | A | DSG1 |
| 18 | 29046606 | G | A | DSG3 |
| 18 | 29790520 | G | A | MEP1B |
| 18 | 29795101 | T | C | MEP1B |
| 18 | 334742 | C | T | COLEC12 |
| 18 | 334994 | A | G | COLEC12 |
| 18 | 335099 | T | C | COLEC12 |
| 18 | 43417684 | G | A | SIGLEC15 |
| 18 | 43417698 | C | G | SIGLEC15 |

| Chr | Position | ref | alt | Gene |
|---|---|---|---|---|
| 18 | 43417812 | C | A | SIGLEC15 |
| 18 | 50432602 | C | G | DCC |
| 18 | 50936935 | A | G | DCC |
| 18 | 52265308 | A | C | DYNAP |
| 18 | 59174759 | C | A | CDH20 |
| 18 | 60021761 | C | T | TNFRSF11A |
| 18 | 60027241 | C | T | TNFRSF11A |
| 18 | 60028921 | G | A | TNFRSF11A |
| 18 | 63530016 | A | G | CDH7 |
| 18 | 64176319 | T | G | CDH19 |
| 18 | 64211251 | C | T | CDH19 |
| 18 | 64235877 | G | A | CDH19 |
| 18 | 7774190 | T | A | PTPRM |
| 19 | 1000665 | G | A | GRIN3B |
| 19 | 1000717 | C | A | GRIN3B |
| 19 | 1000785 | C | T | GRIN3B |
| 19 | 1003162 | C | T | GRIN3B |
| 19 | 1003172 | C | T | GRIN3B |
| 19 | 1003221 | C | A | GRIN3B |
| 19 | 1003657 | G | A | GRIN3B |
| 19 | 1044712 | A | G | ABCA7 |
| 19 | 10449358 | T | C | ICAM3 |
| 19 | 1055191 | G | A | ABCA7 |
| 19 | 10742170 | A | G | SLC44A2 |
| 19 | 10961024 | C | G | C19orf38 |
| 19 | 11222300 | G | A | LDLR |
| 19 | 11233909 | A | C | LDLR |
| 19 | 14153293 | T | C | IL27RA |
| 19 | 14269279 | T | G | LPHN1 |
| 19 | 14499616 | C | T | CD97 |
| 19 | 14507213 | A | C | CD97 |
| 19 | 14507228 | A | C | CD97 |
| 19 | 14758168 | G | A | EMR3 |
| 19 | 14769339 | C | G | EMR3 |
| 19 | 14862458 | G | A | EMR2 |
| 19 | 14875388 | G | A | EMR2 |
| 19 | 14876195 | G | T | EMR2 |
| 19 | 14877799 | G | C | EMR2 |
| 19 | 14910438 | C | T | OR7C1 |
| 19 | 14910654 | T | C | OR7C1 |
| 19 | 14951879 | C | T | OR7A10 |
| 19 | 14951882 | T | A | OR7A10 |
| 19 | 14951884 | T | G | OR7A10 |
| 19 | 14952143 | G | C | OR7A10 |

Figure 23 (Continued)

| Chr | Position | ref | alt | Gene |
|---|---|---|---|---|
| 19 | 15197898 | G | A | OR1I1 |
| 19 | 15198363 | A | C | OR1I1 |
| 19 | 15290007 | C | T | NOTCH3 |
| 19 | 15839365 | C | T | OR10H2 |
| 19 | 15852495 | G | T | OR10H3 |
| 19 | 15918349 | C | T | OR10H1 |
| 19 | 15918802 | C | G | OR10H1 |
| 19 | 16060110 | G | T | OR10H4 |
| 19 | 17471634 | G | A | PLVAP |
| 19 | 17994836 | G | A | SLC5A5 |
| 19 | 18174731 | C | T | IL12RB1 |
| 19 | 18180451 | A | G | IL12RB1 |
| 19 | 18186618 | T | C | IL12RB1 |
| 19 | 18188408 | C | T | IL12RB1 |
| 19 | 18193060 | G | A | IL12RB1 |
| 19 | 2290499 | C | T | LINGO3 |
| 19 | 2396611 | C | T | TMPRSS9 |
| 19 | 2405456 | C | T | TMPRSS9 |
| 19 | 2408530 | G | A | TMPRSS9 |
| 19 | 2416796 | A | G | TMPRSS9 |
| 19 | 2425184 | A | G | TMPRSS9 |
| 19 | 2425196 | G | A | TMPRSS9 |
| 19 | 30021023 | G | C | VSTM2B |
| 19 | 30021131 | G | A | VSTM2B |
| 19 | 33355055 | A | G | SLC7A9 |
| 19 | 33696350 | C | T | LRP3 |
| 19 | 35524607 | G | A | SCN1B |
| 19 | 35718891 | C | T | FAM187B |
| 19 | 35718938 | C | T | FAM187B |
| 19 | 35719020 | C | T | FAM187B |
| 19 | 35719076 | C | T | FAM187B |
| 19 | 35719106 | A | G | FAM187B |
| 19 | 35719438 | G | A | FAM187B |
| 19 | 35790645 | C | A | MAG |
| 19 | 35850022 | A | G | FFAR3 |
| 19 | 35850264 | G | A | FFAR3 |
| 19 | 35863028 | T | C | GPR42 |
| 19 | 36231288 | C | T | IGFLR1 |
| 19 | 36330422 | C | G | NPHS1 |
| 19 | 36336437 | T | C | NPHS1 |
| 19 | 36339247 | C | T | NPHS1 |
| 19 | 36349752 | G | A | KIRREL2 |
| 19 | 36350474 | G | A | KIRREL2 |
| 19 | 38851193 | T | G | CATSPERG |

| Chr | Position | ref | alt | Gene |
|---|---|---|---|---|
| 19 | 38851455 | A | C | CATSPERG |
| 19 | 39993470 | T | A | DLL3 |
| 19 | 39993560 | T | G | DLL3 |
| 19 | 39994711 | T | C | DLL3 |
| 19 | 41884327 | T | C | TMEM91 |
| 19 | 42083739 | A | AGAC | CEACAM21 |
| 19 | 42083849 | C | A | CEACAM21 |
| 19 | 42085873 | A | G | CEACAM21 |
| 19 | 42132193 | T | C | CEACAM4 |
| 19 | 42301685 | A | C | CEACAM3 |
| 19 | 42301689 | T | A | CEACAM3 |
| 19 | 42301763 | A | C | CEACAM3 |
| 19 | 42301854 | A | G | CEACAM3 |
| 19 | 42863035 | A | G | MEGF8 |
| 19 | 42874901 | G | A | MEGF8 |
| 19 | 43031248 | T | G | CEACAM1 |
| 19 | 43031267 | G | A | CEACAM1 |
| 19 | 43031369 | G | A | CEACAM1 |
| 19 | 43031434 | T | A | CEACAM1 |
| 19 | 43031514 | G | T | CEACAM1 |
| 19 | 45150614 | G | A | PVR |
| 19 | 45161070 | G | A | PVR |
| 19 | 45179567 | C | T | CEACAM19 |
| 19 | 45321841 | G | A | BCAM |
| 19 | 45322744 | A | G | BCAM |
| 19 | 47127439 | A | G | PTGIR |
| 19 | 47823038 | G | A | C5AR1 |
| 19 | 47823871 | G | T | C5AR1 |
| 19 | 49693558 | A | C | TRPM4 |
| 19 | 49699758 | TGCTGCGGGGGCC | T | TRPM4 |
| 19 | 49930180 | T | C | GFY |
| 19 | 49930295 | C | G | GFY |
| 19 | 49930352 | C | A | GFY |
| 19 | 49930721 | T | C | GFY |
| 19 | 49930786 | C | A | GFY |
| 19 | 501719 | T | C | MADCAM1 |
| 19 | 501767 | C | T | MADCAM1 |

Figure 23 (Continued)

| Chr | Position | ref | alt | Gene |
|---|---|---|---|---|
| 19 | 501801 | A | C | MADCAM1 |
| 19 | 501802 | G | C | MADCAM1 |
| 19 | 501900 | C | A | MADCAM1 |
| 19 | 50462298 | G | C | SIGLEC11 |
| 19 | 50462860 | C | T | SIGLEC11 |
| 19 | 50463030 | C | A | SIGLEC11 |
| 19 | 50463035 | G | T | SIGLEC11 |
| 19 | 50463044 | T | C | SIGLEC11 |
| 19 | 50463982 | T | G | SIGLEC11 |
| 19 | 50464171 | C | G | SIGLEC11 |
| 19 | 50464184 | T | C | SIGLEC11 |
| 19 | 51294098 | C | T | ACPT |
| 19 | 51628529 | A | G | SIGLEC9 |
| 19 | 51628622 | A | C | SIGLEC9 |
| 19 | 51630482 | C | A | SIGLEC9 |
| 19 | 51630485 | C | A | SIGLEC9 |
| 19 | 51728641 | A | G | CD33 |
| 19 | 51728815 | T | C | CD33 |
| 19 | 51729594 | T | C | CD33 |
| 19 | 51841312 | C | T | VSIG10L |
| 19 | 51841417 | C | T | VSIG10L |
| 19 | 51918360 | A | G | SIGLEC10 |
| 19 | 51919263 | G | T | SIGLEC10 |
| 19 | 51919302 | T | C | SIGLEC10 |
| 19 | 51919949 | G | A | SIGLEC10 |
| 19 | 51920103 | G | C | SIGLEC10 |
| 19 | 51920112 | C | T | SIGLEC10 |
| 19 | 51920115 | C | T | SIGLEC10 |
| 19 | 51920196 | G | T | SIGLEC10 |
| 19 | 51960940 | A | G | SIGLEC8 |
| 19 | 52000672 | G | A | SIGLEC12 |
| 19 | 52001485 | G | A | SIGLEC12 |
| 19 | 52004743 | G | A | SIGLEC12 |
| 19 | 52004747 | G | T | SIGLEC12 |
| 19 | 52004903 | G | A | SIGLEC12 |
| 19 | 52033038 | T | G | SIGLEC6 |
| 19 | 52033158 | C | T | SIGLEC6 |
| 19 | 52033206 | G | A | SIGLEC6 |
| 19 | 52130925 | G | A | SIGLEC5 |
| 19 | 52131119 | A | G | SIGLEC5 |
| 19 | 52133292 | A | G | SIGLEC5 |
| 19 | 5223018 | G | A | PTPRS |
| 19 | 52249680 | T | A | FPR1 |
| 19 | 52250216 | A | G | FPR1 |

| Chr | Position | ref | alt | Gene |
|---|---|---|---|---|
| 19 | 53518178 | C | G | ERVV-1 |
| 19 | 53554075 | A | G | ERVV-2 |
| 19 | 53761740 | T | C | VN1R2 |
| 19 | 54578105 | C | T | TARM1 |
| 19 | 54675643 | G | A | TMC4 |
| 19 | 54724061 | A | G | LILRB3 |
| 19 | 54724407 | C | T | LILRB3 |
| 19 | 54724443 | G | A | LILRB3 |
| 19 | 54724458 | A | G | LILRB3 |
| 19 | 54724635 | C | T | LILRB3 |
| 19 | 54724979 | C | T | LILRB3 |
| 19 | 54725798 | G | T | LILRB3 |
| 19 | 54725864 | C | T | LILRB3 |
| 19 | 54725907 | G | C | LILRB3 |
| 19 | 54725913 | C | T | LILRB3 |
| 19 | 54725930 | C | T | LILRB3 |
| 19 | 54726162 | T | G | LILRB3 |
| 19 | 54726241 | C | T | LILRB3 |
| 19 | 54726299 | A | C | LILRB3 |
| 19 | 54726324 | G | C | LILRB3 |
| 19 | 54726347 | T | A | LILRB3 |
| 19 | 54743824 | T | G | LILRA6 |
| 19 | 54744159 | T | C | LILRA6 |
| 19 | 54744195 | G | A | LILRA6 |
| 19 | 54744210 | A | G | LILRA6 |
| 19 | 54744387 | C | T | LILRA6 |
| 19 | 54744794 | G | A | LILRA6 |
| 19 | 54744799 | G | C | LILRA6 |
| 19 | 54744919 | T | A | LILRA6 |
| 19 | 54745497 | G | A | LILRA6 |
| 19 | 54745550 | G | T | LILRA6 |
| 19 | 54745576 | C | G | LILRA6 |
| 19 | 54745907 | A | G | LILRA6 |
| 19 | 54745993 | C | T | LILRA6 |
| 19 | 54746051 | A | C | LILRA6 |
| 19 | 54759361 | T | C | LILRB5 |
| 19 | 54782670 | T | C | LILRB2 |
| 19 | 54782724 | G | A | LILRB2 |
| 19 | 54784122 | T | C | LILRB2 |
| 19 | 54848121 | C | T | LILRA4 |
| 19 | 54848157 | A | G | LILRA4 |
| 19 | 54849399 | T | C | LILRA4 |
| 19 | 54849942 | G | A | LILRA4 |
| 19 | 54871664 | G | C | LAIR1 |

Figure 23 (Continued)

| Chr | Position | ref | alt | Gene | Chr | Position | ref | alt | Gene |
|---|---|---|---|---|---|---|---|---|---|
| 19 | 54872594 | G | A | LAIR1 | 19 | 55258808 | C | T | KIR2DL3 |
| 19 | 54872611 | A | T | LAIR1 | 19 | 55285072 | A | G | KIR2DL1 |
| 19 | 54872698 | C | G | LAIR1 | 19 | 55286650 | T | C | KIR2DL1 |
| 19 | 55085770 | C | A | LILRA2 | 19 | 55317456 | G | A | KIR2DL4 |
| 19 | 55086296 | G | A | LILRA2 | 19 | 55317612 | G | A | KIR2DL4 |
| 19 | 55086890 | C | T | LILRA2 | 19 | 55317633 | G | A | KIR2DL4 |
| 19 | 55087313 | T | G | LILRA2 | 19 | 55317669 | C | G | KIR2DL4 |
| 19 | 55087403 | G | C | LILRA2 | 19 | 55329021 | A | G | KIR3DL1 |
| 19 | 55087462 | C | T | LILRA2 | 19 | 55329854 | G | A | KIR3DL1 |
| 19 | 55087490 | T | C | LILRA2 | 19 | 55330019 | C | T | KIR3DL1 |
| 19 | 55098677 | G | C | LILRA2 | 19 | 55333193 | C | A | KIR3DL1 |
| 19 | 55098680 | A | C | LILRA2 | 19 | 55333256 | C | T | KIR3DL1 |
| 19 | 55098686 | C | A | LILRA2 | 19 | 55333275 | G | T | KIR3DL1 |
| 19 | 55098695 | A | G | LILRA2 | 19 | 55363482 | C | T | KIR3DL2 |
| 19 | 55106663 | A | G | LILRA1 | 19 | 55363504 | G | A | KIR3DL2 |
| 19 | 55106778 | G | A | LILRA1 | 19 | 55365240 | C | A | KIR3DL2 |
| 19 | 55106865 | T | C | LILRA1 | 19 | 55365320 | G | T | KIR3DL2 |
| 19 | 55107223 | G | T | LILRA1 | 19 | 55396913 | G | A | FCAR |
| 19 | 55107227 | A | G | LILRA1 | 19 | 55418054 | A | C | NCR1 |
| 19 | 55107343 | T | C | LILRA1 | 19 | 55527081 | C | T | GP6 |
| 19 | 55107363 | G | T | LILRA1 | 19 | 55536595 | G | A | GP6 |
| 19 | 55143083 | T | C | LILRB1 | 19 | 55710074 | G | A | PTPRH |
| 19 | 55143157 | G | A | LILRB1 | 19 | 55713535 | G | A | PTPRH |
| 19 | 55143199 | C | T | LILRB1 | 19 | 55715309 | C | T | PTPRH |
| 19 | 55143208 | A | C | LILRB1 | 19 | 55715359 | A | G | PTPRH |
| 19 | 55143209 | G | C | LILRB1 | 19 | 55716742 | C | T | PTPRH |
| 19 | 55143452 | T | C | LILRB1 | 19 | 55953906 | T | G | SHISA7 |
| 19 | 55143491 | G | T | LILRB1 | 19 | 5733874 | T | C | CATSPERD |
| 19 | 55144100 | A | G | LILRB1 | 19 | 5744499 | T | C | CATSPERD |
| 19 | 55144207 | C | G | LILRB1 | 19 | 5749171 | A | G | CATSPERD |
| 19 | 55144208 | G | A | LILRB1 | 19 | 5772897 | C | T | CATSPERD |
| 19 | 55144556 | G | A | LILRB1 | 19 | 5772950 | G | A | CATSPERD |
| 19 | 55144623 | C | T | LILRB1 | 19 | 6531285 | G | T | TNFSF9 |
| 19 | 55144710 | A | T | LILRB1 | 19 | 6534841 | G | A | TNFSF9 |
| 19 | 55144711 | G | C | LILRB1 | 19 | 6665020 | T | C | TNFSF14 |
| 19 | 55145454 | G | A | LILRB1 | 19 | 6901891 | G | A | EMR1 |
| 19 | 55146106 | C | G | LILRB1 | 19 | 6903920 | A | G | EMR1 |
| 19 | 55176262 | A | G | LILRB4 | 19 | 6904137 | C | T | EMR1 |
| 19 | 55237603 | G | A | KIR3DL3 | 19 | 6913707 | C | T | EMR1 |
| 19 | 55237677 | C | T | KIR3DL3 | 19 | 6913811 | A | G | EMR1 |
| 19 | 55239168 | G | T | KIR3DL3 | 19 | 6919624 | A | C | EMR1 |
| 19 | 55239176 | G | A | KIR3DL3 | 19 | 6919753 | A | G | EMR1 |
| 19 | 55253450 | T | G | KIR2DL3 | 19 | 6921868 | G | A | EMR1 |
| 19 | 55253567 | A | G | KIR2DL3 | 19 | 6926378 | T | C | EMR1 |

Figure 23 (Continued)

| Chr | Position | ref | alt | Gene |
|---|---|---|---|---|
| 19 | 7743821 | A | G | C19orf59 |
| 19 | 7743845 | T | G | C19orf59 |
| 19 | 7831061 | A | G | CLEC4M |
| 19 | 7831628 | G | A | CLEC4M |
| 19 | 7981568 | C | T | TGFBR3L |
| 19 | 7982478 | C | G | TGFBR3L |
| 19 | 8367709 | C | T | CD320 |
| 19 | 8841461 | G | A | OR2Z1 |
| 19 | 8962389 | G | A | MUC16 |
| 19 | 8979223 | G | C | MUC16 |
| 19 | 8982271 | G | A | MUC16 |
| 19 | 8987218 | G | T | MUC16 |
| 19 | 8993018 | G | A | MUC16 |
| 19 | 8996460 | A | C | MUC16 |
| 19 | 8999445 | C | T | MUC16 |
| 19 | 8999449 | G | T | MUC16 |
| 19 | 9001833 | A | G | MUC16 |
| 19 | 9002504 | T | C | MUC16 |
| 19 | 9002519 | G | C | MUC16 |
| 19 | 9002576 | T | C | MUC16 |
| 19 | 9002597 | C | T | MUC16 |
| 19 | 9002612 | T | G | MUC16 |
| 19 | 9002636 | C | T | MUC16 |
| 19 | 9002659 | C | T | MUC16 |
| 19 | 9002660 | C | T | MUC16 |
| 19 | 9003615 | C | T | MUC16 |
| 19 | 9003618 | C | T | MUC16 |
| 19 | 9003640 | G | T | MUC16 |
| 19 | 9003645 | G | A | MUC16 |
| 19 | 9005616 | G | T | MUC16 |
| 19 | 9006749 | C | T | MUC16 |
| 19 | 9015670 | C | T | MUC16 |
| 19 | 9016693 | A | AGGT | MUC16 |
| 19 | 9017468 | C | T | MUC16 |
| 19 | 9018441 | G | C | MUC16 |
| 19 | 9018508 | T | G | MUC16 |
| 19 | 9018516 | G | T | MUC16 |
| 19 | 9018540 | A | G | MUC16 |
| 19 | 9020153 | C | T | MUC16 |
| 19 | 9024871 | C | T | MUC16 |
| 19 | 9028373 | G | A | MUC16 |
| 19 | 9045821 | G | A | MUC16 |
| 19 | 9045897 | G | T | MUC16 |

| Chr | Position | ref | alt | Gene |
|---|---|---|---|---|
| 19 | 9046876 | G | T | MUC16 |
| 19 | 9047267 | C | T | MUC16 |
| 19 | 9048035 | G | C | MUC16 |
| 19 | 9048170 | G | A | MUC16 |
| 19 | 9048320 | C | T | MUC16 |
| 19 | 9048335 | G | T | MUC16 |
| 19 | 9048342 | C | T | MUC16 |
| 19 | 9048895 | A | C | MUC16 |
| 19 | 9049149 | G | A | MUC16 |
| 19 | 9049322 | G | A | MUC16 |
| 19 | 9049910 | C | T | MUC16 |
| 19 | 9056941 | A | G | MUC16 |
| 19 | 9056982 | G | A | MUC16 |
| 19 | 9056989 | C | G | MUC16 |
| 19 | 9057408 | A | G | MUC16 |
| 19 | 9057687 | A | G | MUC16 |
| 19 | 9057721 | C | T | MUC16 |
| 19 | 9057750 | T | A | MUC16 |
| 19 | 9058624 | G | A | MUC16 |
| 19 | 9058907 | G | C | MUC16 |
| 19 | 9058942 | C | T | MUC16 |
| 19 | 9059159 | T | G | MUC16 |
| 19 | 9059181 | G | A | MUC16 |
| 19 | 9059232 | T | C | MUC16 |
| 19 | 9059307 | C | T | MUC16 |
| 19 | 9060059 | A | C | MUC16 |
| 19 | 9060085 | C | T | MUC16 |
| 19 | 9060541 | C | T | MUC16 |
| 19 | 9060774 | A | G | MUC16 |
| 19 | 9060915 | C | T | MUC16 |
| 19 | 9061560 | G | A | MUC16 |
| 19 | 9062544 | T | G | MUC16 |
| 19 | 9062622 | G | A | MUC16 |
| 19 | 9062847 | A | G | MUC16 |
| 19 | 9065203 | T | C | MUC16 |
| 19 | 9066132 | G | A | MUC16 |
| 19 | 9066140 | T | G | MUC16 |
| 19 | 9066259 | T | C | MUC16 |
| 19 | 9066874 | G | T | MUC16 |
| 19 | 9068374 | A | G | MUC16 |
| 19 | 9069792 | G | A | MUC16 |
| 19 | 9069892 | A | C | MUC16 |
| 19 | 9070186 | C | T | MUC16 |
| 19 | 9070194 | A | G | MUC16 |

Figure 23 (Continued)

| Chr | Position | ref | alt | Gene |
|---|---|---|---|---|
| 19 | 9070225 | G | C | MUC16 |
| 19 | 9070402 | G | T | MUC16 |
| 19 | 9070837 | G | A | MUC16 |
| 19 | 9071763 | T | A | MUC16 |
| 19 | 9072313 | A | G | MUC16 |
| 19 | 9072742 | T | C | MUC16 |
| 19 | 9072975 | G | A | MUC16 |
| 19 | 9074265 | G | A | MUC16 |
| 19 | 9074950 | G | T | MUC16 |
| 19 | 9075021 | G | A | MUC16 |
| 19 | 9075217 | T | A | MUC16 |
| 19 | 9075346 | T | A | MUC16 |
| 19 | 9075565 | C | T | MUC16 |
| 19 | 9075969 | C | T | MUC16 |
| 19 | 9076083 | G | A | MUC16 |
| 19 | 9076293 | T | C | MUC16 |
| 19 | 9076728 | C | T | MUC16 |
| 19 | 9076858 | C | T | MUC16 |
| 19 | 9076929 | T | G | MUC16 |
| 19 | 9076950 | C | A | MUC16 |
| 19 | 9077196 | C | T | MUC16 |
| 19 | 9077436 | G | A | MUC16 |
| 19 | 9077581 | G | T | MUC16 |
| 19 | 9077803 | T | C | MUC16 |
| 19 | 9080462 | C | G | MUC16 |
| 19 | 9080543 | G | A | MUC16 |
| 19 | 9082465 | GGTGTGAAGGTTAACGTCT | G | MUC16 |
| 19 | 9083143 | G | A | MUC16 |
| 19 | 9083174 | G | A | MUC16 |
| 19 | 9083314 | G | A | MUC16 |
| 19 | 9083457 | C | T | MUC16 |
| 19 | 9083576 | C | T | MUC16 |
| 19 | 9083791 | G | A | MUC16 |
| 19 | 9084197 | T | G | MUC16 |
| 19 | 9084233 | C | T | MUC16 |

| Chr | Position | ref | alt | Gene |
|---|---|---|---|---|
| 19 | 9084299 | T | C | MUC16 |
| 19 | 9084481 | C | T | MUC16 |
| 19 | 9084953 | C | A | MUC16 |
| 19 | 9085004 | T | C | MUC16 |
| 19 | 9085958 | A | G | MUC16 |
| 19 | 9086060 | C | T | MUC16 |
| 19 | 9086123 | A | C | MUC16 |
| 19 | 9086145 | G | C | MUC16 |
| 19 | 9086269 | T | C | MUC16 |
| 19 | 9086318 | G | A | MUC16 |
| 19 | 9086533 | T | C | MUC16 |
| 19 | 9087758 | G | A | MUC16 |
| 19 | 9088330 | G | A | MUC16 |
| 19 | 9088694 | G | A | MUC16 |
| 19 | 9088721 | A | T | MUC16 |
| 19 | 9088772 | T | C | MUC16 |
| 19 | 9090182 | T | C | MUC16 |
| 19 | 9090784 | C | T | MUC16 |
| 19 | 9091772 | G | A | MUC16 |
| 19 | 919933 | G | A | KISS1R |
| 19 | 9213396 | G | A | OR7G2 |
| 19 | 9225940 | G | A | OR7G1 |
| 19 | 9225973 | G | A | OR7G1 |
| 19 | 9226159 | TAA | T | OR7G1 |
| 19 | 9226192 | A | G | OR7G1 |
| 19 | 9237622 | T | C | OR7G3 |
| 19 | 9325252 | G | A | OR7D4 |
| 19 | 9325278 | G | A | OR7D4 |
| 19 | 9362297 | C | T | OR7E24 |
| 20 | 10622501 | G | C | JAG1 |
| 20 | 10626016 | T | G | JAG1 |
| 20 | 13830137 | A | C | SEL1L2 |
| 20 | 13912309 | G | A | SEL1L2 |
| 20 | 14306773 | T | G | FLRT3 |
| 20 | 1546911 | C | G | SIRPB1 |
| 20 | 1552430 | T | C | SIRPB1 |
| 20 | 1559259 | C | T | SIRPB1 |
| 20 | 1616137 | G | A | SIRPG |
| 20 | 1616206 | A | G | SIRPG |
| 20 | 1895889 | G | C | SIRPA |
| 20 | 1895949 | A | AGT | SIRPA |
| 20 | 1895963 | A | G | SIRPA |

Figure 23 (Continued)

| Chr | Position | ref | alt | Gene |
|---|---|---|---|---|
| 20 | 1895965 | C | A | SIRPA |
| 20 | 1895990 | G | A | SIRPA |
| 20 | 1896051 | CCGA | C | SIRPA |
| 20 | 1896059 | G | A | SIRPA |
| 20 | 1896060 | T | C | SIRPA |
| 20 | 19261606 | T | C | SLC24A3 |
| 20 | 19261623 | G | A | SLC24A3 |
| 20 | 23016692 | G | C | SSTR4 |
| 20 | 23016970 | T | G | SSTR4 |
| 20 | 23028686 | C | A | THBD |
| 20 | 23028724 | G | A | THBD |
| 20 | 23029695 | G | C | THBD |
| 20 | 23065209 | G | A | CD93 |
| 20 | 24964558 | T | C | APMAP |
| 20 | 25282967 | C | T | ABHD12 |
| 20 | 2945759 | C | T | PTPRA |
| 20 | 33447314 | C | T | GGT7 |
| 20 | 3452041 | C | T | ATRN |
| 20 | 3528101 | A | C | ATRN |
| 20 | 3541382 | T | C | ATRN |
| 20 | 3565356 | T | G | ATRN |
| 20 | 3577062 | G | A | ATRN |
| 20 | 3654128 | G | A | ADAM33 |
| 20 | 3655219 | T | C | ADAM33 |
| 20 | 3675333 | G | A | SIGLEC1 |
| 20 | 3675498 | T | G | SIGLEC1 |
| 20 | 3682126 | C | T | SIGLEC1 |
| 20 | 3684729 | T | C | SIGLEC1 |
| 20 | 3686436 | C | T | SIGLEC1 |
| 20 | 3686676 | C | G | SIGLEC1 |
| 20 | 41818289 | C | G | PTPRT |
| 20 | 4229375 | G | T | ADRA1D |
| 20 | 4229505 | CGCCCGCGCT | C | ADRA1D |
| 20 | 4229514 | T | C | ADRA1D |
| 20 | 44751363 | C | T | CD40 |
| 20 | 44869878 | C | T | CDH22 |
| 20 | 45174465 | C | T | OCSTAMP |
| 20 | 45354829 | C | G | SLC2A10 |
| 20 | 55066633 | T | G | GCNT7 |

| Chr | Position | ref | alt | Gene |
|---|---|---|---|---|
| 20 | 55070268 | A | T | GCNT7 |
| 20 | 58558015 | T | C | CDH26 |
| 20 | 6031477 | C | T | LRRN4 |
| 20 | 6033004 | G | A | LRRN4 |
| 20 | 6033033 | G | A | LRRN4 |
| 20 | 60503350 | A | G | CDH4 |
| 20 | 62737568 | T | C | NPBWR2 |
| 21 | 19651307 | G | A | TMPRSS15 |
| 21 | 19670118 | G | A | TMPRSS15 |
| 21 | 19687517 | T | G | TMPRSS15 |
| 21 | 19704422 | T | A | TMPRSS15 |
| 21 | 19756040 | C | G | TMPRSS15 |
| 21 | 19770562 | T | C | TMPRSS15 |
| 21 | 22710849 | G | A | NCAM2 |
| 21 | 22746187 | T | C | NCAM2 |
| 21 | 31587793 | A | G | CLDN8 |
| 21 | 34715699 | G | C | IFNAR1 |
| 21 | 34721782 | C | T | IFNAR1 |
| 21 | 34787312 | A | G | IFNGR2 |
| 21 | 39671476 | G | A | KCNJ15 |
| 21 | 41137507 | G | C | IGSF5 |
| 21 | 41142892 | T | A | IGSF5 |
| 21 | 41142932 | C | T | IGSF5 |
| 21 | 41143018 | T | A | IGSF5 |
| 21 | 41725625 | C | T | DSCAM |
| 21 | 41725630 | G | C | DSCAM |
| 21 | 42852497 | C | T | TMPRSS2 |
| 21 | 43505436 | G | A | UMODL1 |
| 21 | 43529749 | A | C | UMODL1 |
| 21 | 43531403 | C | G | UMODL1 |
| 21 | 43531553 | A | C | UMODL1 |
| 21 | 43531632 | T | C | UMODL1 |
| 21 | 43531731 | C | T | UMODL1 |
| 21 | 43539293 | G | A | UMODL1 |
| 21 | 43546509 | G | A | UMODL1 |
| 21 | 43803167 | T | C | TMPRSS3 |
| 21 | 43808627 | C | T | TMPRSS3 |
| 21 | 43809092 | C | T | TMPRSS3 |
| 21 | 45656774 | C | T | ICOSLG |
| 21 | 45656920 | C | T | ICOSLG |
| 21 | 45821582 | T | G | TRPM2 |
| 21 | 46309312 | G | A | ITGB2 |
| 22 | 16449784 | C | A | OR11H1 |
| 22 | 19951271 | G | A | COMT |

Figure 23 (Continued)

| Chr | Position | ref | alt | Gene |
|---|---|---|---|---|
| 22 | 20784050 | T | A | SCARF2 |
| 22 | 20785639 | G | A | SCARF2 |
| 22 | 21377650 | G | A | P2RX6 |
| 22 | 24582041 | A | G | SUSD2 |
| 22 | 24622648 | T | C | GGT5 |
| 22 | 24628908 | G | A | GGT5 |
| 22 | 25019155 | T | C | GGT1 |
| 22 | 26688831 | G | T | SEZ6L |
| 22 | 26695077 | G | T | SEZ6L |
| 22 | 26709766 | T | G | SEZ6L |
| 22 | 29469192 | G | A | KREMEN1 |
| 22 | 29517463 | G | T | KREMEN1 |
| 22 | 29533572 | C | G | KREMEN1 |
| 22 | 37319327 | A | C | CSF2RB |
| 22 | 37326443 | G | C | CSF2RB |
| 22 | 37466992 | G | A | TMPRSS6 |
| 22 | 37471208 | G | A | TMPRSS6 |
| 22 | 37485724 | T | C | TMPRSS6 |
| 22 | 37538508 | G | A | IL2RB |
| 22 | 37603745 | G | A | SSTR3 |
| 22 | 40066958 | C | T | CACNA1I |
| 22 | 41075543 | A | G | MCHR1 |
| 22 | 41076970 | G | A | MCHR1 |
| 22 | 42322716 | G | C | TNFRSF13C |
| 22 | 46655948 | T | C | PKDREJ |
| 22 | 46656242 | A | G | PKDREJ |
| 22 | 46656479 | A | G | PKDREJ |
| 22 | 46658438 | A | C | PKDREJ |
| 22 | 46780521 | T | C | CELSR1 |
| 22 | 46782382 | C | T | CELSR1 |
| 22 | 46786315 | T | C | CELSR1 |
| 22 | 46787694 | A | G | CELSR1 |
| 22 | 46787697 | A | G | CELSR1 |
| 22 | 46793592 | A | G | CELSR1 |
| 22 | 46860063 | C | T | CELSR1 |
| 22 | 46929692 | A | G | CELSR1 |
| 22 | 46930013 | C | A | CELSR1 |

| Chr | Position | ref | alt | Gene |
|---|---|---|---|---|
| 22 | 46931077 | G | C | CELSR1 |
| 22 | 46931309 | T | C | CELSR1 |
| 22 | 46931402 | G | C | CELSR1 |
| 22 | 46932788 | C | T | CELSR1 |
| 22 | 46932854 | G | A | CELSR1 |
| 22 | 46932946 | G | A | CELSR1 |
| 22 | 50721492 | C | T | PLXNB2 |
| 22 | 50721497 | T | C | PLXNB2 |
| 22 | 50722134 | T | C | PLXNB2 |
| 22 | 50722167 | T | C | PLXNB2 |
| 22 | 50722408 | T | C | PLXNB2 |
| 22 | 50728062 | T | C | PLXNB2 |
| X | 102979486 | T | C | GLRA4 |
| X | 108708516 | C | T | GUCY2F |
| X | 108708552 | A | G | GUCY2F |
| X | 135426693 | A | G | GPR112 |
| X | 135426968 | C | A | GPR112 |
| X | 135429503 | C | A | GPR112 |
| X | 135430483 | T | C | GPR112 |
| X | 135431236 | T | C | GPR112 |
| X | 135474444 | AGAT | A | GPR112 |
| X | 147088249 | C | T | FMR1NB |
| X | 153032658 | G | A | PLXNB3 |
| X | 153035798 | G | A | PLXNB3 |
| X | 153039502 | G | C | PLXNB3 |
| X | 153689893 | G | A | PLXNA3 |
| X | 153694334 | C | G | PLXNA3 |
| X | 2724760 | T | C | XG |
| X | 40450585 | C | G | ATP6AP2 |
| X | 65244971 | C | T | VSIG4 |
| X | 65382685 | T | C | HEPH |
| X | 65822607 | T | C | EDA2R |
| X | 65824986 | C | T | EDA2R |
| X | 69478942 | T | G | P2RY4 |
| X | 77268502 | G | C | ATP7A |
| X | 78216024 | A | C | P2RY10 | ated to U.S. Provisional Application No. 62/564,454, filed Sep. 28, 2017, and U.S. Provisional Application No. 62/649,429, filed Mar. 28, 2018, each of which is herein incorporated by reference.

UNIVERSAL PLATFORM FOR PREPARING AN INHIBITORY CHIMERIC ANTIGEN RECEPTOR (ICAR)

CROSS-REFERENCE TO RELATED APPLICATIONS

This application claims priority to U.S. Provisional Application No. 62/564,454, filed Sep. 28, 2017, and U.S. Provisional Application No. 62/649,429, filed Mar. 28, 2018, each of which is herein incorporated by reference.

SEQUENCE LISTING

This patent application contains a Sequence Listing which has been submitted electronically in ASCII format and are hereby incorporated herein by reference in its entirety. Said ASCII copy, created Sep. 27, 2018, is named 120575-5003_ST25.txt.

ASCII TABLE

The provisional patent application to which the current application claims priority contains a lengthy table section. A copy of the table was submitted to the U.S. Patent and Trademark Office on compact disc in ASCII format with priority U.S. Provisional Application No. 62/649,429, filed Mar. 28, 2018 and is hereby incorporated by reference, and may be employed in the practice of the invention. Said ASCII table, created Mar. 28, 2018, is as follows: 120575-5003-PR allCandExt1167Genes_5003_PR.txt, 272,719,870 bytes.

FIELD OF THE INVENTION

The invention relates to the field of cancer immunotherapy by adoptive cell transfer, employing activating chimeric antigen receptors (aCARs) recognizing antigens expressed on the surface of tumor cells, inhibitory CARs (iCARs) and protective CARs (pCARs) directed at allelic variants of the same or other cell surface antigens expressed by normal cells but not by the tumor due to loss of heterozygosity (LOH).

BACKGROUND OF THE INVENTION

The identification of targetable antigens that are exclusively expressed by tumor cells but not by healthy tissue is undoubtedly the major challenge in cancer immunotherapy today. Clinical evidence that T cells are capable of eradicating tumor cells comes from numerous studies evaluating highly diverse approaches for harnessing T cells to treat cancer (Rosenberg and Restifo, 2015). These approaches employ bone marrow transplantation with donor lymphocyte infusion, adoptive transfer of tumor-infiltrating lymphocytes (TILs), treatment with T cells genetically redirected at pre-selected antigens via CARs (Gross and Eshhar, 2016a) or T cell receptors (TCRs), the use of immune checkpoint inhibitors or active vaccination. Of these, the use of genetically engineered T cells and different strategies for active immunization entail pre-existing information on candidate antigens which are likely to exert a durable clinical response but minimal adverse effects. Yet, as stated in the title of a recent review by S. Rosenberg, "Finding suitable targets is the major obstacle to cancer gene therapy" (Rosenberg, 2014).

The concept of using chimeric antigen receptors (or CARs) to genetically redirect T cells (or other killer cells of the immune system such as natural killer (NK) cells and cytokine-induced killer cells) against antigens of choice in an MHC-independent manner was first introduced by Gross and Eshhar in the late 1980s (Gross et al., 1989). They are produced synthetically from chimeric genes encoding an extracellular single-chain antibody variable fragment (scFv) fused through a flexible hinge and transmembrane canonic motif to signaling components comprising immunoreceptor tyrosine-based activation motifs of CD3-ζ or FcRγ chains capable of T cell activation. At present, CARs are being examined in dozens of clinical trials and have so far shown exceptionally high efficacy in B cell malignancies (Dotti et al., 2014; Gill and June, 2015; Gross and Eshhar, 2016a). The safety of CAR-T cell therapy is determined, in large, by its ability to discriminate between the tumor and healthy tissue. A major risk and the direct cause for adverse autoimmune effects that have been reported in clinical and preclinical studies is off-tumor, on-target toxicity resulting from extra-tumor expression of the target antigen (dealt with in detail in our recent review (Gross and Eshhar, 2016b) and (Klebanoff et al., 2016)). Concerning this risk, shared, non-mutated cell surface antigens which are currently tested clinically or pre-clinically for CAR therapy can be generally divided into a number of categories according to their tissue distribution and mode of expression:

Strictly tumor-specific antigens. Perhaps the only member in this group which is already being examined clinically is variant III of the epidermal growth factor receptor (EGFRvIII) that is frequently overexpressed in glioblastoma and is also found in non-small cell lung carcinoma and prostate, breast, head and neck and ovarian cancers but not on normal tissue.

Surface antigens expressed on the tumor and on non-vital healthy tissue. Potential CAR antigens in this group are differentiation-related molecules that are mainly restricted to the B cell lineage. Prominent among these (and a target antigen in numerous clinical trials) is CD19, a pan-B cell marker acquired very early in B cell differentiation and involved in signal transduction by the B cell receptor (BCR). Membrane prostate antigens constitute another class of antigens in this category.

Antigens that are typically expressed by non-malignant tumor-promoting cells. One such antigen is fibroblast activation protein (FAP), a cell surface serine protease which is almost invariably expressed by tumor-associated fibroblasts in diverse primary and metastatic cancers. Another antigen is vascular endothelial growth factor (VEGF), which is highly expressed during tumor angiogenesis and is normally expressed on vascular and lymphatic endothelial cells in many vital organs.

Tumor associated antigens (TAAs) shared with vital healthy tissue.

Most other TAAs which are presently evaluated in preclinical and clinical studies are overexpressed by tumors but are also present, usually at lower level, on essential normal tissue.

The broad spectrum of strategies devised to tackle autoimmunity in CAR T cell therapy can be divided into those which seek to eliminate, or suppress transferred T cells once damage is already evident (reactive measures) and those that aim at preventing potential damage in the first place (proactive measures) (Gross and Eshhar, 2016a). Reactive approaches often use suicide genes such as herpes simplex virus thymidine kinase (HSV-tk) and iC9, a fusion polypeptide comprising a truncated human caspase 9 and a mutated FK506-binding protein. Other approaches utilize antibodies to selectively remove engineered cells which go havoc or, as recently demonstrated, a heterodimerizing small-molecule agent which governs the coupling of the CAR recognition moiety to the intracellular signaling domain (Wu et al., 2015). While some proactive measures are designed to limit the in-vivo persistence or function of CAR T cells (for example, the use of mRNA electroporation for gene delivery), others directly address the critical challenge of increasing antigenic selectivity of the rapeutic CARs so as to avoid damage to non-tumor tissue. Two of these raise particular interest, as they can potentially broaden the range of tumor antigens which can be safely targeted by CAR T cells:

Combinatorial (or 'split') antigen recognition. While true tumor-specific surface antigens are rare, combinations of two different antigens, not-necessarily classified as tumor-associated antigens that are co-expressed by a given tumor, can define a new tumor-specific signature. Restricting the activity of CAR T cells to such antigen pairs provides a critical safety gauge and, consequently, extends the spectrum of tumor-specific targets and may be of substantial therapeutic value. Second and third generation CARs have been designed to provide therapeutic T cells with activation and costimulation signals upon engaging a single antigen through the tethering of two or more signaling portions at the CAR endodomain. However, if activation and costimulation are split in the same T-cell between two CARs, each specific for a different antigen, then full blown response would require the cooperation of the two complementary signals that could only be accomplished in the presence of the two antigens. This principle has been demonstrated in several preclinical studies (Kloss et al., 2013; Lanitis et al., 2013; Wilkie et al., 2012; WO 2016/126608).

While undoubtedly intriguing, this approach still faces the need in meticulous titration of the magnitude of both the activating and costimulatory signals so as to reach the optimal balance that would only allow effective on-target, on-tumor T cell reactivity. Whether such balance can be routinely attained in the clinical setting is still questionable.

An entirely new approach for limiting T cell response only to target cells that express a unique combination of two antigens was published recently (Roybal et al., 2016a). Its core element functions as a 'genetic switch' which exploits the mode of action of several cell surface receptors, including Notch. Following binding of such a receptor to its ligand it undergoes dual cleavage resulting in the liberation of its intracellular domain which translocates to the cell nucleus where it functions as a transcription factor. The implementation of this principle entails the co-introduction of two genes to the effector T cells. The first one is expressed constitutively and encodes such a chimeric cleavable receptor equipped with a recognition moiety directed at the first antigen. Engagement with this antigen on the surface of a target cell will turn on the expression of the second gene encoding a conventional CAR which is directed at the second antigen. The target cell will be killed only if it co-expresses this second antigen as well.

Inhibitory CARs. Off-tumor reactivity occurs when the target antigen of CAR-redirected killer cells is shared with normal tissue. If this normal tissue expresses another surface antigen not present on the tumor, then co-expressing in the gene-modified cells an additional CAR targeting this non-shared antigen, which harbors an inhibitory signaling moiety, can prevent T-cell activation by the normal tissue.

Instead of an activating domain (such as FcRγ or CD3-ζ), an iCAR possesses a signaling domain derived from an inhibitory receptor which can antagonize T cell activation, such as CTLA-4, PD-1 or an NK inhibitory receptor. If the normal tissue which shares the candidate aCAR antigen with the tumor expresses another surface antigen not shared with the tumor, an iCAR expressed by the same T cell which targets this non-shared antigen can protect the normal tissue (FIG. 1).

Unlike T cells, each of which expresses a unique two-chain TCR encoded by somatically rearranged gene segments, NK cells do not express antigen-specific receptors. Instead, NK cells express an array of germline-encoded activating and inhibitory receptors which respectively recognize multiple activating and inhibitory ligands at the cell surface of infected and healthy cells. The protective capacity of an iCAR based on NK inhibitory receptors such as KIR3DL1 has been described (U.S. Pat. No. 9,745,368). KIR3DL1 and other NK inhibitory receptors function by dismantling the immunological synapse in a rapid and comprehensive manner. There is compelling evidence that a single NK cell can spare a resistant cell expressing both inhibitory and activating ligands yet kill a susceptible cell it simultaneously engages, which expresses only the activating ligands (Abeyweera et al., 2011; Eriksson et al., 1999; Treanor et al., 2006; Vyas et al., 2001). This exquisite ability is governed by the different spatial organization of signal transduction molecules formed at each of the respective immune synapses which consequently affects the exocytosis of cytolytic granules (see (Huse et al., 2013) for review). More recently, Fedorov et al. (Fedorov et al., 2013a; WO 2015/142314) successfully employed for this purpose the intracellular domains of PD-1 and CTLA-4. Unlike NK inhibitory receptors, the regulatory effects of these iCARs affected the entire cell. Yet, these effects were temporary, allowing full T-cell activation upon subsequent encounter with target cells expressing only the aCAR antigen.

Tissue distribution of the antigens targeted by the iCAR and aCAR dictates the optimal mode of action of the iCAR required for conferring maximal safety without compromising clinical efficacy. For example, if the anatomical sites of the tumor and the normal tissue(s) to be protected do not intersect, transient inhibition (CTLA-4- or PD-1-like) will likely suffice. Yet, if these sites do overlap, only synapse-confined inhibition (e.g., an NK mode of action) will prevent constant paralysis of the rapeutic cells and allow their effective tumoricidal activity. The approach of using iCARs to reduce on-target off-tumor reactivity suffers from a dire lack of antigens downregulated in tumor cells but present on normal tissue.

Next generation sequencing (NGS) allows the determination of the DNA sequence of all protein-coding genes (~1% of the entire genome) in a given tumor biopsy and the comparison of the cancer 'exome' to that of a healthy tissue (usually from white blood cells) of the same patient. Exome sequencing can be completed within several days post-biopsy removal and at relatively low cost. In parallel, transcriptome analysis (RNA-seq) can provide complementary information on the genes that are actually expressed by the same cell sample.

It is becoming increasingly clear that the mutational landscape of each individual tumor is unique (Lawrence et al., 2013; Vogelstein et al., 2013). As a result of nonsynonymous mutations the tumor cell can potentially present a private set of neopeptides to the patient's immune system on one or more of his or her HLA products. Indeed, tremendous efforts are being put in recent years into identifying tumor-specific neoepitopes which can be recognized by the patient's own CD8 or CD4 T cell repertoire and serve as targets for immunotherapy (for review see (Blankenstein et al., 2015; Van Buuren et al., 2014; Heemskerk et al., 2013; Overwijk et al., 2013; Schumacher and Schreiber, 2015)). However, cumulative findings suggest that neoantigen-based T cell immunotherapies are more likely to be effective in cancers displaying higher mutational load, such as melanoma and lung cancers, but may often fail to show benefit in most cancers with fewer mutations (Savage, 2014; Schumacher and Schreiber, 2015). Furthermore, considerable intratumoral heterogeneity (Burrell et al., 2013) entails the simultaneous co-targeting of several antigens so as to avoid emergence of mutation-loss variants, a task which becomes increasingly demanding in view of the scarcity of useful immunogenic neopeptides.

All in all, the urgent need to identify suitable targets for cancer immunotherapy via the adoptive transfer of genetically redirected killer cells is still largely unmet.

BRIEF SUMMARY OF THE INVENTION

In some aspects, the present invention provides a method of identifying a target for preparing an inhibitory chimeric antigen receptor (iCAR) or a protective chimeric antigen receptor (pCAR) capable of preventing or attenuating undesired activation of an effector immune cell, wherein the target is identified by a method comprising:
  (i) identifying a gene with at least two expressed alleles that encodes a protein comprising an extracellular polymorphic epitope;
  (ii) determining that at least one of the expressed alleles exhibits an amino acid sequence change in the extracellular polymorphic epitope sequence relative to an extracellular polymorphic epitope reference sequence;
  (iii) determining that the gene is located in a chromosomal region which undergoes loss of heterozygosity (LOH) in a tumor type; and
  (iv) determining that the gene is expressed in the tissue-of-origin of the tumor type in which the chromosomal region was found to undergo LOH.

In some embodiments, the LOH position is selected from the group consisting of a substitution, deletion, and insertion. In some embodiments, the LOH position is a SNP. In some embodiments, the gene comprising the extracellular polymorphic epitope is an HLA gene.

In some embodiments, the gene comprising the extracellular polymorphic epitope is an HLA-A, HLA-B, HLA-C, HLA-G, HLA-E, HLA-F, HLA-K, HLA-L, HLA-DM, HLA-DO, HLA-DP, HLA_DQ, or HLA-DR gene. In some embodiments, the gene comprising the extracellular polymorphic epitope is an HLA-A gene. In some embodiments, the gene comprising the extracellular polymorphic epitope is an HLA-B gene. In some embodiments, the gene comprising the extracellular polymorphic epitope is an HLA-C gene. In some embodiments, the gene comprising the extracellular polymorphic epitope is an HLA-G gene. In some embodiments, the gene comprising the extracellular polymorphic epitope is an HLA-E gene. In some embodiments, the gene comprising the extracellular polymorphic epitope is an HLA-F gene. In some embodiments, the gene comprising the extracellular polymorphic epitope is an HLA-K gene. In some embodiments, the gene comprising the extracellular polymorphic epitope is an HLA-L gene. In some embodiments, the gene comprising the extracellular polymorphic epitope is an HLA-DM gene. In some embodiments, the gene comprising the extracellular polymorphic epitope is an HLA-DO gene. In some embodiments, the extracellular polymorphic epitope is an HLA-DP gene. In some embodiments, the extracellular polymorphic epitope is an HLA_DQ gene. In some embodiments, the extracellular polymorphic epitope is an HLA-DR gene.

In some embodiments, the gene comprising the extracellular polymorphic epitope is located on chromosome 1. In some embodiments, the gene comprising the extracellular polymorphic epitope is selected from the group consisting of ABCA4, ADAM30, AQP10, ASTN1, C1orf101, CACNA1S, CATSPER4, CD101, CD164L2, CD1A, CD1C, CD244, CD34, CD46, CELSR2, CHRNB2, CLCA2, CLDN19, CLSTN1, CR1, CR2, CRB1, CSF3R, CSMD2, ECE1, ELTD1, EMC1, EPHA10, EPHA2, EPHA8, ERMAP, FCAMR, FCER1A, FCGR1B, FCGR2A, FCGR2B, FCGR3A, FCRL1, FCRL3, FCRL4, FCRL5, FCRL6, GJB4, GPA33, GPR157, GPR37L1, GPR88, HCRTR1, IGSF3, IGSF9, IL22RA1, IL23R, ITGA10, KIAA1324, KIAA2013, LDLRAD2, LEPR, LGR6, LRIG2, LRP8, LRRC52, LRRC8B, LRRN2, LY9, MIA3, MR1, MUC1, MXRA8, NCSTN, NFASC, NOTCH2, NPR1, NTRK1, OPN3, OR10J1, OR10J4, OR10K1, OR10R2, OR10T2, OR10X1, OR11L1, OR14A16, OR14I1, OR14K1, OR2AK2, OR2C3, OR2G2, OR2G3, OR2L2, OR2M7, OR2T12, OR2T27, OR2T1, OR2T3, OR2T29, OR2T33, OR2T34, OR2T35, OR2T3, OR2T4, OR2T5, OR2T6, OR2T7, OR2T8, OR2W3, OR6F1, OR6K2, OR6K3, OR6K6, OR6N1, OR6P1, OR6Y1, PDPN, PEAR1, PIGR, PLXNA2, PTCH2, PTCHD2, PTGFRN, PTPRC, PTPRF, PTGFRN, PVRL4, RHBG, RXFP4, S1PR1, SCNN1D, SDC3, SELE, SELL, SELP, SEMA4A, SEMA6C, SLAMF7, SLAMF9, SLC2A7, SLC5A9, TACSTD2, TAS1R2, TIE1, TLR5, TMEM81, TNFRSF14, TNFRSF1B, TRABD2B, USH2A, VCAM1, and ZP4.

In some embodiments, the gene comprising the extracellular polymorphic epitope is located on chromosome 2. In some embodiments, the gene comprising the extracellular polymorphic epitope is selected from the group consisting of ABCG5, ALK, ASPRV1, ATRAID, CD207, CD8B, CHRNG, CLEC4F, CNTNAP5, CRIM1, CXCR1, DNER, DPP10, EDAR, EPCAM, GPR113, GPR148, GPR35, GPR39, GYPC, IL1RL1, ITGA4, ITGA6, ITGAV, LCT, LHCGR, LRP1B, LRP2, LY75, MARCO, MERTK, NRP2, OR6B2, PLA2R1, PLB1, PROKR1, PROM2, SCN7A, SDC1, SLC23A3, SLC5A6, TGOLN2, THSD7B, TM4SF20, TMEFF2, TMEM178A, TPO, and TRABD2A.

In some embodiments, the gene comprising the extracellular polymorphic epitope is located on chromosome 3. In some embodiments, the gene comprising the extracellular polymorphic epitope is selected from the group consisting of ACKR2, ALCAM, ANO10, ATP13A4, BTLA, CACNA1D, CACNA2D2, CACNA2D3, CASR, CCRL2, CD200, CD200R1, CD86, CD96, CDCP1, CDHR4, CELSR3, CRL1, CLDN11, CLDN18, CLSTN2, CSPG5, CX3CR1, CXCR6, CYP8B1, DCBLD2, DRD3, EPHA6, EPHB3, GABRR3, GP5, GPR128, GPR15, GPR27, GRM2, GRM7, HEG1, HTR3C, HTR3D, HTR3E, IGSF11, IL17RC, IL17RD, IL17RE, IL5RA, IMPG2, ITGA9, ITGB5, KCNMB3, LRIG1, LRRC15, LRRN1, MST1R, NAALADL2, NRROS, OR5AC1, OR5H1, OR5H14, OR5H15, OR5H6, OR5K2, OR5K3, OR5K4, PIGX, PLXNB1, PLXND1, PRRT3, PTPRG, ROBO2, RYK, SEMA5B, SIDT1, SLC22A14, SLC33A1, SLC4A7, SLITRK3, STAB1, SUSD5, TFRC, TLR9, TMEM108, TMEM44, TMPRSS7, TNFSF10, UPK1B, VIPR1, and ZPLD1.

In some embodiments, the gene comprising the extracellular polymorphic epitope is located on chromosome 4. In some embodiments, the gene comprising the extracellular polymorphic epitope is selected from the group consisting of ANTXR2, BTC, CNGA1, CORN, EGF, EMCN, ENPEP, EPHA5, ERVMER34-1, EVC2, FAT1, FAT4, FGFRL1, FRAS1, GPR125, GRID2, GYPA, GYPB, KDR, KIAA0922, KLB, MFSD8, PARM1, PDGFRA, RNF150, TENM3, TLR10, TLR1, TLR6, TMEM156, TMPRSS11A, TMPRSS11B, TMPRSS11E, TMPRSS11F, UGT2A1, and UNC5C.

In some embodiments, the gene comprising the extracellular polymorphic epitope is located on chromosome 5. In some embodiments, the gene comprising the extracellular polymorphic epitope is selected from the group consisting of ADAM19, ADRB2, BTNL3, BTNL8, BTNL9, C5orf15, CATSPER3, CD180, CDH12, CDHR2, COL23A1, CSF1R, F2RL2, FAM174A, FAT2, FGFR4, FLT4, GABRA6, GABRG2, GPR151, GPR98, GRM6, HAVCR1, HAVCR2, IL31RA, IL6ST, IL7R, IQGAP2, ITGA1, ITGA2, KCNMB1, LIFR, LNPEP, MEGF10, NIPAL4, NPR3, NRG2, OR2V1, OR2Y1, OSMR, PCDH12, PCDH1, PCDHA1, PCDHA2, PCDHA4, PCDHA8, PCDHA9, PCDHB10, PCDHB11, PCDHB13, PCDHB14, PCDHB15, PCDHB16, PCDHB2, PCDHB3, PCDHB4, PCDHB5, PCDHB6, PCDHGA1, PCDHGA4, PDGFRB, PRLR, SEMA5A, SEMA6A, SGCD, SLC1A3, SLC22A4, SLC22A5, SLC23A1, SLC36A3, SLC45A2, SLC6A18, SLC6A19, SLCO6A1, SV2C, TENM2, TIMD4, and UGT3A1.

In some embodiments, the gene comprising the extracellular polymorphic epitope is located on chromosome 6. In some embodiments, the gene comprising the extracellular polymorphic epitope is selected from the group consisting of BAI3, BTN1A1, BTN2A1, BTN2A2, BTN3A1, BTN3A2, BTNL2, CD83, DCBLD1, DLL1, DPCR1, ENPP1, ENPP3, ENPP4, EPHA7, GABBR1, GABRR1, GCNT6, GFRAL, GJB7, GLP1R, GPR110, GPR111, GPR116, GPR126, GPR63, GPRC6A, HFE, HLA-A, HLA-B, HLA-C, HLA-DOA, HLA-DPA1, HLA-DPB1, HLA-DQA1, HLA-DQA2, HLA-DQB1, HLA-DQB2, HLA-DRB1, HLA-DRB5, HLA-E, HLA-F, HLA-G, IL20RA, ITPR3, KIAA0319, LMBRD1, LRFN2, LRP11, MAS1L, MEP1A, MICA, MICB, MOG, MUC21, MUC22, NCR2, NOTCH4, OPRM1, OR10C1, OR12D2, OR12D3, OR14J1, OR2B2, OR2B6, OR2J1, OR2W1, OR5V1, PDE10A, PI16, PKHD1, PTCRA, PTK7, RAET1E, RAET1G, ROS1, SDIM1, SLC16A10, SLC22A1, SLC44A4, TAAR2, TREM1, TREML1, and TREML2.

In some embodiments, the gene comprising the extracellular polymorphic epitope is located on chromosome 7. In some embodiments, the gene comprising the extracellular polymorphic epitope is selected from the group consisting of AQP1, C7orf50, CD36, CDHR3, CNTNAP2, DPP6, EGFR, EPHA1, EPHB6, ERVW-1, GHRHR, GJC3, GPNMB, GRM8, HUS1, HYAL4, KIAA1324L, LRRN3, MET, MUC12, MUC17, NPC1L1, NPSR1, OR2A12, OR2A14. OR2A25, OR2A42, OR2A7, OR2A2, OR2AE1, OR2F2, OR6V1, PILRA, PILRB, PKD1L1, PLXNA4, PODXL, PTPRN2, PTPRZ1, RAMP3, SLC29A4, SMO, TAS2R16, TAS2R40, TAS2R4, TFR2, THSD7A, TMEM213, TTYH3, ZAN, and ZP3.

In some embodiments, the gene comprising the extracellular polymorphic epitope is located on chromosome 8. In some embodiments, the gene comprising the extracellular polymorphic epitope is selected from the group consisting of ADAM18, ADAM28, ADAM32, ADAM7, ADAMS, ADRA1A, CDH17, CHRNA2, CSMD1, CSMD3, DCSTAMP, FZD6, GPR124, NRG1, OR4F21, PKHD1L1, PRSS55, SCARA3, SCARA5, SDC2, SLC10A5, SLC39A14, SLC39A4, SLCO5A1, TNFRSF10A, and TNFRSF10B.

In some embodiments, the gene comprising the extracellular polymorphic epitope is located on chromosome 9. In some embodiments, the gene comprising the extracellular polymorphic epitope is selected from the group consisting of ABCA1, AQP7, ASTN2, C9orf135, CA9, CD72, CNTNAP3B, CNTNAP3, CRB2, ENTPD8, GPR144, GRIN3A, IZUMO3, KIAA1161, MAMDC4, MEGF9, MUSK, NOTCH1, OR13C2, OR13C3, OR13C5, OR13C8, OR13C9, OR13D1, OR13F1, OR1B1, OR1J2, OR1K1, OR1L1, OR1L3, OR1L6, OR1L8, OR1N1, OR1N2, OR1Q1, OR2S2, PCSK5, PDCD1LG2, PLGRKT, PTPRD, ROR2, SEMA4D, SLC31A1, TEK, TLR4, TMEM2, and VLDLR.

In some embodiments, the gene comprising the extracellular polymorphic epitope is located on chromosome 10. In some embodiments, the gene comprising the extracellular polymorphic epitope is selected from the group consisting of ABCC2, ADAMS, ADRB1, ANTXRL, ATRNL1, C10orf54, CDH23, CDHR1, CNNM2, COL13A1, COL17A1, ENTPD1, FZD8, FGFR2, GPR158, GRID1, IL15RA, IL2RA, ITGA8, ITGB1, MRC1, NRG3, NPFFR1, NRP1, OPN4, PCDH15, PKD2L1, PLXDC2, PRLHR, RET, RGR, SLC16A9, SLC29A3, SLC39A12, TACR2, TCTN3, TSPAN15, UNC5B, and VSTM4.

In some embodiments, the gene comprising the extracellular polymorphic epitope is located on chromosome 11. In some embodiments, the gene comprising the extracellular polymorphic epitope is selected from the group consisting of AMICA1, ANO1, ANO3, APLP2, C11orf24, CCKBR, CD248, CD44, CD5, CD6, CD82, CDON, CLMP, CRTAM, DCHS1, DSCAML1, FAT3, FOLH1, GDPD4, GDPD5, GRIK4, HEPHL1, HTR3B, IFITM10, IL10RA, KIRREL3, LGR4, LRP4, LRP5, LRRC32, MCAM, MFRP, MMP26, MPEG1, MRGPRE, MRGPRF, MRGPRX2, MRGPRX3, MRGPRX4, MS4A4A, MS4A6A, MTNR1B, MUC15, NAALAD2, NAALADL1, NCAM1, NRXN2, OR10A2, OR10A5, OR10A6, OR10D3, OR10G4, OR10G7, OR10G8, OR10G9, OR10Q1, OR10S1, OR1S1, OR2AG1, OR2AG2, OR2D2, OR4A47, OR4A15, OR4A5, OR4C11, OR4C13, OR4C15, OR4C16, OR4C3, OR4C46, OR4C5, OR4D6, OR4A8P, OR4D9, OR4S2, OR4X1, OR51E1, OR51L1, OR52A1, OR52E1, OR52E2, OR52E4, OR52E6, OR5211, OR5212, OR52J3, OR52L1, OR52N1, OR52N2, OR52N4, OR52W1, OR56131, OR56B4, OR5A1, OR5A2, OR5AK2, OR5AR1, OR5B17, OR5B3, OR5D14, OR5D16, OR5D18, OR5F1, OR511, OR5L2, OR5M11, OR5M3, OR5P2, OR5R1, OR5T2, OR5T3, OR5W2, OR6A2, OR6T1, OR6X1, OR8A1, OR8B12, OR8B2, OR8B3, OR8B4, OR8D1, OR8D2, OR8H1, OR8H2, OR8H3, OR812, OR8J1, OR8J2, OR8J3, OR8K1, OR8K3, OR8K5, OR8U1, OR9G1, OR9G4, OR9Q2, P2RX3, PTPRJ, ROBO3, SIGIRR, SLC22A10, SLC3A2, SLC5A12, SLCO2B1, SORL1, ST14, SYT8, TENM4, TMEM123, TMEM225, TMPRSS4, TMPRSS5, TRIM5, TRPM5, TSPAN18, and ZP1.

In some embodiments, the gene comprising the extracellular polymorphic epitope is located on chromosome 12. In some embodiments, the gene comprising the extracellular polymorphic epitope is selected from the group consisting of ANO4, AVPR1A, BCL2L14, CACNA2D4, CD163, CD163L1, CD27, CD4, CLEC12A, CLEC1B, CLEC2A, CLEC4C, CLEC7A, CLECL1, CLSTN3, GPR133, GPRC5D, ITGA7, ITGB7, KLRB1, KLRC2, KLRC3, KLRC4, KLRF1, KLRF2, LRP1, LRP6, MANSC1, MANSC4, OLR1, OR10AD1, OR10P1, OR2AP1, OR6C1, OR6C2, OR6C3, OR6C4, OR6C6, OR6C74, OR6C76, OR8S1, OR9K2, ORAI1, P2RX4, P2RX7, PRR4, PTPRB, PTPRQ, PTPRR, SCNN1A, SELPLG, SLC2A14, SLC38A4, SLC5A8, SLC6A15, SLC8B1, SLCO1A2, SLCO1B1, SLCO1B7, SLCO1C1, SSPN, STAB2, TAS2R10, TAS2R13, TAS2R14, TAS2R20, TAS2R30, TAS2R31, TAS2R42, TAS2R43, TAS2R46, TAS2R7, TMEM119, TMEM132B, TMEM132C, TMEM132D, TMPRSS12, TNFRSF1A, TSPAN8, and VSIG10.

In some embodiments, the gene comprising the extracellular polymorphic epitope is located on chromosome 13. In some embodiments, the gene comprising the extracellular polymorphic epitope is selected from the group consisting of ATP4B, ATP7B, FLT3, FREM2, HTR2A, KL, PCDH8, RXFP2, SGCG, SHISA2, SLC15A1, SLITRK6, and TNFRSF19.

In some embodiments, the gene comprising the extracellular polymorphic epitope is located on chromosome 14. In some embodiments, the gene comprising the extracellular polymorphic epitope is selected from the group consisting of ADAM21, BDKRB2, C14orf37, CLEC14A, DLK1, FLRT2, GPR135, GPR137C, JAG2, LTB4R2, MMP14, OR11G2, OR11H12, OR11H6, OR4K1, OR4K15, OR4K5, OR4L1, OR4N2, OR4N5, SLC24A4, and SYNDIG1L.

In some embodiments, the gene comprising the extracellular polymorphic epitope is located on chromosome 15. In some embodiments, the gene comprising the extracellular polymorphic epitope is selected from the group consisting of ANPEP, CD276, CHRNA7, CHRNB4, CSPG4, DUOX1, DUOX2, FAM174B, GLDN, IGDCC4, ITGA11, LCTL, LTK, LYSMD4, MEGF11, NOX5, NRG4, OCA2, OR4F4, OR4M2, OR4N4, PRTG, RHCG, SCAMP5, SEMA4B, SEMA6D, SLC24A1, SLC24A5, SLC28A1, SPG11, STRA6, TRPM1, and TYRO3.

In some embodiments, the gene comprising the extracellular polymorphic epitope is located on chromosome 16. In some embodiments, the gene comprising the extracellular polymorphic epitope is selected from the group consisting of ATP2C2, CACNA1H, CD19, CDH11, CDH15, CDH16, CDH3, CDH5, CNGB1, CNTNAP4, GDPD3, GPR56, GPR97, IFT140, IL4R, ITFG3, ITGAL, ITGAM, ITGAX, KCNG4, MMP15, MSLNL, NOMO1, NOMO3, OR2C1, PIEZO1, PKD1, PKD1L2, QPRT, SCNN1B, SEZ6L2, SLC22A31, SLC5A11, SLC7A6, SPN, TMC5, TMC7, TMEM204, TMEM219, and TMEM8A.

In some embodiments, the gene comprising the extracellular polymorphic epitope is located on chromosome 17. In some embodiments, the gene comprising the extracellular polymorphic epitope is selected from the group consisting of ABCC3, ACE, AOC3, ARL17B, ASGR2, C17orf80, CD300A, CD300C, CD300E, CD300LF, CD300LG, CHRNB1, CLEC10A, CNTNAP1, CPD, CXCL16, ERBB2, FAM171A2, GCGR, GLP2R, GP1BA, GPR142, GUCY2D, ITGA2B, ITGA3, ITGAE, ITGB3, KCNJ12, LRRC37A2, LRRC37A3, LRRC37A, LRRC37B, MRC2, NGFR, OR1A2, OR1D2, OR1G1, OR3A1, OR3A2, OR4D1, OR4D2, RNF43, SCARF1, SCN4A, SDK2, SECTM1, SEZ6, SHPK, SLC26A11, SLC5A10, SPACA3, TMEM102, TMEM132E, TNFSF12, TRPV3, TTYH2, and TUSC5.

In some embodiments, the gene comprising the extracellular polymorphic epitope is located on chromosome 18. In some embodiments, the gene comprising the extracellular polymorphic epitope is selected from the group consisting of APCDD1, CDH19, CDH20, CDH7, COLEC12, DCC, DSC1, DSG1, DSG3, DYNAP, MEP1B, PTPRM, SIGLEC15, and TNFRSF11A.

In some embodiments, the gene comprising the extracellular polymorphic epitope is located on chromosome 19. In some embodiments, the gene comprising the extracellular polymorphic epitope is selected from the group consisting of ABCA7, ACPT, BCAM, C19orf38, C19orf59, C5AR1, CATSPERD, CATSPERG, CD22, CD320, CD33, CD97, CEACAM19, CEACAM1, CEACAM21, CEACAM3, CEACAM4, CLEC4M, DLL3, EMR1, EMR2, EMR3, ERVV-1, ERVV-2, FAM187B, FCAR, FFAR3, FPR1, FXYD5, GFY, GP6, GPR42, GRIN3B, ICAM3, IGFLR1, IL12RB1, IL27RA, KIR2DL1, KIR2DL3, KIR2DL4, KIR3DL1, KIR3DL2, KIR3DL3, KIRREL2, KISS1R, LAIR1, LDLR, LILRA1, LILRA2, LILRA4, LILRA6, LILRB1, LILRB2, LILRB3, LILRB4, LILRB5, LINGO3, LPHN1, LRP3, MADCAM1, MAG, MEGF8, MUC16, NCR1, NOTCH3, NPHS1, OR10H1, OR10H2, OR10H3, OR10H4, OR1I1, OR2Z1, OR7A10, OR7C1, OR7D4, OR7E24, OR7G1, OR7G2, OR7G3, PLVAP, PTGIR, PTPRH, PTPRS, PVR, SCN1B, SHISA7, SIGLEC10, SIGLEC11, SIGLEC12, SIGLEC5, SIGLEC6, SIGLEC8, SIGLEC9, SLC44A2, SLC5A5, SLC7A9, SPINT2, TARM1, TGFBR3L, TMC4, TMEM91, TMEM161A, TMPRSS9, TNFSF14, TNFSF9, TRPM4, VN1R2, VSIG10L, VSTM2B, and ZNRF4.

In some embodiments, the gene comprising the extracellular polymorphic epitope is located on chromosome 20. In some embodiments, the gene comprising the extracellular polymorphic epitope is selected from the group consisting of ABHD12, ADAM33, ADRA1D, APMAP, ATRN, CD40, CD93, CDH22, CDH26, CDH4, FLRT3, GCNT7, GGT7, JAG1, LRRN4, NPBWR2, OCSTAMP, PTPRA, PTPRT, SEL1L2, SIGLEC1, SIRPA, SIRPB1, SIRPG, SLC24A3, SLC2A10, SLC4A11, SSTR4, and THBD.

In some embodiments, the gene comprising the extracellular polymorphic epitope is located on chromosome 21. In some embodiments, the gene comprising the extracellular polymorphic epitope is selected from the group consisting of CLDN8, DSCAM, ICOSLG, IFNAR1, IFNGR2, IGSF5, ITGB2, KCNJ15, NCAM2, SLC19A1, TMPRSS15, TMPRSS2, TMPRSS3, TRPM2, and UMODL1.

In some embodiments, the gene comprising the extracellular polymorphic epitope is located on chromosome 22. In some embodiments, the gene comprising the extracellular polymorphic epitope is selected from the group consisting of CACNA1I, CELSR1, COMT, CSF2RB, GGT1, GGT5, IL2RB, KREMEN1, MCHR1, OR11H1, P2RX6, PKDREJ, PLXNB2, SCARF2, SEZ6L, SSTR3, SUSD2, TMPRSS6, and TNFRSF13C.

In some embodiments, the gene comprising the extracellular polymorphic epitope is located on chromosome X. In some embodiments, the gene comprising the extracellular polymorphic epitope is selected from the group consisting of ATP6AP2, ATP7A, CNGA2, EDA2R, FMR1NB, GLRA4, GPR112, GUCY2F, HEPH, P2RY10, P2RY4, PLXNA3, PLXNB3, TLR8, VSIG4, and XG.

In some embodiments, the tumor is selected from the group consisting of a breast tumor, a prostate tumor, an ovarian tumor, a cervical tumor, a skin tumor, a pancreatic tumor, a colorectal tumor, a renal tumor, a liver tumor, a brain tumor, a lymphoma, a leukemia, a lung tumor, and a glioma.

In some embodiments, the tumor is selected from the group consisting of an adrenal gland tumor, a kidney tumor, a melanoma, DLBC, a breast tumor, a sarcoma, an ovary tumor, a lung tumor, a bladder tumor, and a liver tumor. In some embodiments, the adrenal gland tumor is an adrenocortical carcinoma. In some embodiments, the kidney tumor is a chromophobe renal cell carcinoma. In some embodiments, the melanoma is uveal melanoma.

The present invention also provides safe effector cells. In some embodiments, the present invention provides a safe effector immune cell expressing (i) an iCAR or pCAR and (ii) an activating chimeric antigen receptor (aCAR).

In some embodiments, the safe effector immune cell, wherein the aCAR is directed against or specifically binds to a tumor-associated antigen or a non-polymorphic cell surface epitope. In some embodiments, due to the protective effects of the iCAR or pCAR, the aCAR can be directed against any surface protein expressed on a cancer cell.

In some embodiments, the aCAR is directed against or specifically binds to a tumor associated protein, a CAR target as listed in table 1, any cell surface protein that is expressed in a tumor tissue in which the iCAR is also expressed.

In some embodiments, the non-polymorphic cell surface epitope is selected from the group consisting of CD19, CD20, CD22, CD10, CD7, CD49f, CD56, CD74, CAIX ROR1, ROR2, CD30, LewisY, CD33, CD34, CD38, CD123, CD28, CD44v6, CD44, CD41, CD133, CD138, NKG2D-L, CD139, BCMA, GD2, GD3, hTERT, FBP, EGP-2, EGP-40, FR-α, L1-CAM, ErbB2,3,4, EGFRvIII, VEGFR-2, IL-13Ra2, FAP, Mesothelin, c-MET, PSMA, CEA, kRas, MAGE-A1, MUC1, MUC16, PDL1, PSCA, EpCAM, FSHR, AFP, AXL, CD80, CD89, CDH17, CLD18, GPC3, TEM8, TGFB1, NY-ESO-1, WT-1 and EGFR.

The safe effector immune cell, wherein the safe effector immune cell is an autologous or a universal (allogeneic) effector cell.

In some embodiments, the safe effector immune cell is selected from the group consisting of a T cell, a natural killer cell and a cytokine-induced killer cell.

In some embodiments of the safe effector immune cell, the expression level of the iCAR or pCAR is greater than or equal to the expression level of the aCAR.

In some embodiments of the safe effector immune cell, the iCAR or pCAR is expressed by a first vector and the aCAR is expressed by a second vector.

In some embodiments of the safe effector immune cell, the iCAR or pCAR and the aCAR are both expressed by the same vector.

In some embodiments of the safe effector immune cell, the nucleotide sequence encoding for the aCAR is downstream of the nucleotide sequence encoding for the iCAR or pCAR.

In some embodiments of the safe effector immune cell, the nucleotide sequence comprises a viral self-cleaving 2A peptide between the nucleotide sequence encoding for the aCAR and the nucleotide sequence encoding for the iCAR or pCAR.

In some embodiments of the safe effector immune cell, the viral self-cleaving 2A peptide is selected from the group consisting of T2A from *Thosea asigna* virus (TaV), F2A from Foot-and-mouth disease virus (FMDV), E2A from Equine rhinitis A virus (ERAV) and P2A from Porcine teschovirus-1 (PTV1).

In some embodiments of the safe effector immune cell, the nucleotide sequence encoding the aCAR is linked via a flexible linker to the iCAR or pCAR.

In some embodiments of the safe effector immune cell, the aCAR comprises at least one signal transduction element that activates or co-stimulates an effector immune cell.

In some embodiments of the safe effector immune cell, the at least one signal transduction element that activates or co-stimulates an effector immune cell is homolgous to an immunoreceptor tyrosine-based activation motif (ITAM) of for example CD3ζ or FcRγ chains.

In some embodiments of the safe effector immune cell, the at least one signal transduction element that activates or co-stimulates an effector immune cell is homolgous to an activating killer cell immunoglobulin-like receptor (KIR), such as KIR2DS and KIR3DS.

In some embodiments of the safe effector immune cell, the at least one signal transduction element that activates or co-stimulates an effector immune cell is homolgous to or an adaptor molecule, such as DAP12.

In some embodiments of the safe effector immune cell, the at least one signal transduction element that activates or co-stimulates an effector immune cell is homolgous to or a co-stimulatory signal transduction element of CD27, CD28, ICOS, CD137 (4-1BB), CD134 (OX40) or GITR.

The present invention also provides a method for treating cancer in a patient having a tumor characterized by LOH, comprising administering to the patient a safe effector immune cell expressing an iCAR as described herein.

In some embodiments, the invention further provides a method for treating cancer in a patient having a tumor characterized by LOH, comprising administering to the patient a safe effector immune cell as described herein.

In one aspect, the present invention provides a nucleic acid molecule comprising a nucleotide sequence encoding an inhibitory chimeric antigen receptor (iCAR) capable of preventing or attenuating undesired activation of an effector immune cell, wherein the iCAR comprises an extracellular domain that specifically binds to a single allelic variant of a polymorphic cell surface epitope absent from mammalian tumor cells due to loss of heterozygosity (LOH) but present at least on all cells of related mammalian normal tissue and on vital organs; and an intracellular domain comprising at least one signal transduction element that inhibits an effector immune cell. In some embodiments, the iCAR or pCAR target is expressed on all cells that the aCAR target is normally expressed in. In some embodiments, the iCAR or pCAR target is expressed in the vital organ cells the aCAR is expressed in.

In an additional aspect, the present invention provides a vector comprising a nucleic acid molecule of the invention as defined herein, and at least one control element, such as a promoter, operably linked to the nucleic acid molecule.

In another aspect, the present invention provides a method of preparing an inhibitory chimeric antigen receptor (iCAR) capable of preventing or attenuating undesired activation of an effector immune cell, according to the present invention as defined herein, the method comprising: (i) retrieving a list of human genomic variants of protein-encoding genes from at least one database of known variants; (ii) filtering the list of variants retrieved in (i) by: (a) selecting variants resulting in an amino acid sequence variation in the protein encoded by the respective gene as compared with its corresponding reference allele, (b) selecting variants of genes wherein the amino acid sequence variation is in an extracellular domain of the encoded protein, (c) selecting variants of genes that undergo loss of heterozygosity (LOH) at least in one tumor, and (d) selecting variants of genes that are expressed at least in a tissue of origin of the at least one tumor in which they undergo LOH according to (c), thereby obtaining a list of variants having an amino acid sequence variation in an extracellular domain in the protein encoded by the respective gene lost in the at least one tumor due to LOH and expressed at least in a tissue of origin of the at least one tumor; (iii) defining a sequence region comprising at least one single variant from the list obtained in (ii), sub-cloning and expressing the sequence region comprising the at least one single variant and a sequence region comprising the corresponding reference allele thereby obtaining the respective epitope peptides; (iv) selecting an iCAR binding domain, which specifically binds either to the epitope peptide encoded by the cloned sequence region, or to the epitope peptide encoded by the corresponding reference allele, obtained in (iii); and (vii) preparing iCARs as defined herein, each comprising an iCAR binding domain as defined in (iv).

In still another aspect, the present invention provides a method for preparing a safe effector immune cell comprising: (i) transfecting a TCR-engineered effector immune cell directed to a tumor-associated antigen with a nucleic acid molecule comprising a nucleotide sequence encoding an iCAR as defined herein or transducing the cells with a vector defined herein; or (ii) transfecting a naïve effector immune cell with a nucleic acid molecule comprising a nucleotide sequence encoding an iCAR as defined herein and a nucleic acid molecule comprising a nucleotide sequence encoding an aCAR as defined herein; or transducing an effector immune cell with a vector as defined herein.

In yet another aspect, the present invention provides a safe effector immune cell obtained by the method of the present invention as described herein. The safe effector immune cell may be a redirected T cell expressing an exogenous T cell receptor (TCR) and an iCAR, wherein the exogenous TCR is directed to a non-polymorphic cell surface epitope of an antigen or a single allelic variant of a polymorphic cell surface epitope, wherein said epitope is a tumor-associated antigen or is shared at least by cells of related tumor and normal tissue, and the iCAR is as defined herein; or the safe effector immune cell is a redirected effector immune cell such as a natural killer cell or a T cell expressing an iCAR and an aCAR as defined herein.

In a further aspect, the present invention provides a method of selecting a personalized biomarker for a subject having a tumor characterized by LOH, the method comprising (i) obtaining a tumor biopsy from the subject; (ii) obtaining a sample of normal tissue from the subject, e.g., peripheral blood mononuclear cells (PBMCs); and (iii) identifying a single allelic variant of a polymorphic cell surface epitope that is not expressed by cells of the tumor due to LOH, but that is expressed by the cells of the normal tissue, thereby identifying a personalized biomarker for the subject.

In a further aspect, the present invention provides a method for treating cancer in a patient having a tumor characterized by LOH, comprising administering to the patient an effector immune cell as defined herein, wherein the iCAR is directed to a single allelic variant encoding a polymorphic cell surface epitope absent from cells of the tumor due to loss of heterozygosity (LOH) but present at least on all cells of related mammalian normal tissue of the patient.

In still a further aspect, the present invention is directed to a safe effector immune cell as defined herein for use in treating a patient having a tumor characterized by LOH, wherein the iCAR is directed to a single allelic variant encoding a polymorphic cell surface epitope absent from cells of the tumor due to loss of heterozygosity (LOH) but present at least on all cells of related mammalian normal tissue of the patient, including the vital organs of the patient. In some embodiments, the iCAR or pCAR is expressed on all cells that the aCAR target is normally expressed in. In some embodiments, the iCAR or pCAR is expressed in vital organ cells that the aCAR is expressed in.

In yet a further aspect, the present invention is directed to a method for treating cancer in a patient having a tumor characterized by LOH comprising: (i) identifying or receiving information identifying a single allelic variant of a polymorphic cell surface epitope that is not expressed by cells of the tumor due to LOH, but that is expressed by the cells of the normal tissue, (ii) identifying or receiving information identifying a non-polymorphic cell surface epitope of an antigen or a single allelic variant of a polymorphic cell surface epitope, wherein said epitope is a tumor-associated antigen or is shared by cells at least of related tumor and normal tissue in said cancer patient; (iii) selecting or receiving at least one nucleic acid molecule defining an iCAR as defined herein and at least one nucleic acid molecule comprising a nucleotide sequence encoding an aCAR as defined herein, or at least one vector as defined herein, wherein the iCAR comprises an extracellular domain that specifically binds to a cell surface epitope of (i) and the aCAR comprises an extracellular domain that specifically binds to a cell surface epitope of (ii); (iv) preparing or receiving at least one population of safe redirected effector immune cells by transfecting effector immune cells with the nucleic acid molecules of (iii) or transducing effector immune cells with the vectors of (iii); and (v) administering to said cancer patient at least one population of safe redirected immune effector cells of (iv).

In a similar aspect, the present invention provides at least one population of safe redirected immune effector cells for treating cancer in a patient having a tumor characterized by LOH, wherein the safe redirected immune cells are obtained by (i) identifying or receiving information identifying a single allelic variant of a polymorphic cell surface epitope that is not expressed by cells of the tumor due to LOH, but that is expressed by the cells of the normal tissue, (ii) identifying or receiving information identifying a non-polymorphic cell surface epitope of an antigen or a single allelic variant of a polymorphic cell surface epitope, wherein said epitope is a tumor-associated antigen or is shared by cells at least of related tumor and normal tissue in said cancer patient; (iii) selecting or receiving at least one nucleic acid molecule defining an iCAR as defined herein and at least one nucleic acid molecule comprising a nucleotide sequence encoding an aCAR as defined herein, or at least one vector as defined herein, wherein the iCAR comprises an extracellular domain that specifically binds to a cell surface epitope of (i) and the aCAR comprises an extracellular domain that specifically binds to a cell surface epitope of (ii); (iv) preparing or receiving at least one population of safe redirected effector immune cells by transfecting effector immune cells with the nucleic acid molecules of (iii) or transducing effector immune cells with the vectors of (iii).

In another aspect, the present invention is directed to a combination of two or more nucleic acid molecules, each one comprising a nucleotide sequence encoding a different member of a controlled effector immune cell activating system, said nucleic acid molecules being part of or forming a single continues nucleic acid molecule, or comprising two or more separate nucleic acid molecules, wherein the controlled effector immune activating system directs effector immune cells to kill tumor cells that have lost one or more chromosomes or fractions thereof due to Loss of Heterozygosity (LOH) and spares cells of related normal tissue, and wherein (a) the first member comprises an activating chimeric antigen receptor (aCAR) polypeptide comprising a first extracellular domain that specifically binds to a non-polymorphic cell surface epitope of an antigen or to a single allelic variant of a different polymorphic cell surface epitope and said non-polymorphic or polymorphic cell surface epitope is a tumor-associated antigen or is shared by cells of related abnormal and normal mammalian tissue; and (b) the second member comprises a regulatory polypeptide comprising a second extracellular domain that specifically binds to a single allelic variant of a polymorphic cell surface epitope not expressed by an abnormal mammalian tissue due to LOH but present on all cells of related mammalian normal tissue.

BRIEF DESCRIPTION OF THE DRAWINGS

FIG. 2 shows the aCAR/pCAR molecular design and mode of action. Binding of the pCAR to its antigen on normal cells, whether these express the aCAR antigen or not, is expeeted to result in rapid RIP and breaking of the polypeptide into 3 separate fragments.

FIG. 12 shows the proportion of uveal melanoma tumors undergoing LOH for all SNPs.

FIG. 13 provides the TCGA Study Abbreviations (also available at https://gdc.cancer.gov/resources-tcga-users/tcga-code-tables/tcga-study-abbreviations).

FIG. 16 provides data regarding IL-2 secretion as measured by ELISA. iCAR specifically inhibits IL-2 secretion upon interaction with target cells expressing iCAR target.

FIG. 17 shows that iCAR specifically inhibits IL-2 secretion upon interaction with target cells expressing iCAR target as measured by CBA.

FIG. 20 shows specific inhibition of NFAT activation at different E/T ratios.

FIG. 21 provides the sequences for the iCAR and aCAR constructs of FIG. 15.

FIG. 22 provides the 1167 potential iCAR, pCAR and/or aCAR targets.

FIG. 23 provides the 3288 SNPs from the 1167 genes listed in FIG. 22.

DETAILED DESCRIPTION OF THE INVENTION

I. Introduction

Figure 1:
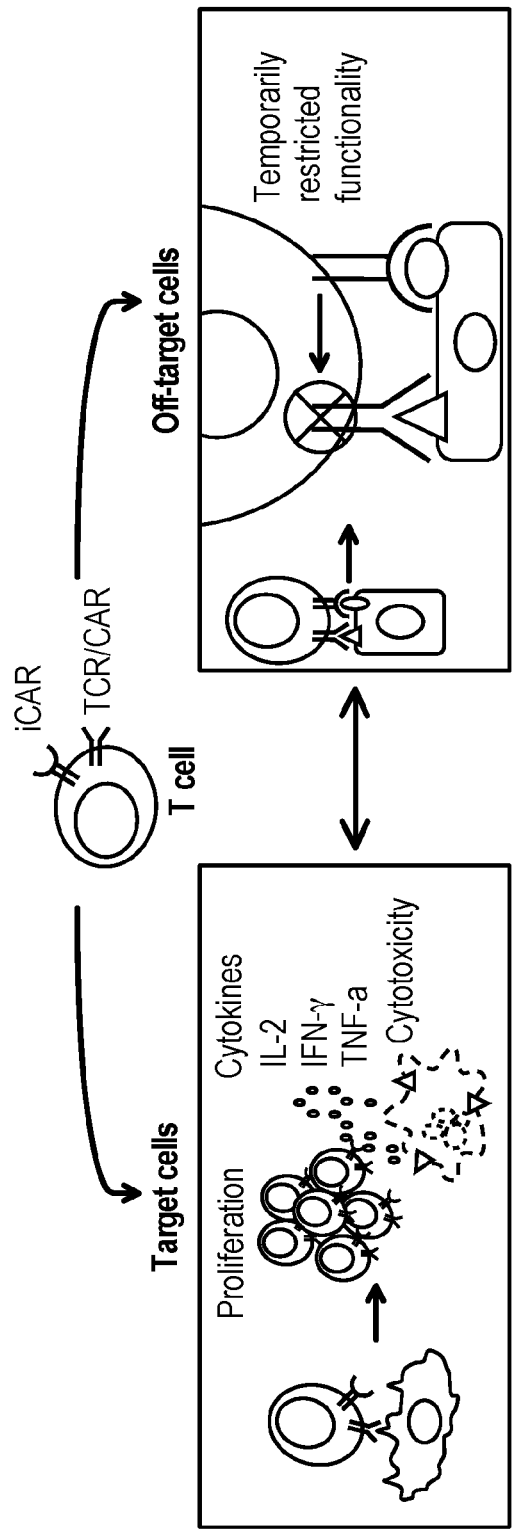
FIG. 1 shows the concept of iCARs (taken from (Fedorov et al., 2013a).

Referring to the revolutionary concept of tumor suppressor genes (TSGs) that had been put forward in 1971 by A. G. Knudson (Knudson Jr., 1971), Devilee, Cleton-Jansen and Cornelisse stated in the opening paragraph of their essay titled 'Ever since Knudson' (Devilee et al., 2001): "Many publications have documented LOH on many different chromosomes in a wide variety of tumors, implicating the existence of multiple TSGs. Knudson's two-hit hypothesis predicts that these LOH events are the second step in the inactivation of both alleles of a TSG". In their seminal review on genetic instabilities in human cancers (Lengauer et al., 1998), Lengauer, Kinzler and Vogelstein wrote: "Karyotypic studies have shown that the majority of cancers have lost or gained chromosomes, and molecular studies indicate that karyotypic data actually underestimate the true extent of such changes. Losses of heterozygosity, that is, losses of a maternal or paternal allele in a tumor, are widespread and are often accompanied by a gain of the opposite allele. A tumor could lose the maternal chromosome 8, for example, while duplicating the paternal chromosome 8, leaving the cell with a normal chromosome 8 karyotype but an abnormal chromosome 8 'allelotype'. The 'average' cancer of the colon, breast, pancreas or prostate may lose 25% of its alleles and it is not unusual for a tumor to have lost over half of its alleles." These observations have since been reinforced and extended to almost all human cancers, including practically all carcinomas, in numerous reports (see (McGranahan et al., 2012) for review). It is now unambiguously established that nearly all individual tumors exhibit multiple losses of full chromosomes, entire chromosomal arms or sub-chromosomal regions of varying size. New algorithms are being rapidly developed (e.g., Sathirapongsasuti et al., 2011) for the determination of the LOH profile in any given cell sample based on the exome sequence data. While statistical bias may at present question the validity of some interpretations (Teo et al., 2012), such algorithms are likely to improve and replace most other methodologies for establishing LOH profiles which had been employed for this purpose in the pre-NGS era Early LOH events can be detected in premalignant cells of the same tissue, but not in surrounding normal cells (Barrett et al., 1999). LOH is irreversible and events can only accumulate, so that tumor heterogeneity reflects the accumulation of losses throughout tumor progression. While tumor subclones can develop which differ in later LOH events, the existence of a minimal LOH signature that is shared by premalignant cells, putative tumor stem cells and all tumor subclones in a given patient, is expected to be the rule. Branches stemming from this 'trunk' LOH pattern would still create a limited set of partially overlapping signatures which, together, cover all tumor cells in the same patient An inevitable outcome of gross LOH events is the concomitant loss of all other genes residing on the deleted chromosomal material, and these naturally include many genes encoding transmembrane proteins. Concerning their identity, a catalog of 3,702 different human cell surface proteins (the 'surfaceome') has been compiled (Da Cunha et al., 2009). The expression of L142% of surfaceome genes display broad tissue distribution while □85 genes are expressed by all tissues examined, which is the hallmark of housekeeping genes. These genes are candidates, the different polymorphic variants of which may serve as targets for the iCARs and aCARs of the present invention More recently, Bausch-Fluck et al. (Bausch-Fluck et al., 2015) applied their Chemoproteomic Cell Surface Capture technology to identify a combined set of 1492 cell surface glycoproteins in 41 human cell types. A large fraction of the surfaceome is expected to be expressed by any given tumor, each exhibiting a distinctive profile. Genes encoding cell surface proteins were found to be slightly enriched for single-nucleotide polymorphisms (SNPs) in their coding regions than all other genes (Da Cunha et al., 2009). Polymorphic in-frame insertions and deletions, which are rarer, further contribute to the number of variants and likely exert more robust structural effects on the polypeptide products than peptide sequence-altering (nonsynonymous) SNPs. Altogether, a typical genome contains 10,000 to 12,000 sites with nonsynonymous variants and 190-210 in-frame insertions/deletions (Abecasis et al., 2010; Auton et al., 2015). These variants are not evenly distributed throughout the genome as highly polymorphic genes such as the HLA locus (http://www.ebi.ac.uk/imgt/hla/stats.html) or certain G-protein-coupled receptor (GPCR) genes (Lee et al., 2003; Rana et al., 2001) create distinct variant 'hotspots'. Another layer of LOH-related hotspots stems from the frequent loss of certain chromosomes, or chromosome arms in different cancers (e.g., 3p and 17p in small-cell lung carcinoma (Lindblad-Toh et al., 2000), 17p and 18q in colorectal cancer (Vogelstein et al., 1989), 17q and 19 in breast cancer (Li et al., 2014; Wang et al., 2004) 9p in melanoma (Stark and Hayward, 2007), 10q in glioblastoma (Ohgaki et al., 2004) and more)

A significant fraction of allelic variations in surface proteins would affect the extracellular portion of the respective gene products, potentially creating distinct allele-restricted epitopes which, in principle, can be recognized and distinguished from other variants by highly-specific mAbs. It is well documented that mAbs can be isolated that discriminate between two variants of the same protein which differ in a single amino acid only (see, for example, an early example of mAbs that recognize point mutation products of the Ras oncogene with exquisite specificity (Carney et al., 1986)). Interestingly, it was shown that two mAbs specific to a single amino acid interchange in a protein epitope can use structurally distinct variable regions from their heavy and light chain V gene pools (Stark and Caton, 1991). Recently, Skora et al. (Skora et al., 2015) reported the isolation of peptide-specific scFvs which can distinguish between HLA-I-bound neopeptides derived from mutated KRAS and EGFR proteins and their wild type counterparts, differing in both cases in one amino acid All taken together, a unique antigenic signature of tumor cells emerges, that can allow their unequivocal discrimination from all other cells in the entire body of the individual patient. It comprises all transmembrane proteins encoded by allelic variants that are absent from the tumor cell surface owing to LOH but are present on normal cells of the cancer tissue of origin or other tissues expressing these genes. Naturally, each gene affected by LOH will be characterized by a distinct pattern of tissue distribution except for true housekeeping genes. The majority of these genes are not expected to be directly involved in tumorigenesis or maintenance of the transformed phenotype and, in this sense, their loss is of a 'passenger' nature The rationale presented above argues that a unique molecular portrayal is inevitably shaped by LOH for almost all tumors, which is marked by the absence of numerous polymorphic surface structures that are present on normal cells. Converting this postulated signature of the individual tumor to a targetable set of antigenic epitopes entails a practicable immunological strategy for translating the recognition of a particular 'absence' into an activating cue capable of triggering target cell killing. Importantly, the incorporation of a safety device to assure that on-target off-tumor reactivity is strictly avoided will be highly favorable in future clinical implementation of this strategy The present invention tackles this challenge through the co-expression in each therapeutic killer cell of a single pair of genes. One partner in this pair encodes an activating CAR (aCAR) and the other encodes a protecting CAR (pCAR) or an inhibitory CAR (iCAR)

II. Select Definitions

The term "nucleic acid molecule" as used herein refers to a DNA or RNA molecule.

The term "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (e.g., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "endogenous" refers to any material from or produced inside an organism, cell, tissue or system.

The term "exogenous" refers to any material introduced from or produced outside an organism, cell, tissue or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

The term "genomic variant" as used herein refers to a change of at least one nucleotide at the genomic level in a sequenced sample compared to the reference or consensus sequence at the same genomic position.

The term "corresponding reference allele" as used herein with reference to a variant means the reference or consensus sequence or nucleotide at the same genomic position as the variant.

The term "extracellular domain" as used herein with reference to a protein means a region of the protein which is outside of the cell membrane.

The term "loss of heterozygosity" or "LOH" as used herein means the loss of chromosomal materials such as a complete chromosome or a part thereof, in one copy of the two chromosomes in a somatic cell.

The term "sequence region" as used herein with reference to a variant or a reference allele means a sequence starting upstream and ending downstream from the position of the variant, which can be translated into an "epitope peptide" that can be recognized by an antibody.

The term "CAR", as that term is used herein, refers to a chimeric polypeptide that shares structural and functional properties with a cell immune-function receptor or adaptor molecule, from e.g., a T cell or a NK cell. CARs include TCARs and NKR-CARs. Upon binding to cognate antigen, a CAR can activate or inactivate the cytotoxic cell in which it is disposed, or modulate the cell's antitumor activity or otherwise modulate the cells immune response.

The term "specific binding" as used herein in the context of an extracellular domain, such as an scFv, that specifically binds to a single allelic variant of a polymorphic cell surface epitope, refers to the relative binding of the scFv to one allelic variant and its failure to bind to the corresponding different allelic variant of the same polymorphic cell surface epitope. Since this depends on the avidity (number of CAR copies on the T cell, number of antigen molecules on the surface of target cells (or cells to be protected) and the affinity of the specific CARs used, a functional definition would be that the specific scFv would provide a significant signal in an ELISA against the single allelic variant of a polymorphic cell surface epitope to which it is specific or cells transfected with a CAR displaying the scFv would be clearly labeled with the single allelic variant of a polymorphic cell surface epitope in a FACS assay, while the same assays using the corresponding different allelic variant of the same polymorphic cell surface epitope would not give any detectable signal.

The term "treating" as used herein refers to means of obtaining a desired physiological effect. The effect may be therapeutic in terms of partially or completely curing a disease and/or symptoms attributed to the disease. The term refers to inhibiting the disease, e.g., arresting its development; or ameliorating the disease, e.g., causing regression of the disease.

As used herein, the terms "subject" or "individual" or "animal" or "patient" or "mammal," refers to any subject, particularly a mammalian subject, for whom diagnosis, prognosis, or therapy is desired, for example, a human.

The phrase "safe effector immune cell" or "safe effector cell" includes those cells described by the invention that express at least one iCAR or pCAR as described herein. In some embodiments, the "safe effector immune cell" or "safe effector cell" is capable of administration to a subject. In some embodiments, the "safe effector immune cell" or "safe effector cell" further expresses an aCAR as described herein. In some embodiments, the "safe effector immune cell" or "safe effector cell" further expresses an iCAR or a pCAR as described herein. In some embodiments, the "safe effector immune cell" or "safe effector cell" further expresses an iCAR or a pCAR as described herein and an aCAR as described herein.

Pharmaceutical compositions for use in accordance with the present invention may be formulated in conventional manner using one or more physiologically acceptable carriers or excipients. The carrier(s) must be "acceptable" in the sense of being compatible with the other ingredients of the composition and not deleterious to the recipient thereof.

The phrase "effective amount" or "therapeutically effective amount" are used interchangeably herein, and refer to an amount of a compound, formulation, material, or composition, as described herein effective to achieve a particular biological result.

The following exemplification of carriers, modes of administration, dosage forms, etc., are listed as known possibilities from which the carriers, modes of administration, dosage forms, etc., may be selected for use with the present invention. Those of ordinary skill in the art will understand, however, that any given formulation and mode of administration selected should first be tested to determine that it achieves the desired results.

Methods of administration include, but are not limited to, parenteral, e.g., intravenous, intraperitoneal, intramuscular, subcutaneous, mucosal (e.g., oral, intranasal, buccal, vaginal, rectal, intraocular), intrathecal, topical and intradermal routes. Administration can be systemic or local. In some embodiments, the pharmaceutical composition is adapted for oral administration.

The term "carrier" refers to a diluent, adjuvant, excipient, or vehicle with which the active agent is administered. The carriers in the pharmaceutical composition may comprise a binder, such as microcrystalline cellulose, polyvinylpyrrolidone (polyvidone or povidone), gum tragacanth, gelatin, starch, lactose or lactose monohydrate; a disintegrating agent, such as alginic acid, maize starch and the like; a lubricant or surfactant, such as magnesium stearate, or sodium lauryl sulphate; and a glidant, such as colloidal silicon dioxide.

The term "peripheral blood mononuclear cell (PBMC)" as used herein refers to any blood cell having a round nucleus, such as a lymphocyte, a monocyte or a macrophage. Methods for isolating PBMCs from blood are readily apparent to those skilled in the art. A non-limiting example is the extraction of these cells from whole blood using ficoll, a hydrophilic polysaccharide that separates layers of blood, with monocytes and lymphocytes forming a buffy coat under a layer of plasma or by leukapheresis, the preparation of leukocyte concentrates with the return of red cells and leukocyte-poor plasma to the donor.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer, glioma, and the like.

III. CAR-T System: iCARs, pCARs, and aCARs

It should be emphasized that the present invention provides a new avenue enabling specific targeting of tumor cells while keeping the normal cells secure. The concept presented herein provides for the identification of new targets for iCARs (or pCARs or protective CARs), these targets defined as comprising single allelic variants of polymorphic cell surface epitopes, which are lost from tumor cells due to LOH of the chromosomal region they reside in, while remaining expressed on normal tissue. Because of the polymorphic variation, it is possible to distinguish the two alleles and target only the allele missing in the tumor cells. Further, the target antigen may not necessarily itself be a tumor suppressor gene, or a gene predicted to be involved with cancer, since it is chosen for being in a region lost by LOH and could therefore simply be linked to such genes. This is conceptually different from the methods employed or suggested to date in cancer therapy, which target tumor associated antigens or antigens downregulated at tumors regardless of polymorphism. The present methods also provide for broadening the selection of aCAR beyond tumor associated antigens, by conferring protection of normal cells through the co-expression of the iCAR and/or pCAR as described herein.

The distinction is crucial because the LOH, being a genomic event, results in a total loss of a specific variant from the tumor with a very rare probability of gaining back the lost allele. If the LOH event occurs very early in the development of tumors, it ensures a uniform target signature in all tumor cells derived from the initial pre-malignant tissue including metastatic tumors. Additionally, LOH occurs in almost all types of cancer and this concept can therefore be relied upon as a universal tool for developing markers relevant to all these cancer types. Since the LOH events are to some extent random, the present invention further provides for selection of personalized tumor markers for each individual cancer patient, based on the specific LOH events which took place in that patient. The tools relied upon to execute this concept, the aCARs and the iCARs, are well-known and can be easily prepared using methods well-known in the art as taught for example, in WO 2015/142314 and in U.S. Pat. No. 9,745,368, both incorporated by reference as if fully disclosed herein.

According to one strategy, the two CARs in every given pair specifically recognize the product of a different allelic variant of the same target gene for which the patient is heterozygous. The basic principle is as follows: the aCAR targets an allelic variant of a selected cell surface protein that is expressed by the given tumor cells and is not affected by LOH while the pCAR or iCAR targets the product encoded by the allelic variant of the same gene that has been lost from these tumor cells due to LOH. In other normal tissues of that individual patient that express the said gene, both alleles are present and are known to be equally functional, that is, expression is biallelic in all tissues (in contrast to other genes which may exhibit random monoallelic expression (Chess, 2012; Savova et al., 2016). In one scenario, the two CARs target two related epitopes residing at the same location on the protein product, which differ by one, or only few amino acids. In another scenario, the aCAR targets a non-polymorphic epitope on the same protein while the pCAR or iCAR is allele-specific. In this case the density of the aCAR epitope on normal cells would generally be two-fold higher than that of the iCAR or pCAR one. In some embodiments, a single nucleic acid vector encodes both the aCAR and iCAR or pCAR.

Another strategy utilizes as the pCAR or iCAR targets the protein products of housekeeping genes. Since, by definition, these genes are expressed on all cells in the body, they are safe targets for pCAR or iCARs. That is, if the pCAR or iCAR targets a membrane product of a housekeeping gene for which the given patient is heterozygous, all cells in the body, except the tumor cells which have lost this allele due to LOH, will be protected. This strategy allows for the uncoupling of the aCAR target gene product from the pCAR or iCAR one. In fact, the aCAR target can then be any non-polymorphic epitope expressed by the tumor. A variation of this strategy would be to utilize a known aCAR targeted to a non-polymorphic tumor-associated antigen, e.g., an aCAR in clinical use or under examination in clinical trials, in combination with an iCAR or pCAR directed against a membrane product of a gene for which the given patient is heterozygous and which is expressed in at least the tissue of origin of the tumor and preferably in additional vital normal tissues in which aCAR target antigen is expressed.

Following the same rationale which allows the uncoupling of the aCAR target antigen from the iCAR/pCAR one, the latter should not necessarily be the product of a housekeeping gene. In some embodiments, the iCAR and/or pCAR be the product of any gene the expression pattern of which is sufficiently wide so as to protect vital normal tissues expressing the aCAR target antigen in addition to the tumor. As a corollary, the aCAR antigen can be, as argued for housekeeping genes, any non-polymorphic epitope expressed by the tumor, not restricted to known 'tumor-associated antigens', a consideration which can vastly expand the list of candidate aCAR targets. In general, for both housekeeping and non-housekeeping genes, the identity of such normal vital tissues and level of expression would serve as important criteria in the prioritization of such candidate aCAR targets Care must be taken to ensure that the inhibitory signal transmitted by the iCAR is strictly and permanently dominant over the aCAR signal and that no cross-recognition between the iCAR and the aCAR occurs. Dominance of the iCAR guarantees that activation of the killer cell upon encounter with normal cells expressing both alleles would be prevented. This default brake would, however, not operate upon engagement with tumor cells: in the absence of its target antigen the iCAR would not deliver inhibitory signals, thus unleashing the anticipated aCAR-mediated cellular activation and subsequent tumor cell lysis The iCAR technology may be based on immune checkpoints. In this regard, the demonstration (Fedorov et al., 2013b; WO 2015/142314) that the regulatory elements of PD-1 and CTLA-4 possess a potent T cell inhibitory capacity when incorporated as iCAR signaling components is encouraging but the generality of these observations was recently questioned (Chicaybam and Bonamino, 2014, 2015). Furthermore, although the precise molecular pathways triggered by these checkpoint proteins are not fully understood, their engagement dampens T-cell activation through both proximal and distal mechanisms, rendering T cells unresponsive to concomitant activating stimuli (Nirschl and Drake, 2013). Hence, although the inactivation status secured by PD-1 and CTLA-4 iCARs is indeed temporary and reversible (Fedorov et al., 2013b), it would not allow T cell activation in tissues expressing both iCAR and aCAR targets. In contrast, the dominance of NK inhibitory receptors over activating receptors assures that healthy cells are spared from NK cell attack through a spatial, rather than temporal mechanism. (Long et al., 2013). There is compelling evidence that a single NK cell can spare a resistant cell expressing both inhibitory and activating ligands yet, kill a susceptible cell it simultaneously engages, which expresses only the activating ligands. This exquisite ability is governed by the different spatial organization of signal transduction molecules formed at each of the respective immune synapses which consequently affects the exocytosis of cytolytic granules (e.g., Abeyweera et al., 2011; Eriksson et al., 1999; Treanor et al., 2006; Vyas et al., 2001; U.S. Pat. No. 9,745,368).

The strategy based on the control asserted by iCARs depends on the dominance of the iCAR activity over the aCAR activity as explained above. In some embodiments, the present invention provides this type of iCAR, termed here a pCAR (for 'protective CAR, see FIG. 2), designed to operate in CAR T cells in a synapse-selective manner and guarantee full dominance over the co-expressed aCAR. In some embodiments, the iCAR provided by the present invention is this particular type of iCAR referred to herein as a protective CAR (pCAR).

In some embodiments, the pCAR of the present invention integrates two technological feats. First, the pCAR allows for uncoupling the activating moiety of the aCAR (FcRγ/CD3-ζ) from the recognition unit and the co-stimulatory element (e.g., CD28, 4-1BB, CD134 (OX40, GITR, IL2Rβ and STAT3 binding motif (YXXQ)) by genetically placing them on two different polypeptide products. Recoupling of these elements, which is mandatory for the aCAR function, will only take place by the addition of a heterodimerizing drug which can bridge the respective binding sites incorporated onto each of the polypeptides separately (FIG. 2B). The reconstruction of a fully functional CAR by bridging similarly split recognition and activating moieties by virtue of a heterodimerizing drug has recently been reported by Wu et al. (Wu et al., 2015). For this purpose, these authors used the FK506 binding protein domain (FKBP, 104 amino acids) and the T2089L mutant of FKBP-rapamycin binding domain (FRB, 89 amino acids) that heterodimerize in the presence of the rapamycin analog AP21967 (Scheme I below). This drug possess 1000-fold less immunosuppressive activity compared to rapamycin (Bayle et al., 2006; Graef et al., 1997; Liberles et al., 1997) and is commercially available (ARGENT™, Regulated Heterodimerization Kit, ARIAD). In some embodiments, the drug is administered orally.

Scheme I. Structure of AP21967

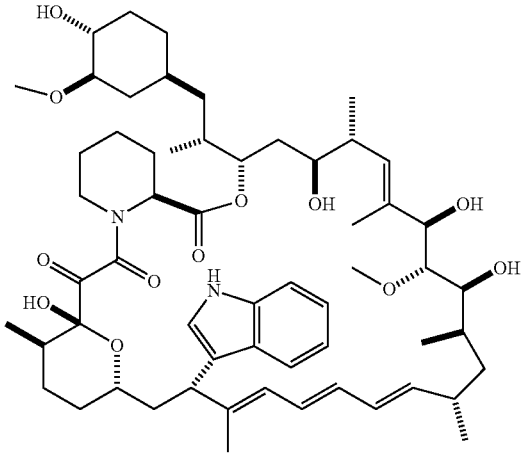

Second, engrafting the pCAR recognition unit and the missing activating domain, respectively, onto the two surfaces of the transmembrane domain of a RIP-controlled receptor which contains the two intramembrane cleavage sites (FIG. 2A). Binding of the pCAR to its antigen will trigger dual cleavage of the encoded polypeptide first by a member of the extracellular disintegrin and metalloproteinase (ADAM) family which removes the ectodomain and then by intracellular γ-secretase, which liberates the intracellular domain of the pCAR. This first cleavage event is predicted to disrupt the ability of the truncated aCAR to gain access to a functional, membrane-anchored configuration of its missing activating element, thus acquiring an operative mode (FIG. 2C). This principle was recently exploited in the development of new genetic switches designed to limit CAR T cell activity to simultaneous recognition of two different antigens on the tumor cell, applying either the Notch receptor (Morsut et al., 2016; Roybal et al., 2016b) or Epithelial cell adhesion molecule (EpCAM, Pizem, Y., M. Sc. thesis under the supervision of the Inventor), two well-studied receptors functioning through RIP. In these studies, binding of the RIP-based CAR to one antigen releases a genetically-engineered intracellular domain which translocates to the cell nucleus where it turns on the expression of the second CAR. Unlike the current invention which utilizes this process solely for disarming any potential aCAR activity in the presence of the protective antigen. In some embodiments, the first cleavage event disrupts the ability of the truncated aCAR to gain access to a functional, membrane-anchored configuration of its missing activating element, thus acquiring an operative mode.

The proposed mode of action described above is predicted to exert local effects so that only aCARs which reside in the same synapse are affected and are no more able to hind their antigen productively and form an immunological synapse. As a result, even when multiple interactions of the aCAR with large numbers of non-tumor cells are likely to take place, they are only expected to be transient and nonfunctional so that the cells are fully capable of further interactions.

Dominance of the pCARs over their aCARs counterparts is inherent to this system as function of the aCARs utterly depends on presence of the pCARs. Relative shortage of pCARs in a given T cell would render the aCARs nonfunctional due to lack of an activating domain. In some embodiments, a shortage of pCARs in a given T cell renders the aCARs non-functional due to lack of an activating domain.

It is critical that both the recognition domain and the activating one are localized to the plasma membrane (Wu et al., 2015). Therefore, the second cleavage, which detaches the activating domain from the plasma membrane, would render this domain nonfunctional and prevent unwanted cellular activation. In some embodiments, the recognition domain and the activating one are localized to the plasma membrane. In some embodiments, the second cleavage detaches the activating domain from the plasma membrane and renders this domain nonfunctional and prevents unwanted cellular activation.

The aCAR and pCAR are designed to function via mutually exclusive mechanisms. The ability of the pCAR to undergo cleavage does not depend on the strength of inhibitory signaling so no completion on signaling outcome will take place. As long as the pCARs are cleaved, the aCARs cannot function, regardless of relative avidity of their interactions with their respective antigens, a scenario which secures another crucial level of safety.

In some embodiments, the mammalian tissue is human tissue and in other embodiments the related mammalian normal tissue is normal tissue from which the tumor developed.

In some embodiments, the effector immune cell is a T cell, a natural killer cell or a cytokine-induced killer cell.

In some embodiments, the at least one signal transduction element capable of inhibiting an effector immune cell is homologous to a signal transduction element of an immune checkpoint protein, such as an immune checkpoint protein selected from the group consisting of PD1; CTLA4; BTLA; 2B4; CD160; CEACAM, such as CEACAM1; KIRs, such as KIR2DL1, KIR2DL2, KIR2DL3, KIR2DL4, KIR2DL5A, KIR2DL5B, KIR3DL1, KIR3DL2, KIR3DL3, LIR1, LIR2, LIR3, LIR5, LIR8 and CD94-NKG2A; LAG3; TIM3; V-domain Ig suppressor of T cell activation (VISTA); STimulator of INterferon Genes (STING); immunoreceptor tyrosine-based inhibitory motif (ITIM)-containing proteins, T cell immunoglobulin and ITIM domain (TIGIT), and adenosine receptor (e.g., A2aR). In some embodiments, the immune checkpoint protein is a negative immune regulator. In some embodiments, the negative immune regulator is selected from the group consisting of 2B4, LAG-3 and BTLA-4.

In some embodiments, immune checkpoint protein is a natural killer cell inhibitory receptor, e.g., KIRs, such as KIR2DL1, KIR2DL2, KIR2DL3, KIR2DL4, KIR2DL5A, KIR2DL5B, KIR3DL1, KIR3DL2, KIR3DL3; or a Leukocyte Ig-like receptor, such as LIR1, LIR2, LIR3, LIR5, LIRE; and CD94-NKG2A, a C-type lectin receptor which forms heterodimers with CD94 and contains 2 ITIMs.

The methods for preparing and using killer cell receptors in iCARs has been described in U.S. Pat. No. 9,745,368, incorporated by reference as if fully disclosed herein.

In some embodiments, the extracellular domain of any one of the above embodiments is fused through a flexible hinge and transmembrane canonic motif to said intracellular domain.

i. Target Identification: aCAR, iCAR and pCAR

The present invention provides methods for identification of aCAR, iCAR and/or pCAR targets based identification of candidate genes having extracellular polymorphic epitopes. In some embodiments, the aCAR can be directed at any extracellular protein expressed on the tumor tissue. In some embodiments, aCAR target is further expressed on non-tumor tissues and the iCAR target is also expressed on non-tumor tissues but is not expressed on tumor tissues.

In some embodiments, the method of identification of candidate genes includes first determining that the gene encodes a transmembrane protein comprising an extracellular polymorphic epitope. In some embodiments, the method of identification of candidate genes further includes determining that the gene has at least two expressed alleles. In some embodiments, these alleles exhibit at least one allelic variation. In some embodiments, the allelic variation includes, for example, the presence of one or more SNPs, insertions, and/or deletions. In some embodiments, the allelic variation found for the gene causes an amino acid change relative to the reference sequence in an extracellular region of the protein. In some embodiments, the gene is located in a chromosomal region which undergoes loss of heterozygosity (LOH). In some embodiments, the gene is located in a chromosomal region which undergoes loss of heterozygosity (LOH) in cancer. In some embodiments, the gene is expressed in a tissue-of-origin of a tumor type in which the corresponding region was found to undergo LOH. In some embodiments, the gene is expressed at least in one or more tissues that the aCAR is expressed in. In some embodiments, the iCAR or pCAR target is expressed in vital organ cells the aCAR is expressed in.

In some embodiments, the target for use in the iCAR and/or pCAR is selected based on identification of a gene having at least one extracellular polymorphic epitope and wherein said gene has at least two expressed alleles. In some embodiments, the target for use in the iCAR and/or pCAR is selected based on identification of a gene having located in a chromosomal region which undergoes loss of heterozygosity. In some embodiments, the target for use in the iCAR and/or pCAR is selected based on identification of a gene having located in a chromosomal region which undergoes loss of heterozygosity in cancer. In some embodiments, the score for a theoretical SNP is calculated and a threshold limit determined. For example, if only 32% of the SNPs had a tumor suppressor gene on the chromosome, then the percentile rank for having one would be 0.68. Further, for example, if the allele had a minor allele fraction of 0.49 (where 0.5 is the highest possible), then the percentile rank would be 0.99. If the rate of LOH was 0.10, and 75% of SNPs had more LOH than that, then the percentile rank would be 0.25. If the ratio of standard deviation of expression values across tissues to the median for the gene harboring this SNP was 1.3 and that is better than 90% of other genes, then the percentile rank is 0.9. The total score for this SNP would then be $0.68*0.99*0.25*0.9=0.15$. In some embodiments, this LOH candidate score can be employed as one method for determining if a candidate gene is a suitable iCAR or pCAR target. In some embodiments, the target can be selected based on this LOH score. In some embodiments, the candidate gene is a determined to be suitable as an iCAR or pCAR target. LOH candidates based on an LOH candidate score of greater than 0.4.

In some embodiments, the target for use in the iCAR and/or pCAR is selected from a gene having at least one extracellular polymorphic epitope. In some embodiments, the target is a gene is located on chromosome 1, chromosome 2, chromosome 3, chromosome 4, chromosome 5, chromosome 6, chromosome 7, chromosome 8, chromosome 9, chromosome 10, chromosome 11, chromosome 12, chromosome 13, chromosome 14, chromosome 15, chromosome 16, chromosome 17, chromosome 18, chromosome 19, chromosome 20, chromosome 21, chromosome 22, or chromosome X.

In some embodiments, the gene comprising the extracellular polymorphic epitope is located on chromosome 1. In some embodiments, the target for use in the iCAR and/or pCAR is selected from the group consisting of ABCA4, ADAM30, AQP10, ASTN1, C1orf101, CACNA1S, CATSPER4, CD101, CD164L2, CD1A, CD1C, CD244, CD34, CD46, CELSR2, CHRNB2, CLCA2, CLDN19, CLSTN1, CR1, CR2, CRB1, CSF3R, CSMD2, ECE1, ELTD1, EMC1, EPHA10, EPHA2, EPHA8, ERMAP, FCAMR, FCER1A, FCGR1B, FCGR2A, FCGR2B, FCGR3A, FCRL1, FCRL3, FCRL4, FCRL5, FCRL6, GJB4, GPA33, GPR157, GPR37L1, GPR88, HCRTR1, IGSF3, IGSF9, IL22RA1, IL23R, ITGA10, KIAA1324, KIAA2013, LDLRAD2, LEPR, LGR6, LRIG2, LRP8, LRRC52, LRRC8B, LRRN2, LY9, MIA3, MR1, MUC1, MXRA8, NCSTN, NFASC, NOTCH2, NPR1, NTRK1, OPN3, OR10J1, OR10J4, OR10K1, OR1OR2, OR10T2, OR10X1, OR11L1, OR14A16, OR14I1, OR14K1, OR2AK2, OR2C3, OR2G2, OR2G3, OR2L2, OR2M7, OR2T12, OR2T27, OR2T1, OR2T3, OR2T29, OR2T33, OR2T34, OR2T35, OR2T3, OR2T4, OR2T5, OR2T6, OR2T7, OR2T8, OR2W3, OR6F1, OR6K2, OR6K3, OR6K6, OR6N1, OR6P1, OR6Y1, PDPN, PEAR1, PIGR, PLXNA2, PTCH2, PTCHD2, PTGFRN, PTPRC, PTPRF, PTGFRN, PVRL4, RHBG, RXFP4, S1PR1, SCNN1D, SDC3, SELE, SELL, SELP, SEMA4A, SEMA6C, SLAMF7, SLAMF9, SLC2A7, SLC5A9, TACSTD2, TAS1R2, T1E1, TLR5, TMEM81, TNFRSF14, TNFRSF1B, TRABD2B, USH2A, VCAM1, and ZP4.

In some embodiments, the gene comprising the extracellular polymorphic epitope is located on chromosome 2. In some embodiments, the target for use in the iCAR and/or pCAR is selected from the group consisting of ABCG5, ALK, ASPRV1, ATRAID, CD207, CD8B, CHRNG, CLEC4F, CNTNAP5, CRIM1, CXCR1, DNER, DPP10, EDAR, EPCAM, GPR113, GPR148, GPR35, GPR39, GYPC, IL1RL1, ITGA4, ITGA6, ITGAV, LCT, LHCGR, LRP1B, LRP2, LY75, MARCO, MERTK, NRP2, OR6B2, PLA2R1, PLB1, PROKR1, PROM2, SCN7A, SDC1, SLC23A3, SLC5A6, TGOLN2, THSD7B, TM4SF20, TMEFF2, TMEM178A, TPO, and TRABD2A.

In some embodiments, the gene comprising the extracellular polymorphic epitope is located on chromosome 3. In some embodiments, the target for use in the iCAR and/or pCAR is selected from the group consisting of ACKR2, ALCAM, ANO10, ATP13A4, BTLA, CACNA1D, CACNA2D2, CACNA2D3, CASR, CCRL2, CD200, CD200R1, CD86, CD96, CDCP1, CDHR4, CELSR3, CHL1, CLDN11, CLDN18, CLSTN2, CSPG5, CX3CR1, CXCR6, CYP8B1, DCBLD2, DRD3, EPHA6, EPHB3, GABRR3, GP5, GPR128, GPR15, GPR27, GRM2, GRM7, HEG1, HTR3C, HTR3D, HTR3E, IGSF11, IL17RC, IL17RD, IL17RE, IL5RA, IMPG2, ITGA9, ITGB5, KCNMB3, LRIG1, LRRC15, LRRN1, MST1R, NAALADL2, NRROS, OR5AC1, OR5H1, OR5H14, OR5H15, OR5H6, OR5K2, OR5K3, OR5K4, PIGX, PLXNB1, PLXND1, PRRT3, PTPRG, ROBO2, RYK, SEMA5B, SIDT1, SLC22A14, SLC33A1, SLC4A7, SLITRK3, STAB1, SUSD5, TFRC, TLR9, TMEM108, TMEM44, TMPRSS7, TNFSF10, UPK1B, VIPR1, and ZPLD1.

In some embodiments, the gene comprising the extracellular polymorphic epitope is located on chromosome 4. In some embodiments, the target for use in the iCAR and/or pCAR is selected from the group consisting of ANTXR2, BTC, CNGA1, CORIN, EGF, EMCN, ENPEP, EPHA5, ERVMER34-1, EVC2, FAT1, FAT4, FGFRL1, FRAS1, GPR125, GRID2, GYPA, GYPB, KDR, KIAA0922, KLB, MFSD8, PARM1, PDGFRA, RNF150, TENM3, TLR10, TLR1, TLR6, TMEM156, TMPRSS11A, TMPRSS11B, TMPRSS11E, TMPRSS11F, UGT2A1, and UNC5C.

In some embodiments, the gene comprising the extracellular polymorphic epitope is located on chromosome 5. In some embodiments, the target for use in the iCAR and/or pCAR is selected from the group consisting of ADAM19, ADRB2, BTNL3, BTNL8, BTNL9, C5orf15, CATSPER3, CD180, CDH12, CDHR2, COL23A1, CSF1R, F2RL2, FAM174A, FAT2, FGFR4, FLT4, GABRA6, GABRG2, GPR151, GPR98, GRM6, HAVCR1, HAVCR2, IL31RA, IL6ST, IL7R, IQGAP2, ITGA1, ITGA2, KCNMB1, LIFR, LNPEP, MEGF10, NIPAL4, NPR3, NRG2, OR2V1, OR2Y1, OSMR, PCDH12, PCDH1, PCDHA1, PCDHA2, PCDHA4, PCDHA8, PCDHA9, PCDHB10, PCDHB11, PCDHB13, PCDHB14, PCDHB15, PCDHB16, PCDHB2, PCDHB3, PCDHB4, PCDHB5, PCDHB6, PCDHGA1, PCDHGA4, PDGFRB, PRLR, SEMA5A, SEMA6A, SGCD, SLC1A3, SLC22A4, SLC22A5, SLC23A1, SLC36A3, SLC45A2, SLC6A18, SLC6A19, SLCO6A1, SV2C, TENM2, TIMD4, and UGT3A1.

In some embodiments, the gene comprising the extracellular polymorphic epitope is located on chromosome 6. In some embodiments, the target for use in the iCAR and/or pCAR is selected from the group consisting of BAI3, BTN1A1, BTN2A1, BTN2A2, BTN3A1, BTN3A2, BTNL2, CD83, DCBLD1, DLL1, DPCR1, ENPP1, ENPP3, ENPP4, EPHA7, GABBR1, GABRR1, GCNT6, GFRAL, GJB7, GLP1R, GPR110, GPR111, GPR116, GPR126, GPR63, GPRC6A, HFE, HLA-A, HLA-B, HLA-C, HLA-DOA, HLA-DPA1, HLA-DPB1, HLA-DQA1, HLA-DQA2, HLA-DQB1, HLA-DQB2, HLA-DRB1, HLA-DRB5, HLA-E, HLA-F, HLA-G, IL20RA, ITPR3, KIAA0319, LMBRD1, LRFN2, LRP11, MAS1L, MEP1A, MICA, MICB, MOG, MUC21, MUC22, NCR2, NOTCH4, OPRM1, OR10C1, OR12D2, OR12D3, OR14J1, OR2B2, OR2B6, OR2J1, OR2W1, OR5V1, PDE10A, PI16, PKHD1, PTCRA, PTK7, RAET1E, RAET1G, ROS1, SDIM1, SLC16A10, SLC22A1, SLC44A4, TAAR2, TREM1, TREML1, and TREML2. In some embodiments, the gene comprising the extracellular polymorphic epitope is located on chromosome 6 and comprises an HLA target. In some embodiments, the target for use in the iCAR and/or pCAR is HLA-A, HLA-B, HLA-C, HLA-DOA, HLA-DPA1, HLA-DPB1, HLA-DQA1, HLA-DQA2, HLA-DQB1, HLA-DQB2, HLA-DRB1, HLA-DRB5, HLA-E, HLA-F, HLA-G. In some embodiments, the target for use in the iCAR and/or pCAR is HLA-A2, In some embodiments, the gene comprising the extracellular polymorphic epitope is located on chromosome 7. In some embodiments, the target for use in the iCAR and/or pCAR is selected from the group consisting of AQP1, C7orf50, CD36, CDHR3, CNTNAP2, DPP6, EGFR, EPHA1, EPHB6, ERVW-1, GHRHR, GJC3, GPNMB, GRM8, HUS1, HYAL4, KIAA1324L, LRRN3, MET, MUC12, MUC17, NPC1L1, NPSR1, OR2A12, OR2A14, OR2A25, OR2A42, OR2A7, OR2A2, OR2AE1, OR2F2, OR6V1, PILRA, PILRB, PKD1L1, PLXNA4, PODXL, PTPRN2, PTPRZ1, RAMP3, SLC29A4, SMO, TAS2R16, TAS2R40, TAS2R4, TFR2, THSD7A, TMEM213, TTYH3, ZAN, and ZP3.

In some embodiments, the gene comprising the extracellular polymorphic epitope is located on chromosome 8. In some embodiments, the target for use in the iCAR and/or pCAR is selected from the group consisting of ADAM18, ADAM28, ADAM32, ADAM7, ADAM9, ADRA1A, CDH17, CHRNA2, CSMD1, CSMD3, DCSTAMP, FZD6, GPR124, NRG1, OR4F21, PKHD1L1, PRSS55, SCARA3, SCARA5, SDC2, SLC10A5, SLC39A14, SLC39A4, SLCO5A1, TNFRSF10A, and TNFRSF10B.

In some embodiments, the gene comprising the extracellular polymorphic epitope is located on chromosome 9. In some embodiments, the target for use in the iCAR and/or pCAR is selected from the group consisting of ABCA1, AQP7, ASTN2, C9orf135, CA9, CD72, CNTNAP3B, CNTNAP3, CRB2, ENTPD8, GPR144, GRIN3A, IZUMO3, KIAA1161, MAMDC4, MEGF9, MUSK, NOTCH1, OR13C2, OR13C3, OR13C5, OR13C8, OR13C9, OR13D1, OR13F1, OR1B1, OR1J2, OR1K1, OR1L1, OR1L3, OR1L6, OR1L8, OR1N1, OR1N2, OR1Q1, OR2S2, PCSK5, PDCD1LG2, PLGRKT, PTPRD, ROR2, SEMA4D, SLC31A1, TEK, TLR4, TMEM2, and VLDLR.

In some embodiments, the gene comprising the extracellular polymorphic epitope is located on chromosome 10. In some embodiments, the target for use in the iCAR and/or pCAR is selected from the group consisting of ABCC2, ADAMS, ADRB1, ANTXRL, ATRNL1, C10orf54, CDH23, CDHR1, CNNM2, COL13A1, COL17A1, ENTPD1, FZD8, FGFR2, GPR158, GRID1, IL15RA, IL2RA, ITGA8, ITGB1, MRC1, NRG3, NPFFR1, NRP1, OPN4, PCDH15, PKD2L1, PLXDC2, PRLHR, RET, RGR, SLC16A9, SLC29A3, SLC39A12, TACR2, TCTN3, TSPAN15, UNC5B, and VSTM4.

In some embodiments, the gene comprising the extracellular polymorphic epitope is located on chromosome 11. In some embodiments, the target for use in the iCAR and/or pCAR is selected from the group consisting of AMICA1, ANO1, ANO3, APLP2, C11orf24, CCKBR, CD248, CD44, CD5, CD6, CD82, CDON, CLMP, CRTAM, DCHS1, DSCAML1, FAT3, FOLH1, GDPD4, GDPD5, GRIK4, HEPHL1, HTR3B, IFITM10, IL10RA, KIRREL3, LGR4, LRP4, LRP5, LRRC32, MCAM, MFRP, MMP26, MPEG1, MRGPRE, MRGPRF, MRGPRX2, MRGPRX3, MRGPRX4, MS4A4A, MS4A6A, MTNR1B, MUC15, NAALAD2, NAALADL1, NCAM1, NRXN2, OR10A2, OR10A5, OR10A6, OR10D3, OR10G4, OR10G7, OR10G8, OR10G9, OR10Q1, OR10S1, OR1S1, OR2AG1, OR2AG2, OR2D2, OR4A47, OR4A15, OR4A5, OR4C11, OR4C13, OR4C15, OR4C16, OR4C3, OR4C46, OR4C5, OR4D6, OR4A8P, OR4D9, OR4S2, OR4X1, OR51E1, OR51L1, OR52A1, OR52E1, OR52E2, OR52E4, OR52E6, OR52I1, OR52I2, OR52J3, OR52L1, OR52N1, OR52N2, OR52N4, OR52W1, OR56B1, OR56B4, OR5A1, OR5A2, OR5AK2, OR5AR1, OR5B17, OR5B3, OR5D14, OR5D16, OR5D18, OR5F1, OR5I1, OR5L2, OR5M11, OR5M3, OR5P2, OR5R1, OR5T2, OR5T3, OR5W2, OR6A2, OR6T1, OR6X1, OR8A1, OR8B12, OR8B2, OR8B3, OR8B4, OR8D1, OR8D2, OR8H1, OR8H2, OR8H3, OR8I2, OR8J1, OR8J2, OR8J3, OR8K1, OR8K3, OR8K5, OR8U1, OR9G1, OR9G4, OR9Q2, P2RX3, PTPRJ, ROBO3, SIGIRR, SLC22A10, SLC3A2, SLC5A12, SLCO2B1, SORL1, ST14, SYT8, TENM4, TMEM123, TMEM225, TMPRSS4, TMPRSS5, TRIM5, TRPM5, TSPAN18, and ZP1.

In some embodiments, the gene comprising the extracellular polymorphic epitope is located on chromosome 12. In some embodiments, the target for use in the iCAR and/or pCAR is selected from the group consisting of ANO4, AVPR1A, BCL2L14, CACNA2D4, CD163, CD163L1, CD27, CD4, CLEC12A, CLEC1B, CLEC2A, CLEC4C, CLEC7A, CLECL1, CLSTN3, GPR133, GPRC5D, ITGA7, ITGB7, KLRB1, KLRC2, KLRC3, KLRC4, KLRF1, KLRF2, LRP1, LRP6, MANSC1, MANSC4, OLR1, OR10AD1, OR10P1, OR2AP1, OR6C1, OR6C2, OR6C3, OR6C4, OR6C6, OR6C74, OR6C76, OR8S1, OR9K2, ORAI1, P2RX4, P2RX7, PRR4, PTPRB, PTPRQ, PTPRR, SCNN1A, SELPLG, SLC2A14, SLC38A4, SLC5A8, SLC6A15, SLC8B1, SLCO1A2, SLCO1B1, SLCO1B7, SLCO1C1, SSPN. STAB2, TAS2R10, TAS2R13, TAS2R14, TAS2R20, TAS2R30, TAS2R31, TAS2R42, TAS2R43, TAS2R46, TAS2R7, TMEM119, TMEM132B, TMEM132C, TMEM132D, TMPRSS12, TNFRSF1A, TSPAN8, and VSIG10.

In some embodiments, the gene comprising the extracellular polymorphic epitope is located on chromosome 13. In some embodiments, the target for use in the iCAR and/or pCAR is selected from the group consisting of ATP4B, ATP7B, FLT3, FREM2, HTR2A, KL, PCDH8, RXFP2, SGCG, SHISA2, SLC15A1, SLITRK6, and TNFRSF19.

In some embodiments, the gene comprising the extracellular polymorphic epitope is located on chromosome 14. In some embodiments, the target for use in the iCAR and/or pCAR is selected from the group consisting of ADAM21, BDKRB2, C14orf37, CLEC14A, DLK1, FLRT2, GPR135, GPR137C, JAG2, LTB4R2, MMP14, OR11G2, OR11H12, OR11H6, OR4K1, OR4K15, OR4K5, OR4L1, OR4N2, OR4N5, SLC24A4, and SYNDIG1L.

In some embodiments, the gene comprising the extracellular polymorphic epitope is located on chromosome 15. In some embodiments, the target for use in the iCAR and/or pCAR is selected from the group consisting of ANPEP, CD276, CHRNA7, CHRNB4, CSPG4, DUOX1, DUOX2, FAM174B, GLDN, IGDCC4, ITGA11, LCTL, LTK, LYSMD4, MEGF11, NOX5, NRG4, OCA2, OR4F4, OR4M2, OR4N4, PRTG, RHCG, SCAMP5, SEMA4B, SEMA6D, SLC24A1, SLC24A5, SLC28A1, SPG11, STRA6, TRPM1, and TYRO3.

In some embodiments, the gene comprising the extracellular polymorphic epitope is located on chromosome 16. In some embodiments, the target for use in the iCAR and/or pCAR is selected from the group consisting of ATP2C2, CACNA1H, CD19, CDH11, CDH15, CDH16, CDH3, CDH5, CNGB1, CNTNAP4, GDPD3, GPR56, GPR97, IFT140, IL4R, ITFG3, ITGAL, ITGAM, ITGAX, KCNG4, MMP15, MSLN, NOMO1, NOMO3, OR2C1, PIEZO1, PKD1, PKD1L2, QPRT, SCNN1B, SEZ6L2, SLC22A31, SLC5A11, SLC7A6, SPN, TMC5, TMC7, TMEM204, TMEM219, and TMEM8A.

In some embodiments, the gene comprising the extracellular polymorphic epitope is located on chromosome 17. In some embodiments, the target for use in the iCAR and/or pCAR is selected from the group consisting of ABCC3, ACE, AOC3, ARL17B, ASGR2, C17orf80, CD300A, CD300C, CD300E, CD300LF, CD300LG, CHRNB1, CLEC10A, CNTNAP1, CPD, CXCL16, ERBB2, FAM171A2, GCGR, GLP2R, GP1BA, GPR142, GUCY2D, ITGA2B, ITGA3, ITGAE, ITGB3, KCNJ12, LRRC37A2, LRRC37A3, LRRC37A, LRRC37B, MRC2, NGFR, OR1A2, OR1D2, OR1G1, OR3A1, OR3A2, OR4D1, OR4D2, RNF43, SCARF1, SCN4A, SDK2, SECTM1, SEZ6, SHPK, SLC26A11, SLC5A10, SPACA3, TMEM102, TMEM132E, TNFSF12, TRPV3, TTYH2, and TUSC5.

In some embodiments, the gene comprising the extracellular polymorphic epitope is located on chromosome 18. In some embodiments, the target for use in the iCAR and/or pCAR is selected from the group consisting of APCDD1, CDH19, CDH20, CDH7, COLEC12, DCC, DSC1, DSG1, DSG3, DYNAP, MEP1B, PTPRM, SIGLEC15, and TNFRSF11A.

In some embodiments, the gene comprising the extracellular polymorphic epitope is located on chromosome 19. In some embodiments, the target for use in the iCAR and/or pCAR is selected from the group consisting of ABCA7, ACPT, BCAM, C19orf38, C19orf59, C5AR1, CATSPERD, CATSPERG, CD22, CD320, CD33, CD97, CEACAM19, CEACAM1, CEACAM21, CEACAM3, CEACAM4, CLEC4M, DLL3, EMR1, EMR2, EMR3, ERVV-1, ERVV-2, FAM187B, FCAR, FFAR3, FPR1, FXYD5, GFY, GP6, GPR42, GRIN3B, ICAM3, IGFLR1, IL12RB1, IL27RA, KIR2DL1, KIR2DL3, KIR2DL4, K1R3DL1, KIR3DL2, KIR3DL3, KIRREL2, KISS1R, LAIR1, LDLR, LILRA1, LILRA2, LILRA4, LILRA6, LILRB1, LILRB2, LILRB3, LILRB4, LILRB5, LINGO3, LPHN1, LRP3, MADCAM1, MAG, MEGF8, MUC16, NCR1, NOTCH3, NPHS1, OR10H1, OR10H2, OR10H3, OR10H4, OR1I1, OR2Z1, OR7A10, OR7C1, OR7D4, OR7E24, OR7G1, OR7G2, OR7G3, PLVAP, PTGIR, PTPRH, PTPRS, PVR, SCN1B, SHISA7, SIGLEC10, SIGLEC11, SIGLEC12, SIGLEC5, SIGLEC6, SIGLEC8, SIGLEC9, SLC44A2, SLC5A5, SLC7A9, SPINT2, TARM1, TGFBR3L, TMC4, TMEM91, TMEM161A, TMPRSS9, TNFSF14, TNFSF9, TRPM4, VN1R2, VSIG10L, VSTM2B, and ZNRF4.

In some embodiments, the gene comprising the extracellular polymorphic epitope is located on chromosome 20. In some embodiments, the target for use in the iCAR and/or pCAR is selected from the group consisting of ABHD12, ADAM33, ADRA1D, APMAP, ATRN, CD40, CD93, CDH22, CDH26, CDH4, FLRT3, GCNT7, GGT7, JAG1, LRRN4, NPBWR2, OCSTAMP, PTPRA, PTPRT, SEL1L2, SIGLEC1, SIRPA, SIRPB1, SIRPG, SLC24A3, SLC2A10, SLC4A11, SSTR4, and THBD.

In some embodiments, the gene comprising the extracellular polymorphic epitope is located on chromosome 21. In some embodiments, the target for use in the iCAR and/or pCAR is selected from the group consisting of CLDN8, DSCAM, ICOSLG, IFNAR1, IFNGR2, IGSF5, ITGB2, KCNJ15, NCAM2, SLC19A1, TMPRSS15, TMPRSS2, TMPRSS3, TRPM2, and UMODL1.

In some embodiments, the gene comprising the extracellular polymorphic epitope is located on chromosome 22. In some embodiments, the target for use in the iCAR and/or pCAR is selected from the group consisting of CACNA1I, CELSR1, COMT, CSF2RB, GGT1, GGT5, IL2RB, KREMEN1, MCHR1, OR11H1, P2RX6, PKDREJ, PLXNB2, SCARF2, SEZ6L, SSTR3, SUSD2, TMPRSS6, and TNFRSF13C.

In some embodiments, the gene comprising the extracellular polymorphic epitope is located on chromosome X. In some embodiments, the target for use in the iCAR and/or pCAR is selected from the group consisting of ATP6AP2, ATP7A, CNGA2, EDA2R, FMR1NB, GLRA4, GPR112, GUCY2F, HEPH, P2RY10, P2RY4, PLXNA3, PLXNB3, TLR8, VSIG4, and XG.

In some embodiments, the aCAR used to treat the cancer is directed against or specifically binds to any membrane protein which is expressed on the tumor tissue as long as the iCAR is expressed on every normal tissue in which the targeted protein is expressed. In some embodiments, the aCAR can specifically bind or be directed to a tumor associated protein, tumor associated antigen and/or antigens in clinical trials, a CAR target as listed in Table 1, as well as any cell surface protein that is expressed in a tumor tissue to which an iCAR can be matched or paired with regard to target binding, according to the criteria listed in the application. In some embodiments, the aCAR can be any expressed protein with an extracellular domain, as long as the iCAR is expressed in the same tissues as the aCAR or in any vital tissues, but is lost in the tumor cells. In some embodiments, the aCAR used to treat the cancer, such as any one of the cancer types recited above, is directed against or specifically binds to, a non-polymorphic cell surface epitope selected from the antigens listed in Table 1, such as CD19. In some embodiments, the aCAR, iCAR, and/or pCAR target is any target with an extracellular domain. In some embodiments, the aCAR used to treat the cancer, is directed against or specifically binds to, a non-polymorphic cell surface epitope selected from but not limited to the following list of antigens: CD19, CD20, CD22, CD10, CD7, CD49f, CD56, CD74, CAIX Igκ, ROR1, ROR2, CD30, LewisY, CD33, CD34, CD38, CD123, CD28, CD44v6, CD44, CD41, CD133, CD138, NKG2D-L, CD139, BCMA, GD2, GD3, hTERT, FBP, EGP-2, EGP-40, FR-α, L1-CAM, ErbB2,3,4, EGFRvIII, VEGFR-2, IL-13Ra2, FAP, Mesothelin, c-MET, PSMA, CEA, kRas, MAGE-A1, MUC1MUC16, PDL1, PSCA, EpCAM, FSHR, AFP, AXL, CD80 CD89, CDH17, CLD18, GPC3, TEM8, TGFB1, NY-ESO-1 WT-1 and EGFR. In some embodiments, the aCAR, iCAR, and/or pCAR target is an antigen listed in Table 1.

TABLE 1

CAR target antigens, including some evaluated in trials registered in ClinicalTrials.gov

| | Antigen | Key structural/functional features | Malignancy | Potential off-tumor targets |
|---|---|---|---|---|
| Hematologic malignancies | CD19 | Pan-B cell marker involved in signal transduction by the BCR | ALL, CLL, NHL, HL, PLL | normal B cells |
| | CD20 | Tetra-transmembrane, regulation of Ca transport and B-cell activation | CLL, NHL | normal B cells |
| | CD22 | B-lineage specific adhesion receptor, sialic acid-binding Ig-type lectin family | ALL, NHL | normal B cells |
| | Igκ | Ig light chain isotype expressed by approx. 65% of normal human B cells | CLL, NHL, MM | normal B cells |
| | ROR1 | Type I orphan-receptor tyrosine-kinase-like, survival-signaling receptor in tumors | CLL, NHL | pancreas; adipose cells |
| | CD30 | TNFR member, pleiotropic effects on cell growth and survival involving NF-κB | NHL, TCL, HL | resting CD8 T cells; activated B and Th2 cells |

TABLE 1-continued

CAR target antigens, including some evaluated in trials registered in ClinicalTrials.gov

| | Antigen | Key structural/functional features | Malignancy | Potential off-tumor targets |
|---|---|---|---|---|
| | Lewis$^Y$ | (CD174) a membrane oligosaccharide harboring two fucose groups | AML, MM | early myeloid progenitor cells |
| | CD33 | Sialic acid-binding Ig-type lectin serving as adhesion molecule of the myelomonocytic lineage | AML | hematopoietic progenitors; myelo-monocytic precursors; monocytes |
| | CD123 | The α chain of the IL-3 receptor | AML | BM myeloid progenitors; DCs, B cells; mast cells, monocytes; macro-phages; megakar.; endothelial cells |
| | NKG2D-L | Ligands for the NK and T-cell activating receptor NKG2D, bearing similarity to MHC-I molecules; upregulated during inflammation | AML, MM | gastrointestinal epithelium, endothelial cells and fibroblasts; |
| | CD139 | Syndecan-1, cell surface heparan sulfate proteoglycan, ECM receptor | MM | precursor & plasma B cells; epithelia |
| | BCMA | TNFR member, binds BAFF and APRIL, involved in proliferation signaling | MM | B cells |
| | TACI | | MM | Mono-nuclear cells, heart |
| Solid tumors | GD2 | Disialoganglioside | NB; sarcomas; solid tumors | skin; neurons |
| | FR-α | GPI-linked folate receptor, functions in the uptake of reduced folate cofactors | ovarian cancer | apical surface in kidney, lung, thyroid, kidney & breast epithelia |
| | L1-CAM | CD 171, neuronal cell adhesion molecule of the Ig superfamily | NB | CNS; sympathetic ganglia; adrenal medulla |
| | ErbB2 | HER2, Member of the EGFR family of receptor tyrosine-protein kinases | brain, CNS, glioma, GBM, H&N, solid tumors | gastrointestinal, respiratory, reproductive & urinary tracts epithelia, skin, breast & placenta; hematopoietic cells |
| | EGFRvIII | Splice variant, in-frame deletion in the amplified EGFR gene encoding a truncated extracellular domain that constantly delivers pro-survival signals | brain, CNS, gliomas, GBM | none |
| | VEGFR-2 | type III transmembrane kinase receptor of the Ig superfamily, regulates vascular endothelial function | solid tumors | vascular and lymphatic endothelia |
| | IL-13Rα2 | The α chain of one of the two IL-13 receptors | brain, CNS, gliomas, GBM | astrocytes; brain; H&N tissue |
| | FAP | Cell surface serine protease | Mesothelioma | fibroblasts in chronic inflammation, wound healing, tissue remodeling |
| | Mesothelin | 40-kDa cell surface glycoprotein with unknown function | mesothelioma, pancreatic, ovarian | peritoneal, pleural, and pericardial mesothelial surfaces |
| | c-MET | hepatocyte growth factor receptor (HGFR), disulfide linked α-β heterodimeric receptor tyrosine kinase | TNBC | liver, gastrointestinal tract, thyroid, kidney, brain |
| | PSMA | type II membrane glycoprotein possessing N-Acetylated alpha-linked acidic dipeptidase and folate hydrolase activity | prostate | apical surface of normal prostate and intestinal epithelium and renal proximal tubular cells |
| | CEA | surface glycoprotein, member of the Ig superfamily and of the CEA-related family of cell adhesion molecules | colorectal, breast, solid tumors | apical epithelial surface: colon, stomach, esophagus & tongue |
| | EGFR | ErbB1, Her1, receptor tyrosine kinases signaling cell differentiation and proliferation upon ligand binding | Solid tumors | tissues of epithelial, mesenchymal & neuronal origin |
| | 5T4 | tumor-associated antigen which is expressed on the cell surface of m | Solid tumors | tissues of epithelial origin |
| | GPC3 | heparan sulfate proteoglycan, | Solid tumors | Urine tissue |
| | ROR1 | Receptor Tyrosine Kinase Like Orphan Receptor | Solid tumors as well as CLL | Urine, pancrease, colon, ovary, brain, monocytes |
| | MUC genes (MUC-1, MUC-16) | O-glycosylated protein that play an essential role in forming protective mucous barriers on epithelial surfaces | Solid tumors | Colon, kidney, lung, breast, pancrease urine |
| | PDL1 | an immune inhibitory receptor ligand that is expressed by hematopoietic and non-hematopoietic cells | lung | Spleen, breast |

TABLE 2

Other CAR target antigens

| | Antigen | Key structural/functional features | Malignancy |
|---|---|---|---|
| Hem. Malig. | CD38 | a surface cyclic ADP ribose hydrolase involved in transmembrane signaling and cell adhesion | CLL, NHL, MM |
| | CS1 | Cell surface signaling lymphocytic activation molecule (SLAM) | MM |
| Solid tumors | PSCA | GPI-anchored membrane glycoprotein of the Thy-1/Ly-6 family | prostate, bladder, pancreatic |
| | CD44v6 | alternatively spliced variant 6 of the hyaluronate receptor CD44 | H&N, liver, pancreatic, gastric, breast, colon; AML, NHL, MM |
| | CD44v7/8 | alternatively spliced variant 7/8 of the hyaluronate receptor CD44 | breast, cervical |
| | MUC1 | densely glycosylated member of the mucin family of glycoproteins | colon, lung, pancreas, breast, ovarian, prostate, kidney, stomach, H&N |
| | L-11rα | the α subunit of the IL-11 recepto | colon, gastric, breast, prostate; osteosarcoma |
| | EphA2 | erythropoietin-producing hepatocellular carcinoma A2 (EphA2) receptor, a member of the Eph family of receptor tyrosine kinases | Glioma; breast, colon, ovarian, prostate, pancreatic |
| | CAIX | transmembrane zinc metalloenzyme | RCC; tumors under hypoxia |
| | CSPG4 | high molecular weight melanoma-associated antigen, cell surface proteoglycan | RCC; tumors under hypoxia | ii. Recognition Moiety: aCAR, iCAR and pCAR

The present invention also provides for recognition moieties designed to provide specific binding to the target. The recognition moiety allows for directing the specific and targeted binding of the aCAR, iCAR and/or pCAR. In some embodiments, the recognition moiety designed to provide specific binding to the target provides specific binding to an extracellular polymorphic epitope. In some embodiments, the recognition moiety is part of an extracellular domain of the aCAR, iCAR and/or pCAR. In some embodiments, the extracellular domain comprises an antibody, derivative or fragment thereof, such as a humanized antibody; a human antibody; a functional fragment of an antibody; a single-domain antibody, such as a Nanobody; a recombinant antibody; and a single chain variable fragment (ScFv). In some embodiments, the extracellular domain comprises an antibody mimetic, such as an affibody molecule; an affilin; an affimer; an affitin; an alphabody; an anticalin; an avimer; a DARPin; a fynomer; a Kunitz domain peptide; and a monobody. In some embodiments, the extracellular domain comprises an aptamer.

Generally, any relevant technology may be used to engineer a recognition moiety that confers to the aCARs and pCAR or iCARs specific binding to their targets. For example, recognition moieties comprising this iCAR-aCAR Library may be derived from a master recognition moiety pool ideally selected from a combinatorial display library, so that:

Collectively, the selected recognition moieties target the cell-surface products of an array of genes which reside on each of the two arms of all 22 human autosomes. The shorter the distance between neighboring genes the fuller the coverage hence, the greater the universality of use.

For each of the selected genes a set of allele-specific recognition moieties is isolated, each allowing rigorous discrimination between different allelic variants that are prevalent in the human population. The greater the number of targeted variants, the greater the number of therapeutic gene pairs that can be offered to patients.

A given allelic product can become a potential pCAR or iCAR target in one patient and a useful aCAR target in another patient harboring the same allele, depending on the particular LOH pattern in each case. Hence, as suitable recognition moiety genes are identified, each will be engrafted onto both a pCAR or an iCAR and an aCAR gene scaffold. It is therefore desirable that all recognition moieties directed at allelic variants of the same gene possess binding affinities of a similar range. Within such a given set of recognition moieties, all possible combinations of pCAR-aCAR or iCAR-aCAR pairs can be pre-assembled so as to assure the highest coverage of potential allelic compositions of that gene in the entire population.

In some embodiments, the patient is heterozygous for the major allele and a minor one, the products of which differ in a single position along the encoded polypeptide as a result of a nonsynonymous SNP or, less frequently, an indel. In some other embodiments, a patient is heterozygous for two minor alleles which differ from the major one in two separate positions. Depending on the particular LOH event involving the said gene in individual patients, a given variant epitope can serve as an iCAR target in one patient and an aCAR target in another. In some embodiments, the variant epitope that can serve as an iCAR target is not the major allele variant. In some embodiments, the variant epitope that can serve as the iCAR target is a minor allele.

The identification of a variant-specific mAb (say, a mAb specific to the epitope encoded by the minor allele 'a') is well known in the art and is similar, in principle, to the identification of a mAb against any conventional antigenic determinant, and can usually best be accomplished via high throughput screening of a recombinant antibody scFv library, utilizing, for example, phage (Barbas et al., 2004), ribosome (Hanes et al., 1997) or yeast (Chao et al., 2006) display technologies. The antigen employed for library screening can either be a synthetic peptide spanning the position of variation between the two alleles (typically 15-20 amino acid in length or more), a recombinant full-length polypeptide which can either be commercially available or tailor-synthesized by one of the many companies operating in this field, or even entire cells expressing the said allelic variant at high level by virtue of gene transfection (e.g., electroporation of mRNA encoding the full-length cDNA cloned as template for in-vitro mRNA transcription in the pGEM4Z/A64 vector (Boczkowski et al., 2000)), following a subtraction step performed on the same cells not expressing this allele. These methods are well-known and described in e.g., Molecular Cloning: A Laboratory Manual (Fourth Edition) Green and Sambrook, Cold Spring Harbor Laboratory Press; Antibodies: A Laboratory Manual (Second Edition), Edited by Edward A. Greenfield, 2012 CSH laboratory press; Using Antibodies, A laboratory manual by Ed Harlow and David Lane, 1999 CSH laboratory press.

By definition, the corresponding epitope (at the same position) which is encoded by the major allele ('A'), creates a unique antigenic determinant that differs from that created by 'a' in the identity of a single amino acid (SNP) or length (indel; for example, insertion or deletion). This determinant can, in principle, be recognized by a different set of mAbs identified by the same, or other, antibody display screening technology. The ability of distinct members in each of the two sets of identified mAbs to distinguish between the two epitopes or variants, for example, an antibody from the first set binds the product of allele 'a' but not of 'A' and an Ab from the second set reciprocally binds 'A' but not 'a' can be determined using conventional binding assays such as ELISA or flow cytometry (Skora et al., 2015) or other technique for cell staining. Alternatively, once an 'a'-binding Ab is identified which does not bind 'A' and its protein sequence is determined, a computational method can potentially be used to predict the sequence of a 'complementary' antibody scFv which binds 'A' but not 'a'. For such a computational method see, for example (Sela-Culang et al., 2015a,b).

In some embodiments, for example with regard to the HLA-class I locus genes HLA-A, HLA-B, and HLA-C as the target genes, there are numerous allele-specific monoclonal antibodies available, for example, but not limited to, the antibodies listed in Example 3.

In some embodiments, the target for use in generation of a recognition moiety comprises at least one extracellular polymorphic epitope. In some embodiments, the target is the product of a gene that is located on chromosome 1, chromosome 2, chromosome 3, chromosome 4, chromosome 5, chromosome 6, chromosome 7, chromosome 8, chromosome 9, chromosome 10, chromosome 11, chromosome 12, chromosome 13, chromosome 14, chromosome 15, chromosome 16, chromosome 17, chromosome 18, chromosome 19, chromosome 20, chromosome 21, chromosome 22, or chromosome X.

In some embodiments, the recognition moiety for use in the aCAR provides specify to at least one extracellular polymorphic epitope in a gene product from a gene selected from chromosome 1. In some embodiments, the recognition moiety for use in the aCAR provides specifity to at least one extracellular polymorphic epitope in a gene product from a gene selected from the group consisting of ABCA4, ADAM30, AQP10, ASTN1, C1orf101, CACNA1S, CATSPER4, CD101, CD164L2, CD1A, CD1C, CD244, CD34, CD46, CELSR2, CHRNB2, CLCA2, CLDN19, CLSTN1, CR1, CR2, CRB1, CSF3R, CSMD2, ECE1, ELTD1, EMC1, EPHA10, EPHA2, EPHA8, ERMAP, FCAMR, FCER1A, FCGR1B, FCGR2A, FCGR2B, FCGR3A, FCRL1, FCRL3, FCRL4, FCRL5, FCRL6, GJB4, GPA33, GPR157, GPR37L1, GPR88, HCRTR1, IGSF3, IGSF9, IL22RA1, IL23R, ITGA10, KIAA1324, KIAA2013, LDLRAD2, LEPR, LGR6, LRIG2, LRP8, LRRC52, LRRC8B, LRRN2, LY9, MIA3, MR1, MUC1, MXRA8, NCSTN, NFASC, NOTCH2, NPR1, NTRK1, OPN3, OR10J1, OR10J4, OR10K1, OR1OR2, OR10T2, OR10X1, OR11L1, OR14A16, OR14I1, OR14K1, OR2AK2, OR2C3, OR2G2, OR2G3, OR2L2, OR2M7, OR2T12, OR2T27, OR2T1, OR2T3, OR2T29, OR2T33, OR2T34, OR2T35, OR2T3, OR2T4, OR2T5, OR2T6, OR2T7, OR2T8, OR2W3, OR6F1, OR6K2, OR6K3, OR6K6, OR6N1, OR6P1, OR6Y1, PDPN, PEAR1, PIGR, PLXNA2, PTCH2, PTCHD2, PTGFRN, PTPRC, PTPRF, PTGFRN, PVRL4, RHBG, RXFP4, S1PR1, SCNN1D, SDC3, SELE, SELL, SELP, SEMA4A, SEMA6C, SLAMF7, SLAMF9, SLC2A7, SLC5A9, TACSTD2, TAS1R2, TIE1, TLR5, TMEM81, TNFRSF14, TNFRSF1B, TRABD2B, USH2A, VCAM1, and ZP4.

In some embodiments, the recognition moiety for use in the iCAR or pCAR provides specifity to at least one extracellular polymorphic epitope in a gene product from a gene selected from chromosome 1. In some embodiments, the recognition moiety for use in the iCAR or pCAR provides specifity to at least one extracellular polymorphic epitope in a gene product from a gene selected from the group consisting of ABCA4, ADAM30, AQP10, ASTN1, C1orf101, CACNA1S, CATSPER4, CD101, CD164L2, CD1A, CD1C, CD244, CD34, CD46, CELSR2, CHRNB2, CLCA2, CLDN19, CLSTN1, CR1, CR2, CRB1, CSF3R, CSMD2, ECE1, ELTD1, EMC1, EPHA10, EPHA2, EPHA8, ERMAP, FCAMR, FCER1A, FCGR1B, FCGR2A, FCGR2B, FCGR3A, FCRL1, FCRL3, FCRL4, FCRL5, FCRL6, GJB4, GPA33, GPR157, GPR37L1, GPR88, HCRTR1, IGSF3, IGSF9, IL22RA1, IL23R, ITGA10, KIAA1324, KIAA2013, LDLRAD2, LEPR, LGR6, LRIG2, LRP8, LRRC52, LRRC8B, LRRN2, LY9, MIA3, MR1, MUC1, MXRA8, NCSTN, NFASC, NOTCH2, NPR1, NTRK1, OPN3, OR10J1, OR10J4, OR10K1, OR10R2, OR10T2, OR10X1, OR11L1, OR14A16, OR14I1, OR14K1, OR2AK2, OR2C3, OR2G2, OR2G3, OR2L2, OR2M7, OR2T12, OR2T27, OR2T1, OR2T3, OR2T29, OR2T33, OR2T34, OR2T35, OR2T3, OR2T4, OR2T5, OR2T6, OR2T7, OR2T8, OR2W3, OR6F1, OR6K2, OR6K3, OR6K6, OR6N1, OR6P1, OR6Y1, PDPN, PEAR1, PIGR, PLXNA2, PTCH2, PTCHD2, PTGFRN, PVRL4, RHBG, RXFP4, S1PR1, SCNN1D, SDC3, SELE, SELL, SELP, SEMA4A, SEMA6C, SLAMF7, SLAMF9, SLC2A7, SLC5A9, TACSTD2, TAS1R2, TIE1, TLR5, TMEM81, TNFRSF14, TNFRSF1B, TRABD2B, USH2A, VCAM1, and ZP4.

In some embodiments, the recognition moiety for use in the aCAR provides specifity to at least one extracellular polymorphic epitope in a gene product from a gene selected from chromosome 2. In some embodiments, the recognition moiety for use in the aCAR provides specifity to at least one extracellular polymorphic epitope in a gene product from a gene selected from the group consisting of ABCG5, ALK, ASPRV1, ATRAID, CD207, CD8B, CHRNG, CLEC4F, CNTNAP5, CRIM1, CXCR1, DNER, DPP10, EDAR, EPCAM, GPR113, GPR148, GPR35, GPR39, GYPC, IL1RL1, ITGA4, ITGA6, ITGAV, LCT, LHCGR, LRP1B, LRP2, LY75, MARCO, MERTK, NRP2, OR6B2, PLA2R1, PLB1, PROKR1, PROM2, SCN7A, SDC1, SLC23A3, SLC5A6, TGOLN2, THSD7B, TM4SF20, TMEFF2, TMEM178A, TPO, and TRABD2A.

In some embodiments, the recognition moiety for use in the iCAR or pCAR provides specifity to at least one extracellular polymorphic epitope in a gene product from a gene selected from chromosome 2. In some embodiments, the recognition moiety for use in the iCAR or pCAR provides specifity to at least one extracellular polymorphic epitope in a gene product from a gene selected from the group consisting of ABCG5, ALK, ASPRV1, ATRAID, CD207, CD8B, CHRNG, CLEC4F, CNTNAP5, CRIM1, CXCR1, DNER, DPP10, EDAR, EPCAM, GPR113, GPR148, GPR35, GPR39, GYPC, IL1RL1, ITGA4, ITGA6, ITGAV, LCT, LHCGR, LRP1B, LRP2, LY75, MARCO, MERTK, NRP2, OR6B2, PLA2R1, PLB1, PROKR1, PROM2, SCN7A, SDC1, SLC23A3, SLC5A6, TGOLN2, THSD7B, TM4SF20, TMEFF2, TMEM178A, TPO, and TRABD2A.

In some embodiments, the recognition moiety for use in the aCAR provides specifity to at least one extracellular polymorphic epitope in a gene product from a gene selected from chromosome 3. In some embodiments, the recognition moiety for use in the aCAR provides specifity to at least one extracellular polymorphic epitope in a gene product from a gene selected from the group consisting of ACKR2, ALCAM, ANO10, ATP13A4, BTLA, CACNA1D, CACNA2D2, CACNA2D3, CASR, CCRL2, CD200, CD200R1, CD86, CD96, CDCP1, CDHR4, CELSR3, CHL1, CLDN11, CLDN18, CLSTN2, CSPG5, CX3CR1, CXCR6, CYP8B1, DCBLD2, DRD3, EPHA6, EPHB3, GABRR3, GP5, GPR128, GPR15, GPR27, GRM2, GRM7, HEG1, HTR3C, HTR3D, HTR3E, IGSF11, IL17RC, IL17RD, IL17RE, IL5RA, IMPG2, ITGA9, ITGB5, KCNMB3, LRIG1, LRRC15, LRRN1, MST1R, NAALADL2, NRROS, OR5AC1, OR5H1, OR5H14, OR5H15, OR5H6, OR5K2, OR5K3, OR5K4, PIGX, PLXNB1, PLXND1, PRRT3, PTPRG, ROBO2, RYK, SEMA5B, SIDT1, SLC22A14, SLC33A1, SLC4A7, SLITRK3, STAB1, SUSD5, TFRC, TLR9, TMEM108, TMEM44, TMPRSS7, TNFSF10, UPK1B, VIPR1, and ZPLD1.

In some embodiments, the recognition moiety for use in the iCAR or pCAR provides specifity to at least one extracellular polymorphic epitope in a gene product from a gene selected from chromosome 3. In some embodiments, the recognition moiety for use in the iCAR or pCAR provides specifity to at least one extracellular polymorphic epitope in a gene product from a gene selected from the group consisting of ACKR2, ALCAM, ANO10, ATP13A4, BTLA, CACNA1D, CACNA2D2, CACNA2D3, CASR, CCRL2, CD200, CD200R1, CD86, CD96, CDCP1, CDHR4, CELSR3, CHL1, CLDN11, CLDN18, CLSTN2, CSPG5, CX3CR1, CXCR6, CYP8B1, DCBLD2, DRD3, EPHA6, EPHB3, GABRR3, GP5, GPR128, GPR15, GPR27, GRM2, GRM7, HEG1, HTR3C, HTR3D, HTR3E, IGSF11, IL17RC, IL17RD, IL17RE, IL5RA, IMPG2, ITGA9, ITGB5, KCNMB3, LRIG1, LRRC15, LRRN1, MST1R, NAALADL2, NRROS, OR5AC1, OR5H1, OR5H14, OR5H15, OR5H6, OR5K2, OR5K3, OR5K4, PIGX, PLXNB1, PLXND1, PRRT3, PTPRG, ROBO2, RYK, SEMA5B, SIDT1, SLC22A14, SLC33A1, SLC4A7, SLITRK3, STAB1, SUSD5, TFRC, TLR9, TMEM108, TMEM44, TMPRSS7, TNFSF10, UPK1B, VIPR1, and ZPLD1.

In some embodiments, the recognition moiety for use in the aCAR provides specifity to at least one extracellular polymorphic epitope in a gene product from a gene selected from chromosome 4. In some embodiments, the recognition moiety for use in the aCAR provides specifity to at least one extracellular polymorphic epitope in a gene product from a gene selected from the group consisting of ANTXR2, BTC, CNGA1, CORIN, EGF, EMCN, ENPEP, EPHA5, ERVMER34-1, EVC2, FAT1, FAT4, FGFRL1, FRAS1, GPR125, GRID2, GYPA, GYPB, KDR, KIAA0922, KLB, MFSD8, PARM1, PDGFRA, RNF150, TENM3, TLR10, TLR1, TLR6, TMEM156, TMPRSS11A, TMPRSS11B, TMPRSS11E, TMPRSS11F, UGT2A1, and UNC5C.

In some embodiments, the recognition moiety for use in the iCAR or pCAR provides specifity to at least one extracellular polymorphic epitope in a gene product from a gene selected from chromosome 4. In some embodiments, the recognition moiety for use in the iCAR or pCAR provides specifity to at least one extracellular polymorphic epitope in a gene product from a gene selected from the group consisting of ANTXR2, BTC, CNGA1, CORIN, EGF, EMCN, ENPEP, EPHA5, ERVMER34-1, EVC2, FAT1, FAT4, FGFRL1, FRAS1, GPR125, GRID2, GYPA, GYPB, KDR, KIAA0922, KLB, MFSD8, PARM1, PDGFRA, RNF150, TENM3, TLR10, TLR1, TLR6, TMEM156, TMPRSS11A, TMPRSS11B, TMPRSS11E, TMPRSS11F, UGT2A1, and UNC5C.

In some embodiments, the recognition moiety for use in the aCAR provides specifity to at least one extracellular polymorphic epitope in a gene product from a gene selected from chromosome 5. In some embodiments, the recognition moiety for use in the aCAR provides specifity to at least one extracellular polymorphic epitope in a gene product from a gene selected from the group consisting of ADAM19, ADRB2, BTNL3, BTNL8, BTNL9, C5orf15, CATSPER3, CD180, CDH12, CDHR2, COL23A1, CSF1R, F2RL2, FAM174A, FAT2, FGFR4, FLT4, GABRA6, GABRG2, GPR151, GPR98, GRM6, HAVCR1, HAVCR2, IL31RA, IL6ST, IL7R, IQGAP2, ITGA1, ITGA2, KCNMB1, LIFR, LNPEP, MEGF10, NIPAL4, NPR3, NRG2, OR2V1, OR2Y1, OSMR, PCDH12, PCDH1, PCDHA1, PCDHA2, PCDHA4, PCDHA8, PCDHA9, PCDHB10, PCDHB11, PCDHB13, PCDHB14, PCDHB15, PCDHB16, PCDHB2, PCDHB3, PCDHB4, PCDHB5, PCDHB6, PCDHGA1, PCDHGA4, PDGFRB, PRLR, SEMA5A, SEMA6A, SGCD, SLC1A3, SLC22A4, SLC22A5, SLC23A1, SLC36A3, SLC45A2, SLC6A18, SLC6A19, SLCO6A1, SV2C, TENM2, TIMD4, and UGT3A1.

In some embodiments, the recognition moiety for use in the iCAR or pCAR provides specifity to at least one extracellular polymorphic epitope in a gene product from a gene selected from chromosome 5. In some embodiments, the recognition moiety for use in the iCAR or pCAR provides specifity to at least one extracellular polymorphic epitope in a gene product from a gene selected from the group consisting of ADAM19, ADRB2, BTNL3, BTNL8, BTNL9, C5orf15, CATSPER3, CD180, CDH12, CDHR2, COL23A1, CSF1R, F2RL2, FAM174A, FAT2, FGFR4, FLT4, GABRA6, GABRG2, GPR151, GPR98, GRM6, HAVCR1, HAVCR2, IL31RA, IL6ST, IL7R, IQGAP2, ITGA1, ITGA2, KCNMB1, LIFR, LNPEP, MEGF10, NIPAL4, NPR3, NRG2, OR2V1, OR2Y1, OSMR, PCDH12, PCDH1, PCDHA1, PCDHA2, PCDHA4, PCDHA8, PCDHA9, PCDHB10, PCDHB11, PCDHB13, PCDHB14, PCDHB15, PCDHB16, PCDHB2, PCDHB3, PCDHB4, PCDHB5, PCDHB6, PCDHGA1, PCDHGA4, PDGFRB, PRLR, SEMA5A, SEMA6A, SGCD, SLC1A3, SLC22A4, SLC22A5, SLC23A1, SLC36A3, SLC45A2, SLC6A18, SLC6A19, SLCO6A1, SV2C, TENM2, TIMD4, and UGT3A1.

In some embodiments, the recognition moiety for use in the aCAR provides specifity to at least one extracellular polymorphic epitope in a gene product from a gene selected from chromosome 6. In some embodiments, the recognition moiety for use in the aCAR provides specifity to at least one extracellular polymorphic epitope in a gene product from a gene selected from the group consisting of BAI3, BTN1A1, BTN2A1, BTN2A2, BTN3A1, BTN3A2, BTNL2, CD83, DCBLD1, DLL1, DPCR1, ENPP1, ENPP3, ENPP4, EPHA7, GABBR1, GABRR1, GCNT6, GFRAL, GJB7, GLP1R, GPR110, GPR111, GPR116, GPR126, GPR63, GPRC6A, HFE, HLA-A, HLA-B, HLA-C, HLA-DOA, HLA-DPA1, HLA-DPB1, HLA-DQA1, HLA-DQA2, HLA-DQB1, HLA-DQB2, HLA-DRB1, HLA-DRB5, HLA-E, HLA-F, HLA-G, IL20RA, ITPR3, KIAA0319, LMBRD1, LRFN2, LRP11, MAS1L, MEP1A, MICA, MICB, MOG, MUC21, MUC22, NCR2, NOTCH4, OPRM1, OR10C1, OR12D2, OR12D3, OR14J1, OR2B2, OR2B6, OR2J1, OR2W1, OR5V1, PDE10A, PI16, PKHD1, PTCRA, PTK7, RAET1E, RAET1G, ROS1, SDIM1, SLC16A10, SLC22A1, SLC44A4, TAAR2, TREM1, TREML1, and TREML2.

In some embodiments, the recognition moiety for use in the iCAR or pCAR provides specifity to at least one extracellular polymorphic epitope in a gene product from a gene selected from chromosome 6. In some embodiments, the recognition moiety for use in the iCAR or pCAR provides specifity to at least one extracellular polymorphic epitope in a gene product from a gene selected from the group consisting of BAI3, BTN1A1, BTN2A1, BTN2A2, BTN3A1, BTN3A2, BTNL2, CD83, DCBLD1, DLL1, DPCR1, ENPP1, ENPP3, ENPP4, EPHA7, GABBR1, GABRR1, GCNT6, GFRAL, GJB7, GLP1R, GPR110, GPR111, GPR116, GPR126, GPR63, GPRC6A, HFE, HLA-A, HLA-B, HLA-C, HLA-DOA, HLA-DPA1, HLA-DPB1, HLA-DQA1, HLA-DQA2, HLA-DQB1, HLA-DQB2, HLA-DRB1, HLA-DRB5, HLA-E, HLA-F, HLA-G, IL20RA, ITPR3, KIAA0319, LMBRD1, LRFN2, LRP11, MAS1L, MEP1A, MICA, MICB, MOG, MUC21, MUC22, NCR2, NOTCH4, OPRM1, OR10C1, OR12D2, OR12D3, OR14J1, OR2B2, OR2B6, OR2J1, OR2W1, OR5V1, PDE10A, PI16, PKHD1, PTCRA, PTK7, RAET1E, RAET1G, ROS1, SDIM1, SLC16A10, SLC22A1, SLC44A4, TAAR2, TREM1, TREML1, and TREML2.

In some embodiments, the recognition moiety for use in the aCAR provides specifity to at least one extracellular polymorphic epitope in a gene product from a gene selected from chromosome 7. In some embodiments, the recognition moiety for use in the aCAR provides specifity to at least one extracellular polymorphic epitope in a gene product from a gene selected from the group consisting of AQP1, C7orf50, CD36, CDHR3, CNTNAP2, DPP6, EGFR, EPHA1, EPHB6, ERVW-1, GHRHR, GJC3, GPNMB, GRM8, HUS1, HYAL4, KIAA1324L, LRRN3, MET, MUC12, MUC17, NPC1L1, NPSR1, OR2A12, OR2A14, OR2A25, OR2A42, OR2A7, OR2A2, OR2AE1, OR2F2, OR6V1, PILRA, PILRB, PKD1L1, PLXNA4, PODXL, PTPRN2, PTPRZ1, RAMP5, SLC29A4, SMO, TAS2R16, TAS2R40, TAS2R4, TFR2, THSD7A, TMEM213, TTYH3, ZAN, and ZP3.

In some embodiments, the recognition moiety for use in the iCAR or pCAR provides specifity to at least one extracellular polymorphic epitope in a gene product from a gene selected from chromosome 7. In some embodiments, the recognition moiety for use in the iCAR or pCAR provides specifity to at least one extracellular polymorphic epitope in a gene product from a gene selected from the group consisting of AQP1, C7orf50, CD36, CDHR3, CNTNAP2, DPP6, EGFR, EPHA1, EPHB6, ERVW-1, GHRHR, GJC3, GPNMB, GRM8, HUS1, HYAL4, KIAA1324L, LRRN3, MET, MUC12, MUC17, NPC1L1, NPSR1, OR2A12, OR2A14, OR2A25, OR2A42, OR2A7, OR2A2, OR2AE1, OR2F2, OR6V1, PILRA, PILRB, PKD1L1, PLXNA4, PODXL, PTPRN2, PTPRZ1, RAMP3, SLC29A4, SMO, TAS2R16, TAS2R40, TAS2R4, TFR2, THSD7A, TMEM213, TTYH3, ZAN, and ZP3.

In some embodiments, the recognition moiety for use in the aCAR provides specifity to at least one extracellular polymorphic epitope in a gene product from a gene selected from chromosome 8. In some embodiments, the recognition moiety for use in the aCAR provides specifity to at least one extracellular polymorphic epitope in a gene product from a gene selected from the group consisting of ADAM18, ADAM28, ADAM32, ADAM7, ADAM9, ADRA1A, CDH17, CHRNA2, CSMD1, CSMD3, DCSTAMP, FZD6, GPR124, NRG1, OR4F21, PKHD1L1, PRSS55, SCARA3, SCARA5, SDC2, SLC10A5, SLC39A14, SLC39A4, SLCO5A1, TNFRSF10A, and TNFRSF10B.

In some embodiments, the recognition moiety for use in the iCAR or pCAR provides specifity to at least one extracellular polymorphic epitope in a gene product from a gene selected from chromosome 8. In some embodiments, the recognition moiety for use in the iCAR or pCAR provides specifity to at least one extracellular polymorphic epitope in a gene product from a gene selected from the group consisting of ADAM18, ADAM28, ADAM32, ADAM7, ADAM9, ADRA1A, CDH17, CHRNA2, CSMD1, CSMD3, DCSTAMP, FZD6, GPR124, NRG1, OR4F21, PKHD1L1, PRSS55, SCARA3, SCARA5, SDC2, SLC10A5, SLC39A14, SLC39A4, SLCO5A1, TNFRSF10A, and TNFRSF10B.

In some embodiments, the recognition moiety for use in the aCAR provides specifity to at least one extracellular polymorphic epitope in a gene product from a gene selected from chromosome 9. In some embodiments, the recognition moiety for use in the aCAR provides specifity to at least one extracellular polymorphic epitope in a gene product from a gene selected from the group consisting of ABCA1, AQP7, ASTN2, C9orf135, CA9, CD72, CNTNAP3B, CNTNAP3, CRB2, ENTPD8, GPR144, GRIN3A, IZUMO3, KIAA1161, MAMDC4, MEGF9, MUSK, NOTCH1, OR13C2, OR13C3, OR13C5, OR13C8, OR13C9, OR13D1, OR13F1, OR1B1, OR1J2, OR1K1, OR1L1, OR1L3, OR1L6, OR1L8, OR1N1, OR1N2, OR1Q1, OR2S2, PCSK5, PDCD1LG2, PLGRKT, PTPRD, ROR2, SEMA4D, SLC31A1, TEK, TLR4, TMEM2, and VLDLR.

In some embodiments, the recognition moiety for use in the iCAR or pCAR provides specifity to at least one extracellular polymorphic epitope in a gene product from a gene selected from chromosome 9. In some embodiments, the recognition moiety for use in the iCAR or pCAR provides specifity to at least one extracellular polymorphic epitope in a gene product from a gene selected from the group consisting of ABCA1, AQP7, ASTN2, C9orf135, CA9, CD72, CNTNAP3B, CNTNAP3, CRB2, ENTPD8, GPR144, GRIN3A, IZUMO3, KIAA1161, MAMDC4, MEGF9, MUSK, NOTCH1, OR13C2, OR13C3, OR13C5, OR13C8, OR13C9, OR13D1, OR13F1, OR1B1, OR1J2, OR1K1, OR1L1, OR1L3, OR1L6, OR1L8, OR1N1, OR1N2, OR1Q1, OR2S2, PCSK5, PDCD1LG2, PLGRKT, PTPRD, ROR2, SEMA4D, SLC31A1, TEK, TLR4, TMEM2, and VLDLR.

In some embodiments, the recognition moiety for use in the aCAR provides specifity to at least one extracellular polymorphic epitope in a gene product from a gene selected from chromosome 10. In some embodiments, the recognition moiety for use in the aCAR provides specifity to at least one extracellular polymorphic epitope in a gene product from a gene selected from the group consisting of ABCC2, ADAM8, ADRB1, ANTXRL, ATRNL1, C10orf54, CDH23, CDHR1, CNNM2, COL13A1, COL17A1, ENTPD1, FZD8, FGFR2, GPR158, GRID1, IL15RA, IL2RA, ITGA8, ITGB1, MRC1, NRG3, NPFFR1, NRP1, OPN4, PCDH15, PKD2L1, PLXDC2, PRLHR, RET, RGR, SLC16A9, SLC29A3, SLC39A12, TACR2, TCTN3, TSPAN15, UNC5B, and VSTM4.

In some embodiments, the recognition moiety for use in the iCAR or pCAR provides specifity to at least one extracellular polymorphic epitope in a gene product from a gene selected from chromosome 10. In some embodiments, the recognition moiety for use in the iCAR or pCAR provides specifity to at least one extracellular polymorphic epitope in a gene product from a gene selected from the group consisting of ABCC2, ADAM8, ADRB1, ANTXRL, ATRNL1, C10orf54, CDH23, CDHR1, CNNM2, COL13A1, COL17A1, ENTPD1, FZD8, FGFR2, GPR158, GRID1, IL15RA, IL2RA, ITGA8, ITGB1, MRC1, NRG3, NPFFR1, NRP1, OPN4, PCDH15, PKD2L1, PLXDC2, PRLHR, RET, RGR, SLC16A9, SLC29A3, SLC39A12, TACR2, TCTN3, TSPAN15, UNC5B, and VSTM4.

In some embodiments, the recognition moiety for use in the aCAR provides specifity to at least one extracellular polymorphic epitope in a gene product from a gene selected from chromosome 11. In some embodiments, the recognition moiety for use in the aCAR provides specifity to at least one extracellular polymorphic epitope in a gene product from a gene selected from the group consisting of AMICAL ANO1, ANO3, APLP2, C11orf24, CCKBR, CD248, CD44, CD5, CD6, CD82, CDON, CLMP, CRTAM, DCHS1, DSCAML1, FAT3, FOLH1, GDPD4, GDPD5, GRIK4, HEPHL1, HTR3B, IFITM10, IL10RA, KIRREL3, LGR4, LRP4, LRP5, LRRC32, MCAM, MFRP, MMP26, MPEG1, MRGPRE, MRGPRF, MRGPRX2, MRGPRX3, MRGPRX4, MS4A4A, MS4A6A, MTNR1B, MUC15, NAALAD2, NAALADL1, NCAM1, NRXN2, OR10A2, OR10A5, OR10A6, OR10D3, OR10G4, OR10G7, OR10G8, OR10G9, OR10Q1, OR10S1, OR1S1, OR2AG1, OR2AG2, OR2D2, OR4A47, OR4A15, OR4A5, OR4C11, OR4C13, OR4C15, OR4C16, OR4C3, OR4C46, OR4C5, OR4D6, OR4A8P, OR4D9, OR4S2, OR4X1, OR51E1, OR51L1, OR52A1, OR52E1, OR52E2, OR52E4, OR52E6, OR52I1, OR52I2, OR52J3, OR52L1, OR52N1, OR52N2, OR52N4, OR52W1, OR56B1, OR56B4, OR5A1, OR5A2, OR5AK2, OR5AR1, OR5B17, OR5B3, OR5D14, OR5D16, OR5D18, OR5F1, OR5I1, OR5L2, OR5M11, OR5M3, OR5P2, OR5R1, OR5T2, OR5T3, OR5W2, OR6A2, OR6T1, OR6X1, OR8A1, OR8B12, OR8B2, OR8B3, OR8B4, OR8D1, OR8D2, OR8H1, OR8H2, OR8I2, OR8J1, OR8J2, OR8J3, OR8K1, OR8K3, OR8K5, OR8U1, OR9G1, OR9G4, OR9Q2, P2RX3, PTPRJ, ROBO3, SIGIRR, SLC22A10, SLC3A2, SLC5A12, SLCO2B1, SORL1, ST14, SYT8, TENM4, TMEM123, TMEM225, TMPRSS4, TMPRSS5, TRIM5, TRPM5, TSPAN18, and ZP1.

In some embodiments, the recognition moiety for use in the iCAR or pCAR provides specifity to at least one extracellular polymorphic epitope in a gene product from a gene selected from chromosome 11. In some embodiments, the recognition moiety for use in the iCAR or pCAR provides specifity to at least one extracellular polymorphic epitope in a gene product from a gene selected from the group consisting of AMICAL ANO1, ANO3, APLP2, C11orf24, CCKBR, CD248, CD44, CD5, CD6, CD82, CDON, CLMP, CRTAM, DCHS1, DSCAML1, FAT3, FOLH1, GDPD4, GDPD5, GRIK4, HEPHL1, HTR3B, IFITM10, IL10RA, KIRREL3, LGR4, LRP4, LRP5, LRRC32, MCAM, MFRP, MMP26, MPEG1, MRGPRE, MRGPRF, MRGPRX2, MRGPRX3, MRGPRX4, MS4A4A, MS4A6A, MTNR1B, MUC15, NAALAD2, NAALADL1, NCAM1, NRXN2, OR10A2, OR10A5, OR10A6, OR10D3, OR10G4, OR10G7, OR10G8, OR10G9, OR10Q1, OR10S1, OR1S1, OR2AG1, OR2AG2, OR2D2, OR4A47, OR4A15, OR4A5, OR4C11, OR4C13, OR4C15, OR4C16, OR4C3, OR4C46, OR4C5, OR4D6, OR4A8P, OR4D9, OR4S2, OR4X1, OR51E1, OR51L1, OR52A1, OR52E1, OR52E2, OR52E4, OR52E6, OR52I1, OR52I2, OR52J3, OR52L1, OR52N1, OR52N2, OR52N4, OR52W1, OR56B1, OR56B4, OR5A1, OR5A2, OR5AK2, OR5AR1, OR5B17, OR5B3, OR5D14, OR5D16, OR5D18, OR5F1, OR5I1, OR5L2, OR5M11, OR5M3, OR5P2, OR5R1, OR5T2, OR5T3, OR5W2, OR6A2, OR6T1, OR6X1, OR8A1, OR8B12, OR8B2, OR8B3, OR8B4, OR8D1, OR8D2, OR8H1, OR8H2, OR8H3, OR8I2, OR8J1, OR8J2, OR8J3, OR8K1, OR8K3, OR8K5, OR8U1, OR9G1, OR9G4, OR9Q2, P2RX3, PTPRJ, ROBO3, SIGIRR, SLC22A10, SLC3A2, SLC5A12, SLCO2B1, SORL1, ST14, SYT8, TENM4, TMEM123, TMEM225, TMPRSS4, TMPRSS5, TRIM5, TRPM5, TSPAN18, and ZP1.

In some embodiments, the recognition moiety for use in the aCAR provides specifity to at least one extracellular polymorphic epitope in a gene product from a gene selected from chromosome 12. In some embodiments, the recognition moiety for use in the aCAR provides specifity to at least one extracellular polymorphic epitope in a gene product from a gene selected from the group consisting of ANO4, AVPR1A, BCL2L14, CACNA2D4, CD163, CD163L1, CD27, CD4, CLEC12A, CLEC1B, CLEC2A, CLEC4C, CLEC7A, CLECL1, CLSTN3, GPR133, GPRC5D, ITGA7, ITGB7, KLRB1, KLRC2, KLRC3, KLRC4, KLRF1, KLRF2, LRP1, LRP6, MANSC1, MANSC4, OLR1, OR10AD1, OR10P1, OR2AP1, OR6C1, OR6C2, OR6C3, OR6C4, OR6C6, OR6C74, OR6C76, OR8S1, OR9K2, ORAI1, P2RX4, P2RX7, PRR4, PTPRB, PTPRQ, PTPRR, SCNN1A, SELPLG, SLC2A14, SLC38A4, SLC5A8, SLC6A15, SLC8B1, SLCO1A2, SLCO1B1, SLCO1B7, SLCO1C1, SSPN, STAB2, TAS2R10, TAS2R13, TAS2R14, TAS2R20, TAS2R30, TAS2R31, TAS2R42, TAS2R43, TAS2R46, TAS2R7, TMEM119, TMEM132B, TMEM132C, TMEM132D, TMPRSS12, TNFRSF1A, TSPAN8, and VSIG10.

In some embodiments, the recognition moiety for use in the iCAR or pCAR provides specifity to at least one extracellular polymorphic epitope in a gene product from a gene selected from chromosome 12. In some embodiments, the recognition moiety for use in the iCAR or pCAR provides specifity to at least one extracellular polymorphic epitope in a gene product from a gene selected from the group consisting of ANO4, AVPR1A, BCL2L14, CACNA2D4, CD163, CD163L1, CD27, CD4, CLEC12A, CLEC1B, CLEC2A, CLEC4C, CLEC7A, CLECL1, CLSTN3, GPR133, GPRC5D, ITGA7, ITGB7, KLRB1, KLRC2, KLRC3, KLRC4, KLRF1, KLRF2, LRP1, LRP6, MANSC1, MANSC4, OLR1, OR10AD1, OR10P1, OR2AP1, OR6C1, OR6C2, OR6C3, OR6C4, OR6C6, OR6C74, OR6C76, OR8S1, OR9K2, ORAI1, P2RX4, P2RX7, PRR4, PTPRB, PTPRQ, PTPRR, SCNN1A, SELPLG, SLC2A14, SLC38A4, SLC5A8, SLC6A15, SLC8B1, SLCO1A2, SLCO1B1, SLCO1B7, SLCO1C1, SSPN, STAB2. TAS2R10, TAS2R13, TAS2R14, TAS2R20, TAS2R30, TAS2R31, TAS2R42, TAS2R43, TAS2R46, TAS2R7, TMEM119, TMEM132B, TMEM132C, TMEM132D, TMPRSS12, TNFRSF1A, TSPAN8, and VSIG10.

In some embodiments, the recognition moiety for use in the aCAR provides specifity to at least one extracellular polymorphic epitope in a gene product from a gene selected from chromosome 13. In some embodiments, the recognition moiety for use in the aCAR provides specifity to at least one extracellular polymorphic epitope in a gene product from a gene selected from the group consisting of ATP4B, ATP7B, FLT3, FREM2, HTR2A, KL, PCDH8, RXFP2, SGCG, SHISA2, SLC15A1, SLITRK6, and TNFRSF19.

In some embodiments, the recognition moiety for use in the iCAR or pCAR provides specifity to at least one extracellular polymorphic epitope in a gene product from a gene selected from chromosome 13. In some embodiments, the recognition moiety for use in the iCAR or pCAR provides specifity to at least one extracellular polymorphic epitope in a gene product from a gene selected from the group consisting of ATP4B, ATP7B, FLT3, FREM2, HTR2A, KL, PCDH8, RXFP2, SGCG, SHISA2, SLC15A1, SLITRK6, and TNFRSF19.

In some embodiments, the recognition moiety for use in the aCAR provides specifity to at least one extracellular polymorphic epitope in a gene product from a gene selected from chromosome 14. In some embodiments, the recognition moiety for use in the aCAR provides specifity to at least one extracellular polymorphic epitope in a gene product from a gene selected from the group consisting of ADAM21, BDKRB2, C14orf37, CLEC14A, DLK1, FLRT2, GPR135, GPR137C, JAG2, LTB4R2, MMP14, OR11G2, OR11H12, OR11H6, OR4K1, OR4K15, OR4K5, OR4L1, OR4N2, OR4N5, SLC24A4, and SYNDIG1L.

In some embodiments, the recognition moiety for use in the iCAR or pCAR provides specifity to at least one extracellular polymorphic epitope in a gene product from a gene selected from chromosome 14. In some embodiments, the recognition moiety for use in the iCAR or pCAR provides specifity to at least one extracellular polymorphic epitope in a gene product from a gene selected from the group consisting of ADAM21, BDKRB2, C14orf37, CLEC14A, DLK1, FLRT2, GPR135, GPR137C, JAG2, LTB4R2, MMP14, OR11G2, OR11H12, OR11H6, OR4K1, OR4K15, OR4K5, OR4L1, OR4N2, OR4N5, SLC24A4, and SYNDIG1L.

In some embodiments, the recognition moiety for use in the aCAR provides specifity to at least one extracellular polymorphic epitope in a gene product from a gene selected from chromosome 15. In some embodiments, the recognition moiety for use in the aCAR provides specifity to at least one extracellular polymorphic epitope in a gene product from a gene selected from the group consisting of ANPEP, CD276, CHRNA7, CHRNB4, CSPG4, DUOX1, DUOX2, FAM174B, GLDN, IGDCC4, ITGA11, LCTL, LTK, LYSMD4, MEGF11, NOX5, NRG4, OCA2, OR4F4, OR4M2, OR4N4, PRTG, RHCG, SCAMP5, SEMA4B, SEMA6D, SLC24A1, SLC24A5, SLC28A1, SPG11, STRA6, TRPM1, and TYRO3.

In some embodiments, the recognition moiety for use in the iCAR or pCAR provides specifity to at least one extracellular polymorphic epitope in a gene product from a gene selected from chromosome 15. In some embodiments, the recognition moiety for use in the iCAR or pCAR provides specifity to at least one extracellular polymorphic epitope in a gene product from a gene selected from the group consisting of ANPEP, CD276, CHRNA7, CHRNB4, CSPG4, DUOX1, DUOX2, FAM174B, GLDN, IGDCC4, ITGA11, LCTL, LTK, LYSMD4, MEGF11, NOX5, NRG4, OCA2, OR4F4, OR4M2, OR4N4, PRTG, RHCG, SCAMP5, SEMA4B, SEMA6D, SLC24A1, SLC24A5, SLC28A1, SPG11, STRA6, TRPM1, and TYRO3.

In some embodiments, the recognition moiety for use in the aCAR provides specifity to at least one extracellular polymorphic epitope in a gene product from a gene selected from chromosome 16. In some embodiments, the recognition moiety for use in the aCAR provides specifity to at least one extracellular polymorphic epitope in a gene product from a gene selected from the group consisting of ATP2C2, CACNA1H, CD19, CDH11, CDH15, CDH16, CDH3, CDH5, CNGB1, CNTNAP4, GDPD3, GPR56, GPR97, IFT140, IL4R, ITFG3, ITGAL, ITGAM, ITGAX, KCNG4, MMP15, MSLNL, NOMO1, NOMO3, OR2C1, PIEZO1, PKD1, PKD1L2, QPRT, SCNN1B, SEZ6L2, SLC22A31, SLC5A11, SLC7A6, SPN, TMC5, TMC7, TMEM204, TMEM219, and TMEM8A.

In some embodiments, the recognition moiety for use in the iCAR or pCAR provides specifity to at least one extracellular polymorphic epitope in a gene product from a gene selected from chromosome 16. In some embodiments, the recognition moiety for use in the iCAR or pCAR provides specifity to at least one extracellular polymorphic epitope in a gene product from a gene selected from the group consisting of ATP2C2, CACNA1H, CD19, CDH11, CDH15, CDH16, CDH3, CDH5, CNGB1, CNTNAP4, GDPD3, GPR56, GPR97, IFT140, IL4R, ITFG3, ITGAL, ITGAM, ITGAX, KCNG4, MMP15, MSLNL, NOMO1, NOMO3, OR2C1, PIEZO1, PKD1, PKD1L2, QPRT, SCNN1B, SEZ6L2, SLC22A31, SLC5A11, SLC7A6, SPN, TMC5, TMC7, TMEM204, TMEM219, and TMEM8A.

In some embodiments, the recognition moiety for use in the aCAR provides specifity to at least one extracellular polymorphic epitope in a gene product from a gene selected from chromosome 17. In some embodiments, the recognition moiety for use in the aCAR provides specifity to at least one extracellular polymorphic epitope in a gene product from a gene selected from the group consisting of ABCC3, ACE, AOC3, ARL17B, ASGR2, C17orf80, CD300A, CD300C, CD300E, CD300LF, CD300LG, CHRNB1, CLEC10A, CNTNAP1, CPD, CXCL16, ERBB2, FAM171A2, GCGR, GLP2R, GP1BA, GPR142, GUCY2D, ITGA2B, ITGA3, ITGAE, ITGB3, KCNJ12, LRRC37A2, LRRC37A3, LRRC37A, LRRC37B, MRC2, NGFR, OR1A2, OR1D2, OR1G1, OR3A1, OR3A2, OR4D1, OR4D2, RNF43, SCARF1, SCN4A, SDK2, SECTM1, SEZ6, SHPK, SLC26A11, SLC5A10, SPACA3, TMEM102, TMEM132E, TNFSF12, TRPV3, TTYH2, and TUSC5.

In some embodiments, the recognition moiety for use in the iCAR or pCAR provides specifity to at least one extracellular polymorphic epitope in a gene product from a gene selected from chromosome 17. In some embodiments, the recognition moiety for use in the iCAR or pCAR provides specifity to at least one extracellular polymorphic epitope in a gene product from a gene selected from the group consisting of ABCC3, ACE, AOC3, ARL17B, ASGR2, C17orf80, CD300A, CD300C, CD300E, CD300LF, CD300LG, CHRNB1, CLEC10A, CNTNAP1, CPD, CXCL16, ERBB2, FAM171A2, GCGR, GLP2R, GP1BA, GPR142, GUCY2D, ITGA2B, ITGA3, ITGAE, ITGB3, KCNJ12, LRRC37A2, LRRC37A3, LRRC37A, LRRC37B, MRC2, NGFR, OR1A2, OR1D2, OR1G1, OR3A1, OR3A2, OR4D1, OR4D2, RNF43, SCARF1, SCN4A, SDK2, SECTM1, SEZ6, SHPK, SLC26A11, SLC5A10, SPACA3, TMEM102, TMEM132E, TNFSF12, TRPV3, TTYH2, and TUSC5.

In some embodiments, the recognition moiety for use in the aCAR provides specifity to at least one extracellular polymorphic epitope in a gene product from a gene selected from chromosome 18. In some embodiments, the recognition moiety for use in the aCAR provides specifity to at least one extracellular polymorphic epitope in a gene product from a gene selected from the group consisting of APCDD1, CDH19, CDH20, CDH7, COLEC12, DCC, DSC1, DSG1, DSG3, DYNAP, MEP1B, PTPRM, SIGLEC15, and TNFRSF11A.

In some embodiments, the recognition moiety for use in the iCAR or pCAR provides specifity to at least one extracellular polymorphic epitope in a gene product from a gene selected from chromosome 18. In some embodiments, the recognition moiety for use in the iCAR or pCAR provides specifity to at least one extracellular polymorphic epitope in a gene product from a gene selected from the group consisting of APCDD1, CDH19, CDH20, CDH7, COLEC12, DCC, DSC1, DSG1, DSG3, DYNAP, MEP1B, PTPRM, SIGLEC15, and TNFRSF11A.

In some embodiments, the recognition moiety for use in the aCAR provides specifity to at least one extracellular polymorphic epitope in a gene product from a gene selected from chromosome 19. In some embodiments, the recognition moiety for use in the aCAR provides specifity to at least one extracellular polymorphic epitope in a gene product from a gene selected from the group consisting of ABCA7, ACPT, BCAM, C19orf38, C19orf59, C5AR1, CATSPERD, CATSPERG, CD22, CD320, CD33, CD97, CEACAM19, CEACAM1, CEACAM21, CEACAM3, CEACAM4, CLEC4M, DLL3, EMR1, EMR2, EMR3, ERVV-1, ERVV-2, FAM187B, FCAR, FFAR3, FPR1, FXYD5, GFY, GP6, GPR42, GRIN3B, ICAM3, IGFLR1, IL12RB1, IL27RA, KIR2DL1, KIR2DL3, KIR2DL4, KIR3DL1, KIR3DL2, KIR3DL3, KIRREL2, KISS1R, LAIR1, LDLR, LILRA1, LILRA2, LILRA4, LILRA6, LILRB1, LILRB2, LILRB3, LILRB4, LILRB5, LINGO3, LPHN1, LRP3, MADCAM1, MAG, MEGF8, MUC16, NCR1, NOTCH3, NPHS1, OR10H1, OR10H2, OR10H3, OR10H4, OR1I1, OR2Z1, OR7A10, OR7C1, OR7D4, OR7E24, OR7G1, OR7G2, OR7G3, PLVAP, PTGIR, PTPRH, PTPRS, PVR, SCN1B, SHISA7, SIGLEC10, SIGLEC11, SIGLEC12, SIGLEC5, SIGLEC6, SIGLEC8, SIGLEC9, SLC44A2, SLC5A5, SLC7A9, SPINT2, TARM1, TGFBR3L, TMC4, TMEM91, TMEM161A, TMPRSS9, TNFSF14, TNFSF9, TRPM4, VN1R2, VSIG10L, VSTM2B, and ZNRF4.

In some embodiments, the recognition moiety for use in the iCAR or pCAR provides specifity to at least one extracellular polymorphic epitope in a gene product from a gene selected from chromosome 19. In some embodiments, the recognition moiety for use in the iCAR or pCAR provides specifity to at least one extracellular polymorphic epitope in a gene product from a gene selected from the group consisting of ABCA7, ACPT, BCAM, C19orf38, C19orf59, C5AR1, CATSPERD, CATSPERG, CD22, CD320, CD33, CD97, CEACAM19, CEACAM1, CEACAM21, CEACAM3, CEACAM4, CLEC4M, DLL3, EMR1, EMR2, EMR3, ERVV-1, ERVV-2, FAM187B, FCAR, FFAR3, FPR1, FXYD5, GFY, GP6, GPR42, GRIN3B, ICAM3, IGFLR1, IL12RB1, IL27RA, KIR2DL1, KIR2DL3, KIR2DL4, KIR3DL1, KIR3DL2, KIR3DL3, KIRREL2, KISS1R, LAIR1, LDLR, LILRA1, LILRA2, LILRA4, LILRA6, LILRB1, LILRB2, LILRB3, LILRB4, LILRB5, LINGO3, LPHN1, LRP3, MADCAM1, MAG, MEGF8, MUC16, NCR1, NOTCH3, NPHS1, OR10H1, OR10H2, OR10H3, OR10H4, OR1I1, OR2Z1, OR7A10, OR7C1, OR7D4, OR7E24, OR7G1, OR7G2, OR7G3, PLVAP, PTGIR, PTPRH, PTPRS, PVR, SCN1B, SHISA7, SIGLEC10, SIGLEC11, SIGLEC12, SIGLEC5, SIGLEC6, SIGLEC8, SIGLEC9, SLC44A2, SLC5A5, SLC7A9, SPINT2, TARM1, TGFBR3L, TMC4, TMEM91, TMEM161A, TMPRSS9, TNFSF14, TNFSF9, TRPM4, VN1R2, VSIG10L, VSTM2B, and ZNRF4.

In some embodiments, the recognition moiety for use in the aCAR provides specifity to at least one extracellular polymorphic epitope in a gene product from a gene selected from chromosome 20. In some embodiments, the recognition moiety for use in the aCAR provides specifity to at least one extracellular polymorphic epitope in a gene product from a gene selected from the group consisting of ABHD12, ADAM33, ADRA1D, APMAP, ATRN, CD40, CD93, CDH22, CDH26, CDH4, FLRT3, GCNT7, GGT7, JAG1, LRRN4, NPBWR2, OCSTAMP, PTPRA, PTPRT, SEL1L2, SIGLEC1, SIRPA, SIRPB1, SIRPG, SLC24A3, SLC2A10, SLC4A11, SSTR4, and THBD.

In some embodiments, the recognition moiety for use in the iCAR or pCAR provides specifity to at least one extracellular polymorphic epitope in a gene product from a gene selected from chromosome 20. In some embodiments, the recognition moiety for use in the iCAR or pCAR provides specifity to at least one extracellular polymorphic epitope in a gene product from a gene selected from the group consisting of ABHD12, ADAM33, ADRA1D, APMAP, ATRN, CD40, CD93, CDH22, CDH26, CDH4, FLRT3, GCNT7, GGT7, JAG1, LRRN4, NPBWR2, OCSTAMP, PTPRA, PTPRT, SEL1L2, SIGLEC1, SIRPA, SIRPB1, SIRPG, SLC24A3, SLC2A10, SLC4A11, SSTR4, and THBD.

In some embodiments, the recognition moiety for use in the aCAR provides specifity to at least one extracellular polymorphic epitope in a gene product from a gene selected from chromosome 21. In some embodiments, the recognition moiety for use in the aCAR provides specifity to at least one extracellular polymorphic epitope in a gene product from a gene selected from the group consisting of CLDN8, DSCAM, ICOSLG, IFNAR1, IFNGR2, IGSF5, ITGB2, KCNJ15, NCAM2, SLC19A1, TMPRSS15, TMPRSS2, TMPRSS3, TRPM2, and UMODL1.

In some embodiments, the recognition moiety for use in the iCAR or pCAR provides specifity to at least one extracellular polymorphic epitope in a gene product from a gene selected from chromosome 21. In some embodiments, the recognition moiety for use in the iCAR or pCAR provides specifity to at least one extracellular polymorphic epitope in a gene product from a gene selected from the group consisting of CLDN8, DSCAM, ICOSLG, IFNAR1, IFNGR2, IGSF5, ITGB2, KCNJ15, NCAM2, SLC19A1, TMPRSS15, TMPRSS2, TMPRSS3, TRPM2, and UMODL1.

In some embodiments, the recognition moiety for use in the aCAR provides specifity to at least one extracellular polymorphic epitope in a gene product from a gene selected from chromosome 22. In some embodiments, the recognition moiety for use in the aCAR provides specifity to at least one extracellular polymorphic epitope in a gene product from a gene selected from the group consisting of CACNA1I, CELSR1, COMT, CSF2RB, GGT1, GGT5, IL2RB, KREMEN1, MCHR1, OR11H1, P2RX6, PKDREJ, PLXNB2, SCARF2, SEZ6L, SSTR3, SUSD2, TMPRSS6, and TNFRSF13C.

In some embodiments, the recognition moiety for use in the iCAR or pCAR provides specifity to at least one extracellular polymorphic epitope in a gene product from a gene selected from chromosome 22. In some embodiments, the recognition moiety for use in the iCAR or pCAR provides specifity to at least one extracellular polymorphic epitope in a gene product from a gene selected from the group consisting of CACNA1I, CELSR1, COMT, CSF2RB, GGT1, GGT5, IL2RB, KREMEN1, MCHR1, OR11H1, P2RX6, PKDREJ, PLXNB2, SCARF2, SEZ6L, SSTR3, SUSD2, TMPRSS6, and TNFRSF13C.

In some embodiments, the recognition moiety for use in the aCAR provides specifity to at least one extracellular polymorphic epitope in a gene product from a gene selected from chromosome X. In some embodiments, the recognition moiety for use in the aCAR provides specifity to at least one extracellular polymorphic epitope in a gene product from a gene selected from the group consisting of ATP6AP2, ATP7A, CNGA2, EDA2R, FMR1NB, GLRA4, GPR112, GUCY2F, HEPH, P2RY10, P2RY4, PLXNA3, PLXNB3, TLR8, VSIG4, and XG.

In some embodiments, the recognition moiety for use in the iCAR or pCAR provides specifity to at least one extracellular polymorphic epitope in a gene product from a gene selected from chromosome X. In some embodiments, the recognition moiety for use in the iCAR or pCAR provides specifity to at least one extracellular polymorphic epitope in a gene product from a gene selected from the group consisting of ATP6AP2, ATP7A, CNGA2, EDA2R, FMR1NB, GLRA4, GPR112, GUCY2F, HEPH, P2RY10, P2RY4, PLXNA3, PLXNB3, TLR8, VSIG4, and XG.

The sequences encoding the variable regions of these antibodies can easily be cloned from the relevant hybridoma and used for constructing genes encoding scFvs against any desired target, including for example, scFvs against specific HLA Class-I allelic epitope variants, and which would be suitable for incorporation into a CAR construct using tools widely available as disclosed e.g., in Molecular Cloning: A Laboratory Manual (Fourth Edition) Green and Sambrook, Cold Spring Harbor Laboratory Press; Antibodies: A Laboratory Manual (Second Edition), Edited by Edward A. Greenfield, 2012 CSH laboratory press; Using Antibodies, A laboratory manual by Ed Harlow and David Lane, 1999 CSH laboratory press.

The present invention provides a database comprising DNA sequences of polymorphic variants lost in tumor cells due to LOH, and that encode cell-surface products, wherein the variation at the DNA sequence results in a variation at the amino acid sequence in an extracellular domain of the encoded protein. The information was retrieved from several databases open to the general public, such as TCGA, available on the public National Institute of Health TCGA data portal (https://gdc.cancer.gov/), which provides, inter alia, data that can be used to infer relative copy number of the gene in a variety of tumor types and the cbio portal for TCGA data at http://www.cbioportal.org (Cerami et al., 2012, Gao et al., 2013); the Exome Aggregation Consortium (ExAC) database (exac.broadinstitute.org, Lek et al., 2016), providing, inter alia, allele frequencies of SNP variants in various populations; the Genotype-Tissue Expression (GTEX) database v6p (dbGaP Accession phs000424.v6.p1) (https://gtexportal.org/home, Consortium G T. Human genomics, 2015) which includes tissue expression data for genes; and databases providing structural information of proteins, such as the Human Protein Atlas (Uhlen et al., 2015); the Cell Surface Protein Atlas (Bausch-Fluck et al., 2015), a mass-spectrometry based database of N-glycosylated cell-surface proteins, and the UniProt database (www.uniprot.org/downloads).

The present invention further provides a method for genome-wide identification of genes that encode expressed cell-surface proteins that undergo LOH. The identified genes must meet the following criteria: 1) The gene encodes a transmembrane protein—therefore having a portion expressed on the cell surface to allow the iCAR or pCAR binding; 2) The gene has at least two expressed alleles (in at least one ethnic population checked); 3) The allelic variation found for that gene causes an amino acid change relative to the reference sequence in an extracellular region of the protein; 4) The gene is located in a chromosomal region which undergoes LOH in cancer; 5) The gene is expressed in a tissue-of-origin of a tumor type in which the corresponding region was found to undergo LOH.

In principle genes as described above, suitable to encode targets for iCAR or pCAR binding may be identified by any method known in the art, and not only by database mining. For example, the concept of LOH is not new and LOH information for specific genes, chromosomes, or genomic/chromosomal regions in specific tumors has already been published in the literature and candidate genes can therefore be derived from the available publications. Alternatively, such information can be found by whole genome hybridizations with chromosomal markers such as microsatellite probes (Medintz et al., 2000, *Genome Res.* 2000 August; 10(8): 1211-1218) or by any other suitable method (Ramos and Amorim, 2015, J. Bras. Patol. Med. Lab. 51(3):198-196).

Similarly, information regarding allelic variants is publicly available in various databases, and can also be easily obtained for a personalized case by genomic sequencing of a suspected region. Also, information regarding protein structure and expression pattern is publicly available and easily accessible as described above.

Accordingly, as information regarding the various criteria for many genes and SNPs is publicly available and the techniques for retrieving it are generally known, the main novelty of the application is using LOH as a criterion for choosing a target for iCAR or pCAR recognition, and the concept of personalizing treatment based on a specific allele lost in a specific patient.

As a non-limiting example, it was found according to the present invention that HLA genes, including non-classical HLA-I and HLA-II genes (e.g., HLA-A, HLA-B HLA-C, HLA-E, HLA-F, HLA-G, HLA-DM, HLA-DO, HLA-DP, HLA-DQ, HLA-DR HLA-K and/or HLA-L) LOH, at varying frequencies, is a relatively frequent event in many tumor types (see FIGS. 10A-C), which would make these genes good candidates to be used as targets for iCAR/pCAR recognition for the purpose of the present invention.

The recognition of the aCAR target on normal cells in any healthy essential tissue in the absence of the pCAR or iCAR target would be detrimental and is strictly forbidden. In this respect, the concept of pCAR-aCAR or iCAR-aCAR pairs, as proposed here, constitutes a fail-safe activation switch, as: i) cells not expressing the selected gene (in case the aCAR and the pCAR or iCAR target different products of the same gene) will not be targeted due to absence of the aCAR target antigen; ii) normal cells expressing this same gene will co-express both alleles and will not be targeted owing to the dominance of the pCAR or iCAR; iii) in case the pCAR or iCAR targets the product of a polymorphic housekeeping gene, all cells in the body will be protected; and iv) only tumor cells which express the aCAR target but not the pCAR or iCAR one will be attacked. In some embodiments, the recognition of the aCAR target on normal cells in any healthy essential tissue in the absence of the pCAR or iCAR target would be detrimental. In some embodiments, cells not expressing the selected gene (in case the aCAR and the pCAR or iCAR target different products of the same gene) will not be targeted due to absence of the aCAR target antigen. In some embodiments, normal cells expressing this same gene will co-express both alleles and will not be targeted owing to the dominance of the pCAR or iCAR. In some embodiments, when the pCAR or iCAR targets the product of a polymorphic housekeeping gene, all cells in the body will be protected. In some embodiments, only tumor cells which express the aCAR target but not the pCAR or iCAR one will be attacked. In some embodiments, cells that express both the aCAR/iCAR pair targets or both aCAR/pCAR pair tarets will be protected.

As emphasized above, according to the invention there must be permanent dominance of the inhibitory signal over the activating signal. It is therefore necessary to ensure that no aCAR gene is expressed in a given killer cell, at any time, in the absence of its iCAR partner. This may be implemented through the tandem assembly of these iCAR-aCAR gene pairs as single-chain products or via a suitable bi-cistronic modality based, for example, on an internal ribosome entry site or on one of several viral self-cleaving 2A peptides. As suggested by the vast bulk of data reported on bi-cistronic expression, the iCAR gene will always be positioned upstream of its aCAR partner to guarantee favorable stoichiometry. Another option would be engineering the killer cells to express both aCAR and iCAR or pCAR by transfecting or transducing the killer cell with two independent constructs, each construct coding for either aCAR or iCAR/pCAR. Of course, this is not an issue when using a pCAR-aCAR gene pair. In some embodiments, the inhibitory signal is dominant over the activating signal. In some embodiments, the aCAR and iCAR or pCAR are expressed simultaneously in the same cell.

Another attractive option for assuring iCAR dominance is detaching the aCAR recognition moiety from its activating/costimulatory portion so that both entities can only be assembled into one functional receptor in the presence of a heterodimerizing small molecule. The ability to tightly control the operative state of such split receptors by precise timing, dosage and location was recently demonstrated in the context of antitumor CARs (Wu et al., 2015).

In addition, the expected dominance is also likely to be intrinsic to the particular composition of the iCAR signaling elements incorporated into the intracellular portion in the selected iCAR design that should 'compete' with the signaling strength of the chosen aCAR platform. This capacity will also be influenced by the relative affinities of the two recognition moieties for their respective target epitopes (which was dealt with above) and the overall avidities of their interactions. Concerning the latter, the proposed strategy secures both a favorable iCAR/aCAR stoichiometry and a balanced distribution of their respective target epitopes on normal cells. Again, this is not an issue when using a pCAR-aCAR gene pair.

To further assure safety, other conventional means currently implemented in the field of CAR and TCR immunotherapy can be employed, such as the use of suicide genes or the use of mRNA electroporation for transient expression.

While LOH often leaves the cells with only one allele of a given gene, it is frequently accompanied by duplication of the remaining chromosome, or chromosome part, resulting in 'copy number neutral'-LOH (Lo et al., 2008; O'Keefe et al., 2010; Sathirapongsasuti et al., 2011). Under these circumstances, the emergence of epitope-loss variants requires two independent events and is thus less likely. Expressing several pCAR-aCAR or iCAR-aCAR pairs in different fractions of the gene-modified cells will prevent the appearance of mutational escapees even in 'copy number loss' LOH cases, in which only a single copy of the target allele has been retained. Yet, as single-copy genes may become essential, their functional loss would be far less likely.

In view of the above, in one aspect, the present invention provides a nucleic acid molecule comprising a nucleotide sequence encoding an inhibitory chimeric antigen receptor (iCAR) capable of preventing or attenuating undesired activation of an effector immune cell, wherein the iCAR comprises an extracellular domain that specifically binds to a single allelic variant of a polymorphic cell surface epitope absent from mammalian tumor cells due to loss of heterozygosity (LOH) but present at least on all cells of related mammalian normal tissue, or on vital organs the aCAR is expressed in; and an intracellular domain comprising at least one signal transduction element that inhibits an effector immune cell.

In some embodiments, the polymorphic cell surface epitope is part of an antigen encoded by a tumor suppressor gene or a gene genetically linked to a tumor suppressor gene, since such genes are likely to be lost due to LOH in tumors. Additionally, the polymorphic cell surface epitope may be part of an antigen encoded by a gene normally residing on a chromosome or chromosomal arm that often undergo LOH in cancer cells such as, but not limited to, chromosomal arms 3p, 6p, 9p, 10q, 17p, 17q, or 18q, or chromosome 19. These epitopes can readily be identified in the relevant databases as described herein.

In some embodiments, the polymorphic cell surface epitope is of a housekeeping gene product, such as the unclassified AP2S1, CD81, GPAA1, LGALS9, MGAT2, MGAT4B, VAMP3; the cell adhesion proteins CTNNA1 NM_001903, CTNNB1, CTNNBIP1 NM_020248, CTNNBL1 NM_030877, CTNND1 NM_001085458 delta catenin; the channels and transporters ABCB10 NM_012089, ABCB7 NM_004299, ABCD3 NM_002857, ABCE1 NM_002939, ABCF1 NM_001090, ABCF2 NM_005692, ABCF3 NM_018358, CALM1[1][7] Calmodulin grasps calcium ions, MFSD11 NM_024311 similar to MSFD10 aka TETRAN or tetracycline transporter-like protein[1], MFSD12 NM_174983, MFSD3 NM_138431, MFSD5 NM_032889, SLC15A4 NM_145648, SLC20A1 NM_005415, SLC25A11[1] mitochondrial oxoglutarate/malate carrier, SLC25A26 NM_173471, SLC25A28 NM_031212, SLC25A3 NM_002635, SLC25A32 NM_030780, SLC25A38 NM_017875, SLC25A39 NM_016016, SLC25A44 NM_014655, SLC25A46 NM_138773, SLC25A5 NM_001152, SLC27A4 NM_005094, SLC30A1 NM_021194, SLC30A5 NM_022902, SLC30A9 NM_006345, SLC35A2 NM_005660, SLC35A4 NM_080670, SLC35B1 NM_005827. SLC35B2 NM_178148, SLC35C2 NM_015945, SLC35E1 NM_024881, SLC35E3 NM_018656, SLC35F5 NM_025181, SLC38A2 NM_018976, SLC39A1 NM_014437, SLC39A3 NM_144564, SLC39A7 NM_006979, SLC41A3 NM_017836, SLC46A3 NM_181785, SLC48A1 NM_017842, the receptors ACVR1 NM_001105 similar to ACVRL1 TGF Beta receptor family Rendu-Osler-Weber syndrome, ACVR1B NM_004302, CD23[1] FCER2 low affinity IgE receptor (lectin); and the HLA/immunoglobulin/cell recognition group BAT1 aka DDX39B which is involved in RNA splicing, BSG Basigin Immunoglobulin Superfamily, extracelluar metalloproteinase, MIF macrophage migration inhibitory factor, and/or TAPBP [Wikipedia]. In some embodiments, the housekeeping gene is an HLA type I, a G-protein-coupled receptor (GPCR), an ion channel or a receptor tyrosine kinase, preferably an HLA-A, HLA-B, HLA-C. In some embodiments, the housekeeping gene is HLA-A. In some embodiments, the housekeeping gene is HLA-B. In some embodiments, the housekeeping gene is HLA-C.

Any relevant technology may be used to engineer a recognition moiety that confers to the aCARs and pCAR or iCARs specific binding to their targets. In some embodiments, the extracellular domain comprises (i) an antibody, derivative or fragment thereof, such as a humanized antibody; a human antibody; a functional fragment of an antibody; a single-domain antibody, such as a Nanobody; a recombinant antibody; and a single chain variable fragment (ScFv); (ii) an antibody mimetic, such as an affibody molecule; an affilin; an affimer; an affitin; an alphabody; an anticalin; an avimer; a DARPin; a fynomer; a Kunitz domain peptide; and a monobody; or (iii) an aptamer. Preferably, the extracellular domain comprises an ScFv.

In some embodiments, the aCAR comprising an extracellular domain that specifically binds to a non-polymorphic cell surface epitope of an antigen or a single allelic variant of a polymorphic cell surface epitope. In some embodiments, the aCAR extracellular domain binds to an epitope that is a tumor-associated antigen epitope. In some embodiments, the aCAR extracellular domain binds to an epitope that is a tumor-associated antigen is shared at least by cells of related tumor and normal tissue, and an intracellular domain comprising at least one signal transduction element that activates and/or co-stimulates an effector immune cell. In some embodiments, the aCAR used to treat the cancer is directed against or specifically binds to any membrane protein which is expressed on the tumor tissue as long as the iCAR target is expressed on every normal tissue in which the targeted aCAR protein is expressed. In some embodiments, the aCAR is directed against or specifically binds to, a non-polymorphic cell surface epitope selected from but not limited to the following list of antigens: CD19, CD20, CD22, CD10, CD7, CD49f, CD56, CD74, CAIX Igκ, ROR1, ROR2, CD30, LewisY, CD33, CD34, CD38, CD123, CD28, CD44v6, CD44, CD41, CD133, CD138, NKG2D-L, CD139, BCMA, GD2, GD3, hTERT, FBP, EGP-2, EGP-40, FR-α, L1-CAM, ErbB2,3,4, EGFRvIII, VEGFR-2, IL-13Ra2, FAP, Mesothelin, c-MET, PSMA, CEA, kRas, MAGE-AL MUC1MUC16, PDL1, PSCA, EpCAM, FSHR, AFP, AXL, CD80 CD89, CDH17, CLD18, GPC3, TEM8, TGFB1, NY-ESO-1, WT-1 and EGFR In some embodiments, the aCAR binds to CD19. In some embodiments, the aCAR directed against or specifically binds to, a non-polymorphic cell surface epitope of CD19.

In some embodiments, the iCAR is directed against or specifically binds to a single allelic variant of an antigen not including the ephrin receptors (e.g., EPHA 7) and claudins. In some embodiments, the iCAR is directed against or specifically binds to an epitope encoded by a single allelic variant of an HLA gene (HLA-A gene, HLA-B gene or HLA-C gene.

iii. Intracellular Domains: aCAR, iCAR and pCAR

The present invention also provides for intracellular domains as part of the aCAR, iCAR, and/or pCAR. In some embodiments, the intracellular domain comprises at least one signal transduction element. In some embodiments, the intracellular domain comprises at least one signal transduction element that inhibits an effector immune cell.

Generally, any relevant technology may be used to engineer a signal transduction element that confers to the aCARs and pCAR or iCARs the ability to induce a cellular function, including for example, the ability to inhibit an effector immune cell or to activate or co-stimulate an effector immune cell.

In some embodiments, the at least one signal transduction element is capable of inhibiting an effector immune cell. In some embodiments, the at least one signal transduction element capable of inhibiting an effector immune cell is homologous to a signal transduction element of an immune checkpoint protein. In some embodiments, the immune checkpoint protein is selected from the group consisting of PD1, CTLA4, BTLA, 2B4, CD160, CEACAM (including for example, CEACAM1), KIRs (including for example KIR2DL1, KIR2DL2, KIR2DL3, KIR2DL4, KIR2DL5A, KIR2DL5B, KIR3DL1, KIR3DL2, KIR3DL3, LIR1, LIR2, LIR3, LIR5, LIR8 and CD94), NKG2A; LAGS; TIM3; V-domain Ig suppressor of T cell activation (VISTA); STimulator of INterferon Genes (STING); immunoreceptor tyrosine-based inhibitory motif (ITIM)-containing proteins, T cell immunoglobulin and ITIM domain (TIGIT), and adenosine receptor (e.g. A2aR). In some embodiments, the immune checkpoint protein is a negative immune regulator. In some embodiments, the negative immune regulator is selected from the group consisting of 2B4, LAG-3 and BTLA-4.

In some embodiments, the signal transduction element is capable of activating or co-stimulating an effector immune cell. In some embodiments, the signal transduction element is an activating domain. In some embodiments, the signal transduction element is a co-stimulatory domain. In some embodiments, the signal transduction element that activates or co-stimulates an effector immune cell is homologous to an immunoreceptor tyrosine-based activation motif (ITAM), an activating killer cell immunoglobulin-like receptor, or an adaptor molecule, and/or a co-stimulatory signal transduction element. In some embodiments, the signal transduction element that activates or co-stimulates an effector immune cell is homologous to an immunoreceptor tyrosine-based activation motif (ITAM). In some embodiments, the ITAM is from a protein including but not limited to CD3ζ or FcRγ chains. In some embodiments, the signal transduction element that activates or co-stimulates an effector immune cell is homologous to an an activating killer cell immunoglobulin-like receptor (KIR). In some embodiments, the KIR includes, for example, but is not limited to KIR2DS and KIR3DS. In some embodiments, the signal transduction element that activates or co-stimulates an effector immune cell is homologous to an adaptor molecule. In some embodiments, the adaptor molecule includes, for example, but is not limited to DAPI 2. In some embodiments, the signal transduction element that activates or co-stimulates an effector immune cell is homologous to a co-stimulatory signal transduction element. In some embodiments, the co-stimulatory signal transduction element is from a protein including but not limited to CD27, CD28, ICOS, CD137 (4-1BB), CD134 (OX40), and/or GITR. In some embodiments, the aCAR comprise a signal transduction element.

In some embodiments, the extracellular domain is fused through a flexible hinge and transmembrane canonic motif to said intracellular domain.

In some embodiments, the use of a pCAR allows for uncoupling for uncoupling the activating moiety of the aCAR (FcRγ/CD3-0 from the recognition unit and the co-stimulatory element (e.g., CD28, 4-1BB). In some embodiments, these elements are genetically placed on two different polypeptide products. In some embodiments, recoupling of these elements, which is mandatory for the aCAR function, will only take place by the addition of a heterodimerizing drug which can bridge the respective binding sites incorporated onto each of the polypeptides separately.

Instead of an activating domain (such as FcRγ or CD3-ζ), an iCAR possesses a signaling domain derived from an inhibitory receptor which can antagonize T cell activation. In some embodiments, the iCAR possesses a signaling domain derived from an inhibitory receptor which can antagonize T cell activation. In some embodiments, the iCAR signaling domain is derived from an inhibitory receptor, including for example but not limited to, a CTLA-4, a PD-1 or an NK inhibitory receptor.

iv. CAR-T Vector Construction (aCAR; iCAR; pCAR)

In some embodiments, the aCAR is encoded by a first nucleic acid vector and the iCAR or pCAR is encoded by a second nucleic acid vector. In some embodiments, the aCAR is encoded by a first nucleic acid vector and the iCAR or pCAR is encoded by a second nucleic acid vector. In some embodiments, the aCAR is encoded by a first nucleic acid vector and the iCAR or pCAR is encoded by a second nucleic acid vector. In some embodiments, the nucleotide sequence encoding for the iCAR or pCAR is on a second vector.

In some embodiments, the present invention provides a vector comprising a nucleic acid molecule of the invention as defined in any one of the above embodiments, and at least one control element, such as a promoter, operably linked to the nucleic acid molecule.

In some embodiments, the vector is a lentiviral (LV) vector. In some embodiments, the LV vector is a commercially available LV vector. In some embodiments, the LV vector includes but is not limited to pLVX-Puro, pLVX-IRES-Puro/Neo/Hygro, pLVx-EF1a-IRES (TAKARA), and/or pcLV-EF1a (Sirion). In some embodiments, the LV vector is pLVX-Puro. In some embodiments, the LV vector is pLVX-IRES-Puro/Neo/Hygro. In some embodiments, the LV vector is pLVx-EF1a-IRES (TAKARA). In some embodiments, the LV vector is pcLV-EF1a (Sirion). In some embodiments, the vector comprises an EF1 promoter. In some embodiments, the vector comprises a CMV promoter. In some embodiments, the vector comprises an PGK promoter. In some embodiments, the vector comprises a CD8 hinge. In some embodiments, the vector comprises a CD28 TM and 41BB costimulatory domain.

In some embodiments, the vector further comprises a nucleic acid molecule comprising a nucleotide sequence encoding an aCAR comprising an extracellular domain specifically binding a non-polymorphic cell surface epitope of an antigen or a single allelic variant of a polymorphic cell surface epitope, wherein said epitope is a tumor-associated antigen or is shared at least by cells of related tumor and normal tissue, and an intracellular domain comprising at least one signal transduction element that activates and/or co-stimulates an effector immune cell.

In some embodiments, the extracellular domain of the aCAR encoded by the nucleic acid comprised in the vector specifically binds to a non-polymorphic cell surface epitope of an antigen and the extracellular domain of the iCAR specifically binds a single allelic variant of a polymorphic cell surface epitope of a different antigen than that to which the extracellular domain of said aCAR binds.

In some embodiments, the extracellular domain of the iCAR encoded by the nucleic acid comprised in the vector, is directed against or specifically binds to a single allelic variant of HLA genes, including for example, HLA-A gene, HLA-B gene or HLA-C gene; or against a single allelic variant of a gene listed Table 8.

In some embodiments, the extracellular domain of the aCAR encoded by the nucleic acid comprised in the vector, is directed against or specifically binds to, a non-polymorphic cell surface epitope selected from the antigens listed in Table 1, such as CD19. In some embodiments, the aCAR target is any target with an extracellular domain.

In some embodiments, the extracellular domain of the iCAR encoded by the nucleic acid comprised in the vector, is directed against or specifically binds to a single allelic variant of HLA genes, including for example, HLA-A gene, HLA-B gene or HLA-C gene or against a single allelic variant of a gene listed Table 8; and the extracellular domain of the aCAR encoded by the nucleic acid comprised in the vector, is directed against or specifically binds to, a non-polymorphic cell surface epitope selected from the antigens listed in Table 1, such as CD19. In some embodiments, the aCAR target is any target with an extracellular domain.

In some embodiments, the at least one signal transduction element of the aCAR that activates or co-stimulates an effector immune cell is homologous to an immunoreceptor tyrosine-based activation motif (ITAM) of for example CD3t or FcRγ chains; a transmembrane domain of an activating killer cell immunoglobulin-like receptor (KIR) comprising a positively charged amino acid residue, or a positively charged side chain or an activating KIR transmembrane domain of e.g., KIR2DS and KIR3DS, or an adaptor molecule such as DAP12; or a co-stimulatory signal transduction element of for example CD27, CD28, ICOS, CD137 (4-1BB) or CD134 (OX40).

In some embodiments, the iCAR or pCAR is expressed by a first vector and the aCAR is expressed by a second vector. In some embodiments, the iCAR or pCAR and the aCAR are both expressed by the same vector.

In some embodiments, the nucleotide sequence of the vector comprises an internal ribosome entry site (IRES) between the nucleotide sequence encoding for the aCAR and the nucleotide sequence encoding for the iCAR. In general, the nucleotide sequence encoding for the aCAR and the nucleotide sequence encoding for the iCAR can be in any sequential order, but in particular embodiments, the nucleotide sequence encoding for the aCAR is downstream of the nucleotide sequence encoding for the iCAR.

In some embodiments, the nucleotide sequences encoding for the aCAR iand the iCAR are encoded on a single vector. In some embodiments, the vector comprises an internal ribosome entry site (IRES) between the nucleotide sequence encoding for the aCAR and the nucleotide sequence encoding for the iCAR. In some embodiments, the nucleotide sequence encoding for the aCAR is downstream of the nucleotide sequence encoding for the iCAR. In some embodiments, the nucleotide sequence comprises a viral self-cleaving 2A peptide located between the nucleotide sequence encoding for the aCAR and the nucleotide sequence encoding for the iCAR. In some embodiments, the nucleotide sequence of the vector comprises a viral self-cleaving 2A peptide between the nucleotide sequence encoding for the aCAR and the nucleotide sequence encoding for the iCAR. In some embodiments, the viral self-cleaving 2A peptide includes but is not limited to T2A from *Thosea asigna* virus (TaV), F2A from Foot-and-mouth disease virus (FMDV), E2A from Equine rhinitis A virus (ERAV) and/or P2A from Porcine teschovirus-1 (PTV1). In some embodiments, the viral self-cleaving 2A peptide is T2A from *Thosea asigna* virus (TaV). In some embodiments, the viral self-cleaving 2A peptide is F2A from Foot-and-mouth disease virus (FMDV). In some embodiments, the viral self-cleaving 2A peptide is E2A from Equine rhinitis A virus (ERAV). In some embodiments, the viral self-cleaving 2A peptide is P2A from Porcine teschovirus-1 (PTV1).

In some embodiments, the vector comprises a nucleotide sequence encoding the constitutive aCAR linked via a flexible linker to said iCAR.

The immune cells may be transfected with the appropriate nucleic acid molecule described herein by e.g., RNA transfection or by incorporation in a plasmid fit for replication and/or transcription in a eukaryotic cell or a viral vector. In some embodiments, the vector is selected from a retroviral or lentiviral vector.

Combinations of retroviral vector and an appropriate packaging line can also be used, where the capsid proteins will be functional for infecting human cells. Several amphotropic virus-producing cell lines are known, including PA12 (Miller, et al. (1985) *Mol. Cell. Biol.* 5:431-437); PA317 (Miller, et al. (1986) *Mol. Cell. Bioi.* 6:2895-2902); and CRIP (Danos, et ai. (1988) *Proc. Nati. Acad. Sci.* USA 85:6460-6464). Alternatively, non-amphotropic particles can be used, such as, particles pseudotyped with VSVG, RD 114 or GAL V envelope. Cells can further be transduced by direct co-culture with producer cells, e.g., by the method of Bregni, et ai. (1992) *Blood* 80: 1418-1422, or culturing with viral supernatant alone or concentrated vector stocks, e.g., by the method of Xu, et ai. (1994) *Exp. Hemat.* 22:223-230; and Hughes, et ai. (1992) *J Clin. Invest.* 89: 1817.

In another aspect, the present invention provides a method of preparing an inhibitory chimeric antigen receptor (iCAR) capable of preventing or attenuating undesired activation of an effector immune cell, according to the present invention as defined above, the method comprising: (i) retrieving a list of human genomic variants of protein-encoding genes from at least one database of known variants; (ii) filtering the list of variants retrieved in (i) by: (a) selecting variants resulting in an amino acid sequence variation in the protein encoded by the respective gene as compared with its corresponding reference allele, (b) selecting variants of genes wherein the amino acid sequence variation is in an extracellular domain of the encoded protein, (c) selecting variants of genes that undergo loss of heterozygosity (LOH) at least in one tumor, and (d) selecting variants of genes that are expressed at least in a tissue of origin of the at least one tumor in which they undergo LOH according to (c), thereby obtaining a list of variants having an amino acid sequence variation in an extracellular domain in the protein encoded by the respective gene lost in the at least one tumor due to LOH and expressed at least in a tissue of origin of the at least one tumor; (iii) defining a sequence region comprising at least one single variant from the list obtained in (ii), sub-cloning and expressing the sequence region comprising the at least one single variant and a sequence region comprising the corresponding reference allele thereby obtaining the respective epitope peptides; (iv) selecting an iCAR binding domain, which specifically binds either to the epitope peptide encoded by the cloned sequence region, or to the epitope peptide encoded by the corresponding reference allele, obtained in (iii); and (vii) preparing iCARs as defined herein above, each comprising an iCAR binding domain as defined in (iv).

In some embodiments, the candidate variants of genes that are selected undergo LOH in at least 2%, 5%, 10%, 20%, 30%, 40%, 50%, 60%, 70%, 80%, 90% or 100% in a certain tumor type.

In some embodiments, the minor allele frequency for each variant selected equals or exceeds 1, 2, 3, 4 or 5% in at least one population.

In another aspect, the present invention is directed to a combination of two or more nucleic acid molecules, each one comprising a nucleotide sequence encoding a different member of a controlled effector immune cell activating system, said nucleic acid molecules being part of or forming a single continues nucleic acid molecule, or comprising two or more separate nucleic acid molecules, wherein the controlled effector immune activating system directs effector immune cells to kill tumor cells that have lost one or more chromosomes or fractions thereof due to Loss of Heterozygosity (LOH) and spares cells of related normal tissue, and wherein (a) the first member comprises an activating chimeric antigen receptor (aCAR) polypeptide comprising a first extracellular domain that specifically binds to a non-polymorphic cell surface epitope of an antigen or to a single allelic variant of a different polymorphic cell surface epitope and said non-polymorphic or polymorphic cell surface epitope is a tumor-associated antigen or is shared by cells of related abnormal and normal mammalian tissue; and (b) the second member comprises a regulatory polypeptide comprising a second extracellular domain that specifically binds to a single allelic variant of a polymorphic cell surface epitope not expressed by an abnormal mammalian tissue due to LOH but present on all cells of related mammalian normal tissue.

In some embodiments, the first member is selected from: (a) a constitutive aCAR further comprising an intracellular domain comprising at least one signal transduction element that activates and/or co-stimulates an effector immune cell; and (b) a conditional aCAR further comprising an intracellular domain comprising a first member of a binding site for a heterodimerizing small molecule and optionally at least one co-stimulatory signal transduction element, but lacking an activating signal transduction element; and the second member is: (c) an inhibiting chimeric antigen receptor (iCAR) further comprising an intracellular domain comprising at least one signal transduction element that inhibits an effector immune cell; or (d) a protective chimeric antigen receptor (pCAR) further comprising an extracellular regulatory region comprising a substrate for a sheddase; a transmembrane canonic motif comprising a substrate for an intramembrane-cleaving protease; and an intracellular domain, said intracellular domain comprising at least one signal transduction element that activates and/or co-stimulates an effector immune cell and a second member of a binding site for a heterodimerizing small molecule.

In some embodiments (i) the extracellular domain of the iCAR or pCAR specifically binds a single allelic variant of a polymorphic cell surface epitope of an antigen, which is a different antigen than that to which the extracellular domain of the aCAR binds; (ii) the extracellular domain of said pCAR or iCAR specifically binds a single allelic variant of a different polymorphic cell surface epitope of the same antigen to which the extracellular domain of said aCAR binds; or (iii) the extracellular domain of said pCAR or iCAR specifically binds a different single allelic variant of the same polymorphic cell surface epitope to which the extracellular domain of said aCAR binds.

In some pCAR embodiments, the substrate for a sheddase is a substrate for a disintegrin and metalloproteinase (ADAM) or a beta-secretase 1 (BACE1). In some embodiments, the substrate forms part of the extracellular domain and comprises Lin 12/Notch repeats and an ADAM protease cleavage site.

It is generally accepted that there is no consistent sequence motif predicting ADAM cleavage, but Caescu et al. (Caescu et al., 2009) disclose in Table 3 a large number of ADAM10 and/or ADAM17 substrate sequences, which are hereby incorporated by reference as if fully disclosed herein, and which may serve as a substrate for ADAM in the pCAR of the present invention. In some embodiments, the ADAM substrate sequences are those of amyloid precursor protein, BTC, CD23, Collagen, DII-1, Ebola glycoprotein, E-cadherin, EGF, Epiregulin, Fas Ligand, growth hormone receptor, HB-EGF, type II interleukin-1 receptor, IL-6 receptor, L-selectin, N-cadherin, Notch, p55 TNF receptor, p75 TNF receptor, Pmel17, Prion protein, receptor-type protein tyrosine phosphatase Z, TGF-α, TNF or TR (Caescu et al., 2009).

It may be advantageous to use an ADAM10 cleavage sequence in the pCAR of the present invention because ADAM 10 is constitutively present at comparably high levels on e.g., lymphocytes. In contrast to ADAM10, the close relative TACE/ADAM17 is detected at only low levels on unstimulated cells. ADAM17 surface expression on T cell blasts is rapidly induced by stimulation (Ebsen et al., 2013).

Hemming et al. (Hemming et al., 2009) report that no consistent sequence motif predicting BACE1 cleavage has been identified in substrates versus non-substrates, but discloses in Table 1 a large number of BACE1 substrates having BAC1 cleavage sequences, which are hereby incorporated by reference as if fully disclosed herein, and which may serve as a substrate for BACE1 in the pCAR of the present invention.

In some pCAR embodiments, the substrate for an intramembrane-cleaving protease is a substrate for an SP2, a γ-secretase, a signal peptide peptidase (spp), a spp-like protease or a rhomboid protease.

Rawson et al. (Rawson, 2013) disclose that SP2 substrates have at least one type 2 membrane-spanning helix and include a helix-destabilizing motif, such as an Asp-Pro motif in a SP2 substrate. This paper discloses in Table 1 a number of SP2 substrates having SP2-cleavage sequences, which are hereby incorporated by reference as if fully disclosed herein, and which may serve as a substrate for SP2 in the pCAR of the present invention.

Haapasalo and Kovacs (Haapasalo and Kovacs, 2011) teach that amyloid-β protein precursor (AβPP) is a substrate for presenilin (PS)-dependent γ-secretase (PS/γ-secretase), and that at least 90 additional proteins have been found to undergo similar proteolysis by this enzyme complex. γ-secretase substrates have some common features: most substrate proteins are type-I transmembrane proteins; the PS/γ-secretase-mediated γ-like cleavage (corresponding to the &- cleavage in AβPP, which releases AICD) takes place at or near the boundary of the transmembrane and cytoplasmic domains. The &-like cleavage site flanks a stretch of hydrophobic amino acid sequence rich in lysine and/or arginine residues. It appears that PS/γ-secretase cleavage is not dependent on a specific amino acid target sequence at or adjacent to the cleavage site, but rather perhaps on the conformational state of the transmembrane domain. Haapasalo and Kovacs disclose in Table 1 a list of γ-secretase substrates, the cleavage sequences of which are hereby incorporated by reference as if fully disclosed herein, and which may serve as a substrate for γ-secretases in the pCAR of the present invention.

Voss et al. (Voss et al., 2013) teach that so far no consensus cleavage site based on primary sequence elements within the substrate has been described for GxGD aspartyl proteases (spps). Transmembrane domains of membrane proteins preferentially adopt an α-helical confirmation in which their peptide bonds are hardly accessible to proteases. In order to make transmembrane domains susceptible for intramembrane proteolysis it was therefore postulated that their α-helical content needs to be reduced by helix destabilizing amino acids. Consistent with this hypothesis, various signal peptides have been shown to contain helix destabilizing amino acids within their h-region which critically influence their proteolytic processing by SPP. In addition, polar residues within the h-region of signal peptides may influence cleavage by SPP, as for instance serine and cysteine residues within the signal peptide of various HCV strains are critical for SPP cleavage. Whether these polar residues also simply affect the helical content of the signal peptides or the hydroxyl or sulfhydryl group in particular is required to trigger cleavage by SPP is not yet fully understood. Similarly, cleavage of the Bri2 transmembrane domain by SPPL2b is significantly increased when the α-helical content of the Bri2 transmembrane domain is reduced. Interestingly, only one amino acid residue out of four residues with a putative helix destabilizing potency significantly reduced the α-helical content of the Bri2 transmembrane domain in a phospholipid-based environment. This suggests that destabilization of an α-helical transmembrane domain is not simply caused by certain amino acid residues but that rather context and position of these amino acids determine their helix destabilizing potential and thus the accessibility of transmembrane domains to intramembrane proteolysis by SPP/SPPLs. Voss et al. further disclose in Table 1 a list of spp and spp-like substrates, the cleavage sequences of which are hereby incorporated by reference as if fully disclosed herein, and which may serve as a substrate for spp in the pCAR of the present invention.

Bergbold et al. (Bergbold and Lemberg, 2013) teach that for rhomboid proteases, two different models for substrate recognition have been suggested. In the first model, the conformational flexibility of the substrate peptide backbone combined with immersion of the membrane in the vicinity of the rhomboid active site is sufficient to provide specificity. For the well-characterized *Drosophila* substrate Spitz, a glycine-alanine motif has been shown to serve as a helix break that allows unfolding of the transmembrane domain into the rhomboid active site. The second model suggests that rhomboid proteases primarily recognize a specific sequence surrounding the cleavage site, and that transmembrane helix-destabilizing residues are a secondary feature required for some substrates only. The specific sequence has not yet been identified. Bergbold et al. disclose in Table 3 a list of rhomboid protease substrates, the cleavage sequences of which are hereby incorporated by reference as if fully disclosed herein, and which may serve as a substrate for rhomboid proteases in the pCAR of the present invention.

In view of the above, since in most cases no consensus motif has yet been established for the intramembrane-cleaving proteases, and since assays for identifying intramembrane-cleaving protease substrates are well known in the art as described in literature cited herein above, the pCAR may comprise an amino acid sequence identified as such and may further comprise transmembrane helix-destabilizing residues.

In some embodiments, the substrate forms part of the transmembrane canonic motif and is homologous to/derived from a transmembrane domain of Notch, ErbB4, E-cadherin, N-cadherin, ephrin-B2, amyloid precursor protein or CD44.

In some embodiments, the comprises a nucleotide sequence encoding an extracellular domain and an intracellular domain of said conditional aCAR as separate proteins, wherein each domain is independently fused to a transmembrane canonic motif and comprises a different member of a binding site for a heterodimerizing small molecule.

In some embodiments, the each one of the first and second member of the binding site for a heterodimerizing small molecule is derived from a protein selected from: (i) Tacrolimus (FK506) binding protein (FKBP) and FKBP; (ii) FKBP and calcineurin catalytic subunit A (CnA); (iii) FKBP and cyclophilin; (iv) FKBP and FKBP-rapamycin associated protein (FRB); (v) gyrase B (GyrB) and GyrB; (vi) dihydrofolate reductase (DHFR) and DHFR; (vii) DmrB homodimerization domain (DmrB) and DmrB; (viii) a PYL protein (a.k.a. abscisic acid receptor and as RCAR) and ABI; and (ix) GAI *Arabidopsis thaliana* protein (a.k.a Gibberellic Acid Insensitive and DELLA protein GAI; GAI) and GID1 *Arabidopsis thaliana* protein (also known as Gibberellin receptor GID1; GID1).

v. Construction of Effector Cells

In still another aspect, the present invention provides a method for preparing a safe effector immune cell comprising: (i) transfecting a TCR-engineered effector immune cell directed to a tumor-associated antigen with a nucleic acid molecule comprising a nucleotide sequence encoding an iCAR or pCAR as defined herein above or transducing the cells with a vector or (ii) transfecting a naïve effector immune cell with a nucleic acid molecule comprising a nucleotide sequence encoding an iCAR or pCAR as defined herein above and a nucleic acid molecule comprising a nucleotide sequence encoding an aCAR as defined herein above; or transducing an effector immune cell with a vector as defined herein above.

In some embodiments, the immune cell for use in engineering includes but is not limited to a T-cell, a natural killer cell, or a cytokine-induced killer cell. In some embodiments, the immune cell for use in engineering includes but is not limited to a Jurkat T-cell, a Jurkat-NFAT T-cell, and/or a peripheral blood mononuclear cell (PB MC).

In yet another aspect, the present invention provides a safe effector immune cell obtained by the method of the present invention as described above. The safe effector immune cell may be a redirected T cell expressing an exogenous T cell receptor (TCR) and an iCAR or pCAR, wherein the exogenous TCR is directed to a non-polymorphic cell surface epitope of an antigen or a single allelic variant of a polymorphic cell surface epitope, wherein said epitope is a tumor-associated antigen or is shared at least by cells of related tumor and normal tissue, and the iCAR or pCAR is as defined above; or the safe effector immune cell is a redirected effector immune cell such as a natural killer cell or a T cell expressing an iCAR or pCAR and an aCAR as defined above.

In some embodiments, the safe effector immune cell, expresses on its surface an aCAR comprising an extracellular domain that specifically binds to a non-polymorphic cell surface epitope of an antigen and an iCAR or pCAR comprising an extracellular domain that specifically binds a single allelic variant of a polymorphic cell surface epitope of a different antigen to which the extracellular domain of said aCAR binds. In some embodiments, the extracellular domain of the iCAR or pCAR specifically hinds a single allelic variant of a different polymorphic cell surface epitope are of the same antigen to which the extracellular domain of said aCAR binds; or the extracellular domain of the iCAR or pCAR specifically binds a different single allelic variant of the same polymorphic cell surface epitope area to which the extracellular domain of said aCAR binds.

In some embodiments, the extracellular domain of the aCAR expressed on the cell surface specifically binds to a non-polymorphic cell surface epitope selected from the antigens listed in Table 1, such as CD19. In some embodiments, the target is any target with an extracellular domain.

In some embodiments, the extracellular domain of the iCAR and or pCAR expressed on the cell surface is directed against or specifically binds to a single allelic variant of an HLA-A, HLA-B, HLA-C, HLA-G, HLA-E, HLA-F, HLA-K, HLA-L, HLA-DM, HLA-DO, HLA-DP, HLA_DQ, or HLA-DR gene or against a single allelic variant of a gene listed Table 8.

In some embodiments, the extracellular domain of the iCAR and/or pCAR expressed on the cell surface is directed against or specifically binds to a single allelic variant of an HLA-A gene, HLA-B gene or HLA-C gene or against a single allelic variant of a gene listed Table 8; and the extracellular domain of the aCAR expressed on the cell surface is directed against or specifically binds to, a non-polymorphic cell surface epitope selected from the antigens listed in Table 1, such as, for example, but not limited to, CD19. In some embodiments, the aCAR target is any target with an extracellular domain.

In some embodiments, the aCAR and the iCAR are present on the cell surface as separate proteins.

In some embodiments, the expression level on the cell surface of the nucleotide sequence encoding the iCAR is greater than or equal to the expression level of the nucleotide sequence encoding the aCAR.

In some embodiments, the extracellular domain of the iCAR and/or pCAR expressed on the cell surface is directed against or specifically binds to a single allelic variant of an at least one extracellular polymorphic epitope.

In some embodiments, the extracellular domain of the iCAR and/or pCAR expressed on the cell surface is directed against or specifically binds to a single allelic variant of a gene selected from the group consisting of ABCA4, ADAM30, AQP10, ASTN1, C1orf101, CACNA1S, CATSPER4, CD101, CD164L2, CD1A, CD1C, CD244, CD34, CD46, CELSR2, CHRNB2, CLCA2, CLDN19, CLSTN1, CR1, CR2, CRB1, CSF3R, CSMD2, ECE1, ELTD1, EMC1, EPHA10, EPHA2, EPHA8, ERMAP, FCAMR, FCER1A, FCGR1B, FCGR2A, FCGR2B, FCGR3A, FCRL1, FCRL3, FCRL4, FCRL5, FCRL6, GJB4, GPA33, GPR157, GPR37L1, GPR88, HCRTR1, IGSF3, IGSF9, IL22RA1, IL23R, ITGA10, KIAA1324, KIAA2013, LDLRAD2, LEPR, LGR6, LRIG2, LRP8, LRRC52, LRRC8B, LRRN2, LY9, MIA3, MR1, MUC1, MXRA8, NCSTN, NFASC, NOTCH2, NPR1, NTRK1, OPN3, OR10J1, OR10J4, OR10K1, OR1OR2, OR10T2, OR10X1, OR11L1, OR14A16, OR14I1, OR14K1, OR2AK2, OR2C3, OR2G2, OR2G3, OR2L2, OR2M7, OR2T12, OR2T27, OR2T1, OR2T3, OR2T29, OR2T33, OR2T34, OR2T35, OR2T3, OR2T4, OR2T5, OR2T6, OR2T7, OR2T8, OR2W3, OR6F1, OR6K2, OR6K3, OR6K6, OR6N1, OR6P1, OR6Y1, PDPN, PEAR1, PIGR, PLXNA2, PTCH2, PTCHD2, PTGFRN, PTPRC, PTPRF, PTGFRN, PVRL4, RHBG, RXFP4, S1PR1, SCNN1D, SDC3, SELE, SELL, SELP, SEMA4A, SEMA6C, SLAMF7, SLAMF9, SLC2A7, SLC5A9, TACSTD2, TAS1R2, TIE1, TLR5, TMEM81, TNFRSF14, TNFRSF1B, TRABD2B, USH2A, VCAM1, and ZP4.

In some embodiments, the extracellular domain of the iCAR and/or pCAR expressed on the cell surface is directed against or specifically binds to a single allelic variant of a gene selected from the group consisting of ABCG5, ALK, ASPRV1, ATRAID, CD207, CD8B, CHRNG, CLEC4F, CNTNAP5, CRIM1, CXCR1, DNER, DPP10, EDAR, EPCAM, GPR113, GPR148, GPR35, GPR39, GYPC, IL1RL1, ITGA4, ITGA6, ITGAV, LCT, LHCGR, LRP1B, LRP2, LY75, MARCO, MERTK, NRP2, OR6B2, PLA2R1, PLB1, PROKR1, PROM2, SCN7A, SDC1, SLC23A3, SLC5A6, TGOLN2, THSD7B, TM4SF20, TMEFF2, TMEM178A, TPO, and TRABD2A.

In some embodiments, the extracellular domain of the iCAR and/or pCAR expressed on the cell surface is directed against or specifically binds to a single allelic variant of a gene selected from the group consisting of ACKR2, ALCAM, ANO10, ATP13A4, BTLA, CACNA1D, CACNA2D2, CACNA2D3, CASR, CCRL2, CD200, CD200R1, CD86, CD96, CDCP1, CDHR4, CELSR3, CRL1, CLDN11, CLDN18, CLSTN2, CSPG5, CX3CR1, CXCR6, CYP8B1, DCBLD2, DRD3, EPHA6, EPHB3, GABRR3, GP5, GPR128, GPR15, GPR27, GRM2, GRM7, HEG1, HTR3C, HTR3D, HTR3E, IGSF11, IL17RC, IL17RD, IL17RE, IL5RA, IMPG2, ITGA9, ITGB5, KCNMB3, LRIG1, LRRC15, LRRN1, MST1R, NAALADL2, NRROS, OR5AC1, OR5H1, OR5H14, OR5H15, OR5H6, OR5K2, OR5K3, OR5K4, PIGX, PLXNB1, PLXND1, PRRT3, PTPRG, ROBO2, RYK, SEMA5B, SIDT1, SLC22A14, SLC33A1, SLC4A7, SLITRK3, STAB1, SUSD5, TFRC, TLR9, TMEM108, TMEM44, TMPRSS7, TNFSF10, UPK1B, VIPR1, and ZPLD1.

In some embodiments, the extracellular domain of the iCAR and/or pCAR expressed on the cell surface is directed against or specifically binds to a single allelic variant of a gene selected from the group consisting of ANTXR2, BTC, CNGA1, CORIN, EGF, EMCN, ENPEP, EPHA5, ERVMER34-1, EVC2, FAT1, FAT4, FGFRL1, FRAS1, GPR125, GRID2, GYPA, GYPB, KDR, KIAA0922, KLB, MFSD8, PARM1, PDGFRA, RNF150, TENM3, TLR10, TLR1, TLR6, TMEM156, TMPRSS11A, TMPRSS11B, TMPRSS11E, TMPRSS11F, UGT2A1, and UNC5C.

In some embodiments, the extracellular domain of the iCAR and/or pCAR expressed on the cell surface is directed against or specifically binds to a single allelic variant of a gene selected from the group consisting of ADAM19, ADRB2, BTNL3, BTNL8, BTNL9, C5orf15, CATSPER3, CD180, CDH12, CDHR2, COL23A1, CSF1R, F2RL2, FAM174A, FAT2, FGFR4, FLT4, GABRA6, GABRG2, GPR151, GPR98, GRM6, HAVCR1, HAVCR2, IL31RA, IL6ST, IL7R, IQGAP2, ITGAL ITGA2, KCNMB1, LIFR, LNPEP, MEGF10, NIPAL4, NPR3, NRG2, OR2V1, OR2Y1, OSMR, PCDH12, PCDH1, PCDHA1, PCDHA2, PCDHA4, PCDHA8, PCDHA9, PCDHB10, PCDHB11, PCDHB13, PCDHB14, PCDHB15, PCDHB16, PCDHB2, PCDHB3, PCDHB4, PCDHB5, PCDHB6, PCDHGA1, PCDHGA4, PDGFRB, PRLR, SEMA5A, SEMA6A, SGCD, SLC1A3. SLC22A4, SLC22A5, SLC23A1 SLC36A3, SLC45A2, SLC6A18, SLC6A19, SLCO6A1, SV2C, TENM2, TIMD4, and UGT3A1.

In some embodiments, the extracellular domain of the iCAR and/or pCAR expressed on the cell surface is directed against or specifically binds to a single allelic variant of a gene selected from the group consisting of BAI3, BTN1A 1, BTN2A1, BTN2A2, BTN3A1, BTN3A2, BTNL2, CD83, DCBLD1, DLL1, DPCR1, ENPP1, ENPP3, ENPP4, EPHA7, GABBR1, GABRR1, GCNT6, GFRAL, GJB7, GLP1R, GPR110, GPR111, GPR116, GPR126, GPR63, GPRC6A, HFE, HLA-A, HLA-B, HLA-C, HLA-DOA, HLA-DPA1, HLA-DPB1, HLA-DQA1, HLA-DQA2, HLA-DQB1, HLA-DQB2, HLA-DRB1, HLA-DRB5, HLA-E, HLA-F, HLA-G, IL20RA, ITPR3, KIAA0319, LMBRD1, LRFN2, LRP11, MAS1L, MEP1A, MICA, MICB, MOG, MUC21, MUC22, NCR2, NOTCH4, OPRM1, OR10C1, OR12D2, OR12D3, OR14J1, OR2B2, OR2B6, OR2J1, OR2W1, OR5V1, PDE10A, PI16, PKHD1, PTCRA, PTK7, RAET1E, RAET1G, ROS1, SDIM1, SLC16A10, SLC22A1, SLC44A4, TAAR2, TREM1, TREML1, and TREML2.

In some embodiments, the extracellular domain of the iCAR and/or pCAR expressed on the cell surface is directed against or specifically binds to a single allelic variant of a gene selected from the group consisting of AQP1, C7orf50, CD36, CDHR3, CNTNAP2, DPP6, EGFR, EPHA1, EPHB6, ERVW-1, GHRHR, GJC3, GPNMB, GRM8, HUS1, HYAL4, KIAA1324L, LRRN3, MET, MUC12, MUC17, NPC1L1, NPSR1, OR2A12, OR2A14, OR2A25, OR2A42, OR2A7, OR2A2, OR2AE1, OR2F2, OR6V1, PILRA, PILRB, PKD1L1, PLXNA4, PODXL, PTPRN2, PTPRZ1, RAMP3, SLC29A4, SMO, TAS2R16, TAS2R40, TAS2R4, TFR2, THSD7A, TMEM213, TTYH3, ZAN, and ZP3.

In some embodiments, the extracellular domain of the iCAR and/or pCAR expressed on the cell surface is directed against or specifically binds to a single allelic variant of a gene selected from the group consisting of ADAM18, ADAM28, ADAM32, ADAM7, ADAM9, ADRA1A, CDH17, CHRNA2, CSMD1, CSMD3, DCSTAMP, FZD6, GPR124, NRG1, OR4F21, PKHD1L1, PRSS55, SCARA3, SCARA5, SDC2, SLC10A5, SLC39A14, SLC39A4, SLCO5A1, TNFRSF10A, and TNFRSF10B.

In some embodiments, the extracellular domain of the iCAR and/or pCAR expressed on the cell surface is directed against or specifically binds to a single allelic variant of a gene selected from the group consisting of ABCA1, AQP7, ASTN2, C9orf135, CA9, CD72, CNTNAP3B, CNTNAP3, CRB2, ENTPD8, GPR144, GRIN3A, IZUMO3, KIAA1161, MAMDC4, MEGF9, MUSK, NOTCH1, OR13C2, OR13C3, OR13C5, OR13C8, OR13C9, OR13D1, OR13F1, OR1B1, OR1J2, OR1K1, OR1L1, OR1L3, OR1L6, OR1L8, OR1N1, OR1N2, OR1Q1, OR2S2, PCSK5, PDCD1LG2, PLGRKT, PTPRD, ROR2, SEMA4D, SLC31A1, TEK, TLR4, TMEM2, and VLDLR.

In some embodiments, the extracellular domain of the iCAR and/or pCAR expressed on the cell surface is directed against or specifically binds to a single allelic variant of a gene selected from the group consisting of ABCC2, ADAMS, ADRB1, ANTXRL, ATRNL1, C10orf54, CDH23, CDHR1, CNNM2, COL13A1, COL17A1, ENTPD1, FZD8, FGFR2, GPR158, GRID1, IL15RA, IL2RA, ITGA8, ITGB1, MRC1, NRG3, NPFFR1, NRP1, OPN4, PCDH15, PKD2L1, PLXDC2, PRLHR, RET, RGR, SLC16A9, SLC29A3, SLC39A12, TACR2, TCTN3, TSPAN15, UNC5B, and VSTM4.

In some embodiments, the extracellular domain of the iCAR and/or pCAR expressed on the cell surface is directed against or specifically binds to a single allelic variant of a gene selected from the group consisting of AMICA1, ANO1, ANO3, APLP2, C11orf24, CCKBR, CD248, CD44, CD5, CD6, CD82, CDON, CLMP, CRTAM, DCHS1, DSCAML1, FAT3, FOLH1, GDPD4, GDPD5, GRIK4, HEPHL1, HTR3B, IFITM10, IL10RA, KIRREL3, LGR4, LRP4, LRP5, LRRC32, MCAM, MFRP, MMP26, MPEG1, MRGPRE, MRGPRF, MRGPRX2, MRGPRX3, MRGPRX4, MS4A4A, MS4A6A, MTNR1B, MUC15, NAALAD2, NAALADL1, NCAM1, NRXN2, OR10A2, OR10A5, OR10A6, OR10D3, OR10G4, OR10G7, OR10G8, OR10G9, OR10Q1, OR10S1, OR1S1, OR2AG1, OR2AG2, OR2D2, OR4A47, OR4A15, OR4A5, OR4C11, OR4C13, OR4C15, OR4C16, OR4C3, OR4C46, OR4C5, OR4D6, OR4A8P, OR4D9, OR4S2, OR4X1, OR51E1, OR51L1, OR52A1, OR52E1, OR52E2, OR52E4, OR52E6, OR52I1, OR52I2, OR52J3, OR52L1, OR52N1, OR52N2, OR52N4, OR52W1, OR56B1, OR56B4, OR5A1, OR5A2, OR5AK2, OR5AR1, OR5B17, OR5B3, OR5D14, OR5D16, OR5D18, OR5F1, OR5I1, OR5L2, OR5M11, OR5M3, OR5P2, OR5R1, OR5T2, OR5T3, OR5W2, OR6A2, OR6T1, OR6X1, OR8A1, OR8B12, OR8B2, OR8B3, OR8B4, OR8D1, OR8D2, OR8H1, OR8H2, OR8H3, OR8I2, OR8J1, OR8J2, OR8J3, OR8K1, OR8K3, OR8K5, OR8U1, OR9G1, OR9G4, OR9Q2, P2RX3, PTPRJ, ROBO3, SIGIRR, SLC22A10, SLC3A2, SLC5A12, SLCO2B1, SORL1, ST14, SYT8, TENM4, TMEM123, TMEM225, TMPRSS4, TMPRSS5, TRIM5, TRPM5, TSPAN18, and ZP1.

In some embodiments, the extracellular domain of the iCAR and/or pCAR expressed on the cell surface is directed against or specifically binds to a single allelic variant of a gene selected from the group consisting of ANO4, AVPR1A, BCL2L14, CACNA2D4, CD163, CD163L1, CD27, CD4, CLEC12A, CLEC1B, CLEC2A, CLEC4C, CLEC7A, CLECL1, CLSTN3, GPR133, GPRC5D, ITGA7, ITGB7, KLRB1, KLRC2, KLRC3, KLRC4, KLRF1, KLRF2, LRP1, LRP6, MANSC1, MANSC4, OLR1, OR10AD1, OR10P1, OR2AP1, OR6C1, OR6C2, OR6C3, OR6C4, OR6C6, OR6C74, OR6C76, OR8S1, OR9K2, ORAI1, P2RX4, P2RX7, PRR4, PTPRB, PTPRQ, PTPRR, SCNN1A, SELPLG, SLC2A14, SLC38A4, SLC5A8, SLC6A15, SLC8B1, SLCO1A2, SLCO1B1, SLCO1B7, SLCO1C1, SSPN, STAB2, TAS2R10, TAS2R13, TAS2R14, TAS2R20, TAS2R30, TAS2R31, TAS2R42, TAS2R43, TAS2R46, TAS2R7, TMEM119, TMEM132B, TMEM132C, TMEM132D, TMPRSS12, TNFRSF1A, TSPAN8, and VS1G10.

In some embodiments, the extracellular domain of the iCAR and/or pCAR expressed on the cell surface is directed against or specifically binds to a single allelic variant of a gene selected from the group consisting of ATP4B, ATP7B, FLT3, FREM2, HTR2A, KL, PCDH8, RXFP2, SGCG, SHISA2, SLC15A1, SLITRK6, and TNFRSF19.

In some embodiments, the recognition moiety for use in the aCAR, iCAR and/or pCAR provides specifity to at least one extracellular polymorphic epitope in a gene product from a gene selected from the group consisting of ADAM21, BDKRB2, C14orf37, CLEC14A, DLK1, FLRT2, GPR135, GPR137C, JAG2, LTB4R2, MMP14, OR11G2, OR11H12, OR11H6, OR4K1, OR4K15, OR4K5, OR4L1, OR4N2, OR4N5, SLC24A4, and SYNDIG1L.

In some embodiments, the extracellular domain of the iCAR and/or pCAR expressed on the cell surface is directed against or specifically binds to a single allelic variant of a gene selected from the group consisting of ANPEP, CD276, CHRNA7, CHRNB4, CSPG4, DUOX1, DUOX2, FAM174B, GLDN, IGDCC4, ITGA11, LCTL, LTK, LYSMD4, MEGF11, NOX5, NRG4, OCA2, OR4F4, OR4M2, OR4N4, PRTG, RHCG, SCAMP5, SEMA4B, SEMA6D, SLC24A1, SLC24A5, SLC28A1, SPG11, STRA6, TRPM1, and TYRO3.

In some embodiments, the extracellular domain of the iCAR and/or pCAR expressed on the cell surface is directed against or specifically binds to a single allelic variant of a gene selected from the group consisting of ATP2C2, CACNA1H, CD19, CDH11, CDH15, CDH16, CDH3, CDH5, CNGB1, CNTNAP4, GDPD3, GPR56, GPR97, IFT140, IL4R, ITFG3, ITGAL, ITGAM, ITGAX, KCNG4, MMP15, MSLNL, NOMO1, NOMO3, OR2C1, PIEZO1, PKD1, PKD1L2, QPRT, SCNN1B, SEZ6L2, SLC22A31, SLC5A11, SLC7A6, SPN, TMC5, TMC7, TMEM204, TMEM219, and TMEM8A.

In some embodiments, the extracellular domain of the iCAR and/or pCAR expressed on the cell surface is directed against or specifically binds to a single allelic variant of a gene selected from the group consisting of ABCC3, ACE, AOC3, ARL17B, ASGR2, C17orf80, CD300A, CD300C, CD300E, CD300LF, CD300LG, CHRNB1, CLEC10A, CNTNAP1, CPD, CXCL16, ERBB2, FAM171A2, GCGR, GLP2R, GP1BA, GPR142, GUCY2D, ITGA2B, ITGA3, ITGAE, ITGB3, KCNJ12, LRRC37A2, LRRC37A3, LRRC37A, LRRC37B, MRC2, NGFR, OR1A2, OR1D2, OR1G1, OR3A1, OR3A2, OR4D1, OR4D2, RNF43, SCARF1, SCN4A, SDK2, SECTM1, SEZ6, SHPK, SLC26A11, SLC5A10, SPACA3, TMEM102, TMEM132E, TNFSF12, TRPV3, TTYH2, and TUSC5.

In some embodiments, the extracellular domain of the iCAR and/or pCAR expressed on the cell surface is directed against or specifically binds to a single allelic variant of a gene selected from the group consisting of APCDD1, CDH19, CDH20, CDH7, COLEC12, DCC, DSC1, DSG1, DSG3, DYNAP, MEP1B, PTPRM, SIGLEC15, and TNFRSF11A.

In some embodiments, the extracellular domain of the iCAR and/or pCAR expressed on the cell surface is directed against or specifically binds to a single allelic variant of a gene selected from the group consisting of ABCA7, ACPT, BCAM, C19orf38, C19orf59, C5AR1, CATSPERD, CATSPERG, CD22, CD320, CD33, CD97, CEACAM19, CEACAM1, CEACAM21, CEACAM3, CEACAM4, CLEC4M, DLL3, EMR1, EMR2, EMR3, ERVV-1, ERVV-2, FAM187B, FCAR, FFAR3, FPR1, FXYD5, GFY, GP6, GPR42, GRIN3B, ICAM3, IGFLR1, IL12RB1, IL27RA, KIR2DL1, KIR2DL3, KIR2DL4, KIR3DL1, KIR3DL2, KIR3DL3, KIRREL2, KISS1R, LAIR1, LDLR, LILRA1, LILRA2, LILRA4, LILRA6, LILRB1, LILRB2, LILRB3, LILRB4, LILRB5, LINGO3, LPHN1, LRP3, MADCAM1, MAG, MEGF8, MUC16, NCR1, NOTCH3, NPHS1, OR10HL OR10H2, OR10H3, OR10H4, OR1I1, OR2Z1, OR7A10, OR7C1, OR7D4, OR7E24, OR7G1, OR7G2, OR7G3, PLVAP, PTGIR, PTPRH, PTPRS, PVR, SCN1B, SHISA7, SIGLEC10, SIGLEC11, SIGLEC12, SIGLEC5, SIGLEC6, SIGLEC8, SIGLEC9, SLC44A2, SLC5A5, SLC7A9, SPINT2, TARM1, TGFBR3L, TMC4, TMEM91, TMEM161A, TMPRSS9, TNFSF14, TNFSF9, TRPM4, VN1R2, VSIG10L, VSTM2B, and ZNRF4.

In some embodiments, the extracellular domain of the iCAR and/or pCAR expressed on the cell surface is directed against or specifically binds to a single allelic variant of a gene selected from the group consisting of ABHD12, ADAM33, ADRA1D, APMAP, ATRN, CD40, CD93, CDH22, CDH26, CDH4, FLRT3, GCNT7, GGT7, JAG1, LRRN4, NPBWR2, OCSTAMP, PTPRA, PTPRT, SEL1L2, SIGLEC1, SIRPA, SIRPB1, SIRPG, SLC24A3, SLC2A10, SLC4A11, SSTR4, and THBD.

In some embodiments, the extracellular domain of the iCAR and/or pCAR expressed on the cell surface is directed against or specifically binds to a single allelic variant of a gene selected from the group consisting of CLDN8, DSCAM, ICOSLG, IFNAR1, IFNGR2, IGSF5, ITGB2, KCNJ15, NCAM2, SLC19A1, TMPRSS15, TMPRSS2, TMPRSS3, TRPM2, and UMODL1.

In some embodiments, the extracellular domain of the iCAR and/or pCAR expressed on the cell surface is directed against or specifically binds to a single allelic variant of a gene selected from the group consisting of CACNA1I, CELSR1, COMT, CSF2RB, GGT1, GGT5, IL2RB, KREMEN1, MCHR1, OR11H1, P2RX6, PKDREJ, PLXNB2, SCARF2, SEZ6L. SSTR3, SUSD2, TMPRSS6, and TNFRSF13C.

In some embodiments, the extracellular domain of the iCAR and/or pCAR expressed on the cell surface is directed against or specifically binds to a single allelic variant of a gene selected from the group consisting of ATP6AP2, ATP7A, CNGA2, EDA2R, FMR1NB, GLRA4, GPR112, GUCY2F, HEPH, P2RY10, P2RY4, PLXNA3, PLXNB3, TLR8, VSIG4, and XG.

In some embodiments, the extracellular domain of the iCAR and/or pCAR expressed on the cell surface is directed against or specifically binds to a single allelic variant of HLA-A2. In some embodiments, the extracellular domain of the iCAR and/or pCAR expressed on the cell surface is directed against or specifically binds to a single allelic variant of CD20. In some embodiments, the iCAR will be directed toward HLA-A2. In some embodiments, the iCAR will be directed toward CD20. In some embodiments, the aCAR with be directed toward CD19. In some embodiments, the iCAR/aCAR set will be HLA-A2 and CD19 respectively. In some embodiments, the iCAR/aCAR set will include CD20 and CD19 respectively.

vi. Preparation of Target Cells

In some embodiments, the target cells are prepared and tested in an in vitro system. In some embodiments, an in vitro recombinant system will be established for testing the functionality of the iCAR and/or pCAR constructs in inhibiting the activity of the aCAR towards the off-target cells. In some embodiments, target cells expressing the aCAR epitope, iCAR epitope or both will be produced. In some embodiments, target cells expressing the aCAR epitope, pCAR epitope or both will be produced. In some embodiments, the recombinant cells expressing the aCAR epitope will represent the on-target 'on-tumor' cells while the cells expressing both aCAR and iCAR epitopes would represent the on target 'off-tumor' healthy cells.

In some embodiments, the iCAR/aCAR set will be HLA-A2 and CD19 respectively, recombinant cells expressing HLA-A2, CD19 or both will be produced by transfecting cell line (e.g., Hela, Hela-Luciferase or Raji) with expression vector coding for these genes. For detection of recombinant CD19 and HLA-A2 expression, both genes will be fused to a protein tag (e.g., HA or Flag or Myc etc). In some embodiments, the iCAR/aCAR target set will be CD20/CD19 and the recombinant cells will express CD19, CD20 or both.

In some embodiments, the expression vector comprising the iCAR/aCAR target set is transfected into a cell. In some embodiments, the expression vector is transfected into a cell to produce the target and off-tumor effects.

In some embodiments, the expression vector codes for a gene selected from the group consisting of ABCA4, ADAM30, AQP10, ASTN1, C1orf101, CACNA1S, CATSPER4, CD101, CD164L2, CD1A, CD1C, CD244, CD34, CD46, CELSR2, CHRNB2, CLCA2, CLDN19, CLSTN1, CR1, CR2, CRB1, CSF3R, CSMD2, ECE1, ELTD1, EMC1, EPHA10, EPHA2, EPHA8, ERMAP, FCAMR, FCER1A, FCGR1B, FCGR2A, FCGR2B, FCGR3A, FCRL1, FCRL3, FCRL4, FCRL5, FCRL6, GJB4, GPA33, GPR157, GPR37L1, GPR88, HCRTR1, IGSF3, IGSF9, IL22RA1, IL23R, ITGA10, KIAA1324, KIAA2013, LDLRAD2, LEPR, LGR6, LRIG2, LRP8, LRRC52, LRRC8B, LRRN2, LY9, MIA3, MR1, MUC1, MXRA8, NCSTN, NFASC, NOTCH2, NPR1, NTRK1, OPN3, OR10J1, OR10J4, OR10K1, OR10R2, OR10T2, OR10X1, OR11L1, OR14A16, OR14I1, OR14K1, OR2AK2, OR2C3, OR2G2, OR2G3, OR2L2, OR2M7, OR2T12, OR2T27, OR2T1, OR2T3, OR2T29, OR2T33, OR2T34, OR2T35, OR2T3, OR2T4, OR2T5, OR2T6, OR2T7, OR2T8, OR2W3, OR6F1, OR6K2, OR6K3, OR6K6, OR6N1, OR6P1, OR6Y1, PDPN, PEAR1, PIGR, PLXNA2, PTCH2, PTCHD2, PTGFRN, PTPRC, PTPRF, PTGFRN, PVRL4, RHBG, RXFP4, S1PR1, SCNN1D, SDC3, SELE, SELL, SELP, SEMA4A, SEMA6C, SLAMF7, SLAMF9, SLC2A7, SLC5A9, TACSTD2, TAS1R2, TIE1, TLR5, TMEM81, TNFRSF14, TNFRSF1B, TRABD2B, USH2A, VCAM1, and ZP4.

In some embodiments, the expression vector codes for a gene selected from the group consisting of ABCG5, ALK, ASPRV1, ATRAID, CD207, CD8B, CHRNG, CLEC4F, CNTNAP5, CRIM1, CXCR1, DNER, DPP10, EDAR, EPCAM, GPR113, GPR148, GPR35, GPR39, GYPC, IL1RL1, ITGA4, ITGA6, ITGAV, LCT, LHCGR, LRP1B, LRP2, LY75, MARCO, MERTK, NRP2, OR6B2, PLA2R1, PLB1, PROKR1, PROM2, SCN7A, SDC1, SLC23A3, SLC5A6, TGOLN2, THSD7B, TM4SF20, TMEFF2, TMEM178A, TPO, and TRABD2AD2A.

In some embodiments, the expression vector codes for a gene selected from the group consisting of ACKR2, ALCAM, ANO10, ATP13A4, BTLA, CACNA1D, CACNA2D2, CACNA2D3, CASR, CCRL2, CD200, CD200R1, CD86, CD96, CDCP1, CDHR4, CELSR3, CHL1, CLDN11, CLDN18, CLSTN2, CSPG5, CX3CR1, CXCR6, CYP8B1, DCBLD2, DRD3, EPHA6, EPHB3, GABRR3, GP5, GPR128, GPR15, GPR27, GRM2, GRM7, HEG1, HTR3C, HTR3D, HTR3E, IGSF11, IL17RC, IL17RD, IL17RE, IL5RA, IMPG2, ITGA9, ITGB5, KCNMB3, LRIG1, LRRC15, LRRN1, MST1R, NAALADL2, NRROS, OR5AC1, OR5H1, OR5H14, OR5H15, OR5H6, OR5K2, OR5K3, OR5K4, PIGX, PLXNB1, PLXND1, PRRT3, PTPRG, ROBO2, RYK, SEMA5B, SIDT1, SLC22A14, SLC33A1, SLC4A7, SLITRK3, STAB1, SUSD5, TFRC, TLR9, TMEM108, TMEM44, TMPRSS7, TNFSF10, UPK1B, VIPR1, and ZPLD1.

In some embodiments, the expression vector codes for a gene selected from the group consisting of ANTXR2, BTC, CNGA1, CORIN, EGF, EMCN, ENPEP, EPHA5, ERVMER34-1, EVC2, FAT1, FAT4, FGFRL1, FRAS1, GPR125, GRID2, GYPA, GYPB, KDR, KIAA0922, KLB, MFSD8, PARM1, PDGFRA, RNF150, TENM3, TLR10, TLR1, TLR6, TMEM156, TMPRSS11A, TMPRSS11B, TMPRSS11E, TMPRSS11F, UGT2A1, and UNC5C.

In some embodiments, the expression vector codes for a gene selected from the group consisting of ADAM19, ADRB2, BTNL3, BTNL8, BTNL9, C5orf15, CATSPER3, CD180, CDH12, CDHR2, COL23A1, CSF1R, F2RL2, FAM174A, FAT2, FGFR4, FLT4, GABRA6, GABRG2, GPR151, GPR98, GRM6, HAVCR1, HAVCR2, IL31RA, IL6ST, IL7R, IQGAP2, ITGA1, ITGA2, KCNMB1, LIFR, LNPEP, MEGF10, NIPAL4, NPR3, NRG2, OR2V1, OR2Y1, OSMR, PCDH12, PCDH1, PCDHA1, PCDHA2, PCDHA4, PCDHA8, PCDHA9, PCDHB10, PCDHB11, PCDHB13, PCDHB14, PCDHB15, PCDHB16, PCDHB2, PCDHB3, PCDHB4, PCDHB5, PCDHB6, PCDHGA1, PCDHGA4, PDGFRB, PRLR, SEMA5A, SEMA6A, SGCD, SLC1A3, SLC22A4, SLC22A5, SLC23A1, SLC36A3, SLC45A2, SLC6A18, SLC6A19, SLCO6A1, SV2C, TENM2, TIMD4, and UGT3A1.

In some embodiments, the expression vector codes for a gene selected from the group consisting of BAI3, BTN1A1, BTN2A1, BTN2A2, BTN3A1, BTN3A2, BTNL2, CD83, DCBLD1, DLL1, DPCR1, ENPP1, ENPP3, ENPP4, EPHA7, GABBR1, GABRR1, GCNT6, GFRAL, GJB7, GLP1R, GPR110, GPR111, GPR116, GPR126, GPR63, GPRC6A, HFE, HLA-A, HLA-B, HLA-C, HLA-DOA, HLA-DPA1, HLA-DPB1, HLA-DQA1, HLA-DQA2, HLA-DQB1, HLA-DQB2, HLA-DRB1, HLA-DRB5, HLA-E, HLA-F, HLA-G, IL20RA, ITPR3, KIAA0319, LMBRD1, LRFN2, LRP11, MAS1L, MEP1A, MICA, MICB, MOG, MUC21, MUC22, NCR2, NOTCH4, OPRM1, OR10C1, OR12D2, OR12D3, OR14J1, OR2B2, OR2B6, OR2J1, OR2W1, OR5V1, PDE10A, PI16, PKHD1, PTCRA, PTK7, RAET1E, RAET1G, ROS1, SDIM1, SLC16A10, SLC22A1, SLC44A4, TAAR2, TREM1, TREML1, and TREML2.

In some embodiments, the expression vector codes for a gene selected from the group consisting of AQP1, C7orf50, CD36, CDHR3, CNTNAP2, DPP6, EGFR, EPHA1, EPHB6, ERVW-1, GHRHR, GJC3, GPNMB, GRM8, HUS1, HYAL4, KIAA1324L, LRRN3, MET, MUC12, MUC17, NPC1L1, NPSR1, OR2A12, OR2A14, OR2A25, OR2A42, OR2A7, OR2A2, OR2AE1, OR2F2, OR6V1, PILRA, PILRB, PKD1L1, PLXNA4, PODXL, PTPRN2, PTPRZ1, RAMP3, SLC29A4, SMO, TAS2R16, TAS2R40, TAS2R4, TFR2, THSD7A, TMEM213, TTYH3, ZAN, and ZP3.

In some embodiments, the expression vector codes for a gene selected from the group consisting of ADAM18, ADAM28, ADAM32, ADAM7, ADAMS, ADRA1A, CDH17, CHRNA2, CSMD1, CSMD3, DCSTAMP, FZD6, GPR124, NRG1, OR4F21, PKHD1L1, PRSS55, SCARA3, SCARA5, SDC2, SLC10A5, SLC39A14, SLC39A4, SLCO5A1, TNFRSF10A, and TNFRSF10B.

In some embodiments, the expression vector codes for a gene selected from the group consisting of ABCA1, AQP7, ASTN2, C9orf135, CA9, CD72, CNTNAP3B, CNTNAP3, CRB2, ENTPD8, GPR144, GRIN3A, IZUMO3, KIAA1161, MAMDC4, MEGF9, MUSK, NOTCH1, OR13C2, OR13C3, OR13C5, OR13C8, OR13C9, OR13D1, OR13F1, OR1B1, OR1J2, OR1K1, OR1L1, OR1L3, OR1L6, OR1L8, OR1N1, OR1N2, OR1Q1, OR2S2, PCSK5, PDCD1LG2, PLGRKT, PTPRD, ROR2, SEMA4D, SLC31A1, TEK, TLR4, TMEM2, and VLDLR.

In some embodiments, the expression vector codes for a gene selected from the group consisting of ABCC2, ADAMS, ADRB1, ANTXRL, ATRNL1, C10orf54, CDH23, CDHR1, CNNM2, COL13A1, COL17A1, ENTPD1, FZD8, FGFR2, GPR158, GRID1, IL15RA, IL2RA, ITGA8, ITGB1, MRC1, NRG3, NPFFR1, NRP1, OPN4, PCDH15, PKD2L1, PLXDC2, PRLHR, RET, RGR, SLC16A9, SLC29A3, SLC39A12, TACR2, TCTN3, TSPAN15, UNC5B, and VSTM4.

In some embodiments, the expression vector codes for a gene selected from the group consisting of AMICA1, ANO1, ANO3, APLP2, C11orf24, CCKBR, CD248, CD44, CD5, CD6, CD82, CDON, CLMP, CRTAM, DCHS1, DSCAML1, FAT3, FOLH1, GDPD4, GDPD5, GRIK4, HEPHL1, HTR3B, IFITM10, IL10RA, KIRREL3, LGR4, LRP4, LRP5, LRRC32, MCAM, MFRP, MMP26, MPEG1, MRGPRE, MRGPRF, MRGPRX2, MRGPRX3, MRGPRX4, MS4A4A, MS4A6A, MTNR1B, MUC15, NAALAD2, NAALADL1, NCAM1, NRXN2, OR10A2, OR10A5, OR10A6, OR10D3, OR10G4, OR10G7, OR10G8, OR10G9, OR10Q1, OR10S1, OR1S1, OR2AG1, OR2AG2, OR2D2, OR4A47, OR4A15, OR4A5, OR4C11, OR4C13, OR4C15, OR4C16, OR4C3, OR4C46, OR4C5, OR4D6, OR4A8P, OR4D9, OR4S2, OR4X1, OR51E1, OR51L1, OR52A1, OR52E1, OR52E2, OR52E4, OR52E6, OR52I1, OR52I2, OR52I3, OR52L1, OR52N1, OR52N2, OR52N4, OR52W1, OR56B1, OR56B4, OR5A1, OR5A2, OR5AK2, OR5AR1, OR5B17, OR5B3, OR5D14, OR5D16, OR5D18, OR5F1, OR5I1, OR5L2, OR5M11, OR5M3, OR5P2, OR5R1, OR5T2, OR5T3, OR5W2, OR6A2, OR6T1, OR6X1, OR8A1, OR8B12, OR8B2, OR8B3, OR8B4, OR8D1, OR8D2, OR8H1, OR8H2, OR8H3, OR8I2, OR8J1, OR8J2, OR8J3, OR8K1, OR8K3, OR8K5, OR8U1, OR9G1, OR9G4, OR9Q2, P2RX3, PTPRJ, ROBO3, SIGIRR, SLC22A10, SLC3A2, SLC5A12, SLCO2B1, SORL1, ST14, SYT8, TENM4, TMEM123, TMEM225, TMPRSS4, TMPRSS5, TRIM5, TRPM5, TSPAN18, and ZP1.

In some embodiments, the expression vector codes for a gene selected from the group consisting of ANO4, AVPR1A, BCL2L14, CACNA2D4, CD163, CD163L1, CD27, CD4, CLEC12A, CLEC1B, CLEC2A, CLEC4C, CLEC7A, CLECL1, CLSTN3, GPR133, GPRC5D, ITGA7, ITGB7, KLRB1, KLRC2, KLRC3, KLRC4, KLRF1, KLRF2, LRP1, LRP6, MANSC1, MANSC4, OLR1, OR10AD1, OR10P1, OR2AP1, OR6C1, OR6C2, OR6C3, OR6C4, OR6C6, OR6C74, OR6C76, OR8S1, OR9K2, ORAI1, P2RX4, P2RX7, PRR4, PTPRB, PTPRQ, PTPRR, SCNN1A, SELPLG, SLC2A14, SLC38A4, SLC5A8, SLC6A15, SLC8B1, SLCO1A2, SLCO1B1, SLCO1B7, SLCO1C1, SSPN, STAB2, TAS2R10, TAS2R13, TAS2R14, TAS2R20, TAS2R30, TAS2R31, TAS2R42, TAS2R43, TAS2R46, TAS2R7, TMEM119, TMEM132B, TMEM132C, TMEM132D, TMPRSS12, TNFRSF1A, TSPAN8, and VSIG10.

In some embodiments, the expression vector codes for a gene selected from the group consisting of ATP4B, ATP7B, FLT3, FREM2, HTR2A, KL, PCDH8, RXFP2, SGCG, SHISA2, SLC15A1, SLITRK6, and TNFRSF19.

In some embodiments, the expression vector codes for a gene selected from the group consisting of ADAM21. BDKRB2, C14orf37, CLEC14A, DLK1, FLRT2, GPR135, GPR137C, JAG2, LTB4R2, MMP14, OR11G2, OR11H12, OR11H6, OR4K1, OR4K15, OR4K5, OR4L1, OR4N2, OR4N5, SLC24A4, and SYNDIG1L.

In some embodiments, the expression vector codes for a gene selected from the group consisting of ANPEP, CD276, CHRNA7, CHRNB4, CSPG4, DUOX1, DUOX2, FAM174B, GLDN, IGDCC4, ITGA11, LCTL, LTK, LYSMD4, MEGF11, NOX5, NRG4, OCA2, OR4F4, OR4M2, OR4N4, PRTG, RHCG, SCAMP5, SEMA4B, SEMA6D, SLC24A1, SLC24A5, SLC28A1, SPG11, STRA6, TRPM1, and TYRO3.

In some embodiments, the expression vector codes for a gene selected from the group consisting of ATP2C2, CACNA1H, CD19, CDH11, CDH15, CDH16, CDH3, CDH5, CNGB1, CNTNAP4, GDPD3, GPR56, GPR97, IFT140, IL4R, ITFG3, ITGAL, ITGAM, ITGAX, KCNG4, MMP15, MSLNL, NOMO1, NOMO3, OR2C1, PIEZO1, PKD1, PKD1L2, QPRT, SCNN1B, SEZ6L2, SLC22A31, SLC5A11, SLC7A6, SPN, TMC5, TMC7, TMEM204, TMEM219, and TMEM8A.

In some embodiments, the expression vector codes for a gene selected from the group consisting of ABCC3, ACE, AOC3, ARL17B, ASGR2, C17orf80, CD300A, CD300C, CD300E, CD300LF, CD300LG, CHRNB1, CLEC10A, CNTNAP1, CPD, CXCL16, ERBB2, FAM171A2, GCGR, GLP2R, GP1BA, GPR142, GUCY2D, ITGA2B, ITGA3, ITGAE, ITGB3, KCNJ12, LRRC37A2, LRRC37A3, LRRC37A, LRRC37B, MRC2, NGFR, OR1A2, OR1D2, OR1G1, OR3A1, OR3A2, OR4D1, OR4D2, RNF43, SCARF1, SCN4A, SDK2, SECTM1, SEZ6, SHPK, SLC26A11, SLC5A10, SPACA3, TMEM102, TMEM132E, TNFSF12, TRPV3, TTYH2, and TUSC5.

In some embodiments, the expression vector codes for a gene selected from the group consisting of APCDD1 CDH19, CDH20, CDH7, COLEC12, DCC, DSC1, DSG1, DSG3, DYNAP, MEP1B, PTPRM, S1GLEC15, and TNFRSF11A.

In some embodiments, the expression vector codes for a gene selected from the group consisting of ABCA7, ACPT, BCAM, C19orf38, C19orf59, C5AR1, CATSPERD, CATSPERG, CD22, CD320, CD33, CD97, CEACAM19, CEACAM1, CEACAM21, CEACAM3, CEACAM4, CLEC4M, DLL3, EMR1, EMR2, EMR3, ERVV-1, ERVV-2, FAM187B, FCAR, FFAR3, FPR1, FXYD5, GFY, GP6, GPR42, GRIN3B, ICAM3, IGFLR1, IL12RB1, IL27RA, KIR2DL1, KIR2DL3, KIR2DL4, KIR3DL1, KIR3DL2, KIR3DL3, KIRREL2, KISS1R, LAIR1, LDLR, LILRA1, LILRA2, LILRA4, LILRA6, LILRB1, LILRB2, LILRB3, LILRB4, LILRB5, LINGO3, LPHN1, LRP3, MADCAM1, MAG, MEGF8, MUC16, NCR1, NOTCH3, NPHS1, OR10H1, OR10H2, OR10H3, OR10H4, OR1I1, OR2Z1, OR7A10, OR7C1, OR7D4, OR7E24, OR7G1, OR7G2, OR7G3, PLVAP, PTGIR, PTPRH, PTPRS, PVR, SCN1B, SHISA7, SIGLEC10, SIGLEC11, SIGLEC12, SIGLEC5, SIGLEC6, SIGLEC8, SIGLEC9, SLC44A2, SLC5A5, SLC7A9, SPINT2, TARM1, TGFBR3L, TMC4, TMEM91, TMEM161A, TMPRSS9, TNFSF14, TNFSF9, TRPM4, VN1R2, VSIG10L, VSTM2B, and ZNRF4.

In some embodiments, the expression vector codes for a gene selected from the group consisting of ABHD12, ADAM33, ADRA1D, APMAP, ATRN, CD40, CD93, CDH22, CDH26, CDH4, FLRT3, GCNT7, GGT7, JAG1, LRRN4, NPBWR2, OCSTAMP, PTPRA, PTPRT, SEL1L2, SIGLEC1, SIRPA, SIRPB1, SIRPG, SLC24A3, SLC2A10, SLC4A11, SSTR4, and THBD.

In some embodiments, the expression vector codes for a gene selected from the group consisting of CLDN8. DSCAM, ICOSLG, IFNAR1, IFNGR2, IGSF5, ITGB2, KCNJ15, NCAM2, SLC19A1, TMPRSS15, TMPRSS2, TMPRSS3, TRPM2, and UMODL1.

In some embodiments, the expression vector codes for a gene selected from the group consisting of CACNA11, CELSR1, COMT, CSF2RB, GGT1, GGT5, IL2RB, KREMEN1, MCHR1, OR11H1, P2RX6, PKDREJ, PLXNB2, SCARF2, SEZ6L, SSTR3, SUSD2, TMPRSS6, and TNFRSF13C.

In some embodiments, the expression vector codes for a gene selected from the group consisting of ATP6AP2, ATP7A, CNGA2, EDA2R, FMR1NB, GLRA4, GPR112, GUCY2F, HEPH, P2RY10, P2RY4, PLXNA3, PLXNB3, TLR8, VSIG4, and XG.

In some embodiments, the safe effector immune cells used for treating cancer as defined above express on their surface an aCAR comprising an extracellular domain that specifically binds to a tumor-associated antigen or a cell surface epitope of an antigen and an iCAR comprising an extracellular domain that specifically binds a single allelic variant of a polymorphic cell surface epitope of an antigen expressed at least in a tissue of origin of the tumor, such as any of those listed above, which is a different antigen than that to which the extracellular domain of said aCAR binds. In some embodiments, the iCAR is expressed in the same tissue as the aCAR is expressed in. In some embodiments, the aCAR and iCAR are different alleles of the same gene. In some embodiments, the aCAR and iCAR are different proteins, and hence are different alleles.

A. In Vitro Assays

In some embodiments, the iCAR and/or pCAR will be tested for activity in effects, including effectiveness and ability to inhibit, using a variety of assays. In some embodiments, the inhibitory effect of the iCAR and/or pCAR will be tested in-vitro and/or in-vivo. In some embodiments, the inhibitory effect of the iCAR and/or pCAR will be tested in-vitro. In some embodiments, the inhibitory effect of the iCAR and/or pCAR will be tested in-vivo. In some embodiments, the in vitro assays measure cytokine secretion and/or cytotoxicity effects. In some embodiments, the in vivo assays will evaluate the iCAR and/or pCAR inhibition and protection to on-target off tumor xenografts. In some embodiments, the in vivo assays will evaluate the iCAR and/or pCAR inhibition and protection to on-target off tumor tissue and/or viral organs.

i. Luciferase Cytotoxicity Assay

In some embodiments, the iCAR and/or pCAR are evaluated using a luciferase cytotoxicity assay. Generally, for a luciferase cytotoxic assay, recombinant target cells (which can be referred to as "T") are engineered to express firefly luciferase. In some embodiments, commercial Hela-Luc cells can be transfected with DNA coding for the target proteins. The in vitro luciferase assay can be performed according to the Bright-Glo Luciferase assay (commercially available from Promega or BPS Biosciences or other commercial vendors). Transduced effector (E) T cells (which have been transduced with both iCAR or pCAR and aCAR or aCAR or mock CAR) can be incubated for 24-48 hrs with recombinant target cells expressing HLA-A2, CD19 or both CD19 and HLA-A2, or CD20, or both CD20 and CD19 to be tested in different effector to target ratios. In some embodiments, the iCAR/aCAR or pCAR/aCAR pair comprises any of aCAR, pCAR and/or iCAR with the components as described above. In some embodiments, the iCAR/aCAR pair comprises an HLA-A2 targeted iCAR and a CD19 targeted aCAR. In some embodiments, the iCAR/aCAR pair comprises a CD20 targeted iCAR and a CD19 targeted aCAR. Cell killing will be quantified indirectly by estimating the number of live cells with the Bright-Glo Luciferase system.

In some embodiments, the 'off-tumor' cytotoxicity can be optimized by sorting transduced T cell populations according to iCAR/aCAR expression level or by selecting sub population of recombinant target cells according to their target expression, including for example, expression of the gene product encoding for at least one extracellular polymorphic epitope. In some embodiments, the aCAR, iCAR, and/or pCAR target is any target with an extracellular domain. In some embodiments, the sorting is based on CD19 or HLA-A2 expression level.

In some embodiments, the iCAR and/or pCAR is examined to determine whether the iCAR transduced T cells can discriminate between the 'on-tumor' cells (e.g., tumor cells) and 'off-tumor' cells (e.g., non-tumor cells) in vitro. Generally, this is tested by examining the killing effect of transduced T cells incubated with a mix of 'on-tumor' and 'off-tumor' cells at a ratio of 1:1. In some embodiments, the ratio is 1:2, 1:3, 1:4, 1:5, 1:6, 1:7, or 1:8. The on tumor recombinant cells can be distinguished from the 'off-tumor' recombinant cells by luciferase expression in embodiments where only one cell population will be engineered to express the luciferase gene at a time). Killing can be quantified after 24-48 hrs of co-incubation using the Bright-Glo Luciferase assay (Promega).

In some embodiments, the iCAR/aCAR and/or pCAR/aCAR transduced T cells exhibit about 10%, about 20%, about 30%, about 40%, about 50%, about 60%, about 70%, about 80%, about 90%, and/or about 95% less off-tumor cell killing as compared to T cells transduced with aCAR but not transduced with the iCAR and/or pCAR. In some embodiments, the iCAR/aCAR and/or pCAR/aCAR transduced T cells exhibit about 1-fold, about 2-fold, about 3-fold, about 4-fold, about 5-fold, or about 10-fold less off-tumor cell killing as compared to T cells transduced with aCAR but not transduced with the iCAR and/or pCAR.

ii. Caspase 3

In some embodiments, caspase 3-detection assays are employed to examine the iCAR and/or pCAR to determine the level of apoptis of the 'on-tumor' cells (e.g., tumor cells) and 'off-tumor' cells (e.g., non-tumor cells) in vitro. In some embodiments, caspase 3-detection of cytotoxic lymphocyte (CTL) induced apoptosis by an antibody to activated cleaved caspase 3 is examined.

Generally, one of the pathways by which CTLs kill target cells is by inducing apoptosis through the Fas ligand. The CASP3 protein is a member of the cysteine-aspartic acid protease (caspase) family. Typically, sequential activation of caspases plays a significant role in the execution-phase of cell apoptosis and as such, cleavage of pro-caspase 3 to caspase 3 results in conformational change and expression of catalytic activity. The cleaved activated form of caspase 3 can be recognized specifically by a monoclonal antibody.

In some embodiments, transduced T cells can be incubated with either 'on-tumor' (e.g., mimicking tumor) and 'off-tumor' cells (e.g., mimicking non-tumor) recombinant cells. In some embodiments, the 'on-tumor' (e.g., tumor) and 'off-tumor' cells (e.g., non-tumor) recombinant cells have been previously labeled with CFSE ((5(6)-Carboxyfluorescein N-hydroxysuccinimidyl ester)) or other cell tracer dye (e.g., CellTrace Violet). In some embodiments, co-incubation of target cells with effector cells occurs for about 1 hour to 6 about hours, about 2 hours to about 5 hours, or about 2 to about 4 hrs. In some embodiments, target cell apoptosis is quantified by flow cytometry. Cells can be permeabilized and fixed by an inside staining kit (Miltenyi or BD bioscience) and stained with an antibody for activated caspase 3 (BD bioscience).

In some embodiments, the iCAR/aCAR and/or pCAR/aCAR transduced T cells induce about 10%, about 20%, about 30%, about 40%, about 50%, about 60%, about 70%, about 80%, about 90%, and/or about 95% less off-tumor cell apoptosis as compared to T cells transduced with aCAR but not transduced with the iCAR and/or pCAR. In some embodiments, the aCAR/iCAR and/or aCAR/pCAR transduced T cells induce about 1-fold, about 2-fold, about 3-fold, about 4-fold, about 5-fold, or about 10-fold less off-tumor cell apoptosis as compared to T cells transduced with aCAR but not transduced with the iCAR and/or pCAR.

iii. Time-Lapse Microscopy

Time Lapse Micros CTL—

Time lapse microscopy of the iCAR and/or pCAR transduced T cells can be employed in order to discern target binding. In some embodiments, target cells will be labeled with a reporter gene (for example but not limited to a fluorescent protein such as mCherry). In some embodiments, transduced T cells are incubated with either 'on-tumor' or 'off-tumor' cells for up to 5 days. In some embodiments, time lapse microscopy can be used to visualize killing. In some embodiments, flow cytometry analysis using viable cell number staining and CountBright beads (Invitrogen) for determining target cell number at end-point time will be conducted.

In some embodiments, in order to determine if the aCAR/iCAR or aCAR/pCAR transduced T cells can discern targets in vitro, each recombinant target cells ('on-tumor' or 'off-tumor') is labeled with a different reporter protein (for example GFP and mCherry). In some embodiments, any report protein pair would work, so long as the reporter pair contains two reporters which are easily distinguishable. In some embodiments, transduced T cells (Effector cells) will be co-incubated with the recombinant cells (target cells) at a 1:1 ratio of E/T. In some embodiments, the ration of effector to target (E/T) includes but is not limited to 16:1, 12:1, 10:1, 8:1, 6:1, 4:1, 2:1, or 1:1. In some embodiments, the cell fate is then examined by microscopy imaging.

iv. Cytokine release

Cytokine release can be examined in order to determine T cells activation. In some embodiments, iCAR/aCAR and/or pCAR/aCAR transduced T cells are incubated with the recombinant target cells and cytokine production for one or more cytokines is quantified, for example, either by measuring cytokine secretion in cell culture supernatant according to BioLegend's ELISA MAXTM Deluxe Set kit or by flow cytometry analysis of the percentage of T cells producing cytokines. For the flow cytometry analysis, a Golgi stop is generally employed to prevent the secretion of the cytokines. In some embodiments, following a 6 hour and 18 hour to 24 hour incubation of the transduced T cells with target cells, T cells will be permeabilized and fixed by an inside staining kit (Miltenyi) and stained with antibodies for the T cell markers (CD3 and CD8) and for one or more cytokines. In some embodiments, the cytokines include but are not limited to IL-2, INFγ, and/or TNFα.

v. CD107a Staining

Staining for CD107a can also be examined in order to determine cytolytic activity of the transduced T cells. Generally, degranulating of T cells can be identified by the surface expression of CD107a, a lysosomal associated membrane protein (LAMP-1), and surface expression of LAMP-1 has been shown to correlate with CD8 T cell cytotoxicity. Further, this molecule is located on the luminal side of lysosomes. Typically, upon activation, CD107a is transferred to the cell membrane surface of activated lymphocytes. Moreover, CD107a is expressed on the cell surface transiently and is rapidly re-internalized via the endocytic pathway. Therefore, while not being bound by theory, CD107a detection is maximized by antibody staining during cell stimulation and by the addition of monensin (for example, to prevent acidification and subsequent degradation of endocytosed CD107a antibody complexes).

In some embodiments, the aCAR/iCAR and/or aCAR/pCAR transduced transduced T cells are incubated with the target cells for about 6 ours to about 24 hrs and CD107a expression on the CD8 T cells is examined. In some embodiments, the target cells expresso only one target protein recognized by aCAR (as in tumor cells) or target cells expressing both target proteins recognized by aCAR and iCAR (as in normal cells). In some embodiments, the iCAR and/or pCAR transduced T cells are incubated with the target cells for about 6 ours to about 24 hrs in the presence of monensin and CD107a expression on the CD8 T cells is followed by flow cytometry using conjugated antibodies against the T cell surface markers (for example, CD3 and CD8) and a conjugated antibody for CD107a.

vi. Quantitation of Secreted Cytokines by ELISA

In some embodiments, following co-cultivation of transduced T-cells (Jurkat, or primary T-cells) expressing iCAR or aCAR or both aCAR and iCAR with modified target cells, expressing iCAR or aCAR or both aCAR and iCAR antigens on their cell surface, conditioned medium will be collected, and cytokine's concentration will be measured by cytokine ELISA. In some embodiments, the cytokine is selected from the group consisting of IL-2, INFγ and/or TNFα. In some embodiments, the cytokine is selected from the group consisting of IL-2. In some embodiments, the cytokine is selected from the group consisting of INFγ. In some embodiments, the cytokine is selected from the group consisting of TNFα. In some embodiments, a decrease of about 20%, about 25%, about 30%, about 35%, about 40%, about 45%, about 50%, about 55%, about 60%, about 65%, about 70%, about 75%, about 80%, about 85%, about 90%, about 95%, or about 99% is demonstrated with dual CAR (aCAR/iCAR) transduced cells.

vii. Cytokines Secretion Measured by Cytometric Bead Array (CBA) Assay

Cytometric Bead Array (CBA) is used to measure a variety of soluble and intracellular proteins, including cytokines, chemokines and growth factors. In some embodiments, T-cells (primary T-cells or Jurkat cells) transduced with aCAR or both aCAR and iCAR constructs (Effector cells) are stimulated with modified target cells expressing both iCAR and aCAR or aCAR or iCAR target antigens on their cell surface. In some embodiments, the effector to target ratio ranges from 20:1 up to 1:1. In some embodiments, the effector to target ratio ranges from 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, or 1:1. In some embodiments, following several hours of co-incubation the effector cells produce and secrete cytokines which indicate their effector state. In some embodiments, the supernatant of the reaction is collected, and secreted IL-2 was measured and quantified by multiplex CBA assay.

In some embodiments, a decrease of about 20%, about 25%, about 30%, about 35%, about 40%, about 45%, about 50%, about 55%, about 60%, about 65%, about 70%, about 75%, about 80%, about 85%, about 90%, about 95%, or about 99% is demonstrated with dual CAR (aCAR/iCAR) transduced cells were co-incubated with target cells expressing both target antigens as compared to IL-2 secretion resulted from co-incubation of the same effector cells with target cells expressing only one target. In some embodiments, a decrease of about 20%, about 25%, about 30%, about 35%, about 40%, about 45%, about 50%, about 55%, about 60%, about 65%, about 70%, about 75%, about 80%, about 85%, about 90%, about 95%, or about 99% in IL-2 secretion was demonstrated when dual CAR (aCAR/iCAR) transduced cells were co-incubated with target cells expressing both target antigens as compared to IL-2 secretion resulted from co-incubation of the same effector cells with target cells expressing only one target. In some embodiments, a decrease of 86%. In some embodiments, the aCAR is a CD19 aCAR. In some embodiments, the iCAR is an HLA-A2 iCAR. In some embodiments, the iCAR is a CD20 iCAR. In some embodiments, the aCAR/iCAR pair is CD19 aCAR and HLA-A2 iCAR. In some embodiments, the aCAR/iCAR pair is CD19 aCAR and a CD20 iCAR viii. T-Cell Degranulation Assay as Measured by CD107a Staining In some embodiments, degranulating of T cells can be identified by the surface expression of CD107a, a lysosomal associated membrane protein (LAMP-1). In some embodiments, surface expression of LAMP-1 has been shown to correlate with CD8 T cell cytotoxicity. In some embodiments, granulation (CD107a) is a marker for killing potential.

B. In Vivo Assays

In some embodiments, the iCAR/aCAR and/or iCAR/pCAR pairs are tested for effectiveness in vivo. In some embodiments, NOD/SCID/γc- or similar mice are inoculated intravenously with tumor cells. In some embodiments, the tumor cells are CD19 positive NALM 6 (ATCC, human B-ALL cell line) cells that are engineered to express firefly luciferase. In some embodiments, for establishment of and/or differentiation between 'on-target' cells and 'off-tumor' cells, NALM 6 can be engineered to express the iCAR and/or pCAR epitope thereby representing the healthy cells. In some embodiments, the iCAR and/or pCAR epitope comprises at least one extracellular polymorphic epitope. In some embodiments, the iCAR and/or pCAR epitope is from HLA-A2 or CD20. Other cells that could be employed in these assays include but are not limited to Raji or any other recombinant cell lines. In some embodiments, such assays can be in a PDX (patient derived xenograft) model.

For the assay, mice will be divided into study groups; one group will be injected with the NALM 6 cells while the other will be injected with the NALM-6 expressing the iCAR epitope. Several days later, mice will be infused intravenously with T cells transduced with aCAR, aCAR/iCAR and a control group of untransduced T cells or no T cells. Mice will be sacrificed and tumor burden will be quantified according to total flux.

According to one embodiment of the assay, in order to test whether the T cells expressing the iCAR and/or pCAR construct could discriminate between the target cells and off target cells in vivo within the same organism, mice are injected with a 1:1 mixture of the 'on-tumor'/'off-tumor' NALM-6 cells, followed by injection of transduced T cells expressing either the aCAR alone or both aCAR and iCAR. With this embodiment, upon sacrifice of the mice the presence of the 'on-tumor' and 'off-tumor cells in the spleen and bone marrow will be analyzed by flow cytometry for the two markers, CD19 and the iCAR epitope.

i. In Vivo CTL Assay in Human Xenograft Mouse Models

In some embodiments, to test whether T-cells expressing both aCAR and iCAR constructs discriminate between the target cells and 'off-target' cells within the same organism and effectively kill the target cells while sparing the 'off-target' cells will be assessed by an in-vivo CTL In some embodiments, transduced T-cells with iCAR or aCAR or both iCAR and aCAR will be injected i.v. to naïve NOD/SCID/γc- or similar mice and up to several hours later, target cells expressing iCAR, aCAR or both will be injected. In some embodiments, these targets will be labeled with either CFSE/CPDE or similar cell trace dye in different concentrations (high, medium and low) which will allow further discrimination between them. In some embodiments, percentage of specific killing will be calculated, as described in Example 5.

ii. Tumor Growth Kinetics in Human Xenograft Mouse Models

In some embodiments, the tumor cells express either the iCAR target, aCAR target or both. In some embodiments, an aCAR tumor cell line could be the CD19 positive NALM 6 (ATCC, human BALL cell line). In some embodiments, tumor cells that express both the aCAR and iCAR (i.e. 'off-tumor' cells) are NALM 6 engineered to express the iCAR epitope (for example HLA-A2) thereby representing the healthy cells. In some embodiments, NALM 6 and NAlM 6-HLA-A2 can also be engineered to express a reporter gene (e.g. firefly luciferase), for easy detection.

In some embodiments, monitoring will be conducted by measuring tumor volume by mechanical means (caliper) and also by using in-vivo imaging systems (IVIS). In some embodiments, tumor burden can be quantified, and infiltrating T-cell populations can be analyzed by FACS.

iii. Toxicity and Tumor Growth Kinetics in Transgenic Mouse Models

In some embodiments, transgenic mice that express the human aCAR and iCAR targets will also be used to determine the efficacy of the transduced T-cells. In some embodiments, system will allow us to monitor efficacy and toxicity issues.

C. In Vivo Uses: Treatment, Biomarkers

In yet another aspect, the present invention provides a method of selecting a personalized biomarker for a subject having a tumor characterized by LOH, the method comprising (i) obtaining a tumor biopsy from the subject; (ii) obtaining a sample of normal tissue from the subject, e.g., PBMCs; and (iii) identifying a single allelic variant of a polymorphic cell surface epitope that is not expressed by cells of the tumor due to LOH, but that is expressed by the cells of the normal tissue, thereby identifying a personalized biomarker for the subject.

In some embodiments, the biomarker is used to customize a treatment of the subject, so the method further comprises the steps of treating cancer in a patient having a tumor characterized by LOH, comprising administering to the patient an effector immune cell as defined above, wherein the iCAR is directed to the single allelic variant identified in (iii). In some embodiments, the present invention provides a method of selecting a personalized biomarker for a subject having a tumor characterized by LOH, the method comprising (i) obtaining a tumor biopsy from the subject; (ii) obtaining a sample of normal tissue from the subject, e.g. PBMCs; (iii) identifying a single allelic variant of a polymorphic cell surface epitope that is not expressed by cells of the tumor due to LOH, but that is expressed by the cells of the normal tissue, based on the LOH candidate score, wherein an allelic variant is identified as a personalized biomarker for the subject.

In a further aspect, the present invention provides a method for treating cancer in a patient having a tumor characterized by LOH, comprising administering to the patient an effector immune cell as defined above, wherein the iCAR is directed to a single allelic variant encoding a polymorphic cell surface epitope absent from cells of the tumor due to loss of heterozygosity (LOH) hut present at least on all cells of related mammalian normal tissue of the patient.

In a similar aspect, the present invention provides a method of reducing tumor burden in a subject having a tumor characterized by LOH, comprising administering to the patient an effector immune cell as defined above, wherein the iCAR is directed to a single allelic variant encoding a polymorphic cell surface epitope absent from cells of the tumor due to loss of heterozygosity (LOH) but present at least on all cells of related mammalian normal tissue of the patient or at least on vital tissues the aCAR is expressed in.

In another similar aspect, the present invention provides a method of increasing survival of a subject having a tumor characterized by LOH, comprising administering to the patient an effector immune cell as defined above, wherein the iCAR is directed to a single allelic variant encoding a polymorphic cell surface epitope absent from cells of the tumor due to loss of heterozygosity (LOH) but present at least on all cells of related mammalian normal tissue of the patient.

In still a further aspect, the present invention is directed to a safe effector immune cell as defined above for use in treating, reducing tumor burden in, or increasing survival of, a patient having a tumor characterized by LOH, wherein the iCAR is directed to a single allelic variant encoding a polymorphic cell surface epitope absent from cells of the tumor due to loss of heterozygosity (LOH) but present at least on all cells of related mammalian normal tissue of the patient.

In yet a further aspect, the present invention is directed to a method for treating cancer in a patient having a tumor characterized by LOH comprising: (i) identifying or receiving information identifying a single allelic variant of a polymorphic cell surface epitope that is not expressed by cells of the tumor due to LOH, but that is expressed by the cells of the normal tissue, (ii) identifying or receiving information identifying a non-polymorphic cell surface epitope of an antigen or a single allelic variant of a polymorphic cell surface epitope, wherein said epitope is a tumor-associated antigen or is shared by cells at least of related tumor and normal tissue in said cancer patient; (iii) selecting or receiving at least one nucleic acid molecule defining an iCAR as defined herein above and at least one nucleic acid molecule comprising a nucleotide sequence encoding an aCAR as defined herein above, or at least one vector as defined herein above, wherein the iCAR comprises an extracellular domain that specifically binds to a cell surface epitope of (i) and the aCAR comprises an extracellular domain that specifically binds to a cell surface epitope of (ii); (iv) preparing or receiving at least one population of safe redirected effector immune cells by transfecting effector immune cells with the nucleic acid molecules of (iii) or transducing effector immune cells with the vectors of (iii); and (v) administering to said cancer patient at least one population of safe redirected immune effector cells of (iv).

In a similar aspect, the present invention provides at least one population of safe redirected immune effector cells for treating cancer in a patient having a tumor characterized by LOH, wherein the safe redirected immune cells are obtained by (i) identifying or receiving information identifying a single allelic variant of a polymorphic cell surface epitope that is not expressed by cells of the tumor due to LOH, but that is expressed by the cells of the normal tissue, (ii) identifying or receiving information identifying a non-polymorphic cell surface epitope of an antigen or a single allelic variant of a polymorphic cell surface epitope, wherein said epitope is a tumor-associated antigen or is shared by cells at least of related tumor and normal tissue in said cancer patient; (iii) selecting or receiving at least one nucleic acid molecule defining an iCAR as defined herein above and at least one nucleic acid molecule comprising a nucleotide sequence encoding an aCAR as defined herein above, or at least one vector as defined herein above, wherein the iCAR comprises an extracellular domain that specifically hinds to a cell surface epitope of (i) and the aCAR comprises an extracellular domain that specifically binds to a cell surface epitope of (ii); (iv) preparing or receiving at least one population of safe redirected effector immune cells by transfecting effector immune cells with the nucleic acid molecules of (iii) or transducing effector immune cells with the vectors of (iii).

In some embodiments referring to any one of the above embodiments directed to treatment of cancer or safe immune effector cells for use in treatment of cancer, (i) the extracellular domain of the iCAR specifically binds a single allelic variant of a polymorphic cell surface epitope of an antigen, which is a different antigen than that to which the extracellular domain of the aCAR binds; (ii) the extracellular domain of said iCAR specifically binds a single allelic variant of a different polymorphic cell surface epitope of the same antigen to which the extracellular domain of said aCAR binds; or (iii) the extracellular domain of said iCAR specifically binds a different single allelic variant of the same polymorphic cell surface epitope to which the extracellular domain of said aCAR binds.

In some embodiments, the treating results in reduced on-target, off-tumor reactivity, as compared with a treatment comprising administering to the cancer patient at least one population of immune effector cells expressing an aCAR of (iii) but lacking and iCAR of (iii).

In some embodiments, the safe effector immune cells used for treating cancer as defined above express on their surface an aCAR comprising an extracellular domain that specifically binds to a tumor-associated antigen or a non-polymorphic cell surface epitope of an antigen and an iCAR comprising an extracellular domain that specifically binds a single allelic variant of a polymorphic cell surface epitope of an antigen expressed at least in a tissue of origin of the tumor or of a housekeeping protein, which is a different antigen than that to which the extracellular domain of said aCAR binds.

In some embodiments, the safe effector immune cells used for treating cancer as defined above express on their surface an aCAR comprising an extracellular domain that specifically binds to a tumor-associated antigen or a non-polymorphic cell surface epitope of an antigen and an iCAR comprising an extracellular domain that specifically binds a single allelic variant of a polymorphic cell surface epitope of an antigen expressed at least in a tissue of origin of the tumor or of a housekeeping protein, such as an HLA genes (including for example, HLA-A, HLA-B, HLA-C, HLA-G, HLA-E, HLA-F, HLA-K, HLA-L, HLA-DM, HLA-DO, HLA-DP, HLA-DQ, or HLA-DR) which is a different antigen than that to which the extracellular domain of said aCAR binds.

In some embodiments, the safe effector immune cells used for treating cancer as defined above express on their surface an aCAR comprising an extracellular domain that specifically binds to a tumor-associated antigen or a non-polymorphic cell surface epitope of an antigen and an iCAR comprising an extracellular domain that specifically binds a single allelic variant of a polymorphic cell surface epitope of an antigen expressed at least in a tissue of origin of the tumor, such as an HLA-A, which is a different antigen than that to which the extracellular domain of said aCAR binds.

In some embodiments, more than one population of immune effector cells are administered, and the different populations express different pairs of aCARs and iCARs having specific binding to cell surface epitopes of different gene products.

In some embodiments, the safe effector immune cells used in the method of treating cancer are selected from T cells, natural killer cells or cytokine-induced killer cells. In some embodiments, the safe effector immune cell is autologous or universal (allogeneic) effector cells. In some embodiments, the iCAR used in any one of the methods of treating cancer defined above is directed to all tissues of the patient on which the target-antigen of the aCAR is present, wherein the target antigen of the aCAR is a non-polymorphic cell surface epitope of an antigen or a single allelic variant of a polymorphic cell surface epitope is present, and said epitope is a tumor-associated antigen or is shared at least by cells of related tumor and normal tissue.

In some embodiments, the cancer is selected from Acute Myeloid Leukemia [LAML], Adrenocortical carcinoma [ACC], Bladder Urothelial Carcinoma [BLCA], Brain Lower Grade Glioma [LGG], Breast invasive carcinoma [BRCA], Cervical squamous cell carcinoma and endocervical adenocarcinoma [CESC], Cholangiocarcinoma [CHOL], Colon adenocarcinoma [COAD], Esophageal carcinoma [ESCA], Glioblastoma multiforme [GBM], Head and Neck squamous cell carcinoma [HNSC], Kidney Chromophobe [KICH], Kidney renal clear cell carcinoma [KIRC], Kidney renal papillary cell carcinoma [KIRP], Liver hepatocellular carcinoma [LIHC], Lung adenocarcinoma [LUAD], Lung squamous cell carcinoma [LUSC], Lymphoid Neoplasm Diffuse Large B-cell Lymphoma [DLBC], Mesothelioma [MESO], Ovarian serous cystadenocarcinoma [OV], Pancreatic adenocarcinoma [PAAD], Pheochromocytoma and Paraganglioma [PCPG], Prostate adenocarcinoma [PRAD], Rectum adenocarcinoma [READ], Sarcoma [SARC], Skin Cutaneous Melanoma [SKCM], Stomach adenocarcinoma [STAD], Testicular Germ Cell Tumors [TGCT], Thymoma [THYM], Thyroid carcinoma [THCA], Uterine Carcinosarcoma [UCS], Uterine Corpus Endometrial Carcinoma [UCEC], Uveal Melanoma [UVM].

In some embodiments, the iCAR and/or pCAR for use in the treatment of cancer is any iCAR and/or pCAR described herein. In some embodiments, the iCAR and/or pCAR used to treat the cancer, such as any one of the cancer types recited above, is directed against or specifically binds to a single allelic variant of an HLA genes (including for example, HLA-A, HLA-B, HLA-C, HLA-G, HLA-E, HLA-F, HLA-K, HLA-L, HLA-DM, HLA-DO, HLA-DP, HLA-DQ, or HLA-DR, HLA-B gene or HLA-C gene or against a single allelic variant of a gene listed Table 8 In some embodiments, the iCAR used to treat the cancer, such as any one of the cancer types recited above, is directed against or specifically binds to a single allelic variant of an HLA-A gene, HLA-B gene or HLA-C gene or against a single allelic variant of a gene listed Table 8; and the aCAR used to treat the cancer, such as any one of the cancer types recited above, is directed against or specifically hinds to, a non-polymorphic cell surface epitope selected from the antigens listed in Table 1, such as CD19.

For oral administration, the pharmaceutical preparation may be in liquid form, for example, solutions, syrups or suspensions, or may be presented as a drug product for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The pharmaceutical compositions may take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well-known in the art.

Preparations for oral administration may be suitably formulated to give controlled release of the active compound.

For buccal administration, the compositions may take the form of tablets or lozenges formulated in conventional manner. The compositions may be formulated for parenteral administration by injection, e.g., by bolus injection or continuous infusion. Formulations for injection may be presented in unit dosage form, e.g., in ampoules or in multidose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen free water, before use.

The compositions may also be formulated in rectal compositions such as suppositories or retention enemas, e.g., containing conventional suppository bases such as cocoa butter or other glycerides.

For administration by inhalation, the compositions for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin, for use in an inhaler or insufflator may be formulated containing a powder mix of the compound and a suitable powder base such as lactose or starch.

For purposes of clarity, and in no way limiting the scope of the teachings, unless otherwise indicated, all numbers expressing quantities, percentages or proportions, and other numerical values recited herein, should be interpreted as being preceded in all instances by the term "about." Accordingly, the numerical parameters recited in the present specification are approximations that may vary depending on the desired outcome. For example, each numerical parameter may be construed in light of the number of reported significant digits and by applying ordinary rounding techniques.

The term "about" as used herein means that values of 10% or less above or below the indicated values are also included.

EXEMPLARY EMBODIMENTS

In some embodiments, the methods of the present invention provide for the following exemplary embodiments.

1. A nucleic acid molecule comprising a nucleotide sequence encoding an inhibitory chimeric antigen receptor (iCAR) or protective chimeric antigen receptor (pCAR) capable of preventing or attenuating undesired activation of an effector immune cell, wherein the iCAR or pCAR comprises an extracellular domain that specifically binds to a single allelic variant of a polymorphic cell surface epitope absent from mammalian tumor cells due to loss of heterozygosity (LOH) but present at least on all cells of related mammalian normal tissue; and an intracellular domain comprising at least one signal transduction element that inhibits an effector immune cell.

2. The nucleic acid molecule, wherein the polymorphic cell surface epitope is of a housekeeping gene product, such as an HLA gene, a G-protein-coupled receptor (GPCR), an ion channel or a receptor tyrosine kinase, preferably an HLA-A, HLA-B or HLA-C; or a polymorphic cell surface epitope of a gene selected from Table 8.

3. The nucleic acid molecule, wherein said extracellular domain comprises (i) an antibody, derivative or fragment thereof, such as a humanized antibody; a human antibody; a functional fragment of an antibody; a single-domain antibody, such as a Nanobody; a recombinant antibody; and a single chain variable fragment (ScFv); (ii) an antibody mimetic, such as an affibody molecule; an affilin; an affimer; an affitin; an alphabody; an anticalin; an avimer; a DARPin; a fynomer; a Kunitz domain peptide; and a monobody; or (iii) an aptamer.

4. The nucleic acid molecule, wherein said mammalian tissue is human tissue and said related mammalian normal tissue is normal tissue from which the tumor developed.

5. The nucleic acid molecule, wherein said effector immune cell is a T cell, a natural killer cell or a cytokine-induced killer cell.

6. The nucleic acid molecule, wherein said at least one signal transduction element capable of inhibiting an effector immune cell is homologous to a signal transduction element of an immune checkpoint protein.

7. The nucleic acid molecules, wherein said immune checkpoint protein is selected from the group consisting of PD1; CTLA4; BTLA; 2B4; CD160; CEACAM, such as CEACAM1; KIRs, such as KIR2DL1, KIR2DL2, KIR2DL3, KIR2DL4, KIR2DL5A, KIR2DL5B, KIR3DL1, KIR3DL2, KIR3DL3, LIR1, LIR2, LIR3, LIR5, LIR8 and CD94—NKG2A; LAG3; TIM3; V-domain Ig suppressor of T cell activation (VISTA); STimulator of INterferon Genes (STING); immunoreceptor tyrosine-based inhibitory motif (ITIM)-containing proteins, T cell immunoglobulin and ITIM domain (TIGIT), and adenosine receptor (e.g. A2aR).

8. The nucleic acid molecule of wherein said extracellular domain is fused through a flexible hinge and transmembrane canonic motif to said intracellular domain.

9. A vector comprising a nucleic acid molecule and at least one control element, such as a promoter, operably linked to the nucleic acid molecule.

10. The vector, further comprising a nucleic acid molecule comprising a nucleotide sequence encoding an aCAR comprising an extracellular domain specifically binding a non-polymorphic cell surface epitope of an antigen or a single allelic variant of a polymorphic cell surface epitope, wherein said epitope is a tumor-associated antigen or is shared at least by cells of related tumor and normal tissue, and an intracellular domain comprising at least one signal transduction element that activates and/or co-stimulates an effector immune cell.

11. The vector, wherein the extracellular domain of the aCAR specifically binds to a non-polymorphic cell surface epitope of an antigen and the extracellular domain of the iCAR specifically binds a single allelic variant of a polymorphic cell surface epitope of a different antigen than that to which the extracellular domain of said aCAR binds.

12. The vector, wherein the extracellular domain of the aCAR specifically binds to a non-polymorphic cell surface epitope selected from the antigens listed in Table 1, such as CD19.

13. The vector, wherein said at least one signal transduction element that activates or co-stimulates an effector immune cell is homologous to an immunoreceptor tyrosine-based activation motif (ITAM) of for example CD3ζ or FcRγ chains; an activating killer cell immunoglobulin-like receptor (KIR), such as KIR2DS and KIR3DS, or an adaptor molecule such as DAP12; or a co-stimulatory signal transduction element of for example CD27, CD28, ICOS, CD137 (4-1BB) or CD134 (OX40).

14. The vector, wherein the nucleotide sequence comprises an internal ribosome entry site (IRES) between the nucleotide sequence encoding for the aCAR and the nucleotide sequence encoding for the iCAR 15. The vector, wherein the nucleotide sequence encoding for the aCAR is downstream of the nucleotide sequence encoding for the iCAR.

16. The vector, wherein the nucleotide sequence comprises a viral self-cleaving 2A peptide between the nucleotide sequence encoding for the aCAR and the nucleotide sequence encoding for the iCAR.

17. The vector, wherein the viral self-cleaving 2A peptide is selected from the group consisting of T2A from *Thosea asigna* virus (TaV), F2A from Foot-and-mouth disease virus (FMDV), E2A from Equine rhinitis A virus (ERAV) and P2A from Porcine teschovirus-1 (PTV1).

18. The vector, comprising a nucleotide sequence encoding said constitutive aCAR linked via a flexible linker to said iCAR.

19. A method of preparing an inhibitory chimeric antigen receptor (iCAR) capable of preventing or attenuating undesired activation of an effector immune cell, the method comprising:
  (i) retrieving a list of human genomic variants of protein-encoding genes from at least one database of known variants;
  (ii) filtering the list of variants retrieved in (i) by:
    (a) selecting variants resulting in an amino acid sequence variation in the protein encoded by the respective gene as compared with its corresponding reference allele,
    (b) selecting variants of genes wherein the amino acid sequence variation is in an extracellular domain of the encoded protein,
    (c) selecting variants of genes that undergo loss of heterozygosity (LOH) at least in one tumor, and
    (d) selecting variants of genes that are expressed at least in a tissue of origin of the at least one tumor in which they undergo LOH according to (c), thereby obtaining a list of variants having an amino acid sequence variation in an extracellular domain in the protein encoded by the respective gene lost in the at least one tumor due to LOH and expressed at least in a tissue of origin of the at least one tumor;
  (iii) defining a sequence region comprising at least one single variant from the list obtained in (ii), sub-cloning and expressing the sequence region comprising the at least one single variant and a sequence region comprising the corresponding reference allele thereby obtaining the respective epitope peptides;
  (iv) selecting an iCAR binding domain, which specifically binds either to the epitope peptide encoded by the cloned sequence region, or to the epitope peptide encoded by the corresponding reference allele, obtained in (iii); and
  (vii) preparing iCARs as defined in any one of claims 1 to 8, each comprising an iCAR binding domain as defined in (iv).

20. The method, wherein the minor allele frequency for each variant equals or exceeds 1, 2, 3, 4 or 5%.

21. A method for preparing a safe effector immune cell comprising: (i) transfecting a TCR-engineered effector immune cell directed to a tumor-associated antigen with a nucleic acid molecule comprising a nucleotide sequence encoding an iCAR or transducing the cells with a vector; or (ii) transfecting a naïve effector immune cell with a nucleic acid molecule comprising a nucleotide sequence encoding an iCAR and a nucleic acid molecule comprising a nucleotide sequence encoding an aCAR; or transducing an effector immune cell with a vector.

22. A safe effector immune cell obtained by the method.

23. The safe effector immune cell, expressing on its surface an aCAR comprising an extracellular domain that specifically binds to a non-polymorphic cell surface epitope of an antigen and an iCAR comprising an extracellular domain that specifically binds a single allelic variant of a polymorphic cell surface epitope of a different antigen to which the extracellular domain of said aCAR binds.

24. The safe effector immune cell, wherein the extracellular domain of the aCAR specifically binds to a non-polymorphic cell surface epitope selected from the antigens listed in Table 1, such as CD19.

25. The safe effector immune cell, wherein the aCAR and the iCAR are present on the cell surface as separate proteins.

26. The safe effector immune cell, wherein the expression level of said nucleotide sequence encoding the iCAR is greater than or equal to the expression level of the nucleotide sequence encoding the aCAR.

27. A method of selecting a personalized biomarker for a subject having a tumor characterized by LOH, the method comprising
  (i) obtaining a tumor biopsy from the subject;
  (ii) obtaining a sample of normal tissue from the subject, e.g. PBMCs;
  (iii) identifying a single allelic variant of a polymorphic cell surface epitope that is not expressed by cells of the tumor due to LOH, but that is expressed by the cells of the normal tissue,
  thereby identifying a personalized biomarker for the subject.

28. A method for treating cancer in a patient having a tumor characterized by LOH, comprising administering to the patient an effector immune cell, wherein the iCAR is directed to a single allelic variant encoding a polymorphic cell surface epitope absent from cells of the tumor due to loss of heterozygosity (LOH) but present at least on all cells of related mammalian normal tissue of the patient.

29. A safe effector immune cell for use in treating patient having a tumor characterized by LOH, wherein the iCAR is directed to a single allelic variant encoding a polymorphic cell surface epitope absent from cells of the tumor due to loss of heterozygosity (LOH) but present at least on all cells of related mammalian normal tissue of the patient.

30. The safe effector immune cell, wherein the treating results in reduced on-target, off-tumor reactivity, as compared with a treatment comprising administering to the cancer patient at least one population of immune effector cells expressing an aCAR of (iii) but lacking and iCAR of (iii).

31. The safe effector immune cell, expressing on its surface an aCAR comprising an extracellular domain that specifically binds to a tumor-associated antigen or a non-polymorphic cell surface epitope of an antigen and an iCAR comprising an extracellular domain that specifically binds a single allelic variant of a polymorphic cell surface epitope of an antigen expressed at least in a tissue of origin of the tumor or of a housekeeping protein, such as an HLA-A, which is a different antigen than that to which the extracellular domain of said aCAR binds.

32. The safe effector immune cell, which is an autologous or a universal (allogeneic) effector cell.

33. The safe effector immune cell, selected from a T cell, natural killer cell or cytokine-induced killer cell.

34. A combination of two or more nucleic acid molecules, each one comprising a nucleotide sequence encoding a different member of a controlled effector immune cell activating system, said nucleic acid molecules forming a single continues nucleic acid molecule or comprising two or more separate nucleic acid molecules, wherein the controlled effector immune activating system directs effector immune cells to kill tumor cells that have lost one or more chromosomes or fractions thereof due to Loss of Heterozygosity (LOH) and spares cells of related normal tissue, and wherein
(a) the first member comprises an activating chimeric antigen receptor (aCAR) polypeptide comprising a first extracellular domain that specifically binds to a non-polymorphic cell surface epitope of an antigen or to a single allelic variant of a different polymorphic cell surface epitope and said non-polymorphic or polymorphic cell surface epitope is a tumor-associated antigen or is shared by cells of related abnormal and normal mammalian tissue; and
(b) the second member comprises a regulatory polypeptide comprising a second extracellular domain that specifically binds to a single allelic variant of a polymorphic cell surface epitope not expressed by an abnormal mammalian tissue due to LOH but present on all cells of related mammalian normal tissue.

35. The combination, wherein the first member is selected from:
(a) a constitutive aCAR further comprising an intracellular domain comprising at least one signal transduction element that activates and/or co-stimulates an effector immune cell; and
(b) a conditional aCAR further comprising an intracellular domain comprising a first member of a binding site for a heterodimerizing small molecule and optionally at least one co-stimulatory signal transduction element, but lacking an activating signal transduction element; and the second member is:
(c) an inhibiting chimeric antigen receptor (iCAR) further comprising an intracellular domain comprising at least one signal transduction element that inhibits an effector immune cell; or
(d) a protective chimeric antigen receptor (pCAR) further comprising an extracellular regulatory region comprising a substrate for a sheddase; a transmembrane canonic motif comprising a substrate for an intramembrane-cleaving protease; and an intracellular domain, said intracellular domain comprising at least one signal transduction element that activates and/or co-stimulates an effector immune cell and a second member of a binding site for a heterodimerizing small molecule.

36. The combination, wherein:
(i) the extracellular domain of the iCAR or pCAR specifically binds a single allelic variant of a polymorphic cell surface epitope of an antigen, which is a different antigen than that to which the extracellular domain of the aCAR binds
(ii) the extracellular domain of said pCAR or iCAR specifically binds a single allelic variant of a different polymorphic cell surface epitope of the same antigen to which the extracellular domain of said aCAR binds; or
(iii) the extracellular domain of said pCAR or iCAR specifically binds a different single allelic variant of the same polymorphic cell surface epitope to which the extracellular domain of said aCAR binds.

37. The combination, wherein said substrate for a sheddase is a substrate for a disintegrin and metalloproteinase (ADAM) or a beta-secretase 1 (BACE1).

38. The combination, wherein said substrate forms part of the extracellular domain and comprises Lin 12/Notch repeats and an ADAM protease cleavage site.

39. The combination, wherein said substrate for an intramembrane-cleaving protease is a substrate for an SP2, a γ-secretase, a signal peptide peptidase (spp), a spp-like protease or a rhomboid protease.

40. The combination, wherein said substrate forms part of the transmembrane canonic motif and is homologous to/derived from a transmembrane domain of Notch, ErbB4, E-cadherin, N-cadherin, ephrin-B2, amyloid precursor protein or CD44.

41. The combination, comprising a nucleotide sequence encoding an extracellular domain and an intracellular domain of said conditional aCAR as separate proteins, wherein each domain is independently fused to a transmembrane canonic motif and comprises a different member of a binding site for a heterodimerizing small molecule.

42. The combination, wherein each one of said first and second member of said binding site for a heterodimerizing small molecule is derived from a protein selected from:
(i) Tacrolimus (FK506) binding protein (FKBP) and FKBP;
(ii) FKBP and calcineurin catalytic subunit A (CnA);
(iii) FKBP and cyclophilin;
(iv) FKBP and FKBP-rapamycin associated protein (FRB);
(v) gyrase B (GyrB) and GyrB;
(vi) dihydrofolate reductase (DHFR) and DHFR;
(vii) DmrB homodimerization domain (DmrB) and DmrB;
(viii) a PYL protein (a.k.a. abscisic acid receptor and as RCAR) and ABI;
(ix) GAI *Arabidopsis thaliana* protein (a.k.a Gibberellic Acid Insensitive and DELLA protein GAI; GAI) and GID1 *Arabidopsis thaliana* protein (also known as Gibberellin receptor GID1; GID1).

Lengthy Tables

The patent application contains a lengthy table section. Copies of the tables are submitted concurrently herewith on CD-ROM.

EXAMPLES

With regard to the examples, the following terminology is employed.

When the term chromosome is employed, this generally refers to the chromosome the SNP lies on. For the SNP analysis, position refers to the genomic position of the SNP (assembly GRCh37.p13). The snp_id when used refers to the dbSNP rs ID, where one exists.

The term "ref" refers to the reference nucleotide allele. The term "alt" refers to the alternative nucleotide allele.

The term "quality" refers to the quality score from Exome Aggregation Consortium (ExAC). The term "filter_status" refers to filter information from ExAC.

The term "allele_frequency" refers to the global allele frequency from ExAC. The term "max_allele_frequency" refers to the global allele frequency of most common alternative allele (generally, this is only relevant when the SNP has more than two alternative alleles at the same site, and this can often mean sequencing errors anyway).

The term "het_allele_count" refers to the number of participants in ExAC who were heterozygotes. The term "AFR_AF" refers to minor allele frequency from African genomes. The term "AMR_AF" refers to minor allele frequency in Latino genomes. The term "EAS_AF" refers to minor allele frequency in East Asian genomes. The term "FIN_AF" refers to minor allele frequency in Finnish genomes. The term "NFE_AF" refers to minor allele frequency in Non-Finnish-European genomes. The term "OTH_AF" refers to minor allele frequency in Other genomes. The term "SAS_AF" refers to minor allele frequency in South Asian genomes.

The term "max_AF" refers to maximum minor allele frequency amongst the populations categorized in ExAC (0.5 is maximum allowable allele frequency).

The term "gene" refers to the HUGO symbol of the gene in which the SNP falls.

The term "hgnc_ID" refers to the HUGO Gene Nomenclature Committee numeric ID of the gene in which the SNP falls.

The term "consequence" refers to the impact of the SNP on the translated protein product. Can be one of several, including: missense_variant, frameshift_variant, inframe_deletion, stop_gained.

The term "protein_consequence" reports the amino acid substitution and the location thereof on the reference protein transcript (e.g. p. Arg482Gln).

The term "aa_affected" refers to the numeric location of the affected amino acid on the consensus protein transcript.

The term "allele_1" refers to the amino acid encoded by the reference allele.

The term "allele_2" refers to the amino acid encoded by the alternative allele.

The term "sift_score" refers to the score and interpretation of the predicted functional effect of the amino acid substitution by the SIFT algorithm. Uses version sift5.2.2. Scores range from 0-1. A low score means than an amino acid substitution is more likely to be tolerated.

The term "polyphen_score" refers to the score and interpretation of the predicted functional effect of the amino acid substitution by the polyphen algorithm. Uses PolyPhen (v2.2.2). Scores range from 0-1. A low score means than an amino acid substitution is more likely to be deleterious.

The term "polyphen_numeric" refers to the extracted numeric only score from the polyphen algorithm.

The term "protein_domains_affected" refers to the predicted protein domains based on the following algorithms: Gene3D, hmmpanther, Prosite.

The term "BLOSUM_score" refers to the score for the amino acid substitution based on the BLOSUM62 matrix from https://www.ncbi.nlm.nih.gov/IEB/ToolBox/C_DOC/lxr/source/data/BLOSUM62. A negative score indicates an amino acid substitution that has occurred less frequently over time in evolution (more likely to affect protein function).

The term "allele_1_one_letter" refers to the one letter amino acid code of the reference amino acid allele.

The term "allele_2_one_letter" refers to the one letter amino acid code of the alternative amino acid allele.

The term "mono_allelic_expression" refers to whether or not the gene that the SNP falls in undergoes mono-allelic expression in humans. The database established by Savova et al. was used for this annotation[7]. A 1 in this column indicates that the gene displays mono-allelic expression. A 0 in this column indicates that the gene did not display mono-allelic expression in the Savova et al. database. An NA in this column means that the gene was not annotated in the Savova et al. paper.

The term "extracellular" refers to whether or not the SNP falls in an extracellular domain of the affected protein. A 1 in this column indicates that the SNP is in an extracellular domain and a 0 indicates that it is not. Uniprot was used for annotation of protein domains.

The term "Pdb_id" refers to the protein databank ID of the affected protein if it exists. In the case where many protein databank entries exist for one protein, only the first ID is included.

The term "aa_context_21aa_allele_1" refers to A 21 amino acid window surrounding the SNP amino acid on the consensus protein sequence. The sequence consists of the 10 amino acids from the preceding part of the consensus protein sequence. A check was made to ensure that the reference amino acid matched the consensus protein sequence at the affected position. If these two amino acids were not the same, then the entry reads "discrepancy with uniprot fasta based on consensus isoform".

The term "aa_context_21aa_allele_2: The same amino acid window as above, but inserting amino acid allele 2 into the middle.

The term "gtex_mean: Average gene expression across tissues (in RPKM). This consists of the mean value of the median RPKM values across tissues from GTEX. For example, if the values for a given gene were Lung (median)= 3, Breast (median)=2, Pancreas (median)=5, then the value reported in this entry would be 3.33.

The term "gtex_min: The lowest gene expression for a tissue across all tissues. This value is derived from the list of the median values of gene expression across all tissues. For example, if the values for a given gene were Lung (median). 3, Breast (median)=2, Pancreas (median)=5, then the value reported in this entry would be 2.

The term "gtex_max: The highest gene expression for a tissue across all tissues. This value is derived from the list of the median values of gene expression across all tissues. For example, if the values for a given gene were Lung (median) =3, Breast (median)=2, Pancreas (median)=5, then the value reported in this entry would be 5.

The term "gtex_std_dev: The standard deviation of gene expression values across tissues for a given gene. For example, if the values for a given gene were Lung (median). 3, Breast (median)=2, Pancreas (median)=5, then the value reported in this entry would be 1.5.

The term "cell_surface_protein_atlas: A binary marker for whether or not the protein was annotated as a membrane protein in the cell surface protein atlas (wlab.ethz.ch/cspa/). A 1 indicates that the gene was annotated as a membrane protein in this database.

The term "human_protein_atlas_membrane_proteins: A binary marker for whether or not the protein was annotated as a membrane protein in the human protein atlas (https://www.proteinatlas.org/). A 1 indicates that the gene was annotated as a membrane protein in this database.

The term "subcellular_map_proteome_membrane_proteins: A binary marker for whether or not the protein was annotated as a membrane protein in the subcellular map of the proteome (http://science.sciencemag.org/content/early/2017/05/10/science.aal3321/). A 1 indicates that the gene was annotated as a membrane protein in this database.

The term "n_membrane_databases_w_gene: The total number of databases with the gene annotated as a gene that is expressed on the cell membrane. Maximum=3, minimum=0.

The term "membrane_protein_call: A textual interpretation of the number of membrane databases that the included the gene. If the gene was included in one database, then the call is a "low-confidence" membrane protein. If the gene was included in two databases, then the call is a "medium-confidence" membrane protein. If the gene was included in three databases, then the call is a "high-confidence" membrane protein.

The term "ratio_gtex_std_dev_to_mean: The ratio of the standard deviation of gene expression across tissues over the mean gene expression across tissues. For example, if the values for a given gene were Lung (median)=3, Breast (median)=2, Pancreas (median)=5, then the value reported in this entry would be 1.5/3.33=0.45. This is meant to be a measure of the uniformity of expression across tissues. A low value indicates that the gene is uniformly expressed. A high value suggests that the gene tends to be expressed in some tissues and not others.

The term "universally_expressed: A binary marker of whether a gene seems to be universally expressed. A gene is said to be universally expressed if the gtex_mean is >10, the gtex_min. The term ">1, and ratio_gtex_std_dev_to_mean<1. A 1 in this column indicates that the gene in question met these criteria.

The term "disease: the TCGA barcode for the disease analyzed for LOH data in this row of the spreadsheet.

The term "mean_expression_in_tissue: The mean gene expression in the tissue analyzed. Several tissue categorizations may map onto a single TCGA tumor type. The mapping from tissues in GTEX to TCGA tumor types is given in the file "tcga_disease_tissue_lookup.txt". A representative sample is given below:

| tcga_disease | gtex_tissues |
| --- | --- |
| ace | Adrenal.Gland |
| blca | Bladder |
| brca | Breast . . . Mammary.Tissue |
| cesc | Cervix . . . Endocervix, Cervix . . . Ectocervix |

The term "mean_expression_in_other_tissues: The mean gene expression in all other tissues except for the tissue analyzed. For example, if the gene being analyzed was PSMA (a prostate specific gene), then this value would be very low when the tumor type analyzed was PRAD (prostate adenocarcinoma).

The term "cohens_d: The Cohen's d measure of the separation of the expression in the tissue analyzed vs all other tissues. This is meant to be a measure of how much this gene is uniquely expressed in the tissue analyzed. A high Cohen's d would suggest that this gene is uniquely expressed in the tissue analyzed and therefore might be a good aCAR target.

The term "proportion_w_LOH_relative: The proportion of tumors in the tumor type analyzed that display evidence of LOH. The threshold for calling a genomic segment suggesting LOH was −0.1 (in relative copy number units). The relative copy number of a segment was the log of the copy number signal in the tumor divided by the copy number signal in the matched normal. These data were obtained from the cbio portal and the technique was validated in part 1.

The term "CI_95_low_relative: The lower boundary of the 95% confidence interval on the proportion of tumors undergoing LOH at this locus. The prop.test function in R was used for this calculation. This function calculates a binomial confidence interval with Yates' continuity correction.

The term "CI_95_high_relative: The upper boundary of the 95% confidence interval on the proportion of tumors undergoing LOH at this locus. The prop.test function in R was used for this calculation. This function calculates a binomial confidence interval with Yates' continuity correction.

The term "mutsig_hits_on_chr: The genes on the same chromosome as the SNP that pass statistical significance (q-value<0.25) for being drivers in cancer. The Mutsig 2.0 algorithm was used. The format is "Gene symbol, q=q-value; Gene symbol 2, . . . "

The term "tsg_on_chr_mutated_in_disease: A binary indicator variable for whether or not one of the genes passing statistically significance from mutsig is a tumor suppressor gene. The list of tumor suppressor genes used for this annotation was the list from the table published by Vogelstein et al[9]. A 1 in this column indicates that the gene is annotated as a tumor suppressor gene.

The term "hallmark_tsg_on_chr_mutated_in_disease: A binary indicator variable for whether any of the genes identified as significantly mutated in the tumor type analyzed and on the same chromosome as the SNP are "hallmark" tumor suppressor genes. "Hallmark" tumor suppressor genes are a small list of very-well validated tumor suppressor genes that are more likely to be mutated early in tumor development. These genes were: TP53, PTEN, APC, MLL3, MLL2, VHL, CDKN2A, and RB1. A 1 in this column indicates that one of these hallmark TSGs exists on the same chromosome as the SNP in question and is significantly mutated in the tumor type analyzed.

The term "gistic_deletion_n_peaks: The number of GISTIC peaks on the chromosome on which the SNP falls. A higher number suggests (loosely) that there are more selective forces driving loss of genetic material on this chromosome.

The term "gistic_deletion_best_q_value: The lowest GISTIC q-value for genomic loss on the chromosome on which the SNP falls. A very low q-value suggests that there is a significant selective pressure to lose genomic material somewhere on the chromosome.

The term "proportion_of_patients_eligible: The estimated proportion of patients who would have i) germline heterozygosity of the SNP and ii) LOH of the SNP in tumor. The estimate of the proportion of patients with germline heterozygosity of the SNP assumes Hardy-Weinberg equilibrium, using the equation proportion heterozygote=2pq. Where p is the global allelic fraction of the SNP and q=1-p.

The term "proportion_of_patients_eligible_max_ethnicity_targeted: The estimated proportion of patients who would have i) germline heterozygosity of the SNP and ii) LOH of the SNP in tumor. The estimate of the proportion of patients with germline heterozygosity of the SNP assumes Hardy-Weinberg equilibrium, using the equation proportion heterozygote=2pq. Where p is the maximum population-restricted allelic fraction of the SNP and q=1-p. For example, in some cases the population used might be African and in some cases it might be South Asian.

The term "cumulative_score: A score that quantifies the degree to which a SNP is a good candidate for an iCAR target. Scores range from 0 to theoretical 1. For more information on the calculation of this score, please see the section titled "Cumulative score to rank candidate SNPs."

Example 1. Assessment of Rate of LOH of HLA Genes Across Cancers

Introduction

A therapeutic strategy is proposed to address vulnerabilities incurred by genomic loss in cancer cells. The proposed strategy uses a combination of activating-CAR T-cells (aCAR) and inhibitory-CAR T-cells (iCAR) to more safely target tumors that have lost genomic segments encoding cell-membrane proteins heterozygous for the maternal and paternal alleles (i.e., with polymorphic protein coding changes).

iCARs can decrease off-tumor toxicity of CAR-T therapy without decreasing anti-tumor efficacy if the target of the iCAR is expressed only by non-tumor tissues. One such scenario in which iCAR targets are expressed only by non-tumor cells occurs when the iCAR antigen is encoded by a portion of the genome that has been deleted in tumor cells. One gene family that is highly polymorphic and known to be expressed on all cells is HLA.

Figure 4:
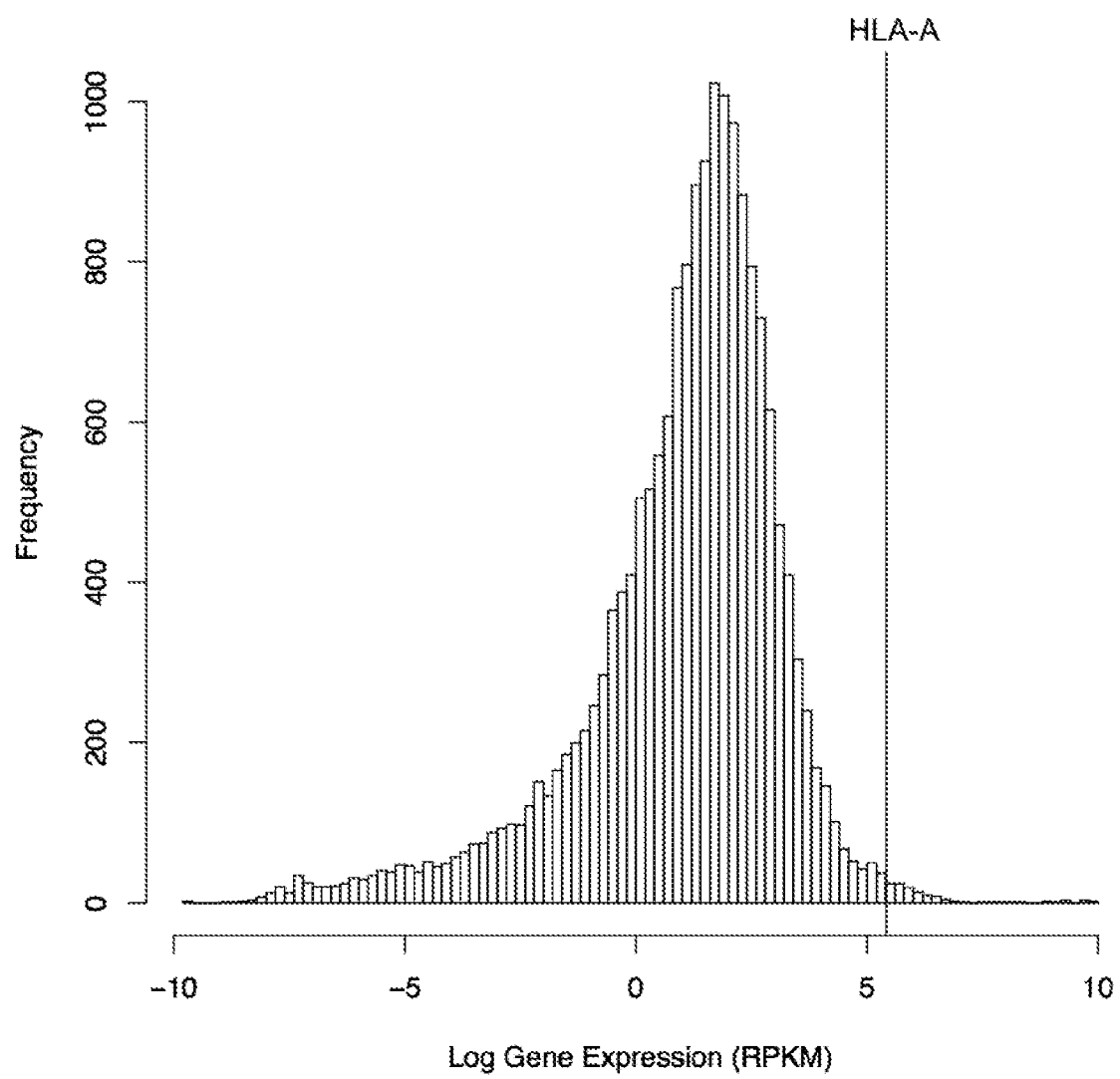
FIG. 4 shows expression of HLA-A relative to all other protein coding genes in the genome. The value for each gene reflects the mean RPKM value of tissue medians obtained from GTEX (gtexportal.org)

The HLA proteins are nearly universally expressed by mammalian cells to allow for the presentation of non-self antigens to cells of the immune system. HLA genes also tend to be quantitatively highly expressed, making them more amenable to therapeutic targeting. The RNA expression of the HLA genes is higher than 99.3 percent of other protein coding genes in the genome (FIG. 4). The mean tissue expression of HLA genes and their genomic locations is included in Table 3 as well as the lengthy table provided herewith on CD-ROM.

The goal of this section is to identify cancer types in which the HLA gene undergoes frequent deletion. Secondary analyses include attempts to identify drivers of genomic loss at the HLA locus.

Figure 5:
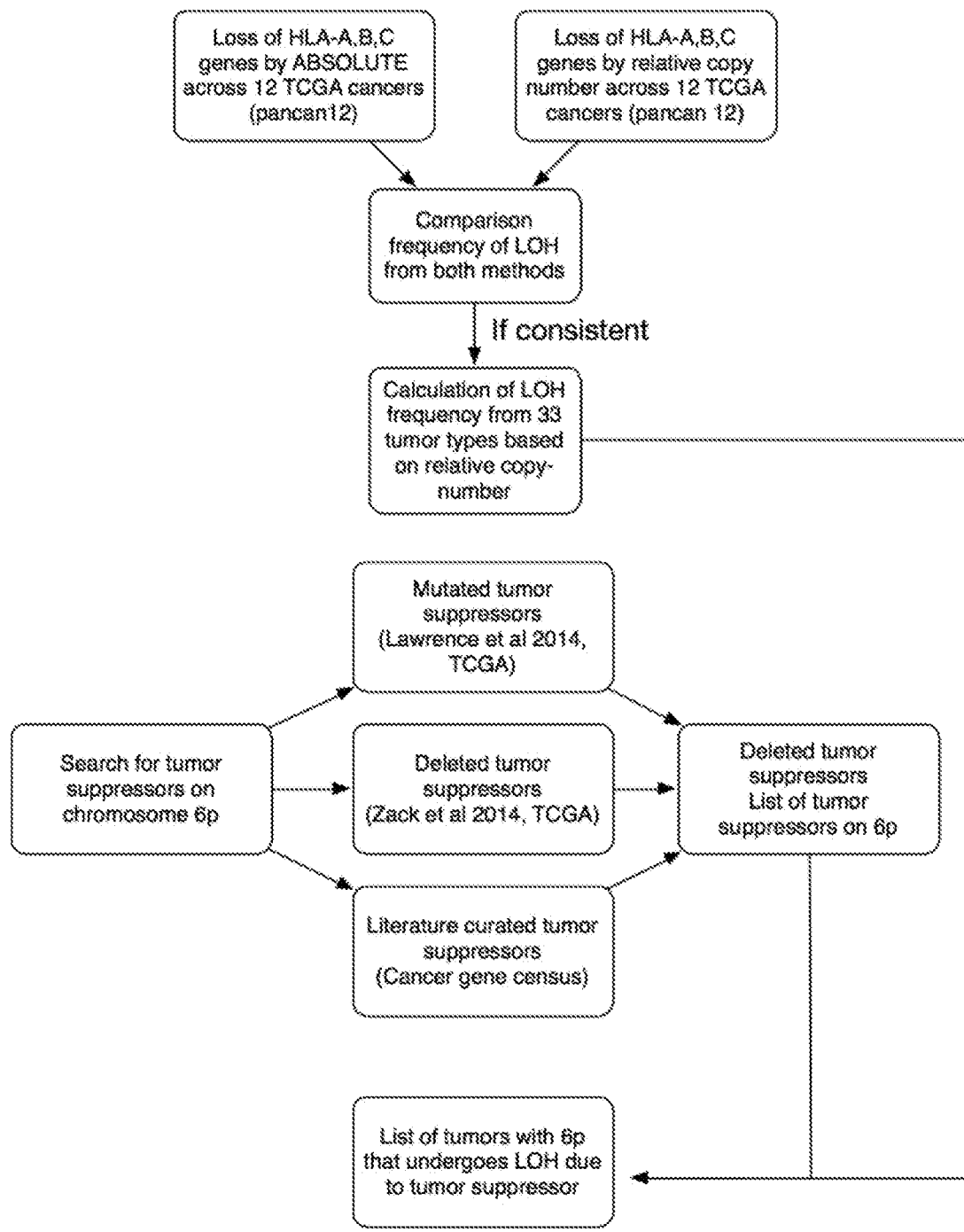
FIG. 5 shows a proposed workflow for analysis of HLA protein loss-of-heterozygosity across cancers in Example 5.

We executed a detailed plan for identifying cancers with selective pressures that drove frequent copy-loss of HLA genes (FIG. 5).

Figure 6:
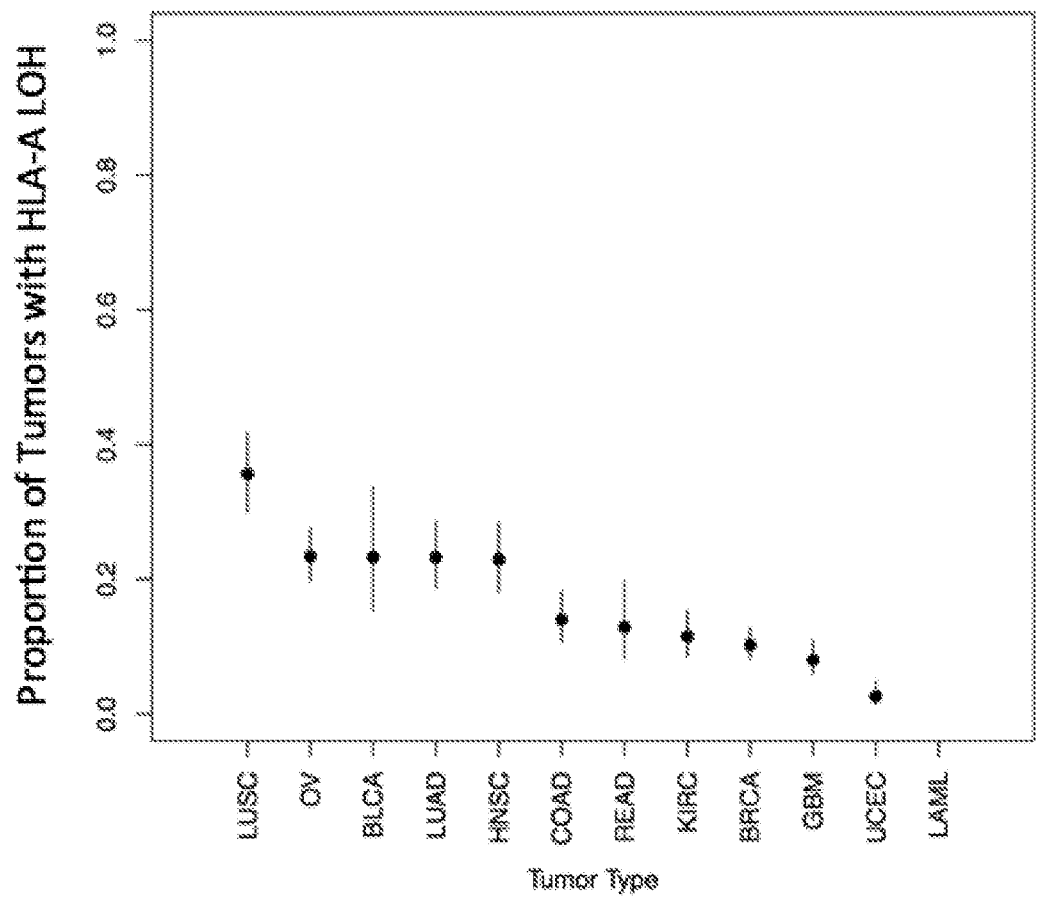
FIG. 6 shows Frequency of LOH in the pancan12 dataset using ABSOLUTE processed copy number data. Lines represent 95% binomial confidence intervals for frequency.
Figure 7:
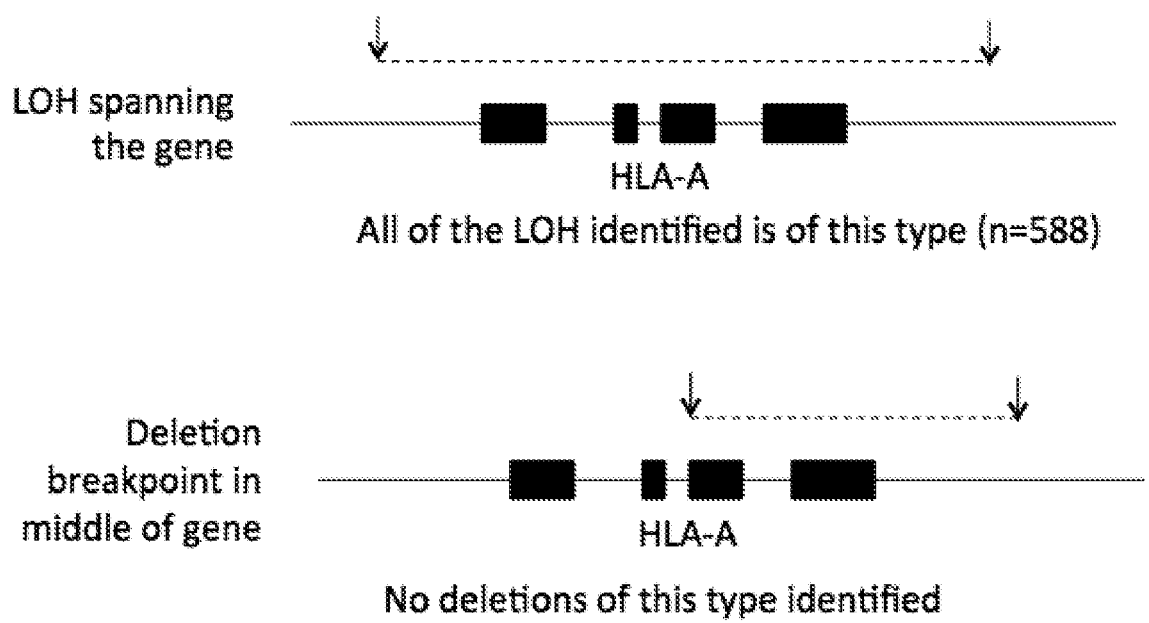
FIG. 7 shows the types of LOH observed in HLA-A. Of 588 episodes of HLA-A LOH, none involved a breakpoint within the HLA-A gene.
Figure 8:
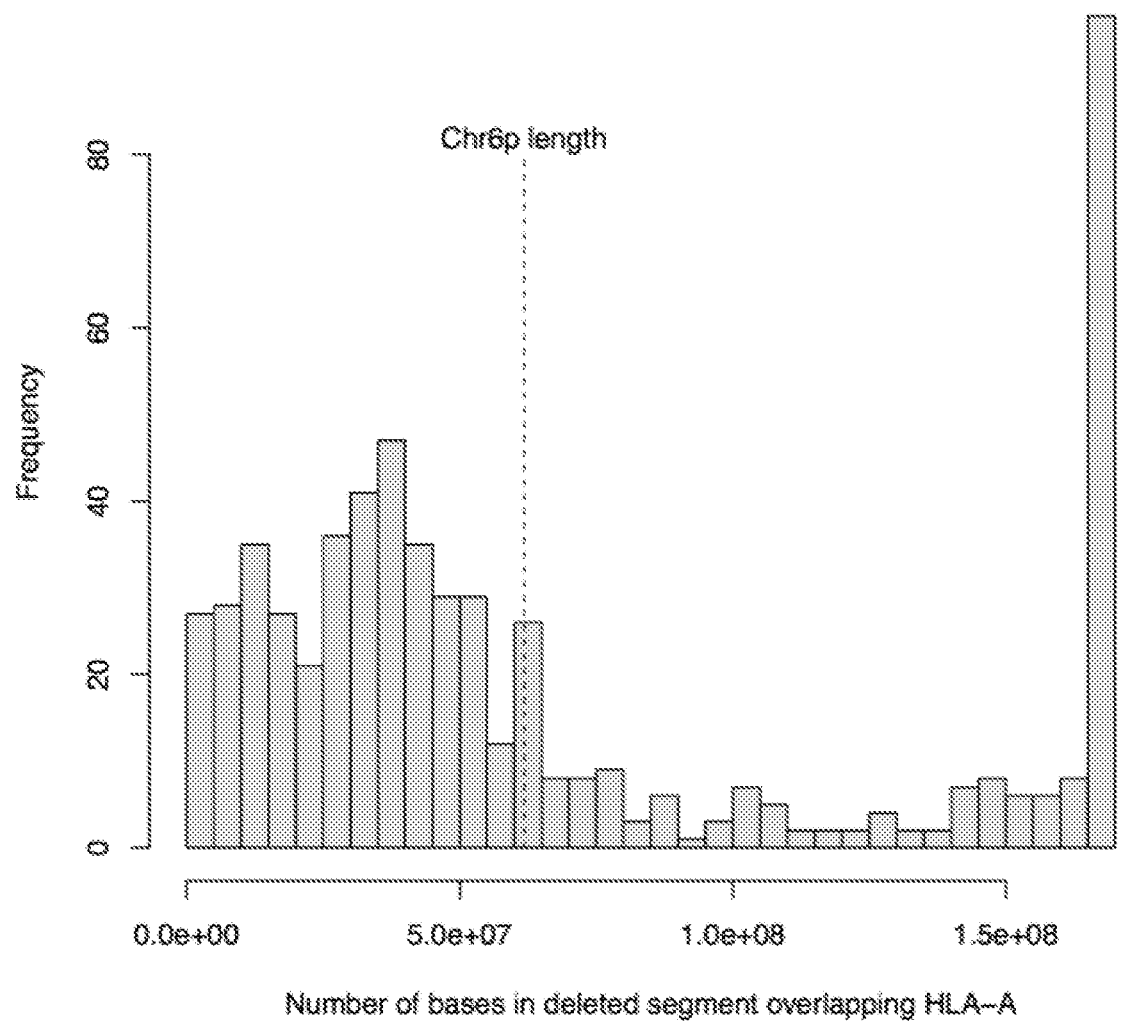
FIG. 8 shows the distribution of length (in basepairs) of deletions encompassing HLA-A. A large fraction of these deletions are greater than the length of chromosome 6p.
Figure 11:
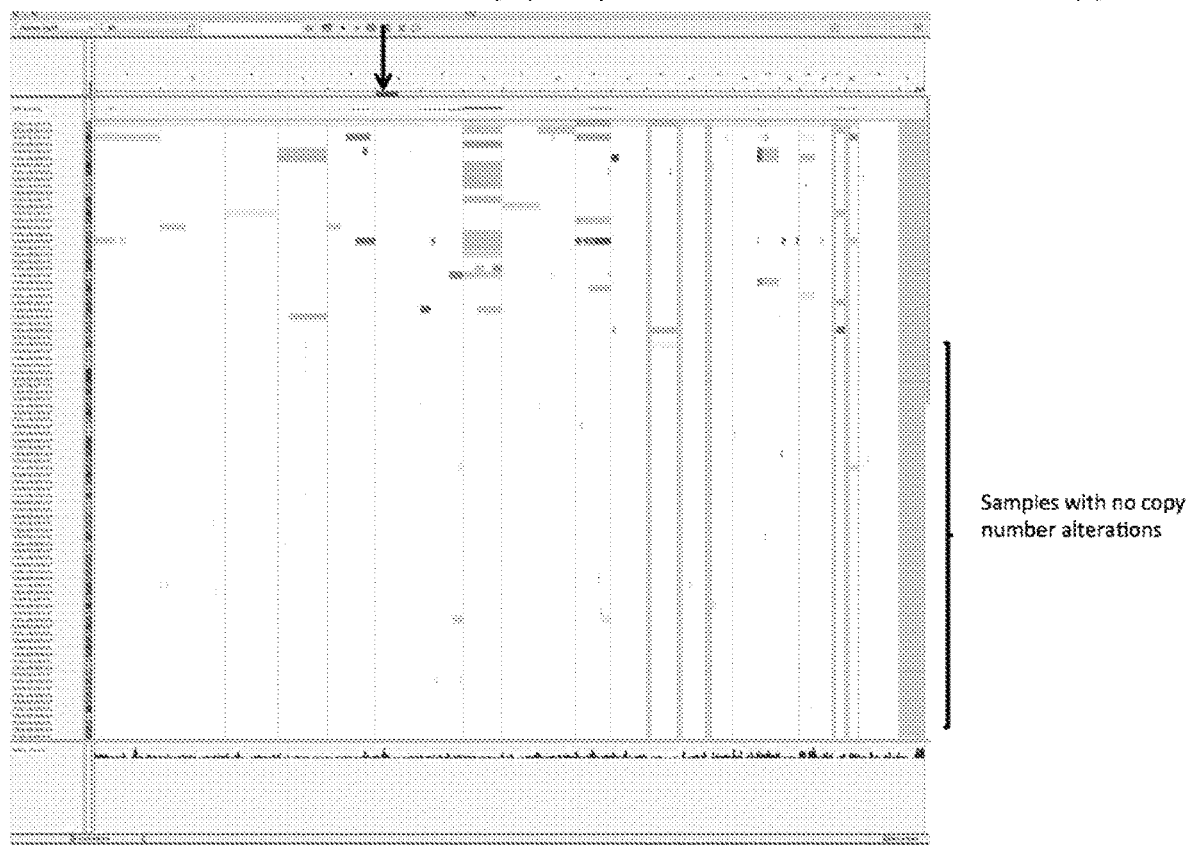
FIG. 11 shows the IGV screenshot of AML copy number profiles sorted for deletion of chromosome 6p. Blue indicates deletion, red indicates amplification. There are no deletions of HLA-A.

Frequency of HLA Loss Across Tumor Types Using ABSOLUTE Data:

We used copy number profiles from the TCGA that had been processed by the ABSOLUTE algorithm to assess ground-truth estimates of the rate of allelic loss of HLA-A. Publicly available ABSOLUTE segmented copy-number data were downloaded from (https://www.synapse.org/#!Synapse:syn1710464.2)[1]. The ABSOLUTE algorithm outputs the integer copy level of each allelic segment within a single cancer genome. In the case of loss of a single copy of chromosome 6 (harboring the HLA locus), then the allelic copy numbers would be: 1 for the retained segment and 0 for the segment that was lost. In the case of copy-neutral loss of heterozygosity, then the retained segment would have copy number 2 and the lost segment would have copy number 0. Publically available copy number data processed by ABSOLUTE were available for 12 tumor types (Table 4). Lung squamous cell carcinoma (LUSC) had the highest frequency of HLA-A LOH compared to the other tumor types (FIG. 6). Uterine/endometrial cancers (UCEC) had the lowest frequency of HLA-A LOH of all the evaluable tumors (AML samples were not included due to ABSOLUTE data not being available). Of 588 deletions of the HLA-A gene, none had an intragenic breakpoint (FIG. 7). Most deletions of HLA-A genes encompassed large portions of the chromosome (FIG. 8). While ABSOLUTE copy number data were not available for AML samples, manual inspection of the relative copy number data in these samples revealed no deletions (FIG. 11).

Validation of Relative Copy Number Data Compared to ABSOLUTE Copy Number Data:

We sought to obtain the frequency of LOH of as many tumor types as were publicly available. However, these data had not been processed by ABSOLUTE and the raw data to process by ABSOLUTE are not publicly available. Instead, we used relative copy number data on 32 tumor types from TCGA (FIG. 13). These data were downloaded from cbioportal (cbioportal.org/data_sets.jsp). The relative copy number data were obtained from Affymetrix SNP 6.0 arrays of tumor samples.

In order to determine whether accurate estimates of LOH could be obtained from relative copy number data, we computed the rate of LOH with relative data for the tumors that had already had LOH data from ABSOLUTE. These data consisted of a segmented copy number file. Each segment is assigned a relative copy-ratio. The copy ratio is defined as the log of the ratio of density of signal in tumor compared to the matched normal (in Affymetrix arrays). The normalization to a matched control (usually from peripheral blood) helps to remove any germline copy-number variants from mistakenly being interpreted as somatic. A segment is said to have undergone genomic loss if the relative copy number of that genomic segment is below a given threshold. For example, if the relative copy number of segment 321 is −0.4 and the threshold for copy-loss is −0.3, then segment 321 is said to have undergone copy-loss and because we lack direct allelic information, it is said to have undergone LOH as well.

Figure 9:
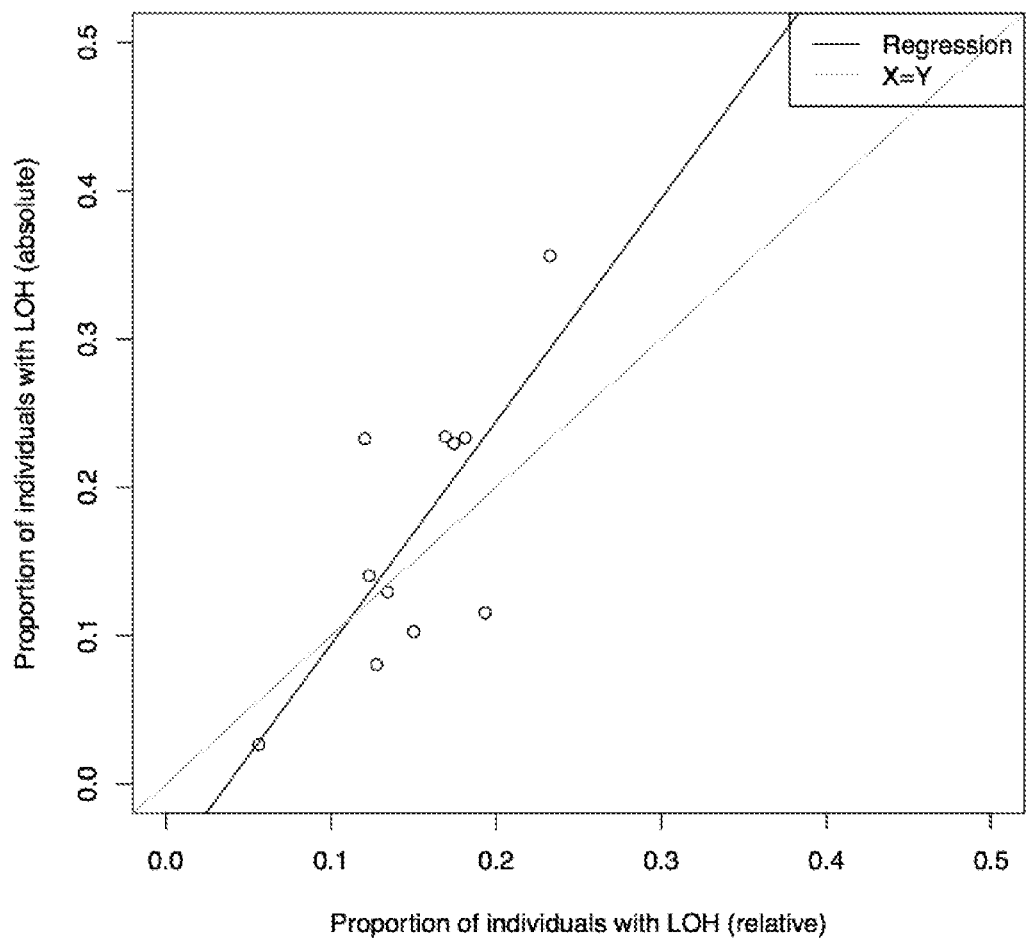
FIG. 9 shows the correlation between fraction of patients that have LOH of HLA-A in relative and ABSOLUTE copy number data with a threshold of −0.1.

We first attempted to determine the optimal copy number cutoff for labeling relative copy number segments as having undergone LOH. The concordance of ABSOLUTE and relative copy number estimates of LOH was highest with a cutoff of −0.1 for relative copy number (Table 5 and FIG. 9). This threshold also happens to be the threshold used by the TCGA copy number group to define copy-loss in the TCGA Tumorscape portal (http://portals.broadinstitute.org/tcga/home). The correlation between the fraction of individuals with HLA-A LOH in relative data vs ABSOLUTE data was 0.55. This reasonably high correlation enabled us to move forward with the analysis of all tumor types with relative copy number data available.

Figure 3A:
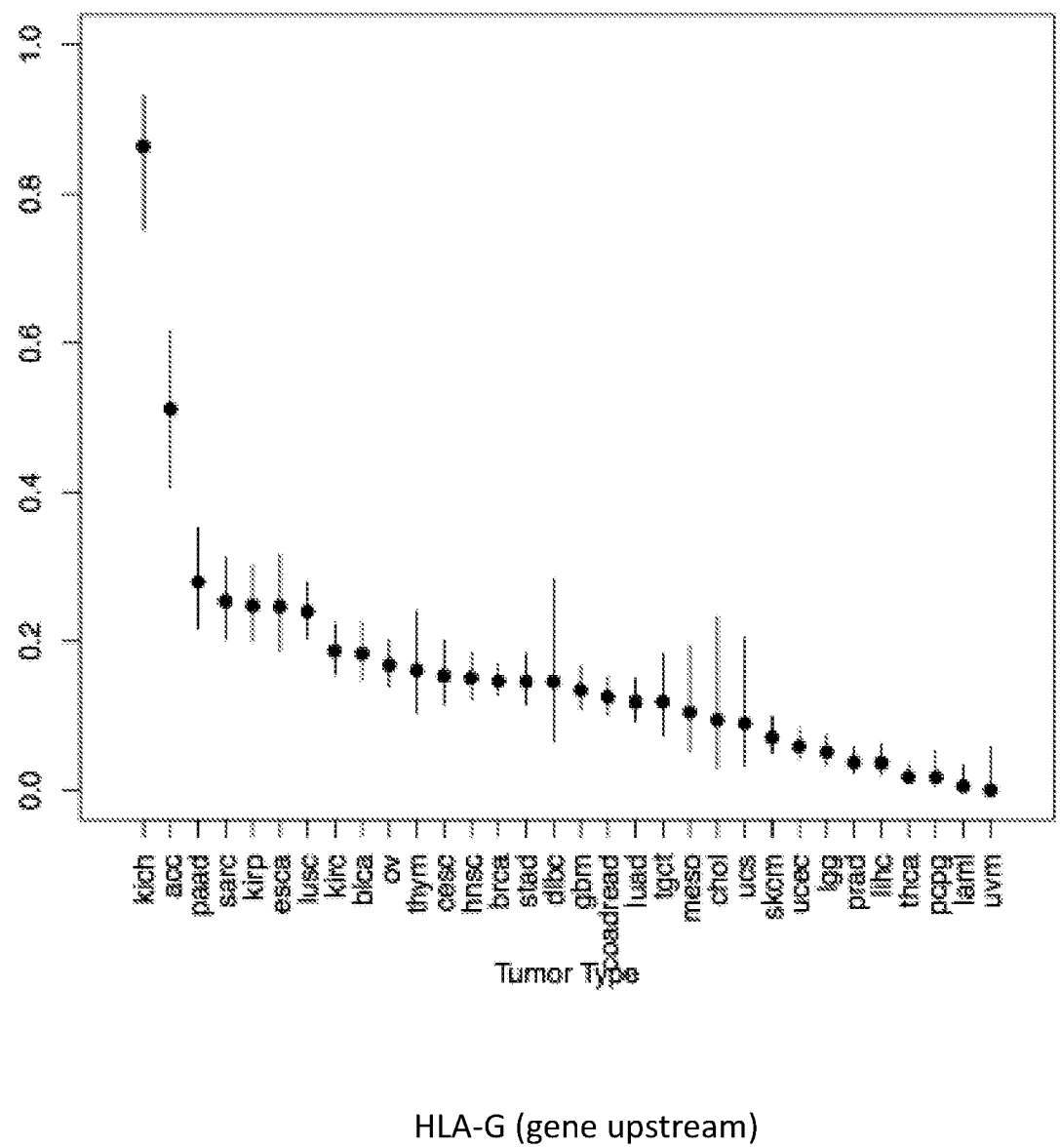
FIGS. 3A-C show the percentage of tumor samples undergoing LOH in the chromosomal region coding for the HLA class I locus. A. HLA-G, B. HLA-A, C. ZNRD1, in tumor types from the TCGA database. Kidney Chromophobe [KICH], Adrenocortical carcinoma [ACC], Pancreatic adenocarcinoma [PAAD], Sarcoma [SARC], Kidney renal papillary cell carcinoma [KIRP], Esophageal carcinoma [ESCA], Lung squamous cell carcinoma [LUSC], Kidney renal clear cell carcinoma [KIRC], Bladder Urothelial Carcinoma [BLCA], Ovarian serous cystadenocarcinoma [OV], Thymoma [THYM], Cervical squamous cell carcinoma and endocervical adenocarcinoma [CESC], Head and Neck squamous cell carcinoma [HNSC], Breast invasive carcinoma [BRCA], Stomach adenocarcinoma [STAD], Lymphoid Neoplasm Diffuse Large B-cell Lymphoma [DLBC], Glioblastoma multiforme [GBM], Colon adenocarcinoma [COAD], Rectum adenocarcinoma [READ], Lung adenocarcinoma [LUAD], Testicular Germ Cell Tumors [TGCT], Mesothelioma [MESO], Cholangiocarcinoma [CHOL], Uterine Carcinosarcoma [UCS], Skin Cutaneous Melanoma [SKCM], Uterine Corpus Endometrial Carcinoma [UCEC], Brain Lower Grade Glioma [LGG], Prostate adenocarcinoma [PRAD], Liver hepatocellular carcinoma [LIHC], Thyroid carcinoma [THCA], Pheochromocytoma and Paraganglioma [PCPG], Acute Myeloid Leukemia [LAML], Uveal Melanoma [UVM]
Figure 3B:
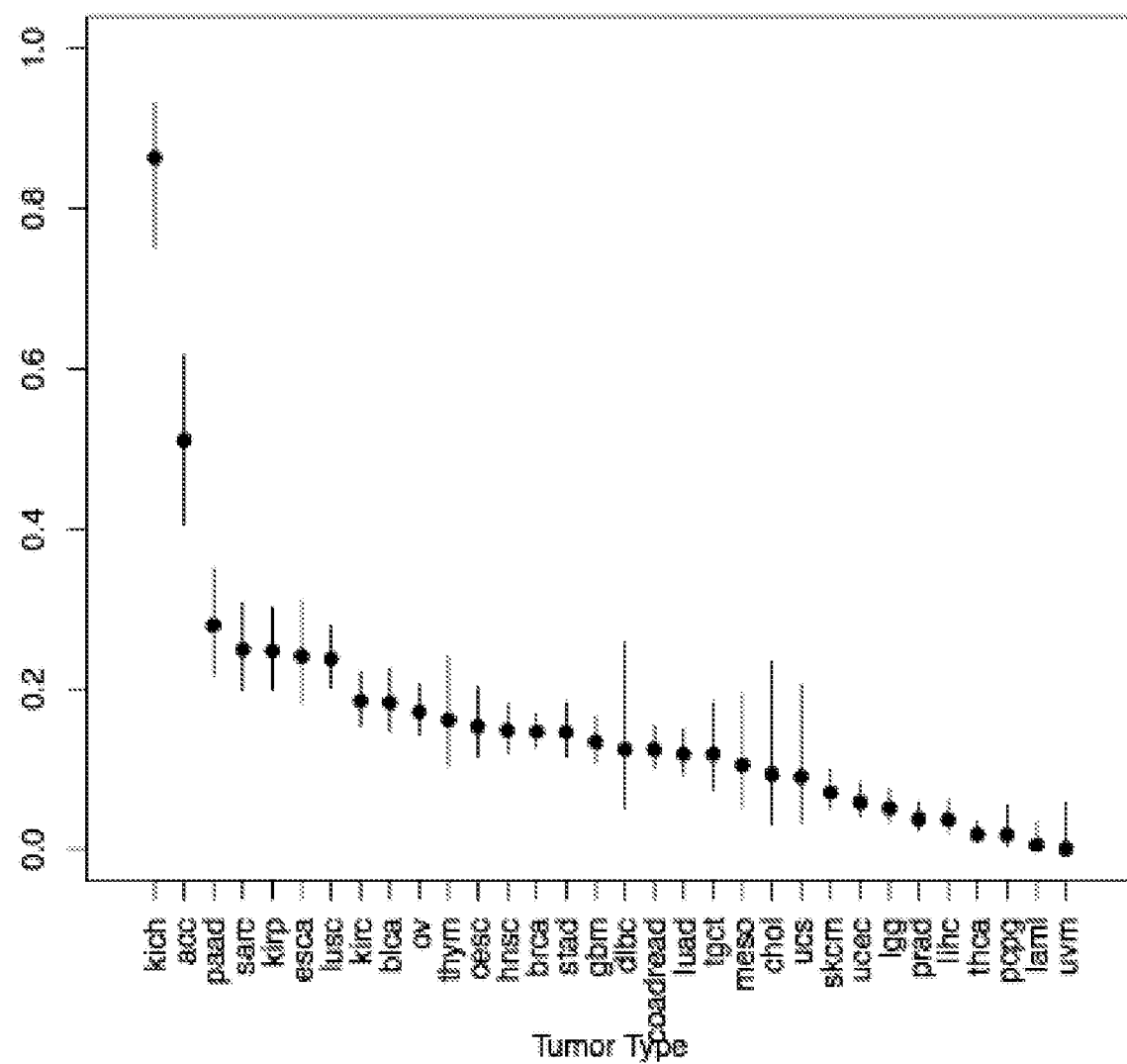
Figure 3C:
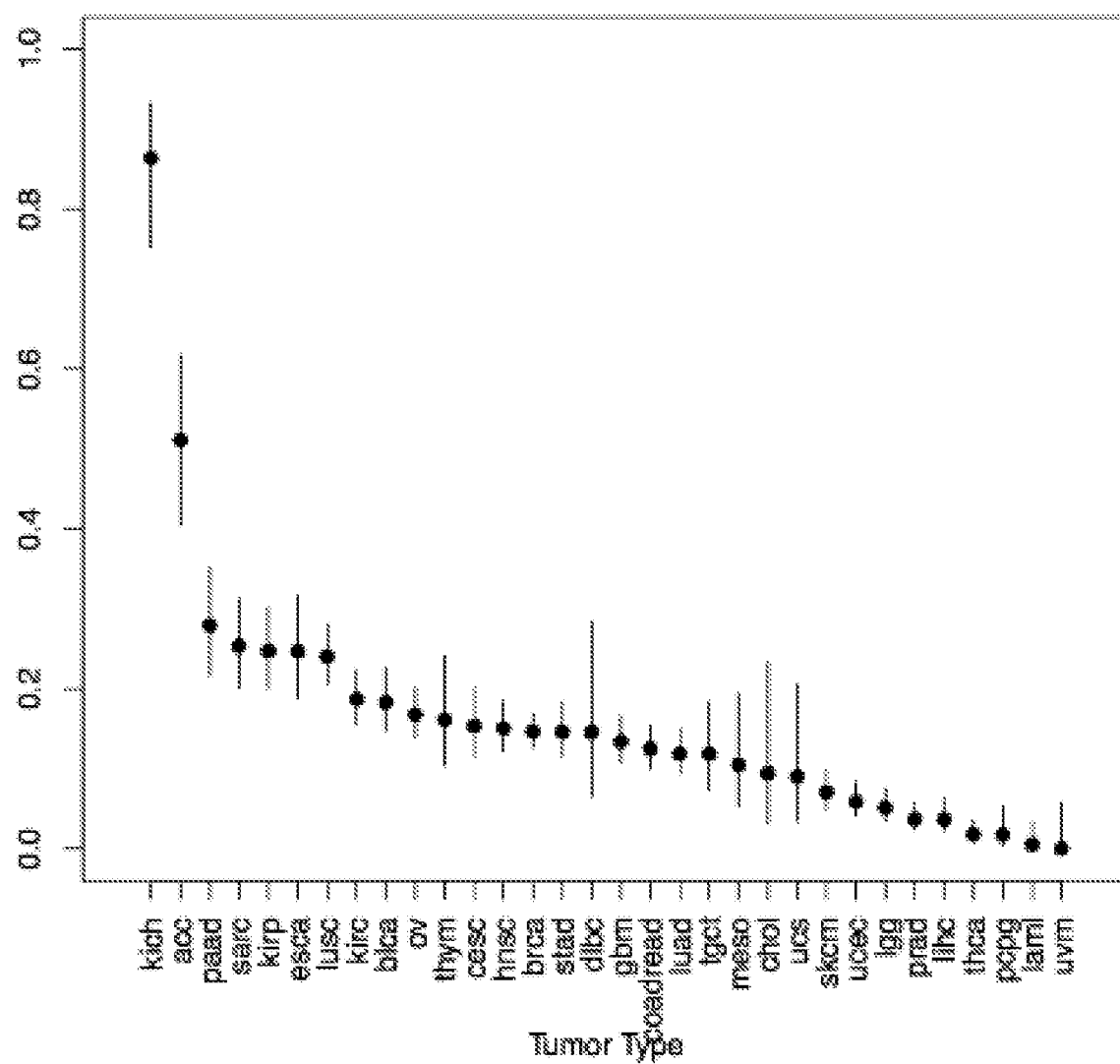
Figure 10A:
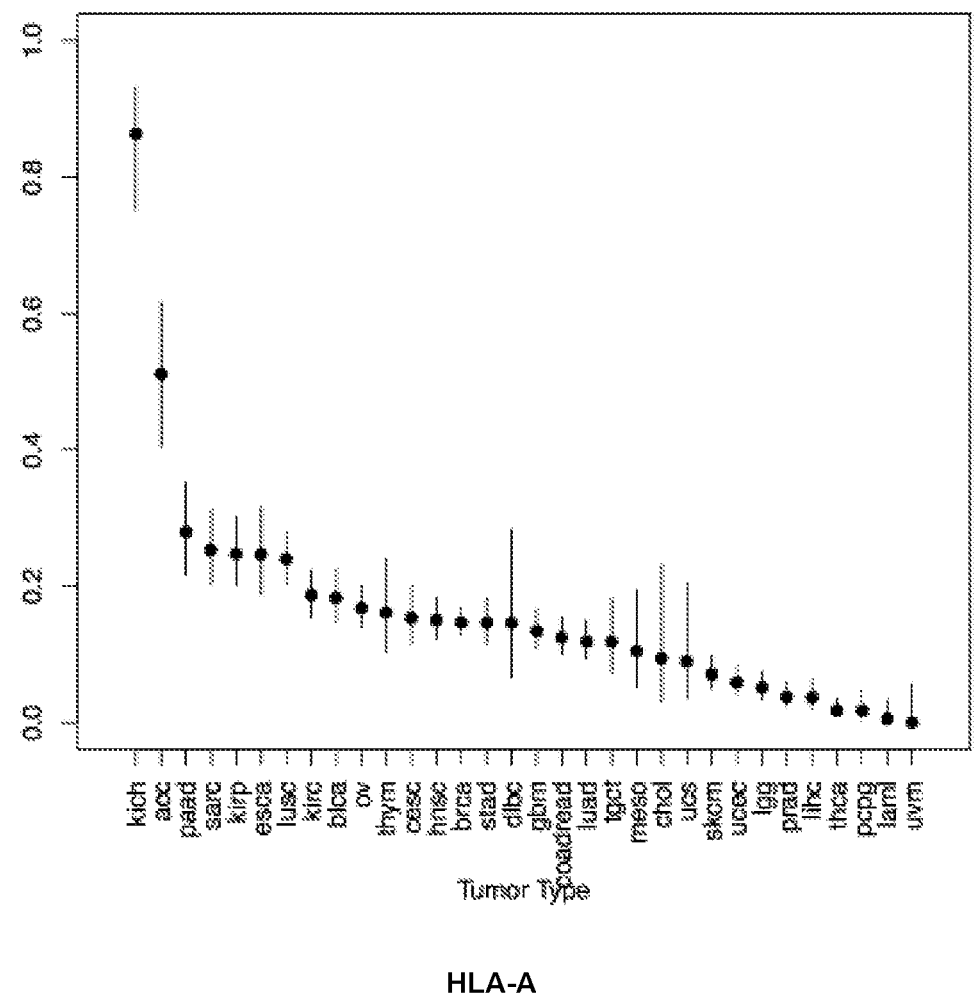
FIG. 10A-10C shows the comparison of rate of LOH of HLA-A, HLA-B and HLA-C across 32 cancers reveals a nearly identical pattern of LOH.
Figure 10B:
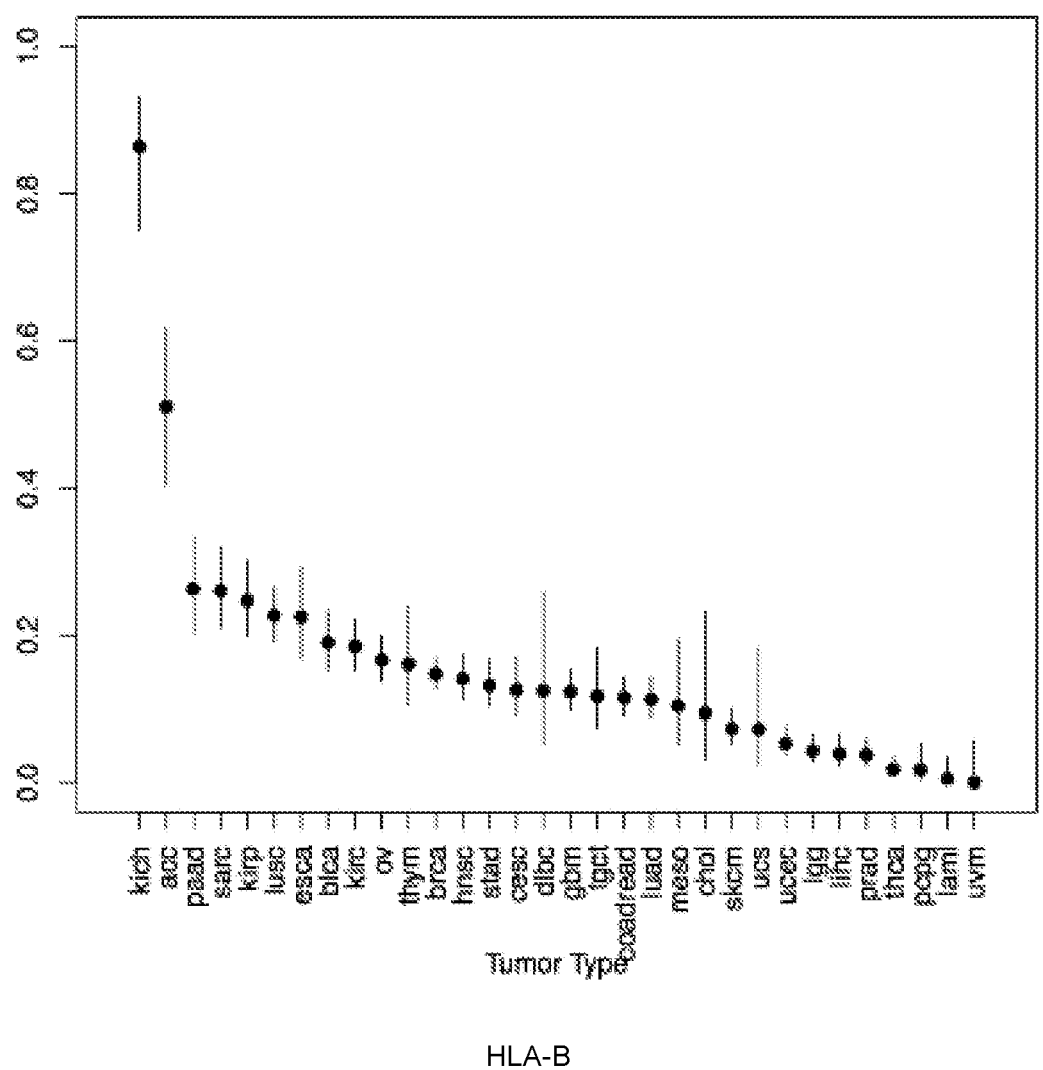
Figure 10C:
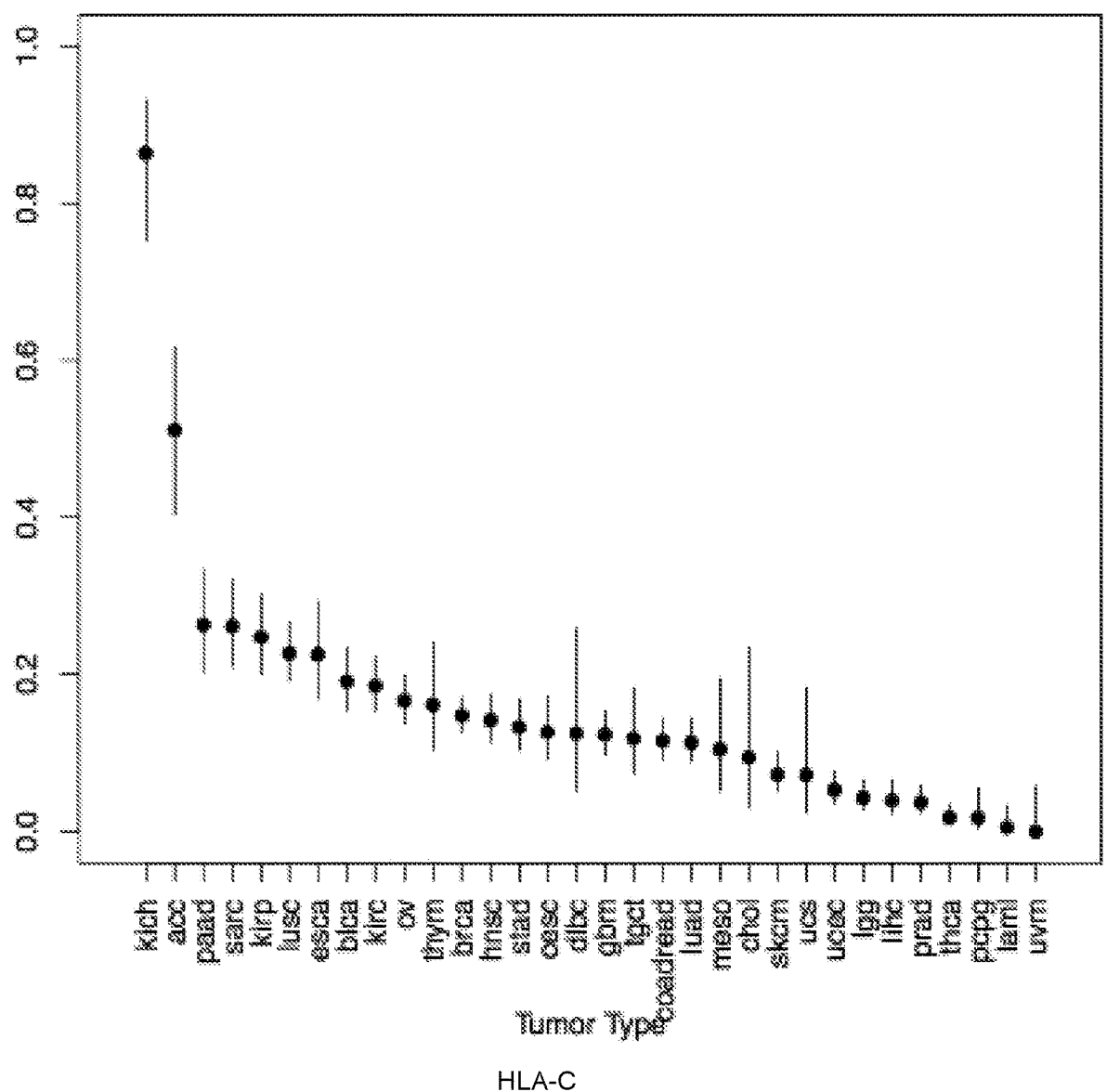

Fraction of Patients with HLA-LOH Across 32 Tumor Types Using Relative Copy Number Data The portion of patients that had LOH of HLA-A was computed for all 32 tumors available from TCGA (FIG. 10A; COAD and READ were analyzed together). The tumor with the highest rate of HLA-A LOH was kidney chromophobe cancer. The tumor with the lowest rate of HLA-A LOH was uveal melanoma (Table 6). To ensure that the rate of LOH we had derived in these analyses was robust to small perturbation of genomic position, we analyzed the rate of LOH of the upstream and downstream genes of HLA-A to see if their rate of HLA-LOH was similar to HLA-A. As expected, the rate of LOH of the upstream and downstream genes, HLA-G and ZNRD1 respectively was exactly the same as for HLA-A. (FIG. 3A-C). These data demonstrate that the HLA-A LOH calls are robust to small deviations in genomic position. Next, we sought to determine whether the other HLA genes (A, B, C) had similar rates of LOH compared to HLA-A. These genes all fall within a 1.3 Mb region on chromosome 6p. In genomic distance, this is a small region. We repeated the HLA-A analysis on HLA-B and HLA-C. The pattern of LOH was nearly identical between all three HLA genes across the 32 tumors analyzed (FIG. 10A-C).

Addition of Selection Pressure to HLA-A LOH Rates

Intratumoral genomic heterogeneity is a recently appreciated feature of nearly all human cancers analyzed to date[2,3]. Therapies targeted to genetic alterations only present in a fraction of tumor cells may only affect the tumor cells harboring said alterations. An iCAR strategy that targets antigens not present on tumor cells may protect some tumor cells from aCAR attack if the antigen is not clonally deleted. We therefore sought to identify tumors in which HLA genes were likely to undergo clonal LOH. LOH that occurs early in evolution is likely to be driven by selective forces in tumor initiation and/or maintenance. We therefore looked for tumor suppressors on chromosome 6 (harboring HLA locus) in three ways. First, we looked for genes that were significantly mutated on chromosome 6 in each of the tumor types assessed[4]. The spreadsheet reports the genes with significant mutation on chromosome 6 under the "chr6_mutsig_sig_genes" column.

Second, we looked for regions of significantly deleted genes, signifying likely deleted tumor suppressors. We used the results of GISTIC2.0 run on these data. The spreadsheet reports the number of GISTIC deletion peaks on chromosome 6 (q<0.25) and the lowest q-value of these deletion peaks. Generally, the more GISTIC deletion peaks and the lower the q-value, the stronger the selection pressure. However, it is also possible to have the scenario where one very strong GISTIC peak predominates and the number of peaks would be small, but the significance of the driver is for certain. In general, the lowest q-value should be the strongest correlate of tumor suppressor driver presence on a given chromosome.

Third, we overlapped the set of genes that were significantly mutated in each tumor with a list of known tumor suppressor genes to determine if any of the mutated genes was likely to drive loss of chromosome $6^5$. We were able to identify two tumor types with possible mutational drivers. In adrenocortical carcinoma, the DAXX gene was significantly mutated (q=0.0571) and in Diffuse Large B Cell Lymphoma, the TNFAIP3 gene was significantly mutated (q=0.00278). DAXX encodes a histone chaperone, mutations of which are associated with longer telomeres in adrenocortical carcinoma[6]. TNFAIP3 encodes a negative regulator of NF-kappaB signaling. Mutations of this gene occurring in DLBCL have been shown to therefore increase NF-kappaB signaling[7].

TABLE 3

Genomic loci analyzed for LOH. Genomic coordinates are in the hg19 human genome assembly.

| Gene | Protein | Chromosome | Start Position | End Position | RNA Expression (RPKM) |
|---|---|---|---|---|---|
| HLA-A | HLA-A | 6 | 29941260 | 29945884 | 226.6 |
| HLA-B | HLA-B | 6 | 31353872 | 31357188 | 422.4 |
| HLA-C | HLA-C | 6 | 31268749 | 31272130 | 193.4 |

TABLE 4

Tumor types with ABSOLUTE data

| Disease Name | TCGA Abbreviation | Number of Samples | Number of Samples Finished ABSOLUTE |
|---|---|---|---|
| Bladder urothelial carcinoma | BLCA | 138 | 90 |
| Breast invasive carcinoma | BRCA | 880 | 750 |
| Colon adenocarcinoma | COAD | 422 | 349 |
| Glioblastoma multiforme | GBM | 580 | 485 |
| Head and Neck squamous cell carcinoma | HNSC | 310 | 270 |
| Kidney renal clear cell carcinoma | KIRC | 497 | 373 |
| Acute Myeloid Leukemia | LAML | 200 | 0 |
| Lung adenocarcinoma | LUAD | 357 | 292 |
| Lung squamous cell carcinoma | LUSC | 344 | 261 |
| Ovarian serous cystadenocarcinoma | OV | 567 | 457 |
| Rectum adenocarcinoma | READ | 164 | 147 |
| Uterine corpus endometrial carcinoma | UCEC | 498 | 378 |

TABLE 5

Correlation (Pearson) of LOH rate by relative copy number data vs ABSOLUTE copy number data. Correlation peaks for a threshold value of −0.1.

| Deletion threshold | Correlation ($r^2$) |
|---|---|
| 0 | 0.01 |
| −0.05 | 0.49 |
| −0.1 | 0.55 |
| −0.15 | 0.53 |
| −0.2 | 0.46 |
| −0.25 | 0.44 |
| −0.3 | 0.21 |
| −0.35 | 0.10 |
| −0.4 | 0.07 |
| −0.45 | 0.09 |
| −0.5 | 0.08 |

TABLE 6

Numbers and rates of LOH for all 32 cancers in the TCGA dataset.

| TCGA Abbreviation | Total samples (n) | Number with LOH (n) | Fraction with LOH |
|---|---|---|---|
| KICH | 66 | 57 | 0.863636364 |
| ACC | 90 | 46 | 0.511111111 |
| PAAD | 184 | 51 | 0.277173913 |
| KIRP | 288 | 73 | 0.253472222 |
| LUSC | 501 | 124 | 0.24750499 |
| SARC | 257 | 63 | 0.245136187 |
| ESCA | 184 | 45 | 0.244565217 |
| KIRC | 528 | 98 | 0.185606061 |
| BLCA | 408 | 73 | 0.178921569 |
| OV | 579 | 96 | 0.165803109 |
| THYM | 123 | 20 | 0.162601626 |
| HNSC | 522 | 81 | 0.155172414 |
| CESC | 295 | 45 | 0.152542373 |
| STAD | 441 | 66 | 0.149659864 |
| BRCA | 1080 | 159 | 0.147222222 |
| DLBC | 48 | 7 | 0.145833333 |
| LUAD | 516 | 65 | 0.125968992 |
| COADREAD | 616 | 77 | 0.125 |
| GBM | 577 | 72 | 0.124783362 |
| TGCT | 150 | 18 | 0.12 |
| CHOL | 36 | 4 | 0.111111111 |
| MESO | 87 | 9 | 0.103448276 |
| UCS | 56 | 5 | 0.089285714 |
| UCEC | 539 | 31 | 0.057513915 |
| LGG | 513 | 24 | 0.046783626 |
| PRAD | 492 | 19 | 0.038617886 |
| SKCM | 104 | 4 | 0.038461538 |
| LIHC | 370 | 14 | 0.037837838 |
| PCPG | 162 | 3 | 0.018518519 |
| THCA | 499 | 9 | 0.018036072 |
| UVM | 80 | 0 | 0 |
| LAML | 0 | 0 | NA |

Based on the above, we concluded that HLA region LOH is a common event in many tumors, however and the percentage of LOH varies between tumor types. Therefore, HLA genes are good candidates for iCAR targets.

References for Example 1

1. Zack T I, Schumacher S E, Carter S L, Cherniack A D, Saksena G, Tabak B, Lawrence M S, Zhsng C Z, Wala J, Mermel C H, Sougnez C, Gabriel S B, Hernandez B, Shen H, Laird P W, Getz G, Meyerson M, Beroukhim R. Pan-cancer patterns of somatic copy number alteration. *Nature genetics.* 2013; 45:1134-1140
2. Gibson W J, Hoivik E A, Halle M K, Taylor-Weiner A, Cherniack A D, Berg A, Holst F, Zack T I, Werner H M, Staby K M, Rosenberg M, Stefansson I M, Kusonmano K, Chevalier A, Mauland K K, Trovik J, Krakstad C, Giannakis M, Hodis E, Woie K, Bjorge L, Vintermyr O K, Wala J A, Lawrence M S, Getz G, Carter S L, Beroukhim R, Salvesen H B. The genomic landscape and evolution of endometrial carcinoma progression and abdominopelvic metastasis. *Nature genetics.* 2016; 48:848-855
3. Gerlinger M, Rowan A J, Horswell S, Math M, Larkin J, Endesfelder D, Gronroos E, Martinez P, Matthews N, Stewart A, Tarpey P, Varela I, Phillimore B, Begum S, McDonald N Q Butler A, Jones D, Raine K, Latimer C, Santos C R, Nohadani M, Eklund A C, Spencer-Dene B, Clark C, Pickering L, Stamp G, Gore M, Szallasi Z, Downward J, Futreal P A, Swanton C. Intratumor heterogeneity and branched evolution revealed by multiregion sequencing. *The New England journal of medicine.* 2012; 366:883-892
4. Lawrence M S, Stojanov P, Mermel C H, Robinson J T, Garraway L A, Golub T R, Meyerson M, Gabriel S B, Lander E S, Getz G. Discovery and saturation analysis of cancer genes across 21 tumour types. *Nature.* 2014; 505:495-501
5. Vogelstein B, Papadopoulos N, Velculescu V E, Zhou S, Diaz L A, Jr., Kinzler K W. Cancer genome landscapes. *Science.* 2013; 339:1546-1558
6. Zheng S, Cherniack A D, Dewal N, Moffitt R A, Danilova L, Murray B A, Lerario A M, Else T, Knijnenburg T A, Ciriello G, Kim S, Assie G, Morozova O, Akbani R, Shih J, Hoadley K A, Choueiri T K, Waldmann J, Mete O, Robertson A G, Wu H T, Raphael B J, Shao L, Meyerson M, Demeure M J, Beuschlein F, Gill A J, Sidhu S B, Almeida M Q Fragoso M, Cope L M, Kebebew E, Habra M A, Whitsett T G, Bussey K J, Rainey W E, Asa S L, Bertherat J, Fassnacht M, Wheeler D A, Cancer Genome Atlas Research N, Hammer G D, Giordano T J, Verhaak R G W. Comprehensive pan-genomic characterization of adrenocortical carcinoma. *Cancer cell.* 2016; 29:723-736
7. Compagno M, Lim W K, Grunn A, Nandula S V, Brahmachary M, Shen Q Bertoni F, Ponzoni M, Scandurra M, Califano A, Bhagat G, Chadburn A, Dalla-Favera R, Pasqualucci L. Mutations of multiple genes cause deregulation of nf-kappab in diffuse large b-cell lymphoma. *Nature.* 2009; 459:717-721

Example 2. Genome-Wide Identification of Germline Alleles that Encode Expressed Cell-Surface Proteins that Undergo Loss of Heterozygosity Introduction Inhibitory-CAR-T cells can decrease off-tumor toxicity of CAR-T therapy without decreasing anti-tumor efficacy if the target of the iCAR is expressed only by non-tumor tissues. One such scenario in which iCAR targets will be expressed only by non-tumor cells is where the iCAR antigen is encoded by a portion of the genome that has been deleted in tumor cells. The goal of this section of the workflow is to identify such alleles.

Allele Identification:

We used the Exome Aggregation Consortium (ExAC) database as an input to the analysis (exac.broadinstitute.org). The ExAC database is a compilation of exomes from various population-level sequencing studies totaling 60,706 exomes[1]. ExAC contains information about each variant including the number of counts of the reference allele compared to the alternative allele (allelic frequency). The allelic frequency information is extended to subpopulations within the database as detailed in Table 7.

TABLE 7

Subpopulations within the ExAC database.

| Population ancestry | Population Abbreviation | Number of Individuals |
|---|---|---|
| African | AFR | 5,203 |
| Latino | AMR | 5,789 |
| East Asian | EAS | 4,327 |
| Finnish | FIN | 3,307 |
| Non-Finnish European | NFE | 33,370 |
| South Asian | SAS | 8,256 |
| Other | OTH | 454 |

Note:
Not all positions in genome have sufficient coverage in exome such that all individuals in this table are represented.
Source: http://exac.broadinstitute.org/faq.

The following filters were applied to variants from the ExAC database: i) the variant must affect the amino acid composition of the encoded protein ii) the variant must have a minor allele frequency of greater than 0.05 (5%) in at least one of the populations in Table 6. The analysis corrected for scenarios where the minor allele had an allele fraction greater than 0.5 (50%). If more than three alleles at a site were observed, then the most prevalent substitution was used (these sites are often sites of sequencing error and should be interpreted with caution).

A SNP was counted as having an impact on the composition of the protein if any of the SNP produced any of the following variant classes: 'missense_variant', 'inframe_deletion', 'start_lose,' 'stop_gained', 'inframe_insertion', 'stop_retained_variant', 'frameshift_variant', 'stop_lost', 'coding_sequence_variant', 'protein_altering_variant'. The analysis started with 9,362,319 variants and 29,904 variants passed these two filters. These variants fell in 10,302 genes. All alleles matching these two filters were included in the analysis.

Identification of Expressed Genes:

We used the Genotype-Tissue Expression (GTEX) database v6p (dbGaP Accession phs000424.v6.p1) for the identification of genes that are expressed in various tissue types (https://gtexportal.org/home/)[2]. The GTEX database consists of RNA-sequencing of 8,555 human samples from diverse healthy tissue types. Several annotations were obtained from this database. First, we determined the average expression of each gene across all tissues. The mean expression for each gene was calculated by taking the per-tissue median expression data and computing the mean of these values across tissues. These data were obtained from the file GTEx_Analysis_v6p_RNA-seq_RNA-SeQCv1.1.8_gene_median_rpkm.gct from available at https://gtexportal.org/home/datasets.

The mean expression of each gene corresponding to each tumor type was also included. To obtain these data we created a mapping of tumor types to corresponding normal tissues. For example, the pancreatic cancer TCGA data would be annotated with pancreas tissue from GTEX. In some cases, the mapping was more approximate. For example, the glioblastomas expression data were mapped from all tissues annotated as brain in GTEX. A table with these mappings (titled tcga_disease_tissue_lookup.txt) is attached Several measures were computed to assess the homogeneity or overexpression of each gene in each tissue/tumor type. For each tumor type, a cohen's-D score was computed to establish possible over-expression of the gene. Genes overexpressed in particular tissues, are likely to be good aCAR targets. Conversely, we measured the standard deviation of gene expression across tissues and compared this to the mean expression across all tissues. When this ratio was low, the gene is evenly expressed across all tissues. Genes with even expression across all tissues are likely to be better iCAR targets.

A gene was called "universally expressed" if it met the following criteria: (i) the mean express across tissues was greater than 10 RPKM. (ii) The tissues with the least expression had an RPKM greater than 1. (iii) The ratio of the standard deviation in median RPKM across tissues compared to the mean RPKM was less than 1. Only 1,092 genes were annotated as universally expressed.

Candidates were selected only based on the UniProt annotation. For transmembrane proteins, there is usually clear prediction for segments of the protein that are extracellular.

Table 8 presents a list of 1167 good candidate genes identified by the above method having extracellular polymorphic epitopes sorted according to chromosome location.

Annotation of Alleles

Impact of Allele on Protein Function:

For an iCAR to effectively recognize only cancer cells that have lost one allele of a membrane protein, the protein's structure out to be sufficiently different based on which allele is encoded. Several measures were taken to quantify the effect of each SNP on the resulting protein. First, the reported SNP variant class (e.g. missense, nonsense) was reported in the column 'consequence'. The effect on the consensus protein translation was included in the 'protein_consequence' (e.g., p. Arg482Gln) column. The SIFT algorithm attempts to predict whether a protein variant will have an effect on the protein structure, and therefore function[6]. The score can range from 0 (deleterious) to 1 (benign). SIFT scores (version sift5.2.2) were included for every SNP for which a score was available. Scores are not available for frameshift mutations for example. PolyPhen (v2.2.2) was also used to make prediction on the possibility that a variant may affect protein structure and function. The Polyphen algorithm reports scores in the opposite manner of SIFT, with a score of 0 corresponding to benign and a score of 1 corresponding to deleterious.

One classic measure of an amino acids substitution probability of inducing a structural change is to use the BLOSUM62 substitution matrix. We downloaded the BLOSUM62 matrix from https://www.ncbi.nlm.nih.gov/IEB/ToolBox/C_DOC/lxr/source/data/BLOSUM62. Each SNP was annotated with the BLOSUM62 score corresponding to its substitution.

Classification of Allele as Falling in the Extracellular Portion of the Protein:

For an iCAR to recognize an allele, the allele must fall on the extracellular portion of the protein. For each SNP, we extracted the position of the amino acid affected in the consensus translation and compared this to domains annotated as extracellular from the Uniprot database. The Uniprot database was downloaded from www.uniprot.org/downloads. Many false negatives are possible due to a lack of characterization of the domains of all proteins. A total of 3288 SNPs in 1167 genes were annotated as extracellular (Table 8).

Annotations of Peptide Context of SNP:

The peptide context of the alleles analyzed will likely matter when trying to generate antibodies that recognize these sequences. We include for reference the 10 amino acids preceding and flanking the amino acid encoded by the SNP (21 amino acid sequence total). The uniprot database was used for the consensus amino acid sequence. We annotate any conflicts where the uniprot database sequence did not match the amino acid encoded by either SNP at the predicted position, so as not to include any false sequences. These 21 amino acid sequences could be useful as input to B-cell epitope prediction programs such as Bepipred.

Cancer-Specific Annotations:

Proportion of Tumors Undergoing LOH

Finding patients whose tumors could benefit from the proposed therapy would require an iCAR target would be a SNP that undergoes loss of heterozygosity (LOH) in a large fraction of tumors. Segments copy number files were downloaded from the cbio cancer genomics portal http://www.cbioportal.org/[8]. As an example, the proportion of uveal melanoma tumors undergoing LOH for all SNPs is shown in FIG. 12.

Potential Driver Alterations on Chromosomes Harboring Candidate SNPs

One possible mechanism of resistance genomically targeted therapy is if one of the intended genomic alterations in only present in a fraction of the cancer cells. One mechanism to attempt to identify targets likely to be present in the earliest stages of tumor development is to identify driver events for each tumor. The most frequent mechanism of tumor suppressor gene inactivation is mutation and subsequent LOH of the non-mutated chromosome. We attempted to find driver genes, particularly tumor suppressor genes (TSGs) likely to undergo this process in each tumor type. We used the results of MUTSIG 2.0 run on all tumors in this analysis to identify genes significantly mutated in each tumor type. We annotated whether or not one of the genes that was significantly mutated was included in a list of "hallmark" tumor suppressor genes including TP53, PTEN, APC, MLL3, MLL2, VHL, CDKN2A, RB1. Finally, the list of driver genes, TSG, and "hallmark" TSGs were annotated onto a SNP if they fell on the same chromosome as the SNP.

While mutations in driver genes that subsequently undergo LOH is one mechanism that may mark events likely to occur early in tumor evolution, focal deletion of genomic segments containing a tumor suppressor gene is another. We used the GISTIC algorithm to identify regions of DNA that undergo genomic deletion at a rate higher than average. The GISTIC algorithm identifies "peaks" of statistical significance along chromosome arms that suggest a negative selective pressure on these regions. For each SNP, we recorded the number of deletion peaks on the chromosome that the SNP fell on. We also recorded the lowest q-value of any of these peaks. A lower q-value suggests stronger selective pressure.

Cumulative Score to Rank Candidate SNPs:

In an effort to provide a continuous "score" for the candidate SNPs, we combined several different metrics that should be associated with better SNP candidates. The score consists of the product of the percentile rank of each of the following:
1. proportion of tumors with LOH at that SNP (higher is better) 2. prevalence of the allele (higher is better) 3. ratio of the standard deviation of expression values across tissues to the median (lower is better, more consistent) 4. whether or not there is a tumor suppressor gene on the chromosome (having one is better than not having one)

To illustrate, we will calculate the score for a theoretical SNP. If only 32% of the SNPs had a tumor suppressor gene on the chromosome, then the percentile rank for having one would be 0.68. If the allele had a minor allele fraction of 0.49 (where 0.5 is the highest possible), then the percentile rank would be 0.99. If the rate of LOH was 0.10, and 75% of SNPs had more LOH than that, then the percentile rank would be 0.25. If the ratio of standard deviation of expression values across tissues to the median for the gene harboring this SNP was 1.3 and that is better than 90% of other genes, then the percentile rank is 0.9. The total score for this SNP would then be 0.68*0.99*0.25*0.9=0.15.

Any SNP with a score greater than 0.4 was considered "top-hit".

TABLE 8

Exemplary iCAR Targets

| Chr. No. | Gene |
|---|---|
| 1 | ABCA4 |
| 1 | ADAM30 |
| 1 | ASTN1 |
| 1 | C1orf101 |
| 1 | CACNA1S |
| 1 | CATSPER4 |
| 1 | CD101 |
| 1 | CD164L2 |
| 1 | CD1A |
| 1 | CD1C |
| 1 | CD244 |
| 1 | CD34 |
| 1 | CELSR2 |
| 1 | CHRNB2 |
| 1 | CLCA2 |
| 1 | CLSTN1 |
| 1 | CR1 |
| 1 | CR2 |
| 1 | CRB1 |
| 1 | CSF3R |
| 1 | CSMD2 |
| 1 | ECE1 |
| 1 | ELTD1 |
| 1 | EMC1 |
| 1 | EPHA10 |
| 1 | EPHA2 |
| 1 | ERMAP |
| 1 | FCAMR |
| 1 | FCER1A |
| 1 | FCGR1B |
| 1 | FCGR2A |
| 1 | FCGR2B |
| 1 | FCGR3A |
| 1 | FCRL1 |
| 1 | FCRL3 |
| 1 | FCRL4 |
| 1 | FCRL5 |
| 1 | FCRL6 |
| 1 | GJB4 |
| 1 | GPA33 |
| 1 | GPR157 |
| 1 | GPR37L1 |
| 1 | GPR88 |
| 1 | HCRTR1 |
| 1 | IGSF3 |
| 1 | IGSF9 |

TABLE 8-continued

Exemplary iCAR Targets

| Chr. No. | Gene |
|---|---|
| 1 | IL22RA1 |
| 1 | ITGA10 |
| 1 | KIAA1324 |
| 1 | KIAA2013 |
| 1 | LDLRAD2 |
| 1 | LEPR |
| 1 | LRIG2 |
| 1 | LRP8 |
| 1 | LRRC52 |
| 1 | LRRC8B |
| 1 | LRRN2 |
| 1 | LY9 |
| 1 | MR1 |
| 1 | MUC1 |
| 1 | MXRA8 |
| 1 | NCSTN |
| 1 | NFASC |
| 1 | NOTCH2 |
| 1 | NPR1 |
| 1 | NTRK1 |
| 1 | OPN3 |
| 1 | OR10J1 |
| 1 | OR10J4 |
| 1 | OR10K1 |
| 1 | OR10R2 |
| 1 | OR10T2 |
| 1 | OR10X1 |
| 1 | OR11L1 |
| 1 | OR14A16 |
| 1 | OR14I1 |
| 1 | OR14K1 |
| 1 | OR2AK2 |
| 1 | OR2C3 |
| 1 | OR2G2 |
| 1 | OR2G3 |
| 1 | OR2L2 |
| 1 | OR2M7 |
| 1 | OR2T1 |
| 1 | OR2T12 |
| 1 | OR2T27 |
| 1 | OR2T29 |
| 1 | OR2T3 |
| 1 | OR2T33 |
| 1 | OR2T34 |
| 1 | OR2T35 |
| 1 | OR2T4 |
| 1 | OR2T5 |
| 1 | OR2T6 |
| 1 | OR2T7 |
| 1 | OR2T8 |
| 1 | OR2W3 |
| 1 | OR6F1 |
| 1 | OR6K2 |
| 1 | OR6K3 |
| 1 | OR6K6 |
| 1 | OR6N1 |
| 1 | OR6P1 |
| 1 | OR6Y1 |
| 1 | PEAR1 |
| 1 | PIGR |
| 1 | PLXNA2 |
| 1 | PTCH2 |
| 1 | PTCHD2 |
| 1 | PTGFRN |
| 1 | PTPRC |
| 1 | PTPRF |
| 1 | PVRL4 |
| 1 | RXFP4 |
| 1 | S1PR1 |
| 1 | SCNN1D |
| 1 | SDC3 |
| 1 | SELE |
| 1 | SELL |
| 1 | SELP |
| 1 | SEMA4A |
| 1 | SEMA6C |

TABLE 8-continued

Exemplary iCAR Targets

| Chr. No. | Gene |
| --- | --- |
| 1 | SLAMF7 |
| 1 | SLAMF9 |
| 1 | SLC2A7 |
| 1 | SLC5A9 |
| 1 | TACSTD2 |
| 1 | TAS1R2 |
| 1 | TIE1 |
| 1 | TLR5 |
| 1 | TMEM81 |
| 1 | TNFRSF14 |
| 1 | TNFRSF1B |
| 1 | TRABD2B |
| 1 | USH2A |
| 1 | VCAM1 |
| 1 | ZP4 |
| 2 | ABCG5 |
| 2 | ALK |
| 2 | ASPRV1 |
| 2 | ATRAID |
| 2 | CD207 |
| 2 | CHRNG |
| 2 | CLEC4F |
| 2 | CNTNAP5 |
| 2 | CRIM1 |
| 2 | CXCR1 |
| 2 | DNER |
| 2 | DPP10 |
| 2 | EDAR |
| 2 | EPCAM |
| 2 | GPR113 |
| 2 | GPR148 |
| 2 | GPR35 |
| 2 | GPR39 |
| 2 | IL1RL1 |
| 2 | ITGA4 |
| 2 | ITGA6 |
| 2 | ITGAV |
| 2 | LCT |
| 2 | LHCGR |
| 2 | LRP1B |
| 2 | LRP2 |
| 2 | LY75 |
| 2 | MARCO |
| 2 | MERTK |
| 2 | NRP2 |
| 2 | OR6B2 |
| 2 | PLA2R1 |
| 2 | PLB1 |
| 2 | PROKR1 |
| 2 | PROM2 |
| 2 | SCN7A |
| 2 | SDC1 |
| 2 | TGOLN2 |
| 2 | THSD7B |
| 2 | TMEFF2 |
| 2 | TMEM178A |
| 2 | TPO |
| 2 | TRABD2A |
| 3 | ACKR2 |
| 3 | ALCAM |
| 3 | ANO10 |
| 3 | ATP13A4 |
| 3 | CACNA1D |
| 3 | CACNA2D2 |
| 3 | CACNA2D3 |
| 3 | CASR |
| 3 | CCRL2 |
| 3 | CD200 |
| 3 | CD200R1 |
| 3 | CD86 |
| 3 | CD96 |
| 3 | CDCP1 |
| 3 | CDHR4 |
| 3 | CELSR3 |
| 3 | CHL1 |
| 3 | CLDN11 |
| 3 | CLDN18 |
| 3 | CLSTN2 |
| 3 | CSPG5 |
| 3 | CX3CR1 |
| 3 | CXCR6 |
| 3 | DCBLD2 |
| 3 | DRD3 |
| 3 | EPHB3 |
| 3 | GABRR3 |
| 3 | GP5 |
| 3 | GPR128 |
| 3 | GPR15 |
| 3 | GPR27 |
| 3 | GRM2 |
| 3 | GRM7 |
| 3 | HEG1 |
| 3 | HTR3C |
| 3 | HTR3D |
| 3 | HTR3E |
| 3 | IGSF11 |
| 3 | IL17RC |
| 3 | IL17RD |
| 3 | IL17RE |
| 3 | IL5RA |
| 3 | IMPG2 |
| 3 | ITGA9 |
| 3 | ITGB5 |
| 3 | KCNMB3 |
| 3 | LRIG1 |
| 3 | LRRC15 |
| 3 | LRRN1 |
| 3 | MST1R |
| 3 | NAALADL2 |
| 3 | NRROS |
| 3 | OR5AC1 |
| 3 | OR5H1 |
| 3 | OR5H14 |
| 3 | OR5H15 |
| 3 | OR5H6 |
| 3 | OR5K2 |
| 3 | OR5K3 |
| 3 | OR5K4 |
| 3 | PLXNB1 |
| 3 | PLXND1 |
| 3 | PRRT3 |
| 3 | PTPRG |
| 3 | ROBO2 |
| 3 | RYK |
| 3 | SEMA5B |
| 3 | SIDT1 |
| 3 | SLC22A14 |
| 3 | SLC33A1 |
| 3 | SLC4A7 |
| 3 | SLITRK3 |
| 3 | STAB1 |
| 3 | SUSD5 |
| 3 | TFRC |
| 3 | TLR9 |
| 3 | TMEM44 |
| 3 | TMPRSS7 |
| 3 | TNFSF10 |
| 3 | UPK1B |
| 3 | VIPR1 |
| 3 | ZPLD1 |
| 4 | ANTXR2 |
| 4 | BTC |
| 4 | CNGA1 |
| 4 | CORIN |
| 4 | EGF |
| 4 | EMCN |
| 4 | ENPEP |
| 4 | EPHA5 |
| 4 | ERVMER34-1 |
| 4 | EVC2 |
| 4 | FAT1 |
| 4 | FAT4 |

TABLE 8-continued

Exemplary iCAR Targets

| Chr. No. | Gene |
|---|---|
| 4 | FGFRL1 |
| 4 | FRAS1 |
| 4 | GPR125 |
| 4 | GRID2 |
| 4 | GYPA |
| 4 | GYPB |
| 4 | KDR |
| 4 | KIAA0922 |
| 4 | KLB |
| 4 | MFSD8 |
| 4 | PARM1 |
| 4 | PDGFRA |
| 4 | RNF150 |
| 4 | TENM3 |
| 4 | TLR1 |
| 4 | TLR10 |
| 4 | TLR6 |
| 4 | TMEM156 |
| 4 | TMPRSS11A |
| 4 | TMPRSS11B |
| 4 | TMPRSS11E |
| 4 | TMPRSS11F |
| 4 | UNC5C |
| 5 | ADAM19 |
| 5 | ADRB2 |
| 5 | BTNL3 |
| 5 | BTNL8 |
| 5 | BTNL9 |
| 5 | C5orf15 |
| 5 | CATSPER3 |
| 5 | CD180 |
| 5 | CDH12 |
| 5 | CDHR2 |
| 5 | COL23A1 |
| 5 | CSF1R |
| 5 | F2RL2 |
| 5 | FAM174A |
| 5 | FAT2 |
| 5 | FGFR4 |
| 5 | FLT4 |
| 5 | GABRA6 |
| 5 | GABRG2 |
| 5 | GPR151 |
| 5 | GPR98 |
| 5 | GRM6 |
| 5 | HAVCR1 |
| 5 | HAVCR2 |
| 5 | IL31RA |
| 5 | IL6ST |
| 5 | IL7R |
| 5 | ITGA1 |
| 5 | ITGA2 |
| 5 | KCNMB1 |
| 5 | LIFR |
| 5 | LNPEP |
| 5 | MEGF10 |
| 5 | NIPAL4 |
| 5 | OR2V1 |
| 5 | OR2Y1 |
| 5 | OSMR |
| 5 | PCDH1 |
| 5 | PCDH12 |
| 5 | PCDHA1 |
| 5 | PCDHA2 |
| 5 | PCDHA4 |
| 5 | PCDHA8 |
| 5 | PCDHA9 |
| 5 | PCDHB10 |
| 5 | PCDHB11 |
| 5 | PCDHB13 |
| 5 | PCDHB14 |
| 5 | PCDHB15 |
| 5 | PCDHB16 |
| 5 | PCDHB2 |
| 5 | PCDHB3 |
| 5 | PCDHB4 |
| 5 | PCDHB5 |
| 5 | PCDHB6 |
| 5 | PCDHGA1 |
| 5 | PCDHGA4 |
| 5 | PDGFRB |
| 5 | PRLR |
| 5 | SEMA5A |
| 5 | SEMA6A |
| 5 | SGCD |
| 5 | SLC1A3 |
| 5 | SLC22A4 |
| 5 | SLC22A5 |
| 5 | SLC36A3 |
| 5 | SLC6A18 |
| 5 | SLC6A19 |
| 5 | SLCO6A1 |
| 5 | SV2C |
| 5 | TENM2 |
| 5 | TIMD4 |
| 5 | UGT3A1 |
| 6 | BAI3 |
| 6 | BTN1A1 |
| 6 | BTN2A1 |
| 6 | BTN2A2 |
| 6 | BTN3A2 |
| 6 | BTNL2 |
| 6 | CD83 |
| 6 | DCBLD1 |
| 6 | DLL1 |
| 6 | DPCR1 |
| 6 | ENPP1 |
| 6 | ENPP3 |
| 6 | ENPP4 |
| 6 | EPHA7 |
| 6 | GABBR1 |
| 6 | GABRR1 |
| 6 | GCNT6 |
| 6 | GFRAL |
| 6 | GJB7 |
| 6 | GLP1R |
| 6 | GPR110 |
| 6 | GPR111 |
| 6 | GPR116 |
| 6 | GPR126 |
| 6 | GPR63 |
| 6 | GPRC6A |
| 6 | HFE |
| 6 | HLA-A |
| 6 | HLA-B |
| 6 | HLA-C |
| 6 | HLA-DPA1 |
| 6 | HLA-DPB1 |
| 6 | HLA-DQA1 |
| 6 | HLA-DQA2 |
| 6 | HLA-DQB1 |
| 6 | HLA-DQB2 |
| 6 | HLA-DRB1 |
| 6 | HLA-DRB5 |
| 6 | HLA-E |
| 6 | HLA-F |
| 6 | HLA-G |
| 6 | IL20RA |
| 6 | ITPR3 |
| 6 | KIAA0319 |
| 6 | LMBRD1 |
| 6 | LRFN2 |
| 6 | LRP11 |
| 6 | MAS1L |
| 6 | MEP1A |
| 6 | MICA |
| 6 | MICB |
| 6 | MUC21 |
| 6 | MUC22 |
| 6 | NCR2 |
| 6 | NOTCH4 |
| 6 | OPRM1 |

TABLE 8-continued

Exemplary iCAR Targets

| Chr. No. | Gene |
|---|---|
| 6 | OR10C1 |
| 6 | OR12D2 |
| 6 | OR12D3 |
| 6 | OR14J1 |
| 6 | OR2B2 |
| 6 | OR2B6 |
| 6 | OR2J1 |
| 6 | OR2W1 |
| 6 | OR5V1 |
| 6 | PKHD1 |
| 6 | PTCRA |
| 6 | RAET1E |
| 6 | RAET1G |
| 6 | ROS1 |
| 6 | SDIM1 |
| 6 | SLC22A1 |
| 6 | SLC44A4 |
| 6 | TAAR2 |
| 6 | TREM1 |
| 6 | TREML1 |
| 6 | TREML2 |
| 7 | AQP1 |
| 7 | CD36 |
| 7 | CDHR3 |
| 7 | CNTNAP2 |
| 7 | DPP6 |
| 7 | EGFR |
| 7 | EPHA1 |
| 7 | EPHB6 |
| 7 | ERVW-1 |
| 7 | GHRHR |
| 7 | GJC3 |
| 7 | GPNMB |
| 7 | GRM8 |
| 7 | HYAL4 |
| 7 | KIAA1324L |
| 7 | LRRN3 |
| 7 | MET |
| 7 | MUC12 |
| 7 | MUC17 |
| 7 | NPC1L1 |
| 7 | NPSR1 |
| 7 | OR2A12 |
| 7 | OR2A14 |
| 7 | OR2A2 |
| 7 | OR2A25 |
| 7 | OR2A42 |
| 7 | OR2A7 |
| 7 | OR2AE1 |
| 7 | OR2F2 |
| 7 | OR6V1 |
| 7 | PILRA |
| 7 | PKD1L1 |
| 7 | PLXNA4 |
| 7 | PODXL |
| 7 | PTPRN2 |
| 7 | PTPRZ1 |
| 7 | RAMP3 |
| 7 | SLC29A4 |
| 7 | SMO |
| 7 | TAS2R16 |
| 7 | TAS2R4 |
| 7 | TAS2R40 |
| 7 | TFR2 |
| 7 | THSD7A |
| 7 | TMEM213 |
| 7 | TTYH3 |
| 7 | ZAN |
| 7 | ZP3 |
| 8 | ADAM18 |
| 8 | ADAM28 |
| 8 | ADAM32 |
| 8 | ADAM7 |
| 8 | ADAM9 |
| 8 | CDH17 |
| 8 | CHRNA2 |

TABLE 8-continued

Exemplary iCAR Targets

| Chr. No. | Gene |
|---|---|
| 8 | CSMD1 |
| 8 | CSMD3 |
| 8 | DCSTAMP |
| 8 | FZD6 |
| 8 | GPR124 |
| 8 | NRG1 |
| 8 | OR4F21 |
| 8 | PKHD1L1 |
| 8 | PRSS55 |
| 8 | SCARA3 |
| 8 | SCARA5 |
| 8 | SDC2 |
| 8 | SLC10A5 |
| 8 | SLC39A14 |
| 8 | SLC39A4 |
| 8 | SLCO5A1 |
| 8 | TNFRSF10A |
| 8 | TNFRSF10B |
| 9 | ABCA1 |
| 9 | AQP7 |
| 9 | C9orf135 |
| 9 | CA9 |
| 9 | CD72 |
| 9 | CNTNAP3 |
| 9 | CNTNAP3B |
| 9 | ENTPD8 |
| 9 | GPR144 |
| 9 | GRIN3A |
| 9 | IZUMO3 |
| 9 | KIAA1161 |
| 9 | MAMDC4 |
| 9 | MEGF9 |
| 9 | MUSK |
| 9 | NOTCH1 |
| 9 | OR13C2 |
| 9 | OR13C3 |
| 9 | OR13C5 |
| 9 | OR13C8 |
| 9 | OR13C9 |
| 9 | OR13D1 |
| 9 | OR13F1 |
| 9 | OR1B1 |
| 9 | OR1J2 |
| 9 | OR1K1 |
| 9 | OR1L1 |
| 9 | OR1L3 |
| 9 | OR1L6 |
| 9 | OR1L8 |
| 9 | OR1N1 |
| 9 | OR1N2 |
| 9 | OR1Q1 |
| 9 | OR2S2 |
| 9 | PCSK5 |
| 9 | PLGRKT |
| 9 | PTPRD |
| 9 | ROR2 |
| 9 | SEMA4D |
| 9 | SLC31A1 |
| 9 | TEK |
| 9 | TLR4 |
| 9 | TMEM2 |
| 9 | VLDLR |
| 10 | ABCC2 |
| 10 | ADAM8 |
| 10 | ADRB1 |
| 10 | ANTXRL |
| 10 | ATRNL1 |
| 10 | C10orf54 |
| 10 | CDH23 |
| 10 | CDHR1 |
| 10 | CNNM2 |
| 10 | COL13A1 |
| 10 | COL17A1 |
| 10 | ENTPD1 |
| 10 | FGFR2 |
| 10 | FZD8 |

TABLE 8-continued

Exemplary iCAR Targets

| Chr. No. | Gene |
|---|---|
| 10 | GPR158 |
| 10 | GRID1 |
| 10 | IL15RA |
| 10 | IL2RA |
| 10 | ITGA8 |
| 10 | ITGB1 |
| 10 | MRC1 |
| 10 | NPFFR1 |
| 10 | NRP1 |
| 10 | OPN4 |
| 10 | PCDH15 |
| 10 | PKD2L1 |
| 10 | PLXDC2 |
| 10 | PRLHR |
| 10 | RGR |
| 10 | SLC29A3 |
| 10 | SLC39A12 |
| 10 | TACR2 |
| 10 | TCTN3 |
| 10 | TSPAN15 |
| 10 | UNC5B |
| 10 | VSTM4 |
| 11 | AMICA1 |
| 11 | ANO3 |
| 11 | APLP2 |
| 11 | C11orf24 |
| 11 | CCKBR |
| 11 | CD248 |
| 11 | CD44 |
| 11 | CD5 |
| 11 | CD6 |
| 11 | CDON |
| 11 | CLMP |
| 11 | CRTAM |
| 11 | DCHS1 |
| 11 | DSCAML1 |
| 11 | FAT3 |
| 11 | FOLH1 |
| 11 | GDPD4 |
| 11 | GDPD5 |
| 11 | GRIK4 |
| 11 | HEPHL1 |
| 11 | HTR3B |
| 11 | IFITM10 |
| 11 | IL10RA |
| 11 | KIRREL3 |
| 11 | LGR4 |
| 11 | LRP4 |
| 11 | LRP5 |
| 11 | LRRC32 |
| 11 | MCAM |
| 11 | MFRP |
| 11 | MPEG1 |
| 11 | MRGPRE |
| 11 | MRGPRF |
| 11 | MRGPRG |
| 11 | MRGPRX2 |
| 11 | MRGPRX3 |
| 11 | MRGPRX4 |
| 11 | MS4A4A |
| 11 | MTNR1B |
| 11 | MUC15 |
| 11 | NAALAD2 |
| 11 | NAALADL1 |
| 11 | NCAM1 |
| 11 | NRXN2 |
| 11 | OR10A2 |
| 11 | OR10A5 |
| 11 | OR10A6 |
| 11 | OR10D3 |
| 11 | OR10G4 |
| 11 | OR10G7 |
| 11 | OR10G8 |
| 11 | OR10G9 |
| 11 | OR10Q1 |
| 11 | OR10S1 |

TABLE 8-continued

Exemplary iCAR Targets

| Chr. No. | Gene |
|---|---|
| 11 | OR1S1 |
| 11 | OR2AG1 |
| 11 | OR2AG2 |
| 11 | OR2D2 |
| 11 | OR4A15 |
| 11 | OR4A47 |
| 11 | OR4A5 |
| 11 | OR4A8P |
| 11 | OR4C11 |
| 11 | OR4C13 |
| 11 | OR4C15 |
| 11 | OR4C16 |
| 11 | OR4C3 |
| 11 | OR4C46 |
| 11 | OR4C5 |
| 11 | OR4D6 |
| 11 | OR4D9 |
| 11 | OR4S2 |
| 11 | OR4X1 |
| 11 | OR51E1 |
| 11 | OR51L1 |
| 11 | OR52A1 |
| 11 | OR52E1 |
| 11 | OR52E2 |
| 11 | OR52E4 |
| 11 | OR52E6 |
| 11 | OR52I1 |
| 11 | OR52I2 |
| 11 | OR52J3 |
| 11 | OR52L1 |
| 11 | OR52N1 |
| 11 | OR52N2 |
| 11 | OR52N4 |
| 11 | OR52W1 |
| 11 | OR56B1 |
| 11 | OR56B4 |
| 11 | OR5A1 |
| 11 | OR5A2 |
| 11 | OR5AK2 |
| 11 | OR5AR1 |
| 11 | OR5B17 |
| 11 | OR5B3 |
| 11 | OR5D14 |
| 11 | OR5D16 |
| 11 | OR5D18 |
| 11 | OR5F1 |
| 11 | OR5I1 |
| 11 | OR5L2 |
| 11 | OR5M11 |
| 11 | OR5M3 |
| 11 | OR5P2 |
| 11 | OR5R1 |
| 11 | OR5T2 |
| 11 | OR5T3 |
| 11 | OR5W2 |
| 11 | OR6A2 |
| 11 | OR6T1 |
| 11 | OR6X1 |
| 11 | OR8A1 |
| 11 | OR8B12 |
| 11 | OR8B2 |
| 11 | OR8B3 |
| 11 | OR8B4 |
| 11 | OR8D1 |
| 11 | OR8D2 |
| 11 | OR8H1 |
| 11 | OR8H2 |
| 11 | OR8H3 |
| 11 | OR8I2 |
| 11 | OR8J1 |
| 11 | OR8J2 |
| 11 | OR8J3 |
| 11 | OR8K1 |
| 11 | OR8K3 |
| 11 | OR8K5 |
| 11 | OR8U1 |

TABLE 8-continued

Exemplary iCAR Targets

| Chr. No. | Gene |
|---|---|
| 11 | OR9G1 |
| 11 | OR9G4 |
| 11 | OR9Q2 |
| 11 | P2RX3 |
| 11 | PTPRJ |
| 11 | ROBO3 |
| 11 | SIGIRR |
| 11 | SLC22A10 |
| 11 | SLC3A2 |
| 11 | SLC5A12 |
| 11 | SLCO2B1 |
| 11 | SORL1 |
| 11 | ST14 |
| 11 | SYT8 |
| 11 | TENM4 |
| 11 | TMEM123 |
| 11 | TMPRSS4 |
| 11 | TMPRSS5 |
| 11 | TRPM5 |
| 11 | TSPAN18 |
| 11 | ZP1 |
| 12 | ANO4 |
| 12 | AVPR1A |
| 12 | CACNA2D4 |
| 12 | CD163 |
| 12 | CD163L1 |
| 12 | CD27 |
| 12 | CD4 |
| 12 | CLEC12A |
| 12 | CLEC2A |
| 12 | CLEC4C |
| 12 | CLEC7A |
| 12 | CLECL1 |
| 12 | CLSTN3 |
| 12 | GPR133 |
| 12 | GPRC5D |
| 12 | ITGA7 |
| 12 | ITGB7 |
| 12 | KLRB1 |
| 12 | KLRC2 |
| 12 | KLRC3 |
| 12 | KLRC4 |
| 12 | KLRF1 |
| 12 | KLRF2 |
| 12 | LRP1 |
| 12 | LRP6 |
| 12 | MANSC1 |
| 12 | MANSC4 |
| 12 | OLR1 |
| 12 | OR10AD1 |
| 12 | OR10P1 |
| 12 | OR2AP1 |
| 12 | OR6C1 |
| 12 | OR6C2 |
| 12 | OR6C3 |
| 12 | OR6C4 |
| 12 | OR6C6 |
| 12 | OR6C74 |
| 12 | OR6C76 |
| 12 | OR8S1 |
| 12 | OR9K2 |
| 12 | ORAI1 |
| 12 | P2RX4 |
| 12 | P2RX7 |
| 12 | PTPRB |
| 12 | PTPRQ |
| 12 | SCNN1A |
| 12 | SELPLG |
| 12 | SLC38A4 |
| 12 | SLC5A8 |
| 12 | SLC6A15 |
| 12 | SLC8B1 |
| 12 | SLCO1B1 |
| 12 | SLCO1B7 |
| 12 | SSPN |
| 12 | STAB2 |
| 12 | TAS2R10 |
| 12 | TAS2R13 |
| 12 | TAS2R20 |
| 12 | TAS2R30 |
| 12 | TAS2R31 |
| 12 | TAS2R42 |
| 12 | TAS2R43 |
| 12 | TAS2R46 |
| 12 | TAS2R7 |
| 12 | TMEM119 |
| 12 | TMEM132B |
| 12 | TMEM132C |
| 12 | TMEM132D |
| 12 | TMPRSS12 |
| 12 | TNFRSF1A |
| 12 | TSPAN8 |
| 12 | VSIG10 |
| 13 | ATP4B |
| 13 | ATP7B |
| 13 | FLT3 |
| 13 | FREM2 |
| 13 | KL |
| 13 | PCDH8 |
| 13 | SGCG |
| 13 | SHISA2 |
| 13 | SLC15A1 |
| 13 | SLITRK6 |
| 13 | TNFRSF19 |
| 14 | ADAM21 |
| 14 | BDKRB2 |
| 14 | C14orf37 |
| 14 | CLEC14A |
| 14 | DLK1 |
| 14 | FLRT2 |
| 14 | GPR135 |
| 14 | GPR137C |
| 14 | JAG2 |
| 14 | LTB4R2 |
| 14 | MMP14 |
| 14 | OR11G2 |
| 14 | OR11H12 |
| 14 | OR11H6 |
| 14 | OR4K1 |
| 14 | OR4K15 |
| 14 | OR4K5 |
| 14 | OR4L1 |
| 14 | OR4N2 |
| 14 | OR4N5 |
| 14 | OR4Q2 |
| 14 | SLC24A4 |
| 14 | SYNDIG1L |
| 15 | ANPEP |
| 15 | CD276 |
| 15 | CHRNA7 |
| 15 | CHRNB4 |
| 15 | CSPG4 |
| 15 | DUOX1 |
| 15 | DUOX2 |
| 15 | FAM174B |
| 15 | GLDN |
| 15 | IGDCC4 |
| 15 | ITGA11 |
| 15 | LCTL |
| 15 | LTK |
| 15 | LYSMD4 |
| 15 | MEGF11 |
| 15 | NRG4 |
| 15 | OCA2 |
| 15 | OR4F4 |
| 15 | OR4M2 |
| 15 | OR4N4 |
| 15 | PRTG |
| 15 | RHCG |
| 15 | SCAMP5 |
| 15 | SEMA4B |
| 15 | SEMA6D |

TABLE 8-continued

Exemplary iCAR Targets

| Chr. No. | Gene |
| --- | --- |
| 15 | SLC24A1 |
| 15 | SLC28A1 |
| 15 | TRPM1 |
| 15 | TYRO3 |
| 16 | ATP2C2 |
| 16 | CACNA1H |
| 16 | CD19 |
| 16 | CDH11 |
| 16 | CDH16 |
| 16 | CDH3 |
| 16 | CDH5 |
| 16 | CNGB1 |
| 16 | CNTNAP4 |
| 16 | GDPD3 |
| 16 | GPR56 |
| 16 | GPR97 |
| 16 | IL4R |
| 16 | ITFG3 |
| 16 | ITGAL |
| 16 | ITGAM |
| 16 | ITGAX |
| 16 | KCNG4 |
| 16 | MMP15 |
| 16 | MSLNL |
| 16 | NOMO1 |
| 16 | NOMO3 |
| 16 | OR2C1 |
| 16 | PKD1 |
| 16 | PKD1L2 |
| 16 | SCNN1B |
| 16 | SEZ6L2 |
| 16 | SLC22A31 |
| 16 | SLC5A11 |
| 16 | SLC7A6 |
| 16 | SPN |
| 16 | TMC5 |
| 16 | TMC7 |
| 16 | TMEM204 |
| 16 | TMEM219 |
| 16 | TMEM8A |
| 17 | ABCC3 |
| 17 | ACE |
| 17 | AOC3 |
| 17 | ASGR2 |
| 17 | C17orf80 |
| 17 | CD300A |
| 17 | CD300C |
| 17 | CD300E |
| 17 | CD300LG |
| 17 | CHRNB1 |
| 17 | CLEC10A |
| 17 | CNTNAP1 |
| 17 | CPD |
| 17 | CXCL16 |
| 17 | FAM171A2 |
| 17 | GCGR |
| 17 | GLP2R |
| 17 | GP1BA |
| 17 | GPR142 |
| 17 | GUCY2D |
| 17 | ITGA2B |
| 17 | ITGA3 |
| 17 | ITGAE |
| 17 | ITGB3 |
| 17 | KCNJ12 |
| 17 | LRRC37A |
| 17 | LRRC37A2 |
| 17 | LRRC37A3 |
| 17 | LRRC37B |
| 17 | MRC2 |
| 17 | NGFR |
| 17 | OR1A2 |
| 17 | OR1D2 |
| 17 | OR1G1 |
| 17 | OR3A1 |
| 17 | OR3A2 |

TABLE 8-continued

Exemplary iCAR Targets

| Chr. No. | Gene |
| --- | --- |
| 17 | OR4D1 |
| 17 | OR4D2 |
| 17 | RNF43 |
| 17 | SCN4A |
| 17 | SDK2 |
| 17 | SECTM1 |
| 17 | SEZ6 |
| 17 | SLC26A11 |
| 17 | SPACA3 |
| 17 | TMEM102 |
| 17 | TMEM132E |
| 17 | TNFSF12 |
| 17 | TRPV3 |
| 17 | TTYH2 |
| 17 | TUSC5 |
| 18 | APCDD1 |
| 18 | CDH19 |
| 18 | CDH20 |
| 18 | CDH7 |
| 18 | COLEC12 |
| 18 | DCC |
| 18 | DSC1 |
| 18 | DSG1 |
| 18 | DSG3 |
| 18 | DYNAP |
| 18 | MEP1B |
| 18 | PTPRM |
| 18 | SIGLEC15 |
| 18 | TNFRSF11A |
| 19 | ABCA7 |
| 19 | ACPT |
| 19 | BCAM |
| 19 | C19orf38 |
| 19 | C19orf59 |
| 19 | C5AR1 |
| 19 | CATSPERD |
| 19 | CATSPERG |
| 19 | CD320 |
| 19 | CD33 |
| 19 | CD97 |
| 19 | CEACAM1 |
| 19 | CEACAM19 |
| 19 | CEACAM21 |
| 19 | CEACAM3 |
| 19 | CEACAM4 |
| 19 | CLEC4M |
| 19 | DLL3 |
| 19 | EMR1 |
| 19 | EMR2 |
| 19 | EMR3 |
| 19 | ERVV-1 |
| 19 | ERVV-2 |
| 19 | FAM187B |
| 19 | FCAR |
| 19 | FFAR3 |
| 19 | FPR1 |
| 19 | GFY |
| 19 | GP6 |
| 19 | GPR42 |
| 19 | GRIN3B |
| 19 | ICAM3 |
| 19 | IGFLR1 |
| 19 | IL12RB1 |
| 19 | IL27RA |
| 19 | KIR2DL1 |
| 19 | KIR2DL3 |
| 19 | KIR2DL4 |
| 19 | KIR3DL1 |
| 19 | KIR3DL2 |
| 19 | KIR3DL3 |
| 19 | KIRREL2 |
| 19 | KISS1R |
| 19 | LAIR1 |
| 19 | LDLR |
| 19 | LILRA1 |
| 19 | LILRA2 |

TABLE 8-continued

Exemplary iCAR Targets

| Chr. No. | Gene |
|---|---|
| 19 | LILRA4 |
| 19 | LILRA6 |
| 19 | LILRB1 |
| 19 | LILRB2 |
| 19 | LILRB3 |
| 19 | LILRB4 |
| 19 | LILRB5 |
| 19 | LINGO3 |
| 19 | LPHN1 |
| 19 | LRP3 |
| 19 | MADCAM1 |
| 19 | MAG |
| 19 | MEGF8 |
| 19 | MUC16 |
| 19 | NCR1 |
| 19 | NOTCH3 |
| 19 | NPHS1 |
| 19 | OR10H1 |
| 19 | OR10H2 |
| 19 | OR10H3 |
| 19 | OR10H4 |
| 19 | OR1I1 |
| 19 | OR2Z1 |
| 19 | OR7A10 |
| 19 | OR7C1 |
| 19 | OR7D4 |
| 19 | OR7E24 |
| 19 | OR7G1 |
| 19 | OR7G2 |
| 19 | OR7G3 |
| 19 | PLVAP |
| 19 | PTGIR |
| 19 | PTPRH |
| 19 | PTPRS |
| 19 | PVR |
| 19 | SCN1B |
| 19 | SHISA7 |
| 19 | SIGLEC10 |
| 19 | SIGLEC11 |
| 19 | SIGLEC12 |
| 19 | SIGLEC5 |
| 19 | SIGLEC6 |
| 19 | SIGLEC8 |
| 19 | SIGLEC9 |
| 19 | SLC44A2 |
| 19 | SLC5A5 |
| 19 | SLC7A9 |
| 19 | TARM1 |
| 19 | TGFBR3L |
| 19 | TMC4 |
| 19 | TMEM91 |
| 19 | TMPRSS9 |
| 19 | TNFSF14 |
| 19 | TNFSF9 |
| 19 | TRPM4 |
| 19 | VN1R2 |
| 19 | VSIG10L |
| 19 | VSTM2B |
| 20 | ABHD12 |
| 20 | ADAM33 |
| 20 | ADRA1D |
| 20 | APMAP |
| 20 | ATRN |
| 20 | CD40 |
| 20 | CD93 |
| 20 | CDH22 |
| 20 | CDH26 |
| 20 | CDH4 |
| 20 | FLRT3 |
| 20 | GCNT7 |
| 20 | GGT7 |
| 20 | JAG1 |
| 20 | LRRN4 |
| 20 | NPBWR2 |
| 20 | OCSTAMP |
| 20 | PTPRA |
| 20 | PTPRT |
| 20 | SEL1L2 |
| 20 | SIGLEC1 |
| 20 | SIRPA |
| 20 | SIRPB1 |
| 20 | SIRPG |
| 20 | SLC24A3 |
| 20 | SLC2A10 |
| 20 | SSTR4 |
| 20 | THBD |
| 21 | CLDN8 |
| 21 | DSCAM |
| 21 | ICOSLG |
| 21 | IFNAR1 |
| 21 | IFNGR2 |
| 21 | IGSF5 |
| 21 | ITGB2 |
| 21 | KCNJ15 |
| 21 | NCAM2 |
| 21 | TMPRSS15 |
| 21 | TMPRSS2 |
| 21 | TMPRSS3 |
| 21 | TRPM2 |
| 21 | UMODL1 |
| 22 | CACNA1I |
| 22 | CELSR1 |
| 22 | COMT |
| 22 | CSF2RB |
| 22 | GGT1 |
| 22 | GGT5 |
| 22 | IL2RB |
| 22 | KREMEN1 |
| 22 | MCHR1 |
| 22 | OR11H1 |
| 22 | P2RX6 |
| 22 | PKDREJ |
| 22 | PLXNB2 |
| 22 | SCARF2 |
| 22 | SEZ6L |
| 22 | SSTR3 |
| 22 | SUSD2 |
| 22 | TMPRSS6 |
| 22 | TNFRSF13C |
| X | ATP6AP2 |
| X | ATP7A |
| X | EDA2R |
| X | FMR1NB |
| X | GLRA4 |
| X | GPR112 |
| X | GUCY2F |
| X | HEPH |
| X | P2RY10 |
| X | P2RY4 |
| X | PLXNA3 |
| X | PLXNB3 |
| X | VSIG4 |
| X | XG |

References for Example 2

1. Lek M, Karczewski K J, Minikel E V, Samocha K E, Banks E, Fennell T, O'Donnell-Luria A H, Ware J S, Hill A J, Cummings B B, Tukiainen T, Birnbaum D P, Kosmicki J A, Duncan L E, Estrada K, Zhao F, Zou J, Pierce-Hoffman E, Berghout J, Cooper D N, Deflaux N, DePristo M, Do R, Flannick J, Fromer M, Gauthier L, Goldstein J, Gupta N, Howrigan D, Kiezun A, Kurki M I, Moonshine A L, Natarajan P, Orozco L, Peloso G M, Poplin R, Rivas M A, Ruano-Rubio V. Rose S A, Ruderfer D M, Shakir K, Stenson P D, Stevens C, Thomas B P, Tiao G, Tusie-Luna M T, Weisburd B, Won H H, Yu D, Altshuler D M, Ardissino D, Boehnke M, Danesh J, Donnelly S, Elosua R, Florez J C, Gabriel S B, Getz G, Glatt S J, Hultman C M, Kathiresan S, Laakso M, McCarroll S, McCarthy M I, McGovern D, McPherson R, Neale B M, Palotie A, Purcell S M, Saleheen D, Scharf J M, Sklar P, Sullivan P F, Tuomilehto J, Tsuang M T, Watkins H C, Wilson J G, Daly M J, MacArthur D G, Exome Aggregation C. Analysis of protein-coding genetic variation in 60,706 humans. *Nature.* 2016; 536:285-291
2. Consortium G T. Human genomics. The genotype-tissue expression (gtex) pilot analysis: Multitissue gene regulation in humans. *Science.* 2015; 348:648-660
3.
6. Ng P C, Henikoff S. Sift: Predicting amino acid changes that affect protein function. *Nucleic acids research.* 2003; 31:3812-3814
7.
8. Cerami E, Gao J, Dogrusoz U, Gross B E, Sumer S O, Aksoy B A, Jacobsen A, Byrne C J, Heuer M L, Larsson E, Antipin Y, Reva B, Goldberg A P, Sander C, Schultz N. The cbio cancer genomics portal: An open platform for exploring multidimensional cancer genomics data. *Cancer discovery.* 2012; 2:401-404

Example 3. DNA Sequencing Analysis for Verification of HLA LOH in KICH Samples

Library Preparation and Sequencing
Purpose—based on the in-silico analysis, KICH cancer was chosen as the first tumor type for wet verification of the HLA LOH prediction. The aim was to identify the HLA genotype for each patient based on DNA derived from normal tissue, and then to analyse the HLA allotype in the cancer tissue in an attempt to identify loss of one of the HLA alleles.

For that matter, HLA allotype was determined for DNA derived from 6 frozen matche KICH samples (Normal and Cancer) RC-001-RC003, TNEABA11, TNEABNWE, 2rDFRAUB, 2RDFRNQG, IOWT5AVJ, IOWT5N74. In addition, two DNA matched samples OG-001-OG-002 (Normal and Cancer) were also analysed. A DNA library was prepared sequence analysis was conducted in order to identify the sample's HLA typing. DNA was extracted from 6 frozen matched KICH samples (Normal and tumor) and a library was prepared as described below.

TruSight HLA Sequencing libraries were prepared using TruSight® HLA v2 Sequencing Panel (Illumina, San Diego, Calif., U.S.A.) at Genotypic Technology Pvt. Ltd., Bangalore, India.

Briefly, HLA Amplicons were generated using the primers provided in the TruSight HLA Sequencing Kit. Amplicons were confirmed on Agarose Gel followed by cleanup of the amplicons using Aample Purification Beads provided in the kit. Amplicons were normalized and fragmented by Tagmentation reaction. Post Tagmentation different amplicons of each individual sample were pooled and proceeded for enrichment PCR. Barcoding of the samples was done during enrichment PCR using Nextera X T Index Kit v2 (Illumina). Final PCR product was purified using Sample Purification Beads followed by quality control check of the libraries. Libraries were quantified by Qubit fluorometer (Thermo Fisher Scientific, MA, USA) and its fragment size distribution was analyzed on Agilent Bioanalyzer.

Illumina Adapter Sequences:

5' -AATGATACGGCGACCACCGAGATCTACAC [i5] TCGTCGGCAGCG TC

5' -CAAGCAGAAGACGGCATACGAGAT [i7] GTCTCGTGGGCTCGG

[i5, i71—Unique dual index sequence to identify sample-specific sequencing data

The table below depict the HLA genotype of the above samples.

As seen below, we can infer the lost allele from the analysis, for example, patient #RC001 exhibits loss of HLA-A30 allele in the tumor samples and becomes hemizygout to HLA-32; patient #RC003 lost HLA-1 in the tumor sample and becomes hemizygout to HLA-30. The identified lost allele will determine the relevant iCAR for each patient. Cases where tumor samples were contaminated with normal cells, could exhibit clear HLA allele loss in this method.

TABLE 9

HLA genotype of the matched KICH samples

| Sample_ID | HLA-A | HLA-B | HLA-C |
|---|---|---|---|
| OG_001_NAT_NORMAL | 02:06:01:— | 7:02:01 | 03:04:01:— |
|  | 24:02:01:— | 15:01:01:— | 07:02:01:— |
| OG_001_TUM_TUMOR | 02:06:01:— | 7:02:01 | 03:04:01:— |
|  | 24:02:01:— | 15:01:01:— | 07:02:01:— |
| OG_002_NAT_NORMAL | 02:01:01:— | 15:01:01:— | 3:03:01 |
|  | 24:02:01:— | 55:01:01 | X |
| OG_002_TUM_TUMOR | 02:01:01:— | 15:01:01:— | 3:03:01 |
|  | 24:02:01:— | 55:01:01 | X |
| RC_002_NAT_A_NORMAL | 03:01:01:— | 7:02:01 | 06:02:01:— |
|  | 68:02:01:— | 58:02:01 | 7:18:00 |
| RC_002_TUM_A_TUMOR | 03:01:01:— | 7:02:01 | 06:02:01:— |
|  | 68:02:01:— | 58:02:01 | 7:18:00 |
| RC_003_NAT_A_NORMAL | 01:01:01:01 | 7:02:01 | 07:01:01:— |
|  | 30:04:01 | 49:01:01 | 07:02:01:— |
| RC_003_TUM_A_TUMOR | 30:04:01 | 7:02:01 | 07:01:01:— |
|  | X | 49:01:01 | 07:02:01:— |
| RC_001_NAT_B_NORMAL | 30:04:01 | 53:01:01 | 04:01:01:— |
|  | 32:01:01 | 58:02:01 | 06:02:01:— |
| RC_001_TUM_B_TUMOR | 32:01:01 | 53:01:01 | 04:01:01:— |
|  | X | 58:02:01 | 06:02:01:— |
| 2RDFRAUB_Tumor | 03:01:01:— | 7:02:01 | 07:02:01:— |
|  | 32:01:01 | 38:01:01 | 12:03:01:— |
| SO_7534_SET3_2RDFRNQG_Normal | 03:01:01:— | 7:02:01 | 07:02:01:— |
|  | 32:01:01 | 38:01:01 | 12:03:01:— |

TABLE 9-continued

| HLA genotype of the matched KICH samples | | | |
|---|---|---|---|
| Sample_ID | HLA-A | HLA-B | HLA-C |
| IOWT5AVJ_Tumor | 34:02:01 | 15:03:01:— | 02:10:01:— |
| | 68:01:01:— | 81:01:00 | 8:04:01 |
| IOWT5N74_Normal | 34:02:01 | 15:03:01:— | 02:10:01:— |
| | 68:01:01:— | 81:01:00 | 8:04:01 |
| TNEAB1L_Tumor | 02:01:01:— | 8:01:01 | 03:04:01:— |
| | 03:01:01:— | 40:01:02 | 07:01:01:— |
| TNEABNWE_Normal | 02:01:01:— | 8:01:01 | 03:04:01:— |
| | 03:01:01:— | 40:01:02 | 07:01:01:— |

X—no variant reads

Exome Sequencing

In addition to the HLA sequencing, we also performed exome sequencing in order to confirm HLA-LOH and to identify additional LOH events across the genome The Illumina paired end raw reads (150X2, HiSeq) were quality checked using FastQC. Illumina raw reads were processed by Trim Galore software for adapter clipping and low quality base trimming using parameters of minimum read length 50 bp and minimum base quality 30. The processed reads were aligned to the reference human genome (hg19) using Bowtie2. Then aligned .bam files for each of the samples were processed to get the final PCR duplicate removed .bam files and alignment quality was checked using Qualimap.

Variants were identified using SAMtools and BCFtools. In this case, joint genotyping is done to identify variants in each pair of samples (each normal and tumor pair). Therefore, for each pair a merged .vcf is generated. Potential variants are identified from each of these merged .vcf files using read depth threshold>20 and mapping quality>30. From each pair of the filtered merged .vcf, sample-wise .vcf files were generated. The filtered variants were further annotated for genes, protein change and the impact of the variations using Variant Studio.

The below table describes the extent of chromosome loss for the above samples. RC001, RC002 and RC003 exhibit extensive chromosome loss including chromosome 6 which codes for HLA genes, hence, for these samples, HLA can be used as iCAR target, in addition to many other targets coded on chromosomes 1, 2, 3, 4 (for RC002), 5, 6, 8 (for RC003), 9 (RC001, RC002), 10 (RC001, RC003), 11 (RC003), 13 (RC001, RC003), 14 (RC002), 17 (RC001, RC003), 19 (RC001), 21 (RC001, RC003), 22(RC001, RC002).

TABLE 10

| | chromosome loss | | | | | | | |
|---|---|---|---|---|---|---|---|---|
| Chr | RC001 | RC002 | RC003 | OG001 | OG002 | 2RD | IOW | TNE |
| 1 | ++ | ++ | ++ | | | | | |
| 2 | ++ | + | ++ | | | + | | |
| 3 | ++ | ++ | | | | + | | |
| 4 | | ++ | | | | | | |
| 5 | ++ | ++ | | | | | | |
| 6 | ++ | + | ++ | | | | | + |
| 7 | | | | | | | | |
| 8 | | | ++ | | | | | |
| 9 | ++ | ++ | | | | | | ++ |
| 10 | ++ | | ++ | | | | | |
| 11 | | | ++ | | | | | |
| 12 | | | | | | | | + |
| 13 | ++ | | ++ | | | | | |
| 14 | | + | | | | + | | |
| 15 | | | | | | + | | |
| 16 | | | | | | | | |
| 17 | ++ | | ++ | | | | | |
| 18 | | | | | | | | |
| 19 | ++ | | | | | | | |
| 20 | | | | | | | | |
| 21 | ++ | | ++ | | | | | |
| 22 | ++ | ++ | | | | | | ++ |

Figure 14:
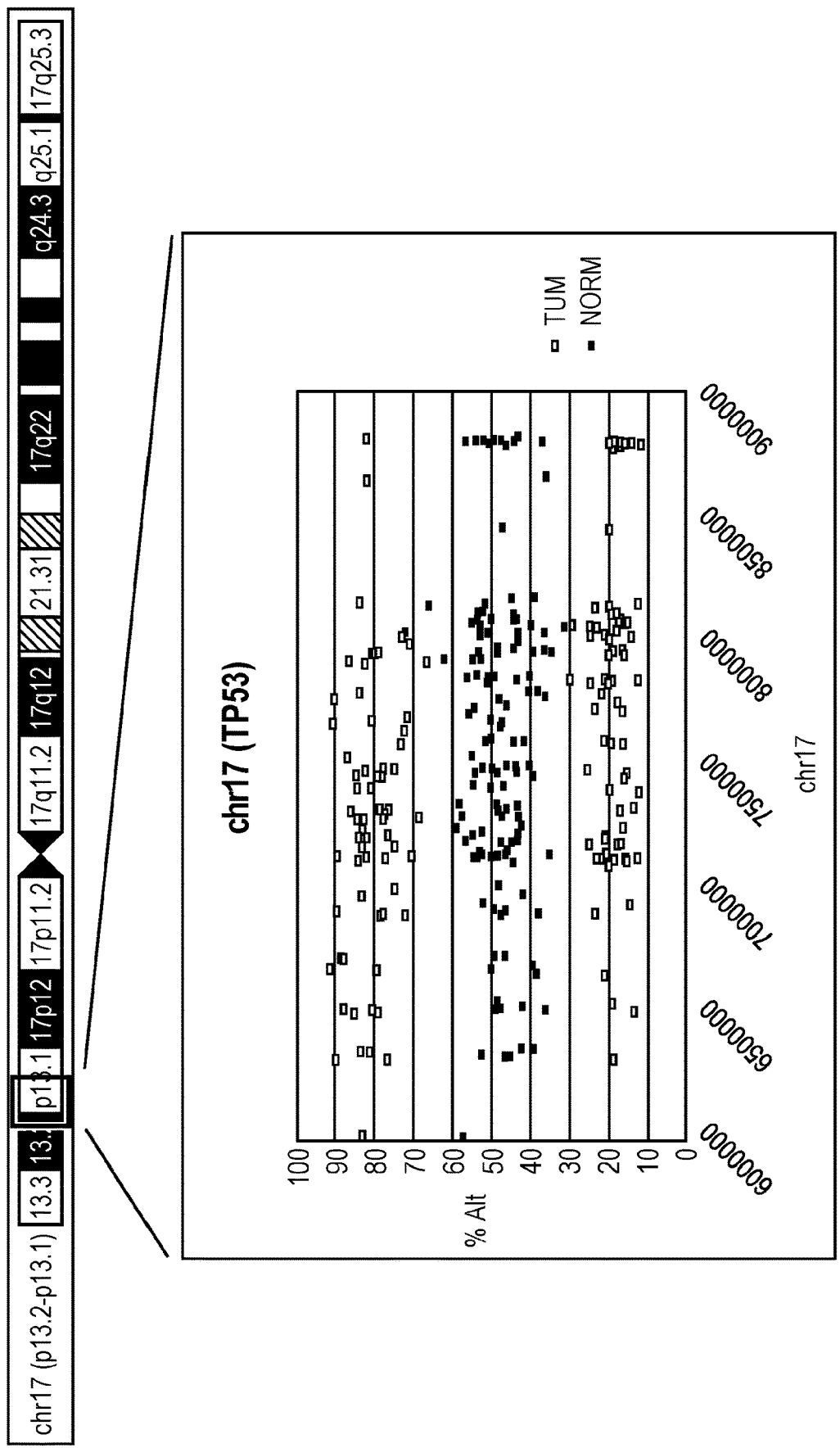
FIG. 14 depicts the loss of a chromosomal region adjacent to the tumor suppressor protein TP53, coded on chromosome 17. Genes coded on chromosome 17 which were identified as iCAR targets can be used to treat patient RC001.

+ LOH (Chr loss) for about 50% of the cells
++ LOH (Chr loss) for almost 100% of the cells For RC001, FIG. 14 depict the loss of a chromosomal region adjacent to the tumor suppressor protein TP53, coded on chromosome 17. Genes coded on chromosome 17 which were identified as iCAR targets can be used to treat patient RC001.

Abbreviations: ADP, adenosine diphosphate; ALL, acute lymphoblastic leukemia; AML, acute myelogenous leukemia; APRIL, a proliferation-inducing ligand; BAFF, B cell activation factor of the TNF family; BCMA, B cell maturation antigen; BCR, B cell receptor; BM, hone marrow; CAIX, carbonic anhydrase IX; CAR, chimeric antigen receptor; CEA, carcinoembryonic antigen; CLL, chronic lymphocytic leukemia; CNS, central nervous system; CSPG4, chondroitin sulfate proteoglycan 4; DC, dendritic cell; ECM, extracellular matrix; EGFR, epidermal growth factor receptor; EGFRvIII, variant III of the EGFR; EphA2, erythropoietin-producing hepatocellular carcinoma A2; FAP, fibroblast activation protein; FR-α, folate receptor-alpha; GBM, glioblastoma multiforme; GPI, glycophosphatidylinositol; H&N, head and neck; HL, Hodgkin's lymphoma; Ig, immunoglobulin; L1-CAM, L1 cell adhesion molecule; MM, multiple myeloma; NB, neuroblastoma; NF-KB, nuclear factor-KB; NHL, non-Hodgkin's lymphoma; NK, natural killer; NKG2D-L, NKG2D ligand; PBMC, peripheral blood mononuclear cell; PC, plasma cell; PLL, prolymphocytic leukemia; PSCA, prostate stem cell antigen; PSMA, prostate-specific membrane antigen; RCC, renal cell carcinomas; ROR1, receptor tyrosine kinase-like orphan receptor 1; TCL, T cell leukemia/lymphoma; Th2, T helper 2; TNBC, triple-negative breast cancer; TNFR, tumor necrosis factor receptor; VEGFR-2, vascular endothelial growth factor-2.

References

Abecasis, G. R., Altshuler, D., Auton, A., Brooks, L. D., Durbin, R. M., Gibbs, R. A., Hurles, M. E., and McVean, G. A. (2010). A map of human genome variation from population-scale sequencing. Nature 467, 1061-1073.

Abeyweera, T. P., Merino, E., and Huse, M. (2011). Inhibitory signaling blocks activating receptor clustering and induces cytoskeletal retraction in natural killer cells. J. Cell Biol. 192, 675-690.

Auton, A., Abecasis, G. R., Altshuler, D. M., Durbin, R. M., Bentley, D. R., Chakravarti, A., Clark, A. G., Donnelly, P., Eichler, E. E., Flicek, P., et al. (2015). A global reference for human genetic variation. Nature 526, 68-74.

Barbas, Carlos F., Dennis R. Burton, Jamie K. Scott, G. J. S. 2004. *Phage display: a laboratory manual*. Cold Spring Harbor Laboratory Press.

Bausch-Fluck, D., Hofmann, A., Bock, T., Frei, A. P., Cerciello, F., Jacobs, A., Moest, H., Omasits, U., Gundry, R. L., Yoon, C., et al. (2015). A mass spectrometric-derived cell surface protein atlas. PLoS One 10.

Bayle, J. H., Grimley, J. S., Stankunas, K., Gestwicki, J. E., Wandless, T. J., and Crabtree, G. R. (2006). Rapamycin analogs with differential binding specificity permit orthogonal control of protein activity. Chem. Biol. 13, 99-107.

Bergbold, N., and Lemberg, M. K. (2013). Emerging role of rhomboid family proteins in mammalian biology and disease. Biochim. Biophys. Acta 1828, 2840-2848.

Blankenstein, T., Leisegang, M., Uckert, W., and Schreiber, H. (2015). Targeting cancer-specific mutations by T cell receptor gene therapy. Curr. Opin. Immunol. 33, 112-119.

Boczkowski, D., S. K. Nair, J. H. Nam, H. K. Lyerly, and E. Gilboa. 2000. Induction of tumor immunity and cytotoxic T lymphocyte responses using dendritic cells transfected with messenger RNA amplified from tumor cells. *Cancer Res* 60: 1028-34.

Barrett, M. T., Sanchez, C. A., Prevo, Burrell, R. A., McGranahan, N., Bartek, J., and Swanton, C. (2013). The causes and consequences of genetic heterogeneity in cancer evolution. Nature 501, 338-345.

Van Buuren, M. M., Calis, J. J. A., and Schumacher, T. N. M. (2014). High sensitivity of cancer exome-based CD8 T cell neo-antigen identification. Oncoimmunology 3.

Caescu, C. I., Jeschke, G. R., and Turk, B. E. (2009). Active-site determinants of substrate recognition by the metalloproteinases TACE and ADAM10. Biochem. J. 424, 79-88.

Carney, W. P., Petit, D., Hamer, P., Der, C. J., Finkel, T., Cooper, G. M., Lefebvre, M., Mobtaker, H., Delellis, R., and Tischler, A. S. (1986). Monoclonal antibody specific for an activated RAS protein. Proc. Natl. Acad. Sci. U.S.A 83, 7485-7489.

Cerami E, et al. The cbio cancer genomics portal: An open platform for exploring multidimensional cancer genomics data. Cancer discovery. 2012; 2:401-404.

Chao, G., W. L. Lau, B. J. Hackel, S. L. Sazinsky, S. M. Lippow, and K. D. Wittrup. 2006. Isolating and engineering human antibodies using yeast surface display. Nat. Protoc. 1.

Chess, A. (2012). Mechanisms and consequences of widespread random monoallelic expression. Nat. Rev. Genet. 13, 421-428.

Chicaybam, L., and Bonamino, M. H. (2014). Abstract 2797: Construction and validation of an activating and inhibitory chimeric antigen receptor (CAR) system. Cancer Res. 74, 2797-2797.

Chicaybam, L., and Bonamino, M. II. (2015). Abstract 3156: Construction and validation of an activating and inhibitory chimeric antigen receptor (CAR) system. Cancer Res. 75, 3156-3156.

Consortium G T. Human genomics. The genotype-tissue expression (gtex) pilot analysis: Multitissue gene regulation in humans. Science. 2015; 348:648-660.

Da Cunha, J. P. C., Galante, P. A. F., De Souza, J. E., De Souza, R. F., Carvalho, P. M., Ohara, D. T., Moura, R. P., Oba-Shinja, S. M., Marie, S. K. N., Silva Jr., W. A., et al. (2009). Bioinformatics construction of the human cell surfaceome. Proc. Natl. Acad. Sci. U.S.A 106, 16752-16757.

Devilee, P., Cleton-Jansen, A.-M., and Cornelisse, C. J. (2001). Ever since Knudson. Trends Genet. 17, 569-573.

Dotti, G., Gottschalk, S., Savoldo, B., and Brenner, M. K. (2014). Design and development of therapies using chimeric antigen receptor-expressing T cells. Immunol. Rev. 257, 107-126.

Ebsen, H., Schröder, A., Kabelitz, D., and Janssen, O. (2013). Differential surface expression of ADAM10 and ADAM17 on human T lymphocytes and tumor cells. PLoS One 8, e76853.

Eriksson, M., Leitz, G., Fallman, E., Axner, O., Ryan, J. C., Nakamura, M. C., and Sentman, C. L. (1999). Inhibitory receptors alter natural killer cell interactions with target cells yet allow simultaneous killing of susceptible targets. J. Exp. Med. 190, 1005-1012.

Fedorov, V. D., Themeli, M., and Sadelain, M. (2013a). PD-1- and CTLA-4-based inhibitory chimeric antigen receptors (iCARs) divert off-target immunotherapy responses. Sci. Transl. Med. 5, 215ra172.

Fedorov, V. D., Themeli, M., and Sadelain, M. (2013b). PD-1- and CTLA-4-based inhibitory chimeric antigen receptors (iCARs) divert off-target immunotherapy responses. In Science Translational Medicine, (Affiliation: Center for Cell Engineering, Memorial Sloan-Kettering Cancer Center (MSKCC), New York, N.Y. 10065, United States; Affiliation: Tri-Institutional MSTP Program (MSKCC, Rockefeller University, Weill-Cornell Medical College), New York, N.Y. 10065, Un).

Feenstra, M., Veltkamp, M., van Kuik, J., Wiertsema, S., Slootweg, P., van den Tweel, J., de Weger, R., and Tilanus, M. (1999). HLA class I expression and chromosomal deletions at 6p and 15q in head and neck squamous cell carcinomas. Tissue Antigens 54, 235-245.

Gao J. et al, Integrative analysis of complex cancer genomics and clinical profiles using the cBio Portal. Sci Signal. 2013 2; 6(269)

Gill, S., and June, C. H. (2015). Going viral: chimeric antigen receptor T-cell therapy for hematological malignancies. Immunol. Rev. 263, 68-89.

Gordon, W. R., Zimmerman, B., He, L., Miles, L. J., Huang, J., Tiyanont, K., McArthur, D. G., Aster, J. C., Perrimon, N., Loparo, J. J., et al. (2015). Mechanical Allostery: Evidence for a Force Requirement in the Proteolytic Activation of Notch. Dev. Cell 33, 729-736.

Graef, I. A., Holsinger, L. J., Diver, S., Schreiber, S. L., and Crabtree, G. R. (1997). Proximity and orientation underlie signaling by the non-receptor tyrosine kinase ZAP70. EMBO J. 16, 5618-5628.

Gross, G., and Eshhar, Z. (2016a). Therapeutic Potential of T-Cell Chimeric Antigen Receptors in Cancer Treatment: Counteracting Off-Tumor Toxicities for Safe CAR T-Cell Therapy. Annu. Rev. Pharmacol. Toxicol. 2016.56:59-83.

Gross, G., and Eshhar, Z. (2016b). Therapeutic Potential of T Cell Chimeric Antigen Receptors (CARs) in Cancer Treatment: Counteracting Off-Tumor Toxicities for Safe CAR T Cell Therapy. Annu. Rev. Pharmacol. Toxicol. 56, 59-83.

Gross, G., Waks, T., and Eshhar, Z. (1989). Expression of immunoglobulin-T-cell receptor chimeric molecules as functional receptors with antibody-type specificity. Proc Natl Acad Sci USA 86, 10024-10028.

Haapasalo, A., and Kovacs, D. M. (2011). The many substrates of presenilin/γ-secretase. J. Alzheimers. Dis. 25, 3-28.

Hanes, J., and A. Plückthun. 1997. In vitro selection and evolution of functional proteins by using ribosome display. *Proc. Natl. Acad. Sci. U.S.A* 94.

Heemskerk, B., Kvistborg, P., and Schumacher, T. N. M. (2013). The cancer antigenome. EMBO J. 32, 194-203.

Hemming, M. L., Elias, J. E., Gygi, S. P., and Selkoe, D. J. (2009). Identification of beta-secretase (BACE1) substrates using quantitative proteomics. PLoS One 4, e8477.

Huse, M., Catherine Milanoski, S., and Abeyweera, T. P. (2013). Building tolerance by dismantling synapses: inhibitory receptor signaling in natural killer cells. Immunol. Rev. 251, 143-153.

Jiménez, P., Canton, J., Collado, A., Cabrera, T., Serrano, A., Real, L. M., García, A., Ruiz-Cabello, F., and Garrido, F. (1999). Chromosome loss is the most frequent mechanism contributing to HLA haplotype loss in human tumors. Int. J. Cancer 83, 91-97.

Klebanoff, C. A., Rosenberg, S. A., and Restifo, N. P. (2016). Prospects for gene-engineered T cell immunotherapy for solid cancers. Nat. Med. 22, 26-36.

Kloss, C. C., Condomines, M., Cartellieri, M., Bachmann, M., and Sadelain, M. (2013). Combinatorial antigen recognition with balanced signaling promotes selective tumor eradication by engineered T cells. Nat. Biotechnol. 31, 71-75.

Knudson Jr., A. G. (1971). Mutation and cancer: statistical study of retinoblastoma. Proc. Natl. Acad. Sci. U.S.A 68, 820-823.

Lanitis, E., Poussin, M., Klattenhoff, A. W., Song, D., Sandaltzopoulos, R., June, C. H., and Powell Jr, D. J. (2013). Chimeric antigen receptor T cells with dissociated signaling domains exhibit focused anti-tumor activity with reduced potential for toxicity. Cancer Immunol. Res. 1, 10.1158/2326-6066. CIR-13-0008.

Lawrence, M. S., Stojanov, P., Polak, P., Kryukov, G. V, Cibulskis, K., Sivachenko, A., Carter, S. L., Stewart, C., Mermel, C. H., Roberts, S. A., et al. (2013). Mutational heterogeneity in cancer and the search for new cancer-associated genes. Nature 499, 214-218.

Lee, A., Rana, B. K., Schiffer, H. H., Schork, N. J., Brann, M. R., Insel, P. A., and Weiner, D. M. (2003). Distribution analysis of nonsynonymous polymorphisms within the G-protein-coupled receptor gene family. Genomics 81, 245-248.

Lek M, et al., Exome Aggregation C. Analysis of protein-coding genetic variation in 60,706 humans. Nature. 2016; 536:285-291.

Lengauer, C., Kinzler, K. W., and Vogelstein, B. (1998). Genetic instabilities in human cancers. Nature 396, 643-649.

Li, H., Yang, B., Xing, K., Yuan, N., Wang, B., Chen, Z., He, W., and Zhou, J. (2014). A preliminary study of the relationship between breast cancer metastasis and loss of heterozygosity by using exome sequencing. Sci. Rep. 4.

Liberles, S. D., Diver, S. T., Austin, D. J., and Schreiber, S. L. (1997). Inducible gene expression and protein translocation using nontoxic ligands identified by a mammalian three-hybrid screen. Proc. Natl. Acad. Sci. 94, 7825-7830.

Lindblad-Toh, K., Tanenbaum, D. M., Daly, M. J., Winchester, E., Lui, W.-O., Villapakkam, A., Stanton, S. E., Larsson, C., Hudson, T. J., Johnson, B. E., et al. (2000). Loss-of-heterozygosity analysis of small-cell lung carcinomas using single-nucleotide polymorphism arrays. Nat. Biotechnol. 18, 1001-1005.

Lo, K. C., Bailey, D., Burkhardt, T. Gardina, P., Turpaz, Y., and Cowell, J. K. (2008). Comprehensive analysis of loss of heterozygosity events in glioblastoma using the 100K SNP mapping arrays and comparison with copy number abnormalities defined by BAC array comparative genomic hybridization. Genes Chromosom. Cancer 47, 221-237.

Long, E. O., Sik Kim, H., Liu, D., Peterson, M. E., and Rajagopalan, S. (2013). Controlling natural killer cell responses: Integration of signals for activation and inhibition. Annu. Rev. Immunol. 31, 227-258.

Maleno, I., López-Nevot, M. A., Cabrera, T., Salinero, J., and Garrido, F. (2002). Multiple mechanisms generate HLA class I altered phenotypes in laryngeal carcinomas: high frequency of HLA haplotype loss associated with loss of heterozygosity in chromosome region 6p21. Cancer Immunol. Immunother. 51, 389-396.

Maleno, I., Cabrera, C. M., Cabrera, T., Paco, L., Lopez-Nevot, M. A., Collado, A., Fernón, A., and Garrido, F. (2004). Distribution of HLA class I altered phenotypes in colorectal carcinomas: high frequency of HLA haplotype loss associated with loss of heterozygosity in chromosome region 6p21. Immunogenetics 56, 244-253.

Maleno, I., Romero, J. M., Cabrera, T., Paco, L., Aptsiauri, N., Cozar, J. M., Tallada, M., López-Nevot, M. A., and Garrido, F. (2006). LOH at 6p21.3 region and HLA class I altered phenotypes in bladder carcinomas. Immunogenetics 58, 503-510.

Maleno, I., Aptsiauri, N., Cabrera, T., Gallego, A., Paschen, A., López-Nevot, M. A., and Garrido, F. (2011). Frequent loss of heterozygosity in the β2-microglobulin region of chromosome 15 in primary human tumors. Immunogenetics 63, 65-71.

McGranahan, N., Burrell, R. A., Endesfelder, D., Novelli, M. R., and Swanton, C. (2012). Cancer chromosomal instability: Therapeutic and diagnostic challenges. EMBO Rep. 13, 528-538.

Morsut, L., Roybal, K. T., Xiong, X., Gordley, R. M., Coyle, S. M., Thomson, M., and Lim, W. A. (2016). Engineering Customized Cell Sensing and Response Behaviors Using Synthetic Notch Receptors. Cell 164, 780-791.

Ng P C, Henikoff S. Sift: Predicting amino acid changes that affect protein function. Nucleic acids research. 2003; 31:3812-3814.

Nirschl, C. J., and Drake, C. G. (2013). Molecular pathways: Coexpression of immune checkpoint molecules: Signaling pathways and implications for cancer immunotherapy. Clin. Cancer Res. 19, 4917-4924.

O'Keefe, C., McDevitt, M. A., and Maciejewski, J. P. (2010). Copy neutral loss of heterozygosity: A novel chromosomal lesion in myeloid malignancies. Blood 115, 2731-2739.

Ohgaki, H., Dessen, P., Jourde, B., Horstmann, S., Nishikawa, T., Di Patre, P.-L., Burkhard, C., Schüler, D., Probst-Hensch, N. M., Maiorka, P. C., et al. (2004). Genetic pathways to glioblastoma: a population-based study. Cancer Res. 64, 6892-6899.

Overwijk, W. W., Wang, E., Marincola, F. M., Rammensee, H. G., and Restifo, N. P. (2013). Mining the mutanome: developing highly personalized Immunotherapies based on mutational analysis of tumors. J. Immunother. Cancer 1, 11.

Rana, B. K., Shiina, T., and Insel, P. A. (2001). Genetic variations and polymorphisms of G protein-coupled receptors: functional and therapeutic implications. Annu. Rev. Pharmacol. Toxicol. 41, 593-624.

Rawson, R. B. (2013). The site-2 protease. Biochim. Biophys. Acta 1828, 2801-2807.

Rosenberg, S. A. (2014). Finding suitable targets is the major obstacle to cancer gene therapy. Cancer Gene Ther. 21, 45-47.

Rosenberg, S. A., and Restifo, N. P. (2015). Adoptive cell transfer as personalized immunotherapy for human cancer. Science 348, 62-68.

Roybal, K. T., Rupp, L. J., Morsut, L., Walker, W. J., McNally, K. A., Park, J. S., and Lim, W. A. (2016a). Precision Tumor Recognition by T Cells With Combinatorial Antigen-Sensing Circuits. Cell.

Roybal, K. T., Rupp, L. J., Morsut, L., Walker, W. J., McNally, K. A., Park, J. S., and Lim, W. A. (2016b). Precision Tumor Recognition by T Cells With Combinatorial Antigen-Sensing Circuits. Cell 164, 770-779.

Sathirapongsasuti, J. F., Lee, H., Horst, B. A. J., Brunner, G., Cochran, A. J., Binder, S., Quackenbush, J., and Nelson, S. F. (2011). Exome sequencing-based copy-number variation and loss of heterozygosity detection: ExomeCNV. Bioinformatics 27, 2648-2654.

Savage, P. A. (2014). Tumor antigenicity revealed. Trends Immunol. 35, 47-48.

Savova, V., Chun, S., Sohail, M., McCole, R. B., Witwicki, R., Gai, L., Lenz, T. L., Wu, C.-T., Sunyaev, S. R., and Gimelbrant, A. A. (2016). Genes with monoallelic expression contribute disproportionately to genetic diversity in humans. Nat. Genet. 48, 231-237.

Schumacher, T. N., and Schreiber, R. D. (2015). Neoantigens in cancer immunotherapy. Science (80-.). 348, 69-74.

Sela-Culang, I., Y. Ofran, and B. Peters. 2015a. Antibody specific epitope prediction—Emergence of a new paradigm. Curr. Opin. Virol. 11.

Sela-Culang, I., S. Ashkenazi, B. Peters, and Y. Ofran. 2015b. PEASE: Predicting B-cell epitopes utilizing antibody sequence. Bioinformatics 31.

Skora, A. D., Douglass, J., Hwang, M. S., Tam, A. J., Blosser, R. L., Gabelli, S. B., Cao, J., Diaz, L. A., Papadopoulos, N., Kinzler, K. W., et al. (2015). Generation of MANAbodies specific to HLA-restricted epitopes encoded by somatically mutated genes. Proc. Natl. Acad. Sci. U.S.A 112, 9967-9972.

Stark, M., and Hayward, N. (2007). Genome-wide loss of heterozygosity and copy number analysis in melanoma using high-density single-nucleotide polymorphism arrays. Cancer Res. 67, 2632-2642.

Stark, S. E., and Caton, A. J. (1991). Antibodies that are specific for a single amino acid interchange in a protein epitope use structurally distinct variable regions. J. Exp. Med. 174, 613-624.

Teo, S. M., Pawitan, Y., Ku, C. S., Chia, K. S., and Salim, A. (2012). Statistical challenges associated with detecting copy number variations with next-generation sequencing. Bioinformatics 28, 2711-2718.

Thul P J, et al. A subcellular map of the human proteome. Science. 2017; 356.

Treanor, B., Lanigan, P. M. P., Kumar, S., Dunsby, C., Munro, 1., Auksorius, E., Culley, F. J., Purbhoo, M. A., Phillips, D., Neil, M. A. A., et al. (2006). Microclusters of inhibitory killer immunoglobulin-like receptor signaling at natural killer cell immunological synapses. J. Cell Biol. 174, 153-161.

Uhlen M, et al. Tissue-based map of the human proteome. Science. 2015; 347:1260419.

Vogelstein, B., Fearon, E. R., Kern, S. E., Hamilton, S. R., Preisinger, A. C., Nakamura, Y., and White, R. (1989). Allelotype of colorectal carcinomas. Science (80-.). 244, 207-211.

Vogelstein, B., Papadopoulos, N., Velculescu, V. E., Zhou, S., Diaz Jr., L. A., and Kinzler, K. W. (2013). Cancer genome landscapes. Science (80-.). 340, 1546-1558.

Voss, M., Schröder, B., and Fluhrer, R. (2013). Mechanism, specificity, and physiology of signal peptide peptidase (SPP) and SPP-like proteases. Biochim. Biophys. Acta 1828, 2828-2839.

Vyas, Y. M., Mehta, K. M., Morgan, M., Maniar, H., Butros, L., Jung, S., Burkhardt, J. K., and Dupont, B. (2001). Spatial organization of signal transduction molecules in the NK cell immune synapses during MHC class I-regulated noncytolytic and cytolytic interactions. J. Immunol. 167, 4358-4367.

Wang, Z. C., Lin, M., Wei, L.-J., Li, C., Miron, A., Lodeiro, G., Harris, L., Ramaswamy, S., Tanenbaum, D. M., Meyerson, M., et al. (2004). Loss of heterozygosity and its correlation with expression profiles in subclasses of invasive breast cancers. Cancer Res. 64, 64-71.

Wilkie, S., Van Schalkwyk, M. C. I., Hobbs, S., Davies, D. M., Van, D. S., Pereira, A. C. P., Burbridge, S. E., Box, C., Eccles, S. A., and Maher, J. (2012). Dual targeting of ErbB2 and MUC in breast cancer using chimeric antigen receptors engineered to provide complementary signaling. J. Clin. Immunol. 32, 1059-1070.

Wu, C.-Y., Roybal, K. T., Puchner, E. M., Onuffer, J., and Lim, W. A. (2015). Remote control of therapeutic T cells through a small molecule-gated chimeric receptor. Science (80-.). 350, aab4077.

Yeung, J. T., Hamilton, R. L., Ohnishi, K., Ikeura, M., Potter, D. M., Nikiforova, M. N., Ferrone, S., Jakacki, R. I., Pollack, I. F., and Okada, H. (2013). LOH in the HLA class I region at 6p21 is associated with shorter survival in newly diagnosed adult glioblastoma. Clin. Cancer Res. 19, 1816-1826.

Example 4. Verification of LOH at the Protein Level

LOH can be detected at the protein level by differential staining of normal vs. tumor cell samples using allele specific antibodies. For example, verification of HLA-LOH in cancer samples, can be done using commercial HLA antibodies specific to the patient's HLA allotype. Table 11 below details an example for available allele-specific antibodies, which can be used.

Samples will be subjected to immuno-histochemistry (IHC) staining as described in the IHC protocol below.

TABLE 11

Allele-specific anti-HLA antibodies

| Antibody | Manufacturer |
|---|---|
| Anti-human HLA-A2 APC (BB7.2) | eBiosciences |
| Anti-human HLA-A2 PE-cy7 (BB7.2) | eBiosciences |
| Anti-human HLA-A3 FITC (GAP A3) | eBiosciences |
| Anti-human HL A-A3 PE (GAP A3) | eBiosciences |
| Mouse Anti-HLA Class 1 Antigen A25, A32 Antibody | US Biological |
| HLA Class 1 Antigen A30, A31 | MyBioSource |
| mouse anti-human HLA-B7-PE (BB7.1) | Millipore |
| HLA-A2 antibody (BB7.2) | Novus |
| HLA B7 antibody (BB7.1) | Novus |
| Mouse anti-human HLA-B27-FITC (clone HLA.ABC.m3) | Millipore |

IHC protocol
Frozen Tissues Samples—

Frozen tissues are often fixed in a formalin-based solution, and embedded in OCT (Optimal Cutting Temperature compound), that enables cryosectioning of the sample. Tissues in OCT are kept frozen at −80° C. Frozen blocks are removed from −80° C. prior to sectioning, equilibrated in cryostat chamber, and cut to thin sections (often 5-15 µm thick). Sections are mounted on a histological slide. Slides can be stored at −20° C. to −80° C. Prior to
IHC Staining, Slides are Thawed at Room Temperature (RT) for 10-20 Min.
Paraffin-Embedded Tissues—

Tissues are embedded in a Formaldehyde Fixative Solution. Prior to addition of the paraffin wax, tissues are dehydrated by gradual immersion in increasing concentrations of ethanol (70%, 90%, 100%) and xylene for specific times and durations at RT. Then, the tissues are embedded in paraffin wax.

The paraffin-embedded tissues are cut in a microtome to a 5-15 µm thick sections, floated in a 56° C. water bath, and mounted on a histological slide. Slides can be kept at RT.

Prior to IHC staining, paraffin-embedded sections require a rehydration step. REHYDRATION—sections are rehydrated by immersion in xylene (2×10 min), followed by decreasing concentrations of ethanol—100%×2, each for 10 min 95% ethanol—5 min 70% ethanol—5 min 50% ethanol—5 min Rinsing in dH2O.

Immunofluorescence Detection:
Protocol:
1. Rehydrate slides in wash buffer (PBSX1) for 10 min. Drain the wash buffer.
2. Perform antigen retrieval—if needed (heat-induced antigen retrieval or enzymatic retrieval).
3. For intracellular antigens, perform permeabilization—incubate the slides in 0.1% triton X-100 in PB for 10 min at RT.
4. BLOCKING—Block the tissue in blocking buffer for 30 min. at RT. Blocking buffer depends on the detection method, usually 5% animal serum in PBSX1, or 1% BSA in PBSX1
5. PRIMARY ANTIBODY—Dilute primary antibody in incubation buffer (e.g., 1% BSA, 1% donkey serum in PBS, other incubation buffers can also be used), according to antibody manufacturer instructions. Incubate the tissue in diluted primary antibody at 4° C. overnight. The primary antibody may be a monoclonal anti-HLA-A, anti-HLA-B or anti-HLA-C allele-specific antibody as detailed above.

If a conjugated primary antibody is used, protect from light, and proceed to step 8.

As a negative control, incubate the tissue with incubation buffer only, with no primary antibody.

Also, perform isotype matched control of the monoclonal antibody used in the experiment.
6. 6. WASH—wash slides in wash buffer—3×5-15 min.
7. 7. SECONDARY ANTIBODY—Dilute secondary antibody in incubation buffer according to antibody manufacturer instructions. Incubate the tissue in diluted secondary antibody for 30-60 min at RT. Protect from light.
8. 8. WASH—wash slides in wash buffer—3×5-15 min.
9. 9. DAPI staining—Dilute DAPI incubation buffer (~300 nM—3 µM). Add 300 µl of DAPI solution to each section. Incubate at RT for 5-10 min.
10. 10. WASH—wash slide once with X1 PBS.
11. 11. Mount with an antifade mounting media.
12. 12. Keep slides protected from light.
13. 13. Visualize slides using a fluorescence microscope.

Chromogenic Detection:
Protocol:
1. 1. Rehydrate slides in wash buffer (PBSX1) for 10 min. Drain the wash buffer.
2. 2. Perform antigen retrieval—if needed—see above.
3. 3. For HRP reagents, block endogenous peroxidase activity with 3.0% hydrogen peroxide in methanol for at least 15 min.
4. 4. Wash the sections by immersing them in dH2O for 5 min.
5. 5. For intracellular antigens, perform permeabilization—incubate the slides in 0.1% triton X-100 in PBSX1 for 10 min at RT.
6. 6. BLOCKING—Block the tissue in blocking buffer for 30 min. at RT. Blocking buffer depends on the detection method, usually 5% animal serum in PBSX1, or 1% BSA in PBSX1.
7. 7. PRIMARY ANTIBODY—Dilute primary antibody in incubation buffer (e.g., 1% BSA, 1% donkey serum in PBS, other incubation buffers can also be used), according to antibody manufacturer instructions. Incubate the tissue in diluted primary antibody at 4° C. overnight
8. 8. WASH—wash slides in wash buffer—3×5-15 min.
9. 9. SECONDARY ANTIBODY—Incubate the tissue in HRP-conjugated secondary antibody for 30-60 min at RT.
10. 10. WASH—wash slides in wash buffer 3×5-15 min.
11. 11. Add ABC-HRP reagent according to manufacturer guidelines. Incubate at RT for 60 min.
12. 12. Prepare DAB solution (or other chromogen) according to manufacturer guidelines, and apply to tissue sections. The chromogenic reaction turns the epitope sites brown (usually few seconds—10 minutes). Proceed to the next step when the intensity of the signal is appropriate for imaging
13. 13. WASH—wash slides in wash buffer—3×5-15 min.
14. 14. Wash slides in dH2O—2×5-15 min.
15. 15. Nuclei staining—add Hematoxylin solution. Incubate at RT for 5 min.
16. 16. Dehydrate tissue sections—95% ethanol—2×2 min. 100% ethanol—2×2 min. Xylene—2×2 min.
17. 17. Mount with an antifade mounting media
18. 18. Visualize slides using a bright-field illumination Example 5. CAR-T Design and Construction The purpose of the study is to create a synthetic receptor which will inhibit the on-target 'off-tumor' effect of CAR-T therapy. To that extent a library of CAR constructs composed of activating and inhibitory CARs was established.

The first set of constructs included an inhibitory CAR directed at HLA type I sequence (HLA-A2) and an activating CAR directed at tumor antigen (CD19). The next set of constructs to be used for the sake of proof of concept, includes activating CAR sequences directed at CD19 and an inhibitory CAR sequences directed at CD20. Additional constructs directed at target antigens identified by future bioinformatics analysis will be constructed. Target candidates will be prioritized according to set forth criteria (exemplary criteria include but are not limited to, target expression pattern, target expression level, antigenicity and more). A CD19 aCAR, CD20 iCAR, and HLA-A2 iCAR have been constructed, as described in FIGS. 15 and 21.

iCAR constructs were designed and synthesized using commercial DNA synthesis. The transmembrane and intracellular domains up to the first annotated extracellular domain of PD-1 (amino acid 145-288) was fused downstream to HLA-A2 scFv (DNA sequence coding for HLA-A2, was retrieved from hybridoma BB7.2, (ATCC cat #: HB-82), producing anti HLA-A2).

Similar constructs with CTLA4 (amino acids 161-223) or with other sequences derived from additional negative immune regulators (for example 2B4, LAG-3 and BTLA-4) will be designed and their signaling sequences will be fused downstream to the HLA-A2 scFv.

Figure 15:
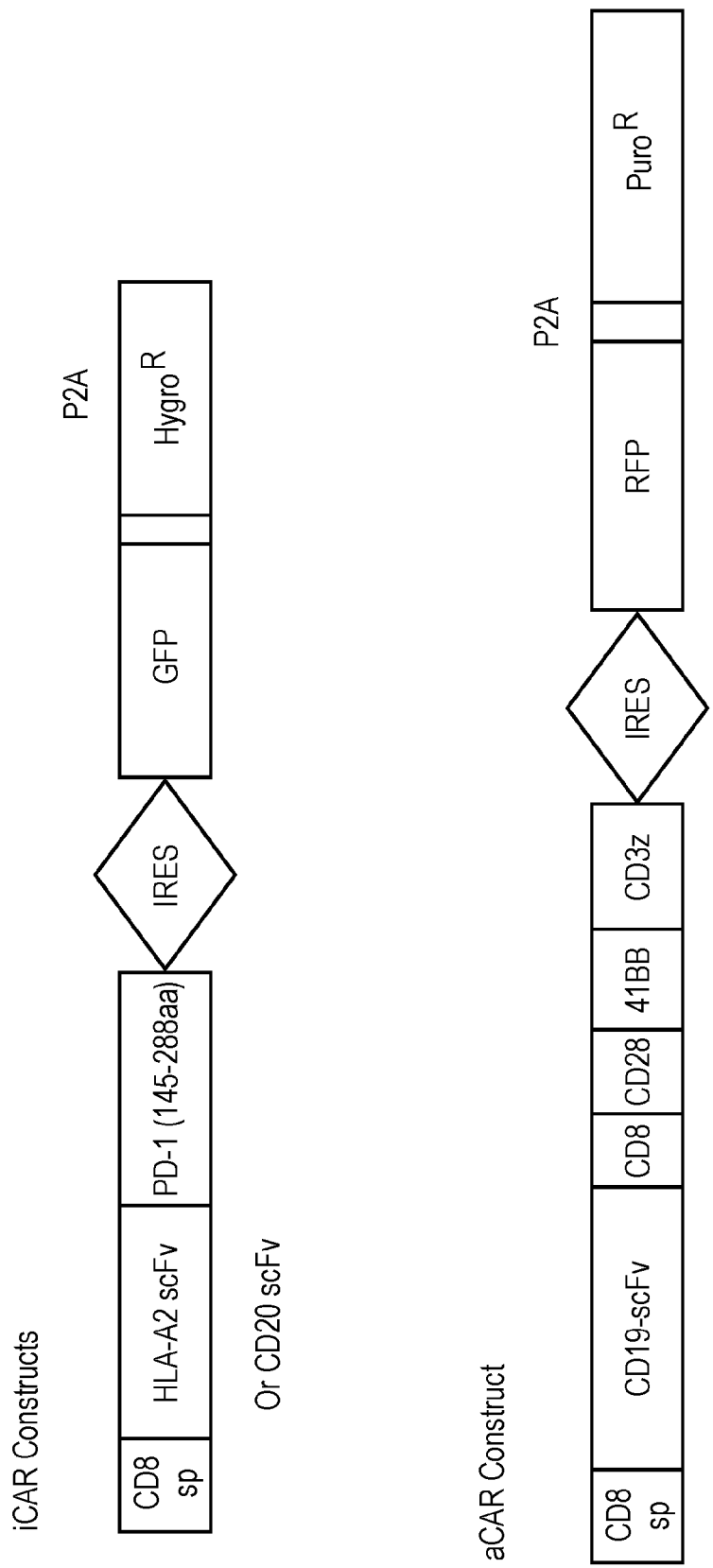
FIG. 15 provides a schematic diagram of iCAR and aCAR constructs.

For iCAR detection and sorting, a reporter gene (e.g., eGFP) was integrated downstream to the iCAR sequence via IRES sequences and followed by an antibiotic resistance gene (i.e., hygromycin) separated by P2A sequence, as illustrated in FIG. 15.

For the aCAR construct, CD19 scFV was fused to 2nd generation CAR construct composed of CD8 hinge sequence followed by CD28 transmembrane and 41BB co-stimulation 1 and CD3ζ. Additional aCAR constructs composed of other signaling or structural element will also be designed and constructed (e.g. CD28 hinge, CD28 signaling domain or both CD28 and 41BB signaling domains). For aCAR detection and sorting, RFP a reporter gene was integrated downstream to the aCAR sequence via IRES sequences followed by antibiotic resistance gene (Puromycin resistance) separated by P2A sequence (FIG. 15).

Both aCAR and iCAR sequences were cloned into lentivirus transfer vector and then used for viral particle production using HEK-293T packaging cells.

Example 6. Production of Effector Cells

To study the effect of the iCAR constructs on modulating CD19 CAR activation, recombinant Jurkat effector cells were constructed as detailed in Table 12 below. Jurkat (ATCC TIB152), a CD4+ T-cell line and Jurkat-NFAT (a Jurkat cell-line purchased from BPS Biosciences, engineered to express a firefly luciferase protein, under the control of NFAT response elements) were transduced using retronectin-coated (Takara) lentiviral vector bound plates or in the presence of polybrene. Transduced cells were further subjected to antibiotic selection to yield the cell-lines described in Table 12. Following selection, the cells were subjected to flow cytometry analysis to verify the expression of the reporter protein coded on each construct.

TABLE 12 recombinant effector cell-lines

| Recombinant effector cell-line | Parental Cell | Construct 1 (aCAR-RFP) | Construct 2 (iCAR-GFP) |
|---|---|---|---|
| CD 19 aCAR Jurkat | Jurkat | CD 19 aCAR | — |
| CD19aCAR/HLA-A2 iCAR Jurkat | Jurkat | CD 19 aCAR | HLA-A2 iCAR |
| HLA-A2 iCAR Jurkat | Jurkat | — | HLA-A2 iCAR |
| CD19aCAR/CD20 iCAR Jurkat | Jurkat | CD 19 aCAR | CD20 iCAR |
| CD20 iCAR Jurkat | Jurkat | — | CD20 iCAR |
| CD 19 aCAR Jurkat-NFAT | Jurkat-NFAT | CD 19 aCAR | — |
| CD19aCAR/HLA-A2 iCAR Jurkat-NFAT | Jurkat-NFAT | CD 19 aCAR | HLA-A2 iCAR |
| HLA-A2 iCAR Jurkat-NFAT | Jurkat-NFAT | — | HLA-A2 iCAR |
| CD19aCAR/CD20 iCAR Jurkat-NFAT | Jurkat-NFAT | CD 19 aCAR | CD20 iCAR |
| CD20 iCAR Jurkat-NFAT | Jurkat-NFAT | — | CD20 iCAR |

In addition, activated T-cells, derived from peripheral blood obtained from healthy donors will be transduced with viral particles coding for aCAR, iCAR or both, at different multiplicity of infection (MOI). FACS selection based on reporter gene expression will be used for sorting and selection of cell population expressing different level of aCAR, iCAR or both.

Example 7. Preparation of Target Cells

An in-vitro recombinant system was established for testing the functionality of iCAR constructs in inhibiting the activity of the aCAR towards off-target cells. For this purpose, target cells expressing the aCAR epitope, iCAR epitope or both were produced. The recombinant cells expressing the aCAR epitope represent the 'on-target' 'on-tumor' cells, while the cells expressing both aCAR and iCAR epitopes represent the 'on-target' 'off-tumor' healthy cells.

As our first iCAR/aCAR set is based on HLA-A2 and CD19 respectively, recombinant cells expressing HLA-A2 or CD19 or both were produced, by transfecting cell line (e.g., Hela, ATCC CRM-CCL-2, Hela-Luciferase—GenTarget SCO32-Bsd or Raji-ATCC CCL-86) with expression vectors coding for these genes.

For detection of recombinant HLA A-2 expression, Myc tag was inserted. For the second iCAR/aCAR set comprised of CD20 iCAR/CD19 aCAR, recombinant cells expressing CD20 or CD19 or both were constructed (target cells are detailed in Table 15).

Example 8. In Vitro Assays

Luciferase Cytotoxic T lymphocyte (CTL) Assay

Assay will be performed using Hela-Luc recombinant target cells described above, engineered to express firefly luciferase and one or two CAR target antigens. In-vitro luciferase assay will be performed according to the Bright-Glo Luciferase assay manufacture's protocol (Promega) and bioluminescence as a readout.

T-cells (transduced with both iCAR and pCAR or iCAR and aCAR or aCAR or mock CAR) will be incubated for 24-48 hrs. with the recombinant target cells expressing HLA-A2 or CD19 or both HLA-A2 and CD19 or CD20 or both CD20 and CD19 in different effector to target ratios. Cell killing will be quantified with the Bright-Glo Luciferase system.

The 'off-tumor' cytotoxicity is optimized by sorting transduced T-cells population according to iCAR/aCAR expression level or by selecting sub population of recombinant target cells according to their CD19, HLA-A2 or CD20 expression level. To test whether iCAR transduced T-cells can discriminate between the 'on-tumor' and 'off-tumor' cells in vitro, we will test the killing effect of transduced T-cells incubated with a mix of 'on-tumor' and 'off-tumor'

TABLE 13

| Set# | Parental cell | Target protein 1 | Target protein 2 | Purpose | Modeling |
|---|---|---|---|---|---|
| 1 | Raji | CD19 | None | A model for cancer cells expressing endogenous CD19 | On-tumor |
|   | Raji | CD19 | HLA-A2 | A model for normal cells expressing endogenous CD19; recombinant HLA-A2 | Off-tumor |
|   | Thp1 | None | HLA_A2 | A model for normal cells expressing endogenous HLA-A2 and negative to CD19 | Negative control |
| 2 | Hela | HLA-A2 | None | A model for normal cells expressing endogenous HLA-A2 and negative to CD19 | Negative control |
|   | Hela | HLA-A2 | CD19 | A model for normal cells expressing recombinant CD19; HLA-A2 | Off-tumor |
| 4 | Hela | CD19 | None | A model for cancer cells expressing recombinant CD19 | On-tumor |
|   | Hela | CD19 | CD20 | A model for normal cells expressing recombinant CD19; CD20 | Off-tumor |
|   | Hela | CD20 | None | A model for normal cells expressing endogenous CD20 and negative to CD19 | Negative control |
| 3 | Hela-Luciferase | HLA-A2 | None | Negative control to be used in killing assay | Negative control |
|   | Hela-Luciferase | HLA-A2 | CD19 | A model for normal cells expressing recombinant CD19; HLA-A2 (killing assay) | Off-tumor |
| 5 | Hela-Luciferase | CD19 | None | A model for cancer cells expressing recombinant CD19 (killing assay) | On-tumor |
|   | Hela-Luciferase | CD19 | CD20 | A model for normal cells expressing recombinant CD19; CD20 (killing assay) | Off-tumor |
|   | Hela-Luciferase | CD20 | None | Negative control (killing assay) | Negative control |

Assays— iCAR's inhibitory effect will be tested both in-vitro and in-vivo.

In the in-vitro assays, we will focus on measuring cytokine secretion and cytotoxicity effects, while in-vivo, we will evaluate the iCAR inhibition and protection to 'on-target off-tumor' xenografts. We will limit T-cells lacking iCAR from contaminating the results by sorting T-cells to be iCAR/aCAR double positive using reporter genes. As a negative control for iCAR blocking activity, we may use T-cells transduced with CAR lacking the scFv domain (i.e. mock transduction).

cells at a ratio of 1:1 and more. The 'on-tumor' recombinant cells will be distinguished from the 'off-tumor' recombinant cells by Luciferase expression (only one cell population will be engineered to express the luciferase gene at a given time). Killing will be quantified after 24-48 hrs of co-incubation.

Caspase 3 Activity Assay—Detection of CTL Induced Apoptosis by an Anti-Activated Caspase 3 (CASP3).

One of the pathways by which cytotoxic T-cells kill target cells is by inducing apoptosis through the Fas ligand. Sequential activation of caspases plays a significant role in the execution-phase of cell apoptosis. Cleavage of pro-caspase 3 to caspase 3 results in conformational change and expression of catalytic activity. The cleaved activated form of caspase 3 can be specifically recognized by a monoclonal antibody.

Transduced T-cells will be co-cultured for 2-4 hrs with either 'on-tumor' or 'off-tumor' recombinant cells, previously labeled with CFSE or other cell tracer dye (e.g. CellTrace Violet). Following cell permeabilization and fixation by an inside staining kit (e.g. Miltenyi or BD bioscience) activated CASP3 will be detected by specific antibody staining (BD bioscience), and apoptotic target cells will be detected and quantified by flow cytometry.

Time Lapse Microscopy CTL

Transduced T-cells will be incubated with either 'on-tumor' or 'off-tumor' cells for up to 5 days. Time lapse microscopy will be used to visualize killing. Alternatively, flow cytometry analysis using viable cell number staining and CountBright beads (Invitrogen) for determining target cells number at end-point time will be conducted.

In order to demonstrate the effectiveness of aCAR/iCAR transduced T-cells in discerning targets in vitro, each recombinant target cells ('on-tumor' or 'off-tumor') is labeled with a different reporter protein (e.g. GFP and mCherry). Transduced T-cells (Effector cells) will be co-incubated with a mix of recombinant cells expressing one or two target antigens (Target cells) at different E/T ratios. Each cell-line's fate will be followed by microscopy imaging.

Cytokine Release

Upon T-cell activation, the cells secrete cytokines which can be quantified and used for evaluating T-cell activation and inhibition. Cytokines can be detected intracellularly by flow cytometry or by measurement of the secreted proteins in the medium by ELISA or Cytometric Bead Array (CBA).

Quantitation of Secreted Cytokines by ELISA

Following co-cultivation of transduced T-cells (Jurkat, or primary T-cells) expressing iCAR or aCAR or both aCA and iCAR with modified target cells, expressing iCAR or aCAR or both aCAR and iCAR antigens on their cell surface, conditioned medium will be collected, and cytokine's concentration will be measured by cytokine ELISA (IL-2, INFγ and or TNFα) according to the manufacture instruction (e.g. BioLegened or similar), and by Cytometric Bead Array (Miltenyi or similar).

iCAR Specific Inhibition as Measured by IL-2 ELISA

Jurkat CD19 aCAR and Jurkat CD19 aCAR/HLA-A2 iCAR effector cells were co-cultured with Raji, Raji-HLA-A2 and Thp 1 target cells and the corresponding supernatants were collected for IL-2 measurement by ELISA, as illustrated in FIG. 16A. Incubation of Jurkat CD19-aCAR/HLA-A2-iCAR with Raji target cells ('tumor') expressing CD19 showed IL-2 secretion, however incubation of these effector cells with Raji-HLA-A2 target cells expressing both CD19 and HLA-A2 ('off-tumor') resulted in more than 80% inhibition of IL-2 secretion. Conversely, IL-2 secretion was not affected when CD19 aCAR Jurkat cells were incubated with Raji or Raji-HLA-A2 target cells (FIG. 16B). This result, together with the NFAT activation assay described below points toward the potency of the iCAR construct to specifically protect normal cells expressing an antigen not expressed on tumor cells.

Quantitation of Cytokine Release by Flow Cytometry

Transduced T-cells (Jurkat, or primary T-cells) expressing iCAR or aCAR or both aCAR and iCAR co-cultured for 6-24 hrs. with recombinant target cells, expressing iCAR or aCAR or both aCAR and iCAR target antigens on their cell surface, will be subjected to Golgi transport blocker (e.g. Brefeldin A, monensin) to enable cytokine intracellular accumulation. T-cells will then be permed and fixed by an inside staining kit (e.g. Miltenyi) and stained with anti CD3 and CD8 and for IL-2 and or INFγ and or TNFα.

Cytokines Secretion Measured by Cytometric Bead Array (CBA) Assay

Cytometric Bead Array (CBA) is used to measure a variety of soluble and intracellular proteins, including cytokines, chemokines and growth factors.

T-cells (primary T-cells or Jurkat cells) transduced with aCAR or both aCAR and iCAR constructs (Effector cells) were stimulated with modified target cells expressing both iCAR and aCAR or aCAR or iCAR target antigens on their cell surface (FIG. 17A). Following several hours of co-incubation the effector cells produce and secrete cytokines which indicate their effector state. The supernatant of the reaction was collected, and secreted IL-2 was measured and quantified by multiplex CBA assay.

As shown in the FIG. 17B, a specific inhibition of IL-2 secretion was demonstrated for aCAR/iCAR transduced Jurkat T-cells co-cultured with target cells expressing both target antigens. A decrease of 86% in IL-2 secretion was demonstrated when dual CAR (aCAR/iCAR) transduced cells were co-incubated with target cells expressing both target antigens as compared to IL-2 secretion resulted from co-incubation of the same effector cells with target cells expressing only one target.

NFAT Activation Assay

Figure 18:
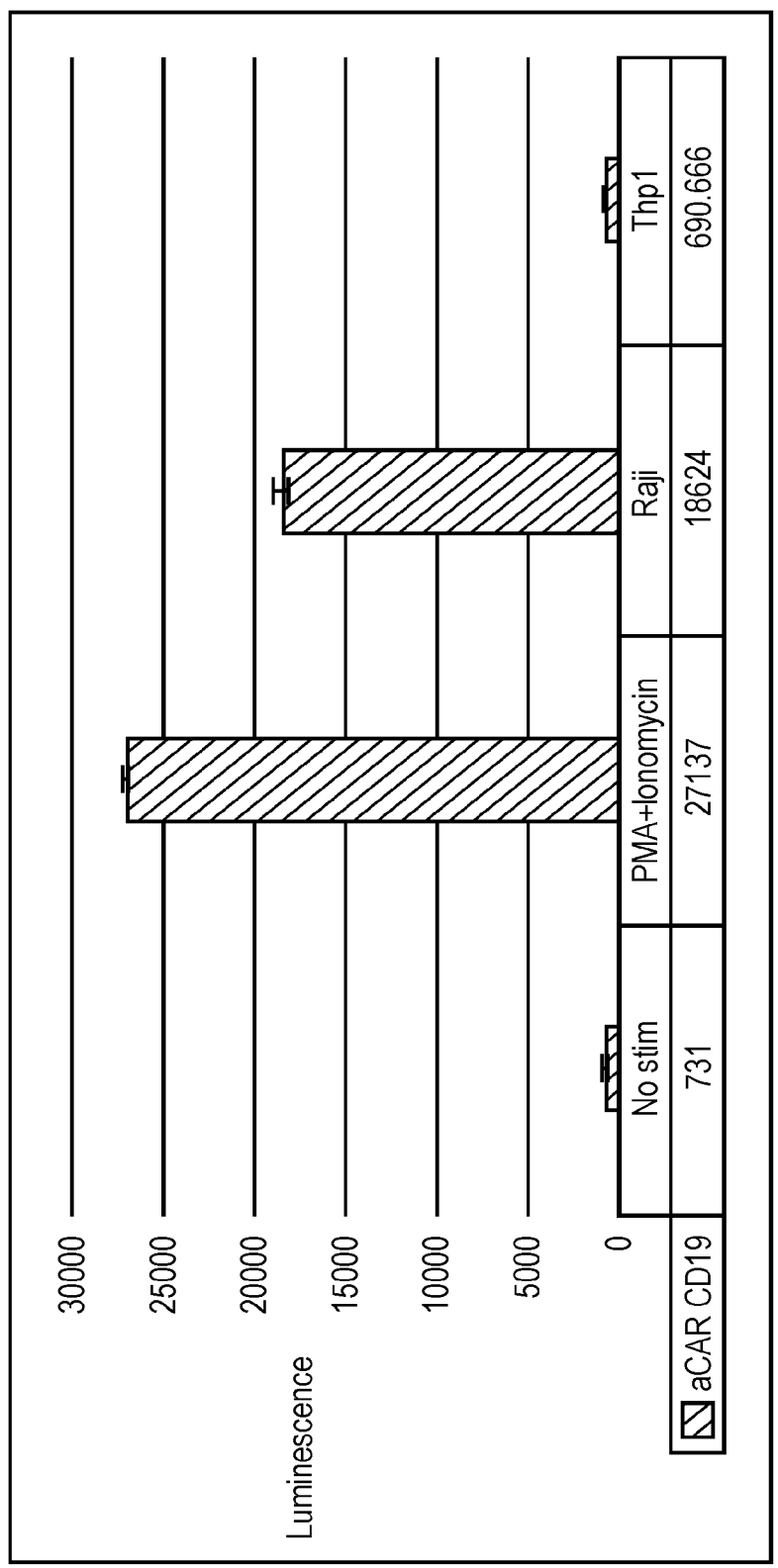
FIG. 18 shows specific activation of CD19 aCAR Jurkat-NFAT by CD19 expressing target cells.

For determination of T-cell activation as measured by NFAT activation, Jurkat-NFAT cells were transduced with different combinations of aCAR and iCAR, as detailed in Table 12. Effector Jurkat-NFAT cell-lines, expressing CD19 aCAR, HLA-A2 iCAR or both, were cocultured with target cells expressing either CD19 (Raji cells-'on-target') both CD19 and HLA-A2 (Raji-HLA-A2 'off-tumor') or HLA-A2 (Thp1 'off tumor') as described in Table 13. As a positive control, effector cells were stimulated in the presence of PMA and Ionomycin, which trigger calcium release required for NFAT signaling. Following 16 hrs. incubation at 37° C., luciferase was quantified using BPS Biosciences kit "One step luciferase assay system" according to the manufacturer's instructions. As expected, Jurkat NFAT cell-line expressing the CD19-CAR construct were specifically activated in the presence of Raji cell-line expressing CD19, while, no activation was shown when these cells were co-cultured with Thp1 cell-line which does not express CD19 (FIG. 18).

Figure 19:
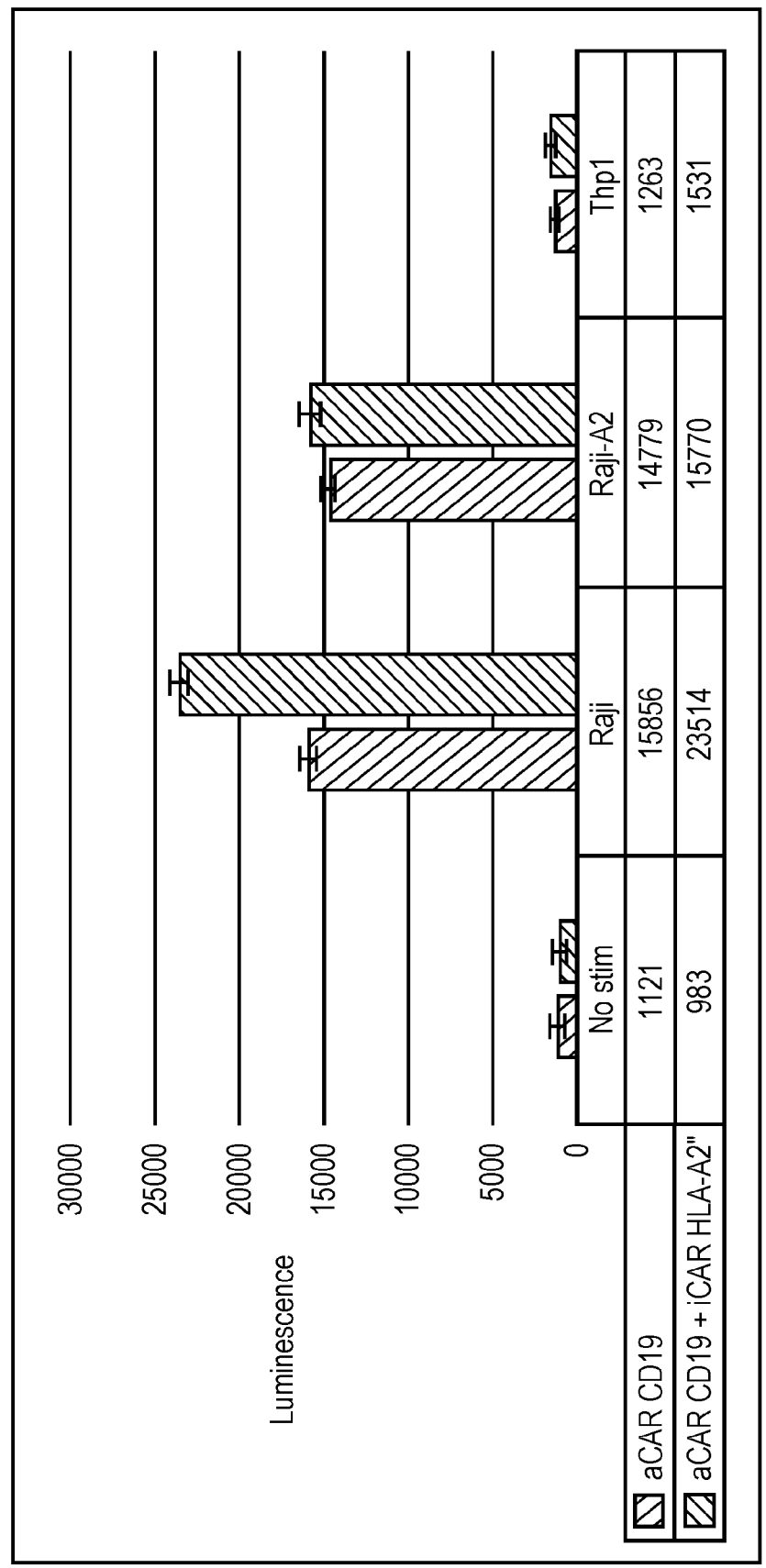
FIG. 19 shows specific inhibition of NFAT activation in CD19 aCAR/HLA-A2 iCAR Jurkat-NFAT

The inhibitory effect of HLA-A2 iCAR on CD19 aCAR induced NFAT activation can be seen in FIG. 21. Jurkat-NFAT-cell line expressing both CD19 aCAR and HLA-A2 iCAR was specifically inhibited when co-incubated with Raji-HLA-A2, expressing CD19 and HLA-A2 as compared to the activation induced by Raji cells expressing CD19 only. In contrast, Jurkat-NFAT cell-line expressing only CD19-CAR was similarly activated by both Raji and Raji-A2 cell-lines. Under these conditions, the inhibition of NFAT activation was calculated as ~30% (FIG. 19).

The effect of different E/T ratios was tested. Assay was repeated several times with E/T ratios of 10:1, 5:1, 1:1. The results given in FIG. 20 indicate that an increased inhibitory effect can be obtained with a higher Elf ratio. The results are presented as a ratio of the mean luminescence value from co-culture each effector cell-line with 'off-tumor' target cells to the mean value from coculture with 'on-target' presenting cells. As shown, Jurkat-NFAT-cell line expressing both CD19 aCAR and HLA-A2 iCAR was specifically inhibited when co-incubated with Raji-HLA-A2 expressing CD19 and HLA-A2 proteins, however, no inhibition was detected when this cell-line was co-cultured with Raji cell-line expressing CD19 only. On the contrary, Jurkat-NFAT cell line expressing CD19 aCAR, was equally activated regardless of the CD19 expressing target cell line it was co-cultured with (Raji or Raji-HLA-A2).

T-Cell Degranulation Assay as Measured by CD107a Staining

Degranulating of T cells can be identified by the surface expression of CD107a, a lysosomal associated membrane protein (LAMP-1). Surface expression of LAMP-1 has been shown to correlate with CD8 T cell cytotoxicity. This molecule is located on the luminal side of lysosomes. Upon activation, CD107a is transferred to the cell membrane surface of activated lymphocytes. CD107a is expressed on the cell surface transiently and is rapidly re-internalized via the endocytic pathway. Therefore, CD107a detection is maximized by antibody staining during cell stimulation and by the addition of monensin (to prevent acidification and subsequent degradation of endocytosed CD107a antibody complexes).

The transduced T cells will be incubated with the target cells for 6-24 hrs in the presence of monensin and will follow CD107a expression on the CD8 T cells by flow cytometry using conjugated antibodies against the T cell surface markers (CD3,CD8) and a conjugated antibody for CD107a.

Granulation (CD107a) as a marker for the killing potential. The most critical function of cytolytic T cells is the ability to kill target cells. Cytotoxic CD8+T lymphocytes mediate the killing of target cells via two major pathways: perforin-granzyme-mediated activation of apoptosis and fas-fas ligand-mediated induction of apoptosis. Induction of these pathways depends on the release of cytolytic granules from the responding CD8+ T cells. Degranulation is a prerequisite to perforin-granzyme-mediated killing and is required for immediate lytic function mediated by responding antigen-specific CD8+ T cells. Cytotoxicity does not require de novo synthesis of proteins by the effector CD8+ T cell; instead, pre-formed lytic granules located within the cytoplasm are released in a polarized fashion toward the target cell. The lytic granules are membrane-bound secretory lysosomes that contain a dense core composed of various proteins, including perforin and granzymes. The granule core is surrounded by a lipid bilayer containing numerous lysosomal-associated membrane glycoproteins (LAMPs), including CD107a (LAMP-1), CD107b (LAMP-2), and CD63 (LAMP-3). During the process of degranulation, the lytic granule membrane merges with the plasma membrane of the activated CD8+ T cell and the contents of the granule are then released into the immunological synapse between the CD8+ T cell and the target cell. As a result of this process, the granular membrane, including CD107a, CD107b, and CD63 glycoproteins therein, is incorporated into the plasma membrane of the responding CD8+ T cell. High-level expression of CD107a and b on the cell surface of activated T cells requires degranulation, because degranulation inhibitors, such as colchicine, dramatically reduce cell-surface expression of CD107a and b. Importantly, these proteins are rarely found on the surface of resting T lymphocytes. Thus, labeling responding cells with antibodies to CD107a and b and measuring their expression by flow cytometry can directly identify degranulating CD8+ T cells (Betts and Koup, 2004).

Experimental Settings:

PBMC's transduced with iCAR+aCAR/aCAR constructs (Effector cells) are stimulated with either PMA+Ionomycin (Positive Control) or modified target cells that express iCAR+aCAR/aCAR/iCAR antigens on their cell surface. During several hours of co-incubation, the effector cells degranulate, CD107a can be detected on the cell surface. This expression is transient and the CD107a is rapidly re-internalized via the endocytic pathway. Therefore, CD107a detection is maximized by antibody staining during cell stimulation and by the addition of monensin (to prevent acidification and subsequent degradation of endocytosed CD107a antibody complexes). BFA is required for optimal cytokine expression.

Example 9. In Vivo Models

In Vivo CTL Assay in Human Xenograft Mouse Models

To test whether T-cells expressing both aCAR and iCAR constructs could discriminate between the target cells and 'off-target' cells within the same organism and effectively kill the target cells while sparing the 'off-target' cells will be assessed by an in-vivo CTL assay.

Transduced T-cells with iCAR or aCAR or both iCAR and aCAR will be injected i.v. to naïve NOD/SCID/γc- or similar mice. Several hours later, target cells expressing iCAR, aCAR or both will be injected. These targets will be labeled with either CFSE/CPDE or similar cell trace dye in different concentrations (high, medium and low) which will allow further discrimination between them. 18 hrs following targets injection, mice will be sacrificed, spleens will be harvested, and the elimination of the specific target will be assessed by FACS. Percentage of specific killing will be calculated according to the formula below:

$$\left\{1 - \left[\left(\frac{\%\ pop_{high}(day1)}{\%\ pop_{high}(day0)}\right) \div \left(\frac{\%\ pop_{medium}(day1)}{\%\ pop_{medium}(day0)}\right)\right]\right\} \times 100$$

Tumor Growth Kinetics in Human Xenograft Mouse Models

NOD/SCID/γc- or similar mice will be inoculated with tumor cells. Inoculation can be i.p/i.v. or s.c. The tumor cells will express either the iCAR target, aCAR target or both. An example for one possible aCAR tumor cell line could be the CD19 positive NALM 6 (ATCC, human BALL cell line). Example of tumor cells that express both the aCAR and iCAR (i.e., 'off-tumor' cells), is the NALM 6 engineered to express the iCAR epitope (for example HLA-A2) thereby representing the healthy cells. NALM 6 and NALM 6-HLA-A2 can also be engineered to express a reporter gene (e.g. firefly luciferase), for easy detection. Mice will be divided into several study groups inoculated with all possible combinations of target cells. As an example, one group will be injected with the NALM 6 cells while the other will be injected with the NALM-6 expressing the iCAR epitope. Several days later, while the tumor has already been established, mice will be infused intravenously with T-cells transduced with aCAR, or aCAR/iCAR, or iCAR. In addition, control groups of untransduced T-cells, no T-cells or T-cells transduced without a signaling domain will also be included. Mice will be monitored until tumor reaches the experimental end point i.e. the maximal allowed tumor volume. Monitoring will be by measuring tumor volume by mechanical means (caliper) and also by using in-vivo imaging systems (IVIS). On the end point day, mice will be sacrificed, tumor burden will be quantified, and infiltrating T-cell populations will be analyzed by FACS. To test whether the T-cells expressing the iCAR construct could discriminate between the target cells and 'off-target' cells within the same organism, we will inject mice with several possible mixtures in several ratios of the 'on-tumor'/'off-tumor NALM-6 cells, followed by injection of transduced T-cells expressing either the aCAR alone or both aCAR and iCAR. Upon sacrifice of the mice the presence of the 'on-tumor' and 'off-tumor cells in the spleen and bone marrow will be analyzed by flow cytometry for the two markers, CD19 and the iCAR epitope.

Toxicity and Tumor Growth Kinetics in Transgenic Mouse Models

Transgenic mice that express the human aCAR and iCAR targets will also be used to determine the efficacy of the transduced T-cells. Under these settings the mice have a fully functional immune system, and the potential toxicity of the iCAR/aCAR transduced T-cells can be evaluated. The CAR construct will contain scFv that matches the human antigens, while the signaling domains will be modified to activate or inhibit murine T-cells. One example for such a model is the HHD-HLA-A2 mice that express only human HLA-A2 molecule while all other proteins are solely murine. The scFv of the CD19 aCAR will be directed in this case to the murine CD19 homolog. Human target cells lacking HLA molecules (e.g. LCL 721.221 cells or C1R-neoATCC® CRL-2369™ or similar) will be used. The targets will be modified to express the murine CD19. This system will allow monitoring of efficacy and toxicity issues.

mAbs Production

Several pairs of preserved and lost allelic variants identified in different tumors are selected and their polypeptide products will serve for the generation of variant specific mAbs using mAb production techniques. The discriminatory power of candidate mAbs will be assayed by double staining and flow cytometry experiments or immunohistochemistry, as determined by binding to recombinant cell-lines expressing the selected alleles.

All headings and section designations are used for clarity and reference purposes only and are not to be considered limiting in any way. For example, those of skill in the art will appreciate the usefulness of combining various aspects from different headings and sections as appropriate according to the spirit and scope of the invention described herein.

All references cited herein are hereby incorporated by reference herein in their entireties and for all purposes to the same extent as if each individual publication or patent or patent application was specifically and individually indicated to be incorporated by reference in its entirety for all purposes.

Many modifications and variations of this application can be made without departing from its spirit and scope, as will be apparent to those skilled in the art. The specific embodiments and examples described herein are offered by way of example only, and the application is to be limited only by the terms of the appended claims, along with the full scope of equivalents to which the claims are entitled.

What is claimed is:

1. A method for preparing a safe effector immune cell expressing (i) an inhibitory chimeric antigen receptor (iCAR) or a protective chimeric antigen receptor (pCAR), and (ii) an activating chimeric antigen receptor (aCAR), the method comprising:
   (i) identifying a gene with at least two expressed alleles that encodes a protein comprising an extracellular polymorphic epitope;
   (ii) determining that at least one of the expressed alleles exhibits an amino acid sequence change in the extracellular polymorphic epitope sequence relative to an extracellular polymorphic epitope reference sequence;
   (iii) determining that the gene is located in a chromosomal region which undergoes loss of heterozygosity (LOH) in a tumor type; and
   (iv) determining that the gene is expressed in the tissue-of-origin of the tumor type in which the chromosomal region was found to undergo LOH.

2. The method of claim 1, wherein the aCAR is directed against or specifically binds to a tumor-associated antigen or a non-polymorphic cell surface epitope.

3. The method of claim 1, wherein the aCAR is directed against or specifically binds to a CAR target selected from the group consisting of CD19, CD20, CD22, IgK, ROR1, CD30, LewisY, CD33, CD123, NKG2D-L, CD139, BCMA, TACI, GD2, FR-a, L1-CAM, ErbB2, EGFRvIII, VEGFR-2, IL-13Ra2, FAP, Mesothelin, c-MET, PSMA, CEA, EGFR, 5T4, GPC3, MUC1, MUC16, PDL1, CD38, CS1, PSCA, CD44v6, CD44v7/8, L-11ra, EphA2, CAIX, and CSPG4.

4. The method of claim 2, wherein the non-polymorphic cell surface epitope is selected from the group consisting of CD 19, CD20, CD22, CDI0, CD7, CD49f, CD56, CD74, CAIX lgK, RORI, ROR2, CD30, LewisY, CD33, CD34, CD38, CD123, CD28, CD44v6, CD44, CD41, CD133, CD138, NKG2D-L, CD139, BCMA, GD2, GD3, hTERT, FBP, EGP-2, EGP-40, FR-α, LI-CAM, ErbB2,3,4, EGFRvIII, VEGFR-2, IL-13Ra2, FAP, Mesothelin, c-MET, PSMA, CEA, kRas, MAGE-A1, MUCI MUC16, PDLI, PSCA, EpCAM, FSHR, AFP, AXL, CD80, CD89, CDH17, CLD18, GPC3, TEM8, TGFBI, NY-ESO-1, WT-I and EGFR.

5. The method of claim 1, wherein the aCAR is directed against or specifically binds to a cell surface protein that is expressed in a tumor tissue in which the iCAR is also expressed.

6. The method of claim 1, wherein the gene comprising the extracellular polymorphic epitope is an HLA gene.

7. The method of claim 1, wherein the gene comprising the extracellular polymorphic epitope is an HLA-A, HLA-B, HLA-C, HLA-G, HLA-E, HLA-F, HLA-K, HLA-L, HLA-DM, HLA-DO, HLA-DP, HLA-DQ, or HLA-DR gene.

8. The method of claim 1, wherein the tumor type is selected from the group consisting of a breast tumor, a prostate tumor, an ovarian tumor, a cervical tumor, a skin tumor, a pancreatic tumor, a colorectal tumor, a renal tumor, a liver tumor, a brain tumor, a lymphoma, a leukemia, a lung tumor, and a glioma.

9. The method of claim 1, wherein the tumor type is selected from the group consisting of an adrenal gland tumor, a kidney tumor, a melanoma, DLBC, a breast tumor, a sarcoma, an ovary tumor, a lung tumor, a bladder tumor, and a liver tumor.

10. The method of claim 2, wherein the tumor-associated antigen is associated with a tumor selected from the group consisting of a breast tumor, a prostate tumor, an ovarian tumor, a cervical tumor, a skin tumor, a pancreatic tumor, a colorectal tumor, a renal tumor, a liver tumor, a brain tumor, a lymphoma, a leukemia, a lung tumor, and a glioma.

11. The method of claim 2, wherein the tumor-associated antigen is associated with a tumor selected from the group consisting of an adrenal gland tumor, a kidney tumor, a melanoma, DLBC, a breast tumor, a sarcoma, an ovary tumor, a lung tumor, a bladder tumor, and a liver tumor.

* * * * *

SEQUENCE LISTING

```
<160> NUMBER OF SEQ ID NOS: 10

<210> SEQ ID NO 1
<211> LENGTH: 3432
<212> TYPE: DNA
<213> ORGANISM: Artificial Sequence
<220> FEATURE:
<223> OTHER INFORMATION: CD19 aCAR_IRES_RFP_P2A_Puro Synthetic DNA

<400> SEQUENCE: 1
atggccttac cagtgaccgc cttgctcctg ccgctggcct tgctgctcca cgccgccagg     60
ccggacatcc agatgacaca gactacatcc tccctgtctg cctctctggg agacagagtc    120
accatcagtt gcagggcaag tcaggacatt agtaaatatt taaattggta tcagcagaaa    180
ccagatggaa ctgttaaact cctgatctac catacatcaa gattacactc aggagtccca    240
tcaaggttca gtggcagtgg gtctggaaca gattattctc tcaccattag caacctggag    300
caagaagata ttgccactta cttttgccaa cagggtaata cgcttccgta cacgttcgga    360 gggggggacca agctggagat cacaggtggc ggtggctcgg gcggtggtgg gtcgggtggc    420
ggcggatctg aggtgaaact gcaggagtca ggacctggcc tggtggcgcc ctcacagagc    480
ctgtccgtca catgcactgt ctcagggttc tcattacccg actatggtgt aagctggatt    540
cgccagcctc cacgaaaggg tctggagtgg ctgggagtaa tatggggtag tgaaaccaca    600
tactataatt cagctctcaa atccagactg accatcatca aggacaactc caagagccaa    660
gttttcttaa aaatgaacag tctgcaaact gatgacacag ccatttacta ctgtgccaaa    720
cattattact acggtggtag ctatgctatg gactactggg gccaaggaac ctcagtcacc    780
```

```
gtctcctcaa ccactacccc agcaccgagg ccacccaccc cggctcctac catcgcctcc    840
cagcctctgt ccctgcgtcc ggaggcatgt agacccgcag ctggtggggc cgtgcatacc    900
cggggtcttg acttcgcctg cgatatctac atttgggccc ctctggctgg tacttgcggg    960
gtcctgctgc tttcactcgt gatcactctt tactgtaagc gcggtcggaa gaagctgctg   1020
tacatcttta agcaacccct catgaggcct gtgcagacta ctcaagagga ggacggctgt   1080
tcatgccggt tcccagagga ggaggaaggc ggctgcgaac tgcgcgtgaa attcagccgc   1140
agcgcagatg ctccagccta caagcagggg cagaaccagc tctacaacga actcaatctt   1200
ggtcggagag aggagtacga cgtgctggac aagcggagag acgggaccc agaaatgggc    1260 gggaagccgc gcagaaagaa tccccaagag ggcctgtaca cgagctcca aaaggataag    1320 atggcagaag cctatagcga gattggtatg aaagggaac gcagaagagg caaaggccac    1380
gacggactgt accagggact cagcaccgcc accaaggaca cctatgacgc tcttcacatg   1440
caggccctgc cgcctcggtg agcggccgca aattccgccc ctctccctcc cccccccta   1500 acgttactgg ccgaagccgc ttggaataag gccggtgtgc gtttgtctat atgttatttt   1560
ccaccatatt gccgtctttt ggcaatgtga gggcccggaa acctggccct gtcttcttga   1620
cgagcattcc tagggtctt tccctctcg ccaaaggaat gcaaggtctg ttgaatgtcg    1680
tgaaggaagc agttcctctg gaagcttctt gaagacaaac aacgtctgta gcgacccttt   1740
gcaggcagcg gaacccccca cctggcgaca ggtgcctctg cggccaaaag ccacgtgtat   1800
aagatacacc tgcaaaggcg gcacaacccc agtgccacgt tgtgagttgg atagttgtgg   1860
aaagagtcaa atggctctcc tcaagcgtat tcaacaaggg gctgaaggat gcccagaagg   1920 tacccccattg tatgggatct gatctggggc ctcggtgcac atgctttaca tgtgtttagt   1980
cgaggttaaa aaaacgtcta ggccccccga accacgggga cgtggttttc ctttgaaaaa   2040
cacgataata ccatggtgtc taagggcgaa gagctgatta aggagaacat gcacatgaag   2100
ctgtacatgg agggcaccgt gaacaaccac cacttcaagt gcacatccga gggcgaaggc   2160
aagccctacg agggcaccca gaccatgaga atcaaggtgg tcgagggcgg ccctctcccc   2220 ttcgcctttcg acatcctggc taccagcttc atgtacggca gcagaacctt catcaaccac   2280
acccagggca tccccgactt ctttaagcag tccttccctg agggcttcac atgggagaga   2340
gtcaccacat acgaagacgg gggcgtgctg accgctaccc aggacaccag cctccaggac   2400
ggctgcctca tctacaacgt caagatcaga ggggtgaact tcccatccaa cggccctgtg   2460
atgcagaaga aaacactcgg ctgggaggcc aacaccgaga tgctgtaccc cgctgacggc   2520
ggcctggaag cagaagcga catggccctg aagctcgtgg gcgggggcca cctgatctgc   2580
aacttcaaga ccacatacag atccaagaaa cccgctaaga acctcaagat gcccggcgtc   2640
tactatgtgg accacagact ggaaagaatc aaggaggccg acaaagagac ctacgtcgag   2700
cagcacgagg tggctgtggc cagatactgc gacctcccta gcaaactggg gcacaaactt   2760
aatggatccg gcgcgacaaa ctttagcttg ctgaagcaag ctggtgacgt ggaggagaat   2820
cccggcccta tggccaccga gtacaagccc acggtgcgcc tcgccacccg gacgacgtc    2880 ccccgggccc tacgcaccct cgccgccgcg ttcgccgact accccgccac gcgccacacc   2940
gtcgatccgg accgccacat cgagcgggtc accgagctgc aagaactctt cctcacgcgc   3000
gtcgggctcg acatcggcaa ggtgtgggtc gcggacgacg gcgccgcggt ggcggtctgg   3060
accacgccga gagcgtcga agcggggcg gtgttcgccg agatcggccc cgcgcatggcc    3120 gagttgagcg gttcccggct ggccgcgcag caacagatgg aaggcctcct ggcgccgcac   3180
```

-continued

```
cggcccaagg agcccgcgtg gttcctggcc accgtcggcg tctcgcccga ccaccagggc    3240
aagggtctgg gcagcgccgt cgtgctcccc ggagtggagg cggccgagcg cgccggggtg    3300
cccgccttcc tggagacctc cgcgccccgc aacctcccct tctacgagcg gctcggcttc    3360
accgtcaccg ccgacgtcga ggtgcccgaa ggaccgcgca cctggtgcat gacccgcaag    3420
cccggtgcct ga                                                        3432
```

<210> SEQ ID NO 2
<211> LENGTH: 486
<212> TYPE: PRT
<213> ORGANISM: Artificial Sequence
<220> FEATURE:
<223> OTHER INFORMATION: CD19 aCAR Synthetic protein

<400> SEQUENCE: 2

```
Met Ala Leu Pro Val Thr Ala Leu Leu Leu Pro Leu Ala Leu Leu Leu
  1               5                  10                  15

His Ala Ala Arg Pro Asp Ile Gln Met Thr Gln Thr Thr Ser Ser Leu
             20                  25                  30

Ser Ala Ser Leu Gly Asp Arg Val Thr Ile Ser Cys Arg Ala Ser Gln
         35                  40                  45

Asp Ile Ser Lys Tyr Leu Asn Trp Tyr Gln Gln Lys Pro Asp Gly Thr
     50                  55                  60

Val Lys Leu Leu Ile Tyr His Thr Ser Arg Leu His Ser Gly Val Pro
 65                  70                  75                  80

Ser Arg Phe Ser Gly Ser Gly Ser Gly Thr Asp Tyr Ser Leu Thr Ile
                 85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Ser Gly Gly Gly Ser Glu
    130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ile Lys Asp Asn Ser Lys Ser Gln Val Phe Leu Lys
    210                 215                 220

Met Asn Ser Leu Gln Thr Asp Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320
```

Val Leu Leu Leu Ser Leu Val Ile Thr Leu Tyr Cys Lys Arg Gly Arg
            325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
            355                 360                 365

Glu Gly Gly Cys Glu Leu Arg Val Lys Phe Ser Arg Ser Ala Asp Ala
            370                 375                 380

Pro Ala Tyr Lys Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
            435                 440                 445

Gly Met Lys Gly Glu Arg Arg Arg Gly Lys Gly His Asp Gly Leu Tyr
            450                 455                 460

Gln Gly Leu Ser Thr Ala Thr Lys Asp Thr Tyr Asp Ala Leu His Met
465                 470                 475                 480

Gln Ala Leu Pro Pro Arg
                485

<210> SEQ ID NO 3
<211> LENGTH: 237
<212> TYPE: PRT
<213> ORGANISM: Artificial Sequence
<220> FEATURE:
<223> OTHER INFORMATION: RFP Synthetic Protein

<400> SEQUENCE: 3

Met Val Ser Lys Gly Glu Glu Leu Ile Lys Glu Asn Met His Met Lys
1               5                   10                  15

Leu Tyr Met Glu Gly Thr Val Asn Asn His His Phe Lys Cys Thr Ser
            20                  25                  30

Glu Gly Glu Gly Lys Pro Tyr Glu Gly Thr Gln Thr Met Arg Ile Lys
        35                  40                  45

Val Val Glu Gly Gly Pro Leu Pro Phe Ala Phe Asp Ile Leu Ala Thr
    50                  55                  60

Ser Phe Met Tyr Gly Ser Arg Thr Phe Ile Asn His Thr Gln Gly Ile
65                  70                  75                  80

Pro Asp Phe Phe Lys Gln Ser Phe Pro Glu Gly Phe Thr Trp Glu Arg
                85                  90                  95

Val Thr Thr Tyr Glu Asp Gly Gly Val Leu Thr Ala Thr Gln Asp Thr
            100                 105                 110

Ser Leu Gln Asp Gly Cys Leu Ile Tyr Asn Val Lys Ile Arg Gly Val
            115                 120                 125

Asn Phe Pro Ser Asn Gly Pro Val Met Gln Lys Lys Thr Leu Gly Trp
            130                 135                 140

Glu Ala Asn Thr Glu Met Leu Tyr Pro Ala Asp Gly Gly Leu Glu Gly
145                 150                 155                 160

Arg Ser Asp Met Ala Leu Lys Leu Val Gly Gly His Leu Ile Cys
                165                 170                 175

Asn Phe Lys Thr Thr Tyr Arg Ser Lys Lys Pro Ala Lys Asn Leu Lys
            180                 185                 190

Met Pro Gly Val Tyr Tyr Val Asp His Arg Leu Glu Arg Ile Lys Glu
            195                 200                 205

Ala Asp Lys Glu Thr Tyr Val Glu Gln His Gly Val Ala Val Ala Arg
            210                 215                 220

Tyr Cys Asp Leu Pro Ser Lys Leu Gly His Lys Leu Asn
225                 230                 235

<210> SEQ ID NO 4
<211> LENGTH: 200
<212> TYPE: PRT
<213> ORGANISM: Artificial Sequence
<220> FEATURE:
<223> OTHER INFORMATION: Puromycin resistance Synthetic Protein

<400> SEQUENCE: 4

Met Ala Thr Glu Tyr Lys Pro Thr Val Arg Leu Ala Thr Arg Asp Asp
1               5                   10                  15

Val Pro Arg Ala Val Arg Thr Leu Ala Ala Ala Phe Ala Asp Tyr Pro
            20                  25                  30

Ala Thr Arg His Thr Val Asp Pro Asp Arg His Ile Glu Arg Val Thr
        35                  40                  45

Glu Leu Gln Glu Leu Phe Leu Thr Arg Val Gly Leu Asp Ile Gly Lys
    50                  55                  60

Val Trp Val Ala Asp Asp Gly Ala Ala Val Ala Val Trp Thr Thr Pro
65                  70                  75                  80

Glu Ser Val Glu Ala Gly Ala Val Phe Ala Glu Ile Gly Pro Arg Met
                85                  90                  95

Ala Glu Leu Ser Gly Ser Arg Leu Ala Ala Gln Gln Met Glu Gly
            100                 105                 110

Leu Leu Ala Pro His Arg Pro Lys Glu Pro Ala Trp Phe Leu Ala Thr
        115                 120                 125

Val Gly Val Ser Pro Asp His Gln Gly Lys Gly Leu Gly Ser Ala Val
    130                 135                 140

Val Leu Pro Gly Val Glu Ala Ala Glu Arg Ala Gly Val Pro Ala Phe
145                 150                 155                 160

Leu Glu Thr Ser Ala Pro Arg Asn Leu Pro Phe Tyr Glu Arg Leu Gly
                165                 170                 175

Phe Thr Val Thr Ala Asp Val Glu Val Pro Glu Gly Pro Arg Thr Trp
            180                 185                 190

Cys Met Thr Arg Lys Pro Gly Ala
        195                 200

<210> SEQ ID NO 5
<211> LENGTH: 3669
<212> TYPE: DNA
<213> ORGANISM: Artificial Sequence
<220> FEATURE:
<223> OTHER INFORMATION: CD20 iCAR_IRES_GFP_P2A_Hygro Synthetic DNA

<400> SEQUENCE: 5
atggcactgc ctgtgaccgc cctgctgctg ccactggccc tgctgctgca cgcagccagg     60
cccgacatcg tgctgacaca gagcccagca atcctgtccg cctctcctgg agagaaggtg    120
accatgacat gccgcgccag ctcctctgtg aactacatgg attggtatca gaagaagcct    180
ggcagctccc caaagccctg gatctacgcc accagcaatc tggcctccgg cgtgccagca    240
cggttcagcg gctccggctc tggcaccagc tattccctga caatctccag agtggaggca    300
gaggacgcag caacctacta ttgccagcag tggtctttca acccccctac ctttggcggc    360

-continued

```
ggcacaaagc tggagatcaa gggctctaca agcggaggag gctctggagg aggcagcgga    420
ggcggcggct ctagcgaggt gcagctgcag cagagcggag cagagctggt gaagcctgga    480
gcctccgtga agatgtcttg taaggccagc ggctacacct tcacatccta taatatgcac    540
tgggtgaagc agacccccagg acagggcctg gagtggatcg gagcaatcta cccaggaaac    600
ggcgacacaa gctataatca gaagtttaag ggcaaggcca ccctgacagc cgataagtcc    660
tctagcaccg cctacatgca gctgtcctct ctgacatccg aggactctgc cgattactat    720
tgtgcccggt ccaactacta tggcagctcc tactggttct ttgacgtgtg gggagcaggc    780
accacagtga ccgtgtctag caccgagagg agagcagagg tgcccacagc acccccatct    840
ccaagcccta ggccagcagg acagttccag accctggtgg tgggagtggt gggaggcctg    900
ctgggctctc tggtgctgct ggtgtgggtg ctggccgtga tctgcagcag gccgcccgc    960
ggcaccatcg gcgccaggcg cacaggccag cctctgaagg aggaccttc cgccgtgcca    1020
gtgttctctg tggactacgg cgagctggat tttcagtggc gggagaaaac cccagagcca    1080
cctgtgccct gcgtgcctga gcagaccgag tatgccacaa tcgtgtttcc atccggaatg    1140
ggcacaagct cccctgcaag gagaggcagc gccgacggac cacggtccgc ccagccactg    1200
cggcccgagg atggccactg ttcttggccc ctgtgacgcc cctctccccc ccccccctct    1260
ccctcccccc cccctaacgt tactggccga agccgcttgg aataaggccg gtgtgcgttt    1320
gtctatatgt tattttccac catattgccg tcttttggca atgtgagggc ccggaaacct    1380
ggccctgtct tcttgacgag cattcctagg ggtctttccc ctctcgccaa aggaatgcaa    1440
ggtctgttga atgtcgtgaa ggaagcagtt cctctggaag cttcttgaag acaaacaacg    1500
tctgtagcga ccctttgcag gcagcggaac cccccacctg gcgacaggtg cctctgcggc    1560
caaaagccac gtgtataaga tacacctgca aaggcggcac aacccagtg ccacgttgtg    1620
agttggatag ttgtggaaag agtcaaatgg ctctcctcaa gcgtattcaa caaggggctg    1680
aaggatgccc agaaggtacc ccattgtatg ggatctgatc tggggcctcg gtgcacatgc    1740
tttacatgtg tttagtcgag gttaaaaaaa cgtctaggcc ccccgaacca cggggacgtg    1800
gttttccttt gaaaaacacg atgataaggc ttgccacaac ccgtaccaaa gatggtgtcc    1860
aagggagagg agctgttcac cggagtggtg cccatcctgg tggagctgga cggcgatgtg    1920
aatggccaca gtttagcgt gtccggagag ggagagggcg acgcaaccta cggcaagctg    1980
acactgaagt tcatctgcac cacaggcaag ctgcccgtgc cttggccaac cctggtgacc    2040
acactgacat acggcgtgca gtgttttctt cgctatcccg accacatgaa gcagcacgat    2100
ttctttaaga gcgccatgcc tgagggctac gtgcaggagc ggaccatctt ctttaaggac    2160
gatggcaact ataagaccag agccgaggtg aagttcgagg gcgacacact ggtgaacagg    2220
atcgagctga agggcatcga ctttaaggag gatggcaata tcctgggcca caagctggag    2280
tacaactata ttcccacaa cgtgtacatc atggccgata gcagaagaa cggcatcaag    2340
gtcaatttca gatcagaca caatatcgag gacggctctg tgcagctggc cgatcactac    2400
cagcagaaca ccccaatcgg cgacggaccc gtgctgctgc ctgataatca ctatctgtct    2460
acacagagcg ccctgtccaa ggaccccaac gagaagaggg atcacatggt gctgctggag    2520
tttgtgaccg cagcaggaat cacactggga atggacgagc tgtataaggg cagcggcgcc    2580
accaacttct ccctgctgaa gcaggcaggc gacgtggagg agaatccagg acctatggat    2640
agaagcggca agccagagct gaccgccaca tccgtgagaa gttcctgat cgagaagttt    2700
gactctgtga gcgatctgat gcagctgtcc gagggagagg agtccagggc cttctctttt    2760
```

```
gatgtgggcg gcaggggata cgtgctgagg gtgaatagct gcgccgacgg cttctataag    2820
gatagatacg tgtatagaca ctttgcctcc gccgccctgc caatcccaga ggtgctggac    2880
atcggcgagt tttccgagtc tctgacctac tgtatcagcc ggagagccca gggagtgacc    2940
ctgcaggatc tgcctgagac agagctgcca gccgtgctgc agccagtggc agaggctatg    3000
gacgcaatcg ccgccgccga cctgtctcag acaagcggct tcggccctt tggcccacag    3060 ggcatcggcc agtacaccac atggagggac ttcatctgcg ccatcgccga tcctcacgtg    3120
tatcactggc agaccgtgat ggacgataca gtgagcgcct ccgtggcaca ggccctggac    3180
gagctgatgc tgtgggccga ggattgtcca gaggtgcgcc acctggtgca cgcagacttt    3240
ggcagcaaca atgtgctgac cgataatggc cggatcacag ccgtgatcga ctggtccgag    3300
gccatgttcg gcgattctca gtacgaggtg ccaacatct tcttttggag gccttggctg    3360
gcctgcatgg agcagcagac ccgctatttt gagaggcgcc accctgagct ggccggctct    3420
ccacggctga gagcatacat gctgcgcatc ggcctggacc agctgtatca gagcctggtg    3480
gatggcaatt tcgacgatgc agcatgggca cagggccggt gcgacgcaat cgtgagatcc    3540
ggcgccggca ccgtgggccg gacacagatc gcacggcgga gccgccgt gtggaccgac    3600 ggatgcgtgg aggtgctggc cgattctggc aacaggcgcc caagcacaag gccccgcgcc    3660
aaggagtga                                                            3669
```

<210> SEQ ID NO 6
<211> LENGTH: 411
<212> TYPE: PRT
<213> ORGANISM: Artificial Sequence
<220> FEATURE:
<223> OTHER INFORMATION: CD20 iCAR Synthetic Protein

<400> SEQUENCE: 6

```
Met Ala Leu Pro Val Thr Ala Leu Leu Leu Pro Leu Ala Leu Leu Leu
1               5                   10                  15

His Ala Ala Arg Pro Asp Ile Val Leu Thr Gln Ser Pro Ala Ile Leu
            20                  25                  30

Ser Ala Ser Pro Gly Glu Lys Val Thr Met Thr Cys Arg Ala Ser Ser
        35                  40                  45

Ser Val Asn Tyr Met Asp Trp Tyr Gln Lys Pro Gly Ser Ser Pro
    50                  55                  60

Lys Pro Trp Ile Tyr Ala Thr Ser Asn Leu Ala Ser Gly Val Pro Ala
65                  70                  75                  80

Arg Phe Ser Gly Ser Gly Ser Gly Thr Ser Tyr Ser Leu Thr Ile Ser
                85                  90                  95

Arg Val Glu Ala Glu Asp Ala Ala Thr Tyr Tyr Cys Gln Gln Trp Ser
            100                 105                 110

Phe Asn Pro Pro Thr Phe Gly Gly Gly Thr Lys Leu Glu Ile Lys Gly
        115                 120                 125

Ser Thr Ser Gly Gly Gly Ser Gly Gly Gly Ser Gly Gly Gly Gly Ser
    130                 135                 140

Ser Glu Val Gln Leu Gln Gln Ser Gly Ala Glu Leu Val Lys Pro Gly
145                 150                 155                 160

Ala Ser Val Lys Met Ser Cys Lys Ala Ser Gly Tyr Thr Phe Thr Ser
                165                 170                 175

Tyr Asn Met His Trp Val Lys Gln Thr Pro Gly Gln Gly Leu Glu Trp
            180                 185                 190
```

```
Ile Gly Ala Ile Tyr Pro Gly Asn Gly Asp Thr Ser Tyr Asn Gln Lys
            195                 200                 205

Phe Lys Gly Lys Ala Thr Leu Thr Ala Asp Lys Ser Ser Ser Thr Ala
    210                 215                 220

Tyr Met Gln Leu Ser Ser Leu Thr Ser Glu Asp Ser Ala Asp Tyr Tyr
225                 230                 235                 240

Cys Ala Arg Ser Asn Tyr Tyr Gly Ser Ser Tyr Trp Phe Phe Asp Val
                245                 250                 255

Trp Gly Ala Gly Thr Thr Val Thr Val Ser Ser Thr Glu Arg Arg Ala
            260                 265                 270

Glu Val Pro Thr Ala His Pro Ser Pro Ser Pro Arg Pro Ala Gly Gln
    275                 280                 285

Phe Gln Thr Leu Val Val Gly Val Val Gly Leu Leu Gly Ser Leu
290                 295                 300

Val Leu Leu Val Trp Val Leu Ala Val Ile Cys Ser Arg Ala Ala Arg
305                 310                 315                 320

Gly Thr Ile Gly Ala Arg Arg Thr Gly Gln Pro Leu Lys Glu Asp Pro
                325                 330                 335

Ser Ala Val Pro Val Phe Ser Val Asp Tyr Gly Glu Leu Asp Phe Gln
                340                 345                 350

Trp Arg Glu Lys Thr Pro Glu Pro Pro Val Pro Cys Val Pro Glu Gln
            355                 360                 365

Thr Glu Tyr Ala Thr Ile Val Phe Pro Ser Gly Met Gly Thr Ser Ser
    370                 375                 380

Pro Ala Arg Arg Gly Ser Ala Asp Gly Pro Arg Ser Ala Gln Pro Leu
385                 390                 395                 400

Arg Pro Glu Asp Gly His Cys Ser Trp Pro Leu
                405                 410

<210> SEQ ID NO 7
<211> LENGTH: 239
<212> TYPE: PRT
<213> ORGANISM: Artificial Sequence
<220> FEATURE:
<223> OTHER INFORMATION: GFP Synthetic Protein

<400> SEQUENCE: 7

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140
```

```
Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
            195                 200                 205

Ser Lys Asp Pro Asn Glu Lys Arg Asp His Met Val Leu Leu Glu Phe
        210                 215                 220

Val Thr Ala Ala Gly Ile Thr Leu Gly Met Asp Glu Leu Tyr Lys
225                 230                 235

<210> SEQ ID NO 8
<211> LENGTH: 344
<212> TYPE: PRT
<213> ORGANISM: Artificial Sequence
<220> FEATURE:
<223> OTHER INFORMATION: Hygromycin resistance Synthetic Protein

<400> SEQUENCE: 8

Met Asp Arg Ser Gly Lys Pro Glu Leu Thr Ala Thr Ser Val Glu Lys
1               5                   10                  15

Phe Leu Ile Glu Lys Phe Asp Ser Val Ser Asp Leu Met Gln Leu Ser
            20                  25                  30

Glu Gly Glu Glu Ser Arg Ala Phe Ser Phe Asp Val Gly Gly Arg Gly
        35                  40                  45

Tyr Val Leu Arg Val Asn Ser Cys Ala Asp Gly Phe Tyr Lys Asp Arg
50                  55                  60

Tyr Val Tyr Arg His Phe Ala Ser Ala Ala Leu Pro Ile Pro Glu Val
65                  70                  75                  80

Leu Asp Ile Gly Glu Phe Ser Glu Ser Leu Thr Tyr Cys Ile Ser Arg
                85                  90                  95

Arg Ala Gln Gly Val Thr Leu Gln Asp Leu Pro Glu Thr Glu Leu Pro
            100                 105                 110

Ala Val Leu Gln Pro Val Ala Glu Ala Met Asp Ala Ile Ala Ala Ala
        115                 120                 125

Asp Leu Ser Gln Thr Ser Gly Phe Gly Pro Phe Gly Pro Gln Gly Ile
130                 135                 140

Gly Gln Tyr Thr Thr Trp Arg Asp Phe Ile Cys Ala Ile Ala Asp Pro
145                 150                 155                 160

His Val Tyr His Trp Gln Thr Val Met Asp Asp Thr Val Ser Ala Ser
                165                 170                 175

Val Ala Gln Ala Leu Asp Glu Leu Met Leu Trp Ala Glu Asp Cys Pro
            180                 185                 190

Glu Val Arg His Leu Val His Ala Asp Phe Gly Ser Asn Asn Val Leu
        195                 200                 205

Thr Asp Asn Gly Arg Ile Thr Ala Val Ile Asp Trp Ser Glu Ala Met
210                 215                 220

Phe Gly Asp Ser Gln Tyr Glu Val Ala Asn Ile Phe Phe Trp Arg Pro
225                 230                 235                 240

Trp Leu Ala Cys Met Glu Gln Gln Thr Arg Tyr Phe Glu Arg Arg His
                245                 250                 255

Pro Glu Leu Ala Gly Ser Pro Arg Leu Arg Ala Tyr Met Leu Arg Ile
            260                 265                 270
```

```
Gly Leu Asp Gln Leu Tyr Gln Ser Leu Val Asp Gly Asn Phe Asp Asp
            275                 280                 285
Ala Ala Trp Ala Gln Gly Arg Cys Asp Ala Ile Val Arg Ser Gly Ala
290                 295                 300
Gly Thr Val Gly Arg Thr Gln Ile Ala Arg Arg Ser Ala Ala Val Trp
305                 310                 315                 320
Thr Asp Gly Cys Val Glu Val Leu Ala Asp Ser Gly Asn Arg Pro
                325                 330                 335
Ser Thr Arg Pro Arg Ala Lys Glu
            340

<210> SEQ ID NO 9
<211> LENGTH: 3696
<212> TYPE: DNA
<213> ORGANISM: Artificial Sequence
<220> FEATURE:
<223> OTHER INFORMATION: HLA-A2 iCAR_IRES_ GFP_P2A_Hygro Synthetic DNA

<400> SEQUENCE: 9
atggcactgc cagtgaccgc cctgctgctg cctctggccc tgctgctgca cgcagccaga      60
cccgagcaga agctgatctc cgaggaggac ctgcaggtgc agctgcagca gtctggacct     120
gagctggtga agccaggagc ctccgtgaag atgtcttgca aggccagcgg ctacaccttc     180
acatcttatc acatccagtg ggtgaagcag cggcccggac agggcctgga gtggatcgga     240
tggatctacc caggcgacgg ctccacacag tataacgaga agttcaaggg caagaccaca     300
ctgaccgccg ataagagcag cagcaccgcc tacatgctgc tgagcagcct gaccagcgag     360
gacagcgcca tctactttg cgccagggag ggcacatact atgctatgga ctattgggc     420 cagggcacca gcgtgacagt gtctagcgga ggaggaggct ccggaggagg aggctctggc     480
ggcggcggca gcgacgtgct gatgacccag acaccactga gcctgccgt gagcctgggc     540 gatcaggtga gcatctcctg tagatcctct cagagcatcg tgcactccaa cggcaatacc     600
tacctggagt ggtatctgca gaagccaggc cagtccccca gctgctgat ctataaggtg     660 tctaatcggt tcagcggcgt gcctgacaga ttttctggca gcggctccgg caccgacttc     720
accctgaaga tcagccgggt ggaggcagag gatctgggcg tgtactattg tttccagggc     780
tcccacgtgc cacgcacctt tggcggcggc acaaagctgg agatcaagac cgagaggaga     840
gcagaggtgc ccacagcaca cccatctcca gccctaggc cagcaggaca gttccagacc     900
ctggtggtgg gagtggtggg aggcctgctg gctctctgg tgctgctggt gtgggtgctg     960
gccgtgatct gcagcagggc cgcccgcggc accatcggcg ccaggcgcac aggccagcct    1020
ctgaaggagg acccttccgc cgtgccagtg ttctctgtgg actacggcga gctggatttt    1080
cagtggcggg agaaaacccc agagccacct gtgccctgcg tgcctgagca gaccgagtat    1140
gccacaatcg tgtttccatc cggaatgggc acaagctccc ctgcaaggag aggcagcgcc    1200
gacggaccac ggtccgccca gccactgcgg cccgaggatg ccactgttc ttggcccctg    1260 tgacgcccct ctccccccc ccctctcccc tccccccccc ctaacgttac tggccgaagc    1320
cgcttggaat aaggccggtg tgcgtttgtc tatatgttat tttccaccat attgccgtct    1380
tttggcaatg tgagggcccg gaaacctggc cctgtcttct tgacgagcat tcctagggt    1440 cttttcccctc tcgccaaagg aatgcaaggt ctgttgaatg tcgtgaagga agcagttcct    1500
ctggaagctt cttgaagaca aacaacgtct gtagcgaccc tttgcaggca gcggaacccc    1560
ccacctggcg acaggtgcct ctgcggccaa aagccacgtg tataagatac acctgcaaag    1620
```

|                                                                        |      |
| ---------------------------------------------------------------------- | ---- |
| gcggcacaac cccagtgcca cgttgtgagt tggatagttg tggaaagagt caaatggctc       | 1680 |
| tcctcaagcg tattcaacaa ggggctgaag gatgcccaga aggtacccca ttgtatggga       | 1740 |
| tctgatctgg ggcctcggtg cacatgcttt acatgtgttt agtcgaggtt aaaaaaacgt       | 1800 |
| ctaggccccc cgaaccacgg ggacgtggtt ttcctttgaa aaacacgatg ataaggcttg       | 1860 |
| ccacaacccg taccaaagat ggtgtccaag ggagaggagc tgttcaccgg agtggtgccc       | 1920 |
| atcctggtgg agctggacgg cgatgtgaat ggccacaagt ttagcgtgtc cggagaggga       | 1980 |
| gagggcgacg caacctacgg caagctgaca ctgaagttca tctgcaccac aggcaagctg       | 2040 |
| cccgtgcctt ggccaaccct ggtgaccaca ctgacatacg gcgtgcagtg ttttctcgc        | 2100 |
| tatcccgacc acatgaagca gcacgatttc tttaagagcg ccatgcctga gggctacgtg       | 2160 |
| caggagcgga ccatcttctt taaggacgat ggcaactata agaccagagc cgaggtgaag       | 2220 |
| ttcgagggcg acacactggt gaacaggatc gagctgaagg gcatcgactt taaggaggat       | 2280 |
| ggcaatatcc tgggccacaa gctggagtac aactataatt cccacaacgt gtacatcatg       | 2340 |
| gccgataagc agaagaacgg catcaaggtc aatttcaaga tcagacacaa tatcgaggac       | 2400 |
| ggctctgtgc agctggccga tcactaccag cagaacaccc caatcggcga cggacccgtg       | 2460 |
| ctgctgcctg ataatcacta tctgtctaca cagagcgccc tgtccaagga ccccaacgag       | 2520 |
| aagagggatc acatggtgct gctggagttt gtgaccgcag caggaatcac actgggaatg       | 2580 |
| gacgagctgt ataagggcag cggcgccacc aacttctccc tgctgaagca ggcaggcgac       | 2640 |
| gtggaggaga atccaggacc tatggataga agcggcaagc cagagctgac cgccacatcc       | 2700 |
| gtggagaagt tcctgatcga gaagtttgac tctgtgagcg atctgatgca gctgtccgag       | 2760 |
| ggagaggagt ccagggcctt ctcttttgat gtgggcggca ggggatacgt gctgagggtg       | 2820 |
| aatagctgcg ccgacggctt ctataaggat agatacgtgt atagacactt tgcctccgcc       | 2880 |
| gccctgccaa tccagaggt gctggacatc ggcgagtttt ccgagtctct gacctactgt        | 2940 |
| atcagccgga gagcccaggg agtgaccctg caggatctgc ctgagacaga gctgccagcc       | 3000 |
| gtgctgcagc cagtggcaga ggctatggac gcaatcgccg ccgccgacct gtctcagaca       | 3060 |
| agcggcttcg gccttttggg cccacagggc atcggccagt acaccacatg gagggacttc       | 3120 |
| atctgcgcca tcgccgatcc tcacgtgtat cactggcaga ccgtgatgga cgatacagtg       | 3180 |
| agcgcctccg tggcacaggc cctggacgag ctgatgctgt gggccgagga ttgtccagag       | 3240 |
| gtgcgccacc tggtgcacgc agactttggc agcaacaatg tgctgaccga taatggccgg       | 3300 |
| atcacagccg tgatcgactg gtccgaggcc atgttcggcg attctcagta cgaggtggcc       | 3360 |
| aacatcttct tttggaggcc ttggctgcc tgcatggagc agcagaccccg ctattttgag       | 3420 |
| aggcgccacc ctgagctggc cggctctcca cggctgagag catacatgct gcgcatcggc       | 3480 |
| ctggaccagc tgtatcagag cctggtggat ggcaatttcg acgatgcagc atgggcacag       | 3540 |
| ggccggtgcg acgcaatcgt gagatccggc gccggcaccg tgggccggac acagatcgca       | 3600 |
| cggcggagcg ccgccgtgtg gaccgacgga tgcgtggagg tgctggccga ttctggcaac       | 3660 |
| aggcgcccaa gcacaaggcc ccgcgccaag gagtga                                 | 3696 |

<210> SEQ ID NO 10
<211> LENGTH: 420
<212> TYPE: PRT
<213> ORGANISM: Artificial Sequence
<220> FEATURE:
<223> OTHER INFORMATION: HLA-A2 iCAR Synthetic Protein

```
<400> SEQUENCE: 10

Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Gln
            20                  25                  30

Val Gln Leu Gln Gln Ser Gly Pro Glu Leu Val Lys Pro Gly Ala Ser
        35                  40                  45

Val Lys Met Ser Cys Lys Ala Ser Gly Tyr Thr Phe Thr Ser Tyr His
    50                  55                  60

Ile Gln Trp Val Lys Gln Arg Pro Gly Gln Gly Leu Glu Trp Ile Gly
65                  70                  75                  80

Trp Ile Tyr Pro Gly Asp Gly Ser Thr Gln Tyr Asn Glu Lys Phe Lys
                85                  90                  95

Gly Lys Thr Thr Leu Thr Ala Asp Lys Ser Ser Ser Thr Ala Tyr Met
            100                 105                 110

Leu Leu Ser Ser Leu Thr Ser Glu Asp Ser Ala Ile Tyr Phe Cys Ala
        115                 120                 125

Arg Glu Gly Thr Tyr Tyr Ala Met Asp Tyr Trp Gly Gln Gly Thr Ser
    130                 135                 140

Val Thr Val Ser Ser Gly Gly Gly Ser Gly Gly Gly Ser Gly
145                 150                 155                 160

Gly Gly Gly Ser Asp Val Leu Met Thr Gln Thr Pro Leu Ser Leu Pro
                165                 170                 175

Val Ser Leu Gly Asp Gln Val Ser Ile Ser Cys Arg Ser Ser Gln Ser
            180                 185                 190

Ile Val His Ser Asn Gly Asn Thr Tyr Leu Glu Trp Tyr Leu Gln Lys
        195                 200                 205

Pro Gly Gln Ser Pro Lys Leu Leu Ile Tyr Lys Val Ser Asn Arg Phe
    210                 215                 220

Ser Gly Val Pro Asp Arg Phe Ser Gly Ser Gly Ser Gly Thr Asp Phe
225                 230                 235                 240

Thr Leu Lys Ile Ser Arg Val Glu Ala Glu Asp Leu Gly Val Tyr Tyr
                245                 250                 255

Cys Phe Gln Gly Ser His Val Pro Arg Thr Phe Gly Gly Gly Thr Lys
            260                 265                 270

Leu Glu Ile Lys Thr Glu Arg Arg Ala Glu Val Pro Thr Ala His Pro
        275                 280                 285

Ser Pro Ser Pro Arg Pro Ala Gly Gln Phe Gln Thr Leu Val Val Gly
    290                 295                 300

Val Val Gly Gly Leu Leu Gly Ser Leu Val Leu Leu Val Trp Val Leu
305                 310                 315                 320

Ala Val Ile Cys Ser Arg Ala Ala Arg Gly Thr Ile Gly Ala Arg Arg
                325                 330                 335

Thr Gly Gln Pro Leu Lys Glu Asp Pro Ser Ala Val Pro Val Phe Ser
            340                 345                 350

Val Asp Tyr Gly Glu Leu Asp Phe Gln Trp Arg Glu Lys Thr Pro Glu
        355                 360                 365

Pro Pro Val Pro Cys Val Pro Glu Gln Thr Glu Tyr Ala Thr Ile Val
    370                 375                 380

Phe Pro Ser Gly Met Gly Thr Ser Ser Pro Ala Arg Arg Gly Ser Ala
385                 390                 395                 400
```

-continued

```
Asp Gly Pro Arg Ser Ala Gln Pro Leu Arg Pro Glu Asp Gly His Cys
            405                 410                 415
Ser Trp Pro Leu
        420
```